United States Patent
Schönfeld et al.

(10) Patent No.: US 12,173,068 B2
(45) Date of Patent: *Dec. 24, 2024

(54) ANTI-SEMA3A ANTIBODIES AND USES THEREOF

(71) Applicant: BAYER AKTIENGESELLSCHAFT, Leverkusen (DE)

(72) Inventors: Dorian Schönfeld, Cologne (DE); Karoline Dröbner, Velbert (DE); Ernst Weber, Langenfeld (DE); Katharina Filarsky, Düsseldorf (DE); Philipp Ellinger, Solingen (DE); Fionnuala Mary McAleese Eser, Lagenfeld (DE); Ingo Flamme, Reichshof (DE); Winfried Wunderlich, Bovenden (DE); Antje Schmidt, Göttingen (DE); Yalda Sedaghat, Hamburg (DE); Kenneth Young, Hamburg (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/399,934

(22) Filed: Dec. 29, 2023

(65) Prior Publication Data
US 2024/0254222 A1    Aug. 1, 2024

Related U.S. Application Data

(63) Continuation of application No. 17/706,543, filed on Mar. 28, 2022.

(30) Foreign Application Priority Data

Mar. 30, 2021   (EP) .................................... 21165960

(51) Int. Cl.
| | |
|---|---|
| *C07K 16/28* | (2006.01) |
| *A61K 39/395* | (2006.01) |
| *A61P 9/10* | (2006.01) |
| *A61P 13/12* | (2006.01) |
| *C07K 16/18* | (2006.01) |
| *A61K 39/00* | (2006.01) |

(52) U.S. Cl.
CPC ...... *C07K 16/2803* (2013.01); *A61K 39/3955* (2013.01); *A61P 9/10* (2018.01); *A61P 13/12* (2018.01); *C07K 16/18* (2013.01); *A61K 2039/505* (2013.01); *C07K 2317/33* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,634,665 A | 1/1987 | Axel et al. |
| 4,657,760 A | 4/1987 | Kung et al. |

(Continued)

FOREIGN PATENT DOCUMENTS

| | | |
|---|---|---|
| AU | 2016346595 A1 | 6/2018 |
| EP | 2955195 A1 | 12/2015 |

(Continued)

OTHER PUBLICATIONS

Kipriyanov, Sergey M., and Fabrice Le Gall. "Generation and production of engineered antibodies." Molecular biotechnology 26.1 (2004): 39-60. (Year: 2004).*

(Continued)

*Primary Examiner* — Michael Szperka
*Assistant Examiner* — Lia E Taylor
(74) *Attorney, Agent, or Firm* — Harness, Dickey & Pierce, P.L.C.

(57) ABSTRACT

The present disclosure relates to an isolated antibody or antigen-binding fragment thereof that binds to human Sema3A. The isolated antibody or antigen-binding fragment according to the present disclosure i) binds to human Sema3A of the sequence of SEQ ID NO: 600 with a dissociation constant (KD)≤50 nM, ≤20 nM, ≤10 nM, ≤1 nM, or ≤0.1 nM; ii) cross-reacts with mouse, cynomolgus, rat, pig and/or dog Sema3A, particularly wherein said isolated antibody or antigen-binding fragment thereof binds to mouse, cynomolgus, rat, pig and/or dog Sema3A with a dissociation constant (KD)≤50 nM, ≤20 nM, ≤10 nM, ≤1 nM, or ≤0.1 nM; iii) binds to human Sema3A of the sequence of SEQ ID NO: 600 with a binding activity as measured by surface plasmon resonance (SPR) of ≥60%, ≥70%, ≥80%, or ≥90%; iv) inhibits the activity of human Sema3A of the sequence of SEQ ID NO: 600 in an in vitro mesangial cell migration assay with an EC50 of ≤10 nM, ≤5 nM, ≤2.5 nM, or ≤1 nM; v) inhibits the activity of human Sema3A of the sequence of SEQ ID NO: 600 in an in vitro growth cone collapse assay with an EC50 of ≤50 nM, ≤25 nM, ≤10 nM, or ≤5 nM; vi) inhibits the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM and/or vii) exhibits an increased potency against cellular Sema3A, of the sequence of SEQ ID NO: 600, induced HUVEC repulsion.

9 Claims, 15 Drawing Sheets

Figure 1A:
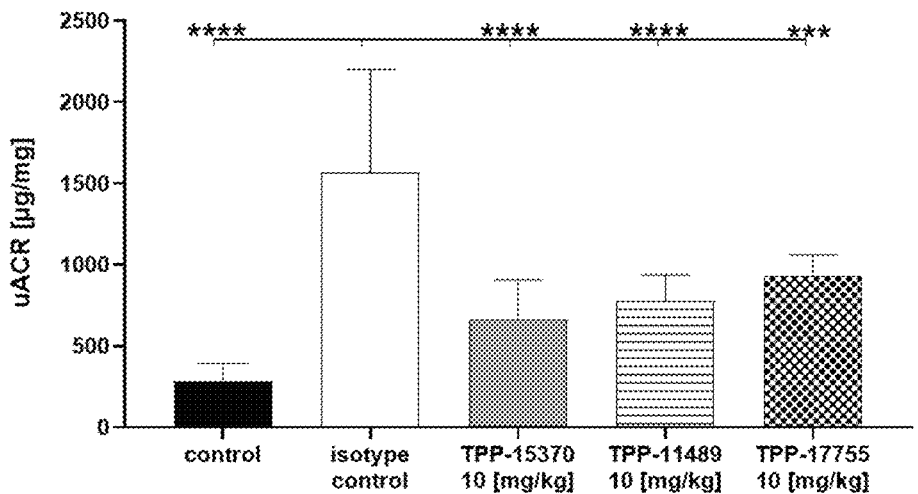

Specification includes a Sequence Listing.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,968,615 | A | 11/1990 | Koszinowski et al. |
| 5,168,062 | A | 12/1992 | Stinski |
| 5,179,017 | A | 1/1993 | Axel et al. |
| 5,206,344 | A | 4/1993 | Katre et al. |
| 5,208,020 | A | 5/1993 | Chari et al. |
| 5,225,212 | A | 7/1993 | Martin et al. |
| 5,225,539 | A | 7/1993 | Winter |
| 5,416,064 | A | 5/1995 | Chari et al. |
| 5,585,089 | A | 12/1996 | Queen et al. |
| 5,635,483 | A | 6/1997 | Pettit et al. |
| 5,693,761 | A | 12/1997 | Queen et al. |
| 5,693,762 | A | 12/1997 | Queen et al. |
| 5,766,886 | A | 6/1998 | Studnicka et al. |
| 5,780,588 | A | 7/1998 | Pettit et al. |
| 5,821,337 | A | 10/1998 | Carter et al. |
| 5,859,205 | A | 1/1999 | Adair et al. |
| 6,180,370 | B1 * | 1/2001 | Queen ............... A61P 19/02 435/69.6 |
| 6,300,064 | B1 | 10/2001 | Knappik et al. |
| 6,602,684 | B1 | 8/2003 | Umana et al. |
| 6,982,321 | B2 | 1/2006 | Winter |
| 6,989,250 | B2 | 1/2006 | Soderlind et al. |
| 7,087,409 | B2 | 8/2006 | Barbas, III et al. |
| 7,498,298 | B2 | 3/2009 | Doronina et al. |
| 7,527,791 | B2 | 5/2009 | Adams et al. |
| 9,879,075 | B2 * | 1/2018 | Goshima ............. A61P 37/02 |
| 2005/0014934 | A1 | 1/2005 | Hinton et al. |
| 2005/0123546 | A1 | 6/2005 | Umana et al. |

FOREIGN PATENT DOCUMENTS

| | | |
|---|---|---|
| WO | WO-9708320 A1 | 3/1997 |
| WO | WO-199730087 A1 | 8/1997 |
| WO | WO-199858964 A1 | 12/1998 |
| WO | WO-199922764 A1 | 5/1999 |
| WO | WO-2003011878 A2 | 2/2003 |
| WO | WO-2004056312 A2 | 7/2004 |
| WO | WO-2008077546 A1 | 7/2008 |
| WO | WO-2008112640 A2 | 9/2008 |
| WO | WO-2017074013 A1 | 5/2017 |
| WO | WO-2020225400 A1 | 11/2020 |
| WO | WO-2020261281 A1 | 12/2020 |

OTHER PUBLICATIONS

Janeway, Charles A. "Immunobiology: The Immune System in Health and Disease." 2001 (Year: 2001).*

Almagro, Juan C. et al., "Humanization of antibodies" Frontiers in Bioscience 13, Jan. 2008, (15 pages).

Bebbington, C.R. et al., "High-Level Expression of a Recombinant Antibody From Myeloma Cells Using a Glutamine Synthetase Gene as an Amplifiable Selectable Marker", Bio/Technology, vol. 10, Feb. 1992, (7 pages).

Bird, Robert E. et al., "Single-Chain Antigen-Binding Proteins", Science vol. 242, Oct. 21, 1988, (4 pages).

Bruggemann, Marianne, et al., Human Antibody Production in Transgenic Animals, Arch. Immunol. Ther. Exp., vol. 63, 2015. (8 pages).

Carlsson, Roland et al., "n-CoDeR concept: unique types of antibodies for diagnostic use and therapy" Expert Rev. Mol. Diagn., vol. 1, 2001. (7 pages).

Carter, Paul J., "Potent antibody therapeutics by design", Nature Reviews Immunology, vol. 6, May 2006. (16 pages).

Chari, Ravi V.J., et al., "Immunoconjugates Containing Novel Maytansinoids: Promising Anticancer Drugs", Cancer Research, vol. 52, Jan. 1992. (5 pages).

Chothia, Cyrus et al., "Canonical Structures for the Hypervariable Regions of Immunoglobulins", J. Mol. Biol., vol. 196, 1987. (17 pages).

Dall'Acqua, William F. et al., "Antibody humanization by framework shuffling", Methods, vol. 36, Jan. 17, 2005. (18 pages).

Durocher, Yves et al., "High-level and high-throughput recombinant protein production by transient transfection of suspension-growing human 293-EBNA1 cells" Nucleic Acids Research, vol. 30, 2002. (9 pages).

Fan, Lianchun et al., "Improving the Efficiency of CHO Cell Line Generation Using Glutamine Synthetase Gene Knockout Cells" Biotechnology and Bioengineering, vol. 109, 2012. (9 pages).

Frenzel, Andre et al., "Phage display-derived human antibodies in clinical development and therapy" MABS, vol. 8, 2016. (19 pages).

Guyer, Ruth L. et al., "Immunoglobulin Binding By Mouse Intestinal Epithelial Cell Receptors" The Journal of Immunology, vol. 117, Aug. 1976. (7 pages).

Hoet et al., "Generation of high-affinity human antibodies by combining donor-derived and synthetic complementarity-determining-region diversity" Nature Biotechnology, vol. 23, Mar. 2005. (5 pages).

Huston, James S. et al., "Protein engineering of antibody binding sites: Recovery of specific activity in an anti-digoxin single-chain Fv analogue produced in *Escherichia coli*" Proc. Natl. Acad. Sci. USA, vol. 85, Aug. 1988. (5 pages).

Jones, Peter T. et al., "Replacing the complementarity-determining regions in a human antibody with those from a mouse" Nature, vol. 321, May 1986. (4 pages).

Kanda, Yutaka et al., "Comparison of Cell Lines for Stable Production of Fucose-Negative Antibodies With Enhanced ADCC" Biotechnology and Bioengineering, vol. 94, 2006. (10 pages).

Kashmiri et al., "SDR grafting—a new approach to antibody humanization" Methods, vol. 36, 2005. (10 pages).

Kaufman, Randal J. & Sharp, Phillip A., "Amplification and Expression of Sequences Cotransfected with a Modular Dihydrofolate Reductase Complementary DNA Gene" J. Mol. Biol., vol. 159, 1982. (21 pages).

Khorana H. G. et al., "Studies on Polynucleotides, CIII: Total Synthesis of the Structural Gene for an Alanine Transfer Ribonucleic Acid from Yeast" J. Mol. Biol., vol. 72, 1972. (9 pages).

Kim, J.K. et al., "Identifying amino acid residues that influence plasma clearance of murine IgG1 fragments by site-directed mutagenesis" Eur. J. Immunol., vol. 24, 1994. (7 pages).

Klimka, A et al., "Human anti-CD30 recombinant antibodies by guided phage antibody selection using cell panning" British Journal of Cancer, vol. 83, 2000. (9 pages).

Knappik, Achim et al., "Fully Synethic Human Combinatorial Antibody Libraries (HuCAL) Based on Modular Consensus Frameworks and CDRs Randomized with Trinucleotides" J. Mol. Biol. vol 296, 2000. (30 pages).

Kohler et al., "Continuous cultures of fused cells secreting antibody of predefined specificity" Nature, vol. 256, Aug. 1975. (3 pages).

Krebs, Barbara et al., "High throughput generation and engineering of recombinant human antibodies" Journal of Immunological Methods, vol. 254, 2001. (18 pages).

Liu, C. et al., "Eradication of large colon tumor xenografts by targeted delivery of maytansinoids" Proc. Natl. Acad. Sci. USA, vol. 93, Aug. 1996. (6 pages).

McCafferty, John et al., "Phage antibodies: filamentous phage displaying antibody variable domains" Naturem vol. 348, Dec. 1990. (3 pages).

Mikule, Keith et al., "Growth Cone Collapse Induced by Semaphorin 3A Requires 12/15-Lipoxygenase" The Journal of Neuroscience, vol. 22, Jun. 2002. (10 pages).

Nelson, Aaron L. et al., "Development trends for human monoclonal antibody therapeutics" Nature Reviews, vol. 9, Oct. 2010. (8 pages).

Nose, Masato et al., "Biological significance of carbohydrate chains on monoclonal antibodies" Proc. Natl. Acad. Sci. USA, vol. 80, Nov. 1983. (5 pages).

Okazaki, Akira et al., "Fucose Depletion from Human IgG1 Oligosaccharide Enhances Binding Enthalpy and Association Rate Between IgG1 and FcγRIIIa" J. Mol. Biol., vol. 336, 2004. (11 pages).

Osbourn, Jane et al., "From rodent reagents to human therapeutics using antibody guided selection" Methods, vol. 36, 2005. (8 pages).

(56) References Cited

OTHER PUBLICATIONS

Padlan, Eduardo A., "A Possible Procedure for Reducing The Immunogenicity of Antibody Variable Domains While Preserving Their Ligand-Binding Properties" Molecular Immunology, vol. 28, 1991. (10 pages).

Pluckthun, A., "Antibodies from *Escherichia coli*" The Pharmacology of Monoclonal Antibodies, edition 113, 1994. (47 pages).

Presta, Leonard G., "Antibody engineering" Structural Biology, vol. 2, 1992. (4 pages).

Queen, Cary et al., "A humanized antibody that binds to the interleukin 2 receptor" Proc. Natl. Acad. Sci. USA, vol. 86, Dec. 1989. (5 pages).

Riechmann, Lutz et al., "Reshaping human antibodies for therapy" Nature, vol. 332, Mar. 1988. (5 pages).

Ripka, James et al., "Two Chinese Hamster Ovary Glycosylation Mutants Affected in the Conversion of GDP-Mannose to GDP-Fucose", Archives of Biochemistry and Biophysics, vol. 249, Apr. 1986. (13 pages).

Soderlind, Eskil et al., "Recombining germline-derived CDR sequences for creating diverse single-framework antibody libraries" Nature Biotechnology, vol. 18, Aug. 2000. (5 pages).

Urlaub, Gail et al., "Deletion of the Diploid Dihydrofolate Reductase Locus from Cultured Mammalian Cells", Cell, vol. 33, Jun. 1983. (8 pages).

Urlaub, Gail et al., "Isolation of Chinese hamster cell mutants deficient in dihydrofolate reductase activity" Proc. Natl. Acad. Sci. USA, vol. 77, Jul. 1980. (5 pages).

Virnekas, Bernhard et al., "Trinucleotide phosphoramidites: ideal reagents for the synthesis of mixed oligonucleotides for random mutagenesis" Nucleic Acids Research, vol. 22, 1994. (8 pages).

Winkelhake, Jeffrey L., "Effects of Exoglycosidase Treatments on Autochthonous Antibody Survival Time in The Circulation" The Journal of Biological Chemistry, vol. 251, Feb. 1976. (7 pages).

Wright, Ann & Morrison, Sherie L., "Effect of glycosylation on antibody function: implications for genetic engineering" TIBTECH, vol. 15, Jan. 1997. (7 pages).

Yamane-Ohnuki, Naoko et al., "Establishment of FUT8 Knockout Chinese Hamster Ovary Cells: An Ideal Hoset Cell Line for Producing Completely Defucosylated Antibodies With Enhanced Antibody-Dependent Cellular Cytotoxicity" Biotechnology and Bioengineering, vol. 87, Sep. 2004. (9 pages).

Zapata, Gerardo et al., "Engineering linear F(ab')2 fragments for efficient production in *Escherichia coli* and enhanced antiproliferative activity" Protein Engineering, vol. 8, 1995. (6 pages).

\* cited by examiner

SEQUENCE LISTING

Sequence total quantity: 885
SEQ ID NO: 1             moltype = AA   length = 124
FEATURE                  Location/Qualifiers
REGION                   1..124
                         note = antibody sequence
source                   1..124
                         mol_type = protein
                         organism = synthetic construct
SEQUENCE: 1
EVQLLESGGG LVQPGGSLRL SCAASGFTFS SYPMGWVRQA PGKGLEWVAG IDDDGDSDTR    60
YAPAVKGRAT ISRDNSKNTV YLQMNSLRAE DTAVYYCAKH TGIGANSAGS IDAWGQGTLV   120
TVSS                                                                124

SEQ ID NO: 2             moltype = AA   length = 5
FEATURE                  Location/Qualifiers
REGION                   1..5
                         note = antibody sequence
source                   1..5
                         mol_type = protein
                         organism = synthetic construct
SEQUENCE: 2
SYPMG                                                                 5

SEQ ID NO: 3             moltype = AA   length = 18
FEATURE                  Location/Qualifiers
REGION                   1..18
                         note = antibody sequence
source                   1..18
                         mol_type = protein
                         organism = synthetic construct
SEQUENCE: 3
GIDDDGDSDT RYAPAVKG                                                  18

SEQ ID NO: 4             moltype = AA   length = 14
FEATURE                  Location/Qualifiers
REGION                   1..14
                         note = antibody sequence
source                   1..14
                         mol_type = protein
                         organism = synthetic construct
SEQUENCE: 4
HTGIGANSAG SIDA                                                      14

SEQ ID NO: 5             moltype = AA   length = 108
FEATURE                  Location/Qualifiers
REGION                   1..108
                         note = antibody sequence
source                   1..108
                         mol_type = protein
                         organism = synthetic construct

```
SEQUENCE: 5
SYELTQPPSV SVSPGQTARI TCSGGGSYTG SYYYGWYQQK PGQAPVTVIY YNNKRPSDIP    60
ERFSGSLSGT TNTLTISGVQ AEDEADYYCG SADNSGDAFG TGTKVTVL                108

SEQ ID NO: 6              moltype = AA   length = 13
FEATURE                   Location/Qualifiers
REGION                    1..13
                          note = antibody sequence
source                    1..13
                          mol_type = protein
                          organism = synthetic construct
SEQUENCE: 6
SGGGSYTGSY YYG                                                      13

SEQ ID NO: 7              moltype = AA   length = 7
FEATURE                   Location/Qualifiers
REGION                    1..7
                          note = antibody sequence
source                    1..7
                          mol_type = protein
                          organism = synthetic construct
SEQUENCE: 7
YNNKRPS                                                              7

SEQ ID NO: 8              moltype = AA   length = 9
FEATURE                   Location/Qualifiers
REGION                    1..9
                          note = antibody sequence
source                    1..9
                          mol_type = protein
                          organism = synthetic construct
SEQUENCE: 8
GSADNSGDA                                                            9

SEQ ID NO: 9              moltype = DNA  length = 372
FEATURE                   Location/Qualifiers
misc_feature              1..372
                          note = antibody sequence
source                    1..372
                          mol_type = other DNA
                          organism = synthetic construct
SEQUENCE: 9
gaagttcagc tgctggaatc tggcggcgga ctggttcaac ctggcggatc tctgagactg    60
agctgtgccg ccagcggctt cacctttagc agctatccta tgggctgggt ccgacaggcc   120
cctggcaaag gacttgaatg ggtggccgga atcgacgacg atggcgatag cgatacaaga   180
tacgcccctg ccgtgaaggg cagagccacc atctccagag acaacagcaa gaacaccgtg   240
tacctgcaga tgaacagcct gagagccgag gacaccgccg tgtactattg tgccaagcac   300
acaggcatcg gcgccaattc tgccggctct attgatgcct ggggccaggg aacactggtc   360
acagtttctt ca                                                      372

SEQ ID NO: 10             moltype = DNA  length = 15
FEATURE                   Location/Qualifiers
misc_feature              1..15
                          note = antibody sequence
source                    1..15
                          mol_type = other DNA
                          organism = synthetic construct
SEQUENCE: 10
agctatccta tgggc                                                    15

SEQ ID NO: 11             moltype = DNA  length = 54
FEATURE                   Location/Qualifiers
misc_feature              1..54
                          note = antibody sequence
source                    1..54
                          mol_type = other DNA
                          organism = synthetic construct
SEQUENCE: 11
ggcatcgacg acgatggcga tagcgataca agatacgccc ctgccgtgaa gggc         54

SEQ ID NO: 12             moltype = DNA  length = 42
FEATURE                   Location/Qualifiers
misc_feature              1..42
                          note = antibody sequence
source                    1..42
                          mol_type = other DNA
                          organism = synthetic construct
SEQUENCE: 12
cacacaggca tcggcgccaa ttctgccggc tctattgatg cc                      42
```

```
SEQ ID NO: 13            moltype = DNA  length = 324
FEATURE                  Location/Qualifiers
misc_feature             1..324
                         note = antibody sequence
source                   1..324
                         mol_type = other DNA
                         organism = synthetic construct
SEQUENCE: 13
agctatgagc tgacacagcc tccaagcgtg tccgtgtctc ctggacagac cgccagaatc    60
acatgtagcg gcggaggcag ctacaccggc agctactact atggctggta tcagcagaag   120
cccgacagg ccctgtgac cgtgatctac tacaacaaca gcggcccag cgacatcccc      180
gagagatttt ctggctctct gagcggcacc accaacacac tgacaatctc tggcgtgcag   240
gccgaggacg aggccgatta ctattgtggc agcgccgata tagcggcga cgcctttggc    300
accggcacca agttacagt gcta                                           324

SEQ ID NO: 14            moltype = DNA  length = 39
FEATURE                  Location/Qualifiers
misc_feature             1..39
                         note = antibody sequence
source                   1..39
                         mol_type = other DNA
                         organism = synthetic construct
SEQUENCE: 14
agcggcggag gcagctacac cggcagctac tactatggc                           39

SEQ ID NO: 15            moltype = DNA  length = 21
FEATURE                  Location/Qualifiers
misc_feature             1..21
                         note = antibody sequence
source                   1..21
                         mol_type = other DNA
                         organism = synthetic construct
SEQUENCE: 15
tacaacaaca gcggcccag c                                               21

SEQ ID NO: 16            moltype = DNA  length = 27
FEATURE                  Location/Qualifiers
misc_feature             1..27
                         note = antibody sequence
source                   1..27
                         mol_type = other DNA
                         organism = synthetic construct
SEQUENCE: 16
ggcagcgccg ataatagcgg cgacgcc                                        27

SEQ ID NO: 17            moltype = AA  length = 453
FEATURE                  Location/Qualifiers
REGION                   1..453
                         note = antibody sequence
source                   1..453
                         mol_type = protein
                         organism = synthetic construct
SEQUENCE: 17
EVQLLESGGG LVQPGGSLRL SCAASGFTFS SYPMGWVRQA PGKGLEWVAG IDDDGDSDTR    60
YAPAVKGRAT ISRDNSKNTV YLQMNSLRAE DTAVYYCAKH TGIGANSAGS IDAWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPG                                453

SEQ ID NO: 18            moltype = AA  length = 214
FEATURE                  Location/Qualifiers
REGION                   1..214
                         note = antibody sequence
source                   1..214
                         mol_type = protein
                         organism = synthetic construct
SEQUENCE: 18
SYELTQPPSV SVSPGQTARI TCSGGGSYTG SYYYGWYQQK PGQAPVTVIY YNNKRPSDIP    60
ERFSGSLSGT TNTLTISGVQ AEDEADYYCG SADNSGDAFG TGTKVTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 19            moltype = DNA  length = 1359
FEATURE                  Location/Qualifiers
misc_feature             1..1359
```

```
                        note = antibody sequence
source                  1..1359
                        mol_type = other DNA
                        organism = synthetic construct
SEQUENCE: 19
gaagttcagc tgctggaatc tggcggcgga ctggttcaac ctggcggatc tctgagactg    60
agctgtgccg ccagcggctt cacctttagc agctatccta tgggctgggt ccgacaggcc   120
cctggcaaag gacttgaatg ggtggccggc atcgacgacg atggcgatag cgatacaaga   180
tacgccctg ccgtgaaggg cagagccacc atctccagag acaacagcaa gaacaccgtg    240
tacctgcaga tgaacagcct gagagccgag gacaccgccg tgtactattg tgccaagcac   300
acaggcatcg gcgccaattc tgccggctct attgatgcct ggggccaggg aacactggtc   360
acagtttctt cagccagcac caagggcccc agcgtgttcc ctctggcccc tagcagcaag   420
agcacatctg gcggaacagc cgccctgggc tgctcgtga aggactactt ccccgagccc     480
gtgaccgtgt cctggaactc tggcgctctg acaagcggcg tgcacacctt ccagcgcac    540
ctgcagagca gcggcctgta ctctctgagc agcgtcgtga cagtgcccag cagctctctg   600
ggcacccaga cctacatctg caacgtgaac cacaagccca gcaacaccaa ggtggacaag   660
aaggtggaac ccaagagctg cgacaagacc cacacctgtc cccttgtcc tgcccccgaa    720
ctgctgggga gcccttccgt gttcctgttc cccccaaagc ccaaggacac cctgatgatc   780
agccggaccc ccgaagtgac ctgcgtggtg gtggatgtgt cccacgagga ccctgaagtg   840
aagttcaatt ggtacgtgga cggcgtggaa gtgcacaacg ccaagaccaa gcctagagag   900
gaacagtaca acagcaccta ccgggtggtg tccgtgctga cagtgctgca ccaggactgg   960
ctgaacggca aagagtacaa gtgcaaggtg tccaacaagg ccctgcctgc ccccatcgag  1020
aaaaccatca gcaaggccaa ggccagccc cgcgaacccc aggtgtacac actgccccca   1080
agcagggacg agctgaccaa gaaccaggtg tccctgacct gtctcgtgaa aggcttctac  1140
ccctccgata tcgccgtgga atgggagagc aacggccagc cgagaacaa ctacaagacc   1200
accccccctg tgctggacag cgacggctca ttcttcctgt acagcaagct gaccgtggac  1260
aagtcccggt ggcagcaggg caacgtgttc agctgcagcg tgatgcacga ggccctgcac  1320
aaccactaca cccagaagtc cctgagcctg agcctggc                          1359

SEQ ID NO: 20           moltype = DNA  length = 642
FEATURE                 Location/Qualifiers
misc_feature            1..642
                        note = antibody sequence
source                  1..642
                        mol_type = other DNA
                        organism = synthetic construct
SEQUENCE: 20
agctatgagc tgacacagcc tccaagcgtg tccgtgtctc ctggacagac cgccagaatc     60
acatgtagcg gcggaggcag ctacaccggc agctactact atggctggta tcagcagaag   120
cccggacagg cccctgtgac cgtgatctac tacaacaaca gcggcccag cgacatcccc    180
gagagatttt ctggctctct gagcggcacc accaacacac tgacaatctc tggcgtgcag   240
gccgaggacg aggccgatta ctattgtggc agcgccgata tagcggcga cgcctttggc    300
accggcacca aagttacagt gctaggccag cctaaagccg gaccctgtc                360
cctccaagca gcgaggaact gcaggccaac aaggccaccc tcgtgtgcct gatcagcgac   420
ttctatcctg gcgccgtgac cgtggcctgg aaggccgata gctctcctgt gaaggccggc   480
gtggaaacca ccaccccctag caagcagagc aacaacaaat acgccgccag cagctacctg  540
agcctgaccc ccgagcagtg gaagtccacc agatcctaca gctgccaagt gacccacgag   600
ggcagcaccg tggaaaagac agtggcccct accgagtgca gc                      642

SEQ ID NO: 21           moltype = AA  length = 124
FEATURE                 Location/Qualifiers
REGION                  1..124
                        note = antibody sequence
source                  1..124
                        mol_type = protein
                        organism = synthetic construct
SEQUENCE: 21
EVQLLESGGG LVQPGGSLRL SCAASGFTFS SYPMGWVRQA PGKGLEWVAG IDDDGDSDTR    60
YAPAVKGRAT ISRDNSKNTV YLQMNSLRAE DTAVYYCAKH TGIGANSAGS IDAWGQGTLV   120
TVSS                                                                124

SEQ ID NO: 22           moltype = AA  length = 5
FEATURE                 Location/Qualifiers
REGION                  1..5
                        note = antibody sequence
source                  1..5
                        mol_type = protein
                        organism = synthetic construct
SEQUENCE: 22
SYPMG                                                                 5

SEQ ID NO: 23           moltype = AA  length = 18
FEATURE                 Location/Qualifiers
REGION                  1..18
                        note = antibody sequence
source                  1..18
                        mol_type = protein
                        organism = synthetic construct
SEQUENCE: 23
```

```
GIDDDGDSDT RYAPAVKG                                                        18

SEQ ID NO: 24          moltype = AA   length = 14
FEATURE                Location/Qualifiers
REGION                 1..14
                       note = antibody sequence
source                 1..14
                       mol_type = protein
                       organism = synthetic construct
SEQUENCE: 24
HTGIGANSAG SIDA                                                            14

SEQ ID NO: 25          moltype = AA   length = 108
FEATURE                Location/Qualifiers
REGION                 1..108
                       note = antibody sequence
source                 1..108
                       mol_type = protein
                       organism = synthetic construct
SEQUENCE: 25
SYELTQPPSV SVSPGQTARI TCSGGGSYTG SYYYGWYQQK PGQAPVTVIY YNNKRPSDIP           60
ERFSGSLSGT TNTLTISGVQ AEDEADYYCG SADNSGDAFG TGTKVTVL                       108

SEQ ID NO: 26          moltype = AA   length = 13
FEATURE                Location/Qualifiers
REGION                 1..13
                       note = antibody sequence
source                 1..13
                       mol_type = protein
                       organism = synthetic construct
SEQUENCE: 26
SGGGSYTGSY YYG                                                             13

SEQ ID NO: 27          moltype = AA   length = 7
FEATURE                Location/Qualifiers
REGION                 1..7
                       note = antibody sequence
source                 1..7
                       mol_type = protein
                       organism = synthetic construct
SEQUENCE: 27
YNNKRPS                                                                     7

SEQ ID NO: 28          moltype = AA   length = 9
FEATURE                Location/Qualifiers
REGION                 1..9
                       note = antibody sequence
source                 1..9
                       mol_type = protein
                       organism = synthetic construct
SEQUENCE: 28
GSADNSGDA                                                                   9

SEQ ID NO: 29          moltype = DNA   length = 372
FEATURE                Location/Qualifiers
misc_feature           1..372
                       note = antibody sequence
source                 1..372
                       mol_type = other DNA
                       organism = synthetic construct
SEQUENCE: 29
gaagttcagc tgctggaatc tggcggcgga ctggttcaac ctggcggatc tctgagactg           60
agctgtgccg ccagcggctt caccttttagc agctatccta tgggctgggt ccgacaggcc        120
cctggcaaag gacttgaatg ggtggccggc atcgacgacg atggcgatag cgatacaaga         180
tacgccctg ccgtgaaggg cagagccacc atctccagag acaacagcaa gaacaccgtg          240
tacctgcaga tgaacagcct gagagccgag gacaccgccg tgtactattg tgccaagcac         300
acaggcatcg gcgccaattc tgccggctct attgatgcct ggggccaggg aacactggtc         360
acagtttctt ca                                                             372

SEQ ID NO: 30          moltype = DNA   length = 15
FEATURE                Location/Qualifiers
misc_feature           1..15
                       note = antibody sequence
source                 1..15
                       mol_type = other DNA
                       organism = synthetic construct
SEQUENCE: 30
agctatccta tgggc                                                           15
```

```
SEQ ID NO: 31              moltype = DNA   length = 54
FEATURE                    Location/Qualifiers
misc_feature               1..54
                           note = antibody sequence
source                     1..54
                           mol_type = other DNA
                           organism = synthetic construct
SEQUENCE: 31
ggcatcgacg acgatggcga tagcgataca agatacgccc ctgccgtgaa gggc      54

SEQ ID NO: 32              moltype = DNA   length = 42
FEATURE                    Location/Qualifiers
misc_feature               1..42
                           note = antibody sequence
source                     1..42
                           mol_type = other DNA
                           organism = synthetic construct
SEQUENCE: 32
cacacaggca tcggcgccaa ttctgccggc tctattgatg cc                   42

SEQ ID NO: 33              moltype = DNA   length = 324
FEATURE                    Location/Qualifiers
misc_feature               1..324
                           note = antibody sequence
source                     1..324
                           mol_type = other DNA
                           organism = synthetic construct
SEQUENCE: 33
agctatgagc tgacacagcc tccaagcgtg tccgtgtctc tggacagac cgccagaatc   60
acatgtagcg gcggaggcag ctacaccggc agctactact atggctggta tcagcagaag  120
cccggacagg cccctgtgac cgtgatctac tacaacaaca gcggcccag cgacatcccc  180
gagagatttt ctggctctct gagcggcacc accaacacac tgacaatctc tggcgtgcag  240
gccgaggacg aggccgatta ctattgtggc agcgccgata tagcggcga cgcctttggc  300
accggcacca aagttacagt gcta                                       324

SEQ ID NO: 34              moltype = DNA   length = 39
FEATURE                    Location/Qualifiers
misc_feature               1..39
                           note = antibody sequence
source                     1..39
                           mol_type = other DNA
                           organism = synthetic construct
SEQUENCE: 34
agcggcggag gcagctacac cggcagctac tactatggc                       39

SEQ ID NO: 35              moltype = DNA   length = 21
FEATURE                    Location/Qualifiers
misc_feature               1..21
                           note = antibody sequence
source                     1..21
                           mol_type = other DNA
                           organism = synthetic construct
SEQUENCE: 35
tacaacaaca gcggcccag c                                           21

SEQ ID NO: 36              moltype = DNA   length = 27
FEATURE                    Location/Qualifiers
misc_feature               1..27
                           note = antibody sequence
source                     1..27
                           mol_type = other DNA
                           organism = synthetic construct
SEQUENCE: 36
ggcagcgccg ataatagcgg cgacgcc                                    27

SEQ ID NO: 37              moltype = AA    length = 448
FEATURE                    Location/Qualifiers
REGION                     1..448
                           note = antibody sequence
source                     1..448
                           mol_type = protein
                           organism = synthetic construct
SEQUENCE: 37
EVQLLESGGG LVQPGGSLRL SCAASGFTFS SYPMGWVRQA PGKGLEWVAG IDDDGDSDTR   60
YAPAVKGRAT ISRDNSKNTV YLQMNSLRAE DTAVYYCAKH TGIGANSAGS IDAWGQGTLV  120
TVSSAKTTPP SVYPLAPGSA AQTNSMVTLG CLVKGYFPEP VTVTWNSGSL SSGVHTFPAV  180
LQSDLYTLSS SVTVPSSTWP SETVTCNVAH PASSTKVDKK IVPRDCGCKP CICTVPEVSS  240
VFIFPPKPKD VLTITLTPKV TCVVVDISKD DPEVQFSWFV DDVEVHTAQT QPREEQFNST  300
FRSVSELPIM HQDWLNGKEF KCRVNSAAFP APIEKTISKT KGRPKAPQVY TIPPPKEQMA  360
```

```
KDKVSLTCMI TDFFPEDITV EWQWNGQPAE NYKNTQPIMD TDGSYFVYSK LNVQKSNWEA    420
GNTFTCSVLH EGLHNHHTEK SLSHSPGK                                      448

SEQ ID NO: 38           moltype = AA  length = 214
FEATURE                 Location/Qualifiers
REGION                  1..214
                        note = antibody sequence
source                  1..214
                        mol_type = protein
                        organism = synthetic construct
SEQUENCE: 38
SYELTQPPSV SVSPGQTARI TCSGGGSYTG SYYYGWYQQK PGQAPVTVIY YNNKRPSDIP    60
ERFSGSLSGT TNTLTISGVQ AEDEADYYCG SADNSGDAFG TGTKVTVLGQ PKSSPSVTLF    120
PPSSEELETN KATLVCTITD FYPGVVTVDW KVDGTPVTQG METTQPSKQS NNKYMASSYL    180
TLTARAWERH SSYSCQVTHE GHTVEKSLSR ADCS                                214

SEQ ID NO: 39           moltype = DNA  length = 1344
FEATURE                 Location/Qualifiers
misc_feature            1..1344
                        note = antibody sequence
source                  1..1344
                        mol_type = other DNA
                        organism = synthetic construct
SEQUENCE: 39
gaagttcagc tgctggaatc tggcggcgga ctggttcaac tggcggatc tctgagactg     60
agctgtgccg ccagcggctt cacctttagc agctatccta tgggctgggt ccgacaggcc   120
cctggcaaag gacttgaatg ggtgccggc atcgacacg atggcgatag cgatacaaga    180
tacgccctg ccgtgaaggg cagagccacc atctccagag acaacagcaa gaacaccgtg   240
tacctgcaga tgaacagcct gagagccgag gacaccgccg tgtactattg tgccaagcac   300
acaggcatcg gcgccaattc tgccggctct attgatgcct ggggccaggg aacactggtc   360
acagttttctt cagccaagac cacccccccc agcgtgtacc ctctggctcc tggatctgcc   420
gcccagacca acagcatggt caccctgggc tgcctcgtga agggctactt ccctgagcct   480
gtgaccgtga cctggaacag cggctctctg tctagcggcg tgcacacctt ccagccgtg    540
ctgcagagcg acctgtacac cctgagcagc agcgtgaccg tgcctagcag cacctggcct   600
agcgagacga tgacctgcaa cgtggcccac cctgccagca gcacaaaggt ggacaagaaa   660
atcgtgcccc gggactgcgg ctgcaagccc tgtatctgta ccgtgcccga ggtgtccagc   720
gtgttcatct tccacccaa gcccaaggac gtgctgacca tccctgac ccccaaagtg   780
acctgtgtgg tggtggacat cagcaaggac gaccccgagg tgcagttcag ttggttcgtg   840
gacgacgtgg aagtgcacac agcccagacc cagcccaagg aggaacagtt caacagcacg   900
ttcagaagcg tgtccgagct gcccatcatg caccaggact ggctgaacgg caaagagttc   960
aagtgcaagg tgaacagcgc cgccttccct gcccccatcg agaaaaccat ctccaagacc   1020
aagggcagac ccaaggcccc tcaggtgtac acaatccccc caccccaaga cagatggcc   1080
aaggacagag tgtccctgac ctgcatgatc accgatttct tcccagagga catcaccgtg   1140
gaatggcagt ggaacggcca gcccgccgag aactacaaga caccccagcc tatcatggac   1200
accgacggca gctactcgt gtacagcaag ctgaacgtgc agaagtccaa ctgggaggcc   1260
ggcaacacct tcacctgtag cgtgctgcac gagggcctgc acaatcacca caccgagaag   1320
tccctgtccc acagccctgg caag                                         1344

SEQ ID NO: 40           moltype = DNA  length = 642
FEATURE                 Location/Qualifiers
misc_feature            1..642
                        note = antibody sequence
source                  1..642
                        mol_type = other DNA
                        organism = synthetic construct
SEQUENCE: 40
agctatgagc tgacacagcc tccaagcgtg tccgtgtctc ctggacagac cgccagaatc    60
acatgtagcg gcgaggcag ctacaccggc agctactact atggctggta tcagcagaag   120
cccggacagg cccctgtgac cgtgatctac tacaacagca gcagcccag cgacatcccc   180
gagagatttt ctggctctct gagcggcacc accaacacac tgacaatctc tggcgtgcag   240
gccgaggacg aggccgatta ctattgtggc agcgccgata tagcggcga cgcctttggc   300
accggcacca agttacagt gctaggcag cccaagagca gccctagcgt gaccctgttc   360
cctccaagca gcgaggaact ggaaacaaac aaggccaccc tcgtgtgcac catcaccgac   420
ttctaccccg gcgtcgtgac cgtggactgg aaggtggacg gcaccccag gacccgagg   480
atggaaacca cccagcccag caagcagagc aacaacaagt acatggccag cagctacctg   540
accctgaccg ccagagcctg ggagagacac agctcctaca gctgccaagt gacccacgag   600
ggccacaccg tggaaaagag cctgagcaga gccgactgca gc                     642

SEQ ID NO: 41           moltype = AA  length = 120
FEATURE                 Location/Qualifiers
REGION                  1..120
                        note = antibody sequence
source                  1..120
                        mol_type = protein
                        organism = synthetic construct
SEQUENCE: 41
EVQLLESGGG LVQPGGSLRL SCAASGFTFS SYGMHWVRQA PGKGLEWVSA IGTGGDTYYA    60
DSVMGRFTIS RDNSKNTLYL QMNSLRAEDT AVYYCARRDD YTSRDAFDVW GQGTLVTVSS   120
```

| | | |
|---|---|---|
| SEQ ID NO: 42<br>FEATURE<br>REGION<br><br>source<br><br><br>SEQUENCE: 42<br>SYGMH | moltype = AA   length = 5<br>Location/Qualifiers<br>1..5<br>note = antibody sequence<br>1..5<br>mol_type = protein<br>organism = synthetic construct | <br><br><br><br><br><br><br><br>5 |
| SEQ ID NO: 43<br>FEATURE<br>REGION<br><br>source<br><br><br>SEQUENCE: 43<br>AIGTGGDTYY ADSVMG | moltype = AA   length = 16<br>Location/Qualifiers<br>1..16<br>note = antibody sequence<br>1..16<br>mol_type = protein<br>organism = synthetic construct | <br><br><br><br><br><br><br><br>16 |
| SEQ ID NO: 44<br>FEATURE<br>REGION<br><br>source<br><br><br>SEQUENCE: 44<br>RDDYTSRDAF DV | moltype = AA   length = 12<br>Location/Qualifiers<br>1..12<br>note = antibody sequence<br>1..12<br>mol_type = protein<br>organism = synthetic construct | <br><br><br><br><br><br><br><br>12 |
| SEQ ID NO: 45<br>FEATURE<br>REGION<br><br>source<br><br><br>SEQUENCE: 45<br>QSVLTQPPSA SGTPGQRVTI SCSGSSSNIG SNTVNWYQQL PGTAPKLLIY YDDLLPSGVP<br>DRFSGSKSGT SASLAISGLR SEDEADYYCA AWDDSLNGYV VFGGGTKLTV L | moltype = AA   length = 111<br>Location/Qualifiers<br>1..111<br>note = antibody sequence<br>1..111<br>mol_type = protein<br>organism = synthetic construct | <br><br><br><br><br><br><br><br>60<br>111 |
| SEQ ID NO: 46<br>FEATURE<br>REGION<br><br>source<br><br><br>SEQUENCE: 46<br>SGSSSNIGSN TVN | moltype = AA   length = 13<br>Location/Qualifiers<br>1..13<br>note = antibody sequence<br>1..13<br>mol_type = protein<br>organism = synthetic construct | <br><br><br><br><br><br><br><br>13 |
| SEQ ID NO: 47<br>FEATURE<br>REGION<br><br>source<br><br><br>SEQUENCE: 47<br>YDDLLPS | moltype = AA   length = 7<br>Location/Qualifiers<br>1..7<br>note = antibody sequence<br>1..7<br>mol_type = protein<br>organism = synthetic construct | <br><br><br><br><br><br><br><br>7 |
| SEQ ID NO: 48<br>FEATURE<br>REGION<br><br>source<br><br><br>SEQUENCE: 48<br>AAWDDSLNGY VV | moltype = AA   length = 12<br>Location/Qualifiers<br>1..12<br>note = antibody sequence<br>1..12<br>mol_type = protein<br>organism = synthetic construct | <br><br><br><br><br><br><br><br>12 |
| SEQ ID NO: 49<br>FEATURE<br>misc_feature<br><br>source<br><br><br>SEQUENCE: 49 | moltype = DNA   length = 360<br>Location/Qualifiers<br>1..360<br>note = antibody sequence<br>1..360<br>mol_type = other DNA<br>organism = synthetic construct | |

```
gaagttcagc tgctggaatc tggcggcgga ctggttcaac ctggcggatc tctgagactg   60
agctgtgccg ccagcggctt cacctttagc agctatggca tgcactgggt ccgacaggcc  120
cctggcaaag gacttgaatg ggtgtccgcc atcggcacag gcgcgatac ctactatgcc   180
gatagcgtga tgggcagatt caccatcagc cgggacaaca gcaagaacac cctgtacctg  240
cagatgaaca gcctgagagc cgaggacacc gccgtgtact attgcgccag aagggacgac  300
tacaccagca gggatgcctt cgatgtgtgg ggccagggaa cactggttac cgtttcttca  360

SEQ ID NO: 50            moltype = DNA   length = 15
FEATURE                  Location/Qualifiers
misc_feature             1..15
                         note = antibody sequence
source                   1..15
                         mol_type = other DNA
                         organism = synthetic construct
SEQUENCE: 50
agctatggca tgcac                                                    15

SEQ ID NO: 51            moltype = DNA   length = 48
FEATURE                  Location/Qualifiers
misc_feature             1..48
                         note = antibody sequence
source                   1..48
                         mol_type = other DNA
                         organism = synthetic construct
SEQUENCE: 51
gccatcggca caggcggcga tacctactat gccgatagcg tgatgggc                48

SEQ ID NO: 52            moltype = DNA   length = 36
FEATURE                  Location/Qualifiers
misc_feature             1..36
                         note = antibody sequence
source                   1..36
                         mol_type = other DNA
                         organism = synthetic construct
SEQUENCE: 52
agggacgact acaccagcag ggatgccttc gatgtg                             36

SEQ ID NO: 53            moltype = DNA   length = 333
FEATURE                  Location/Qualifiers
misc_feature             1..333
                         note = antibody sequence
source                   1..333
                         mol_type = other DNA
                         organism = synthetic construct
SEQUENCE: 53
cagtctgttc tgacacagcc tcctagcgcc tctggcacac tggacagag agtgaccatc    60
agctgtagcg gcagcagctc caacatcggc agcaacaccg tgaactggta tcagcagctg  120
cctggcacag cccctaaaact gctgatctac tacgacgacc tgctgcctag cggcgtgccc  180
gatagatttt ctggcagcaa gagcggcaca agcgccagcc tggctatctc tggactgaga  240
tctgaggacg aggccgacta ctattgcgcc gcctgggacg atagcctgaa cggctatgtg  300
gttttcggcg gaggcaccaa gctgaccgtg cta                                333

SEQ ID NO: 54            moltype = DNA   length = 39
FEATURE                  Location/Qualifiers
misc_feature             1..39
                         note = antibody sequence
source                   1..39
                         mol_type = other DNA
                         organism = synthetic construct
SEQUENCE: 54
agcggcagca gctccaacat cggcagcaac accgtgaac                          39

SEQ ID NO: 55            moltype = DNA   length = 21
FEATURE                  Location/Qualifiers
misc_feature             1..21
                         note = antibody sequence
source                   1..21
                         mol_type = other DNA
                         organism = synthetic construct
SEQUENCE: 55
tacgacgacc tgctgcctag c                                             21

SEQ ID NO: 56            moltype = DNA   length = 36
FEATURE                  Location/Qualifiers
misc_feature             1..36
                         note = antibody sequence
source                   1..36
                         mol_type = other DNA
                         organism = synthetic construct
```

```
SEQUENCE: 56
gccgcctggg acgatagcct gaacggctat gtggtt                              36

SEQ ID NO: 57            moltype = AA  length = 449
FEATURE                  Location/Qualifiers
REGION                   1..449
                         note = antibody sequence
source                   1..449
                         mol_type = protein
                         organism = synthetic construct
SEQUENCE: 57
EVQLLESGGG LVQPGGSLRL SCAASGFTFS SYGMHWVRQA PGKGLEWVSA IGTGGDTYYA     60
DSVMGRFTIS RDNSKNTLYL QMNSLRAEDT AVYYCARRDD YTSRDAFDVW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPG                                     449

SEQ ID NO: 58            moltype = AA  length = 217
FEATURE                  Location/Qualifiers
REGION                   1..217
                         note = antibody sequence
source                   1..217
                         mol_type = protein
                         organism = synthetic construct
SEQUENCE: 58
QSVLTQPPSA SGTPGQRVTI SCSGSSSNIG SNTVNWYQQL PGTAPKLLIY YDDLLPSGVP     60
DRFSGSKSGT SASLAISGLR SEDEADYYCA AWDDSLNGYV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 59            moltype = DNA  length = 1347
FEATURE                  Location/Qualifiers
misc_feature             1..1347
                         note = antibody sequence
source                   1..1347
                         mol_type = other DNA
                         organism = synthetic construct
SEQUENCE: 59
gaagttcagc tgctggaatc tggcggcgga ctggttcaac ctggcggatc tctgagactg     60
agctgtgccg ccagcggctt caccttttagc agctatggca tgcactgggt ccgacaggcc    120
cctggcaaag gacttgaatg ggtgtccgcc atcggcacag gcggcgatac ctactatgcc    180
gatagcgtga tgggcagatt caccatcagc cgggacaaca gcaagaacac cctgtacctg    240
cagatgaaca gcctgagagc cgaggacacc gccgtgtact attgcgccag aagggacgac    300
tacaccagca gggatgcctt cgatgtgtgg ggccagggaa cactggttac cgtttcttca    360
gccagcacca agggcccag cgtgttccct ctgcccccta gcagcaagag cacatctggc    420
ggaacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagcc gctctctggg cacccagacc    600
tacatctgca acgtgaacca caagcccagc aacaccaagg tggacaagaa ggtgaaaccc    660
aagagctgcg acaagaccca cacctgtccc cttgtcctgc ccccgaact gctgggagc    720
ccttccgtgt tcctgttccc cccaaagccc aaggacaccc tgatgatcag ccggacccc    780
gaagtgacct gcgtggtggt ggatgtgtcc cacgaggacc ctgaagtgaa gttcaattgg    840
tacgtggacg gcgtggaagt gcacaacgcc aagaccaagc ctagagagga acagtacaac    900
agcacctacc gggtggtgtc cgtgctgaca gtgctgcacc aggactggct gaacggcaaa    960
gagtacaagt gcaaggtgtc caacaaggcc ctgcctgccc catcgagaa accatcagc    1020
aaggccaagg gccagcccg cgaaccccag gtgtacacca tgccccaag caggggacgag    1080
ctgaccaaga accaggtgtc cctgacctgt ctcgtgaaag gcttctaccc ctccgatatc    1140
gccgtggaat gggagagcaa cggccagccc gagaacaact acaagaccac ccccctgtg    1200
ctggacagca cggctcatt cttcctgtac agcaagctga ccgtggacaa gtcccggtgg    1260
cagcagggca acgtgttcag ctgcagcgtg atgcacgagg ccctgcacaa ccactacacc    1320
cagaagtccc tgagcctgag ccctggc                                       1347

SEQ ID NO: 60            moltype = DNA  length = 651
FEATURE                  Location/Qualifiers
misc_feature             1..651
                         note = antibody sequence
source                   1..651
                         mol_type = other DNA
                         organism = synthetic construct
SEQUENCE: 60
cagtctgttc tgacacagcc tcctagcgcc tctggcacac tggacagag agtgaccatc      60
agctgtagcg gcagcagctc caacatcggc agcaacaccg tgaactggta tcagcagctg    120
cctggcacag cccctaaact gctgatctac tacgacgacc tgctgcctag cggcgtgccc    180
gatagatttt ctggcagcaa gagcggcaca agcgccagcc tggctatctc tggactgaga    240
tctgaggacg aggccgacta ctattgcgcc gcctgggacg atagcctgaa cggctatgtg    300
gttttcggcg gaggcaccaa gctgaccgtg ctaggccagc ctaaagccgc ccctagcgtg    360
```

```
accctgttcc ctccaagcag cgaggaactg caggccaaca aggccaccct cgtgtgcctg    420
atcagcgact tctatcctgg cgccgtgacc gtgccctgga aggccgatag ctctcctgtg    480
aaggccggcg tggaaaccac caccccctagc aagcagagca acaacaaata cgccgccagc   540
agctacctga gcctgacccc cgagcagtgg aagtcccaca gatcctacag ctgccaagtg    600
acccacgagg gcagcaccgt ggaaaagaca gtggccccta ccgagtgcag c             651
```

```
SEQ ID NO: 61              moltype = AA   length = 123
FEATURE                    Location/Qualifiers
REGION                     1..123
                           note = antibody sequence
source                     1..123
                           mol_type = protein
                           organism = synthetic construct
SEQUENCE: 61
EVQLLESGGG LVQPGGSLRL SCAASGFTFS SYEMNWVRQA PGKGLEWVSG ISWNSGSIGY     60
ADSVKGRFTI SRDNSKNTLY LQMNSLRAED TAVYYCARSG YSSSWFDPDF DYWGQGTLVT    120
VSS                                                                 123

SEQ ID NO: 62              moltype = AA   length = 5
FEATURE                    Location/Qualifiers
REGION                     1..5
                           note = antibody sequence
source                     1..5
                           mol_type = protein
                           organism = synthetic construct
SEQUENCE: 62
SYEMN                                                                 5

SEQ ID NO: 63              moltype = AA   length = 17
FEATURE                    Location/Qualifiers
REGION                     1..17
                           note = antibody sequence
source                     1..17
                           mol_type = protein
                           organism = synthetic construct
SEQUENCE: 63
GISWNSGSIG YADSVKG                                                   17

SEQ ID NO: 64              moltype = AA   length = 14
FEATURE                    Location/Qualifiers
REGION                     1..14
                           note = antibody sequence
source                     1..14
                           mol_type = protein
                           organism = synthetic construct
SEQUENCE: 64
SGYSSSWFDP DFDY                                                      14

SEQ ID NO: 65              moltype = AA   length = 111
FEATURE                    Location/Qualifiers
REGION                     1..111
                           note = antibody sequence
source                     1..111
                           mol_type = protein
                           organism = synthetic construct
SEQUENCE: 65
QSVLTQPPSA SGTPGQRVTI SCTGSSSNIG AGYDVHWYQQ LPGTAPKLLI YGNSNRPSGV     60
PDRFSGSKSG TSASLAISGL RSEDEADYYC SSYAGSNPYV VFGGGTKLTV L             111

SEQ ID NO: 66              moltype = AA   length = 14
FEATURE                    Location/Qualifiers
REGION                     1..14
                           note = antibody sequence
source                     1..14
                           mol_type = protein
                           organism = synthetic construct
SEQUENCE: 66
TGSSSNIGAG YDVH                                                      14

SEQ ID NO: 67              moltype = AA   length = 7
FEATURE                    Location/Qualifiers
REGION                     1..7
                           note = antibody sequence
source                     1..7
                           mol_type = protein
                           organism = synthetic construct
SEQUENCE: 67
GNSNRPS                                                               7
```

```
SEQ ID NO: 68              moltype = AA   length = 11
FEATURE                    Location/Qualifiers
REGION                     1..11
                           note = antibody sequence
source                     1..11
                           mol_type = protein
                           organism = synthetic construct
SEQUENCE: 68
SSYAGSNPYV V                                                                  11

SEQ ID NO: 69              moltype = DNA   length = 369
FEATURE                    Location/Qualifiers
misc_feature               1..369
                           note = antibody sequence
source                     1..369
                           mol_type = other DNA
                           organism = synthetic construct
SEQUENCE: 69
gaagttcagc tgctggaatc tggcggcgga ctggttcaac ctggcggatc tctgagactg      60
agctgtgccg ccagcggctt cacctttagc agctacgaga tgaactgggt ccgacaggcc     120
cctggcaaag gccttgaatg ggtgtccggc atcagctgga atagcggctc tatcggctac     180
gccgacagcg tgaagggcag attcaccatc agcggggaca acagcaagaa caccctgtac     240
ctgcagatga acagcctgag agccgaggac accgccgtgt actactgtgc cagaagcggc     300
tacagcagct cttggtttga ccccgacttc gactattggg ccagggcac actggtcaca      360
gtctcttca                                                             369

SEQ ID NO: 70              moltype = DNA   length = 15
FEATURE                    Location/Qualifiers
misc_feature               1..15
                           note = antibody sequence
source                     1..15
                           mol_type = other DNA
                           organism = synthetic construct
SEQUENCE: 70
agctacgaga tgaac                                                       15

SEQ ID NO: 71              moltype = DNA   length = 51
FEATURE                    Location/Qualifiers
misc_feature               1..51
                           note = antibody sequence
source                     1..51
                           mol_type = other DNA
                           organism = synthetic construct
SEQUENCE: 71
ggcatcagct ggaatagcgg ctctatcggc tacgccgaca gcgtgaaggg c                51

SEQ ID NO: 72              moltype = DNA   length = 42
FEATURE                    Location/Qualifiers
misc_feature               1..42
                           note = antibody sequence
source                     1..42
                           mol_type = other DNA
                           organism = synthetic construct
SEQUENCE: 72
agcggctaca gcagctcttg gtttgacccc gacttcgact at                         42

SEQ ID NO: 73              moltype = DNA   length = 333
FEATURE                    Location/Qualifiers
misc_feature               1..333
                           note = antibody sequence
source                     1..333
                           mol_type = other DNA
                           organism = synthetic construct
SEQUENCE: 73
cagtctgttc tgacacagcc tcctagcgcc tctggcacac tggacagag agtgaccatc       60
agctgtaccg gcagcagctc caatatcgga gccggctatg acgtgcactg gtatcagcag     120
ctgcctggca gcccctaa actgctgatc tacggcaaca gcaacagacc cagcggcgtg       180
cccgatagat tttccggctc taagagcggc acaagcgcca gctggctat ctctggactg      240
agatctgagg acgaggccga ctactactgc agcagctatg ccggcagcaa cccctacgtt    300
gtgtttggcg gaggcaccaa gctgaccgtt cta                                   333

SEQ ID NO: 74              moltype = DNA   length = 42
FEATURE                    Location/Qualifiers
misc_feature               1..42
                           note = antibody sequence
source                     1..42
                           mol_type = other DNA
                           organism = synthetic construct
SEQUENCE: 74
```

```
accggcagca gctccaatat cggagccggc tatgacgtgc ac                          42

SEQ ID NO: 75           moltype = DNA   length = 21
FEATURE                 Location/Qualifiers
misc_feature            1..21
                        note = antibody sequence
source                  1..21
                        mol_type = other DNA
                        organism = synthetic construct
SEQUENCE: 75
ggcaacagca acagacccag c                                                 21

SEQ ID NO: 76           moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 76
agcagctatg ccggcagcaa ccccctacgtt gtg                                   33

SEQ ID NO: 77           moltype = AA    length = 452
FEATURE                 Location/Qualifiers
REGION                  1..452
                        note = antibody sequence
source                  1..452
                        mol_type = protein
                        organism = synthetic construct
SEQUENCE: 77
EVQLLESGGG LVQPGGSLRL SCAASGFTFS SYEMNWVRQA PGKGLEWVSG ISWNSGSIGY       60
ADSVKGRFTI SRDNSKNTLY LQMNSLRAED TAVYYCARSG YSSSWFDPDF DYWGQGTLVT      120
VSSASTKGPS VFPLAPSSKS TSGGTAALGC LVKDYFPEPV TVSWNSGALT SGVHTFPAVL      180
QSSGLYSLSS VVTVPSSSLG TQTYICNVNH KPSNTKVDKK VEPKSCDKTH TCPPCPAPEL      240
LGGPSVFLFP PKPKDTLMIS RTPEVTCVVV DVSHEDPEVK FNWYVDGVEV HNAKTKPREE      300
QYNSTYRVVS VLTVLHQDWL NGKEYKCKVS NKALPAPIEK TISKAKGQPR EPQVYTLPPS      360
RDELTKNQVS LTCLVKGFYP SDIAVEWESN GQPENNYKTT PPVLDSDGSF FLYSKLTVDK      420
SRWQQGNVFS CSVMHEALHN HYTQKSLSLS PG                                    452

SEQ ID NO: 78           moltype = AA    length = 217
FEATURE                 Location/Qualifiers
REGION                  1..217
                        note = antibody sequence
source                  1..217
                        mol_type = protein
                        organism = synthetic construct
SEQUENCE: 78
QSVLTQPPSA SGTPGQRVTI SCTGSSSNIG AGYDVHWYQQ LPGTAPKLLI YGNSNRPSGV       60
PDRFSGSKSG TSASLAISGL RSEDEADYYC SSYAGSNPYV VFGGGTKLTV LGQPKAAPSV      120
TLFPPSSEEL QANKATLVCL ISDFYPGAVT VAWKADSSPV KAGVETTTPS KQSNNKYAAS      180
SYLSLTPEQW KSHRSYSCQV THEGSTVEKT VAPTECS                               217

SEQ ID NO: 79           moltype = DNA   length = 1356
FEATURE                 Location/Qualifiers
misc_feature            1..1356
                        note = antibody sequence
source                  1..1356
                        mol_type = other DNA
                        organism = synthetic construct
SEQUENCE: 79
gaagttcagc tgctggaatc tggcggcgga ctggttcaac tggcggatc tctgagactg        60
agctgtgccg ccagcggctt cacctttagc agctacgaga tgaactgggt ccgacaggcc      120
cctggcaaag gccttgaatg ggtgtccggc atcagctgga atagcggctc tatcggctac      180
gccgacagcg tgaagggcag attcaccatc agcgggacac agcaagaca cccctgtac       240
ctgcagatga acagcctgag agccgaggac accgccgtgt actactgtgc cagaagcggc      300
tacagcagct cttggtttga ccccgacttc gactattggg gccagggcac actggtcaca      360
gtctcttcag ccagcaccaa gggccccagc gtgttccctc tggcccctag cagcaagagc      420
acatctggcg gaacagccgc cctgggctgc ctcgtgaagg actactttcc cgagcccgtg      480
accgtgtcct ggaactctgg cgctctgaca agcggcgtgc acacctttcc agctgtg       540
cagagcagcg gcctgtactc tctgagcagc gtcgtgacag tgcccagcag ctctctgggc      600
acccagacct acatctgcaa cgtgaaccac aagcccagca caccaaggt ggacaagaag      660
gtggaaccca gagctgcga caagacccac acctgtcccc cttgtcctgc ccccgaactg      720
ctgggaggcc cttccgtgtt cctgttcccc ccaaagccca aggacaccct gatgatcagc      780
cggacccccg aagtgacctg cgtggtggtg gatgtgtccc acgaggaccc tgaagtgaag      840
ttcaattggt acgtggacgg cgtggaagtg cacaacgcca agaccaagcc tagagaggaa      900
cagtacaaca gcacctaccg ggtggtgtcc gtgacagt gctgcacca ggactggctg       960
aacggcaaag agtacaagtg caaggtgtcc aacaaggccc tgcctgcccc catcgagaaa     1020
accatcagca ggccaaggg ccagcccgc gaaccccagg tgtacacact gccccaagc      1080
agggacgagc tgaccaagaa ccaggtgtcc ctgacctgtc tcgtgaaagg cttctacccc     1140
```

```
tccgatatcg ccgtggaatg ggagagcaac ggccagcccg agaacaacta caagaccacc   1200
ccccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggc                             1356
```

| | |
|---|---|
| SEQ ID NO: 80 | moltype = DNA  length = 651 |
| FEATURE | Location/Qualifiers |
| misc_feature | 1..651 |
| | note = antibody sequence |
| source | 1..651 |
| | mol_type = other DNA |
| | organism = synthetic construct |

SEQUENCE: 80
```
cagtctgttc tgacacagcc tcctagcgcc tctggcacac ctggacagag agtgaccatc    60
agctgtaccg gcagcagctc caatatcgga gccggctatg acgtgcactg gtatcagcag   120
ctgcctggca gccccctaaa actgctgatc tacggcaaca gcaacagacc cagcggcgtg   180
cccgatagat tttccggctc taagagcggc acaagcgcca gcctggctat ctctggactg   240
agatctgagg acgaggccga ctactactgc agcagctatg ccggcagcaa cccctacgtt   300
gtgtttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggccggcg tggaaaccac caccccctag aagcagagca acaacaaata cgccgccagc   540
agctacctga gcctgacccc cgagcagtgg aagtcccaca gatcctacag ctgccaagtg   600
acccacgagg gcagcaccgt ggaaaagaca gtggcccctc ccgagtgcag c             651
```

| | |
|---|---|
| SEQ ID NO: 81 | moltype = AA  length = 116 |
| FEATURE | Location/Qualifiers |
| REGION | 1..116 |
| | note = antibody sequence |
| source | 1..116 |
| | mol_type = protein |
| | organism = synthetic construct |

SEQUENCE: 81
```
EVQLLESGGG LVQTGGSLRL SCAASGFTFS DYAMSWVRQA PGKGLEWVSW IYYDSGSKYY    60
ADSVKGRFTI SRDNSKNTLY LQMNSLRAED TAVYYCAKLN GDFDYWGQGT LVTVSS       116
```

| | |
|---|---|
| SEQ ID NO: 82 | moltype = AA  length = 5 |
| FEATURE | Location/Qualifiers |
| REGION | 1..5 |
| | note = antibody sequence |
| source | 1..5 |
| | mol_type = protein |
| | organism = synthetic construct |

SEQUENCE: 82
```
DYAMS                                                                 5
```

| | |
|---|---|
| SEQ ID NO: 83 | moltype = AA  length = 17 |
| FEATURE | Location/Qualifiers |
| REGION | 1..17 |
| | note = antibody sequence |
| source | 1..17 |
| | mol_type = protein |
| | organism = synthetic construct |

SEQUENCE: 83
```
WIYYDSGSKY YADSVKG                                                   17
```

| | |
|---|---|
| SEQ ID NO: 84 | moltype = AA  length = 7 |
| FEATURE | Location/Qualifiers |
| REGION | 1..7 |
| | note = antibody sequence |
| source | 1..7 |
| | mol_type = protein |
| | organism = synthetic construct |

SEQUENCE: 84
```
LNGDFDY                                                               7
```

| | |
|---|---|
| SEQ ID NO: 85 | moltype = AA  length = 110 |
| FEATURE | Location/Qualifiers |
| REGION | 1..110 |
| | note = antibody sequence |
| source | 1..110 |
| | mol_type = protein |
| | organism = synthetic construct |

SEQUENCE: 85
```
QSVLTQPPSA SGTPGQRVTI SCSGSSSNIG NNDVSWYQQL PGTAPKLLIY ADSHRPSGVP    60
DRFSGSKSGT SASLAISGLR SEDEADYYCG AWDSSLSGYV FGGGTKLTVL              110
```

| | |
|---|---|
| SEQ ID NO: 86 | moltype = AA  length = 13 |
| FEATURE | Location/Qualifiers |

```
REGION                     1..13
                           note = antibody sequence
source                     1..13
                           mol_type = protein
                           organism = synthetic construct
SEQUENCE: 86
SGSSSNIGNN DVS                                                           13

SEQ ID NO: 87              moltype = AA  length = 7
FEATURE                    Location/Qualifiers
REGION                     1..7
                           note = antibody sequence
source                     1..7
                           mol_type = protein
                           organism = synthetic construct
SEQUENCE: 87
ADSHRPS                                                                   7

SEQ ID NO: 88              moltype = AA  length = 11
FEATURE                    Location/Qualifiers
REGION                     1..11
                           note = antibody sequence
source                     1..11
                           mol_type = protein
                           organism = synthetic construct
SEQUENCE: 88
GAWDSSLSGY V                                                             11

SEQ ID NO: 89              moltype = DNA  length = 348
FEATURE                    Location/Qualifiers
misc_feature               1..348
                           note = antibody sequence
source                     1..348
                           mol_type = other DNA
                           organism = synthetic construct
SEQUENCE: 89
gaagttcagc tgctggaatc tggcggcgga ctggttcaaa caggcggctc tctgagactg         60
agctgtgccg cctctggctt caccttcagc gattacgcca tgagctgggt ccgacaggcc       120
cctggaaaag gccttgaatg ggtgtcctgg atctactacg acagcggcag caagtactac       180
gccgacagcg tgaagggcag attcaccatc agccgggaca cagcaagaa cacccctgtac       240
ctgcagatga acagcctgag agccgaggac accgccgtgt actattgcgc caagctgaac       300
ggcgacttcg actattgggg ccagggcaca ctggtcacag tctcttca                    348

SEQ ID NO: 90              moltype = DNA  length = 15
FEATURE                    Location/Qualifiers
misc_feature               1..15
                           note = antibody sequence
source                     1..15
                           mol_type = other DNA
                           organism = synthetic construct
SEQUENCE: 90
gattacgcca tgagc                                                         15

SEQ ID NO: 91              moltype = DNA  length = 51
FEATURE                    Location/Qualifiers
misc_feature               1..51
                           note = antibody sequence
source                     1..51
                           mol_type = other DNA
                           organism = synthetic construct
SEQUENCE: 91
tggatctact acgacagcgg cagcaagtac tacgccgaca gcgtgaaggg c                 51

SEQ ID NO: 92              moltype = DNA  length = 21
FEATURE                    Location/Qualifiers
misc_feature               1..21
                           note = antibody sequence
source                     1..21
                           mol_type = other DNA
                           organism = synthetic construct
SEQUENCE: 92
ctgaacggcg acttcgacta t                                                  21

SEQ ID NO: 93              moltype = DNA  length = 330
FEATURE                    Location/Qualifiers
misc_feature               1..330
                           note = antibody sequence
source                     1..330
                           mol_type = other DNA
```

```
                        organism = synthetic construct
SEQUENCE: 93
cagtctgttc tgacacagcc tcctagcgcc tctggcacac ctggacagag agtgaccatc    60
agctgtagcg gcagcagctc caacatcggc aacaacgacg tgtcctggta tcagcagctg   120
cctggcacag cccctaaaact gctgatctac gccgacagcc acagacccgg cgtgtgcca   180
gatagattca gcggctctaa gagcggcaca tctgccagcc tggccatctc tggactgaga   240
tctgaggaca aggccgacta ctattgcggc gcctgggatt ctagcctgag cggctatgtt   300
tttggcggag gcaccaagct gaccgtgcta                                    330

SEQ ID NO: 94           moltype = DNA  length = 39
FEATURE                 Location/Qualifiers
misc_feature            1..39
                        note = antibody sequence
source                  1..39
                        mol_type = other DNA
                        organism = synthetic construct
SEQUENCE: 94
agcggcagca gctccaacat cggcaacaac gacgtgtcc                           39

SEQ ID NO: 95           moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 95
gccgacagcc acagacctag c                                              21

SEQ ID NO: 96           moltype = DNA  length = 33
FEATURE                 Location/Qualifiers
misc_feature            1..33
                        note = antibody sequence
source                  1..33
                        mol_type = other DNA
                        organism = synthetic construct
SEQUENCE: 96
ggcgcctggg attctagcct gagcggctat gtt                                 33

SEQ ID NO: 97           moltype = AA  length = 445
FEATURE                 Location/Qualifiers
REGION                  1..445
                        note = antibody sequence
source                  1..445
                        mol_type = protein
                        organism = synthetic construct
SEQUENCE: 97
EVQLLESGGG LVQTGGSLRL SCAASGFTFS DYAMSWVRQA PGKGLEWVSW IYYDSGSKYY    60
ADSVKGRFTI SRDNSKNTLY LQMNSLRAED TAVYYCAKLN GDFDYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                         445

SEQ ID NO: 98           moltype = AA  length = 216
FEATURE                 Location/Qualifiers
REGION                  1..216
                        note = antibody sequence
source                  1..216
                        mol_type = protein
                        organism = synthetic construct
SEQUENCE: 98
QSVLTQPPSA SGTPGQRVTI SCSGSSSNIG NNDVSWYQQL PGTAPKLLIY ADSHRPSGVP    60
DRFSGSKSGT SASLAISGLR SEDEADYYCG AWDSSLSGYV FGGGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 99           moltype = DNA  length = 1335
FEATURE                 Location/Qualifiers
misc_feature            1..1335
                        note = antibody sequence
source                  1..1335
                        mol_type = other DNA
                        organism = synthetic construct
SEQUENCE: 99
gaagttcagt gctgctgaatc tggcggcgga ctggttcaaa caggcggctc tctgagactg    60
agctgtgccg cctctggctt caccttcagc gattacgcca tgagctgggt ccgacaggcc   120
```

```
cctggaaaag gccttgaatg ggtgtcctgg atctactacg acagcggcag caagtactac    180
gccgacagcg tgaagggcag attcaccatc agccgggaca acagcaagaa cacccctgtac   240
ctgcagatga acagcctgag agccgaggac accgccgtgt actattgcgc caagctgaac    300
ggcgacttcg actattgggg ccagggcaca ctggtcacag tctcttcagc cagcaccaag    360
ggcccccagcg tgttccctct ggcccctagc agcaagagca catctggcgg aacagccgcc    420
ctgggctgcc tcgtgaagga ctactttccc gagcccgtga ccgtgtcctg gaactctggc    480
gctctgacaa gcggcgtgca cacctttcca gccgtgctgc agagcagcgg cctgtactct    540
ctgagcagcg tcgtgacagt gcccagcagc tctctgggca cccagaccta catctgcaac    600
gtgaaccaca agcccagcaa caccaaggtg gacaagaagg tggaacccaa gagctgcgac    660
aagacccaca cctgtccccc ttgtcctgcc cccgaactgc tgggaggccc ttccgtgttc    720
ctgttccccc caaagcccaa ggacaccctg atgatcagcc ggacccccga agtgacctgc    780
gtggtggtgg atgtgtccca cgaggaccct gaagtgaagt tcaattggta cgtggacggc    840
gtggaagtgc acaacgccaa gaccaagcct agagaggaac agtacaacag cacctaccgg    900
gtggtgtccg tgctgacagt gctgcaccag gactggctga acggcaaaga gtacaagtgc    960
aaggtgtcca acaaggccct gcctgccccc atcgagaaaa ccatcagcaa ggccaagggc   1020
cagccccgcg aaccccaggt gtacacactg ccccaagca gggacgagct gaccaagaac   1080
caggtgtccc tgacctgtct cgtgaaaggc ttctacccct ccgatatcgc cgtggaatgg   1140
gagagcaacg gccagcccga gaacaactac aagaccccc cctgtgct ggacagcgac   1200
ggctcattct tcctgtacag caagctgacc gtggacaagc ccggtggca gcagggcaac   1260
gtgttcagct gcagcgtgat gcacgaggcc ctgcacaacc actacaccca gaagtccctg   1320
agcctgagcc ctggc                                                    1335

SEQ ID NO: 100          moltype = DNA   length = 648
FEATURE                 Location/Qualifiers
misc_feature            1..648
                        note = antibody sequence
source                  1..648
                        mol_type = other DNA
                        organism = synthetic construct
SEQUENCE: 100
cagtctgttc tgacacagcc tcctagcgcc tctggcacac ctggacgaga gtgaccatc     60
agctgtagcg gcagcagctc caacatcggc aacaacgacg tgtcctggta tcagcagctg   120
cctggcacag cccctaaact gctgatctac gccgacagcc acagacctag cggcgtgcca   180
gatagattca gcggctctaa gagcggcaca tctgccagcc tggccatctc tggactgaga   240
tctgaggacg aggccgacta ctattgcgcc gcctgggatt ctagcctgag cggctatgtt   300
tttggcggag gcaccaagct gaccgtgcta ggccagccta agccgcccc tagcgtgacc   360
ctgttccctc caagcagcga ggaactgcag gccaacaagg ccaccctcgt gtgcctgatc   420
agcgacttct atcctggcgc cgtgaccgtg gcctggaagg ccgatagctc tcctgtgaag   480
gccggcgtgg aaaccaccac ccctagcaag cagagcaaca caaatacgc cgccagcagc   540
tacctgagcc tgacccccga gcagtggaag tcccacagat cctacagctg ccaagtgacc   600
cacgagggca gcaccgtgga aaagacagtg gcccctaccg agtgcagc                648

SEQ ID NO: 101          moltype = AA   length = 123
FEATURE                 Location/Qualifiers
REGION                  1..123
                        note = antibody sequence
source                  1..123
                        mol_type = protein
                        organism = synthetic construct
SEQUENCE: 101
EVQLLESGGG LVQPGGSLRL SCAASGFTFS SYEMNWVRQA PGKGLEWVSG ISWNSGSIGY    60
ADSVKGRFTI SRDNSKNTLY LQMNSLRAED TAVYYCARSG YSSSWFDPDF DYWGQGTLVT   120
VSS                                                                 123

SEQ ID NO: 102          moltype = AA   length = 5
FEATURE                 Location/Qualifiers
REGION                  1..5
                        note = antibody sequence
source                  1..5
                        mol_type = protein
                        organism = synthetic construct
SEQUENCE: 102
SYEMN                                                                 5

SEQ ID NO: 103          moltype = AA   length = 17
FEATURE                 Location/Qualifiers
REGION                  1..17
                        note = antibody sequence
source                  1..17
                        mol_type = protein
                        organism = synthetic construct
SEQUENCE: 103
GISWNSGSIG YADSVKG                                                   17

SEQ ID NO: 104          moltype = AA   length = 14
FEATURE                 Location/Qualifiers
REGION                  1..14
                        note = antibody sequence
source                  1..14
```

```
                        mol_type = protein
                        organism = synthetic construct
SEQUENCE: 104
SGYSSSWFDP DFDY                                                       14

SEQ ID NO: 105          moltype = AA   length = 111
FEATURE                 Location/Qualifiers
REGION                  1..111
                        note = antibody sequence
source                  1..111
                        mol_type = protein
                        organism = synthetic construct
SEQUENCE: 105
QSVLTQPPSV SGAPGQRVTI SCTGSSSNIG AGYDVHWYQQ LPGTAPKLLI YGNSNRPSGV     60
PDRFSGSKSG TSASLAITGL QAEDEADYYC SSYAGSNPYV VFGGGTKLTV L             111

SEQ ID NO: 106          moltype = AA   length = 14
FEATURE                 Location/Qualifiers
REGION                  1..14
                        note = antibody sequence
source                  1..14
                        mol_type = protein
                        organism = synthetic construct
SEQUENCE: 106
TGSSSNIGAG YDVH                                                       14

SEQ ID NO: 107          moltype = AA   length = 7
FEATURE                 Location/Qualifiers
REGION                  1..7
                        note = antibody sequence
source                  1..7
                        mol_type = protein
                        organism = synthetic construct
SEQUENCE: 107
GNSNRPS                                                               7

SEQ ID NO: 108          moltype = AA   length = 11
FEATURE                 Location/Qualifiers
REGION                  1..11
                        note = antibody sequence
source                  1..11
                        mol_type = protein
                        organism = synthetic construct
SEQUENCE: 108
SSYAGSNPYV V                                                          11

SEQ ID NO: 109          moltype = DNA   length = 369
FEATURE                 Location/Qualifiers
misc_feature            1..369
                        note = antibody sequence
source                  1..369
                        mol_type = other DNA
                        organism = synthetic construct
SEQUENCE: 109
gaagttcagc tgctggaatc tggcggcgga ctggttcaac ctggcggatc tctgagactg     60
agctgtgccg ccagcggctt cacctttagc agctacgaga tgaactgggt ccgacaggcc    120
cctggcaaag gccttgaatg ggtgtccggc atcagctgga atagcggctc tatcggctac    180
gccgacagcg tgaagggcag attcaccatc agcggggaca cagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttca                                                            369

SEQ ID NO: 110          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 110
agctacgaga tgaac                                                      15

SEQ ID NO: 111          moltype = DNA   length = 51
FEATURE                 Location/Qualifiers
misc_feature            1..51
                        note = antibody sequence
source                  1..51
                        mol_type = other DNA
                        organism = synthetic construct
```

```
SEQUENCE: 111
ggcatcagct ggaatagcgg ctctatcggc tacgccgaca gcgtgaaggg c            51

SEQ ID NO: 112              moltype = DNA   length = 42
FEATURE                     Location/Qualifiers
misc_feature                1..42
                            note = antibody sequence
source                      1..42
                            mol_type = other DNA
                            organism = synthetic construct
SEQUENCE: 112
agcggctaca gcagctcttg gtttgacccc gacttcgact at                      42

SEQ ID NO: 113              moltype = DNA   length = 333
FEATURE                     Location/Qualifiers
misc_feature                1..333
                            note = antibody sequence
source                      1..333
                            mol_type = other DNA
                            organism = synthetic construct
SEQUENCE: 113
cagtctgttc tgacacagcc tccatctgtg tctggcgccc ctggacagag agtgaccatc   60
agctgtacag gcagcagctc caatatcgga gccggctatg acgtgcactg gtatcagcag  120
ctgcctggca gccccctaaa actgctgatc tacgcaacaa gcaacagacc cagcggcgtg  180
cccgatagat tttccggctc taagagcggc acaagcgcca gcctggctat tactggactg  240
caggccgagg acgaggccga ctactactgt tctagctacg ccggcagcaa ccccctacgt  300
gtgtttggcg gaggcaccaa gctgacagtt cta                               333

SEQ ID NO: 114              moltype = DNA   length = 42
FEATURE                     Location/Qualifiers
misc_feature                1..42
                            note = antibody sequence
source                      1..42
                            mol_type = other DNA
                            organism = synthetic construct
SEQUENCE: 114
acaggcagca gctccaatat cggagccggc tatgacgtgc ac                      42

SEQ ID NO: 115              moltype = DNA   length = 21
FEATURE                     Location/Qualifiers
misc_feature                1..21
                            note = antibody sequence
source                      1..21
                            mol_type = other DNA
                            organism = synthetic construct
SEQUENCE: 115
ggcaacagca acagacccag c                                             21

SEQ ID NO: 116              moltype = DNA   length = 33
FEATURE                     Location/Qualifiers
misc_feature                1..33
                            note = antibody sequence
source                      1..33
                            mol_type = other DNA
                            organism = synthetic construct
SEQUENCE: 116
tctagctacg ccggcagcaa ccccctacgt gtg                                33

SEQ ID NO: 117              moltype = AA    length = 452
FEATURE                     Location/Qualifiers
REGION                      1..452
                            note = antibody sequence
source                      1..452
                            mol_type = protein
                            organism = synthetic construct
SEQUENCE: 117
EVQLLESGGG LVQPGGSLRL SCAASGFTFS SYEMNWVRQA PGKGLEWVSG ISWNSGSIGY    60
ADSVKGRFTI SRDNSKNTLY LQMNSLRAED TAVYYCARSG YSSSWFDPDF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PG                                 452

SEQ ID NO: 118              moltype = AA    length = 217
FEATURE                     Location/Qualifiers
REGION                      1..217
                            note = antibody sequence
```

```
source                    1..217
                          mol_type = protein
                          organism = synthetic construct
SEQUENCE: 118
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC SSYAGSNPYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 119            moltype = DNA   length = 1356
FEATURE                   Location/Qualifiers
misc_feature              1..1356
                          note = antibody sequence
source                    1..1356
                          mol_type = other DNA
                          organism = synthetic construct
SEQUENCE: 119
gaagttcagc tgctggaatc tggcggcgga ctggttcaac ctggcggatc tctgagactg    60
agctgtgccg ccagcggctt caccttttagc agctacgaga tgaactgggt ccgacaggcc   120
cctggcaaag gccttgaatg ggtgtccggc atcagctgga atagcggctc tatcggctac   180
gccgacagcg tgaagggcag attcaccatc agccgggaca cagcaagaa caccctgtac    240
ctgcagatga cagcctgag agccgaggac accgccgtgt actactgtgc cagaagcgc    300
tacagcagct cttggtttga ccccgacttc gactattggg gccagggcac actggtcaca   360
gtctcttcag ccagcaccaa gggccccagc gtgttccctc tggcccctag cagcaagagc   420
acatctggcg gaacagccgc cctgggctgc ctcgtgaagg actactttcc gagcccgtg    480
accgtgtcct ggaactctgg cgctctgaca agcggcgtgc actttccc agccgtgctg    540
cagagcagcg gcctgtactc tctgagcagc gtcgtgacag tgcccagcag ctctctgggc   600
acccagacct acatctgcaa cgtgaaccac aagcccagca caccaaggt ggacaagaag    660
gtggaaccca gagctgcga caagacccac acctgtcccc cttgtcctgc ccccgaactg   720
ctgggaggcc cttccgtgtt cctgttcccc caaagtcaag gacaccct gatgatcagc    780
cggacccccg aagtgacctg cgtggtggtg gatgtgtccc acgaggaccc tgaagtgaag   840
ttcaattggt acgtggacgg cgtggaagtg cacaacgcca agaccaagcc tagagaggaa   900
cagtacaaca gcacctaccg ggtggtgtcc gtgctgacag tgctgcacca ggactggctg   960
aacggcaaag agtacaagtg caaggtgtcc aacaaggccc tgcctgccc catcgagaaa   1020
accatcagca aggccaaggg ccagccccgc gaaccccagg tgtacacact gccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
cccctgtgtc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggc                             1356

SEQ ID NO: 120            moltype = DNA   length = 651
FEATURE                   Location/Qualifiers
misc_feature              1..651
                          note = antibody sequence
source                    1..651
                          mol_type = other DNA
                          organism = synthetic construct
SEQUENCE: 120
cagtctgttc tgacacagcc tccatctgtg tctggcgccc tggacagag agtgaccatc    60
agctgtacag gcagcagctc caatatcgga gccggctatg acgtgcactg gtatcagcag   120
ctgcctggca cagcccctaa actgctgatc tacggcaaca gcaacagacc cagcggcgtg   180
cccgatagat tttccggctc taagagcgga acaagcgcca gcctggctat tactggactg   240
caggccgagg acgaggccga ctactactgt tctagctacg ccggcagcaa cccctacgtg   300
gtgtttggcg gaggcaccaa gctgacagtt ctaggccagc cctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggccggct ggaaaccac cacccctagc aagcagagca caacaaata cgccgccagc   540
agctacctga gcctgacccc cgagcagtgg aagtcccaca gatcctacag ctgccaagtg   600
acccacgagg gcagcaccgt ggaaaagaca gtggcccta ccgagtgcag c             651

SEQ ID NO: 121            moltype = AA   length = 120
FEATURE                   Location/Qualifiers
REGION                    1..120
                          note = antibody sequence
source                    1..120
                          mol_type = protein
                          organism = synthetic construct
SEQUENCE: 121
EVQLLESGGG LVQPGGSLRL SCAASGFTFS SYAMSWVRQA PGKGLEWVSA IGTGGDTYYA    60
DSVKGRFTIS RDNSKNTLYL QMNSLRAEDT AVYYCARRDD YTSRDAFDYW GQGTLVTVSS   120

SEQ ID NO: 122            moltype = AA   length = 5
FEATURE                   Location/Qualifiers
REGION                    1..5
                          note = antibody sequence
source                    1..5
                          mol_type = protein
                          organism = synthetic construct
```

```
SEQUENCE: 122
SYAMS                                                                    5

SEQ ID NO: 123          moltype = AA  length = 16
FEATURE                 Location/Qualifiers
REGION                  1..16
                        note = antibody sequence
source                  1..16
                        mol_type = protein
                        organism = synthetic construct
SEQUENCE: 123
AIGTGGDTYY ADSVKG                                                       16

SEQ ID NO: 124          moltype = AA  length = 12
FEATURE                 Location/Qualifiers
REGION                  1..12
                        note = antibody sequence
source                  1..12
                        mol_type = protein
                        organism = synthetic construct
SEQUENCE: 124
RDDYTSRDAF DY                                                           12

SEQ ID NO: 125          moltype = AA  length = 111
FEATURE                 Location/Qualifiers
REGION                  1..111
                        note = antibody sequence
source                  1..111
                        mol_type = protein
                        organism = synthetic construct
SEQUENCE: 125
QSVLTQPPSA SGTPGQRVTI SCSGSSSNIG SNTVNWYQQL PGTAPKLLIY YDDLRPSGVP        60
DRFSGSKSGT SASLAISGLQ SEDEADYYCA AWDDSLNGYV VFGGGTKLTV L                111

SEQ ID NO: 126          moltype = AA  length = 13
FEATURE                 Location/Qualifiers
REGION                  1..13
                        note = antibody sequence
source                  1..13
                        mol_type = protein
                        organism = synthetic construct
SEQUENCE: 126
SGSSSNIGSN TVN                                                          13

SEQ ID NO: 127          moltype = AA  length = 7
FEATURE                 Location/Qualifiers
REGION                  1..7
                        note = antibody sequence
source                  1..7
                        mol_type = protein
                        organism = synthetic construct
SEQUENCE: 127
YDDLRPS                                                                  7

SEQ ID NO: 128          moltype = AA  length = 12
FEATURE                 Location/Qualifiers
REGION                  1..12
                        note = antibody sequence
source                  1..12
                        mol_type = protein
                        organism = synthetic construct
SEQUENCE: 128
AAWDDSLNGY VV                                                           12

SEQ ID NO: 129          moltype = DNA  length = 360
FEATURE                 Location/Qualifiers
misc_feature            1..360
                        note = antibody sequence
source                  1..360
                        mol_type = other DNA
                        organism = synthetic construct
SEQUENCE: 129
gaagttcagc tgctggaatc tggcggcgga ctggttcaac ctggcggatc tctgagactg        60
agctgtgccg ccagcggctt cacctttagc agctacgcca tgagctgggt ccgacaggct       120
cctggcaaag ccttgaatg ggtgtccgcc attggcacag gcggcgatac ctactacgcc        180
gactctgtga aggcagatt caccatcagc cggacaacag caagaacac cctgtacctg         240
cagatgaaca gcctgagagc cgaggacacc gccgtgtact attgcgccag aagggacgac       300
tacaccagca gggacgcctt cgattattgg ggccagggca cactggtcac cgtttcttca       360
```

```
SEQ ID NO: 130              moltype = DNA  length = 15
FEATURE                     Location/Qualifiers
misc_feature                1..15
                            note = antibody sequence
source                      1..15
                            mol_type = other DNA
                            organism = synthetic construct
SEQUENCE: 130
agctacgcca tgagc                                                          15

SEQ ID NO: 131              moltype = DNA  length = 48
FEATURE                     Location/Qualifiers
misc_feature                1..48
                            note = antibody sequence
source                      1..48
                            mol_type = other DNA
                            organism = synthetic construct
SEQUENCE: 131
gccattggca caggcggcga tacctactac gccgactctg tgaagggc                      48

SEQ ID NO: 132              moltype = DNA  length = 36
FEATURE                     Location/Qualifiers
misc_feature                1..36
                            note = antibody sequence
source                      1..36
                            mol_type = other DNA
                            organism = synthetic construct
SEQUENCE: 132
agggacgact acaccagcag ggacgccttc gattat                                   36

SEQ ID NO: 133              moltype = DNA  length = 333
FEATURE                     Location/Qualifiers
misc_feature                1..333
                            note = antibody sequence
source                      1..333
                            mol_type = other DNA
                            organism = synthetic construct
SEQUENCE: 133
cagtctgttc tgacacagcc tcctagcgcc tctggcacac ctggacagag agtgaccatc         60
agctgtagcg gcagcagctc caacatcggc agcaacaccg tgaactggta tcagcagctg        120
cctggcacag cccctaaaact gctgatctac tacgacgacc tgcggcctag cggcgtgcca       180
gatagatttt ctggcagcaa gagcggcacc tctgccagcc tggctatttc tggactgcag        240
agcgaggacg aggccgacta ttattgtgcc gcctgggacg acagcctgaa cggctatgtt        300
gttttcggcg gaggcaccaa gctgaccgtt cta                                     333

SEQ ID NO: 134              moltype = DNA  length = 39
FEATURE                     Location/Qualifiers
misc_feature                1..39
                            note = antibody sequence
source                      1..39
                            mol_type = other DNA
                            organism = synthetic construct
SEQUENCE: 134
agcggcagca gctccaacat cggcagcaac accgtgaac                                39

SEQ ID NO: 135              moltype = DNA  length = 21
FEATURE                     Location/Qualifiers
misc_feature                1..21
                            note = antibody sequence
source                      1..21
                            mol_type = other DNA
                            organism = synthetic construct
SEQUENCE: 135
tacgacgacc tgcggcctag c                                                   21

SEQ ID NO: 136              moltype = DNA  length = 36
FEATURE                     Location/Qualifiers
misc_feature                1..36
                            note = antibody sequence
source                      1..36
                            mol_type = other DNA
                            organism = synthetic construct
SEQUENCE: 136
gccgcctggg acgacagcct gaacggctat gttgtt                                   36

SEQ ID NO: 137              moltype = AA  length = 449
FEATURE                     Location/Qualifiers
REGION                      1..449
                            note = antibody sequence
```

```
source                  1..449
                        mol_type = protein
                        organism = synthetic construct
SEQUENCE: 137
EVQLLESGGG LVQPGGSLRL SCAASGFTFS SYAMSWVRQA PGKGLEWVSA IGTGGDTYYA    60
DSVKGRFTIS RDNSKNTLYL QMNSLRAEDT AVYYCARRDD YTSRDAFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 138          moltype = AA  length = 217
FEATURE                 Location/Qualifiers
REGION                  1..217
                        note = antibody sequence
source                  1..217
                        mol_type = protein
                        organism = synthetic construct
SEQUENCE: 138
QSVLTQPPSA SGTPGQRVTI SCSGSSSNIG SNTVNWYQQL PGTAPKLLIY DDDLRPSGVP    60
DRFSGSKSGT SASLAISGLQ SEDEADYYCA AWDDSLNGYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 139          moltype = DNA  length = 1347
FEATURE                 Location/Qualifiers
misc_feature            1..1347
                        note = antibody sequence
source                  1..1347
                        mol_type = other DNA
                        organism = synthetic construct
SEQUENCE: 139
gaagttcagc tgctggaatc tggcggcgga ctggttcaac ctggcggatc tctgagactg    60
agctgtgccg ccagcggctt cacctttagc agctacgcca tgagctgggt ccgacaggct   120
cctggcaaag ccttgaatg gtgtccgcc attggcacag cggcgatac ctactacgcc     180
gactctgtga agggcagatt caccatcagc cgggacaaca gcaagaacac cctgtacctg   240
cagatgaaca gcctgagagc cgaggacac cgcgtgtact attgcgccag aagggacgac   300
tacaccagca gggacgcctt cgattattgg ggccagggca cactggtcac cgtttcttca   360
gccagcacca agggccccag cgtgttccct ctgcccccta gcagcaagag cacatctggc   420
ggaacagccg ccctgggctg cctcgtgaag gactactttc ccgagcccgt gaccgtgtcc   480
tggaactctg gcgctctgac aagcggcgtg cacacctttc cagccgtgct gcagagcagc   540
ggcctgtact ctctgagcag cgtcgtgaca gtgcccagca gctctctggg cacccagacc   600
tacatctgca acgtgaacca caagcccagc aacaccaagg tggacaagaa ggtgaaaccc   660
aagagctgcg acaagaccca cacctgtccc ccttgtcctg cccccgaact gctggggaggc   720
cctcgtgtgt tcctgttccc ccaaagccc aaggacaccc tgatgatcag ccggaccccc   780
gaagtgacct gcgtggtggt ggatgtgtcc cacgaggacc ctgaagtgaa gttcaattgg   840
tacgtggacg gcgtggaagt gcacaacgcc aagaccaagc ctagagga acagtacaac   900
agcacctacc gggtggtgtc cgtgctgaca gtgctgcacc aggactggct gaacggcaaa   960
gagtacaagt gcaaggtgtc caacaaggcc ctgcctgccc ccatcgagaa aaccatcagc  1020
aaggccaagg gccagcccg gaacccag gtgtacacac tgcccccaag cagggacgag  1080
ctgaccaaga accaggtgtc cctgacctgt ctcgtgaaag gcttctaccc ctccgatatc  1140
gccgtggaat gggagagcaa cggccagccc gagaacaact acaagaccac ccccctgtg  1200
ctggacagcg acggctcatt cttcctgtac agcaagctga ccgtgacaa gtcccggtgg  1260
cagcagggca acgtgttcag ctgcagcgtg atgcacgagg ccctgcacaa ccactacacc  1320
cagaagtccc tgagcctgag ccctggc                                     1347

SEQ ID NO: 140          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 140
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac gacgacc tgcgcctag cggcgtgcca      180
gatagatttt ctggcagcaa gagcggcacc tctgccagcc tggctatttc tggactgcag   240
agcgaggacg aggccgacta ttattgtgcc gcctgggacg acagcctgaa cggctatgtt   300
gttttcggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggctgatag ttcccctgta   480
aaggccggcg tggaaaccac caccccctagc aagcaggagca acaacaaata cgccgccagc   540
agctacctga gcctgacccc cgagcagtgg aagtcccaca gatcctacag ctgccaagtg   600
acccacgagg gcagcaccgt ggaaaagaca gtggccccta ccgagtgcag c            651

SEQ ID NO: 141          moltype = AA  length = 120
```

```
FEATURE                 Location/Qualifiers
REGION                  1..120
                        note = antibody sequence
source                  1..120
                        mol_type = protein
                        organism = synthetic construct
SEQUENCE: 141
EVQLLESGGG LVQPGGSLRL SCAASGFTFY SYAMSWVRQA PGKGLEWVSA IGTGGDTYYA    60
DSVKGRFTIS RDNSKNTLYL QMNSLRAEDT AVYYCARRDD YTSRDAFDYW GQGTLVTVSS   120

SEQ ID NO: 142          moltype = AA   length = 5
FEATURE                 Location/Qualifiers
REGION                  1..5
                        note = antibody sequence
source                  1..5
                        mol_type = protein
                        organism = synthetic construct
SEQUENCE: 142
SYAMS                                                                 5

SEQ ID NO: 143          moltype = AA   length = 16
FEATURE                 Location/Qualifiers
REGION                  1..16
                        note = antibody sequence
source                  1..16
                        mol_type = protein
                        organism = synthetic construct
SEQUENCE: 143
AIGTGGDTYY ADSVKG                                                    16

SEQ ID NO: 144          moltype = AA   length = 12
FEATURE                 Location/Qualifiers
REGION                  1..12
                        note = antibody sequence
source                  1..12
                        mol_type = protein
                        organism = synthetic construct
SEQUENCE: 144
RDDYTSRDAF DY                                                        12

SEQ ID NO: 145          moltype = AA   length = 111
FEATURE                 Location/Qualifiers
REGION                  1..111
                        note = antibody sequence
source                  1..111
                        mol_type = protein
                        organism = synthetic construct
SEQUENCE: 145
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCA AWDDSLNDYV VFGGGTKLTV L            111

SEQ ID NO: 146          moltype = AA   length = 13
FEATURE                 Location/Qualifiers
REGION                  1..13
                        note = antibody sequence
source                  1..13
                        mol_type = protein
                        organism = synthetic construct
SEQUENCE: 146
SGSSSNIGSN TVN                                                       13

SEQ ID NO: 147          moltype = AA   length = 7
FEATURE                 Location/Qualifiers
REGION                  1..7
                        note = antibody sequence
source                  1..7
                        mol_type = protein
                        organism = synthetic construct
SEQUENCE: 147
YDDLRPS                                                               7

SEQ ID NO: 148          moltype = AA   length = 12
FEATURE                 Location/Qualifiers
REGION                  1..12
                        note = antibody sequence
source                  1..12
                        mol_type = protein
                        organism = synthetic construct
SEQUENCE: 148
```

AAWDDSLNDY VV                                                          12

SEQ ID NO: 149          moltype = DNA   length = 360
FEATURE                 Location/Qualifiers
misc_feature            1..360
                        note = antibody sequence
source                  1..360
                        mol_type = other DNA
                        organism = synthetic construct
SEQUENCE: 149
gaagttcagc tgctggaatc tggcggcgga ctggttcaac ctggcggatc tctgagactg   60
agctgtgccg ccagcggctt caccttttac agctacgcca tgagctgggt ccgacaggcc  120
cctggaaaag gccttgaatg ggtgtccgcc atcggcacag cggcgatac ctactatgcc   180
gactctgtga agggcagatt caccatcagc cgggacaaca gcaagaacac cctgtacctg  240
cagatgaaca gcctgagagc cgaggacacc gccgtgtact attgcgccag aagggacgac  300
tacaccagca gggacgcctt cgattattgg ggccagggca cactggtcac cgtttcttca  360

SEQ ID NO: 150          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 150
agctacgcca tgagc                                                    15

SEQ ID NO: 151          moltype = DNA   length = 48
FEATURE                 Location/Qualifiers
misc_feature            1..48
                        note = antibody sequence
source                  1..48
                        mol_type = other DNA
                        organism = synthetic construct
SEQUENCE: 151
gccatcggca caggcggcga tacctactat gccgactctg tgaagggc                48

SEQ ID NO: 152          moltype = DNA   length = 36
FEATURE                 Location/Qualifiers
misc_feature            1..36
                        note = antibody sequence
source                  1..36
                        mol_type = other DNA
                        organism = synthetic construct
SEQUENCE: 152
agggacgact acaccagcag ggacgccttc gattat                             36

SEQ ID NO: 153          moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 153
cagtctgttc tgacacagcc tcctagcgcc tctggcacac ctggacagag agtgaccatc   60
agctgtagcg gcagcagctc caacatcggc agcaacaccg tgaactggta tcagcagctg  120
cctggcacag cccctaaaact gctgatctac tacgacgacc tgcggcctag cggcgtgcca  180
gatagatttt ctggcagcaa gagcggcacc tctgccagcc tggctatttc tggactgcag  240
agcgaggacg aggccgacta ttattgtgcc gcctgggacg acagcctgaa cgactacgtt  300
gtgtttggcg gaggcaccaa gctgaccgtt cta                               333

SEQ ID NO: 154          moltype = DNA   length = 39
FEATURE                 Location/Qualifiers
misc_feature            1..39
                        note = antibody sequence
source                  1..39
                        mol_type = other DNA
                        organism = synthetic construct
SEQUENCE: 154
agcggcagca gctccaacat cggcagcaac accgtgaac                          39

SEQ ID NO: 155          moltype = DNA   length = 21
FEATURE                 Location/Qualifiers
misc_feature            1..21
                        note = antibody sequence
source                  1..21
                        mol_type = other DNA
                        organism = synthetic construct

```
SEQUENCE: 155
tacgacgacc tgcggcctag c                                              21

SEQ ID NO: 156            moltype = DNA  length = 36
FEATURE                   Location/Qualifiers
misc_feature              1..36
                          note = antibody sequence
source                    1..36
                          mol_type = other DNA
                          organism = synthetic construct
SEQUENCE: 156
gccgcctggg acgacagcct gaacgactac gttgtg                              36

SEQ ID NO: 157            moltype = AA   length = 447
FEATURE                   Location/Qualifiers
REGION                    1..447
                          note = antibody sequence
source                    1..447
                          mol_type = protein
                          organism = synthetic construct
SEQUENCE: 157
EVQLLESGGG LVQPGGSLRL SCAASGFTFY SYAMSWVRQA PGKGLEWVSA IGTGGDTYYA     60
DSVKGRFTIS RDNSKNTLYL QMNSLRAEDT AVYYCARRDD YTSRDAFDYW GQGTLVTVSS    120
ASTKGPSVFP LAPCSRSTSE STAALGCLVK DYFPEPVTVS WNSGALTSGV HTFPAVLQSS    180
GLYSLSSVVT VPSSSLGTKT YTCNVDHKPS NTKVDKRVES KYGPPCPPCP APEFLGGPSV    240
FLFPPKPKDT LMISRTPEVT CVVVDVSQED PEVQFNWYVD GVEVHNAKTK PREEQFNSTY    300
RVVSVLTVLH QDWLNGKEYK CKVSNKGLPS SIEKTISKAK GQPREPQVYT LPPSQEEMTK    360
NQVSLTCLVK GFYPSDIAVE WESNGQPENN YKTTPPVLDS DGSFFLYSRL TVDKSRWQEG    420
NVFSCSVMHE ALHNHYTQKS LSLSLGK                                        447

SEQ ID NO: 158            moltype = AA   length = 217
FEATURE                   Location/Qualifiers
REGION                    1..217
                          note = antibody sequence
source                    1..217
                          mol_type = protein
                          organism = synthetic construct
SEQUENCE: 158
QSVLTQPPSA SGTPGQRVTI SCSGSSSNIG SNTVNWYQQL PGTAPKLLIY YDDLRPSGVP     60
DRFSGSKSGT SASLAISGLQ SEDEADYYCA AWDDSLNDYV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 159            moltype = DNA  length = 1341
FEATURE                   Location/Qualifiers
misc_feature              1..1341
                          note = antibody sequence
source                    1..1341
                          mol_type = other DNA
                          organism = synthetic construct
SEQUENCE: 159
gaagttcagc tgctggaatc tggcggcgga ctggttcaac ctggcggatc tctgagactg     60
agctgtgccg ccagcggctt cacctttac agctacgcca tgagctgggt ccgacaggcc    120
cctggaaaag gccttgaatg ggtgtccgcc atcggcacag cggcgatac ctactatgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggccccag cgtgttccct ggcccctt gtagcagaag caccagcgag    420
tctacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagca gcagcctggg caccaagacc    600
tacacctgta acgtggacca caagcccagc aacaccaagg tggacaagcg ggtggaatct    660
aagtacggcc ctccctgccc tccttgccca gcccctgaat tctgggcgg accctccgtg    720
ttcctgttcc ccccaaagcc caaggacacc ctgatgatca gccgacccc cgaagtgcc    780
tgcgtggtgg tggatgtgtc caggaagat cccgaggtgc agttcaattg gtacgtggac    840
ggcgtggaag tgcacaacgc caagaccaag ccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag   1020
ggccagcccc gcgaacccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcagactg accgtggaca agagccggtg gcaggaaggc   1260
aacgtgttca gctgcagcgt gatgcacgag gccctgcaca accactacac ccagaagtcc   1320
ctgtctctga gcctgggcaa g                                             1341

SEQ ID NO: 160            moltype = DNA  length = 651
FEATURE                   Location/Qualifiers
misc_feature              1..651
                          note = antibody sequence
```

```
source                        1..651
                              mol_type = other DNA
                              organism = synthetic construct
SEQUENCE: 160
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactcag    240
agcgaggacg aggccgacta ttattgtgcc gcctgggaca cagcctgaa cgactacgtt    300
gtgtttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact ctatcctgg cgccgtgacc gtggcctgga aggccgatag ctctcctgtg    480
aaggccggcg tggaaaccac caccccctagc aagcagagca caacaaaata cgccgccagc   540
agctacctga gcctgacccc cgagcagtgg aagtcccaca gatcctacag ctgccaagtg   600
acccacgagg gcagcaccgt ggaaaagaca gtgggcccta ccgagtgcag c            651

SEQ ID NO: 161                moltype = AA  length = 120
FEATURE                       Location/Qualifiers
REGION                        1..120
                              note = antibody sequence
source                        1..120
                              mol_type = protein
                              organism = synthetic construct
SEQUENCE: 161
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120

SEQ ID NO: 162                moltype = AA  length = 5
FEATURE                       Location/Qualifiers
REGION                        1..5
                              note = antibody sequence
source                        1..5
                              mol_type = protein
                              organism = synthetic construct
SEQUENCE: 162
SYAMS                                                                 5

SEQ ID NO: 163                moltype = AA  length = 16
FEATURE                       Location/Qualifiers
REGION                        1..16
                              note = antibody sequence
source                        1..16
                              mol_type = protein
                              organism = synthetic construct
SEQUENCE: 163
AIGYGGDTYY ADSVKG                                                    16

SEQ ID NO: 164                moltype = AA  length = 12
FEATURE                       Location/Qualifiers
REGION                        1..12
                              note = antibody sequence
source                        1..12
                              mol_type = protein
                              organism = synthetic construct
SEQUENCE: 164
RDDYTSRDAF DY                                                        12

SEQ ID NO: 165                moltype = AA  length = 111
FEATURE                       Location/Qualifiers
REGION                        1..111
                              note = antibody sequence
source                        1..111
                              mol_type = protein
                              organism = synthetic construct
SEQUENCE: 165
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCA AWDDSLNDIV VFGGGTKLTV L             111

SEQ ID NO: 166                moltype = AA  length = 13
FEATURE                       Location/Qualifiers
REGION                        1..13
                              note = antibody sequence
source                        1..13
                              mol_type = protein
                              organism = synthetic construct
SEQUENCE: 166
SGSSSNIGSN TVN                                                       13

SEQ ID NO: 167                moltype = AA  length = 7
```

```
FEATURE                 Location/Qualifiers
REGION                  1..7
                        note = antibody sequence
source                  1..7
                        mol_type = protein
                        organism = synthetic construct
SEQUENCE: 167
YDDLRPS                                                                     7

SEQ ID NO: 168          moltype = AA  length = 12
FEATURE                 Location/Qualifiers
REGION                  1..12
                        note = antibody sequence
source                  1..12
                        mol_type = protein
                        organism = synthetic construct
SEQUENCE: 168
AAWDDSLNDI VV                                                              12

SEQ ID NO: 169          moltype = DNA  length = 360
FEATURE                 Location/Qualifiers
misc_feature            1..360
                        note = antibody sequence
source                  1..360
                        mol_type = other DNA
                        organism = synthetic construct
SEQUENCE: 169
gaagttcagc tgctggaatc tggcggcgga ctggttcaac ctgcggatc tctgagactg            60
agctgtgccg ccagcggctt cacctttagc agctacgcca tgagctgggt ccgacaggct         120
cctggcaaag gccttgaatg ggtgtccgcc atcggtatg gcggcgatac ctactacgct          180
gactctgtga agggcagatt caccatcagc cggacaaca gcaagaacac cctgtacctg          240
cagatgaaca gcctgagagc cgaggacacc gccgtgtact attgcgccag aagggacgac         300
tacaccagca gggacgcctt cgattattgg ggccagggca cactggtcac cgtttcttca         360

SEQ ID NO: 170          moltype = DNA  length = 15
FEATURE                 Location/Qualifiers
misc_feature            1..15
                        note = antibody sequence
source                  1..15
                        mol_type = other DNA
                        organism = synthetic construct
SEQUENCE: 170
agctacgcca tgagc                                                           15

SEQ ID NO: 171          moltype = DNA  length = 48
FEATURE                 Location/Qualifiers
misc_feature            1..48
                        note = antibody sequence
source                  1..48
                        mol_type = other DNA
                        organism = synthetic construct
SEQUENCE: 171
gccatcggct atggcggcga tacctactac gccgactctg tgaagggc                       48

SEQ ID NO: 172          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 172
agggacgact acaccagcag ggacgccttc gattat                                    36

SEQ ID NO: 173          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 173
cagtctgttc tgacacagcc tcctagcgcc tctggcacac ctggacagag agtgaccatc           60
agctgtagcg gcagcagctc caacatcggc agcaacaccg tgaactggta tcagcagctg         120
cctggcacag cccctaaact gctgatctac tacgacgacc tgcggcctag cggcgtgcca         180
gatagatttt ctggcagcaa gagcggcacc tctgccagcc tggctatttc tggactgcag         240
agcgaggacg aggccgacta ttattgtgcc gcctgggacg acagcctgaa cgacatcgtt         300
gttttcggcg gaggcaccaa gctgaccgtt cta                                      333
```

```
SEQ ID NO: 174           moltype = DNA  length = 39
FEATURE                  Location/Qualifiers
misc_feature             1..39
                         note = antibody sequence
source                   1..39
                         mol_type = other DNA
                         organism = synthetic construct
SEQUENCE: 174
agcggcagca gctccaacat cggcagcaac accgtgaac                                   39

SEQ ID NO: 175           moltype = DNA  length = 21
FEATURE                  Location/Qualifiers
misc_feature             1..21
                         note = antibody sequence
source                   1..21
                         mol_type = other DNA
                         organism = synthetic construct
SEQUENCE: 175
tacgacgacc tgcggcctag c                                                      21

SEQ ID NO: 176           moltype = DNA  length = 36
FEATURE                  Location/Qualifiers
misc_feature             1..36
                         note = antibody sequence
source                   1..36
                         mol_type = other DNA
                         organism = synthetic construct
SEQUENCE: 176
gccgcctggg acgacagcct gaacgacatc gttgtt                                      36

SEQ ID NO: 177           moltype = AA   length = 447
FEATURE                  Location/Qualifiers
REGION                   1..447
                         note = antibody sequence
source                   1..447
                         mol_type = protein
                         organism = synthetic construct
SEQUENCE: 177
EVQLLESGGG LVQPGGSLRL SCAASGFTFS SYAMSWVRQA PGKGLEWVSA IGYGGDTYYA             60
DSVKGRFTIS RDNSKNTLYL QMNSLRAEDT AVYYCARRDD YTSRDAFDYW GQGTLVTVSS            120
ASTKGPSVFP LAPCSRSTSE STAALGCLVK DYFPEPVTVS WNSGALTSGV HTFPAVLQSS            180
GLYSLSSVVT VPSSSLGTKT YTCNVDHKPS NTKVDKRVES KYGPPCPPCP APEFLGGPSV            240
FLFPPKPKDT LMISRTPEVT CVVVDVSQED PEVQFNWYVD GVEVHNAKTK PREEQFNSTY            300
RVVSVLTVLH QDWLNGKEYK CKVSNKGLPS SIEKTISKAK GQPREPQVYT LPPSQEEMTK            360
NQVSLTCLVK GFYPSDIAVE WESNGQPENN YKTTPPVLDS DGSFFLYSRL TVDKSRWQEG            420
NVFSCSVMHE ALHNHYTQKS LSLSLGK                                                447

SEQ ID NO: 178           moltype = AA   length = 217
FEATURE                  Location/Qualifiers
REGION                   1..217
                         note = antibody sequence
source                   1..217
                         mol_type = protein
                         organism = synthetic construct
SEQUENCE: 178
QSVLTQPPSA SGTPGQRVTI SCSGSSSNIG SNTVNWYQQL PGTAPKLLIY YDDLRPSGVP             60
DRFSGSKSGT SASLAISGLQ SEDEADYYCA AWDDSLNDIV VFGGGTKLTV LGQPKAAPSV            120
TLFPPSSEEL QANKATLVCL ISDFYPGAVT VAWKADSSPV KAGVETTTPS KQSNNKYAAS            180
SYLSLTPEQW KSHRSYSCQV THEGSTVEKT VAPTECS                                     217

SEQ ID NO: 179           moltype = DNA  length = 1341
FEATURE                  Location/Qualifiers
misc_feature             1..1341
                         note = antibody sequence
source                   1..1341
                         mol_type = other DNA
                         organism = synthetic construct
SEQUENCE: 179
gaagttcagc tgctggaatc tggcggcgga ctggttcaac tggcggatc tctgagactg             60
agctgtgccg ccagcggctt cacctttagc agctacgcca tgagctgggt ccgacaggct           120
cctggcaaag gccttgaatg ggtgtccgcc atcggctatg gcggcgatac ctactacgcc           180
gactctgtga agggcagatt caccatcagc cgggacaaca gcaagaacac cctgtacctg           240
cagatgaaca gcctgagagc cgaggacacc gccgtgtact attgcgccag aagggacgac           300
tacaccagcc gggacgcctt cgattattgg ggccagggca ctggtcac cgtttcttca            360
gccagcacca agggcccag cgtgttccct ctgcccctt gtagcagaag caccagcgag           420
tctacagccg cccctgggctg cctcgtgaag gactactttc ccgagcccgt gaccgtgtcc           480
tggaactctg gcgctctgac aagcggcgtg cacacctttc agccgtgct gcagagcagc           540
ggcctgtact ctctgagcag cgtcgtgaca gtgcccagca gcctgggc accaagacc             600
tacacctgta acgtggacca caagcccagc aacaccaagg tggacaagcg ggtggaatct           660
```

```
aagtacggcc ctccctgccc tccttgccca gccccctgaat ttctgggcgg accctccgtg    720
ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag   1020
ggccagcccc gcgaacccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca cccccccctgt gctggacaag   1200
gacggctcat tcttcctgta cagcagactg accgtggaca gagccggtg gcaggaaggc   1260
aacgtgttca gctgcagcgt gatgcacgag gccctgcaca accactacac ccagaagtcc   1320
ctgtctctga gcctgggcaa g                                              1341

SEQ ID NO: 180          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 180
cagtctgttc tgacacagcc tcctagcgcc tctggcacac ctggacagag agtgaccatc     60
agctgtagcg gcagcagctc caacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ttattgtgcc gcctggacac acagcctgaa cgacatcgtt    300
gttttcggcg gaggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccccctagc aagcagagca acaacaaata cgccgccagc    540
agctacctga gcctgacccc cgagcagtgg aagtcccaca gatcctcag ctgccaagtg     600
acccacgagg gcagcaccgt ggaaaagaca gtggcccccta ccgagtgcag c            651

SEQ ID NO: 181          moltype = AA  length = 120
FEATURE                 Location/Qualifiers
REGION                  1..120
                        note = antibody sequence
source                  1..120
                        mol_type = protein
                        organism = synthetic construct
SEQUENCE: 181
EVQLLESGGG LVQPGGSLRL SCAASGFTFS SYAMSWVRQA PGKGLEWVSA IGYGGDTYYA     60
DSVKGRFTIS RDNSKNTLYL QMNSLRAEDT AVYYCARRDD YTSRDAFDYW GQGTLVTVSS    120

SEQ ID NO: 182          moltype = AA  length = 5
FEATURE                 Location/Qualifiers
REGION                  1..5
                        note = antibody sequence
source                  1..5
                        mol_type = protein
                        organism = synthetic construct
SEQUENCE: 182
SYAMS                                                                   5

SEQ ID NO: 183          moltype = AA  length = 16
FEATURE                 Location/Qualifiers
REGION                  1..16
                        note = antibody sequence
source                  1..16
                        mol_type = protein
                        organism = synthetic construct
SEQUENCE: 183
AIGYGGDTYY ADSVKG                                                      16

SEQ ID NO: 184          moltype = AA  length = 12
FEATURE                 Location/Qualifiers
REGION                  1..12
                        note = antibody sequence
source                  1..12
                        mol_type = protein
                        organism = synthetic construct
SEQUENCE: 184
RDDYTSRDAF DY                                                          12

SEQ ID NO: 185          moltype = AA  length = 111
FEATURE                 Location/Qualifiers
REGION                  1..111
                        note = antibody sequence
source                  1..111
```

```
                         mol_type = protein
                         organism = synthetic construct
SEQUENCE: 185
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCA AWDDSLNVYP VFGGGTKLTV L            111

SEQ ID NO: 186           moltype = AA   length = 13
FEATURE                  Location/Qualifiers
REGION                   1..13
                         note = antibody sequence
source                   1..13
                         mol_type = protein
                         organism = synthetic construct
SEQUENCE: 186
SGSSSNIGSN TVN                                                       13

SEQ ID NO: 187           moltype = AA   length = 7
FEATURE                  Location/Qualifiers
REGION                   1..7
                         note = antibody sequence
source                   1..7
                         mol_type = protein
                         organism = synthetic construct
SEQUENCE: 187
YDDLRPS                                                              7

SEQ ID NO: 188           moltype = AA   length = 12
FEATURE                  Location/Qualifiers
REGION                   1..12
                         note = antibody sequence
source                   1..12
                         mol_type = protein
                         organism = synthetic construct
SEQUENCE: 188
AAWDDSLNVY PV                                                        12

SEQ ID NO: 189           moltype = DNA   length = 360
FEATURE                  Location/Qualifiers
misc_feature             1..360
                         note = antibody sequence
source                   1..360
                         mol_type = other DNA
                         organism = synthetic construct
SEQUENCE: 189
gaagttcagc tgctggaatc tggcggcgga ctggttcaac ctggcggatc tctgagactg    60
agctgtgccg ccagcggctt cacctttagc agctacgcca tgagctgggt ccgacaggct   120
cctggcaaag gccttgaatg ggtgtccgcc atcggctatg gcgacgatac ctactacgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360

SEQ ID NO: 190           moltype = DNA   length = 15
FEATURE                  Location/Qualifiers
misc_feature             1..15
                         note = antibody sequence
source                   1..15
                         mol_type = other DNA
                         organism = synthetic construct
SEQUENCE: 190
agctacgcca tgagc                                                     15

SEQ ID NO: 191           moltype = DNA   length = 48
FEATURE                  Location/Qualifiers
misc_feature             1..48
                         note = antibody sequence
source                   1..48
                         mol_type = other DNA
                         organism = synthetic construct
SEQUENCE: 191
gccatcggct atggcggcga tacctactac gccgactctg tgaagggc                 48

SEQ ID NO: 192           moltype = DNA   length = 36
FEATURE                  Location/Qualifiers
misc_feature             1..36
                         note = antibody sequence
source                   1..36
                         mol_type = other DNA
                         organism = synthetic construct
SEQUENCE: 192
```

```
agggacgact acaccagcag ggacgccttc gattat                              36

SEQ ID NO: 193           moltype = DNA   length = 333
FEATURE                  Location/Qualifiers
misc_feature             1..333
                         note = antibody sequence
source                   1..333
                         mol_type = other DNA
                         organism = synthetic construct
SEQUENCE: 193
cagtctgttc tgacacagcc tcctagcgcc tctggcacac ctggacagag agtgaccatc   60
agctgtagcg gcagcagctc caacatcggc agcaacaccg tgaactggta tcagcagctg  120
cctggcacag cccctaaact gctgatctac tacgacgacc tgcggcctag cggcgtgcca  180
gatagatttt ctggcagcaa gagcggcacc tctgccagcc tggctatttc tggactgcag  240
agcgaggacg aggccgacta ttattgtgcc gcctgggacg acagcctgaa cgtgtaccct  300
gttttggcg gaggcaccaa gctgaccgtt cta                                333

SEQ ID NO: 194           moltype = DNA   length = 39
FEATURE                  Location/Qualifiers
misc_feature             1..39
                         note = antibody sequence
source                   1..39
                         mol_type = other DNA
                         organism = synthetic construct
SEQUENCE: 194
agcggcagca gctccaacat cggcagcaac accgtgaac                          39

SEQ ID NO: 195           moltype = DNA   length = 21
FEATURE                  Location/Qualifiers
misc_feature             1..21
                         note = antibody sequence
source                   1..21
                         mol_type = other DNA
                         organism = synthetic construct
SEQUENCE: 195
tacgacgacc tgcggcctag c                                             21

SEQ ID NO: 196           moltype = DNA   length = 36
FEATURE                  Location/Qualifiers
misc_feature             1..36
                         note = antibody sequence
source                   1..36
                         mol_type = other DNA
                         organism = synthetic construct
SEQUENCE: 196
gccgcctggg acgacagcct gaacgtgtac cctgtt                             36

SEQ ID NO: 197           moltype = AA   length = 447
FEATURE                  Location/Qualifiers
REGION                   1..447
                         note = antibody sequence
source                   1..447
                         mol_type = protein
                         organism = synthetic construct
SEQUENCE: 197
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 198           moltype = AA   length = 217
FEATURE                  Location/Qualifiers
REGION                   1..217
                         note = antibody sequence
source                   1..217
                         mol_type = protein
                         organism = synthetic construct
SEQUENCE: 198
QSVLTQPPSA SGTPGQRVTI SCSGSSSNIG SNTVNWYQQL PGTAPKLLIY DDLRPSGVP    60
DRFSGSKSGT SASLAISGLQ SEDEADYYCA AWDDSLNVYP VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 199           moltype = DNA   length = 1341
FEATURE                  Location/Qualifiers
```

```
misc_feature            1..1341
                        note = antibody sequence
source                  1..1341
                        mol_type = other DNA
                        organism = synthetic construct
SEQUENCE: 199
gaagttcagc tgctggaatc tggcggcgga ctggttcaac ctggcggatc tctgagactg    60
agctgtgccg ccagcggctt caccttagc agctacgcca tgagctgggt ccgacaggct   120
cctggcaaag gccttgaatg ggtgtccgcc atcggctatg gcggcgatac ctactacgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360
gccagcacca agggccccag cgtgttccct ctggccccct gtagcagaag caccagcgag   420
tctacagccg ccctgggctg cctcgtgaag gactactttc ccgagcccgt gaccgtgtcc   480
tggaactctg gcgctctgac aagcggcgtg cacacctttc cagccgtgct gcagagcagc   540
ggcctgtact ctctgagcag cgtcgtgaca gtgcccagca gcagcctggg caccaagacc   600
tacacctgta acgtggacca caagcccagc aacaccaagg tggacaagcg ggtggaatct   660
aagtacggcc ctccctgccc tccttgccca gcccctgaat ttctgggcgg acccTccgtg   720
ttcctgttcc ccccaaagcc caaggacacc ctgatgatca gccggacccc cgaagtgacc   780
tgcgtggtgg tggatgtgtc ccaggaagat cccgaggtgc agttcaattg gtacgtggac   840
ggcgtggaag tgcacaacgc caagaccaag cccagagagg aacagttcaa cagcacctac   900
cgggtggtgt ccgtgctgac agtgctgcac caggactggc tgaacggcaa agagtacaag   960
tgcaaggtgt ccaacaaggg cctgcccagc tccatcgaga aaaccatcag caaggccaag  1020
ggccagcccc gcgaacccca ggtgtacaca ctgcctccaa gccaggaaga gatgaccaag  1080
aaccaggtgt ccctgacctg tctcgtgaaa ggcttctacc cctccgatat cgccgtggaa  1140
tgggagagca acggccagcc cgagaacaac tacaagacca cccccctgt gctggacgtg  1200
gacggctcat tcttcctgta cagcagactg accgtggaca agagccggtg gcaggaaggc  1260
aacgtgttca gctgcagcgt gatgcacgag gccctgcaca accactacac ccagaagtcc  1320
ctgtctctga gcctgggcaa g                                            1341

SEQ ID NO: 200          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 200
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggaca caggcctgaa cgtgtacctt   300
gtttttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggcgggca tggaaaccac cacccctagc aagcagagca acaacaaata cgccgccagc   540
agctacctga gcctgacccc cgagcagtgg aagtcccaca gatcctcagc tgccaagtg   600
acccacgagg gcagcaccgt ggaaaagaca gtggcccctca ccgagtgcag c           651

SEQ ID NO: 201          moltype = AA  length = 120
FEATURE                 Location/Qualifiers
REGION                  1..120
                        note = antibody sequence
source                  1..120
                        mol_type = protein
                        organism = synthetic construct
SEQUENCE: 201
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120

SEQ ID NO: 202          moltype = AA  length = 5
FEATURE                 Location/Qualifiers
REGION                  1..5
                        note = antibody sequence
source                  1..5
                        mol_type = protein
                        organism = synthetic construct
SEQUENCE: 202
SYAMS                                                                5

SEQ ID NO: 203          moltype = AA  length = 16
FEATURE                 Location/Qualifiers
REGION                  1..16
                        note = antibody sequence
source                  1..16
                        mol_type = protein
                        organism = synthetic construct
SEQUENCE: 203
```

AIGYGGDTYY ADSVKG                                                              16

SEQ ID NO: 204           moltype = AA   length = 12
FEATURE                  Location/Qualifiers
REGION                   1..12
                         note = antibody sequence
source                   1..12
                         mol_type = protein
                         organism = synthetic construct
SEQUENCE: 204
RDDYTSRDAF DY                                                                  12

SEQ ID NO: 205           moltype = AA   length = 111
FEATURE                  Location/Qualifiers
REGION                   1..111
                         note = antibody sequence
source                   1..111
                         mol_type = protein
                         organism = synthetic construct
SEQUENCE: 205
QSVLTQPPSA SGTPGQRVTI SCSGSSSNIG SNTVNWYQQL PGTAPKLLIY YDDLRPSGVP              60
DRFSGSKSGT SASLAISGLQ SEDEADYYCH AWDDSLNDIV VFGGGTKLTV L                      111

SEQ ID NO: 206           moltype = AA   length = 13
FEATURE                  Location/Qualifiers
REGION                   1..13
                         note = antibody sequence
source                   1..13
                         mol_type = protein
                         organism = synthetic construct
SEQUENCE: 206
SGSSSNIGSN TVN                                                                 13

SEQ ID NO: 207           moltype = AA   length = 7
FEATURE                  Location/Qualifiers
REGION                   1..7
                         note = antibody sequence
source                   1..7
                         mol_type = protein
                         organism = synthetic construct
SEQUENCE: 207
YDDLRPS                                                                         7

SEQ ID NO: 208           moltype = AA   length = 12
FEATURE                  Location/Qualifiers
REGION                   1..12
                         note = antibody sequence
source                   1..12
                         mol_type = protein
                         organism = synthetic construct
SEQUENCE: 208
HAWDDSLNDI VV                                                                  12

SEQ ID NO: 209           moltype = DNA   length = 360
FEATURE                  Location/Qualifiers
misc_feature             1..360
                         note = antibody sequence
source                   1..360
                         mol_type = other DNA
                         organism = synthetic construct
SEQUENCE: 209
gaagttcagc tgctggaatc tggcggcgga ctggttcaac tggcggatct tctgagactg              60
agctgtgccg ccagcggctt cacctttagc agctacgcca tgagctgggt ccgacaggct             120
cctggcaaag gccttgaatg ggtgtccgcc atcggctatg gcggcgatac ctactacgcc             180
gactctgtga agggcagatt caccatcagc cggacaacag caagaacac cctgtacctg              240
cagatgaaca gcctgagagc cgaggacacc gccgtgtact attgcgccag aagggacgac             300
tacaccagca gggacgcctt cgattattgg ggccagggca cactggtcac cgtttcttca             360

SEQ ID NO: 210           moltype = DNA   length = 15
FEATURE                  Location/Qualifiers
misc_feature             1..15
                         note = antibody sequence
source                   1..15
                         mol_type = other DNA
                         organism = synthetic construct
SEQUENCE: 210
agctacgcca tgagc                                                               15

SEQ ID NO: 211           moltype = DNA   length = 48

```
FEATURE                 Location/Qualifiers
misc_feature            1..48
                        note = antibody sequence
source                  1..48
                        mol_type = other DNA
                        organism = synthetic construct
SEQUENCE: 211
gccatcggct atggcggcga tacctactac gccgactctg tgaagggc          48

SEQ ID NO: 212          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 212
agggacgact acaccagcag ggacgccttc gattat                        36

SEQ ID NO: 213          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 213
cagtctgttc tgacacagcc tcctagcgcc tctggcacac ctggacagag agtgaccatc    60
agctgtagcg gcagcagctc caacatcggc agcaacaccg tgaactggta tcagcagctg  120
cctggcacag cccctaaaact gctgatctac tacgacgact gcgcctag cggcgtgcca   180
gatagatttt ctggcagcaa gagcggcacc tctgccagcc tggctatttc tggactgcag  240
agcgaggaca ggccgacta ctattgtcac gcctgggacg acagcctgaa cgacatcgtg  300
gttttggcg gaggcaccaa gctgaccgtt cta                               333

SEQ ID NO: 214          moltype = DNA  length = 39
FEATURE                 Location/Qualifiers
misc_feature            1..39
                        note = antibody sequence
source                  1..39
                        mol_type = other DNA
                        organism = synthetic construct
SEQUENCE: 214
agcggcagca gctccaacat cggcagcaac accgtgaac                     39

SEQ ID NO: 215          moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 215
tacgacgacc tgcggcctag c                                        21

SEQ ID NO: 216          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 216
cacgcctggg acgacagcct gaacgacatc gtggtt                        36

SEQ ID NO: 217          moltype = AA  length = 447
FEATURE                 Location/Qualifiers
REGION                  1..447
                        note = antibody sequence
source                  1..447
                        mol_type = protein
                        organism = synthetic construct
SEQUENCE: 217
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
```

NVFSCSVMHE ALHNHYTQKS LSLSLGK                                         447

SEQ ID NO: 218          moltype = AA  length = 217
FEATURE                 Location/Qualifiers
REGION                  1..217
                        note = antibody sequence
source                  1..217
                        mol_type = protein
                        organism = synthetic construct
SEQUENCE: 218
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCH AWDDSLNDIV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 219          moltype = DNA  length = 1341
FEATURE                 Location/Qualifiers
misc_feature            1..1341
                        note = antibody sequence
source                  1..1341
                        mol_type = other DNA
                        organism = synthetic construct
SEQUENCE: 219
gaagttcagc tgctggaatc tggcggcgga ctggttcaac tggcggatc tctgagactg    60
agctgtgccg ccagcggctt cacctttagc agctacgcca tgagctgggt ccgacaggct   120
cctggcaaag gccttgaatg ggtgtccgcc atcggtatg gcgcgatac ctactacgcc    180
gactctgtga aggcagatt caccatcagc cggacaaca gcaagaacac cctgtacctg    240
cagatgaaca gcctgagagc cgaggacacc gccgtgtact attgcgccag aagggacgac   300
tacaccagca gggacgcctt cgattattgg ggccagggca cactggtcac cgtttcttca   360
gccacacca agggccccag cgtgttccct ctggcccctt gtagcagaag caccagcgag   420
tctacagccg ccctgggctg cctcgtgaag gactactttc ccgagcccgt gaccgtgtcc   480
tggaactctg gcgctctgac aagcggcgtg cacacctttc agccgtgct gcagagcagc   540
ggcctgtact ctctgagcag cgtcgtgaca gtgcccagca gcctgggg caccaagacc    600
tacacctgta acgtggacca caagcccagc aacaccaagg tggacaagcg ggtggaatct   660
aagtacggcc ctccctgccc tccttgccca gccctgaat ttctgggcgg accctccgtg   720
ttcctgttcc ccccaaagcc caaggacacc ctgatgatca gccggacccc cgaagtgacc   780
tgcgtggtgg tggatgtgtc ccaggaagat cccgaggtgc agttcaattg gtacgtggac   840
ggcgtggaag tgcacaacgc caagaccaag ccagagagg aacagttcaa cagcacctac   900
cgggtggtgt ccgtgctgac agtgctgcac caggactgcc tgaacggcaa agagtacaag   960
tgcaaggtgt ccaacaaggg cctgcccagc tccatcgaga aaaccatcag caaggccaag  1020
ggccagcccc gcgaaccca ggtgtacaca ctgcctccaa gccaggaaga gatgaccaag  1080
aaccaggtgt ccctgacctg tctcgtgaaa ggcttctacc cctccgatat cgccgtggaa  1140
tgggagagca acggccagcc cgagaacaac tacaagacca cccccctgt cctggacagc  1200
gacggctcat tcttcctgta cagcagactg accgtggaca agagccggtg gcaggaaggc  1260
aacgtgttca gctgcagcgt gatgcacgag gccctgcaca accactacac ccagaagtcc  1320
ctgtctctga gcctgggcaa g                                             1341

SEQ ID NO: 220          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 220
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagattt ctggcagcaa gagcggcacc tctgccagcc tggctatttc tggactgcag   240
agcgaggacg aggccgacta ctattgtcac gcctgggacg acagcctgaa cgacatcgtg   300
gtttttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggccggcg tggaaaccac caccccctagc aagcagaca aacaaatata cgccgccagc   540
agctacctga gcctgacccc cgagcagtgg aagtcccaca gatcctcag ctgccaagtg    600
acccacgagg gcagcaccgt ggaaaagaca gtggcccccta ccgagtgcag c           651

SEQ ID NO: 221          moltype = AA  length = 120
FEATURE                 Location/Qualifiers
REGION                  1..120
                        note = antibody sequence
source                  1..120
                        mol_type = protein
                        organism = synthetic construct
SEQUENCE: 221
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120

SEQ ID NO: 222          moltype = AA  length = 5

```
FEATURE              Location/Qualifiers
REGION               1..5
                     note = antibody sequence
source               1..5
                     mol_type = protein
                     organism = synthetic construct
SEQUENCE: 222
SYAMS                                                                    5

SEQ ID NO: 223       moltype = AA  length = 16
FEATURE              Location/Qualifiers
REGION               1..16
                     note = antibody sequence
source               1..16
                     mol_type = protein
                     organism = synthetic construct
SEQUENCE: 223
AIGYGGDTYY ADSVKG                                                       16

SEQ ID NO: 224       moltype = AA  length = 12
FEATURE              Location/Qualifiers
REGION               1..12
                     note = antibody sequence
source               1..12
                     mol_type = protein
                     organism = synthetic construct
SEQUENCE: 224
RDDYTSRDAF DY                                                           12

SEQ ID NO: 225       moltype = AA  length = 111
FEATURE              Location/Qualifiers
REGION               1..111
                     note = antibody sequence
source               1..111
                     mol_type = protein
                     organism = synthetic construct
SEQUENCE: 225
QSVLTQPPSA SGTPGQRVTI SCSGSSSNIG SNTVNWYQQL PGTAPKLLIY YDDLRPSGVP        60
DRFSGSKSGT SASLAISGLQ SEDEADYYCH AWDDSLNDYP VFGGGTKLTV L                111

SEQ ID NO: 226       moltype = AA  length = 13
FEATURE              Location/Qualifiers
REGION               1..13
                     note = antibody sequence
source               1..13
                     mol_type = protein
                     organism = synthetic construct
SEQUENCE: 226
SGSSSNIGSN TVN                                                          13

SEQ ID NO: 227       moltype = AA  length = 7
FEATURE              Location/Qualifiers
REGION               1..7
                     note = antibody sequence
source               1..7
                     mol_type = protein
                     organism = synthetic construct
SEQUENCE: 227
YDDLRPS                                                                  7

SEQ ID NO: 228       moltype = AA  length = 12
FEATURE              Location/Qualifiers
REGION               1..12
                     note = antibody sequence
source               1..12
                     mol_type = protein
                     organism = synthetic construct
SEQUENCE: 228
HAWDDSLNDY PV                                                           12

SEQ ID NO: 229       moltype = DNA  length = 360
FEATURE              Location/Qualifiers
misc_feature         1..360
                     note = antibody sequence
source               1..360
                     mol_type = other DNA
                     organism = synthetic construct
SEQUENCE: 229
gaagttcagc tgctggaatc tggcggcgga ctggttcaac tggcggatc tctgagactg         60
```

```
agctgtgccg ccagcggctt cacctttagc agctacgcca tgagctgggt ccgacaggct    120
cctggcaaag gccttgaatg ggtgtccgcc atcggctatg gcggcgatac ctactacgcc    180
gactctgtga agggcagatt caccatcagc cggacaaca gcaagaacac cctgtacctg     240
cagatgaaca gcctgagagc cgaggacacc gccgtgtact attgcgccag aagggacgac   300
tacaccagca gggacgcctt cgattattgg ggccagggca cactggtcac cgtttcttca   360

SEQ ID NO: 230           moltype = DNA   length = 15
FEATURE                  Location/Qualifiers
misc_feature             1..15
                         note = antibody sequence
source                   1..15
                         mol_type = other DNA
                         organism = synthetic construct
SEQUENCE: 230
agctacgcca tgagc                                                     15

SEQ ID NO: 231           moltype = DNA   length = 48
FEATURE                  Location/Qualifiers
misc_feature             1..48
                         note = antibody sequence
source                   1..48
                         mol_type = other DNA
                         organism = synthetic construct
SEQUENCE: 231
gccatcggct atggcggcga tacctactac gccgactctg tgaagggc                 48

SEQ ID NO: 232           moltype = DNA   length = 36
FEATURE                  Location/Qualifiers
misc_feature             1..36
                         note = antibody sequence
source                   1..36
                         mol_type = other DNA
                         organism = synthetic construct
SEQUENCE: 232
agggacgact acaccagcag ggacgccttc gattat                              36

SEQ ID NO: 233           moltype = DNA   length = 333
FEATURE                  Location/Qualifiers
misc_feature             1..333
                         note = antibody sequence
source                   1..333
                         mol_type = other DNA
                         organism = synthetic construct
SEQUENCE: 233
cagtctgttc tgacacagcc tcctagcgcc tctggcacac ctggacagag agtgaccatc     60
agctgtagcg gcagcagctc caacatcggc agcaacaccc tgaactggta tcagcagctg   120
cctggcacag cccctaaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggacg acagcctgaa cgactaccct   300
gttttttggcg gaggcaccaa gctgaccgtt cta                                333

SEQ ID NO: 234           moltype = DNA   length = 39
FEATURE                  Location/Qualifiers
misc_feature             1..39
                         note = antibody sequence
source                   1..39
                         mol_type = other DNA
                         organism = synthetic construct
SEQUENCE: 234
agcggcagca gctccaacat cggcagcaac accgtgaac                           39

SEQ ID NO: 235           moltype = DNA   length = 21
FEATURE                  Location/Qualifiers
misc_feature             1..21
                         note = antibody sequence
source                   1..21
                         mol_type = other DNA
                         organism = synthetic construct
SEQUENCE: 235
tacgacgacc tgcggcctag c                                              21

SEQ ID NO: 236           moltype = DNA   length = 36
FEATURE                  Location/Qualifiers
misc_feature             1..36
                         note = antibody sequence
source                   1..36
                         mol_type = other DNA
                         organism = synthetic construct
SEQUENCE: 236
```

```
cacgcctggg acgacagcct gaacgactac cctgtt                                    36

SEQ ID NO: 237          moltype = AA  length = 447
FEATURE                 Location/Qualifiers
REGION                  1..447
                        note = antibody sequence
source                  1..447
                        mol_type = protein
                        organism = synthetic construct
SEQUENCE: 237
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 238          moltype = AA  length = 217
FEATURE                 Location/Qualifiers
REGION                  1..217
                        note = antibody sequence
source                  1..217
                        mol_type = protein
                        organism = synthetic construct
SEQUENCE: 238
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCH AWDDSLNDYP VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 239          moltype = DNA  length = 1341
FEATURE                 Location/Qualifiers
misc_feature            1..1341
                        note = antibody sequence
source                  1..1341
                        mol_type = other DNA
                        organism = synthetic construct
SEQUENCE: 239
gaagttcagc tgctggaatc tggcggcgga ctggttcaac ctggcggatc tctgagactg    60
agctgtgccg ccagcggctt cacctttagc agctacgcca tgagctgggt ccgacaggct   120
cctggcaaag gcctttgaatg ggtgtccgcc atcggctacg gcggcgatac ctactacgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360
gccagcacca agggccccag cgtgttccct ctggccccct gtagcagaag caccagcgag   420
tctacagccg ccctgggctg cctcgtgaag gactactttc ccgagccgt gaccgtgtcc   480
tggaactctg gcgctctgac aagcggcgtg cacacctttc cagccgtgct gcagagcagc   540
ggcctgtact ctctgagcag cgtcgtgaca gtgcccagca gcagcctggg caccaagacc   600
tacacctgta acgtggacca caagcccagc aacaccaagg tggacaagcg ggtggaatct   660
aagtacggcc ctccctgccc tccttgccca gcccctgaat ttctgggcgg accctccgtg   720
ttcctgttcc ccccaaagcc caaggacacc ctgatgatca gccggacccc cgaagtgacc   780
tgcgtggtgg tggatgtgtc caggaagat cccgaggtgc agttcaattg gtacgtggac   840
ggcgtggaag tgcacaacgc caagaccaag cccagagagg aacagttcaa cagcacctac   900
cgggtggtgt ccgtgctgac agtgctgcac caggactggc tgaacggcaa agagtacaag   960
tgcaaggtgt ccaacaaggg cctgcccagc tccatcgaga aaaccatcag caaggccaag  1020
ggccagcccc gcgaacccca ggtgtacaca ctgcctccaa gccaggaaga gatgaccaag  1080
aaccaggtgt ccctgacctg tctcgtgaaa ggcttctacc cctccgatat cgccgtggaa  1140
tgggagagca acgggcagcc cgagaacaac tacaagacca ccccccctgt gctggacagc  1200
gacggctcat tcttcctgta cagcagactg accgtggaca gagccggtg caggaaggc  1260
aacgtgttca gctgcagcgt gatgcacgag gccctgcaca accactacac ccagaagtcc  1320
ctgtctctga gcctgggcaa g                                          1341

SEQ ID NO: 240          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 240
cagtctgttc tgacacagcc tcctagcgcc tctggcacac ctggacagag agtgaccatc    60
agctgtagcg gcagcagctc caacatcggc agcaacaccg tgaactggta tcagcagctc   120
cctggcacag cccctaaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggacg acagcctgaa cgactaccct   300
gttttttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
```

```
atcagcgact tctatcctgg cgccgtgacc gtggcctgga aggccgatag ctctcctgtg    480
aaggccggcg tggaaaccac caccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651
```

| SEQ ID NO: 241 | moltype = AA  length = 120 |
|---|---|
| FEATURE | Location/Qualifiers |
| REGION | 1..120 |
| | note = antibody sequence |
| source | 1..120 |
| | mol_type = protein |
| | organism = synthetic construct |

SEQUENCE: 241
```
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120
```

| SEQ ID NO: 242 | moltype = AA  length = 5 |
|---|---|
| FEATURE | Location/Qualifiers |
| REGION | 1..5 |
| | note = antibody sequence |
| source | 1..5 |
| | mol_type = protein |
| | organism = synthetic construct |

SEQUENCE: 242
```
SYAMS                                                                  5
```

| SEQ ID NO: 243 | moltype = AA  length = 16 |
|---|---|
| FEATURE | Location/Qualifiers |
| REGION | 1..16 |
| | note = antibody sequence |
| source | 1..16 |
| | mol_type = protein |
| | organism = synthetic construct |

SEQUENCE: 243
```
AIGYGGDTYY ADSVKG                                                     16
```

| SEQ ID NO: 244 | moltype = AA  length = 12 |
|---|---|
| FEATURE | Location/Qualifiers |
| REGION | 1..12 |
| | note = antibody sequence |
| source | 1..12 |
| | mol_type = protein |
| | organism = synthetic construct |

SEQUENCE: 244
```
RDDYTSRDAF DY                                                         12
```

| SEQ ID NO: 245 | moltype = AA  length = 111 |
|---|---|
| FEATURE | Location/Qualifiers |
| REGION | 1..111 |
| | note = antibody sequence |
| source | 1..111 |
| | mol_type = protein |
| | organism = synthetic construct |

SEQUENCE: 245
```
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCH AWDDSLNVYP VFGGGTKLTV L            111
```

| SEQ ID NO: 246 | moltype = AA  length = 13 |
|---|---|
| FEATURE | Location/Qualifiers |
| REGION | 1..13 |
| | note = antibody sequence |
| source | 1..13 |
| | mol_type = protein |
| | organism = synthetic construct |

SEQUENCE: 246
```
SGSSSNIGSN TVN                                                        13
```

| SEQ ID NO: 247 | moltype = AA  length = 7 |
|---|---|
| FEATURE | Location/Qualifiers |
| REGION | 1..7 |
| | note = antibody sequence |
| source | 1..7 |
| | mol_type = protein |
| | organism = synthetic construct |

SEQUENCE: 247
```
YDDLRPS                                                                7
```

| SEQ ID NO: 248 | moltype = AA  length = 12 |
|---|---|
| FEATURE | Location/Qualifiers |

```
REGION                   1..12
                         note = antibody sequence
source                   1..12
                         mol_type = protein
                         organism = synthetic construct
SEQUENCE: 248
HAWDDSLNVY PV                                                              12

SEQ ID NO: 249           moltype = DNA  length = 360
FEATURE                  Location/Qualifiers
misc_feature             1..360
                         note = antibody sequence
source                   1..360
                         mol_type = other DNA
                         organism = synthetic construct
SEQUENCE: 249
gaagttcagc tgctggaatc tggcggcgga ctggttcaac ctggcggatc tctgagactg          60
agctgtgccg ccagcggctt cacctttagc agctacgcca tgagctgggt ccgacaggct         120
cctggcaaag gccttgaatg ggtgtccgcc atcggctatg gcggcgatac ctactacgcc         180
gactctgtga agggcagatt caccatcagc cgggacaaca gcaagaacac cctgtacctg         240
cagatgaaca gcctgagagc cgaggacacc gccgtgtact attgcgccag aagggacgac         300
tacaccagca gggacgcctt cgattattgg ggccagggca cactggtcac cgtttcttca         360

SEQ ID NO: 250           moltype = DNA  length = 15
FEATURE                  Location/Qualifiers
misc_feature             1..15
                         note = antibody sequence
source                   1..15
                         mol_type = other DNA
                         organism = synthetic construct
SEQUENCE: 250
agctacgcca tgagc                                                           15

SEQ ID NO: 251           moltype = DNA  length = 48
FEATURE                  Location/Qualifiers
misc_feature             1..48
                         note = antibody sequence
source                   1..48
                         mol_type = other DNA
                         organism = synthetic construct
SEQUENCE: 251
gccatcggct atggcggcga tacctactac gccgactctg tgaagggc                       48

SEQ ID NO: 252           moltype = DNA  length = 36
FEATURE                  Location/Qualifiers
misc_feature             1..36
                         note = antibody sequence
source                   1..36
                         mol_type = other DNA
                         organism = synthetic construct
SEQUENCE: 252
agggacgact acaccagcag ggacgccttc gattat                                    36

SEQ ID NO: 253           moltype = DNA  length = 333
FEATURE                  Location/Qualifiers
misc_feature             1..333
                         note = antibody sequence
source                   1..333
                         mol_type = other DNA
                         organism = synthetic construct
SEQUENCE: 253
cagtctgttc tgacacagcc tcctagcgcc tctggcacac ctggacagag agtgaccatc          60
agctgtagcg gcagcagctc caacatcggc agcaacaccg tgaactggta tcagcagctg         120
cctggcacag cccctaaact gctgatctac tacgacgacc tgcggcctag cggcgtgcca         180
gatagatttt ctggcagcaa gagcggcacc tctgccagcc tggctatttc tggactgcag         240
agcgaggacg aggccgacta ctattgtcac gcctgggacg acagcctgaa cgtgtaccct         300
gttttttggcg gaggcaccaa gctgaccgtt cta                                     333

SEQ ID NO: 254           moltype = DNA  length = 39
FEATURE                  Location/Qualifiers
misc_feature             1..39
                         note = antibody sequence
source                   1..39
                         mol_type = other DNA
                         organism = synthetic construct
SEQUENCE: 254
agcggcagca gctccaacat cggcagcaac accgtgaac                                 39

SEQ ID NO: 255           moltype = DNA  length = 21
```

```
FEATURE                 Location/Qualifiers
misc_feature            1..21
                        note = antibody sequence
source                  1..21
                        mol_type = other DNA
                        organism = synthetic construct
SEQUENCE: 255
tacgacgacc tgcggcctag c                                                 21

SEQ ID NO: 256          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 256
cacgcctggg acgacagcct gaacgtgtac cctgtt                                 36

SEQ ID NO: 257          moltype = AA  length = 447
FEATURE                 Location/Qualifiers
REGION                  1..447
                        note = antibody sequence
source                  1..447
                        mol_type = protein
                        organism = synthetic construct
SEQUENCE: 257
EVQLLESGGG LVQPGGSLRL SCAASGFTFS SYAMSWVRQA PGKGLEWVSA IGYGGDTYYA        60
DSVKGRFTIS RDNSKNTLYL QMNSLRAEDT AVYYCARRDD YTSRDAFDYW GQGTLVTVSS       120
ASTKGPSVFP LAPCSRSTSE STAALGCLVK DYFPEPVTVS WNSGALTSGV HTFPAVLQSS       180
GLYSLSSVVT VPSSSLGTKT YTCNVDHKPS NTKVDKRVES KYGPPCPPCP APEFLGGPSV       240
FLFPPKPKDT LMISRTPEVT CVVVDVSQED PEVQFNWYVD GVEVHNAKTK PREEQFNSTY       300
RVVSVLTVLH QDWLNGKEYK CKVSNKGLPS SIEKTISKAK GQPREPQVYT LPPSQEEMTK       360
NQVSLTCLVK GFYPSDIAVE WESNGQPENN YKTTPPVLDS DGSFFLYSRL TVDKSRWQEG       420
NVFSCSVMHE ALHNHYTQKS LSLSLGK                                          447

SEQ ID NO: 258          moltype = AA  length = 217
FEATURE                 Location/Qualifiers
REGION                  1..217
                        note = antibody sequence
source                  1..217
                        mol_type = protein
                        organism = synthetic construct
SEQUENCE: 258
QSVLTQPPSA SGTPGQRVTI SCSGSSSNIG SNTVNWYQQL PGTAPKLLIY YDDLRPSGVP        60
DRFSGSKSGT SASLAISGLQ SEDEADYYCH AWDDSLNVYP VFGGGTKLTV LGQPKAAPSV       120
TLFPPSSEEL QANKATLVCL ISDFYPGAVT VAWKADSSPV KAGVETTTPS KQSNNKYAAS       180
SYLSLTPEQW KSHRSYSCQV THEGSTVEKT VAPTECS                               217

SEQ ID NO: 259          moltype = DNA  length = 1341
FEATURE                 Location/Qualifiers
misc_feature            1..1341
                        note = antibody sequence
source                  1..1341
                        mol_type = other DNA
                        organism = synthetic construct
SEQUENCE: 259
gaagttcagc tgctggaatc tggcggcgga ctggttcaac tggcggatc tctgagactg         60
agctgtgccg ccagcggctt caccttagc agctacgcca tgagctgggt ccgacaggct        120
cctggcaaag gccttgaatg ggtgtccgcc atcggctatg gcggcgatac ctactacgcc       180
gactctgtga agggcagatt caccatcagc cgggacaaca gcaagaacac cctgtacctg       240
cagatgaaca gcctgagagc cgaggacacc gccgtgtact attgcgccag aagggacgac       300
tacaccagca gggacgcctt cgattattgg ggccagggca cactggtcac cgtttcttca       360
gccacagcca agggccccag cgtgttccct ctggccccct gtagcagaag caccagcgag       420
tctacagccg ccctgggctg cctcgtgaag gactactttc ccgagcccgt gaccgtgtcc       480
tggaactctg gcgctctgac aagcggcgtg cacacctttc cagccgtgct gcagagcagc       540
ggcctgtact ctctgagcag cgtcgtgaca gtgcccagca gcagcctggg caccaagacc       600
tacacctgta acgtggacca caagcccagc aacaccaagg tggacaagcg ggtggaatct       660
aagtacggcc ctccctgccc tccttgccca gcccctgaac ttctgggcgg acccctcgtg       720
ttcctgttcc cccaaagcc caaggacacc ctgatgatca gccggacccc cgaagtgacc       780
tgcgtggtgg tggatgtgtc ccaggaagat cccgaggtgc agttcaattg gtacgtggac       840
ggcgtggaag tgcacaacgc caagaccaag cccagagagg aacagttcaa cagcacctac       900
cgggtggtgt ccgtgctgac agtgctgcac caggactggc tgaacggcaa agagtacaag       960
tgcaaggtgt ccaacaaggg cctgcccagc tccatcgaga aaaccatcag caaggccaag      1020
ggccagcccc gcgaacccca ggtgtacaca ctgcctccaa gccaggaaga gatgaccaag      1080
aaccaggtgt ccctgacctg tctcgtgaaa ggcttctacc cctccgatat cgccgtggaa      1140
tgggagagca acgccagcc cgagaacaac tacaagacca ccccccctgt gctggacagc      1200
gacggctcat tcttcctgta cagcagactg accgtggaca agagcaggtg gcaggaaggc      1260
aacgtgttca gctgcagcgt gatgcacgag gccctgcaca accactacac ccagaagtcc      1320
```

```
ctgtctctga gcctgggcaa g                                                  1341

SEQ ID NO: 260         moltype = DNA  length = 651
FEATURE                Location/Qualifiers
misc_feature           1..651
                       note = antibody sequence
source                 1..651
                       mol_type = other DNA
                       organism = synthetic construct
SEQUENCE: 260
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagca tggctatttc tggactgcag   240
agcgaggacg aggccgacta ctattgtcac gcctgggacg acagcctgaa cgtgtaccct   300
gttttttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga tctctcctgg                480
aaggccggcg tggaaaccac caccccctagc aagcagagca acaacaaata cgccgccagc   540
agctacctga gcctgacccc cgagcagtgg aagtcccaca gatcctacag ctgccaagtg   600
acccacgagg gcagcaccgt ggaaaagaca gtggcccccta ccgagtgcag c            651

SEQ ID NO: 261         moltype = AA  length = 120
FEATURE                Location/Qualifiers
REGION                 1..120
                       note = antibody sequence
source                 1..120
                       mol_type = protein
                       organism = synthetic construct
SEQUENCE: 261
EVQLLESGGG LVQPGGSLRL SCAASGFTFS SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120

SEQ ID NO: 262         moltype = AA  length = 5
FEATURE                Location/Qualifiers
REGION                 1..5
                       note = antibody sequence
source                 1..5
                       mol_type = protein
                       organism = synthetic construct
SEQUENCE: 262
SYAMS                                                                  5

SEQ ID NO: 263         moltype = AA  length = 16
FEATURE                Location/Qualifiers
REGION                 1..16
                       note = antibody sequence
source                 1..16
                       mol_type = protein
                       organism = synthetic construct
SEQUENCE: 263
AIGYGGDTYY ADSVKG                                                     16

SEQ ID NO: 264         moltype = AA  length = 12
FEATURE                Location/Qualifiers
REGION                 1..12
                       note = antibody sequence
source                 1..12
                       mol_type = protein
                       organism = synthetic construct
SEQUENCE: 264
RDDYTSRDAF DY                                                         12

SEQ ID NO: 265         moltype = AA  length = 111
FEATURE                Location/Qualifiers
REGION                 1..111
                       note = antibody sequence
source                 1..111
                       mol_type = protein
                       organism = synthetic construct
SEQUENCE: 265
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCH AWDDSLNVIP VFGGGTKLTV L            111

SEQ ID NO: 266         moltype = AA  length = 13
FEATURE                Location/Qualifiers
REGION                 1..13
                       note = antibody sequence
source                 1..13
```

```
                                mol_type = protein
                                organism = synthetic construct
SEQUENCE: 266
SGSSSNIGSN TVN                                                              13

SEQ ID NO: 267          moltype = AA   length = 7
FEATURE                 Location/Qualifiers
REGION                  1..7
                        note = antibody sequence
source                  1..7
                        mol_type = protein
                        organism = synthetic construct
SEQUENCE: 267
YDDLRPS                                                                      7

SEQ ID NO: 268          moltype = AA   length = 12
FEATURE                 Location/Qualifiers
REGION                  1..12
                        note = antibody sequence
source                  1..12
                        mol_type = protein
                        organism = synthetic construct
SEQUENCE: 268
HAWDDSLNVI PV                                                               12

SEQ ID NO: 269          moltype = DNA   length = 360
FEATURE                 Location/Qualifiers
misc_feature            1..360
                        note = antibody sequence
source                  1..360
                        mol_type = other DNA
                        organism = synthetic construct
SEQUENCE: 269
gaagttcagc tgctggaatc tggcggcgga ctggttcaac ctggcggatc tctgagactg            60
agctgtgccg ccagcggctt cacctttagc agctacgcca tgagctgggt ccgacaggct          120
cctggcaaag gccttgaatg ggtgtccgca tcggctatg gcggcgatac ctactacgcc           180
gactctgtga agggcagatt caccatcagc cgggacaaca gcaagaacac cctgtacctg          240
cagatgaaca gcctgagagc cgaggacacc gccgtgtact attgcgccag aagggacgac          300
tacaccagca gggacgcctt cgattattgg ggccagggca cactggtcac cgtttcttca          360

SEQ ID NO: 270          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 270
agctacgcca tgagc                                                            15

SEQ ID NO: 271          moltype = DNA   length = 48
FEATURE                 Location/Qualifiers
misc_feature            1..48
                        note = antibody sequence
source                  1..48
                        mol_type = other DNA
                        organism = synthetic construct
SEQUENCE: 271
gccatcggct atggcggcga tacctactac gccgactctg tgaagggc                        48

SEQ ID NO: 272          moltype = DNA   length = 36
FEATURE                 Location/Qualifiers
misc_feature            1..36
                        note = antibody sequence
source                  1..36
                        mol_type = other DNA
                        organism = synthetic construct
SEQUENCE: 272
agggacgact acaccagcag ggacgccttc gattat                                     36

SEQ ID NO: 273          moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 273
cagtctgttg tgacacagcc tcctagcgcc tctggcacac tggacagag agtgaccatc            60
```

```
agctgtagcg gcagcagctc aacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggacg acagcctgaa cgtgatccct   300
gttttggcg gaggcaccaa gctgaccgtt cta                                 333
```

| SEQ ID NO: 274 | moltype = DNA   length = 39 |
|---|---|
| FEATURE | Location/Qualifiers |
| misc_feature | 1..39 |
| | note = antibody sequence |
| source | 1..39 |
| | mol_type = other DNA |
| | organism = synthetic construct |

SEQUENCE: 274
```
agcggcagca gctccaacat cggcagcaac accgtgaac                           39
```

| SEQ ID NO: 275 | moltype = DNA   length = 21 |
|---|---|
| FEATURE | Location/Qualifiers |
| misc_feature | 1..21 |
| | note = antibody sequence |
| source | 1..21 |
| | mol_type = other DNA |
| | organism = synthetic construct |

SEQUENCE: 275
```
tacgacgacc tgcggcctag c                                              21
```

| SEQ ID NO: 276 | moltype = DNA   length = 36 |
|---|---|
| FEATURE | Location/Qualifiers |
| misc_feature | 1..36 |
| | note = antibody sequence |
| source | 1..36 |
| | mol_type = other DNA |
| | organism = synthetic construct |

SEQUENCE: 276
```
cacgcctggg acgacagcct gaacgtgatc cctgtt                              36
```

| SEQ ID NO: 277 | moltype = AA   length = 447 |
|---|---|
| FEATURE | Location/Qualifiers |
| REGION | 1..447 |
| | note = antibody sequence |
| source | 1..447 |
| | mol_type = protein |
| | organism = synthetic construct |

SEQUENCE: 277
```
EVQLLESGGG LVQPGGSLRL SCAASGFTFS SYAMSWVRQA PGKGLEWVSA IGYGGDTYYA   60
DSVKGRFTIS RDNSKNTLYL QMNSLRAEDT AVYYCARRDD YTSRDAFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447
```

| SEQ ID NO: 278 | moltype = AA   length = 217 |
|---|---|
| FEATURE | Location/Qualifiers |
| REGION | 1..217 |
| | note = antibody sequence |
| source | 1..217 |
| | mol_type = protein |
| | organism = synthetic construct |

SEQUENCE: 278
```
QSVLTQPPSA SGTPGQRVTI SCSGSSSNIG SNTVNWYQQL PGTAPKLLIY YDDLRPSGVP   60
DRFSGSKSGT SASLAISGLQ SEDEADYYCH AWDDSLNVIP VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217
```

| SEQ ID NO: 279 | moltype = DNA   length = 1341 |
|---|---|
| FEATURE | Location/Qualifiers |
| misc_feature | 1..1341 |
| | note = antibody sequence |
| source | 1..1341 |
| | mol_type = other DNA |
| | organism = synthetic construct |

SEQUENCE: 279
```
gaagttcagc tgctggaatc tggcggcgga ctggttcaac tggcggatc tctgagactg    60
agctgtgccg ccagcggctt cacctttagc agctacgcca tgagctgggt ccgacaggct  120
cctggcaaag gccttgaatg ggtgtccgcc atcggctatg gcggcgatac ctactacgcc  180
gactctgtga aggcgagatt caccatcagc cgggacaaca gcaagaacac cctgtacctg  240
cagatgaaca gcctgagagc cgaggacacc gccgtgtact attgcgccag aagggacgac  300
```

```
tacaccagca gggacgcctt cgattattgg ggccagggca cactggtcac cgtttcttca    360
gccagcacca agggccccag cgtgttccct ctgcccccct gtagcagaag caccagcgag    420
tctacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagcc agcgcctggg caccaagacc    600
tacacctgta acgtggacca caagcccagc aacaccaagg tggacaagcg ggtggaatct    660
aagtacggcc ctcccctgcc tccttgccca gcccctgaat ttctgggcgg accctccgtg    720
ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag   1020
ggccagcccc gcgaacccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcagactg accgtggaca gagccggtg gcaggaaggc    1260
aacgtgttca gctgcagcgt gatgcacgag gccctgcaca accactacac ccagaagtcc   1320
ctgtctctga gcctgggcaa g                                             1341

SEQ ID NO: 280              moltype = DNA  length = 651
FEATURE                     Location/Qualifiers
misc_feature                1..651
                            note = antibody sequence
source                      1..651
                            mol_type = other DNA
                            organism = synthetic construct
SEQUENCE: 280
cagtctgttc tgacacagcc tcctagcgcc tctggcacac ctggacagag agtgaccatc     60
agctgtagcg gcagcagctc caacatcggc agcaacaccg tgaactggta tcagcagctg    120
cctggcacag cccctaaact gctgatctac tacgacgtgt gcgcctag cggcgtgcca      180
gatagatttt ctggcagcaa gagcggcacc tctgccagcc tggctatttc tggactgcag    240
agcgaggacg aggccgacta ctattgtcac gcctgggacg acagcctgaa cgtgatccct    300
gttttggcg gaggcaccaa gctgaccgtt ctaggccagc ctaaagccgc ccctagcgtg    360
accctgttcc ctccaagcag cgaggaactg caggccaccc tggtgtgcct g             420
atcagcgact tctatcctgg cgccgtgacc gtggcctgga aggccgatag ctctcctgtg    480
aaggccggcg tggaaaccac caccccctagc aagcagagca caacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651

SEQ ID NO: 281              moltype = AA  length = 120
FEATURE                     Location/Qualifiers
REGION                      1..120
                            note = antibody sequence
source                      1..120
                            mol_type = protein
                            organism = synthetic construct
SEQUENCE: 281
EVQLLESGGG LVQPGGSLRL SCAASGFTFY SYAMLWVRQA PGKGLEWVSA IGTGGDTYYA     60
DSVKGRFTIS RDNSKNTLYL QMNSLRAEDT AVYYCARRDD YTSRDAFDYW GQGTLVTVSS    120

SEQ ID NO: 282              moltype = AA  length = 5
FEATURE                     Location/Qualifiers
REGION                      1..5
                            note = antibody sequence
source                      1..5
                            mol_type = protein
                            organism = synthetic construct
SEQUENCE: 282
SYAML                                                                  5

SEQ ID NO: 283              moltype = AA  length = 16
FEATURE                     Location/Qualifiers
REGION                      1..16
                            note = antibody sequence
source                      1..16
                            mol_type = protein
                            organism = synthetic construct
SEQUENCE: 283
AIGTGGDTYY ADSVKG                                                     16

SEQ ID NO: 284              moltype = AA  length = 12
FEATURE                     Location/Qualifiers
REGION                      1..12
                            note = antibody sequence
source                      1..12
                            mol_type = protein
                            organism = synthetic construct
SEQUENCE: 284
RDDYTSRDAF DY                                                         12
```

```
SEQ ID NO: 285           moltype = AA  length = 111
FEATURE                  Location/Qualifiers
REGION                   1..111
                         note = antibody sequence
source                   1..111
                         mol_type = protein
                         organism = synthetic construct
SEQUENCE: 285
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCA AWDDSLNDYV VFGGGTKLTV L            111

SEQ ID NO: 286           moltype = AA  length = 13
FEATURE                  Location/Qualifiers
REGION                   1..13
                         note = antibody sequence
source                   1..13
                         mol_type = protein
                         organism = synthetic construct
SEQUENCE: 286
SGSSSNIGSN TVN                                                       13

SEQ ID NO: 287           moltype = AA  length = 7
FEATURE                  Location/Qualifiers
REGION                   1..7
                         note = antibody sequence
source                   1..7
                         mol_type = protein
                         organism = synthetic construct
SEQUENCE: 287
YDDLRPS                                                              7

SEQ ID NO: 288           moltype = AA  length = 12
FEATURE                  Location/Qualifiers
REGION                   1..12
                         note = antibody sequence
source                   1..12
                         mol_type = protein
                         organism = synthetic construct
SEQUENCE: 288
AAWDDSLNDY VV                                                        12

SEQ ID NO: 289           moltype = DNA  length = 360
FEATURE                  Location/Qualifiers
misc_feature             1..360
                         note = antibody sequence
source                   1..360
                         mol_type = other DNA
                         organism = synthetic construct
SEQUENCE: 289
gaagttcagc tgctggaatc tggcggcgga ctggttcaac ctggcggatc tctgagactg    60
agctgtgccg ccagcggctt cacctttac agctacgcca tgctgtgggt ccgacaggcc   120
cctggaaaag gccttgaatg ggtgtccgcc atcggcacag cggcgatac ctactatgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360

SEQ ID NO: 290           moltype = DNA  length = 15
FEATURE                  Location/Qualifiers
misc_feature             1..15
                         note = antibody sequence
source                   1..15
                         mol_type = other DNA
                         organism = synthetic construct
SEQUENCE: 290
agctacgcca tgctg                                                     15

SEQ ID NO: 291           moltype = DNA  length = 48
FEATURE                  Location/Qualifiers
misc_feature             1..48
                         note = antibody sequence
source                   1..48
                         mol_type = other DNA
                         organism = synthetic construct
SEQUENCE: 291
gccatcggca caggcggcga tacctactat gccgactctg tgaagggc                 48

SEQ ID NO: 292           moltype = DNA  length = 36
FEATURE                  Location/Qualifiers
```

```
misc_feature            1..36
                        note = antibody sequence
source                  1..36
                        mol_type = other DNA
                        organism = synthetic construct
SEQUENCE: 292
agggacgact acaccagcag ggacgccttc gattat                             36

SEQ ID NO: 293          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 293
cagtctgttc tgacacagcc tcctagcgcc tctggcacac ctggacagag agtgaccatc   60
agctgtagcg gcagcagctc caacatcggc agcaacaccg tgaactggta tcagcagctg  120
cctggcacag cccctaaact gctgatctac tacgacgacc tgcggcctag cggcgtgcca  180
gatagatttt ctggcagcaa gagcggcacc tctgccagcc tggctatttc tggactgcag  240
agcgaggacg aggccgacta ttattgtgcc gcctgggacg acagcctgaa cgactacgtt  300
gtgtttggcg gaggcaccaa gctgaccgtt cta                               333

SEQ ID NO: 294          moltype = DNA  length = 39
FEATURE                 Location/Qualifiers
misc_feature            1..39
                        note = antibody sequence
source                  1..39
                        mol_type = other DNA
                        organism = synthetic construct
SEQUENCE: 294
agcggcagca gctccaacat cggcagcaac accgtgaac                          39

SEQ ID NO: 295          moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 295
tacgacgacc tgcggcctag c                                             21

SEQ ID NO: 296          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 296
gccgcctggg acgacagcct gaacgactac gttgtg                             36

SEQ ID NO: 297          moltype = AA  length = 447
FEATURE                 Location/Qualifiers
REGION                  1..447
                        note = antibody sequence
source                  1..447
                        mol_type = protein
                        organism = synthetic construct
SEQUENCE: 297
EVQLLESGGG LVQPGGSLRL SCAASGFTFY SYAMLWVRQA PGKGLEWVSA IGTGGDTYYA   60
DSVKGRFTIS RDNSKNTLYL QMNSLRAEDT AVYYCARRDD YTSRDAFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 298          moltype = AA  length = 217
FEATURE                 Location/Qualifiers
REGION                  1..217
                        note = antibody sequence
source                  1..217
                        mol_type = protein
                        organism = synthetic construct
SEQUENCE: 298
QSVLTQPPSA SGTPGQRVTI SCSGSSSNIG SNTVNWYQQL PGTAPKLLIY YDDLRPSGVP   60
```

```
DRFSGSKSGT SASLAISGLQ SEDEADYYCA AWDDSLNDYV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 299            moltype = DNA  length = 1341
FEATURE                   Location/Qualifiers
misc_feature              1..1341
                          note = antibody sequence
source                    1..1341
                          mol_type = other DNA
                          organism = synthetic construct
SEQUENCE: 299
gaagttcagc tgctggaatc tggcggcgga ctggttcaac ctggcggatc tctgagactg      60
agctgtgccg ccagcggctt caccttttac agctacgcca tgctgtgggt ccgacaggcc    120
cctggaaaag gccttgaatg ggtgtccgcc atcggcacag gcggcgatac ctactatgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360
gccagcacca agggcccag cgtgttccct ctggcccctt gtagcagaag caccagcgag    420
tctacagccg ccctgggctg cctcgtgaag gactactttc ccgagccgt gaccgtgtcc    480
tggaactctg gcgctctgac aagcggcgtg cacacctttc cagccgtgct gcagagcagc    540
ggcctgtact ctctgagcag cgtcgtgaca gtgcccagcc agcctgaga ccaagagcc    600
tacacctgta acgtggacca caagcccagc aacaccaagg tggacaagcg ggtgaatct    660
aagtacggcc ctccctgccc tccttgccca gcccctgaat ttctgggcgg accctccgtg    720
ttcctgttcc cccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag   1020
ggccagcccc gcgaacccca ggtgtacaca ctgcctccaa gccaggaaga tgatgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcagactg accgtggaca gagccggtg gcaggaaggc   1260
aacgtgttca gctgcagcgt gatgcacgag gccctgcaca accactacac ccagaagtcc   1320
ctgtctctga gcctgggcaa g                                             1341

SEQ ID NO: 300            moltype = DNA  length = 651
FEATURE                   Location/Qualifiers
misc_feature              1..651
                          note = antibody sequence
source                    1..651
                          mol_type = other DNA
                          organism = synthetic construct
SEQUENCE: 300
cagtctgttc tgacacagcc tcctagcgcc tctggcacac ctggacagag agtgaccatc     60
agctgtagcg gcagcagctc caacatcggc agcaacaccg tgaactggta tcagcagctg    120
cctggcacag cccctaaact gctgatctac tacgacgctc tgcgcctag cggcgtgcca    180
gatagatttt ctggcagcaa gagcggcacc tctgccagcc tggctatttc tggactgcag    240
agcgaggacg aggccgacta ttattgtgcc gcctgggacg acagcctgaa cgactacgtt    300
gtgtttggcg gaggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca caacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651

SEQ ID NO: 301            moltype = AA  length = 120
FEATURE                   Location/Qualifiers
REGION                    1..120
                          note = antibody sequence
source                    1..120
                          mol_type = protein
                          organism = synthetic construct
SEQUENCE: 301
EVQLLESGGG LVQPGGSLRL SCAASGFTFY SYAMLWVRQA PGKGLEWVSA IGTGGDTYYA     60
DSVKGRFTIS RDNSKNTLYL QMNSLRAEDT AVYYCARRDD YTSRDAFDYW GQGTLVTVSS    120

SEQ ID NO: 302            moltype = AA  length = 5
FEATURE                   Location/Qualifiers
REGION                    1..5
                          note = antibody sequence
source                    1..5
                          mol_type = protein
                          organism = synthetic construct
SEQUENCE: 302
SYAML                                                                  5

SEQ ID NO: 303            moltype = AA  length = 16
FEATURE                   Location/Qualifiers
```

```
REGION                   1..16
                         note = antibody sequence
source                   1..16
                         mol_type = protein
                         organism = synthetic construct
SEQUENCE: 303
AIGTGGDTYY ADSVKG                                                      16

SEQ ID NO: 304           moltype = AA  length = 12
FEATURE                  Location/Qualifiers
REGION                   1..12
                         note = antibody sequence
source                   1..12
                         mol_type = protein
                         organism = synthetic construct
SEQUENCE: 304
RDDYTSRDAF DY                                                          12

SEQ ID NO: 305           moltype = AA  length = 111
FEATURE                  Location/Qualifiers
REGION                   1..111
                         note = antibody sequence
source                   1..111
                         mol_type = protein
                         organism = synthetic construct
SEQUENCE: 305
QSVLTQPPSA SGTPGQRVTI SCSGSSSNIG SNTVNWYQQL PGTAPKLLIY YDDLRPSGVP       60
DRFSGSKSGT SASLAISGLQ SEDEADYYCA AWDDSLNVYV VFGGGTKLTV L              111

SEQ ID NO: 306           moltype = AA  length = 13
FEATURE                  Location/Qualifiers
REGION                   1..13
                         note = antibody sequence
source                   1..13
                         mol_type = protein
                         organism = synthetic construct
SEQUENCE: 306
SGSSSNIGSN TVN                                                         13

SEQ ID NO: 307           moltype = AA  length = 7
FEATURE                  Location/Qualifiers
REGION                   1..7
                         note = antibody sequence
source                   1..7
                         mol_type = protein
                         organism = synthetic construct
SEQUENCE: 307
YDDLRPS                                                                 7

SEQ ID NO: 308           moltype = AA  length = 12
FEATURE                  Location/Qualifiers
REGION                   1..12
                         note = antibody sequence
source                   1..12
                         mol_type = protein
                         organism = synthetic construct
SEQUENCE: 308
AAWDDSLNVY VV                                                          12

SEQ ID NO: 309           moltype = DNA  length = 360
FEATURE                  Location/Qualifiers
misc_feature             1..360
                         note = antibody sequence
source                   1..360
                         mol_type = other DNA
                         organism = synthetic construct
SEQUENCE: 309
gaagttcagc tgctggaatc tggcggcgga ctggttcaac ctggcggatc tctgagactg       60
agctgtgccg ccagcggctt cacctttttac agctacgcca tgctgtgggt ccgacaggcc    120
cctggaaaag gccttgaatg ggtgtccgcc atcggcacag gcggcgatac ctactatgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccgca gggacgcctt cgattattgg ggccagggca cactggtcac cgtttcttca    360

SEQ ID NO: 310           moltype = DNA  length = 15
FEATURE                  Location/Qualifiers
misc_feature             1..15
                         note = antibody sequence
source                   1..15
```

```
                            mol_type = other DNA
                            organism = synthetic construct
SEQUENCE: 310
agctacgcca tgctg                                                            15

SEQ ID NO: 311          moltype = DNA  length = 48
FEATURE                 Location/Qualifiers
misc_feature            1..48
                        note = antibody sequence
source                  1..48
                        mol_type = other DNA
                        organism = synthetic construct
SEQUENCE: 311
gccatcggca caggcggcga tacctactat gccgactctg tgaagggc                        48

SEQ ID NO: 312          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 312
agggacgact acaccagcag ggacgccttc gattat                                     36

SEQ ID NO: 313          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 313
cagtctgttc tgacacagcc tcctagcgcc tctggcacac ctggacagag agtgaccatc           60
agctgtagcg gcagcagctc aacatcggc agcaacaccg tgaactggta tcagcagctg          120
cctggcacag cccctaaact gctgatctac tacgacgacc tgcggcctag cggcgtgcca         180
gatagatttt ctggcagcaa gagcggcacc tctgccagcc tggctatttc tggactgcag         240
agcgaggacg aggccgacta ttattgtgcc gcctgggacg acagcctgaa cgtgtacgtt         300
gtgtttggcg gaggcaccaa gctgaccgtt cta                                       333

SEQ ID NO: 314          moltype = DNA  length = 39
FEATURE                 Location/Qualifiers
misc_feature            1..39
                        note = antibody sequence
source                  1..39
                        mol_type = other DNA
                        organism = synthetic construct
SEQUENCE: 314
agcggcagca gctccaacat cggcagcaac accgtgaac                                  39

SEQ ID NO: 315          moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 315
tacgacgacc tgcggcctag c                                                     21

SEQ ID NO: 316          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 316
gccgcctggg acgacagcct gaacgtgtac gttgtg                                     36

SEQ ID NO: 317          moltype = AA  length = 447
FEATURE                 Location/Qualifiers
REGION                  1..447
                        note = antibody sequence
source                  1..447
                        mol_type = protein
                        organism = synthetic construct
SEQUENCE: 317
EVQLLESGGG LVQPGGSLRL SCAASGFTFY SYAMLWVRQA PGKGLEWVSA IGTGGDTYYA           60
```

```
DSVKGRFTIS RDNSKNTLYL QMNSLRAEDT AVYYCARRDD YTSRDAFDYW GQGTLVTVSS    120
ASTKGPSVFP LAPCSRSTSE STAALGCLVK DYFPEPVTVS WNSGALTSGV HTFPAVLQSS    180
GLYSLSSVVT VPSSSLGTKT YTCNVDHKPS NTKVDKRVES KYGPPCPPCP APEFLGGPSV    240
FLFPPKPKDT LMISRTPEVT CVVVDVSQED PEVQFNWYVD GVEVHNAKTK PREEQFNSTY    300
RVVSVLTVLH QDWLNGKEYK CKVSNKGLPS SIEKTISKAK GQPREPQVYT LPPSQEEMTK    360
NQVSLTCLVK GFYPSDIAVE WESNGQPENN YKTTPPVLDS DGSFFLYSRL TVDKSRWQEG    420
NVFSCSVMHE ALHNHYTQKS LSLSLGK                                       447

SEQ ID NO: 318          moltype = AA  length = 217
FEATURE                 Location/Qualifiers
REGION                  1..217
                        note = antibody sequence
source                  1..217
                        mol_type = protein
                        organism = synthetic construct
SEQUENCE: 318
QSVLTQPPSA SGTPGQRVTI SCSGSSSNIG SNTVNWYQQL PGTAPKLLIY DDLRPSGVP     60
DRFSGSKSGT SASLAISGLQ SEDEADYYCA AWDDSLNVYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 319          moltype = DNA  length = 1341
FEATURE                 Location/Qualifiers
misc_feature            1..1341
                        note = antibody sequence
source                  1..1341
                        mol_type = other DNA
                        organism = synthetic construct
SEQUENCE: 319
gaagttcagc tgctggaatc tggcggcgga ctggttcaac ctggcggatc tctgagactg    60
agctgtgccg ccagcggctt cacctttac agctacgcca tgctgtgggt ccgacaggcc   120
cctggaaaag gccttgaatg ggtgtccgca atcggcacag gcggcgatac ctactatgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
taccagca gggacgcctt cgattattgg ggccagggca cactggtcac cgtttcttca   360
gccagcacca agggcccag cgtgttcct ctggcccctt gtagcagaag caccagcgag   420
tctacagccg ccctgggctg cctcgtgaag gactactttc ccgagccgtg accgtgtcc   480
tggaactctg gcgctctgac aagcggcgtg cacacctttc agccgtgct gcagagcagc   540
ggcctgtact ctctgagcag cgtcgtgaca gtgcccagcc agcctgtggg caccaagacc   600
tacacctgta acgtggacca caagcccagc aacaccaagg tggacaagcg ggtggaatct   660
aagtacggcc ctcctgccc tccttgccca gccctgaat ttctgggcgg accctccgtg   720
ttcctgttcc ccccaaagcc caaggacacc ctgatgatca gccggacccc cgaagtgacc   780
tgcgtggtgg tggatgtgtc ccaggaagat cccgaggtgc agttcaattg gtacgtggac   840
ggcgtggaag tgcacaacgc caagaccaag cccagagagg aacagttcaa cagcacctac   900
cgggtggtgt ccgtgctgac agtgctgcac caggactggc tgaacggcaa agagtacaag   960
tgcaaggtgt ccaacaaggg cctgccagc tccatcgaga aaaccatcag caaggccaag  1020
ggccagcccc gcgaaccca ggtgtacaca ctgcctccaa gccaggaaga gatgaccaag  1080
aaccaggtgt ccctgacctg tctcgtgaaa ggcttctacc cctccgatat cgccgtggaa  1140
tgggagagca acggccagcc cgagaacaac tacaagacca ccccccctgt gctggacagc  1200
gacggctcat tcttcctgta cagcagactg accgtggaca gagccggtg gcaggaaggc  1260
aacgtgttca gctgcagcgt gatgcacgag gccctgcaca accactacac ccagaagtcc  1320
ctgtctctga gcctgggcaa g                                           1341

SEQ ID NO: 320          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 320
cagtctgttc tgacacagcc tcctagcgcc tctggcacac tggacagag agtgaccatc    60
agctgtagcg gcagcagctc caacatcggc agcaacaccg tgaactggta tcagcagctg   120
cctggcacag cccctaaact gctgatctac tacgacgcc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgtgtacgtt   300
gtgtttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact ctatcctgg cgccgtgacc gtggcctgga aggccgatag ctctcctgtg   480
aaggccggcg tggaaaccac cacccctagc aagcagagca caacaaata cgccgccagc   540
agctacctga gcctgacccc cgagcagtgg aagtcccaca gatcctacag ctgccaagtg   600
acccacgagg gcagcaccgt ggaaaagaca gtggccccta ccgagtgcag c            651

SEQ ID NO: 321          moltype = AA  length = 120
FEATURE                 Location/Qualifiers
REGION                  1..120
                        note = antibody sequence
source                  1..120
                        mol_type = protein
```

```
                        organism = synthetic construct
SEQUENCE: 321
EVQLLESGGG LVQPGGSLRL SCAASGFTFY SYAMSWVRQA PGKGLEWVSA IGYGGDTYYA      60
DSVKGRFTIS RDNSKNTLYL QMNSLRAEDT AVYYCARRDD YTSRDAFDYW GQGTLVTVSS     120

SEQ ID NO: 322          moltype = AA   length = 5
FEATURE                 Location/Qualifiers
REGION                  1..5
                        note = antibody sequence
source                  1..5
                        mol_type = protein
                        organism = synthetic construct
SEQUENCE: 322
SYAMS                                                                   5

SEQ ID NO: 323          moltype = AA   length = 16
FEATURE                 Location/Qualifiers
REGION                  1..16
                        note = antibody sequence
source                  1..16
                        mol_type = protein
                        organism = synthetic construct
SEQUENCE: 323
AIGYGGDTYY ADSVKG                                                      16

SEQ ID NO: 324          moltype = AA   length = 12
FEATURE                 Location/Qualifiers
REGION                  1..12
                        note = antibody sequence
source                  1..12
                        mol_type = protein
                        organism = synthetic construct
SEQUENCE: 324
RDDYTSRDAF DY                                                          12

SEQ ID NO: 325          moltype = AA   length = 111
FEATURE                 Location/Qualifiers
REGION                  1..111
                        note = antibody sequence
source                  1..111
                        mol_type = protein
                        organism = synthetic construct
SEQUENCE: 325
QSVLTQPPSA SGTPGQRVTI SCSGSSSNIG SNTVNWYQQL PGTAPKLLIY YDDLRPSGVP      60
DRFSGSKSGT SASLAISGLQ SEDEADYYCH AWDDSLNVYP VFGGGTKLTV L              111

SEQ ID NO: 326          moltype = AA   length = 13
FEATURE                 Location/Qualifiers
REGION                  1..13
                        note = antibody sequence
source                  1..13
                        mol_type = protein
                        organism = synthetic construct
SEQUENCE: 326
SGSSSNIGSN TVN                                                         13

SEQ ID NO: 327          moltype = AA   length = 7
FEATURE                 Location/Qualifiers
REGION                  1..7
                        note = antibody sequence
source                  1..7
                        mol_type = protein
                        organism = synthetic construct
SEQUENCE: 327
YDDLRPS                                                                 7

SEQ ID NO: 328          moltype = AA   length = 12
FEATURE                 Location/Qualifiers
REGION                  1..12
                        note = antibody sequence
source                  1..12
                        mol_type = protein
                        organism = synthetic construct
SEQUENCE: 328
HAWDDSLNVY PV                                                          12

SEQ ID NO: 329          moltype = DNA   length = 360
FEATURE                 Location/Qualifiers
misc_feature            1..360
```

```
                             note            = antibody sequence
source                       1..360
                             mol_type        = other DNA
                             organism        = synthetic construct
SEQUENCE: 329
gaagttcagc tgctggaatc tggcggcgga ctggttcaac ctggcggatc tctgagactg    60
agctgtgccg ccagcggctt cacctttac agctacgcca tgagctgggt ccgacaggcc   120
cctggaaaag gccttgaatg ggtgtccgcc atcggctatg cggcgatac ctactacgcc   180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360

SEQ ID NO: 330               moltype = DNA   length = 15
FEATURE                      Location/Qualifiers
misc_feature                 1..15
                             note            = antibody sequence
source                       1..15
                             mol_type        = other DNA
                             organism        = synthetic construct
SEQUENCE: 330
agctacgcca tgagc                                                     15

SEQ ID NO: 331               moltype = DNA   length = 48
FEATURE                      Location/Qualifiers
misc_feature                 1..48
                             note            = antibody sequence
source                       1..48
                             mol_type        = other DNA
                             organism        = synthetic construct
SEQUENCE: 331
gccatcggct atgcggcga tacctactac gccgactctg tgaagggc                  48

SEQ ID NO: 332               moltype = DNA   length = 36
FEATURE                      Location/Qualifiers
misc_feature                 1..36
                             note            = antibody sequence
source                       1..36
                             mol_type        = other DNA
                             organism        = synthetic construct
SEQUENCE: 332
agggacgact acaccagcag ggacgccttc gattat                              36

SEQ ID NO: 333               moltype = DNA   length = 333
FEATURE                      Location/Qualifiers
misc_feature                 1..333
                             note            = antibody sequence
source                       1..333
                             mol_type        = other DNA
                             organism        = synthetic construct
SEQUENCE: 333
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ctattgtcac gcctgggaca cagcctgaa cgtgtaccct   300
gttttttggcg gaggcaccaa gctgaccgtt cta                               333

SEQ ID NO: 334               moltype = DNA   length = 39
FEATURE                      Location/Qualifiers
misc_feature                 1..39
                             note            = antibody sequence
source                       1..39
                             mol_type        = other DNA
                             organism        = synthetic construct
SEQUENCE: 334
agcggcagca gctccaacat cggcagcaac accgtgaac                           39

SEQ ID NO: 335               moltype = DNA   length = 21
FEATURE                      Location/Qualifiers
misc_feature                 1..21
                             note            = antibody sequence
source                       1..21
                             mol_type        = other DNA
                             organism        = synthetic construct
SEQUENCE: 335
tacgacgacc tgcggcctag c                                              21

SEQ ID NO: 336               moltype = DNA   length = 36
FEATURE                      Location/Qualifiers
```

```
misc_feature            1..36
                        note = antibody sequence
source                  1..36
                        mol_type = other DNA
                        organism = synthetic construct
SEQUENCE: 336
cacgcctggg acgacagcct gaacgtgtac cctgtt                                 36

SEQ ID NO: 337          moltype = AA  length = 447
FEATURE                 Location/Qualifiers
REGION                  1..447
                        note = antibody sequence
source                  1..447
                        mol_type = protein
                        organism = synthetic construct
SEQUENCE: 337
EVQLLESGGG LVQPGGSLRL SCAASGFTFY SYAMSWVRQA PGKGLEWVSA IGYGGDTYYA   60
DSVKGRFTIS RDNSKNTLYL QMNSLRAEDT AVYYCARRDD YTSRDAFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 338          moltype = AA  length = 217
FEATURE                 Location/Qualifiers
REGION                  1..217
                        note = antibody sequence
source                  1..217
                        mol_type = protein
                        organism = synthetic construct
SEQUENCE: 338
QSVLTQPPSA SGTPGQRVTI SCSGSSSNIG SNTVNWYQQL PGTAPKLLIY DDDLRPSGVP   60
DRFSGSKSGT SASLAISGLQ SEDEADYYCH AWDDSLNVYP VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 339          moltype = DNA  length = 1341
FEATURE                 Location/Qualifiers
misc_feature            1..1341
                        note = antibody sequence
source                  1..1341
                        mol_type = other DNA
                        organism = synthetic construct
SEQUENCE: 339
gaagttcagc tgctggaatc tggcggcgga ctggttcaac tggcggatc tctgagactg     60
agctgtgccg ccagcggctt cacctttac agctacgcca tgagctgggt ccgacaggcc   120
cctggaaaag gccttgaatg ggtgtccgcc atcggctatg gcggcgatac ctactacgcc   180
gactctgtga aggggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360
gccagcacca agggcccag cgtgttccct ctggcccctt gtagcagaag caccagcgag   420
tctacagccg ccctgggctg cctcgtgaag gactactttc ccgagcccgt gaccgtgtcc   480
tggaactctg gcgctctgac aagcggcgtg cacacctttc cagccgtcg gcagagcagc   540
ggcctgtact ctctgagcag cgtcgtgaca gtgcccagca gcagcctggg caccaagacc   600
tacacctgta acgtggacca caagcccagc aacaccaagg tggacaagcg ggtggaatct   660
aagtacggcc ctccctgccc tccttgccca gcccctgaat ttctgggcgg accctccgtg   720
ttcctgttcc ccccaaagcc caaggacacc ctgatgatca gccggacccc cgaagtgacc   780
tgcgtggtgg tggatgtgtc ccaggaagat cccgaggtgc agttcaattg gtacgtggac   840
ggcgtggaag tgcacaacgc caagaccaag cccagagagg aacagttcaa cagcacctac   900
cgggtggtgt ccgtgctgac agtgctgcac caggactggc tgaacggcaa agagtacaag   960
tgcaaggtgt ccaacaaggg cctgcccagc tccatcgaga aaaccatcag caaggccaag  1020
ggccagcccc gcgaaccca ggtgtacaca ctgcctccaa gccaggaaga gatgaccaag  1080
aaccaggtgt ccctgacctg tctcgtgaaa ggcttctacc cctccgatat cgccgtggaa  1140
tgggagagca acggccagcc cgagaacaac tacaagacca cccccctgt gctggacagc  1200
gacggctcat tcttcctgta cagcagactg accgtggaca gagcggtg caggaaggc  1260
aacgtgttca gctgcagcgt gatgcacgag gccctgcaca accactacac ccagaagtcc  1320
ctgtctctga gcctgggcaa g                                           1341

SEQ ID NO: 340          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 340
cagtctgttc tgacacagcc tcctagcgcc tctggcacac tggacagag agtgaccatc     60
```

```
agctgtagcg gcagcagctc caacatcggc agcaacaccg tgaactggta tcagcagctg    120
cctggcacag cccctaaact gctgatctac tacgacgacc tgcggcctag cggcgtgcca    180
gatagatttt ctggcagcaa gagcggcacc tctgccagcc tggctatttc tggactgcag    240
agcgaggacg aggccgacta ctattgtacc gcctgggacg acagcctgaa cgtgtaccct    300
gttttttggcg gaggcaccaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c              651
```

```
SEQ ID NO: 341          moltype = AA   length = 120
FEATURE                 Location/Qualifiers
REGION                  1..120
                        note = antibody sequence
source                  1..120
                        mol_type = protein
                        organism = synthetic construct
SEQUENCE: 341
EVQLLESGGG LVQPGGSLRL SCAASGFTFY SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120

SEQ ID NO: 342          moltype = AA   length = 5
FEATURE                 Location/Qualifiers
REGION                  1..5
                        note = antibody sequence
source                  1..5
                        mol_type = protein
                        organism = synthetic construct
SEQUENCE: 342
SYAMS                                                                  5

SEQ ID NO: 343          moltype = AA   length = 16
FEATURE                 Location/Qualifiers
REGION                  1..16
                        note = antibody sequence
source                  1..16
                        mol_type = protein
                        organism = synthetic construct
SEQUENCE: 343
AIGYGGDTYY ADSVKG                                                     16

SEQ ID NO: 344          moltype = AA   length = 12
FEATURE                 Location/Qualifiers
REGION                  1..12
                        note = antibody sequence
source                  1..12
                        mol_type = protein
                        organism = synthetic construct
SEQUENCE: 344
RDDYTSRDAF DY                                                         12

SEQ ID NO: 345          moltype = AA   length = 111
FEATURE                 Location/Qualifiers
REGION                  1..111
                        note = antibody sequence
source                  1..111
                        mol_type = protein
                        organism = synthetic construct
SEQUENCE: 345
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCA AWDDSLNDIP VFGGGTKLTV L             111

SEQ ID NO: 346          moltype = AA   length = 13
FEATURE                 Location/Qualifiers
REGION                  1..13
                        note = antibody sequence
source                  1..13
                        mol_type = protein
                        organism = synthetic construct
SEQUENCE: 346
SGSSSNIGSN TVN                                                        13

SEQ ID NO: 347          moltype = AA   length = 7
FEATURE                 Location/Qualifiers
REGION                  1..7
                        note = antibody sequence
source                  1..7
                        mol_type = protein
```

```
                            organism = synthetic construct
SEQUENCE: 347
YDDLRPS                                                                    7

SEQ ID NO: 348           moltype = AA  length = 12
FEATURE                  Location/Qualifiers
REGION                   1..12
                         note = antibody sequence
source                   1..12
                         mol_type = protein
                         organism = synthetic construct
SEQUENCE: 348
AAWDDSLNDI PV                                                             12

SEQ ID NO: 349           moltype = DNA  length = 360
FEATURE                  Location/Qualifiers
misc_feature             1..360
                         note = antibody sequence
source                   1..360
                         mol_type = other DNA
                         organism = synthetic construct
SEQUENCE: 349
gaagttcagc tgctggaatc tggcggcgga ctggttcaac ctggcggatc tctgagactg    60
agctgtgccg ccagcggctt cacctttac agctacgcca tgagctgggt ccgacaggcc   120
cctgaaaaag gccttgaatg ggtgtccgcc atcggctatg cggcgatac ctactacgcc    180
gactctgtga agggcagatt caccatcagc cgggacaaca gcaagaacac cctgtacctg   240
cagatgaaca gcctgagagc cgaggacacc gccgtgtact attgcgccag aagggacgac   300
tacaccagca gggacgcctt cgattattgg ggccagggca cactggtcac cgtttcttca   360

SEQ ID NO: 350           moltype = DNA  length = 15
FEATURE                  Location/Qualifiers
misc_feature             1..15
                         note = antibody sequence
source                   1..15
                         mol_type = other DNA
                         organism = synthetic construct
SEQUENCE: 350
agctacgcca tgagc                                                          15

SEQ ID NO: 351           moltype = DNA  length = 48
FEATURE                  Location/Qualifiers
misc_feature             1..48
                         note = antibody sequence
source                   1..48
                         mol_type = other DNA
                         organism = synthetic construct
SEQUENCE: 351
gccatcggct atgcggcga tacctactac gccgactctg tgaagggc                       48

SEQ ID NO: 352           moltype = DNA  length = 36
FEATURE                  Location/Qualifiers
misc_feature             1..36
                         note = antibody sequence
source                   1..36
                         mol_type = other DNA
                         organism = synthetic construct
SEQUENCE: 352
agggacgact acaccagcag ggacgccttc gattat                                   36

SEQ ID NO: 353           moltype = DNA  length = 333
FEATURE                  Location/Qualifiers
misc_feature             1..333
                         note = antibody sequence
source                   1..333
                         mol_type = other DNA
                         organism = synthetic construct
SEQUENCE: 353
cagtctgttc tgacacagcc tcctagcgcc tctggcacac ctggacagag agtgaccatc    60
agctctagcg gcagcagctc caacatcggc agcaacaccg tgaactggta tcagcagctg   120
cctggcacag cccctaaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgacatccct   300
gttttttggcg gaggcaccaa gctgaccgtt cta                                 333

SEQ ID NO: 354           moltype = DNA  length = 39
FEATURE                  Location/Qualifiers
misc_feature             1..39
                         note = antibody sequence
source                   1..39
```

```
                        mol_type = other DNA
                        organism = synthetic construct
SEQUENCE: 354
agcggcagca gctccaacat cggcagcaac accgtgaac                              39

SEQ ID NO: 355          moltype = DNA   length = 21
FEATURE                 Location/Qualifiers
misc_feature            1..21
                        note = antibody sequence
source                  1..21
                        mol_type = other DNA
                        organism = synthetic construct
SEQUENCE: 355
tacgacgacc tgcggcctag c                                                 21

SEQ ID NO: 356          moltype = DNA   length = 36
FEATURE                 Location/Qualifiers
misc_feature            1..36
                        note = antibody sequence
source                  1..36
                        mol_type = other DNA
                        organism = synthetic construct
SEQUENCE: 356
gccgcctggg acgacagcct gaacgacatc cctgtt                                 36

SEQ ID NO: 357          moltype = AA   length = 447
FEATURE                 Location/Qualifiers
REGION                  1..447
                        note = antibody sequence
source                  1..447
                        mol_type = protein
                        organism = synthetic construct
SEQUENCE: 357
EVQLLESGGG LVQPGGSLRL SCAASGFTFY SYAMSWVRQA PGKGLEWVSA IGYGGDTYYA        60
DSVKGRFTIS RDNSKNTLYL QMNSLRAEDT AVYYCARRDD YTSRDAFDYW GQGTLVTVSS       120
ASTKGPSVFP LAPCSRSTSE STAALGCLVK DYFPEPVTVS WNSGALTSGV HTFPAVLQSS       180
GLYSLSSVVT VPSSSLGTKT YTCNVDHKPS NTKVDKRVES KYGPPCPPCP APEFLGGPSV       240
FLFPPKPKDT LMISRTPEVT CVVVDVSQED PEVQFNWYVD GVEVHNAKTK PREEQFNSTY       300
RVVSVLTVLH QDWLNGKEYK CKVSNKGLPS SIEKTISKAK GQPREPQVYT LPPSQEEMTK       360
NQVSLTCLVK GFYPSDIAVE WESNGQPENN YKTTPPVLDS DGSFFLYSRL TVDKSRWQEG       420
NVFSCSVMHE ALHNHYTQKS LSLSLGK                                           447

SEQ ID NO: 358          moltype = AA   length = 217
FEATURE                 Location/Qualifiers
REGION                  1..217
                        note = antibody sequence
source                  1..217
                        mol_type = protein
                        organism = synthetic construct
SEQUENCE: 358
QSVLTQPPSA SGTPGQRVTI SCSGSSSNIG SNTVNWYQQL PGTAPKLLIY YDDLRPSGVP        60
DRFSGSKSGT SASLAISGLQ SEDEADYYCA AWDDSLNDIP VFGGGTKLTV LGQPKAAPSV       120
TLFPPSSEEL QANKATLVCL ISDFYPGAVT VAWKADSSPV KAGVETTTPS KQSNNKYAAS       180
SYLSLTPEQW KSHRSYSCQV THEGSTVEKT VAPTECS                                217

SEQ ID NO: 359          moltype = DNA   length = 1341
FEATURE                 Location/Qualifiers
misc_feature            1..1341
                        note = antibody sequence
source                  1..1341
                        mol_type = other DNA
                        organism = synthetic construct
SEQUENCE: 359
gaagttcagc tgctggaatc tggcggcgga ctggttcaac ctggcggatc tctgagactg        60
agctgtgccg ccagcggctt caccttttac agctacgcca tgagctgggt ccgacaggcc       120
cctggaaaag gccttgaatg ggtgtccgcc atcggctatg gcggcgatac ctactacgcc       180
gactctgtga aggcagatt caccatcagc cgggacaaca gcaagaacac cctgtacctg       240
cagatgaaca gcctgagagc cgaggacacc gccgtgtact attgcgccag aagggacgac       300
tacaccagca gggacgcctt cgattattgg ggccagggca cactggtcac cgtttcttca       360
gccagcacca agggcccag cgtgttccct ctggcccctt gtagcagaag caccagcgag       420
tctacagccg ccctgggctg cctcgtgaag gactactttc ccgagcccgt gaccgtgtcc       480
tggaactctg gcgctctgac aagcggcgtg cacacctttc cagccgtgct gcagagcagc       540
ggcctgtact ctctgagcag cgtcgtgaca gtgcccagca gcagcctggg caccaagacc       600
tacacctgta acgtggacca caagcccagc aacaccaagg tggacaagcg ggtggaatct       660
aagtacggcc ctccctgccc tccttgccca gccctgaat tctgggcgg accctccgtg       720
ttcctgttcc ccccaaagcc caaggacacc ctgatgatca gccggacccc cgaagtgacc       780
tgcgtggtgg tggatgtgtc ccaggaagat cccgaggtgc agttcaattg gtacgtggac       840
ggcgtggaag tgcacaacgc caagaccaag cccagagagg aacagttcaa cagcacctac       900
cgggtggtgt ccgtgctgac agtgctgcac caggactggc tgaacggcaa agagtacaag       960
```

```
tgcaaggtgt ccaacaaggg cctgcccagc tccatcgaga aaaccatcag caaggccaag   1020
ggccagcccc gcgaacccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca cccccctgt gctggacagc    1200
gacggctcat tcttcctgta cagcagactg accgtggaca gagccggtg gcaggaaggc    1260
aacgtgttca gctgcagcgt gatgcacgag gccctgcaca accactacac ccagaagtcc   1320
ctgtctctga gcctgggcaa g                                              1341

SEQ ID NO: 360           moltype = DNA  length = 651
FEATURE                  Location/Qualifiers
misc_feature             1..651
                         note = antibody sequence
source                   1..651
                         mol_type = other DNA
                         organism = synthetic construct
SEQUENCE: 360
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgacatccct   300
gtttttggcg gaggcaccaa gctgaccgtt ctaggccgc ctaaagccgc ccctagcgtg    360
accctgttcc ctccaagcag cgaggaactg caggccaaca aggccaccct cgtgtgcctg   420
atcagcgact ctatcctggc cgccgtgacc gtggcctgga aggccgatag ctctcctgtg   480
aaggccggcg tggaaaccac caccctagc aagcagagca caacaaata cgccgccagc    540
agctacctga gcctgacccc cgagcagtgg aagtcccaca gatcctacag ctgccaagtg   600
acccacgagg gcagcaccgt ggaaaagaca gtggcccta ccgagtgcag c             651

SEQ ID NO: 361           moltype = AA  length = 120
FEATURE                  Location/Qualifiers
REGION                   1..120
                         note = antibody sequence
source                   1..120
                         mol_type = protein
                         organism = synthetic construct
SEQUENCE: 361
EVQLLESGGG LVQPGGSLRL SCAASGFTFY SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120

SEQ ID NO: 362           moltype = AA  length = 5
FEATURE                  Location/Qualifiers
REGION                   1..5
                         note = antibody sequence
source                   1..5
                         mol_type = protein
                         organism = synthetic construct
SEQUENCE: 362
SYAMS                                                                 5

SEQ ID NO: 363           moltype = AA  length = 16
FEATURE                  Location/Qualifiers
REGION                   1..16
                         note = antibody sequence
source                   1..16
                         mol_type = protein
                         organism = synthetic construct
SEQUENCE: 363
AIGYGGDTYY ADSVKG                                                    16

SEQ ID NO: 364           moltype = AA  length = 12
FEATURE                  Location/Qualifiers
REGION                   1..12
                         note = antibody sequence
source                   1..12
                         mol_type = protein
                         organism = synthetic construct
SEQUENCE: 364
RDDYTSRDAF DY                                                        12

SEQ ID NO: 365           moltype = AA  length = 111
FEATURE                  Location/Qualifiers
REGION                   1..111
                         note = antibody sequence
source                   1..111
                         mol_type = protein
                         organism = synthetic construct
SEQUENCE: 365
QSVLTQPPSA SGTPGQRVTI SCSGSSSNIG SNTVNWYQQL PGTAPKLLIY YDDLRPSGVP    60
DRFSGSKSGT SASLAISGLQ SEDEADYYCA AWDDSLNVIP VFGGGTKLTV L            111
```

| SEQ ID NO: 366 | moltype = AA  length = 13 |
| FEATURE | Location/Qualifiers |
| REGION | 1..13 |
| | note = antibody sequence |
| source | 1..13 |
| | mol_type = protein |
| | organism = synthetic construct |

SEQUENCE: 366
SGSSSNIGSN TVN                                                              13

| SEQ ID NO: 367 | moltype = AA  length = 7 |
| FEATURE | Location/Qualifiers |
| REGION | 1..7 |
| | note = antibody sequence |
| source | 1..7 |
| | mol_type = protein |
| | organism = synthetic construct |

SEQUENCE: 367
YDDLRPS                                                                      7

| SEQ ID NO: 368 | moltype = AA  length = 12 |
| FEATURE | Location/Qualifiers |
| REGION | 1..12 |
| | note = antibody sequence |
| source | 1..12 |
| | mol_type = protein |
| | organism = synthetic construct |

SEQUENCE: 368
AAWDDSLNVI PV                                                               12

| SEQ ID NO: 369 | moltype = DNA  length = 360 |
| FEATURE | Location/Qualifiers |
| misc_feature | 1..360 |
| | note = antibody sequence |
| source | 1..360 |
| | mol_type = other DNA |
| | organism = synthetic construct |

SEQUENCE: 369
gaagttcagc tgctggaatc tggcggcgga ctggttcaac tggcggatc tctgagactg      60
agctgtgccg ccagcggctt caccttttac agctacgcca tgagctgggt ccgacaggcc    120
cctggaaaag gccttgaatg ggtgtccgcc atcggctatg cggcgatac ctactacgcc     180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggccagggca cactggtcac cgtttcttca    360

| SEQ ID NO: 370 | moltype = DNA  length = 15 |
| FEATURE | Location/Qualifiers |
| misc_feature | 1..15 |
| | note = antibody sequence |
| source | 1..15 |
| | mol_type = other DNA |
| | organism = synthetic construct |

SEQUENCE: 370
agctacgcca tgagc                                                            15

| SEQ ID NO: 371 | moltype = DNA  length = 48 |
| FEATURE | Location/Qualifiers |
| misc_feature | 1..48 |
| | note = antibody sequence |
| source | 1..48 |
| | mol_type = other DNA |
| | organism = synthetic construct |

SEQUENCE: 371
gccatcggct atgcggcgga tacctactac gccgactctg tgaagggc                        48

| SEQ ID NO: 372 | moltype = DNA  length = 36 |
| FEATURE | Location/Qualifiers |
| misc_feature | 1..36 |
| | note = antibody sequence |
| source | 1..36 |
| | mol_type = other DNA |
| | organism = synthetic construct |

SEQUENCE: 372
agggacgact acaccagcag ggacgccttc gattat                                     36

| SEQ ID NO: 373 | moltype = DNA  length = 333 |
| FEATURE | Location/Qualifiers |
| misc_feature | 1..333 |

```
                        note = antibody sequence
source                  1..333
                        mol_type = other DNA
                        organism = synthetic construct
SEQUENCE: 373
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgtgatccct   300
gtttttggcg gaggcaccaa gctgaccgtt cta                                 333

SEQ ID NO: 374          moltype = DNA  length = 39
FEATURE                 Location/Qualifiers
misc_feature            1..39
                        note = antibody sequence
source                  1..39
                        mol_type = other DNA
                        organism = synthetic construct
SEQUENCE: 374
agcggcagca gctccaacat cggcagcaac accgtgaac                            39

SEQ ID NO: 375          moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 375
tacgacgacc tgcggcctag c                                               21

SEQ ID NO: 376          moltype = DNA  length = 36
FEATURE                 Location/Qualifiers
misc_feature            1..36
                        note = antibody sequence
source                  1..36
                        mol_type = other DNA
                        organism = synthetic construct
SEQUENCE: 376
gccgcctggg acgacagcct gaacgtgatc cctgtt                               36

SEQ ID NO: 377          moltype = AA  length = 447
FEATURE                 Location/Qualifiers
REGION                  1..447
                        note = antibody sequence
source                  1..447
                        mol_type = protein
                        organism = synthetic construct
SEQUENCE: 377
EVQLLESGGG LVQPGGSLRL SCAASGFTFY SYAMSWVRQA PGKGLEWVSA IGYGGDTYYA    60
DSVKGRFTIS RDNSKNTLYL QMNSLRAEDT AVYYCARRDD YTSRDAFDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                       447

SEQ ID NO: 378          moltype = AA  length = 217
FEATURE                 Location/Qualifiers
REGION                  1..217
                        note = antibody sequence
source                  1..217
                        mol_type = protein
                        organism = synthetic construct
SEQUENCE: 378
QSVLTQPPSA SGTPGQRVTI SCSGSSSNIG SNTVNWYQQL PGTAPKLLIY DDLRPSGVP     60
DRFSGSKSGT SASLAISGLQ SEDEADYYCA AWDDSLNVIP VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 379          moltype = DNA  length = 1341
FEATURE                 Location/Qualifiers
misc_feature            1..1341
                        note = antibody sequence
source                  1..1341
                        mol_type = other DNA
                        organism = synthetic construct
```

```
SEQUENCE: 379
gaagttcagc tgctggaatc tggcggcgga ctggttcaac ctggcggatc tctgagactg    60
agctgtgccg ccagcggctt cacctttac agctacgcca tgagctgggt ccgacaggcc    120
cctgaaaaag gccttgaatg ggtgtccgcc atcggctatg cggcgatac ctactacgcc    180
gactctgtga agggcagatt caccatcagc cgggacaaca gcaagaacac cctgtacctg    240
cagatgaaca gcctgagagc cgaggacacc gccgtgtact attgcgccag aagggacgac    300
tacaccagca gggacgcctt cgattattgg ggcagggca cactggtcac cgtttcttca    360
gccagcacca agggccccag cgtgttccct ctggccccctt gtagcagaag caccagcgag    420
tctacagccg ccctgggctg cctcgtgaag gactactttc ccgagcccgt gaccgtgtcc    480
tggaactctg gcgctctgac aagcggcgtg cacacctttc cagccgtgct gcagagcagc    540
ggcctgtact ctctgagcag cgtcgtgaca gtgcccagca gcagcctggg caccaagacc    600
tacacctgta acgtggacca caagcccagc aacaccaagg tggacaagcg ggtggaatct    660
aagtacggcc ctccctgccc tccttgccca gcccctgaat ttctgggcgg accctccgtg    720
ttcctgttcc ccccaaagcc caaggacacc ctgatgatca gccggacccc cgaagtgacc    780
tgcgtggtgg tggatgtgtc ccaggaagat cccgaggtgc agttcaattg gtacgtggac    840
ggcgtggaag tgcacaacgc caagaccaag cccagagagg aacagttcaa cagcacctac    900
cgggtggtgt ccgtgctgac agtgctgcac caggactggc tgaacggcaa agagtacaag    960
tgcaaggtgt ccaacaaggg cctgcccagc tccatcgaga aaaccatcag caaggccaag   1020
ggccagcccc gcgaacccca ggtgtacaca ctgcctccaa gccaggaaga gatgaccaag   1080
aaccaggtgt ccctgacctg tctcgtgaaa ggcttctacc cctccgatat cgccgtggaa   1140
tgggagagca acggccagcc cgagaacaac tacaagacca ccccccctgt gctggacagc   1200
gacggctcat tcttcctgta cagcagactg accgtggaca gagccggtg gcaggaaggc   1260
aacgtgttca gctgcagcgt gatgcacgag gccctgcaca ccactacac ccagaagtcc   1320
ctgtctctga gcctgggcaa g                                             1341

SEQ ID NO: 380          moltype = DNA    length = 651
FEATURE                 Location/Qualifiers
misc_feature            1..651
                        note = antibody sequence
source                  1..651
                        mol_type = other DNA
                        organism = synthetic construct
SEQUENCE: 380
cagtctgttc tgacacagcc tcctagcgcc tctggcacac ctggacagag agtgaccatc    60
agctgtagcg gcagcagctc caacatcggc agcaacaccg tgaactggta tcagcagctg   120
cctggcacag cccctaaact gctgatctac tacgacgacc tgcggcctag cggcgtgcca   180
gatagatttt ctggcagcaa gagcggcacc tctgccagcc tggctatttc tggactgcag   240
agcgaggacg aggccgacta ttattgtgcc gcctgggacg acagcctgaa cgtgatccct   300
gtttttgggg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggccggcg tggaaaccac caccccctagc aagcagagca caacaaata cgccgccagc   540
agctacctga gcctgaccccc cgagcagtgg aagtcccaca gatcctacag ctgccaagtg   600
acccagagg gcagcaccgt ggaaaagaca gtggccccta ccgagtgcag c              651

SEQ ID NO: 381          moltype = AA    length = 123
FEATURE                 Location/Qualifiers
REGION                  1..123
                        note = antibody sequence
source                  1..123
                        mol_type = protein
                        organism = synthetic construct
SEQUENCE: 381
EVQLLESGGG LVQPGGSLRL SCAASGFTFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSS                                                                 123

SEQ ID NO: 382          moltype = AA    length = 5
FEATURE                 Location/Qualifiers
REGION                  1..5
                        note = antibody sequence
source                  1..5
                        mol_type = protein
                        organism = synthetic construct
SEQUENCE: 382
SYEMN                                                                 5

SEQ ID NO: 383          moltype = AA    length = 17
FEATURE                 Location/Qualifiers
REGION                  1..17
                        note = antibody sequence
source                  1..17
                        mol_type = protein
                        organism = synthetic construct
SEQUENCE: 383
GISWNSGWID YADSVKG                                                   17

SEQ ID NO: 384          moltype = AA    length = 14
FEATURE                 Location/Qualifiers
```

```
REGION                  1..14
                        note = antibody sequence
source                  1..14
                        mol_type = protein
                        organism = synthetic construct
SEQUENCE: 384
SGYSSSWFDP DFDY                                                          14

SEQ ID NO: 385          moltype = AA  length = 111
FEATURE                 Location/Qualifiers
REGION                  1..111
                        note = antibody sequence
source                  1..111
                        mol_type = protein
                        organism = synthetic construct
SEQUENCE: 385
QSVLTQPPSV SGAPGQRVTI SCTGSSSDIG AGYDVHWYQQ LPGTAPKLLI YGNSNRPSGV         60
PDRFSGSKSG TSASLAITGL QAEDEADYYC SSYAGPNPYV VFGGGTKLTV L                 111

SEQ ID NO: 386          moltype = AA  length = 14
FEATURE                 Location/Qualifiers
REGION                  1..14
                        note = antibody sequence
source                  1..14
                        mol_type = protein
                        organism = synthetic construct
SEQUENCE: 386
TGSSSDIGAG YDVH                                                          14

SEQ ID NO: 387          moltype = AA  length = 7
FEATURE                 Location/Qualifiers
REGION                  1..7
                        note = antibody sequence
source                  1..7
                        mol_type = protein
                        organism = synthetic construct
SEQUENCE: 387
GNSNRPS                                                                   7

SEQ ID NO: 388          moltype = AA  length = 11
FEATURE                 Location/Qualifiers
REGION                  1..11
                        note = antibody sequence
source                  1..11
                        mol_type = protein
                        organism = synthetic construct
SEQUENCE: 388
SSYAGPNPYV V                                                             11

SEQ ID NO: 389          moltype = DNA  length = 369
FEATURE                 Location/Qualifiers
misc_feature            1..369
                        note = antibody sequence
source                  1..369
                        mol_type = other DNA
                        organism = synthetic construct
SEQUENCE: 389
gaagttcagc tgctggaatc tggcggcgga ctggttcaac tggcggatc tctgagactg          60
agctgtgccg ccagcggctt caccttcgat agctacgaga tgaactgggt ccgacaggcc        120
cctggcaaag gccttgaatg ggtgtccggc atcagcggct ga atagcggctg gatcgactac     180
gccgacagcg tgaagggcag attcaccatc agccgggaca acagcaagaa caccctgtac        240
ctgcagatga acagcctgag agccgaggac accgccgtgt actactgtgc cagaagcggc        300
tacagcagct cttggtttga ccccgacttc gactattggg gccagggcac actggtcaca        360
gtctcttca                                                                369

SEQ ID NO: 390          moltype = DNA  length = 15
FEATURE                 Location/Qualifiers
misc_feature            1..15
                        note = antibody sequence
source                  1..15
                        mol_type = other DNA
                        organism = synthetic construct
SEQUENCE: 390
agctacgaga tgaac                                                         15

SEQ ID NO: 391          moltype = DNA  length = 51
FEATURE                 Location/Qualifiers
misc_feature            1..51
                        note = antibody sequence
```

```
source                  1..51
                        mol_type = other DNA
                        organism = synthetic construct
SEQUENCE: 391
ggcatcagct ggaatagcgg ctggatcgac tacgccgaca gcgtgaaggg c        51

SEQ ID NO: 392          moltype = DNA  length = 42
FEATURE                 Location/Qualifiers
misc_feature            1..42
                        note = antibody sequence
source                  1..42
                        mol_type = other DNA
                        organism = synthetic construct
SEQUENCE: 392
agcggctaca gcagctcttg gtttgacccc gacttcgact at                  42

SEQ ID NO: 393          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 393
cagtctgttc tgacacagcc tccatctgtg tctggcgccc ctggacagag agtgaccatc   60
agctgtacag gcagcagctc cgatattggc gccggataca gcgtgcactg gtatcagcaa  120
ctgcctggca cagcccctaa gctgctgatc tacggcaaca gcaacagacc tagcggcgtg  180
cccgatagat tcagcggctc taagtctggc acaagcgcca gcctggccat tactggactg  240
caggccgaag atgaggccga ctactactgc agcagctacg ctggccccaa tccttacgtg  300
gtgtttggcg gcggaacaaa gctgaccgtt cta                             333

SEQ ID NO: 394          moltype = DNA  length = 42
FEATURE                 Location/Qualifiers
misc_feature            1..42
                        note = antibody sequence
source                  1..42
                        mol_type = other DNA
                        organism = synthetic construct
SEQUENCE: 394
acaggcagca gctccgatat tggcgccgga tacgacgtgc ac                  42

SEQ ID NO: 395          moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 395
ggcaacagca acagacctag c                                         21

SEQ ID NO: 396          moltype = DNA  length = 33
FEATURE                 Location/Qualifiers
misc_feature            1..33
                        note = antibody sequence
source                  1..33
                        mol_type = other DNA
                        organism = synthetic construct
SEQUENCE: 396
agcagctacg ctggccccaa tccttacgtg gtg                            33

SEQ ID NO: 397          moltype = AA  length = 453
FEATURE                 Location/Qualifiers
REGION                  1..453
                        note = antibody sequence
source                  1..453
                        mol_type = protein
                        organism = synthetic construct
SEQUENCE: 397
EVQLLESGGG LVQPGGSLRL SCAASGFTFD SYEMNWVRQA PGKGLEWVSG ISWNSGWIDY   60
ADSVKGRFTI SRDNSKNTLY LQMNSLRAED TAVYYCARSG YSSSWFDPDF DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                             453

SEQ ID NO: 398          moltype = AA  length = 217
```

```
FEATURE                 Location/Qualifiers
REGION                  1..217
                        note = antibody sequence
source                  1..217
                        mol_type = protein
                        organism = synthetic construct
SEQUENCE: 398
QSVLTQPPSV SGAPGQRVTI SCTGSSSDIG AGYDVHWYQQ LPGTAPKLLI YGNSNRPSGV   60
PDRFSGSKSG TSASLAITGL QAEDEADYYC SSYAGPNPYV VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 399          moltype = DNA  length = 1359
FEATURE                 Location/Qualifiers
misc_feature            1..1359
                        note = antibody sequence
source                  1..1359
                        mol_type = other DNA
                        organism = synthetic construct
SEQUENCE: 399
gaagttcagc tgctggaatc tggcggcgga ctggttcaac tggcggatc tctgagactg     60
agctgtgccg ccagcggctt cacctttcgat agctacgaga tgaactgggt ccgacaggcc  120
cctggcaaag gccttgaatg ggtgtccggc atcagctgga atagcggctg gatcgactac  180
gccgacagcg tgaagggcag attcaccatc agccgggaca acagcaagaa caccctgtac  240
ctgcagatga acagcctgag agccgaggac accgccgtgt actactgtgc cagaagcggc  300
tacagcagct cttggtttga ccccgacttc gactattggg gccagggcac actggtcaca  360
gtctcttcag ccagcaccaa gggcccccagc gtgttccctc tggccccctag cagcaagagc  420
acatctggcg gaacagccgc cctgggctgc ctcgtgaagg actactttcc cgagcccgtg  480
accgtgtcct ggaactctgg cgctctgaca agcggcgtgc acacctttcc agccgtgctg  540
cagagcagcg gcctgtactc tctgagcagc gtcgtgaccg tgcccagcag ctctctgggc  600
acccagacct acatctgcaa cgtgaaccac aagcccagca acaccaaggt ggacaagaag  660
gtggaaccca gagctgcga caagacccac acctgtcccc cttgtcctgc cccgaactg   720
ctgggaggcc cttccgtgtt cctgttcccc caaagcccaa ggacaccct gatgatcagc  780
cggacccccg aagtgacctg cgtggtggtg gatgtgtccc acgaggaccc tgaagtgaag  840
ttcaattggt acgtggacgg cgtggaagtg cacaacgcca agaccaagcc tagagaggaa  900
cagtacaaca gcacctaccg ggtggtgtcc gtgctgacag tgctgcacca ggactggctg  960
aacggcaaag agtacaagtg caaggtgtcc aacaaggccc tgcctgcccc catcgagaaa 1020
accatcagca aggccaaggg ccagccccgc gaacccccagg tgtacacact gccccccaagc 1080
agggacgagc tgaccaagaa ccaggtgtcc ctgacctgtc tcgtgaaagg ctttctaccc 1140
tccgatatcg ccgtgaatg ggagagcaac ggccagcccg agaacaacta caagaccacc 1200
cccctgtgc tggacagcga cggctcattc ttcctgtaca gcaagctgac cgtggacaag 1260
tcccggtggc agcagggcaa cgtgttcagc tgcagcgtga tgcacgaggc cctgcacaac 1320
cactacaccc agaagtccct gagcctgagc cctggcaag                         1359

SEQ ID NO: 400          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 400
cagtctgttc tgacacagcc tccatctgtg tctggcgccc ctggacagag agtgaccatc    60
agctgtacag gcagcagctc cgatattggc gccggatacg acgtgcactg gtatcagcaa  120
ctgcctggca cagccctaa gctgctgatc tacggcaaca gcaacagacc tagcggcgtg  180
cccgatagat tcagcggctc taagtctggc acaagcgcca gcctggccat tactggactg  240
caggccgaag atgaggccga ctactactgc agcagctacg ctggccccaa tccttacgtg  300
gtgtttggcg gcgaaacaaa gctgaccgtt ctaggccagc ctaaagccgc ccctagcgtg  360
acccttgttcc ctccaagcag cgaggaactg caggccaaca aggccaccct cgtgtgcctg  420
atcagcgact tctatcctgg cgccgtgacc gtggcctgga aggccgatag ctctcctgtg  480
aaggccggcg tggaaaccac cacccctagc aagcagagca acaacaaata cgccgccagc  540
agctacctga gcctgacccc cgagcagtgg aagtcccaca gatcctacag ctgccaagtg  600
acccacgagg gcagcaccgt ggaaaagaca gtggcccctga ccgagtgcag c          651

SEQ ID NO: 401          moltype = AA  length = 123
FEATURE                 Location/Qualifiers
REGION                  1..123
                        note = antibody sequence
source                  1..123
                        mol_type = protein
                        organism = synthetic construct
SEQUENCE: 401
EVQLLESGGG LVQPGGSLRL SCAASGFTFD SYEMNWVRQA PGKGLEWVSG ISWNSGWIDY   60
ADSVKGRFTI SRDNSKNTLY LQMNSLRAED TAVYYCARSG YSSSWFDPDF DYWGQGTLVT  120
VSS                                                                 123

SEQ ID NO: 402          moltype = AA  length = 5
FEATURE                 Location/Qualifiers
REGION                  1..5
```

```
                         note = antibody sequence
source                   1..5
                         mol_type = protein
                         organism = synthetic construct
SEQUENCE: 402
SYEMN                                                                    5

SEQ ID NO: 403           moltype = AA  length = 17
FEATURE                  Location/Qualifiers
REGION                   1..17
                         note = antibody sequence
source                   1..17
                         mol_type = protein
                         organism = synthetic construct
SEQUENCE: 403
GISWNSGWID YADSVKG                                                      17

SEQ ID NO: 404           moltype = AA  length = 14
FEATURE                  Location/Qualifiers
REGION                   1..14
                         note = antibody sequence
source                   1..14
                         mol_type = protein
                         organism = synthetic construct
SEQUENCE: 404
SGYSSSWFDP DFDY                                                         14

SEQ ID NO: 405           moltype = AA  length = 111
FEATURE                  Location/Qualifiers
REGION                   1..111
                         note = antibody sequence
source                   1..111
                         mol_type = protein
                         organism = synthetic construct
SEQUENCE: 405
QSVLTQPPSV SGAPGQRVTI SCTGSSSNIG AGYDVHWYQQ LPGTAPKLLI YGNSNRPSGV        60
PDRFSGSKSG TSASLAITGL QAEDEADYYC QSYAGINPYV VFGGGTKLTV L                111

SEQ ID NO: 406           moltype = AA  length = 14
FEATURE                  Location/Qualifiers
REGION                   1..14
                         note = antibody sequence
source                   1..14
                         mol_type = protein
                         organism = synthetic construct
SEQUENCE: 406
TGSSSNIGAG YDVH                                                         14

SEQ ID NO: 407           moltype = AA  length = 7
FEATURE                  Location/Qualifiers
REGION                   1..7
                         note = antibody sequence
source                   1..7
                         mol_type = protein
                         organism = synthetic construct
SEQUENCE: 407
GNSNRPS                                                                  7

SEQ ID NO: 408           moltype = AA  length = 11
FEATURE                  Location/Qualifiers
REGION                   1..11
                         note = antibody sequence
source                   1..11
                         mol_type = protein
                         organism = synthetic construct
SEQUENCE: 408
QSYAGINPYV V                                                            11

SEQ ID NO: 409           moltype = DNA  length = 369
FEATURE                  Location/Qualifiers
misc_feature             1..369
                         note = antibody sequence
source                   1..369
                         mol_type = other DNA
                         organism = synthetic construct
SEQUENCE: 409
gaagttcagc tgctggaatc tggcggcgga ctggttcaac ctggcggatc tctgagactg        60
agctgtgccg ccagcggctt caccttcgat agctacgaga tgaactgggt ccgacaggcc       120
cctggcaaag cccttgaatg ggtgtccggc atcagctgga atagcggctg gatcgactac       180
```

```
gccgacagcg tgaagggcag attcaccatc agccgggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttca                                                            369

SEQ ID NO: 410           moltype = DNA  length = 15
FEATURE                  Location/Qualifiers
misc_feature             1..15
                         note = antibody sequence
source                   1..15
                         mol_type = other DNA
                         organism = synthetic construct
SEQUENCE: 410
agctacgaga tgaac                                                     15

SEQ ID NO: 411           moltype = DNA  length = 51
FEATURE                  Location/Qualifiers
misc_feature             1..51
                         note = antibody sequence
source                   1..51
                         mol_type = other DNA
                         organism = synthetic construct
SEQUENCE: 411
ggcatcagct ggaatagcgg ctggatcgac tacgccgaca cgtgaaggg c               51

SEQ ID NO: 412           moltype = DNA  length = 42
FEATURE                  Location/Qualifiers
misc_feature             1..42
                         note = antibody sequence
source                   1..42
                         mol_type = other DNA
                         organism = synthetic construct
SEQUENCE: 412
agcggctaca gcagctcttg gtttgacccc gacttcgact at                       42

SEQ ID NO: 413           moltype = DNA  length = 333
FEATURE                  Location/Qualifiers
misc_feature             1..333
                         note = antibody sequence
source                   1..333
                         mol_type = other DNA
                         organism = synthetic construct
SEQUENCE: 413
cagtctgttc tgacacagcc tccatctgtg tctggcgccc ctggacagag agtgaccatc    60
agctgtacag gcagcagctc caatatcgga gccggctatg acgtgactg gtatcagcag    120
ctgcctggca cagcccctaa actgctgatc tacggcaaca gcaacagacc cagcggcgtg    180
cccgatgat tttccggctc taagagcggc acaaagccgcca gcctggctat tactgactg    240
caggccgagg acgaggccga ctactactgt cagagctacg ccggcatcaa cccctacgtg    300
gtgtttggcg gaggcaccaa gctgacagtt cta                                 333

SEQ ID NO: 414           moltype = DNA  length = 42
FEATURE                  Location/Qualifiers
misc_feature             1..42
                         note = antibody sequence
source                   1..42
                         mol_type = other DNA
                         organism = synthetic construct
SEQUENCE: 414
acaggcagca gctccaatat cggagccggc tatgacgtgc ac                       42

SEQ ID NO: 415           moltype = DNA  length = 21
FEATURE                  Location/Qualifiers
misc_feature             1..21
                         note = antibody sequence
source                   1..21
                         mol_type = other DNA
                         organism = synthetic construct
SEQUENCE: 415
ggcaacagca acagacccag c                                              21

SEQ ID NO: 416           moltype = DNA  length = 33
FEATURE                  Location/Qualifiers
misc_feature             1..33
                         note = antibody sequence
source                   1..33
                         mol_type = other DNA
                         organism = synthetic construct
SEQUENCE: 416
cagagctacg ccggcatcaa cccctacgtg gtg                                 33
```

```
SEQ ID NO: 417          moltype = AA  length = 453
FEATURE                 Location/Qualifiers
REGION                  1..453
                        note = antibody sequence
source                  1..453
                        mol_type = protein
                        organism = synthetic construct
SEQUENCE: 417
EVQLLESGGG LVQPGGSLRL SCAASGFTFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 418          moltype = AA  length = 217
FEATURE                 Location/Qualifiers
REGION                  1..217
                        note = antibody sequence
source                  1..217
                        mol_type = protein
                        organism = synthetic construct
SEQUENCE: 418
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC QSYAGINPYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 419          moltype = DNA  length = 1359
FEATURE                 Location/Qualifiers
misc_feature            1..1359
                        note = antibody sequence
source                  1..1359
                        mol_type = other DNA
                        organism = synthetic construct
SEQUENCE: 419
gaagttcagc tgctggaatc tggcggcgga ctggttcaac tggcggatc tctgagactg     60
agctgtgccg ccagcggctt caccttcgat agctacgaga tgaactgggt ccgacaggcc   120
cctggcaaag gccttgaatg ggtgtccggc atcagctgga atagcggctg gatcgactac   180
gccgacagcg tgaagggcag attcaccatc agcggacaca gcaagaacac caccctgtac   240
ctgcagatga acagcctgag agccgaggac accgccgtgt actactgtgc cagaagcggc   300
tacagcagct cttggtttga ccccgacttc gactattggg gccagggcac actggtcaca   360
gtctcttcag ccagcaccaa gggcccagc gtgttccctc tggcccctag cagcaagagc   420
acatctggcg gaacagccgc cctgggctgc ctcgtgaagg actactttcc cgagcccgtg   480
accgtgtcct ggaactctgg cgctctgaca agcggcgtgc acacctttcc agccgtgctg   540
cagagcagcg gcctgtactc tctgagcagc gtcgtgacag tgcccagcag ctctctgggc   600
acccagacct acatctgcaa cgtgaaccac aagcccagca caccaaggt ggacaagaag   660
gtggaaccca gagctgcga caagacccac acctgtcccc cttgtcctgc ccccgaacttg   720
ctggaggcc cttccgtgtt cctgttccc ccaaagccca aggacaccct gatgatcagc    780
cggacccccg aagtgacctg cgtggtggtg gatgtgtccc acgaggaccc tgaagtgaag   840
ttcaattggt acgtggacgg cgtggaagtg cacaacgcca agaccaagcc tagagaggaa   900
cagtacaaca gcacctaccg ggtggtgtcc gtgctgacag tgctgcacca ggactggctg   960
aacggcaaag agtacaagtg caaggtgtcc aacaaggccc tgcctgcccc catcgagaaa  1020
accatcagca aggccaaggg ccagccccgc gaacccagg tgtacacact gcccccaagc  1080
agggacgagc tgaccaagaa ccaggtgtcc ctgacctgtc tcgtgaaagg cttctacccc  1140
tccgatatcg ccgtggaatg ggagagcaac ggccagccg agaacaacta caagaccacc  1200
cccctgtgc tggacagcga cggctcattc ttcctgtaca gcaagctgac cgtcgacaag  1260
tccccggtgg cagcagggcaa cgtgttcagc tgcagcgtga tgcacgaggc cctgcacaac  1320
cactacaccc agaagtccct gagcctgagc cctggcaag                         1359

SEQ ID NO: 420          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 420
cagtctgttc tgacacagcc tccatctgtg tctggcgccc tggacagag agtgaccatc     60
agctgtacag gcagcagctc caatatcgga gccggctatg acgtgcactg gtatcagcag   120
ctgcctggca cagcccctaa actgctgatc tacggcaaca gcaaccagacc cagcggctac   180
cccgatagat tttccggctc taagagcggc acaagcgcca gcctggctat tactggactg   240
caggccgagg acgaggccga ctactactgt cagagctacg ccggcatcaa cccctacgtg   300
gtgtttggcg gaggcaccaa gctgaccgtt ctaggccagc ctaaagccgc ccctagcgtg   360
accctgttcc ctccaagcag cgaggaactg caggccaaca aggccaccct cgtgtgcctg   420
atcagcgact ctatcctgg cgccgtgacc gtggcctgga aggccgatag ctcctcctgtg   480
```

```
aaggccggcg tggaaaccac caccccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c              651

SEQ ID NO: 421          moltype = AA   length = 123
FEATURE                 Location/Qualifiers
REGION                  1..123
                        note = antibody sequence
source                  1..123
                        mol_type = protein
                        organism = synthetic construct
SEQUENCE: 421
EVQLLESGGG LVQPGGSLRL SCAASGFDFS SYEMNWVRQA PGKGLEWVSG ISWNSGWIGY     60
ADSVKGRFTI SRDNSKNTLY LQMNSLRAED TAVYYCARSG YSSSWFDPDF DYWGQGTLVT    120
VSS                                                                  123

SEQ ID NO: 422          moltype = AA   length = 5
FEATURE                 Location/Qualifiers
REGION                  1..5
                        note = antibody sequence
source                  1..5
                        mol_type = protein
                        organism = synthetic construct
SEQUENCE: 422
SYEMN                                                                  5

SEQ ID NO: 423          moltype = AA   length = 17
FEATURE                 Location/Qualifiers
REGION                  1..17
                        note = antibody sequence
source                  1..17
                        mol_type = protein
                        organism = synthetic construct
SEQUENCE: 423
GISWNSGWIG YADSVKG                                                    17

SEQ ID NO: 424          moltype = AA   length = 14
FEATURE                 Location/Qualifiers
REGION                  1..14
                        note = antibody sequence
source                  1..14
                        mol_type = protein
                        organism = synthetic construct
SEQUENCE: 424
SGYSSSWFDP DFDY                                                       14

SEQ ID NO: 425          moltype = AA   length = 111
FEATURE                 Location/Qualifiers
REGION                  1..111
                        note = antibody sequence
source                  1..111
                        mol_type = protein
                        organism = synthetic construct
SEQUENCE: 425
QSVLTQPPSV SGAPGQRVTI SCTGSSSNIG AGYDVHWYQQ LPGTAPKLLI YGNSNRPSGV     60
PDRFSGSKSG TSASLAITGL QAEDEADYYC QSYAGPNPYV VFGGGTKLTV L              111

SEQ ID NO: 426          moltype = AA   length = 14
FEATURE                 Location/Qualifiers
REGION                  1..14
                        note = antibody sequence
source                  1..14
                        mol_type = protein
                        organism = synthetic construct
SEQUENCE: 426
TGSSSNIGAG YDVH                                                       14

SEQ ID NO: 427          moltype = AA   length = 7
FEATURE                 Location/Qualifiers
REGION                  1..7
                        note = antibody sequence
source                  1..7
                        mol_type = protein
                        organism = synthetic construct
SEQUENCE: 427
GNSNRPS                                                                7

SEQ ID NO: 428          moltype = AA   length = 11
FEATURE                 Location/Qualifiers
```

```
REGION                  1..11
                        note = antibody sequence
source                  1..11
                        mol_type = protein
                        organism = synthetic construct
SEQUENCE: 428
QSYAGPNPYV V                                                               11

SEQ ID NO: 429          moltype = DNA  length = 369
FEATURE                 Location/Qualifiers
misc_feature            1..369
                        note = antibody sequence
source                  1..369
                        mol_type = other DNA
                        organism = synthetic construct
SEQUENCE: 429
gaagttcagc tgctggaatc tggcggcgga ctggttcaac ctggcggatc tctgagactg          60
agctgtgccg ccagcggctt cgatttcagc agctacgaga tgaactgggt ccgacaggcc         120
cctggcaaag gccttgaatg ggtgtccggc atcagctgga atagcggctg gatcggctac         180
gccgatagcg tgaagggcag attcaccatc agcgggaca cagcaagaa cacctgtac            240
ctgcagatga acagcctgag agccgaggac accgccgtgt actactgtgc cagaagcggc         300
tacagcagct cttggtttga ccccgacttc gactattggg gccagggcac actggtgaca         360
gtctcttca                                                                 369

SEQ ID NO: 430          moltype = DNA  length = 15
FEATURE                 Location/Qualifiers
misc_feature            1..15
                        note = antibody sequence
source                  1..15
                        mol_type = other DNA
                        organism = synthetic construct
SEQUENCE: 430
agctacgaga tgaac                                                           15

SEQ ID NO: 431          moltype = DNA  length = 51
FEATURE                 Location/Qualifiers
misc_feature            1..51
                        note = antibody sequence
source                  1..51
                        mol_type = other DNA
                        organism = synthetic construct
SEQUENCE: 431
ggcatcagct ggaatagcgg ctggatcggc tacgccgata gcgtgaaggg c                   51

SEQ ID NO: 432          moltype = DNA  length = 42
FEATURE                 Location/Qualifiers
misc_feature            1..42
                        note = antibody sequence
source                  1..42
                        mol_type = other DNA
                        organism = synthetic construct
SEQUENCE: 432
agcggctaca gcagctcttg gtttgacccc gacttcgact at                             42

SEQ ID NO: 433          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 433
cagtctgttc tgacacagcc tccatctgtg tctggcgccc ctggacagag agtgaccatc          60
agctacacag gcagcagctc caatatcgga gccggctatg acgtgcactg gtatcagcag         120
ctgcctggca gcccctaa actgctgatc tacggcaaca gcaacagacc cagcggcgtg           180
cccgatagat tttccggctc taagagcggc acaagcgcca gctggctat tactggactg          240
caggccgagg acgaggccga ctactactgt cagtcttacg ctggccccaa tccttacgtg         300
gtgtttggcg gcggaacaaa gctgaccgtt cta                                      333

SEQ ID NO: 434          moltype = DNA  length = 42
FEATURE                 Location/Qualifiers
misc_feature            1..42
                        note = antibody sequence
source                  1..42
                        mol_type = other DNA
                        organism = synthetic construct
SEQUENCE: 434
acaggcagca gctccaatat cggagccggc tatgacgtgc ac                             42
```

```
SEQ ID NO: 435          moltype = DNA   length = 21
FEATURE                 Location/Qualifiers
misc_feature            1..21
                        note = antibody sequence
source                  1..21
                        mol_type = other DNA
                        organism = synthetic construct
SEQUENCE: 435
ggcaacagca acagacccag c                                                21

SEQ ID NO: 436          moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 436
cagtcttacg ctggccccaa tccttacgtg gtg                                   33

SEQ ID NO: 437          moltype = AA   length = 453
FEATURE                 Location/Qualifiers
REGION                  1..453
                        note = antibody sequence
source                  1..453
                        mol_type = protein
                        organism = synthetic construct
SEQUENCE: 437
EVQLLESGGG LVQPGGSLRL SCAASGFDFS SYEMNWVRQA PGKGLEWVSG ISWNSGWIGY      60
ADSVKGRFTI SRDNSKNTLY LQMNSLRAED TAVYYCARSG YSSSWFDPDF DYWGQGTLVT     120
VSSASTKGPS VFPLAPSSKS TSGGTAALGC LVKDYFPEPV TVSWNSGALT SGVHTFPAVL     180
QSSGLYSLSS VVTVPSSSLG TQTYICNVNH KPSNTKVDKK VEPKSCDKTH TCPPCPAPEL     240
LGGPSVFLFP PKPKDTLMIS RTPEVTCVVV DVSHEDPEVK FNWYVDGVEV HNAKTKPREE     300
QYNSTYRVVS VLTVLHQDWL NGKEYKCKVS NKALPAPIEK TISKAKGQPR EPQVYTLPPS     360
RDELTKNQVS LTCLVKGFYP SDIAVEWESN GQPENNYKTT PPVLDSDGSF FLYSKLTVDK     420
SRWQQGNVFS CSVMHEALHN HYTQKSLSLS PGK                                  453

SEQ ID NO: 438          moltype = AA   length = 217
FEATURE                 Location/Qualifiers
REGION                  1..217
                        note = antibody sequence
source                  1..217
                        mol_type = protein
                        organism = synthetic construct
SEQUENCE: 438
QSVLTQPPSV SGAPGQRVTI SCTGSSSNIG AGYDVHWYQQ LPGTAPKLLI YGNSNRPSGV      60
PDRFSGSKSG TSASLAITGL QAEDEADYYC QSYAGPNPYV VFGGGTKLTV LGQPKAAPSV     120
TLFPPSSEEL QANKATLVCL ISDFYPGAVT VAWKADSSPV KAGVETTTPS KQSNNKYAAS     180
SYLSLTPEQW KSHRSYSCQV THEGSTVEKT VAPTECS                              217

SEQ ID NO: 439          moltype = DNA   length = 1359
FEATURE                 Location/Qualifiers
misc_feature            1..1359
                        note = antibody sequence
source                  1..1359
                        mol_type = other DNA
                        organism = synthetic construct
SEQUENCE: 439
gaagttcagc tgctggaatc tggcggcgga ctggttcaac ctggcggatc tctgagactg      60
agctgtgccg ccagcggctt cgatttcagc agctacgaga tgaactgggt ccgacaggcc     120
cctggcaaag gccttgaatg ggtgtccggg atcagctgga atagcggctg gatcggctac     180
gccgatagcg tgaagggcag attcaccatc agcgggaca cagcaagaa caccctgtac       240
ctgcagatga cagcctgag agccgaggac accgccgtgt actactgtgc cagaagcggc     300
tacagcagct cttggtttga ccccgacttc gactattgga gccagggcac actggtgacc     360
gtctcttcag ccagcaccaa gggcccagc gtgttcccc tggcccctag cagcaagagc       420
acatctggcg gaacagccgc cctgggctgc ctcgtgaagg actactttcc cgagcccgtg     480
accgtgtcct ggaactctgg cgctctgaca agcggcgtgc acacctttcc agccgtgctg     540
cagagcagcg gcctgtactc tctgagcagc gtcgtgacag tgcccagcag ctctctgggc     600
acccagacct acatctgcaa cgtgaaccac aagcccagca acaccaaggt ggacaagaag     660
gtggaaccca gagctgcgga caagacccac acctgtcccc cttgtcctgc ccccgaactg     720
ctgggaggcc cttccgtgtt cctgttcccc ccaaagccca aggacaccct gatgatcagc     780
cggaccccg aagtgacctg cgtggtggtg gatgtgtccc acgaggaccc tgaagtgaag     840
ttcaattggt acgtggacgg cgtggaagtg cacaacgcca agaccaagcc tagagaggaa     900
cagtacaaca gcacctaccg ggtggtgtcc gtgctgacag tgctgcacca ggactggctg     960
aacggcaaag agtacaagtg caaggtgtcc aacaaggccc tgcctgcccc catcgagaaa     1020
accatcagca aggccaaggg ccagccccgc gaacccagg tgtacacact gcccccaagc     1080
agggacgagc tgaccaagaa ccaggtgtcc ctgacctgtc tcgtgaaagg cttctacccc     1140
tccgatatcg ccgtggaatg ggagagcaac ggccagccg agaacaacta caagaccacc     1200
cccccctgtg tggacagcga cggctcattc ttcctgtaca gcaagctgac cgtggacaag     1260
```

```
tcccggtggc agcagggcaa cgtgttcagc tgcagcgtga tgcacgaggc cctgcacaac   1320
cactcaccc agaagtccct gagcctgagc cctggcaag                           1359
```

SEQ ID NO: 440          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 440
```
cagtctgttc tgacacagcc tccatctgtg tctggcgccc ctggacagag agtgaccatc   60
agctgtacag gcagcagctc caatatcgga gccggctatg acgtgcactg gtatcagcag   120
ctgcctggca cagccccta actgctgatc tacggcaaca gcaacagacc cagcggctg    180
cccgatagat tttccggctc taagagcggc acaagcgcca gcctggctat tactggactg   240
caggccgagg acgaggccga ctactactgt cagtcttacg ctggccccaa tccttacgtg   300
gtgtttggcg gcggaacaaa gctgaccgtt ctaggccagc ctaaagccgc ccctagcgtg   360
accctgttcc ctccaagcag cgaggaactg caggccaaca ggccacccct cgtgtgctg   420
atcagcgact tctatcctgg cgccgtgacc gtggcctgga aggccgatag ctctcctgtg   480
aaggccggct ggaaaccac cacccctagc aagcagagca caacaaata cgccgccagc   540
agctacctga gcctgacccc cgagcagtgg aagtcccaca gatcctacag ctgccaagtg   600
acccacgagg gcagcaccgt ggaaaagaca gtggccccta ccgagtgcag c           651
```

SEQ ID NO: 441          moltype = AA  length = 123
FEATURE                 Location/Qualifiers
REGION                  1..123
                        note = antibody sequence
source                  1..123
                        mol_type = protein
                        organism = synthetic construct
SEQUENCE: 441
```
EVQLLESGGG LVQPGGSLRL SCAASGFDFS SYEMNWVRQA PGKGLEWVSG ISWNSGWIDY   60
ADSVKGRFTI SRDNSKNTLY LQMNSLRAED TAVYYCARSG YSSSWFDPDF DYWGQGTLVT   120
VSS                                                                123
```

SEQ ID NO: 442          moltype = AA  length = 5
FEATURE                 Location/Qualifiers
REGION                  1..5
                        note = antibody sequence
source                  1..5
                        mol_type = protein
                        organism = synthetic construct
SEQUENCE: 442
SYEMN                                                              5

SEQ ID NO: 443          moltype = AA  length = 17
FEATURE                 Location/Qualifiers
REGION                  1..17
                        note = antibody sequence
source                  1..17
                        mol_type = protein
                        organism = synthetic construct
SEQUENCE: 443
GISWNSGWID YADSVKG                                                 17

SEQ ID NO: 444          moltype = AA  length = 14
FEATURE                 Location/Qualifiers
REGION                  1..14
                        note = antibody sequence
source                  1..14
                        mol_type = protein
                        organism = synthetic construct
SEQUENCE: 444
SGYSSSWFDP DFDY                                                    14

SEQ ID NO: 445          moltype = AA  length = 111
FEATURE                 Location/Qualifiers
REGION                  1..111
                        note = antibody sequence
source                  1..111
                        mol_type = protein
                        organism = synthetic construct
SEQUENCE: 445
```
QSVLTQPPSV SGAPGQRVTI SCTGSSSNIG AGYDVHWYQQ LPGTAPKLLI YGNSNRPSGV   60
PDRFSGSKSG TSASLAITGL QAEDEADYYC QSYAGPNPYV VFGGGTKLTV L            111
```

SEQ ID NO: 446          moltype = AA  length = 14
FEATURE                 Location/Qualifiers
REGION                  1..14

```
                        note = antibody sequence
source                  1..14
                        mol_type = protein
                        organism = synthetic construct
SEQUENCE: 446
TGSSSNIGAG YDVH                                                         14

SEQ ID NO: 447          moltype = AA   length = 7
FEATURE                 Location/Qualifiers
REGION                  1..7
                        note = antibody sequence
source                  1..7
                        mol_type = protein
                        organism = synthetic construct
SEQUENCE: 447
GNSNRPS                                                                 7

SEQ ID NO: 448          moltype = AA   length = 11
FEATURE                 Location/Qualifiers
REGION                  1..11
                        note = antibody sequence
source                  1..11
                        mol_type = protein
                        organism = synthetic construct
SEQUENCE: 448
QSYAGPNPYV V                                                            11

SEQ ID NO: 449          moltype = DNA   length = 369
FEATURE                 Location/Qualifiers
misc_feature            1..369
                        note = antibody sequence
source                  1..369
                        mol_type = other DNA
                        organism = synthetic construct
SEQUENCE: 449
gaagttcagc tgctggaatc tggcggcgga ctggttcaac ctgcggatct tctgagactg        60
agctgtgccg ccagcggctt cgatttcagc agctacgaga tgaactgggt ccgacaggcc       120
cctggcaaag gccttgaatg ggtgtccggc atcagctgga atagcggctg gatcgactac       180
gccgacacgc tgaagggcag attcaccatc agccggacaa acagcaagaa caccctgtac       240
ctgcagatga acagcctgag agccgaggac accgccgtgt actactgtgc cagaagcggc       300
tacagcagct cttggtttga ccccgacttc gactattggg ccagggcac actggtcaca        360
gtctcttca                                                               369

SEQ ID NO: 450          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 450
agctacgaga tgaac                                                        15

SEQ ID NO: 451          moltype = DNA   length = 51
FEATURE                 Location/Qualifiers
misc_feature            1..51
                        note = antibody sequence
source                  1..51
                        mol_type = other DNA
                        organism = synthetic construct
SEQUENCE: 451
ggcatcagct ggaatagcgg ctggatcgac tacgccgaca gcgtgaaggg c                51

SEQ ID NO: 452          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 452
agcggctaca gcagctcttg gtttgacccc gacttcgact at                          42

SEQ ID NO: 453          moltype = DNA   length = 333
FEATURE                 Location/Qualifiers
misc_feature            1..333
                        note = antibody sequence
source                  1..333
                        mol_type = other DNA
```

```
                        organism = synthetic construct
SEQUENCE: 453
cagtctgttc tgacacagcc tccatctgtg tctggcgccc ctggacagag agtgaccatc    60
agctgtacag gcagcagctc caatatcgga gccggctatg acgtgcactg gtatcagcag   120
ctgcctggca cagcccctaa actgctgatc tacggcaaca gcaacagacc cagcggcgtg   180
cccgatagat tttccggctc taagagcggc acaagcgcca gcctggctat tactggactg   240
caggccgagg acgaggccga ctactactgt cagtcttacg ctggccccaa tccttacgtg   300
gtgtttggcg gcggaacaaa gctgaccgtt cta                                333

SEQ ID NO: 454          moltype = DNA  length = 42
FEATURE                 Location/Qualifiers
misc_feature            1..42
                        note = antibody sequence
source                  1..42
                        mol_type = other DNA
                        organism = synthetic construct
SEQUENCE: 454
acaggcagca gctccaatat cggagccggc tatgacgtgc ac                       42

SEQ ID NO: 455          moltype = DNA  length = 21
FEATURE                 Location/Qualifiers
misc_feature            1..21
                        note = antibody sequence
source                  1..21
                        mol_type = other DNA
                        organism = synthetic construct
SEQUENCE: 455
ggcaacagca acagacccag c                                              21

SEQ ID NO: 456          moltype = DNA  length = 33
FEATURE                 Location/Qualifiers
misc_feature            1..33
                        note = antibody sequence
source                  1..33
                        mol_type = other DNA
                        organism = synthetic construct
SEQUENCE: 456
cagtcttacg ctggccccaa tccttacgtg gtg                                 33

SEQ ID NO: 457          moltype = AA  length = 453
FEATURE                 Location/Qualifiers
REGION                  1..453
                        note = antibody sequence
source                  1..453
                        mol_type = protein
                        organism = synthetic construct
SEQUENCE: 457
EVQLLESGGG LVQPGGSLRL SCAASGFDFS SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 458          moltype = AA  length = 217
FEATURE                 Location/Qualifiers
REGION                  1..217
                        note = antibody sequence
source                  1..217
                        mol_type = protein
                        organism = synthetic construct
SEQUENCE: 458
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC QSYAGPNPYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 459          moltype = DNA  length = 1359
FEATURE                 Location/Qualifiers
misc_feature            1..1359
                        note = antibody sequence
source                  1..1359
                        mol_type = other DNA
                        organism = synthetic construct
SEQUENCE: 459
gaagttcagc tgctggaatc tggcggcgga ctggttcaac tggcggatc tctgagactg     60
agctgtgccg ccagcggctt cgatttcagc agctacgaga tgaactgggt ccgacaggcc   120
```

```
cctggcaaag gccttgaatg ggtgtccggc atcagctgga atagcggctg gatcgactac    180
gccgacagcg tgaagggcag attcaccatc agccgggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggccccagc gtgttccctc tggccccta g cagcaagagc    420
acatctggcg gaacagccgc cctgggctgc ctcgtgaagg actactttcc cgagcccgtg    480
accgtgtcct ggaactctgg cgctctgaca agcggcgtgc acacctttcc agccgtgctg    540
cagagcagcg gcctgtactc tctgagcagc gtcgtgacag tgcccagcag ctctctgggc    600
acccagacct acatctgcaa cgtgaaccac aagcccagca acaccaaggt ggacaagaag    660
gtggaaccca gagctgcgca caagaccacc acctgtcccc cttgtcctgc ccccgaactg    720
ctgggaggcc cttccgtgtt cctgttcccc ccaaagccca aggacaccct gatgatcagc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg t gtacacact gcccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagacccc    1200
cccctgtgc t ggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                          1359

SEQ ID NO: 460         moltype = DNA  length = 651
FEATURE                Location/Qualifiers
misc_feature           1..651
                       note = antibody sequence
source                 1..651
                       mol_type = other DNA
                       organism = synthetic construct
SEQUENCE: 460
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca cagcccctaa actgctgatc tacggcaaca gcaacagacc cagcggcgtg    180
cccgatagat tttccggctc taagagcggc acaagcgcca gcctggctat tactggaactg    240
caggccgagg acgaggccga ctactactgt cagtcttacg ctggcccaa t tccttacgtg    300
gtgtttggcg gcggaaacaa agctgaccgt t ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccgagg tggaaaccac cacccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c              651

SEQ ID NO: 461         moltype = AA  length = 123
FEATURE                Location/Qualifiers
REGION                 1..123
                       note = antibody sequence
source                 1..123
                       mol_type = protein
                       organism = synthetic construct
SEQUENCE: 461
EVQLLESGGG LVQPGGSLRL SCAASGFTFD SYEMNWVRQA PGKGLEWVSG ISWNSGWIDY     60
ADSVKGRFTI SRDNSKNTLY LQMNSLRAED TAVYYCARSG YSSSWFDPDF DYWGQGTLVT    120
VSS                                                                  123

SEQ ID NO: 462         moltype = AA  length = 5
FEATURE                Location/Qualifiers
REGION                 1..5
                       note = antibody sequence
source                 1..5
                       mol_type = protein
                       organism = synthetic construct
SEQUENCE: 462
SYEMN                                                                  5

SEQ ID NO: 463         moltype = AA  length = 17
FEATURE                Location/Qualifiers
REGION                 1..17
                       note = antibody sequence
source                 1..17
                       mol_type = protein
                       organism = synthetic construct
SEQUENCE: 463
GISWNSGWID YADSVKG                                                    17

SEQ ID NO: 464         moltype = AA  length = 14
FEATURE                Location/Qualifiers
REGION                 1..14
                       note = antibody sequence
source                 1..14
```

```
                        mol_type = protein
                        organism = synthetic construct
SEQUENCE: 464
SGYSSSWFDP DFDY                                                        14

SEQ ID NO: 465          moltype = AA   length = 111
FEATURE                 Location/Qualifiers
REGION                  1..111
                        note = antibody sequence
source                  1..111
                        mol_type = protein
                        organism = synthetic construct
SEQUENCE: 465
QSVLTQPPSV SGAPGQRVTI SCTGSSSNIG AGYDVHWYQQ LPGTAPKLLI YGNSNRPSGV       60
PDRFSGSKSG TSASLAITGL QAEDEADYYC QSYAGPNPYV VFGGGTKLTV L               111

SEQ ID NO: 466          moltype = AA   length = 14
FEATURE                 Location/Qualifiers
REGION                  1..14
                        note = antibody sequence
source                  1..14
                        mol_type = protein
                        organism = synthetic construct
SEQUENCE: 466
TGSSSNIGAG YDVH                                                        14

SEQ ID NO: 467          moltype = AA   length = 7
FEATURE                 Location/Qualifiers
REGION                  1..7
                        note = antibody sequence
source                  1..7
                        mol_type = protein
                        organism = synthetic construct
SEQUENCE: 467
GNSNRPS                                                                7

SEQ ID NO: 468          moltype = AA   length = 11
FEATURE                 Location/Qualifiers
REGION                  1..11
                        note = antibody sequence
source                  1..11
                        mol_type = protein
                        organism = synthetic construct
SEQUENCE: 468
QSYAGPNPYV V                                                           11

SEQ ID NO: 469          moltype = DNA   length = 369
FEATURE                 Location/Qualifiers
misc_feature            1..369
                        note = antibody sequence
source                  1..369
                        mol_type = other DNA
                        organism = synthetic construct
SEQUENCE: 469
gaagttcagc tgctggaatc tggcggcgga ctggttcaac ctggcggatc tctgagactg      60
agctgtgccg ccagcggctt caccttcgat agctacgaga tgaactgggt ccgacaggcc     120
cctggcaaag gccttgaatg ggtgtccggc atcagctgga atagcggctg gatcgactac     180
gccgacagcg tgaagggcag attcaccatc agcgggaca acagcaagaa cacccctgtac     240
ctgcagatga acagcctgag agccgaggac accgccgtgt actactgtgc cagaagcggc     300
tacagcagct cttggtttga ccccgacttc gactattggg gccagggcac actggtcaca     360
gtctcttca                                                             369

SEQ ID NO: 470          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 470
agctacgaga tgaac                                                       15

SEQ ID NO: 471          moltype = DNA   length = 51
FEATURE                 Location/Qualifiers
misc_feature            1..51
                        note = antibody sequence
source                  1..51
                        mol_type = other DNA
                        organism = synthetic construct
```

```
SEQUENCE: 471
ggcatcagct ggaatagcgg ctggatcgac tacgccgaca gcgtgaaggg c             51

SEQ ID NO: 472              moltype = DNA  length = 42
FEATURE                     Location/Qualifiers
misc_feature                1..42
                            note = antibody sequence
source                      1..42
                            mol_type = other DNA
                            organism = synthetic construct
SEQUENCE: 472
agcggctaca gcagctcttg gtttgacccc gacttcgact at                       42

SEQ ID NO: 473              moltype = DNA  length = 333
FEATURE                     Location/Qualifiers
misc_feature                1..333
                            note = antibody sequence
source                      1..333
                            mol_type = other DNA
                            organism = synthetic construct
SEQUENCE: 473
cagtctgttc tgacacagcc tccatctgtg tctggcgccc ctggacagag agtgaccatc    60
agctgtacag gcagcagctc caatatcgga gccggctatg acgtgcactg gtatcagcag   120
ctgcctggca gccccctaa actgctgatc tacggcaaca gcaacagacc cagcggcgtg    180
cccgatagat tttccggctc taagagcggc acaagcgcca gctggctat tactggactg    240
caggccgagg acgaggccga ctactactgt cagtcttacg ctggccccaa tccttacgtg   300
gtgtttggcg gcggaacaaa gctgaccgtt cta                                333

SEQ ID NO: 474              moltype = DNA  length = 42
FEATURE                     Location/Qualifiers
misc_feature                1..42
                            note = antibody sequence
source                      1..42
                            mol_type = other DNA
                            organism = synthetic construct
SEQUENCE: 474
acaggcagca gctccaatat cggagccggc tatgacgtgc ac                       42

SEQ ID NO: 475              moltype = DNA  length = 21
FEATURE                     Location/Qualifiers
misc_feature                1..21
                            note = antibody sequence
source                      1..21
                            mol_type = other DNA
                            organism = synthetic construct
SEQUENCE: 475
ggcaacagca acagacccag c                                              21

SEQ ID NO: 476              moltype = DNA  length = 33
FEATURE                     Location/Qualifiers
misc_feature                1..33
                            note = antibody sequence
source                      1..33
                            mol_type = other DNA
                            organism = synthetic construct
SEQUENCE: 476
cagtcttacg ctggccccaa tccttacgtg gtg                                 33

SEQ ID NO: 477              moltype = AA  length = 453
FEATURE                     Location/Qualifiers
REGION                      1..453
                            note = antibody sequence
source                      1..453
                            mol_type = protein
                            organism = synthetic construct
SEQUENCE: 477
EVQLLESGGG LVQPGGSLRL SCAASGFTFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 478              moltype = AA  length = 217
FEATURE                     Location/Qualifiers
REGION                      1..217
                            note = antibody sequence
```

```
source                          1..217
                                mol_type = protein
                                organism = synthetic construct
SEQUENCE: 478
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC QSYAGPNPYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 479                  moltype = DNA  length = 1359
FEATURE                         Location/Qualifiers
misc_feature                    1..1359
                                note = antibody sequence
source                          1..1359
                                mol_type = other DNA
                                organism = synthetic construct
SEQUENCE: 479
gaagttcagc tgctggaatc tggcggcgga ctggttcaac ctggcggatc tctgagactg     60
agctgtgccg ccagcggctt caccttcgat agctacgaga tgaactgggt ccgacaggcc    120
cctggcaaag gccttgaatg ggtgtccggc atcagctgga atagcggctg gatcgactac    180
gccgacagcg tgaagggcag attcaccatc agccgggaca cagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggccccagc gtgttccctc tggcccctag cagcaagagc    420
acatctggcg gaacagccgc cctgggctgc ctcgtgaagg actactttcc cgagcccgtg    480
accgtgtcct ggaactctgg cgctctgaca agcggcgtgc actacctttc agccgtgctg    540
cagagcagcg gcctgtactc tctgagcagc gtcgtgacag tgcccagcag ctctctgggc    600
acccagacct acatctgcaa cgtgaaccac aagcccagca caccaaggt ggacaagaag    660
gtggaaccca gagctgcga caagacccac acctgtcccc cttgtcctgc ccccgaactg    720
ctgggaggcc cttccgtgtt cctgttcccc caaagtgc aggacaccct gatgatcagc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgccc catcgagaaa   1020
accatcagca aggccaaggg ccagcccgc gaaccccagg tgtacacact gccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
cccccctgtg tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                         1359

SEQ ID NO: 480                  moltype = DNA  length = 651
FEATURE                         Location/Qualifiers
misc_feature                    1..651
                                note = antibody sequence
source                          1..651
                                mol_type = other DNA
                                organism = synthetic construct
SEQUENCE: 480
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca cagcccctaa actgctgatc tacggcaaca gcaacagacc cagcggcgtg    180
cccgatagat tttccggctc taagagcggc acaagcgcca gcctggctat tactggactg    240
caggccgagg acgaggccga ctactactgt cagtcttacg ctggcccaa tccttacgtg    300
gtgtttggcg gcggaaacaa gctgaccgtt ctaggccagc ctaaagccgc ccctagcgtg    360
accctgttcc ctccaagcag cgaggaactg caggccaaca aggccaccct cgtgtgcctg    420
atcagcgact ctatcctgg cgccgtgacc gtggcctgga aggccgatag ctctcctgtg    480
aaggccggct ggaaaccac caccctagc aagcagagca caacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c            651

SEQ ID NO: 481                  moltype = AA  length = 123
FEATURE                         Location/Qualifiers
REGION                          1..123
                                note = antibody sequence
source                          1..123
                                mol_type = protein
                                organism = synthetic construct
SEQUENCE: 481
EVQLLESGGG LVQPGGSLRL SCAASGFDFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSS                                                                 123

SEQ ID NO: 482                  moltype = AA  length = 5
FEATURE                         Location/Qualifiers
REGION                          1..5
                                note = antibody sequence
source                          1..5
                                mol_type = protein
```

```
                        organism = synthetic construct
SEQUENCE: 482
SYEMN                                                                   5

SEQ ID NO: 483          moltype = AA  length = 17
FEATURE                 Location/Qualifiers
REGION                  1..17
                        note = antibody sequence
source                  1..17
                        mol_type = protein
                        organism = synthetic construct
SEQUENCE: 483
GISWNSGWID YADSVKG                                                     17

SEQ ID NO: 484          moltype = AA  length = 14
FEATURE                 Location/Qualifiers
REGION                  1..14
                        note = antibody sequence
source                  1..14
                        mol_type = protein
                        organism = synthetic construct
SEQUENCE: 484
SGYSSSWFDP DFDY                                                        14

SEQ ID NO: 485          moltype = AA  length = 111
FEATURE                 Location/Qualifiers
REGION                  1..111
                        note = antibody sequence
source                  1..111
                        mol_type = protein
                        organism = synthetic construct
SEQUENCE: 485
QSVLTQPPSV SGAPGQRVTI SCTGSSSNIG AGYDVHWYQQ LPGTAPKLLI YGNSNRPSGV       60
PDRFSGSKSG TSASLAITGL QAEDEADYYC QSYAGPNPYV VFGGGTKLTV L               111

SEQ ID NO: 486          moltype = AA  length = 14
FEATURE                 Location/Qualifiers
REGION                  1..14
                        note = antibody sequence
source                  1..14
                        mol_type = protein
                        organism = synthetic construct
SEQUENCE: 486
TGSSSNIGAG YDVH                                                        14

SEQ ID NO: 487          moltype = AA  length = 7
FEATURE                 Location/Qualifiers
REGION                  1..7
                        note = antibody sequence
source                  1..7
                        mol_type = protein
                        organism = synthetic construct
SEQUENCE: 487
GNSNRPS                                                                 7

SEQ ID NO: 488          moltype = AA  length = 11
FEATURE                 Location/Qualifiers
REGION                  1..11
                        note = antibody sequence
source                  1..11
                        mol_type = protein
                        organism = synthetic construct
SEQUENCE: 488
QSYAGPNPYV V                                                           11

SEQ ID NO: 489          moltype = DNA  length = 369
FEATURE                 Location/Qualifiers
misc_feature            1..369
                        note = antibody sequence
source                  1..369
                        mol_type = other DNA
                        organism = synthetic construct
SEQUENCE: 489
gaagttcagc tgctggaatc tggcggcgga ctggttcaac ctggcggatc tctgagactg       60
agctgtgccg ccagcggctt cgacttcgat agctacgaga tgaactgggt ccgacaggcc     120
cctggcaaag ccttgaatg ggtgtccggc atcagctgga atagcggctg gatcgactac      180
gccgacagcg tgaagggcag attcaccatc agcagggaca acagcaagaa caccctgtac     240
ctgcagatga acagcctgag agccgaggac accgccgtgt actactgtgc cagaagcggc     300
tacagcagct cttggtttga ccccgacttc gactattggg gccagggcac actggtcaca     360
```

```
gtctcttca                                                            369

SEQ ID NO: 490          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 490
agctacgaga tgaac                                                     15

SEQ ID NO: 491          moltype = DNA   length = 51
FEATURE                 Location/Qualifiers
misc_feature            1..51
                        note = antibody sequence
source                  1..51
                        mol_type = other DNA
                        organism = synthetic construct
SEQUENCE: 491
ggcatcagct ggaatagcgg ctggatcgac tacgccgaca gcgtgaaggg c              51

SEQ ID NO: 492          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 492
agcggctaca gcagctcttg gtttgacccc gacttcgact at                       42

SEQ ID NO: 493          moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 493
cagtctgttc tgacacagcc tccatctgtg tctggcgccc ctggacagag agtgaccatc    60
agctgtacag gcagcagctc caatatcgga gccggctatg acgtgcactg gtatcagcag   120
ctgcctggca cagcccctaa actgctgatc tacggcaaca gcaacagacc cagcggcgtg   180
cccgatagat tttccggctc taagagcggc acaagcgcca gcctggctat tactggactg   240
caggccgagg acgaggccga ctactactgt cagtcttacg ctggccccaa tccttacgtg   300
gtgtttggcg gcggaacaaa gctgaccgtt cta                                333

SEQ ID NO: 494          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 494
acaggcagca gctccaatat cggagccggc tatgacgtgc ac                       42

SEQ ID NO: 495          moltype = DNA   length = 21
FEATURE                 Location/Qualifiers
misc_feature            1..21
                        note = antibody sequence
source                  1..21
                        mol_type = other DNA
                        organism = synthetic construct
SEQUENCE: 495
ggcaacagca acagacccag c                                              21

SEQ ID NO: 496          moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 496
cagtcttacg ctggccccaa tccttacgtg gtg                                 33

SEQ ID NO: 497          moltype = AA    length = 453
FEATURE                 Location/Qualifiers
```

```
REGION                       1..453
                             note = antibody sequence
source                       1..453
                             mol_type = protein
                             organism = synthetic construct
SEQUENCE: 497
EVQLLESGGG LVQPGGSLRL SCAASGFDFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 498               moltype = AA  length = 217
FEATURE                      Location/Qualifiers
REGION                       1..217
                             note = antibody sequence
source                       1..217
                             mol_type = protein
                             organism = synthetic construct
SEQUENCE: 498
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC QSYAGPNPYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 499               moltype = DNA  length = 1359
FEATURE                      Location/Qualifiers
misc_feature                 1..1359
                             note = antibody sequence
source                       1..1359
                             mol_type = other DNA
                             organism = synthetic construct
SEQUENCE: 499
gaagttcagc tgctggaatc tggcggcgga ctggttcaac ctggcggatc tctgagactg    60
agctgtgccg ccagcggctt cgacttcgat agctacgaga tgaactgggt ccgacaggcc   120
cctggcaaag gccttgaatg ggtgtccggc atcagctgga atagcggctg gatcgactac   180
gccgacagcg tgaagggcag attcaccatc agccggdaca acagcaagaa caccctgtac   240
ctgcagatga cagcctgag agccgaggac accgccgtgt actactgtgc cagaagcggc   300
tacagcagct cttggtttga ccccgacttc gactattggg gccagggcac actggtcaca   360
gtctcttcag ccagcaccaa gggccccagc gtgttccctc tagccaagagc acatctggcg   420
aacagccgc cctgggctgc tcgtgaagg actactttcc cgagcccgtg   480
accgtgtcct ggaactctgg cgctctgaca agcggcgtgc acacctttcc agccgtgctg   540
cagagcagcg gcctgtactc tctgagcagc gtcgtgacag tgcccagcag ctctctgggc   600
acccagacct acatctgcaa cgtgaaccac aagcccagca acaccaaggt ggacaagaag   660
gtggaaccca gagctgcga caagacccac acctgtcccc cttgtcctgc ccccgaactg   720
ctgggaggcc cttccgtgtt cctgttcccc caaagccca aggacaccct gatgatcagc   780
cggacccccg aagtgacctg cgtggtggtg gatgtgtccc acgaggaccc tgaagtgaag   840
ttcaattggt acgtggacgg cgtggaagtg cacaacgcca agaccaagcc tagagaggaa   900
cagtacaaca gcacctaccg ggtggtgtcc gtgctgacag tgctgcacca ggactggctg   960
aacggcaaag agtacaagtg caaggtgtcc aacaaggccc tgcctgcccc catcgagaaa  1020
accatcagca aggccaaggg ccagccccgc gaacccaggt gtacacact gcccccaagc  1080
agggacgagc tgaccaagaa ccaggtgtcc ctgacctgtc tcgtgaaagg cttctaccc  1140
tccgatatcg ccgtggaatg ggagagcaac ggccagcccg agaacaacta caagaccacc  1200
ccccctgtgc tggacagcga cggctcattc ttcctgtaca gcaagctgac cgtggacaag  1260
tcccggtggc agcagggcaa cgtgttcagc tgcagcgtga tgcacgaggc cctgcacaac  1320
cactacaccc agaagtccct gagcctgagc cctggcaag                         1359

SEQ ID NO: 500               moltype = DNA  length = 651
FEATURE                      Location/Qualifiers
misc_feature                 1..651
                             note = antibody sequence
source                       1..651
                             mol_type = other DNA
                             organism = synthetic construct
SEQUENCE: 500
cagtctgttc tgacacagcc tccatctgtg tctggcgccc tggacagag agtgaccatc    60
agctgtacag gcagcagctc caatatcgga gccggctatg acgtgcactg gtatcagcag   120
ctgcctggca cagcccctaa actgctgatc tacggcaaca gcaacagacc cagcggcgtg   180
cccgatagat ttttcggctc taagagcggc acaagcgcca gctggctat tactggactg   240
caggccgagg acgaggccga ctactactgt cagtcttacg ctggccccaa tccttacgtg   300
gtgtttggcg gcgggaacaa gctgaccgtt ctaggccagc ctaaagcccc cagcgtg     360
accctgttcc ctccaagcag cgaggaactg caggccaaca aggccaccct cgtgtgcctg   420
atcagcgact tctatcctgg cgccgtgacc gtggcctgga aggccgatag ctctcctgtg   480
aaggccggcg tggaaaccac caccctagc aagcagagca caacaaata cgccgccagc   540
agctacctga gcctgacccc cgagcagtgg aagtcccaca gatcctacag ctgccaagtg   600
acccacgagg gcagcaccgt ggaaaagaca gtggccccta ccgagtgcag c           651
```

```
SEQ ID NO: 501          moltype = AA  length = 123
FEATURE                 Location/Qualifiers
REGION                  1..123
                        note = antibody sequence
source                  1..123
                        mol_type = protein
                        organism = synthetic construct
SEQUENCE: 501
EVQLLESGGG LVQPGGSLRL SCAASGFTFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSS                                                                 123

SEQ ID NO: 502          moltype = AA  length = 5
FEATURE                 Location/Qualifiers
REGION                  1..5
                        note = antibody sequence
source                  1..5
                        mol_type = protein
                        organism = synthetic construct
SEQUENCE: 502
SYEMN                                                                 5

SEQ ID NO: 503          moltype = AA  length = 17
FEATURE                 Location/Qualifiers
REGION                  1..17
                        note = antibody sequence
source                  1..17
                        mol_type = protein
                        organism = synthetic construct
SEQUENCE: 503
GISWNSGWID YADSVKG                                                   17

SEQ ID NO: 504          moltype = AA  length = 14
FEATURE                 Location/Qualifiers
REGION                  1..14
                        note = antibody sequence
source                  1..14
                        mol_type = protein
                        organism = synthetic construct
SEQUENCE: 504
SGYSSSWFDP DFDY                                                      14

SEQ ID NO: 505          moltype = AA  length = 111
FEATURE                 Location/Qualifiers
REGION                  1..111
                        note = antibody sequence
source                  1..111
                        mol_type = protein
                        organism = synthetic construct
SEQUENCE: 505
QSVLTQPPSV SGAPGQRVTI SCTGSSSDIG AGYDVHWYQQ LPGTAPKLLI YGNSNRPSGV    60
PDRFSGSKSG TSASLAITGL QAEDEADYYC QSYAGINPYV VFGGGTKLTV L            111

SEQ ID NO: 506          moltype = AA  length = 14
FEATURE                 Location/Qualifiers
REGION                  1..14
                        note = antibody sequence
source                  1..14
                        mol_type = protein
                        organism = synthetic construct
SEQUENCE: 506
TGSSSDIGAG YDVH                                                      14

SEQ ID NO: 507          moltype = AA  length = 7
FEATURE                 Location/Qualifiers
REGION                  1..7
                        note = antibody sequence
source                  1..7
                        mol_type = protein
                        organism = synthetic construct
SEQUENCE: 507
GNSNRPS                                                               7

SEQ ID NO: 508          moltype = AA  length = 11
FEATURE                 Location/Qualifiers
REGION                  1..11
                        note = antibody sequence
source                  1..11
```

```
                        mol_type = protein
                        organism = synthetic construct
SEQUENCE: 508
QSYAGINPYV V                                                         11

SEQ ID NO: 509          moltype = DNA   length = 369
FEATURE                 Location/Qualifiers
misc_feature            1..369
                        note = antibody sequence
source                  1..369
                        mol_type = other DNA
                        organism = synthetic construct
SEQUENCE: 509
gaagttcagc tgctggaatc tggcggcgga ctggttcaac ctggcggatc tctgagactg    60
agctgtgccg ccagcggctt caccttcgat agctacgaga tgaactgggt ccgacaggcc   120
cctggcaaag gccttgaatg ggtgtccggc atcagctgga atagcggctg gatcgactac   180
gccgacagcg tgaagggcag attcaccatc agcgggaca cagcaagaa caccctgtac    240
ctgcagatga acagcctgag agccgaggac accgccgtgt actactgtgc cagaagcggc   300
tacagcagct cttggtttga ccccgacttc gactattggg gccagggcac actggtcaca   360
gtctcttca                                                           369

SEQ ID NO: 510          moltype = DNA   length = 15
FEATURE                 Location/Qualifiers
misc_feature            1..15
                        note = antibody sequence
source                  1..15
                        mol_type = other DNA
                        organism = synthetic construct
SEQUENCE: 510
agctacgaga tgaac                                                     15

SEQ ID NO: 511          moltype = DNA   length = 51
FEATURE                 Location/Qualifiers
misc_feature            1..51
                        note = antibody sequence
source                  1..51
                        mol_type = other DNA
                        organism = synthetic construct
SEQUENCE: 511
ggcatcagct ggaatagcgg ctggatcgac tacgccgaca gcgtgaaggg c              51

SEQ ID NO: 512          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 512
agcggctaca gcagctcttg gtttgacccc gacttcgact at                       42

SEQ ID NO: 513          moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 513
cagtctgttc tgacacagcc tccatctgtg tctggcgccc ctggacagag agtgaccatc    60
agctgtacag gcagcagctc cgatattggc gccggatacg acgtgcactg gtatcagcaa   120
ctgcctggca cagcccctaa gctgctgatc tacggcaaca gcaacagacc tagcggcgtg   180
cccgatagat tcagcggctc taagtctggc acaagcgcca gcctggccat tactggactg   240
caggccgaag atgaggccga ctactactgt cagagctacg ccggcatcaa cccctacgtg   300
gtgtttggcg gaggcaccaa gctgacagtt cta                                333

SEQ ID NO: 514          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 514
acaggcagca gctccgatat tggcgccgga tacgacgtgc ac                       42

SEQ ID NO: 515          moltype = DNA   length = 21
FEATURE                 Location/Qualifiers
misc_feature            1..21
```

```
                        note = antibody sequence
source                  1..21
                        mol_type = other DNA
                        organism = synthetic construct
SEQUENCE: 515
ggcaacagca acagacctag c                                              21

SEQ ID NO: 516          moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 516
cagagctacg ccggcatcaa ccctacgtg gtg                                  33

SEQ ID NO: 517          moltype = AA   length = 453
FEATURE                 Location/Qualifiers
REGION                  1..453
                        note = antibody sequence
source                  1..453
                        mol_type = protein
                        organism = synthetic construct
SEQUENCE: 517
EVQLLESGGG LVQPGGSLRL SCAASGFTFD SYEMNWVRQA PGKGLEWVSG ISWNSGWIDY     60
ADSVKGRFTI SRDNSKNTLY LQMNSLRAED TAVYYCARSG YSSSWFDPDF DYWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                453

SEQ ID NO: 518          moltype = AA   length = 217
FEATURE                 Location/Qualifiers
REGION                  1..217
                        note = antibody sequence
source                  1..217
                        mol_type = protein
                        organism = synthetic construct
SEQUENCE: 518
QSVLTQPPSV SGAPGQRVTI SCTGSSSDIG AGYDVHWYQQ LPGTAPKLLI YGNSNRPSGV     60
PDRFSGSKSG TSASLAITGL QAEDEADYYC QSYAGINPYV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 519          moltype = DNA   length = 1359
FEATURE                 Location/Qualifiers
misc_feature            1..1359
                        note = antibody sequence
source                  1..1359
                        mol_type = other DNA
                        organism = synthetic construct
SEQUENCE: 519
gaagttcagc tgctggaatc tggcggcgga ctggttcaac ctggcggatc tctgagactg     60
agctgtgccg ccagcggctt caccttcgat agctacgaga tgaactgggt ccgacaggcc    120
cctggcaaag gccttgaatg ggtgtccggc atcagctgga atagcggctg gatcgactac    180
gccgacagcg tgaagggcag attcaccatc agcgggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggcccagc gtgttcccc tggccctag cagcaagagc       420
acatctggcg gaacagccgc cctgggctgc ctcgtgaagg actacttcc cgagcccgtg    480
accgtgtcct ggaactctgg cgctctgaca agcggcgtgc acacctttcc agcccgtgc    540
cagagcagcg gcctgtactc tctgagcagc gtcgtgacag tgcccagcag ctctctgggc    600
acccagacct acatctgcaa cgtgaaccac aagcccagca acaccaaggt ggacaagaag    660
gtggaaccca gagctgcgac aagacccac acctgtcccc cttgtcctgc ccccgaactg    720
ctgggaggcc cttccgtgtt cctgttcccc caaagccca aggacaccct gatgatcagc    780
cggacccccg aagtgacctg cgtggtggtg gatgtgtccc acgaggccga tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaaccccagg tgtacacact gccccagagc   1080
agagaggaga tgaccaagaa ccaggtgtcc ctgacctgtc tcgtgaaagg cttctaccc    1140
tccgatatcg ccgtggaatg ggagagcaac ggccagcccg agaacaacta caagaccacc   1200
cccccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                          1359
```

```
SEQ ID NO: 520          moltype = DNA  length = 651
FEATURE                 Location/Qualifiers
misc_feature            1..651
                        note = antibody sequence
source                  1..651
                        mol_type = other DNA
                        organism = synthetic construct
SEQUENCE: 520
cagtctgttc tgacacagcc tccatctgtg tctggcgccc ctggacagag agtgaccatc    60
agctgtacag gcagcagctc cgatattggc gccggatacg acgtgcactg gtatcagcaa   120
ctgcctggca cagcccctaa gctgctgatc tacggcaaca gcaacagacc tagcggcgtg   180
cccgatagat tcagcggctc taagtctggc acaagcgcca gcctggccat tactggactg   240
caggccgaag atgaggccga ctactactgt cagagctacg ccggcatcaa cccctacgtg   300
gtgtttggcg gaggcaccaa gctgacagtt ctaggccagc cctaagcgtg   360
accctgttcc ctccaagcag cgaggaactg caggccaaca aggccaccct cgtgtgcctg   420
atcagcgact ctatcctggc cgccgtgacc gtggcctgga aggccgatag ctctcctgtg   480
aaggccggcg tggaaaccac caccccctagc aagcagagca caacaaaata cgccgccagc   540
agctacctga gcctgacccc cgagcagtgg aagtcccaca gatcctacag ctgccaagtg   600
acccacgagg gcagcaccgt ggaaaagaca gtgggccta ccgagtgcag c              651

SEQ ID NO: 521          moltype = AA  length = 123
FEATURE                 Location/Qualifiers
REGION                  1..123
                        note = antibody sequence
source                  1..123
                        mol_type = protein
                        organism = synthetic construct
SEQUENCE: 521
EVQLLESGGG LVQPGGSLRL SCAASGFDFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSS                                                                 123

SEQ ID NO: 522          moltype = AA  length = 5
FEATURE                 Location/Qualifiers
REGION                  1..5
                        note = antibody sequence
source                  1..5
                        mol_type = protein
                        organism = synthetic construct
SEQUENCE: 522
SYEMN                                                                 5

SEQ ID NO: 523          moltype = AA  length = 17
FEATURE                 Location/Qualifiers
REGION                  1..17
                        note = antibody sequence
source                  1..17
                        mol_type = protein
                        organism = synthetic construct
SEQUENCE: 523
GISWNSGWID YADSVKG                                                   17

SEQ ID NO: 524          moltype = AA  length = 14
FEATURE                 Location/Qualifiers
REGION                  1..14
                        note = antibody sequence
source                  1..14
                        mol_type = protein
                        organism = synthetic construct
SEQUENCE: 524
SGYSSSWFDP DFDY                                                      14

SEQ ID NO: 525          moltype = AA  length = 111
FEATURE                 Location/Qualifiers
REGION                  1..111
                        note = antibody sequence
source                  1..111
                        mol_type = protein
                        organism = synthetic construct
SEQUENCE: 525
QSVLTQPPSV SGAPGQRVTI SCTGSSSDIG AGYDVHWYQQ LPGTAPKLLI YGNSNRPSGV    60
PDRFSGSKSG TSASLAITGL QAEDEADYYC SSYEGINPYV VFGGGTKLTV L             111

SEQ ID NO: 526          moltype = AA  length = 14
FEATURE                 Location/Qualifiers
REGION                  1..14
                        note = antibody sequence
source                  1..14
                        mol_type = protein
```

```
SEQUENCE: 526
TGSSSDIGAG YDVH                                                         14

SEQ ID NO: 527           moltype = AA   length = 7
FEATURE                  Location/Qualifiers
REGION                   1..7
                         note = antibody sequence
source                   1..7
                         mol_type = protein
                         organism = synthetic construct
SEQUENCE: 527
GNSNRPS                                                                  7

SEQ ID NO: 528           moltype = AA   length = 11
FEATURE                  Location/Qualifiers
REGION                   1..11
                         note = antibody sequence
source                   1..11
                         mol_type = protein
                         organism = synthetic construct
SEQUENCE: 528
SSYEGINPYV V                                                            11

SEQ ID NO: 529           moltype = DNA   length = 369
FEATURE                  Location/Qualifiers
misc_feature             1..369
                         note = antibody sequence
source                   1..369
                         mol_type = other DNA
                         organism = synthetic construct
SEQUENCE: 529
gaagttcagc tgctggaatc tggcggcgga ctggttcaac tggcggatc tctgagactg        60
agctgtgccg ccagcggctt cgacttcgat agctacgaga tgaactgggt ccgacaggcc      120
cctggcaaag gccttgaatg ggtgtccggc atcagcggc atagcggctg gatcgactac       180
gccgacagcg tgaagggcag attcaccatc agccgggaca acagcaagaa caccctgtac      240
ctgcagatga acagcctgag agccgaggac accgccgtgt actactgtgc cagaagcggc      300
tacagcagct cttggtttga ccccgacttc gactattggg gccagggcac actggtcaca      360
gtctcttca                                                              369

SEQ ID NO: 530           moltype = DNA   length = 15
FEATURE                  Location/Qualifiers
misc_feature             1..15
                         note = antibody sequence
source                   1..15
                         mol_type = other DNA
                         organism = synthetic construct
SEQUENCE: 530
agctacgaga tgaac                                                        15

SEQ ID NO: 531           moltype = DNA   length = 51
FEATURE                  Location/Qualifiers
misc_feature             1..51
                         note = antibody sequence
source                   1..51
                         mol_type = other DNA
                         organism = synthetic construct
SEQUENCE: 531
ggcatcagct ggaatagcgg ctggatcgac tacgccgaca gcgtgaaggg c                51

SEQ ID NO: 532           moltype = DNA   length = 42
FEATURE                  Location/Qualifiers
misc_feature             1..42
                         note = antibody sequence
source                   1..42
                         mol_type = other DNA
                         organism = synthetic construct
SEQUENCE: 532
agcggctaca gcagctcttg gtttgacccc gacttcgact at                          42

SEQ ID NO: 533           moltype = DNA   length = 333
FEATURE                  Location/Qualifiers
misc_feature             1..333
                         note = antibody sequence
source                   1..333
                         mol_type = other DNA
                         organism = synthetic construct
SEQUENCE: 533
cagtctgttt tgacacagcc tccatctgtg tctggcgccc tggacagag agtgaccatc        60
```

```
agctgtacag gcagcagctc cgatattggc gccggatacg acgtgcactg gtatcagcaa    120
ctgcctggca cagcccctaa gctgctgatc tacggcaaca gcaacagacc tagcggcgtg    180
cccgatagat tcagcggctc taagtctggc acaagcgcca gcctggccat tactggactg    240
caggccgaag atgaggccga ctactactgc agcagctacg agggcatcaa ccccctacgtg   300
gtgtttggcg gcggaacaaa gctgaccgtt cta                                 333

SEQ ID NO: 534           moltype = DNA   length = 42
FEATURE                  Location/Qualifiers
misc_feature             1..42
                         note = antibody sequence
source                   1..42
                         mol_type = other DNA
                         organism = synthetic construct
SEQUENCE: 534
acaggcagca gctccgatat tggcgccgga tacgacgtgc ac                        42

SEQ ID NO: 535           moltype = DNA   length = 21
FEATURE                  Location/Qualifiers
misc_feature             1..21
                         note = antibody sequence
source                   1..21
                         mol_type = other DNA
                         organism = synthetic construct
SEQUENCE: 535
ggcaacagca acagacctag c                                               21

SEQ ID NO: 536           moltype = DNA   length = 33
FEATURE                  Location/Qualifiers
misc_feature             1..33
                         note = antibody sequence
source                   1..33
                         mol_type = other DNA
                         organism = synthetic construct
SEQUENCE: 536
agcagctacg agggcatcaa ccccctacgtg gtg                                 33

SEQ ID NO: 537           moltype = AA   length = 453
FEATURE                  Location/Qualifiers
REGION                   1..453
                         note = antibody sequence
source                   1..453
                         mol_type = protein
                         organism = synthetic construct
SEQUENCE: 537
EVQLLESGGG LVQPGGSLRL SCAASGFDFD SYEMNWVRQA PGKGLEWVSG ISWNSGWIDY     60
ADSVKGRFTI SRDNSKNTLY LQMNSLRAED TAVYYCARSG YSSSWFDPDF DYWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                 453

SEQ ID NO: 538           moltype = AA   length = 217
FEATURE                  Location/Qualifiers
REGION                   1..217
                         note = antibody sequence
source                   1..217
                         mol_type = protein
                         organism = synthetic construct
SEQUENCE: 538
QSVLTQPPSV SGAPGQRVTI SCTGSSSDIG AGYDVHWYQQ LPGTAPKLLI YGNSNRPSGV     60
PDRFSGSKSG TSASLAITGL QAEDEADYYC SSYEGINPYV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 539           moltype = DNA   length = 1359
FEATURE                  Location/Qualifiers
misc_feature             1..1359
                         note = antibody sequence
source                   1..1359
                         mol_type = other DNA
                         organism = synthetic construct
SEQUENCE: 539
gaagttcagc tgctggaatc tggcggcgga ctggttcaac tggcggatc tctgagactg      60
agctgtgccg ccagcggctt cgacttcgat agctacgaga tgaactgggt ccgacaggcc    120
cctggcaaag gccttgaatg ggtgtccggc atcagctgga atagcggctg gatcgactac    180
gccgacagct gaagggcag attcaccatc agccgggaca cagcaagaa caccctgtac     240
ctgcagatga acagcctgag agccgaggac accgccgtgt actactgtgc cagaagcggc    300
```

```
tacagcagct cttggtttga ccccgacttc gactattggg gccagggcac actggtcaca    360
gtctcttcag ccagcaccaa gggcccagc  gtgttcctc  tggcccctag cagcaagagc    420
acatctggcg aacagccgc  cctgggctgc tcgtgaagg  actactttcc cgagcccgtg    480
accgtgtcct ggaactctgg cgctctgaca agcggcgtgc acacctttcc agccgtgctg    540
cagagcagcg gcctgtactc tctgagcagc gtcgtgaca  tgcccagcag ctctctgggc    600
acccagacct acatctgcaa cgtgaaccac aagcccagca caccaaggt  ggacaagaag    660
gtggaaccca agagctgcga caagacccac acctgtcccc cttgtcctgc ccccgaactg    720
ctgggaggcc cttccgtgtt cctgttcccc caaagcccca aggacaccct gatgatcagc    780
cggacccccg aagtgacctg cgtggtggtg gatgtgtccc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggcaagg   ccagcccgc  gaacccccag tgtacacact gcccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
ccccctgtgc tggacagcga cggctcattc ttcctgtaca gcaagctgac cgtggacaag   1260
tcccggtggc agcagggcaa cgtgttcagc tgcagcgtga tgcacgaggc cctgcacaac   1320
cactacaccc agaagtccct gagcctgagc cctggcaag                          1359

SEQ ID NO: 540              moltype = DNA  length = 651
FEATURE                     Location/Qualifiers
misc_feature                1..651
                            note = antibody sequence
source                      1..651
                            mol_type = other DNA
                            organism = synthetic construct
SEQUENCE: 540
cagtctgttc tgacacagcc tccatctgtg tctggcgccc ctggacagag agtgaccatc     60
agctgtacag gcagcagctc cgatattggc gccggatacg acgtgcactg gtatcagcaa    120
ctgcctggca cagcccctaa gctgctgatc tacggcaaca gcaacagacc tagcggcgtg    180
cccgatagat tcagcggctc taagtctggc acaagcgcca gcctggccat tactggactg    240
caggccgaag atgaggccga ctactactgc agcagctacg agggcatcaa ccccgactgg    300
gtgtttggcg gcggaacaaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccctagc  aagcagagca caacaaata  cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c             651

SEQ ID NO: 541              moltype = AA  length = 123
FEATURE                     Location/Qualifiers
REGION                      1..123
                            note = antibody sequence
source                      1..123
                            mol_type = protein
                            organism = synthetic construct
SEQUENCE: 541
EVQLLESGGG LVQPGGSLRL SCAASGFDFS SYEMNWVRQA PGKGLEWVSG ISWNSGWIDY     60
ADSVKGRFTI SRDNSKNTLY LQMNSLRAED TAVYYCARSG YSSSWFDPDF DYWGQGTLVT    120
VSS                                                                 123

SEQ ID NO: 542              moltype = AA  length = 5
FEATURE                     Location/Qualifiers
REGION                      1..5
                            note = antibody sequence
source                      1..5
                            mol_type = protein
                            organism = synthetic construct
SEQUENCE: 542
SYEMN                                                                 5

SEQ ID NO: 543              moltype = AA  length = 17
FEATURE                     Location/Qualifiers
REGION                      1..17
                            note = antibody sequence
source                      1..17
                            mol_type = protein
                            organism = synthetic construct
SEQUENCE: 543
GISWNSGWID YADSVKG                                                   17

SEQ ID NO: 544              moltype = AA  length = 14
FEATURE                     Location/Qualifiers
REGION                      1..14
                            note = antibody sequence
source                      1..14
                            mol_type = protein
                            organism = synthetic construct
SEQUENCE: 544
```

```
SGYSSSWFDP DFDY                                                      14

SEQ ID NO: 545          moltype = AA  length = 111
FEATURE                 Location/Qualifiers
REGION                  1..111
                        note = antibody sequence
source                  1..111
                        mol_type = protein
                        organism = synthetic construct
SEQUENCE: 545
QSVLTQPPSV SGAPGQRVTI SCTGSSSNIG AGYDVHWYQQ LPGTAPKLLI YGASNRPSGV    60
PDRFSGSKSG TSASLAITGL QAEDEADYYC SSYEGPNPYV VFGGGTKLTV L             111

SEQ ID NO: 546          moltype = AA  length = 14
FEATURE                 Location/Qualifiers
REGION                  1..14
                        note = antibody sequence
source                  1..14
                        mol_type = protein
                        organism = synthetic construct
SEQUENCE: 546
TGSSSNIGAG YDVH                                                      14

SEQ ID NO: 547          moltype = AA  length = 7
FEATURE                 Location/Qualifiers
REGION                  1..7
                        note = antibody sequence
source                  1..7
                        mol_type = protein
                        organism = synthetic construct
SEQUENCE: 547
GASNRPS                                                              7

SEQ ID NO: 548          moltype = AA  length = 11
FEATURE                 Location/Qualifiers
REGION                  1..11
                        note = antibody sequence
source                  1..11
                        mol_type = protein
                        organism = synthetic construct
SEQUENCE: 548
SSYEGPNPYV V                                                         11

SEQ ID NO: 549          moltype = DNA  length = 369
FEATURE                 Location/Qualifiers
misc_feature            1..369
                        note = antibody sequence
source                  1..369
                        mol_type = other DNA
                        organism = synthetic construct
SEQUENCE: 549
gaagttcagc tgctggaatc tggcggcgga ctggttcaac ctggcggatc tctgagactg    60
agctgtgccg ccagcggctt cgatttcagc agctacgaga tgaactgggt ccgacaggcc   120
cctggcaaag gccttgaatg ggtgtccggc atcagctgga atagcggctg gatcgactac   180
gccgacagcg tgaagggcag attcaccatc agcggagaca acagcaagaa caccctgtac   240
ctgcagatga acagcctgag agccgaggac accgccgtgt actactgtgc cagaagcggc   300
tacagcagct cttggtttga ccccgacttc gactattggg gccaggcac actggtcaca    360
gtctcttca                                                           369

SEQ ID NO: 550          moltype = DNA  length = 15
FEATURE                 Location/Qualifiers
misc_feature            1..15
                        note = antibody sequence
source                  1..15
                        mol_type = other DNA
                        organism = synthetic construct
SEQUENCE: 550
agctacgaga tgaac                                                     15

SEQ ID NO: 551          moltype = DNA  length = 51
FEATURE                 Location/Qualifiers
misc_feature            1..51
                        note = antibody sequence
source                  1..51
                        mol_type = other DNA
                        organism = synthetic construct
SEQUENCE: 551
ggcatcagct ggaatagcgg ctggatcgac tacgccgaca gcgtgaaggg c              51
```

-continued

```
SEQ ID NO: 552           moltype = DNA  length = 42
FEATURE                  Location/Qualifiers
misc_feature             1..42
                         note = antibody sequence
source                   1..42
                         mol_type = other DNA
                         organism = synthetic construct
SEQUENCE: 552
agcggctaca gcagctcttg gtttgacccc gacttcgact at                          42

SEQ ID NO: 553           moltype = DNA  length = 333
FEATURE                  Location/Qualifiers
misc_feature             1..333
                         note = antibody sequence
source                   1..333
                         mol_type = other DNA
                         organism = synthetic construct
SEQUENCE: 553
cagtctgttc tgacacagcc tccatctgtg tctggcgccc ctggacagag agtgaccatc       60
agctgtacag gcagcagctc caatatcgga gccggctatg acgtgactg gtatcagcag      120
ctgcctggca cagcccctaa actgctgatc tacgcgcca gcaatagacc tagcggcgtg      180
cccgatagat tcagcggctc taagtctggc acaagcgcca gcctggccat tactggactg      240
caggccgaag atgaggccga ctactactgc agcagctacg agggccccaa tccttacgtg      300
gtgtttggcg gcggaacaaa gctgaccgtt cta                                    333

SEQ ID NO: 554           moltype = DNA  length = 42
FEATURE                  Location/Qualifiers
misc_feature             1..42
                         note = antibody sequence
source                   1..42
                         mol_type = other DNA
                         organism = synthetic construct
SEQUENCE: 554
acaggcagca gctccaatat cggagccggc tatgacgtgc ac                          42

SEQ ID NO: 555           moltype = DNA  length = 21
FEATURE                  Location/Qualifiers
misc_feature             1..21
                         note = antibody sequence
source                   1..21
                         mol_type = other DNA
                         organism = synthetic construct
SEQUENCE: 555
ggcgccagca atagacctag c                                                 21

SEQ ID NO: 556           moltype = DNA  length = 33
FEATURE                  Location/Qualifiers
misc_feature             1..33
                         note = antibody sequence
source                   1..33
                         mol_type = other DNA
                         organism = synthetic construct
SEQUENCE: 556
agcagctacg agggccccaa tccttacgtg gtg                                    33

SEQ ID NO: 557           moltype = AA  length = 453
FEATURE                  Location/Qualifiers
REGION                   1..453
                         note = antibody sequence
source                   1..453
                         mol_type = protein
                         organism = synthetic construct
SEQUENCE: 557
EVQLLESGGG LVQPGGSLRL SCAASGFDFS SYEMNWVRQA PGKGLEWVSG ISWNSGWIDY       60
ADSVKGRFTI SRDNSKNTLY LQMNSLRAED TAVYYCARSG YSSSWFDPDF DYWGQGTLVT      120
VSSASTKGPS VFPLAPSSKS TSGGTAALGC LVKDYFPEPV TVSWNSGALT SGVHTFPAVL      180
QSSGLYSLSS VVTVPSSSLG TQTYICNVNH KPSNTKVDKK VEPKSCDKTH TCPPCPAPEL      240
LGGPSVFLFP PKPKDTLMIS RTPEVTCVVV DVSHEDPEVK FNWYVDGVEV HNAKTKPREE      300
QYNSTYRVVS VLTVLHQDWL NGKEYKCKVS NKALPAPIEK TISKAKGQPR EPQVYTLPPS      360
RDELTKNQVS LTCLVKGFYP SDIAVEWESN GQPENNYKTT PPVLDSDGSF FLYSKLTVDK      420
SRWQQGNVFS CSVMHEALHN HYTQKSLSLS PGK                                   453

SEQ ID NO: 558           moltype = AA  length = 217
FEATURE                  Location/Qualifiers
REGION                   1..217
                         note = antibody sequence
source                   1..217
                         mol_type = protein
                         organism = synthetic construct
```

```
SEQUENCE: 558
QSVLTQPPSV SGAPGQRVTI SCTGSSSNIG AGYDVHWYQQ LPGTAPKLLI YGASNRPSGV    60
PDRFSGSKSG TSASLAITGL QAEDEADYYC SSYEGPNPYV VFGGGTKLTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                           217

SEQ ID NO: 559          moltype = DNA   length = 1359
FEATURE                 Location/Qualifiers
misc_feature            1..1359
                        note = antibody sequence
source                  1..1359
                        mol_type = other DNA
                        organism = synthetic construct
SEQUENCE: 559
gaagttcagc tgctggaatc tggcggcgga ctggttcaac ctggcggatc tctgagactg     60
agctgtgccg ccagcggctt cgatttcagc agctacgaga tgaactgggt ccgacaggcc    120
cctggcaaag gccttgaatg ggtgtccggc atcagctgga atagcggctg gatcgactac    180
gccgacagcg tgaagggcag attcaccatc agccgggaca acagcaagaa caccctgtac    240
ctgcagatga acagcctgag agccgaggac accgccgtgt actactgtgc cagaagcggc    300
tacagcagct cttggtttga ccccgacttc gactattggg gccagggcac actggtcaca    360
gtctcttcag ccagcaccaa gggccccagc gtgttccctc tggcccctag cagcaagagc    420
acatctggcg gaacagccgc cctgggctgc ctcgtgaagg actactttcc cgagcccgtg    480
accgtgtcct ggaactctgg cgctctgaca agcggcgtgc acacctttcc agccgtgctg    540
cagagcagcg gcctgtactc tctgagcagc gtcgtgacag tgcccagcag ctctctgggc    600
acccagacct acatctgcaa cgtgaaccac aagcccagca caccaaggt ggacaagaag     660
gtggaaccca agagctgcga caagacccac acctgtcccc cttgtcctgc ccccgaactg    720
ctggggaggcc cttccgtgtt cctgttcccc caaagcccaa ggacaccct gatgatcagc    780
cggaccccg aagtgacctg cgtggtggtg gatgtgtccc acgaggaccc tgaagtgaag     840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa   1020
accatcagca aggccaaggg ccagccccgc gaacccagg tgtacacact gcccccaagc    1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
cccctgtgc tggacagcga cggctcattc ttcctgtaca gcaagctgac cgtggacaag    1260
tcccggtggc agcagggcaa cgtgttcagc tgcagcgtga tgcacgaggc cctgcacaac   1320
cactacaccc agaagtccct gagcctgagc cctggcaag                          1359

SEQ ID NO: 560          moltype = DNA   length = 651
FEATURE                 Location/Qualifiers
misc_feature            1..651
                        note = antibody sequence
source                  1..651
                        mol_type = other DNA
                        organism = synthetic construct
SEQUENCE: 560
cagtctgttc tgacacagcc tccatctgtg tctggcgccc tggacagag agtgaccatc      60
agctgtacag gcagcagctc caatatcgga gccggctatg acgtgcactg gtatcagcag    120
ctgcctggca cagcccctaa actgctgatc tacggcgcca gcaatagacc tagcggcgtg    180
cccgatagat tcagcggctc taagtctggc acaagcgcca gcctggccat tactggactg    240
caggccgaag atgaggccga ctactactgc agcagctacg agggccccaa tccttacgtg    300
gtgtttggcg gcggaacaaa gctgaccgtt ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca acaacaaata cgccgccagc    540
agctacctga gcctgacccc cgagcagtgg aagtcccaca gatcctacag ctgccaagtg    600
acccacgagg gcagcaccgt ggaaaagaca gtggcccta ccgagtgcgc c              651

SEQ ID NO: 561          moltype = AA   length = 123
FEATURE                 Location/Qualifiers
REGION                  1..123
                        note = antibody sequence
source                  1..123
                        mol_type = protein
                        organism = synthetic construct
SEQUENCE: 561
EVQLLESGGG LVQPGGSLRL SCAASGFTFD SYEMNWVRQA PGKGLEWVSG ISWNSGWIDY    60
ADSVKGRFTI SRDNSKNTLY LQMNSLRAED TAVYYCARSG YSSSWFDPDF DYWGQGTLVT   120
VSS                                                                 123

SEQ ID NO: 562          moltype = AA   length = 5
FEATURE                 Location/Qualifiers
REGION                  1..5
                        note = antibody sequence
source                  1..5
                        mol_type = protein
                        organism = synthetic construct
SEQUENCE: 562
SYEMN                                                                 5
```

```
SEQ ID NO: 563          moltype = AA   length = 17
FEATURE                 Location/Qualifiers
REGION                  1..17
                        note = antibody sequence
source                  1..17
                        mol_type = protein
                        organism = synthetic construct
SEQUENCE: 563
GISWNSGWID YADSVKG                                                  17

SEQ ID NO: 564          moltype = AA   length = 14
FEATURE                 Location/Qualifiers
REGION                  1..14
                        note = antibody sequence
source                  1..14
                        mol_type = protein
                        organism = synthetic construct
SEQUENCE: 564
SGYSSSWFDP DFDY                                                     14

SEQ ID NO: 565          moltype = AA   length = 111
FEATURE                 Location/Qualifiers
REGION                  1..111
                        note = antibody sequence
source                  1..111
                        mol_type = protein
                        organism = synthetic construct
SEQUENCE: 565
QSVLTQPPSV SGAPGQRVTI SCTGSSSNIG AGYDVHWYQQ LPGTAPKLLI YGNSNRPSGV    60
PDRFSGSKSG TSASLAITGL QAEDEADYYC SSYAGPNPYV VFGGGTKLTV L            111

SEQ ID NO: 566          moltype = AA   length = 14
FEATURE                 Location/Qualifiers
REGION                  1..14
                        note = antibody sequence
source                  1..14
                        mol_type = protein
                        organism = synthetic construct
SEQUENCE: 566
TGSSSNIGAG YDVH                                                     14

SEQ ID NO: 567          moltype = AA   length = 7
FEATURE                 Location/Qualifiers
REGION                  1..7
                        note = antibody sequence
source                  1..7
                        mol_type = protein
                        organism = synthetic construct
SEQUENCE: 567
GNSNRPS                                                             7

SEQ ID NO: 568          moltype = AA   length = 11
FEATURE                 Location/Qualifiers
REGION                  1..11
                        note = antibody sequence
source                  1..11
                        mol_type = protein
                        organism = synthetic construct
SEQUENCE: 568
SSYAGPNPYV V                                                        11

SEQ ID NO: 569          moltype = DNA   length = 369
FEATURE                 Location/Qualifiers
misc_feature            1..369
                        note = antibody sequence
source                  1..369
                        mol_type = other DNA
                        organism = synthetic construct
SEQUENCE: 569
gaagttcagc tgctggaatc tggcggcgga ctggttcaac tggcggatc tctgagactg    60
agctgtgccg ccagcggctt caccttcgat agctacgaga tgaactgggt ccgacaggcc   120
cctggcaaag ccttgaatg ggtgtccggc atcagctgga atagcggctg gatcgactac    180
gccgacagcg tgaagggcag attcaccatc agccgggaca acagcaagaa caccctgtac   240
ctgcagatga acagcctgag agccgaggac accgccgtgt actactgtgc cagaagcggc   300
tacagcagct cttggtttga ccccgacttc gactattggg gccagggcac actggtcaca   360
gtctcttca                                                           369

SEQ ID NO: 570          moltype = DNA   length = 15
```

```
FEATURE                 Location/Qualifiers
misc_feature            1..15
                        note = antibody sequence
source                  1..15
                        mol_type = other DNA
                        organism = synthetic construct
SEQUENCE: 570
agctacgaga tgaac                                                      15

SEQ ID NO: 571          moltype = DNA   length = 51
FEATURE                 Location/Qualifiers
misc_feature            1..51
                        note = antibody sequence
source                  1..51
                        mol_type = other DNA
                        organism = synthetic construct
SEQUENCE: 571
ggcatcagct ggaatagcgg ctggatcgac tacgccgaca gcgtgaaggg c               51

SEQ ID NO: 572          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 572
agcggctaca gcagctcttg gtttgacccc gacttcgact at                        42

SEQ ID NO: 573          moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 573
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca cagcccctaa actgctgatc tacggcaaca gcaacagacc cagcggcgtg    180
cccgatagat tttccggctc taagagcggc acaagcgcca gcctggctat tactggactg    240
caggccgagg acgaggccga ctactactgt agctcttacg ctggccccaa tccttacgtg    300
gtgtttggcg gcggaacaaa gctgaccgtt cta                                 333

SEQ ID NO: 574          moltype = DNA   length = 42
FEATURE                 Location/Qualifiers
misc_feature            1..42
                        note = antibody sequence
source                  1..42
                        mol_type = other DNA
                        organism = synthetic construct
SEQUENCE: 574
acaggcagca gctccaatat cggagccggc tatgacgtgc ac                        42

SEQ ID NO: 575          moltype = DNA   length = 21
FEATURE                 Location/Qualifiers
misc_feature            1..21
                        note = antibody sequence
source                  1..21
                        mol_type = other DNA
                        organism = synthetic construct
SEQUENCE: 575
ggcaacagca acagacccag c                                               21

SEQ ID NO: 576          moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 576
agctcttacg ctggccccaa tccttacgtg gtg                                  33

SEQ ID NO: 577          moltype = AA    length = 453
FEATURE                 Location/Qualifiers
REGION                  1..453
                        note = antibody sequence
source                  1..453
```

```
                            mol_type = protein
                            organism = synthetic construct
SEQUENCE: 577
EVQLLESGGG LVQPGGSLRL SCAASGFTFD SYEMNWVRQA PGKGLEWVSG ISWNSGWIDY     60
ADSVKGRFTI SRDNSKNTLY LQMNSLRAED TAVYYCARSG YSSSWFDPDF DYWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                 453

SEQ ID NO: 578              moltype = AA  length = 217
FEATURE                     Location/Qualifiers
REGION                      1..217
                            note = antibody sequence
source                      1..217
                            mol_type = protein
                            organism = synthetic construct
SEQUENCE: 578
QSVLTQPPSV SGAPGQRVTI SCTGSSSNIG AGYDVHWYQQ LPGTAPKLLI YGNSNRPSGV     60
PDRFSGSKSG TSASLAITGL QAEDEADYYC SSYAGPNPYV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 579              moltype = DNA  length = 1359
FEATURE                     Location/Qualifiers
misc_feature                1..1359
                            note = antibody sequence
source                      1..1359
                            mol_type = other DNA
                            organism = synthetic construct
SEQUENCE: 579
gaagttcagc tgctggaatc tggcggcgga ctggttcaac ctggcggatc tctgagactg     60
agctgtgccg ccagcggctt caccttcgat agctacgaga tgaactgggt ccgacaggcc    120
cctggcaaag ccttgaatg gtgtccggc atcagctgga atagcggctg gatcgactac    180
gccgacagcg tgaagggcag attcaccatc agccgggaca cagcaagaa caccctgtac    240
ctgcagatga acagcctgag agccgaggac accgccgtgt actactgtgc cagaagcggc    300
tacagcagct cttggtttga ccccgacttc gactattgga gccagggcac actggtcaca    360
gtctcttcag ccagcaccaa gggcccagc gtgttccctc tggcccctag cagcaagagc    420
acatctggcg aacagccgc cctgggctgc ctcgtgaagg actactttcc cgagcccgtg    480
accgtgtcct ggaactctgg cgctctgaca agcggcgtgc acacctttcc agccgtgctg    540
cagagcagcg gcctgtactc tctgagcagc gtcgtgacg tgcccagcag ctctctgggc    600
acccagacct acatctgcaa cgtgaaccac aagcccagca caccaaggt ggacaagaag    660
gtggaaccca gagctgcga caagacccac acctgtcccc cttgtcctgc ccgaactg    720
ctgggaggc cttccgtgtt cctgttccc caaagccca aggacaccct gatgatcagc    780
cggaccccg aagtgacctc cgtggtggtg gatgtgtcc acgaggaccc tgaagtgaag    840
ttcaattggt acgtggacgg cgtggaagtg cacaacgcca agaccaagcc tagagaggaa    900
cagtacaaca gcacctaccg ggtggtgtcc gtgctgacag tgctgcacca ggactggctg    960
aacggcaaag agtacaagtg caaggtgtcc aacaaggccc tgcctgcccc catcgagaaa    1020
accatcagca aggccaaggg ccagccccgc gaacccagg tgtacacact gccccaagc    1080
agggacgagc tgaccaagaa ccaggtgtcc ctgacctgtc tcgtgaaagg cttctacccc    1140
tccgatatcg ccgtggaatg ggagagcaac ggccagcccg agaacaacta caagaccacc    1200
cccctgtgc tggacagcga cggctcattc ttcctgtaca gcaagctgac cgtggacaag    1260
tcccggtggc agcagggcaa cgtgttcagc tgcagcgtga tgcacgaggc cctgcacaac    1320
cactacaccc agaagtccct gagcctgagc cctggcaag                          1359

SEQ ID NO: 580              moltype = DNA  length = 651
FEATURE                     Location/Qualifiers
misc_feature                1..651
                            note = antibody sequence
source                      1..651
                            mol_type = other DNA
                            organism = synthetic construct
SEQUENCE: 580
cagtctgttc tgacacagcc tccatctgtg tctggcgccc ctggacagag agtgaccatc     60
agctgtacag gcagcagctc caatatcgga gccggctatg acgtgcactg gtatcagcag    120
ctgcctggca gcccctaa actgctgatc tacggcaaca gcaacagaca cagcggcgtg    180
cccgatagat tttccggctc taagagcggc acaagcgcca gcctggctat tactggacg    240
caggccgagg acgaggccga ctactactgt agctcttacg ctggccccaa tccttacgtg    300
gtgtttggcg gcggaacaaa gctgaccgtt ctaggcagc ctaaagcgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggtg tggaaaccac cacccctagc aagcagagca caacaaata cgccgcctgc    540
agctacctga gcctgacccc cgagcagtgg aagtcccaca gatcctcag ctgcaagtg    600
acccacgagg gcagcaccgt ggaaaagaca gtgcccccta ccgagtgcag c             651

SEQ ID NO: 581              moltype = AA  length = 990
FEATURE                     Location/Qualifiers
```

```
source                   1..990
                         mol_type = protein
                         organism = Homo sapiens
SEQUENCE: 581
HHHHHHKNNV PRLKLSYKEM LESNNVITFN GLANSSSYHT FLLDEERSRL YVGAKDHIFS     60
FDLVNIKDFQ KIVWPVSYTR RDECKWAGKD ILKECANFIK VLKAYNQTHL YACGTGAFHP    120
ICTYIEIGHH PEDNIFKLEN SHFENGRGKS PYDPKLLTAS LLIDGELYSG TAADFMGRDF    180
AIFRTLGHHH PIRTEQHDSR WLNDPKFISA HLISESDNPE DDKVYFFFRE NAIDGEHSGK    240
ATHARIGQIC KNDFGGHRSL VNKWTTFLKA RLICSVPGPN GIDTHFDELQ DVFLMNFKDP    300
KNPVYGVFT TSSNIFKGSA VCMYSMSDVR RVFLGPYAHR DGPNYQWVPY QGRVPYPRPG    360
TCPSKTFGGF DSTKDLPDDV ITFARSHPAM YNPVFPMNNR PIVIKTDVNY QFTQIVVDRV    420
DAEDGQYDVM FIGTDVGTVL KVVSIPKETW YDLEEVLLEE MTVFREPTAI SAMELSTKQQ    480
QLYIGSTAGV AQLPLHRCDI YGKACAECCL ARDPYCAWDG SACSRYFPTA KRATRAQDIR    540
NGDPLTHCSD LHHDNHHGHS PEERIIYGVE NSSTFLECSP KSQRALVYWQ FQRRNEERKE    600
EIRVDDHIIR TDQGLLLRSL QQKDSGNYLC HAVEHGFIQT LLKVTLEVID TEHLEELLHK    660
DDDGDGSKTK EMSNSMTPSQ KVWYRDFMQL INHPNLNTMD EFCEQVWKRD RKQRRQRPGH    720
TPGNSNKWKH LQENKKGRNR RTHEFERAPR SVDIEGRMDC KSCDKTHTCP PCPAPELLGG    780
PSVFLFPPKP KDTLMISRTP EVTCVVVDVS HEDPEVKFNW YVDGVEVHNA KTKPREEQYN    840
STYRVVSVLT VLHQDWLNGK EYKCKVSNKA LPAPIEKTIS KAKGQPREPQ VYTLPPSRDE    900
LTKNQVSLTC LVKGFYPSDI AVEWESNGQP ENNYKTTPPV LDSDGSFFLY SKLTVDKSRW    960
QQGNVFSCSV MHEALHNHYT QKSLSLSPGK                                    990

SEQ ID NO: 582           moltype = AA   length = 563
FEATURE                  Location/Qualifiers
source                   1..563
                         mol_type = protein
                         organism = Homo sapiens
SEQUENCE: 582
NYQNGKNNVP RLKLSYKEML ESNNVITFNG LANSSSYHTF LLDEERSRLY VGAKDHIFSF     60
DLVNIKDFQK IVWPVSYTRR DECKWAGKDI LKECANFIKV LKAYNQTHLY ACGTGAFHPI    120
CTYIEIGHHP EDNIFKLENS HFENGRGKSP YDPKLLTASL LIDGELYSGT AADFMGRDFA    180
IFRTLGHHHP IRTEQHDSRW LNDPKFISAH LISESDNPED DKVYFFFREN AIDGEHSGKA    240
THARIGQICK NDFGGHRSLV NKWTTFLKAR LICSVPGPNG IDTHFDELQD VFLMNFKDPK    300
NPVYGVFT SSNIFKGSAV CMYSMSDVRR VFLGPYAHRD GPNYQWVPYQ GRVPYPRPGT    360
CPSKTFGGFD STKDLPDDVI TFARSHPAMY NPVFPMNNRP IVIKTDVNYQ FTQIVVDRVD    420
AEDGQYDVMF IGTDVGTVLK VVSIPKETWY DLEEVLLEEM TVFREPTAIS AMELSTKQQQ    480
LYIGSTAGVA QLPLHRCDIY GKACAECCLA RDPYCAWDGS ACSRYFPTAK ARTRAQDIRN    540
GDPLTHCSDG GIEGRMDHHH HHH                                           563

SEQ ID NO: 583           moltype = AA   length = 563
FEATURE                  Location/Qualifiers
source                   1..563
                         mol_type = protein
                         organism = Mus musculus
SEQUENCE: 583
NYANGKNNVP RLKLSYKEML ESNNVITFNG LANSSSYHTF LLDEERSRLY VGAKDHIFSF     60
NLVNIKDFQK IVWPVSYTRR DECKWAGKDI LKECANFIKV LEAYNQTHLY ACGTGAFHPI    120
CTYIEVGHHP EDNIFKLQDS HFENGRGKSP YDPKLLTASL LIDGELYSGT AADFMGRDFA    180
IFRTLGHHHP IRTEQHDSRW LNDPRFISAH LIPESDNPED DKVYFFFREN AIDGEHSGKA    240
THARIGQICK NDFGGHRSLV NKWTTFLKAR LICSVPGPNG IDTHFDELQD VFLMNSKDPK    300
NPIVYGVFTT SSNIFKGSAV CMYSMSDVRR VFLGPYAHRD GPNYQWVPYQ GRVPYPRPGT    360
CPSKTFGGFD STKDLPDDVI TFARSHPAMY NPVFPINNRP IMIKTDVNYQ FTQIVVDRVD    420
AEDGQYDVMF IGTDVGTVLK VVSVPKETWH DLEEILLEEM TVFREPTTIS AMELSTKQQQ    480
LYIGSTAGVA QLPLHRCDIY GKACAECCLA RDPYCAWDGS SCSRYFPTAK ARTRAQDIRN    540
GDPLTHCSDG GIEGRMDHHH HHH                                           563

SEQ ID NO: 584           moltype = AA   length = 563
FEATURE                  Location/Qualifiers
source                   1..563
                         mol_type = protein
                         organism = Rattus norvegicus
SEQUENCE: 584
NYANGKNNVP RLKLSYKEML ESNNVITFNG LANSSSYHTF LLDEERSRLY VGAKDHIFSF     60
NLVNIKDFQK IVWPVSYTRR DECKWAGKDI LKECANFIKV LKAYNQTHLY ACGTGAFHPI    120
CTYIEVGHHP EDNIFKLQDS HFENGRGKSP YDPKLLTASL LIDGELYSGT AADFMGRDFA    180
IFRTLGHHHP IRTEQHDSRW LNDPRFISAH LIPESDNPED DKVYFFFREN AIDGEHSGKA    240
THARIGQICK NDFGGHRSLV NKWTTFLKAR LICSVPGPNG IDTHFDELQD VFLMNSKDPK    300
NPIVYGVFTT SSNIFKGSAV CMYSMSDVRR VFLGPYAHRD GPNYQWVPYQ GRVPYPRPGT    360
CPSKTFGGFD STKDLPDDVI TFARSHPAMY NPVFPINNRP IMIKTDVNYQ FTQIVVDRVD    420
AEDGQYDVMF IGTDVGTVLK VVSVPKETWH DLEEVLLEEM TVFREPTTIS AMELSTKQQQ    480
LYIGSTAGVA QLPLHRCDIY GKACAECCLA RDPYCAWDGS SCSRYFPTAK ARTRAQDIRN    540
GDPLTHCSDG GIEGRMDHHH HHH                                           563

SEQ ID NO: 585           moltype = AA   length = 563
FEATURE                  Location/Qualifiers
source                   1..563
                         mol_type = protein
                         organism = Canis lupus
SEQUENCE: 585
```

```
NYQNGKNNVP RLKLSYKEML ESNSVITFNG LANSSSYHTF LLDEERSRLY VGAKDHIFSF    60
NLVNIKDFQK IVWPVSYTRR DECKWAGKDI QKECANFIKV LKAYNQTHLY ACGTGAFHPI   120
CTYIEIGHHP EDNIFKLEDS HFENGRGKSP YDPKLLTASL LIDGELYSGT AADFMGRDFA   180
IFRTLGHHHP IRTEQHDSRW LNDPRFISAH LIPESDNPED DKVYFFFREN AIDGEHTGKA   240
THARIGQICK NDFGGHRSLV NKWTTFLKAR LICSVPGPNG IDTHFDELQD VFLMNSKDPK   300
NPIVYGVFTT SSNIFKGSAV CMYSMSDVRR VFLGPYAHRD GPNYQWVPYQ GRVPYPRPGT   360
CPSKTFGGFD STKDLPDDVI TFARSHPAMY NPVFPINNRP IMIKTDVNYQ FTQIVVDRVD   420
AEDGQYDVMF IGTDVGTVLK VVSIPKETWH DLEEVLLEEM TVFREPTPIS AMELSTKQHQ   480
LYAGSPAGLA QLPLQRCAAY GRACAECCLA RDPYCAWDGA ACSRYFPAAK ARTRAQDIRN   540
GDPLTHCSDG GIEGRMDHHH HHH                                          563

SEQ ID NO: 586          moltype = AA  length = 563
FEATURE                 Location/Qualifiers
source                  1..563
                        mol_type = protein
                        organism = Macaca fascicularis
SEQUENCE: 586
NYQNGKNNVP RLKLSYKEML ESNNVITFNG LANSSSYHTF LLDEERSRLY VGAKDHIFSF    60
NLVNIKDFQK IVWPVSYTRR DECKWAGKDI LKECANFIKV LKAYNQTHLY ACGTGAFHPI   120
CTYIEIGHHP EDNIFKLENS HFENGRGKSP YDPKLLTASL LIDGELYSGT AADFMGRDFA   180
IFRTLGHHHP IRTEQHDSRW LNDPRFISAH LIPESDNPED DKVYFFFREN AIDGEHSGKA   240
THARIGQICK NDFGGHRSLV NKWTTFLKAR LICSVPGPNG IDTHFDELQD VFLMNFKDPK   300
NPIVYGVFTT SSNIFKGSAV CMYSMSDVRR VFLGPYAHRD GPNYQWVPYQ GRVPYPRPGT   360
CPSKTFGGFD STKDLPDDVI TFARSHPAMY NPVFPINNRP IMIKTDVNYQ FTQIVVDRVD   420
AEDGQYDVMF IGTDVGTVLK VVSIPKETWH DLEEVLLEEM TVFREPTTIS AMELSTKQQQ   480
LYIGSTAGIA QLPLHRCDIY GKACAECCLA RDPYCAWDGS SCSRYFPTAK ARTRAQDIRN   540
GDPLTHCSDG GIEGRMDHHH HHH                                          563

SEQ ID NO: 587          moltype = AA  length = 563
FEATURE                 Location/Qualifiers
source                  1..563
                        mol_type = protein
                        organism = Sus scrofa
SEQUENCE: 587
NYQNGKNNVP RLKLSYKEML ESNNVITFNG LANSSSYHTF LLDEERSRLY VGAKDHIFSF    60
NLVNIKDFQK IVWPVSYTRR DECKWAGKDI LKECANFIKV LKAYNQTHLY ACGTGAFHPI   120
CTYIEIGHHP EDNIFKLEDS HFENGRGKSP YDPKLLTASL LIDGELYSGT AADFMGRDFA   180
IFRTLGHHHP IRTEQHDSRW LNDPRFISAH LIPESDNPED DKVYFFFREN AIDGEHTGKA   240
THARIGQICK NDFGGHRSLV NKWTTFLKAR LICSVPGPNG IDTHFDELQD VFLMNSKDPK   300
NPVVYGVFTT SSNIFKGSAV CMYSMSDVRR VFLGPYAHRD GPNYQWVPYQ GRVPYPRPGT   360
CPSKTFGGFD STKDLPDDVI TFARSHPAMY NPVFPINNRP IMIKTDVNYQ FTQIVVDRVD   420
AEDGQYDVMF IGTDVGTVLK VVSIPKETWH DLEEVLLEEM TVFREPTTIS AMELSTKQQQ   480
LYVGSAAGVA QLPLHRCDIY GKACAECCLA RDPYCAWDGS SCSRYFPTAK ARTRAQDIRN   540
GDPLTHCSDG GIEGRMDHHH HHH                                          563

SEQ ID NO: 588          moltype =     length =
SEQUENCE: 588
000

SEQ ID NO: 589          moltype = AA  length = 5
FEATURE                 Location/Qualifiers
REGION                  1..5
                        note = antibody sequence
SITE                    5
                        note = site - Xaa can be any naturally occurring amino acid
source                  1..5
                        mol_type = protein
                        organism = synthetic construct
SEQUENCE: 589
SYAMX                                                                5

SEQ ID NO: 590          moltype = AA  length = 16
FEATURE                 Location/Qualifiers
REGION                  1..16
                        note = antibody sequence
SITE                    4
                        note = site - Xaa can be any naturally occurring amino acid
SITE                    15
                        note = site - Xaa can be any naturally occurring amino acid
source                  1..16
                        mol_type = protein
                        organism = synthetic construct
SEQUENCE: 590
AIGXGGDTYY ADSVXG                                                   16

SEQ ID NO: 591          moltype = AA  length = 16
FEATURE                 Location/Qualifiers
REGION                  1..16
                        note = antibody sequence
```

| | |
|---|---|
| SITE | 4 |
| | note = site - Xaa can be any naturally occurring amino acid |
| source | 1..16 |
| | mol_type = protein |
| | organism = synthetic construct |

SEQUENCE: 591
AIGXGGDTYY ADSVKG                                                              16

| | |
|---|---|
| SEQ ID NO: 592 | moltype = AA  length = 17 |
| FEATURE | Location/Qualifiers |
| REGION | 1..17 |
| | note = antibody sequence |
| SITE | 8 |
| | note = site - Xaa can be any naturally occurring amino acid |
| SITE | 10 |
| | note = site - Xaa can be any naturally occurring amino acid |
| source | 1..17 |
| | mol_type = protein |
| | organism = synthetic construct |

SEQUENCE: 592
GISWNSGXIX YADSVKG                                                             17

| | |
|---|---|
| SEQ ID NO: 593 | moltype = AA  length = 17 |
| FEATURE | Location/Qualifiers |
| REGION | 1..17 |
| | note = antibody sequence |
| SITE | 10 |
| | note = site - Xaa can be any naturally occurring amino acid |
| source | 1..17 |
| | mol_type = protein |
| | organism = synthetic construct |

SEQUENCE: 593
GISWNSGWIX YADSVKG                                                             17

| | |
|---|---|
| SEQ ID NO: 594 | moltype = AA  length = 12 |
| FEATURE | Location/Qualifiers |
| REGION | 1..12 |
| | note = antibody sequence |
| SITE | 12 |
| | note = site - Xaa can be any naturally occurring amino acid |
| source | 1..12 |
| | mol_type = protein |
| | organism = synthetic construct |

SEQUENCE: 594
RDDYTSRDAF DX                                                                  12

| | |
|---|---|
| SEQ ID NO: 595 | moltype = AA  length = 14 |
| FEATURE | Location/Qualifiers |
| REGION | 1..14 |
| | note = antibody sequence |
| SITE | 6 |
| | note = site - Xaa can be any naturally occurring amino acid |
| source | 1..14 |
| | mol_type = protein |
| | organism = synthetic construct |

SEQUENCE: 595
TGSSSXIGAG YDVH                                                                14

| | |
|---|---|
| SEQ ID NO: 596 | moltype = AA  length = 7 |
| FEATURE | |
| SITE | 5 |
| | note = site - Xaa can be any naturally occurring amino acid |
| source | 1..7 |
| | mol_type = protein |
| | organism = synthetic construct |

SEQUENCE: 596
YDDLXPS                                                                        7

| | |
|---|---|
| SEQ ID NO: 597 | moltype = AA  length = 7 |
| FEATURE | Location/Qualifiers |
| REGION | 1..7 |
| | note = antibody sequence |
| SITE | 2 |
| | note = site - Xaa can be any naturally occurring amino acid |
| source | 1..7 |
| | mol_type = protein |
| | organism = synthetic construct |

SEQUENCE: 597
GXSNRPS                                                                        7

```
SEQ ID NO: 598          moltype = AA  length = 12
FEATURE                 Location/Qualifiers
REGION                  1..12
                        note = antibody sequence
SITE                    1
                        note = site - Xaa can be any naturally occurring amino acid
REGION                  9..11
                        note = site - Xaa can be any naturally occurring amino acid
source                  1..12
                        mol_type = protein
                        organism = synthetic construct
SEQUENCE: 598
XAWDDSLNXX XV                                                                       12

SEQ ID NO: 599          moltype = AA  length = 11
FEATURE                 Location/Qualifiers
REGION                  1..11
                        note = antibody sequence
SITE                    1
                        note = site - Xaa can be any naturally occurring amino acid
SITE                    4
                        note = site - Xaa can be any naturally occurring amino acid
SITE                    6
                        note = site - Xaa can be any naturally occurring amino acid
source                  1..11
                        mol_type = protein
                        organism = synthetic construct
SEQUENCE: 599
XSYXGXNPYV V                                                                        11

SEQ ID NO: 600          moltype = AA  length = 750
FEATURE                 Location/Qualifiers
source                  1..750
                        mol_type = protein
                        organism = Homo sapiens
SEQUENCE: 600
YQNGKNNVPR LKLSYKEMLE SNNVITFNGL ANSSSYHTFL LDEERSRLYV GAKDHIFSFD    60
LVNIKDFQKI VWPVSYTRRD ECKWAGKDIL KECANFIKVL KAYNQTHLYA CGTGAFHPIC   120
TYIEIGHHPE DNIFKLENSH FENGRGKSPY DPKLLTASLL IDGELYSGTA ADFMGRDFAI   180
FRTLGHHHPI RTEQHDSRWL NDPKFISAHL ISESDNPEDD KVYFFFRENA IDGEHSGKAT   240
HARIGQICKN DFGGHRSLVN KWTTFLKARL ICSVPGPNGI DTHFDELQDV FLMNFKDPKN   300
PVVYGVFTTS SNIFKGSAVC MYSMSDVRRV FLGPYAHRDG PNYQWVPYQG RVPYPRPGTC   360
PSKTFGGFDS TKDLPDDVIT FARSHPAMYN PVFPMNNRPI VIKTDVNYQF TQIVVDRVDA   420
EDGQYDVMFI GTDVGTVLKV VSIPKETWYD LEEVLLEEMT VFREPTAISA MELSTKQQQL   480
YIGSTAGVAQ LPLHRCDIYG KACAECCLAR DPYCAWDGSA CSRYFPTAKR RTRRQDIRNG   540
DPLTHCSDLH HDNHHGHSPE ERIIYGVENS STFLECSPKS QRALVYWQFQ RRNEERKEEI   600
RVDDHIIRTD QGLLLRSLQQ KDSGNYLCHA VEHGFIQTLL KVTLEVIDTE HLEELLHKDD   660
DGDGSKTKEM SNSMTPSQKV WYRDFMQLIN HPNLNTMDEF CEQVWKRDRK QRRQRPGHTP   720
GNSNKWKHLQ ENKKGRNRRT HEFERAPRSV                                    750

SEQ ID NO: 601          moltype = AA  length = 752
FEATURE                 Location/Qualifiers
source                  1..752
                        mol_type = protein
                        organism = Mus musculus
SEQUENCE: 601
NYANGKNNVP RLKLSYKEML ESNNVITFNG LANSSSYHTF LLDEERSRLY VGAKDHIFSF    60
NLVNIKDFQK IVWPVSYTRR DECKWAGKDI LKECANFIKV LEAYNQTHLY ACGTGAFHPI   120
CTYIEVGHHP EDNIFKLQDS HFENGRGKSP YDPKLLTASL LIDGELYSGT AADFMGRDFA   180
IFRTLGHHHP IRTEQHDSRW LNDPRFISAH LIPESDNPED DKVYFFFREN AIDGEHSGKA   240
THARIGQICK NDFGGHRSLV NKWTTFLKAR LICSVPGPNG IDTHFDELQD VFLMNSKDPK   300
NPIVYGVFTT SSNIFKGSAV CMYSMSDVRR VFLGPYAHRD GPNYQWVPYQ GRVPYPRPGT   360
CPSKTFGGFD STKDLPDDVI TFARSHPAMY NPVFPINNRP IMIKTDVNYQ FTQIVVDRVD   420
AEDGQYDVMF IGTDVGTVLK VVSVPKETWH DLEEVLLEEM TVFREPTTIS AMELSTKQQQ   480
LYIGSTAGVA QLPLHRCDIY GKACAECCLA RDPYCAWDGS CSRYFPTAK RRTRRQDIRN   540
GDPLTHCSDL QHHDNHHGPS LEERIIYGVE NSSTFLECSP KSQRALVYWQ FQRRNEDRKE   600
EIRMGDHIIR TEQGLLLRSL QKKDSGNYLC HAVEHGFMQT LLKVTLEVID TEHLEELLHK   660
DDDGDGSKIK EMSSSMTPSQ KVWYRDFMQL INHPNLNTMD EFCEQVWKRD RKQRRQRPGH   720
SQGSSNKWKH MQESKKGRNR RTHEFERAPR SV                                 752

SEQ ID NO: 602          moltype = AA  length = 772
FEATURE                 Location/Qualifiers
source                  1..772
                        mol_type = protein
                        organism = Macaca fascicularis
SEQUENCE: 602
MGWLTRIVCL FWGVLLTARA NYQNGKNNVP RKLSYKEML ESNNVITFNG LANSSSYHTF    60
LLDEERSRLY VGAKDHIFSF NLVNIKDFQK IVWPVSYTRR DECKWAGKDI LKECANFIKV   120
```

```
LKAYNQTHLY ACGTGAFHPI CTYIEIGHHP EDNIFKLENS HFENGRGKSP YDPKLLTASL    180
LIDGELYSGT AADFMGRDFA IFRTLGHHHP IRTEQHDSRW LNDPRFISAH LIPESDNPED    240
DKVYFFFREN AIDGEHSGKA THARIGQICK NDFGGHRSLV NKWTTFLKAR LICSVPGPNG    300
IDTHFDELQD VFLMNFKDPK NPIVYGVFTT SSNIFKGSAV CMYSMSDVRR VFLGPYAHRD    360
GPNYQWVPYQ GRVPYPRPGT CPSKTFGGFD STKDLPDDVI TFARSHPAMY NPVFPINNRP    420
IMIKTDVNYQ FTQIVVDRVD AEDGQYDVMF IGTDVGTVLK VVSIPKETWH DLEEVLLEEM    480
TVFREPTTIS AMELSTKQQQ LYIGSTAGIA QLPLHRCDIY GKACAECCLA RDPYCAWDGS    540
SCSRYFPTAK RRTRRQDIRN GDPLTHCSDL QHHDNHHGHS PEERIIYGVE NSSTFLECSP    600
KSQRALVYWQ FQRRNEERKE EIRVDDHIIR TDQGLLLRSL QRKDSGSYLC HAVEHGFIQT    660
LLKVTLEVID TEHLEELLHK DDDGDGSKTK EMSNSMTPSQ KVWYRDFMQL INHPNLNTMD    720
EFCEQVWKRD RKQRRQRPGH TQGNSNKWKH LQENKKGRNR RTHEFERAPR SV            772

SEQ ID NO: 603             moltype = AA  length = 752
FEATURE                    Location/Qualifiers
source                     1..752
                           mol_type = protein
                           organism = Rattus norvegicus
SEQUENCE: 603
NYANGKNNVP RLKLSYKEML ESNNVITFNG LANSSSYHTF LLDEERSRLY VGAKDHIFSF     60
NLVNIKDFQK IVWPVSYTRR DECKWAGKDI LKECANFIKV LKAYNQTHLY ACGTGAFHPI    120
CTYIEVGHHP EDNIFKLQDS HFENGRGKSP YDPKLLTASL LIDGELYSGT AADFMGRDFA    180
IFRTLGHHHP IRTEQHDSRW LNDPRFLSAH LIPESDNPED DKVYFFFREN AIDGEHSGKA    240
THARIGQICK NDFGGHRSLV NKWTTFLKAR LICSVPGPNG IDTHFDELQD VFLMNSKDPK    300
NPIVYGVFTT SSNIFKGSAV CMYSMSDVRR VFLGPYAHRD GPNYQWVPYQ GRVPYPRPGT    360
CPSKTFGGFD STKDLPDDVI TFARSHPAMY NPVFPINNRP IMIKTDVNYQ FTQIVVDRVD    420
AEDGQYDVMF IGTDVGTVLK VVSIPKETWH DLEEVLLEEM TVFREPTTIS AMELSTKQQQ    480
LYIGSTAGVA QLPLHRCDIY GKACAECCLA RDPYCAWDGS SCSRYFPTAK RRTRRQDIRN    540
GDPLTHCSDL QHHDNHHGHS LEERIIYGVE NSSTFLECSP KSQRALVYWQ FQRRNEDRKE    600
EIRVGDHIIR TEQGLLLRSL QKKDSGNYLC HAVEHGFMQT LLKVTLEVID TEHLEELLHK    660
DDDGDGSKTK EMSSSMTPSQ KVWYRDFMQL INHPNLNTMD EFCEQVWKRD RKQRRQRPGH    720
SQGSSNKWKH MQESKKGRNR RTHEFERAPR SV                                  752

SEQ ID NO: 604             moltype = AA  length = 772
FEATURE                    Location/Qualifiers
source                     1..772
                           mol_type = protein
                           organism = Sus scrofa
SEQUENCE: 604
MGWFSRIVCL FWGVLLTARA NYQNGKNNVP RLKLSYKEML ESNNVITFNG LANSSSYHTF     60
LLDEERSRLY VGAKDHIFSF NLVNIKDFQK IVWPVSYTRR DECKWAGKDI LKECANFIKV    120
LKAYNQTHLY ACGTGAFHPI CTYIEIGHHP EDNIFKLEDS HFENGRGKSP YDPKLLTASL    180
LIDGELYSGT AADFMGRDFA IFRTLGHHHP IRTEQHDSRW LNDPRFISAH LIPESDNPED    240
DKVYFFFREN AIDGEHTGKA THARIGQICK NDFGGHRSLV NKWTTFLKAR LICSVPGPNG    300
IDTHFDELQD VFLMNSKDPK NPVVYGVFTT SSNIFKGSAV CMYSMSDVRR VFLGPYAHRD    360
GPNYQWVPYQ GRVPYPRPGT CPSKTFGGFD STKDLPDDVI TFARSHPAMY NPVFPINNRP    420
IMIKTDVNYQ FTQIVVDRVD AEDGQYDVMF IGTDVGTVLK VVSIPKETWH DLEEVLLEEM    480
TVFREPTTIS AMELSTKQQQ LYVGSAAGVA QLPLHRCDIY GKACAECCLA RDPYCAWDGS    540
SCSRYFPTAK RRTRRQDIRN GDPLTHCSDL QHHDNHRGHN FEERIIYGVE NSSTFLECSP    600
KSQRALVYWQ FQRRNEERKE EIRVDDHIIR TEQGLLLRSL QRKDSGSYLC HAVEHGFMQT    660
LLKVTLEVID TEHLEELLHK DDDGDSSKTK EMSNSMTPSQ KIWYRDFMQL INHPNLNTMD    720
EFCEQVWKRD RKQRRQRPGH TQGNSNKWKH LQENKKCRNR RTHEFERAPR SV            772

SEQ ID NO: 605             moltype = AA  length = 772
FEATURE                    Location/Qualifiers
source                     1..772
                           mol_type = protein
                           organism = Canis lupus
SEQUENCE: 605
MGWLARIACL FWGVLLTATA NYQNGKNNVP RLKLSYKEML ESNSVITFNG LANSSSYHTF     60
LLDEERSRLY VGAKDHIFSF NLVNIKDFQK IVWPVSYTRR DECKWAGKDI QKECANFIKV    120
LKAYNQTHLY ACGTGAFHPI CTYIEIGHHP EDNIFKLEDS HFENGRGKSP YDPKLLTASL    180
LIDGELYSGT AADFMGRDFA IFRTLGHHHP IRTEQHDSRW LNDPRFISAH LIPESDNPED    240
DKVYFFFREN AIDGEHTGKA THARIGQICK NDFGGHRSLV NKWTTFLKAR LICSVPGPNG    300
IDTHFDELQD VFLMNSKDPK NPIVYGVFTT SSNIFKGSAV CMYSMSDVRR VFLGPYAHRD    360
GPNYQWVPYQ GRVPYPRPGT CPSKTFGGFD STKDLPDDVI TFARSHPAMY NPVFPINNRP    420
IMIKTDVNYQ FTQIVVDRVD AEDGQYDVMF IGTDVGTVLK VVSIPKETWH DLEEVLLEEM    480
TVFREPTPIS AMELSTKQHQ LYAGSPAGLA QLPLQRCAAY GRACAECCLA RDPYCAWDGA    540
ACSRYFPAAK RRTRRQDIRN GDPLTHCSDL QHHDNHHSHS LEERIIYGVE NSSTFLECSP    600
KSQRALVYWQ FQRRNEERKE EIRVDDHIIR TEQGLLLRSL QRKDSGNYLC HAVEHGFMQT    660
LLKVTLEVID TEHLEELLHK DDDGDGSKTK EISNSMTPSQ KVWYRDFMQL INHPNLNTMD    720
EFCEQVWKRD RKQRRQRPGH TQGNSNKWKH LQENKKGRNR RTHEFERAPR SV            772

SEQ ID NO: 606             moltype =     length =
SEQUENCE: 606
000

SEQ ID NO: 607             moltype =     length =
SEQUENCE: 607
000
```

| | | |
|---|---|---|
| SEQ ID NO: 608 SEQUENCE: 608 | moltype = | length = 000 |
| SEQ ID NO: 609 SEQUENCE: 609 | moltype = | length = 000 |
| SEQ ID NO: 610 SEQUENCE: 610 | moltype = | length = 000 |
| SEQ ID NO: 611 SEQUENCE: 611 | moltype = | length = 000 |
| SEQ ID NO: 612 SEQUENCE: 612 | moltype = | length = 000 |
| SEQ ID NO: 613 SEQUENCE: 613 | moltype = | length = 000 |
| SEQ ID NO: 614 SEQUENCE: 614 | moltype = | length = 000 |
| SEQ ID NO: 615 SEQUENCE: 615 | moltype = | length = 000 |
| SEQ ID NO: 616 SEQUENCE: 616 | moltype = | length = 000 |
| SEQ ID NO: 617 SEQUENCE: 617 | moltype = | length = 000 |
| SEQ ID NO: 618 SEQUENCE: 618 | moltype = | length = 000 |
| SEQ ID NO: 619 SEQUENCE: 619 | moltype = | length = 000 |
| SEQ ID NO: 620 SEQUENCE: 620 | moltype = | length = 000 |
| SEQ ID NO: 621 SEQUENCE: 621 | moltype = | length = 000 |
| SEQ ID NO: 622 SEQUENCE: 622 | moltype = | length = 000 |
| SEQ ID NO: 623 SEQUENCE: 623 | moltype = | length = 000 |
| SEQ ID NO: 624 SEQUENCE: 624 | moltype = | length = 000 |
| SEQ ID NO: 625 SEQUENCE: 625 | moltype = | length = 000 |
| SEQ ID NO: 626 SEQUENCE: 626 | moltype = | length = 000 |
| SEQ ID NO: 627 SEQUENCE: 627 | moltype = | length = |

000

SEQ ID NO: 628              moltype =    length =
SEQUENCE: 628
000

SEQ ID NO: 629              moltype =    length =
SEQUENCE: 629
000

SEQ ID NO: 630              moltype =    length =
SEQUENCE: 630
000

SEQ ID NO: 631              moltype =    length =
SEQUENCE: 631
000

SEQ ID NO: 632              moltype =    length =
SEQUENCE: 632
000

SEQ ID NO: 633              moltype =    length =
SEQUENCE: 633
000

SEQ ID NO: 634              moltype =    length =
SEQUENCE: 634
000

SEQ ID NO: 635              moltype =    length =
SEQUENCE: 635
000

SEQ ID NO: 636              moltype =    length =
SEQUENCE: 636
000

SEQ ID NO: 637              moltype =    length =
SEQUENCE: 637
000

SEQ ID NO: 638              moltype =    length =
SEQUENCE: 638
000

SEQ ID NO: 639              moltype =    length =
SEQUENCE: 639
000

SEQ ID NO: 640              moltype =    length =
SEQUENCE: 640
000

SEQ ID NO: 641              moltype =    length =
SEQUENCE: 641
000

SEQ ID NO: 642              moltype =    length =
SEQUENCE: 642
000

SEQ ID NO: 643              moltype =    length =
SEQUENCE: 643
000

SEQ ID NO: 644              moltype =    length =
SEQUENCE: 644
000

SEQ ID NO: 645              moltype =    length =
SEQUENCE: 645
000

SEQ ID NO: 646              moltype =    length =
SEQUENCE: 646
000

SEQ ID NO: 647              moltype =    length =

| | | |
|---|---|---|
| SEQUENCE: 647 000 | | |
| SEQ ID NO: 648 SEQUENCE: 648 000 | moltype = | length = |
| SEQ ID NO: 649 SEQUENCE: 649 000 | moltype = | length = |
| SEQ ID NO: 650 SEQUENCE: 650 000 | moltype = | length = |
| SEQ ID NO: 651 SEQUENCE: 651 000 | moltype = | length = |
| SEQ ID NO: 652 SEQUENCE: 652 000 | moltype = | length = |
| SEQ ID NO: 653 SEQUENCE: 653 000 | moltype = | length = |
| SEQ ID NO: 654 SEQUENCE: 654 000 | moltype = | length = |
| SEQ ID NO: 655 SEQUENCE: 655 000 | moltype = | length = |
| SEQ ID NO: 656 SEQUENCE: 656 000 | moltype = | length = |
| SEQ ID NO: 657 SEQUENCE: 657 000 | moltype = | length = |
| SEQ ID NO: 658 SEQUENCE: 658 000 | moltype = | length = |
| SEQ ID NO: 659 SEQUENCE: 659 000 | moltype = | length = |
| SEQ ID NO: 660 SEQUENCE: 660 000 | moltype = | length = |
| SEQ ID NO: 661 SEQUENCE: 661 000 | moltype = | length = |
| SEQ ID NO: 662 SEQUENCE: 662 000 | moltype = | length = |
| SEQ ID NO: 663 SEQUENCE: 663 000 | moltype = | length = |
| SEQ ID NO: 664 SEQUENCE: 664 000 | moltype = | length = |
| SEQ ID NO: 665 SEQUENCE: 665 000 | moltype = | length = |
| SEQ ID NO: 666 SEQUENCE: 666 000 | moltype = | length = |

| | | |
|---|---|---|
| SEQ ID NO: 667<br>SEQUENCE: 667 | moltype = | length = 000 |
| SEQ ID NO: 668<br>SEQUENCE: 668 | moltype = | length = 000 |
| SEQ ID NO: 669<br>SEQUENCE: 669 | moltype = | length = 000 |
| SEQ ID NO: 670<br>SEQUENCE: 670 | moltype = | length = 000 |
| SEQ ID NO: 671<br>SEQUENCE: 671 | moltype = | length = 000 |
| SEQ ID NO: 672<br>SEQUENCE: 672 | moltype = | length = 000 |
| SEQ ID NO: 673<br>SEQUENCE: 673 | moltype = | length = 000 |
| SEQ ID NO: 674<br>SEQUENCE: 674 | moltype = | length = 000 |
| SEQ ID NO: 675<br>SEQUENCE: 675 | moltype = | length = 000 |
| SEQ ID NO: 676<br>SEQUENCE: 676 | moltype = | length = 000 |
| SEQ ID NO: 677<br>SEQUENCE: 677 | moltype = | length = 000 |
| SEQ ID NO: 678<br>SEQUENCE: 678 | moltype = | length = 000 |
| SEQ ID NO: 679<br>SEQUENCE: 679 | moltype = | length = 000 |
| SEQ ID NO: 680<br>SEQUENCE: 680 | moltype = | length = 000 |
| SEQ ID NO: 681<br>SEQUENCE: 681 | moltype = | length = 000 |
| SEQ ID NO: 682<br>SEQUENCE: 682 | moltype = | length = 000 |
| SEQ ID NO: 683<br>SEQUENCE: 683 | moltype = | length = 000 |
| SEQ ID NO: 684<br>SEQUENCE: 684 | moltype = | length = 000 |
| SEQ ID NO: 685<br>SEQUENCE: 685 | moltype = | length = 000 |
| SEQ ID NO: 686<br>SEQUENCE: 686 | moltype = | length = 000 |

SEQ ID NO: 687    moltype =    length =
SEQUENCE: 687
000

SEQ ID NO: 688    moltype =    length =
SEQUENCE: 688
000

SEQ ID NO: 689    moltype =    length =
SEQUENCE: 689
000

SEQ ID NO: 690    moltype =    length =
SEQUENCE: 690
000

SEQ ID NO: 691    moltype =    length =
SEQUENCE: 691
000

SEQ ID NO: 692    moltype =    length =
SEQUENCE: 692
000

SEQ ID NO: 693    moltype =    length =
SEQUENCE: 693
000

SEQ ID NO: 694    moltype =    length =
SEQUENCE: 694
000

SEQ ID NO: 695    moltype =    length =
SEQUENCE: 695
000

SEQ ID NO: 696    moltype =    length =
SEQUENCE: 696
000

SEQ ID NO: 697    moltype =    length =
SEQUENCE: 697
000

SEQ ID NO: 698    moltype =    length =
SEQUENCE: 698
000

SEQ ID NO: 699    moltype =    length =
SEQUENCE: 699
000

SEQ ID NO: 700    moltype =    length =
SEQUENCE: 700
000

SEQ ID NO: 701    moltype =    length =
SEQUENCE: 701
000

SEQ ID NO: 702    moltype =    length =
SEQUENCE: 702
000

SEQ ID NO: 703    moltype =    length =
SEQUENCE: 703
000

SEQ ID NO: 704    moltype =    length =
SEQUENCE: 704
000

SEQ ID NO: 705    moltype =    length =
SEQUENCE: 705
000

SEQ ID NO: 706    moltype =    length =
SEQUENCE: 706

-continued

000

SEQ ID NO: 707  moltype =  length =
SEQUENCE: 707
000

SEQ ID NO: 708  moltype =  length =
SEQUENCE: 708
000

SEQ ID NO: 709  moltype =  length =
SEQUENCE: 709
000

SEQ ID NO: 710  moltype =  length =
SEQUENCE: 710
000

SEQ ID NO: 711  moltype =  length =
SEQUENCE: 711
000

SEQ ID NO: 712  moltype =  length =
SEQUENCE: 712
000

SEQ ID NO: 713  moltype =  length =
SEQUENCE: 713
000

SEQ ID NO: 714  moltype =  length =
SEQUENCE: 714
000

SEQ ID NO: 715  moltype =  length =
SEQUENCE: 715
000

SEQ ID NO: 716  moltype =  length =
SEQUENCE: 716
000

SEQ ID NO: 717  moltype =  length =
SEQUENCE: 717
000

SEQ ID NO: 718  moltype =  length =
SEQUENCE: 718
000

SEQ ID NO: 719  moltype =  length =
SEQUENCE: 719
000

SEQ ID NO: 720  moltype =  length =
SEQUENCE: 720
000

SEQ ID NO: 721  moltype =  length =
SEQUENCE: 721
000

SEQ ID NO: 722  moltype =  length =
SEQUENCE: 722
000

SEQ ID NO: 723  moltype =  length =
SEQUENCE: 723
000

SEQ ID NO: 724  moltype =  length =
SEQUENCE: 724
000

SEQ ID NO: 725  moltype =  length =
SEQUENCE: 725
000

SEQ ID NO: 726  moltype =  length =

-continued

SEQUENCE: 726
000

SEQ ID NO: 727         moltype =    length =
SEQUENCE: 727
000

SEQ ID NO: 728         moltype =    length =
SEQUENCE: 728
000

SEQ ID NO: 729         moltype =    length =
SEQUENCE: 729
000

SEQ ID NO: 730         moltype =    length =
SEQUENCE: 730
000

SEQ ID NO: 731         moltype =    length =
SEQUENCE: 731
000

SEQ ID NO: 732         moltype =    length =
SEQUENCE: 732
000

SEQ ID NO: 733         moltype =    length =
SEQUENCE: 733
000

SEQ ID NO: 734         moltype =    length =
SEQUENCE: 734
000

SEQ ID NO: 735         moltype =    length =
SEQUENCE: 735
000

SEQ ID NO: 736         moltype =    length =
SEQUENCE: 736
000

SEQ ID NO: 737         moltype =    length =
SEQUENCE: 737
000

SEQ ID NO: 738         moltype =    length =
SEQUENCE: 738
000

SEQ ID NO: 739         moltype =    length =
SEQUENCE: 739
000

SEQ ID NO: 740         moltype =    length =
SEQUENCE: 740
000

SEQ ID NO: 741         moltype =    length =
SEQUENCE: 741
000

SEQ ID NO: 742         moltype =    length =
SEQUENCE: 742
000

SEQ ID NO: 743         moltype =    length =
SEQUENCE: 743
000

SEQ ID NO: 744         moltype =    length =
SEQUENCE: 744
000

SEQ ID NO: 745         moltype =    length =
SEQUENCE: 745
000

| | | |
|---|---|---|
| SEQ ID NO: 746<br>SEQUENCE: 746<br>000 | moltype = | length = |
| SEQ ID NO: 747<br>SEQUENCE: 747<br>000 | moltype = | length = |
| SEQ ID NO: 748<br>SEQUENCE: 748<br>000 | moltype = | length = |
| SEQ ID NO: 749<br>SEQUENCE: 749<br>000 | moltype = | length = |
| SEQ ID NO: 750<br>SEQUENCE: 750<br>000 | moltype = | length = |
| SEQ ID NO: 751<br>SEQUENCE: 751<br>000 | moltype = | length = |
| SEQ ID NO: 752<br>SEQUENCE: 752<br>000 | moltype = | length = |
| SEQ ID NO: 753<br>SEQUENCE: 753<br>000 | moltype = | length = |
| SEQ ID NO: 754<br>SEQUENCE: 754<br>000 | moltype = | length = |
| SEQ ID NO: 755<br>SEQUENCE: 755<br>000 | moltype = | length = |
| SEQ ID NO: 756<br>SEQUENCE: 756<br>000 | moltype = | length = |
| SEQ ID NO: 757<br>SEQUENCE: 757<br>000 | moltype = | length = |
| SEQ ID NO: 758<br>SEQUENCE: 758<br>000 | moltype = | length = |
| SEQ ID NO: 759<br>SEQUENCE: 759<br>000 | moltype = | length = |
| SEQ ID NO: 760<br>SEQUENCE: 760<br>000 | moltype = | length = |
| SEQ ID NO: 761<br>SEQUENCE: 761<br>000 | moltype = | length = |
| SEQ ID NO: 762<br>SEQUENCE: 762<br>000 | moltype = | length = |
| SEQ ID NO: 763<br>SEQUENCE: 763<br>000 | moltype = | length = |
| SEQ ID NO: 764<br>SEQUENCE: 764<br>000 | moltype = | length = |
| SEQ ID NO: 765<br>SEQUENCE: 765<br>000 | moltype = | length = |

| | | |
|---|---|---|
| SEQ ID NO: 766 SEQUENCE: 766 000 | moltype = | length = |
| SEQ ID NO: 767 SEQUENCE: 767 000 | moltype = | length = |
| SEQ ID NO: 768 SEQUENCE: 768 000 | moltype = | length = |
| SEQ ID NO: 769 SEQUENCE: 769 000 | moltype = | length = |
| SEQ ID NO: 770 SEQUENCE: 770 000 | moltype = | length = |
| SEQ ID NO: 771 SEQUENCE: 771 000 | moltype = | length = |
| SEQ ID NO: 772 SEQUENCE: 772 000 | moltype = | length = |
| SEQ ID NO: 773 SEQUENCE: 773 000 | moltype = | length = |
| SEQ ID NO: 774 SEQUENCE: 774 000 | moltype = | length = |
| SEQ ID NO: 775 SEQUENCE: 775 000 | moltype = | length = |
| SEQ ID NO: 776 SEQUENCE: 776 000 | moltype = | length = |
| SEQ ID NO: 777 SEQUENCE: 777 000 | moltype = | length = |
| SEQ ID NO: 778 SEQUENCE: 778 000 | moltype = | length = |
| SEQ ID NO: 779 SEQUENCE: 779 000 | moltype = | length = |
| SEQ ID NO: 780 SEQUENCE: 780 000 | moltype = | length = |
| SEQ ID NO: 781 SEQUENCE: 781 000 | moltype = | length = |
| SEQ ID NO: 782 SEQUENCE: 782 000 | moltype = | length = |
| SEQ ID NO: 783 SEQUENCE: 783 000 | moltype = | length = |
| SEQ ID NO: 784 SEQUENCE: 784 000 | moltype = | length = |
| SEQ ID NO: 785 SEQUENCE: 785 | moltype = | length = |

```
SEQ ID NO: 786         moltype =    length =
SEQUENCE: 786
000

SEQ ID NO: 787         moltype =    length =
SEQUENCE: 787
000

SEQ ID NO: 788         moltype =    length =
SEQUENCE: 788
000

SEQ ID NO: 789         moltype =    length =
SEQUENCE: 789
000

SEQ ID NO: 790         moltype =    length =
SEQUENCE: 790
000

SEQ ID NO: 791         moltype =    length =
SEQUENCE: 791
000

SEQ ID NO: 792         moltype =    length =
SEQUENCE: 792
000

SEQ ID NO: 793         moltype =    length =
SEQUENCE: 793
000

SEQ ID NO: 794         moltype =    length =
SEQUENCE: 794
000

SEQ ID NO: 795         moltype =    length =
SEQUENCE: 795
000

SEQ ID NO: 796         moltype =    length =
SEQUENCE: 796
000

SEQ ID NO: 797         moltype =    length =
SEQUENCE: 797
000

SEQ ID NO: 798         moltype =    length =
SEQUENCE: 798
000

SEQ ID NO: 799         moltype =    length =
SEQUENCE: 799
000

SEQ ID NO: 800         moltype = AA   length = 117
FEATURE                Location/Qualifiers
REGION                 1..117
                       note = antibody sequence
source                 1..117
                       mol_type = protein
                       organism = synthetic construct
SEQUENCE: 800
EVQLVESGGG LVQPGGSLRL SCAASGFTFS SYYMSWVRQA PGKGLEWVST IIKSGGYAYY    60
PDSVKDRFTI SRDNSKNTLY LQMSSLRAED TAVYYCVRGG QGAMDYWGQG TTVTVSS      117

SEQ ID NO: 801         moltype = AA   length = 5
FEATURE                Location/Qualifiers
REGION                 1..5
                       note = antibody sequence
source                 1..5
                       mol_type = protein
                       organism = synthetic construct
SEQUENCE: 801
SYYMS                                                                 5
```

```
SEQ ID NO: 802              moltype = AA  length = 17
FEATURE                     Location/Qualifiers
REGION                      1..17
                            note = antibody sequence
source                      1..17
                            mol_type = protein
                            organism = synthetic construct
SEQUENCE: 802
TIIKSGGYAY YPDSVKD                                                         17

SEQ ID NO: 803              moltype = AA  length = 8
FEATURE                     Location/Qualifiers
REGION                      1..8
                            note = antibody sequence
source                      1..8
                            mol_type = protein
                            organism = synthetic construct
SEQUENCE: 803
GGQGAMDY                                                                    8

SEQ ID NO: 804              moltype = AA  length = 107
FEATURE                     Location/Qualifiers
REGION                      1..107
                            note = antibody sequence
source                      1..107
                            mol_type = protein
                            organism = synthetic construct
SEQUENCE: 804
EIVLTQSPAT LSLSPGERAT LSCRASQSIG DYLHWYQQKP GQAPRLLIKY ASQSISGIPA          60
RFSGSGSGTD FTLTITSLEP EDFAVYYCQQ GYSFPYTFGG GTKLEIK                        107

SEQ ID NO: 805              moltype = AA  length = 11
FEATURE                     Location/Qualifiers
REGION                      1..11
                            note = antibody sequence
source                      1..11
                            mol_type = protein
                            organism = synthetic construct
SEQUENCE: 805
RASQSIGDYL H                                                               11

SEQ ID NO: 806              moltype = AA  length = 7
FEATURE                     Location/Qualifiers
REGION                      1..7
                            note = antibody sequence
source                      1..7
                            mol_type = protein
                            organism = synthetic construct
SEQUENCE: 806
YASQSIS                                                                     7

SEQ ID NO: 807              moltype = AA  length = 9
FEATURE                     Location/Qualifiers
REGION                      1..9
                            note = antibody sequence
source                      1..9
                            mol_type = protein
                            organism = synthetic construct
SEQUENCE: 807
QQGYSFPYT                                                                   9

SEQ ID NO: 808              moltype = DNA  length = 351
FEATURE                     Location/Qualifiers
misc_feature                1..351
                            note = antibody sequence
source                      1..351
                            mol_type = other DNA
                            organism = synthetic construct
SEQUENCE: 808
gaagtgcagc tggtggaatc tggcggagga ctggttcaac ctggcggctc tctgagactg          60
tcttgtgccg ccagcggctt caccttcagc agctactaca tgagctgggt ccgacaggcc         120
cctggcaaag gacttgaatg ggtgtccacc atcatcaaga gcggcggcta cgcctactat         180
cccgacagcg tgaaggaccg gttcaccatc tccagagaca cagcaagaa cacctgtac           240
ctgcagatga gcagcctgag agccgaggat accgccgtgt actactgtgt tagaggcgga         300
cagggcgcca tggattattg gggccaggga accacagtga ccgtgtcatc a                  351

SEQ ID NO: 809              moltype = DNA  length = 321
FEATURE                     Location/Qualifiers
misc_feature                1..321
```

```
                            note = antibody sequence
source                      1..321
                            mol_type = other DNA
                            organism = synthetic construct
SEQUENCE: 809
gagattgtgc tgacacagtc tcccgccaca ctgtctctta gccctggcga aagagccaca    60
ctgagctgta gagccagcca gagcatcggc gattacctgc actggtatca gcagaagcct   120
ggacaggccc ctcggctgct gattaagtac gccagccagt ccatcagcgg catccctgcc   180
agattttctg gcagcggctc tggcaccgat ttcaccctga ccatcaccag cctggaacct   240
gaggacttcg ccgtgtacta ctgccagcag ggctacagct tcccctacac atttggcgga   300
ggcaccaagc tggaaatcaa a                                              321

SEQ ID NO: 810              moltype = AA  length = 447
FEATURE                     Location/Qualifiers
REGION                      1..447
                            note = antibody sequence
source                      1..447
                            mol_type = protein
                            organism = synthetic construct
SEQUENCE: 810
EVQLVESGGG LVQPGGSLRL SCAASGFTFS SYYMSWVRQA PGKGLEWVST IIKSGGYAYY     60
PDSVKDRFTI SRDNSKNTLY LQMSSLRAED TAVYYCVRGG QGAMDYWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 811              moltype = AA  length = 214
FEATURE                     Location/Qualifiers
REGION                      1..214
                            note = antibody sequence
source                      1..214
                            mol_type = protein
                            organism = synthetic construct
SEQUENCE: 811
EIVLTQSPAT LSLSPGERAT LSCRASQSIG DYLHWYQQKP GQAPRLLIKY ASQSISGIPA     60
RFSGSGSGTD FTLTITSLEP EDFAVYYCQQ GYSFPYTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 812              moltype = DNA  length = 1341
FEATURE                     Location/Qualifiers
misc_feature                1..1341
                            note = antibody sequence
source                      1..1341
                            mol_type = other DNA
                            organism = synthetic construct
SEQUENCE: 812
gaagtgcagc tggtggaatc tggcggagga ctggttcaac ctggcggctc tctgagactg    60
tcttgtgccg ccagcggctt caccttcagc agctactaca tgagctgggt ccgacaggcc   120
cctggcaaag gacttgaatg ggtgtccacc atcatcaaga gcggcggcta cgcctactat   180
cccgacagcg tgaaggaccg gttcaccatc tccagagaca cagcaagaa caccctgtac   240
ctgcagatga gcagcctgag agccgaggat accgccgtgt actactgtgt tagaggcgga   300
cagggcgcca tggattattg gggccaggga accagtgta ccgtgtcatc agccagcacc   360
aagggcccca gcgtgttccc tctggcccct agcagcaaga gcacatctgg cggaacagcc   420
gccctgggct gcctcgtgaa ggactacttt cccgagcccg tgaccgtgtc ctggaactct   480
ggcgctctga caagcggcgt gcacaccttt ccagccgtgc tgcagagcag cggcctgtac   540
tctctgagca gcgtcgtgac agtgcccagc agctctctgg gcacccagac ctacatctgc   600
aacgtgaacc acaagcccag caacaccaag gtggacaaga aggtggaacc caagagctgc   660
gacaagaccc acacctgtcc ccttgtcct gccccgaaac tgctgggagg cccttccgtg   720
ttcctgttcc cccaaagcc aaggacacc ctgatgatca gccggacccc gaagtgacc   780
tgcgtggtgg tggatgtgtc cacgaggac cctgaagtga agttcaattg gtacgtggac   840
ggcgtggaag tgcacaacgc caagaccaag cctagagagg aacagtacaa cagcacctac   900
cgggtggtgt ccgtgctgac agtgctgcac caggactggc tgaacggcaa agagtacaag   960
tgcaaggtgt ccaacaaggc cctgcctgcc cccatcgaga aaaccatcag caaggccaag  1020
ggccagcccc gcgaacccca ggtgtacaca ctgcccccaa gcagggacga gctgaccaag  1080
aaccagtgtc ccctgacctg tctcgtgaaa ggcttctacc cctccgatat cgccgtggaa  1140
tgggagagca acggcagcc cgagaacaac tacaagacca ccccccctgt gctggacagc  1200
gacggctcat tcttcctgta cagcaagctg accgtggaca gtcccggtg gcagcagggc  1260
aacgtgttca gctgcagcgt gatgcacgag gccctgcaca accactacac ccagaagtcc  1320
ctgagcctga gccctggcaa g                                            1341

SEQ ID NO: 813              moltype = DNA  length = 642
FEATURE                     Location/Qualifiers
misc_feature                1..642
                            note = antibody sequence
source                      1..642
```

```
                        mol_type = other DNA
                        organism = synthetic construct
SEQUENCE: 813
gagattgtgc tgacacagtc tcccgccaca ctgtctctta gccctggcga aagagccaca    60
ctgagctgta gagccagcca gagcatcggc gattacctgc actggtatca gcagaagcct   120
ggacaggccc ctcggctgct gattaagtac gccagccagt ccatcagcgg catccctgcc   180
agatttctg gcagcggctc tggcaccgat ttcaccctga ccatcaccag cctggaacct    240
gaggacttcg ccgtgtacta ctgccagcag ggctacagct cccctacac atttggcgga    300
ggcaccaagc tggaaatcaa acgaaccgtg gccgctccca gcgtgttcat cttcccacct   360
agcgacgagc agctgaagtc cggcacagcc tctgtcgtgt gcctgctgaa caacttctac   420
ccccgcgagg ccaaggtgca gtggaaggtg gacaatgccc tgcagagcgg caacagccag   480
gaaagcgtga ccgagcagga cagcaaggac tccacctaca gcctgagcag caccctgacc   540
ctgagcaagg ccgactacga aagcacaag gtgtacgcct gcgaagtgac ccaccagggc    600
ctgtctagcc ccgtgaccaa gagcttcaac cggggcgagt gt                       642

SEQ ID NO: 814          moltype = AA   length = 117
FEATURE                 Location/Qualifiers
REGION                  1..117
                        note = antibody sequence
source                  1..117
                        mol_type = protein
                        organism = synthetic construct
SEQUENCE: 814
EVQLVESGGG LVQPGGSLRL SCAASGFPFS SYYMSWVRQA PGKGLEWVST IIKSGGYAYY    60
PDSVKDRFTI SRDNSKNTLY LQMSSLRAED TAVYYCVRGG QGAMDYWGQG TTVTVSS      117

SEQ ID NO: 815          moltype = AA   length = 5
FEATURE                 Location/Qualifiers
REGION                  1..5
                        note = antibody sequence
source                  1..5
                        mol_type = protein
                        organism = synthetic construct
SEQUENCE: 815
SYYMS                                                                  5

SEQ ID NO: 816          moltype = AA   length = 17
FEATURE                 Location/Qualifiers
REGION                  1..17
                        note = antibody sequence
source                  1..17
                        mol_type = protein
                        organism = synthetic construct
SEQUENCE: 816
TIIKSGGYAY YPDSVKD                                                    17

SEQ ID NO: 817          moltype = AA   length = 8
FEATURE                 Location/Qualifiers
REGION                  1..8
                        note = antibody sequence
source                  1..8
                        mol_type = protein
                        organism = synthetic construct
SEQUENCE: 817
GGQGAMDY                                                               8

SEQ ID NO: 818          moltype = AA   length = 107
FEATURE                 Location/Qualifiers
REGION                  1..107
                        note = antibody sequence
source                  1..107
                        mol_type = protein
                        organism = synthetic construct
SEQUENCE: 818
EIVLTQSPAT LSLSPGERAT LSCRASQSIG DYLHWYQQKP GQAPRLLIKY ASQSISGIPA    60
RFSGSGSGTD FTLTITSLEP EDFAVYYCQQ GYSFPYTFGG GTKLEIK                  107

SEQ ID NO: 819          moltype = AA   length = 11
FEATURE                 Location/Qualifiers
REGION                  1..11
                        note = antibody sequence
source                  1..11
                        mol_type = protein
                        organism = synthetic construct
SEQUENCE: 819
RASQSIGDYL H                                                          11

SEQ ID NO: 820          moltype = AA   length = 7
FEATURE                 Location/Qualifiers
```

| | | |
|---|---|---|
| REGION | 1..7 | |
| | note = antibody sequence | |
| source | 1..7 | |
| | mol_type = protein | |
| | organism = synthetic construct | |

SEQUENCE: 820
YASQSIS                                                                  7

| | | |
|---|---|---|
| SEQ ID NO: 821 | moltype = AA   length = 9 | |
| FEATURE | Location/Qualifiers | |
| REGION | 1..9 | |
| | note = antibody sequence | |
| source | 1..9 | |
| | mol_type = protein | |
| | organism = synthetic construct | |

SEQUENCE: 821
QQGYSFPYT                                                                9

| | | |
|---|---|---|
| SEQ ID NO: 822 | moltype = DNA   length = 351 | |
| FEATURE | Location/Qualifiers | |
| misc_feature | 1..351 | |
| | note = antibody sequence | |
| source | 1..351 | |
| | mol_type = other DNA | |
| | organism = synthetic construct | |

SEQUENCE: 822
```
gaagtgcagc tggtggaatc tggcggagga ctggttcaac ctggcggctc tctgagactg    60
tcttgtgccg cctctggctt cccattcagc agctactaca tgagctgggt ccgacaggcc   120
cctggcaaag gacttgaatg ggtgtccacc atcatcaaga gcggcggcta cgcctactat   180
cccgacagcg tgaaggaccg gttcaccatc agccgggaca acagcaagaa caccctgtac   240
ctgcagatga gcagcctgag agccgaggat accgccgtgt actactgtgt tagaggcgga   300
cagggcgcca tggattattg gggccaggga accacagtga ccgtgtcatc a            351
```

| | | |
|---|---|---|
| SEQ ID NO: 823 | moltype = DNA   length = 321 | |
| FEATURE | Location/Qualifiers | |
| misc_feature | 1..321 | |
| | note = antibody sequence | |
| source | 1..321 | |
| | mol_type = other DNA | |
| | organism = synthetic construct | |

SEQUENCE: 823
```
gagattgtgc tgacacagtc tcccgccaca ctgtctctta gccctggcga aagagccaca    60
ctgagctgta gagccagcca gagcatcggc gattacctac actggtatca gcagaagcct   120
ggacaggccc ctcggctgct gattaagtac gccagccagt ccatcagcgg catccctgcc   180
agatttctg gcagcggctc tggcaccgat ttcaccctga ccatcaccag cctgaaacct   240
gaggacttcg ccgtgtacta ctgccagcag ggctacagct tccctacac atttggcgga   300
ggcaccaagc tggaaatcaa a                                             321
```

| | | |
|---|---|---|
| SEQ ID NO: 824 | moltype = AA   length = 447 | |
| FEATURE | Location/Qualifiers | |
| REGION | 1..447 | |
| | note = antibody sequence | |
| source | 1..447 | |
| | mol_type = protein | |
| | organism = synthetic construct | |

SEQUENCE: 824
```
EVQLVESGGG LVQPGGSLRL SCAASGFPFS SYYMSWVRQA PGKGLEWVST IIKSGGYAYY     60
PDSVKDRFTI SRDNSKNTLY LQMSSLRAED TAVYYCVRGG QGAMDYWGQG TTVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447
```

| | | |
|---|---|---|
| SEQ ID NO: 825 | moltype = AA   length = 214 | |
| FEATURE | Location/Qualifiers | |
| REGION | 1..214 | |
| | note = antibody sequence | |
| source | 1..214 | |
| | mol_type = protein | |
| | organism = synthetic construct | |

SEQUENCE: 825
```
EIVLTQSPAT LSLSPGERAT LSCRASQSIG DYLHWYQQKP GQAPRLLIKY ASQSISGIPA     60
RFSGSGSGTD FTLTITSLEP EDFAVYYCQQ GYSFPYTFGG GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

| | | |
|---|---|---|
| SEQ ID NO: 826 | moltype = DNA   length = 1341 | |

```
FEATURE                 Location/Qualifiers
misc_feature            1..1341
                        note = antibody sequence
source                  1..1341
                        mol_type = other DNA
                        organism = synthetic construct
SEQUENCE: 826
gaagtgcagc tggtggaatc tggcggagga ctggttcaac ctggcggctc tctgagactg    60
tcttgtgccg cctctggctt cccattcagc agctactaca tgagctgggt ccgacaggcc   120
cctggcaaag gacttgaatg ggtgtccacc atcatcaaga gcggcggcta cgcctactat   180
cccgacagcg tgaaggaccg gttcaccatc agccgggaca acagcaagaa caccctgtac   240
ctgcagatga gcagcctgag agccgaggat accgccgtgt actactgtgt tagaggcgga   300
cagggcgcca tggattattg gggccaggga accacagtga ccgtgtcatc agccagcacc   360
aagggcccca gcgtgttccc tctggcccct agcagcaaga gcacatctgg cggaacagcc   420
gccctgggct gcctcgtgaa ggactacttt cccgagcccg tgaccgtgtc ctggaactct   480
ggcgctctga caagcggcgt gcacaccttt ccagccgtgc tgcagagcag cggcctgtac   540
tctctgagca gcgtcgtgac agtgcccagc agctctctgg gcacccagac ctacatctgc   600
aacgtgaacc acaagcccag caacaccaag gtggacaaga aggtggaacc caagagctgc   660
gacaagaccc acacctgtcc cccttgtcct gcccccgaac tgctgggagg cccttccgtg   720
ttcctgttcc ccccaaagcc caaggacacc ctgatgatca gccggacccc cgaagtgacc   780
tgcgtggtgg tggatgtgtc ccacgaggac cctgaagtga agttcaattg gtacgtggac   840
ggcgtggaag tgcacaacgc caagaccaag cctagagagg aacagtacaa cagcacctac   900
cgggtggtgt ccgtgctgac agtgctgcac caggactggc tgaacggcaa agagtacaag   960
tgcaaggtgt ccaacaaggc cctgcctgcc cccatcgaga aaaccatcag caaggccaag  1020
ggccagcccc gcgaacccca ggtgtacaca ctgcccccaa gcagggacga gctgaccaag  1080
aaccaggtgt ccctgacctg tctcgtgaaa ggcttctacc cctccgatat cgccgtggaa  1140
tgggagagca acggccagcc cgagaacaac tacaagacca ccccccctgt gctggacagc  1200
gacggctcat tcttcctgta cagcaagctg accgtggaca gtcccggtg gcagcagggc  1260
aacgtgttca gctgcagcgt gatgcacgag gccctgcaca accactacac ccagaagtcc  1320
ctgagcctga gccctggcaa g                                            1341

SEQ ID NO: 827          moltype = DNA  length = 642
FEATURE                 Location/Qualifiers
misc_feature            1..642
                        note = antibody sequence
source                  1..642
                        mol_type = other DNA
                        organism = synthetic construct
SEQUENCE: 827
gagattgtgc tgacacagtc tcccgccaca ctgtctctta gccctggcga aagagccaca    60
ctgagctgta gagccagcca gagcatcggc gattacctgc actggtatca gcagaagcct   120
ggacaggccc ctcggctgct gattaagtac gccagccagt ccatcagcgg catccctgcc   180
agattttctg gcagcggctc tggcaccgat ttcaccctga ccatcaccag cctggaacct   240
gaggacttcg ccgtgtacta ctgccagcag ggctacagct cccctacac atttggcgga   300
ggcaccaagc tggaaatcaa acgaaccgtg gccgctccca gcgtgttcat cttcccacct   360
agcgacgagc agctgaagtc cggcacagcc tctgtcgtgt gcctgctgaa caacttctac   420
ccccgcgaag ccaaggtgca gtggaaggtg gacaatgcac tgcagagcgg caacagccag   480
gaaagcgtga ccgagcagga cagcaaggac tccacctaca gcctgagcag caccctgacc   540
ctgagcaagg ccgactacga aagcacaag gtgtacgcct gcgaagtgac ccaccagggc   600
ctgtctagcc ccgtgaccaa gagcttcaac cggggcgagt gt                     642

SEQ ID NO: 828          moltype = AA  length = 117
FEATURE                 Location/Qualifiers
REGION                  1..117
                        note = antibody sequence
source                  1..117
                        mol_type = protein
                        organism = synthetic construct
SEQUENCE: 828
EVQLVESGGG LVQLGGSLRL SCAASGFTFS SYYMSWVRQA PGKGLEWVST IIKSGGYAYY    60
PDSVKDRFTI SRDNSKNTLY LQMNSLRAED TAVYYCVKGG QGAMDYWGQG TTVTVSS     117

SEQ ID NO: 829          moltype = AA  length = 5
FEATURE                 Location/Qualifiers
REGION                  1..5
                        note = antibody sequence
source                  1..5
                        mol_type = protein
                        organism = synthetic construct
SEQUENCE: 829
SYYMS                                                                 5

SEQ ID NO: 830          moltype = AA  length = 17
FEATURE                 Location/Qualifiers
REGION                  1..17
                        note = antibody sequence
source                  1..17
                        mol_type = protein
                        organism = synthetic construct
```

```
SEQUENCE: 830
TIIKSGGYAY YPDSVKD                                                      17

SEQ ID NO: 831          moltype = AA  length = 8
FEATURE                 Location/Qualifiers
REGION                  1..8
                        note = antibody sequence
source                  1..8
                        mol_type = protein
                        organism = synthetic construct
SEQUENCE: 831
GGQGAMDY                                                                 8

SEQ ID NO: 832          moltype = AA  length = 107
FEATURE                 Location/Qualifiers
REGION                  1..107
                        note = antibody sequence
source                  1..107
                        mol_type = protein
                        organism = synthetic construct
SEQUENCE: 832
EIVLTQSPAT LSLSPGERAT LSCRASQSIG DYLHWYQQKP GQAPRLLIYY ASQSISGIPA        60
RFSGSGSGTD FTLTISSLEP EDFAVYYCQQ GYSFPYTFGG GTKLEIK                     107

SEQ ID NO: 833          moltype = AA  length = 11
FEATURE                 Location/Qualifiers
REGION                  1..11
                        note = antibody sequence
source                  1..11
                        mol_type = protein
                        organism = synthetic construct
SEQUENCE: 833
RASQSIGDYL H                                                            11

SEQ ID NO: 834          moltype = AA  length = 7
FEATURE                 Location/Qualifiers
REGION                  1..7
                        note = antibody sequence
source                  1..7
                        mol_type = protein
                        organism = synthetic construct
SEQUENCE: 834
YASQSIS                                                                  7

SEQ ID NO: 835          moltype = AA  length = 9
FEATURE                 Location/Qualifiers
REGION                  1..9
                        note = antibody sequence
source                  1..9
                        mol_type = protein
                        organism = synthetic construct
SEQUENCE: 835
QQGYSFPYT                                                                9

SEQ ID NO: 836          moltype = DNA  length = 351
FEATURE                 Location/Qualifiers
misc_feature            1..351
                        note = antibody sequence
source                  1..351
                        mol_type = other DNA
                        organism = synthetic construct
SEQUENCE: 836
gaagtgcagc tggtggaatc tggcggagga ctggttcagc tcggcggatc tctgagactg        60
tcttgtgccg ccagcggctt caccttcagc agctactaca tggctgggt ccgacaggcc       120
cctggcaaag gacttgaatg ggtgtccacc atcatcaaga gcggcggcta cgcctactat       180
cccgacagcg tgaaggaccg gttcaccatc tccagagaca cagcaagaa caccctgtac       240
ctgcagatga acagcctgag agccgaggac accgccgtgt actactgtgt gaaaggtgga       300
cagggcgcca tggactattg gggccaggga acaaacagta ccgtgtcctc a               351

SEQ ID NO: 837          moltype = DNA  length = 321
FEATURE                 Location/Qualifiers
misc_feature            1..321
                        note = antibody sequence
source                  1..321
                        mol_type = other DNA
                        organism = synthetic construct
SEQUENCE: 837
gagattgtgc tgacacagtc tcccgccaca ctgtctctta gccctggcga aagagccaca        60
ctgagctgta gagccagcca gagcatcggc gattacctgc actggtatca gcagaagcct       120
```

```
ggacaggccc ctcggctgct gatctactat gccagccagt ccatcagcgg catccccgcc    180
agattttctg gcagcggctc tggcaccgat tcacccctga ccataagcag cctggaacct    240
gaggacttcg ccgtgtacta ctgccagcag ggctacagct cccctacac atttggcgga    300
ggcaccaagc tggaaatcaa a                                              321
```

```
SEQ ID NO: 838             moltype = AA   length = 447
FEATURE                    Location/Qualifiers
REGION                     1..447
                           note = antibody sequence
source                     1..447
                           mol_type = protein
                           organism = synthetic construct
SEQUENCE: 838
EVQLVESGGG LVQLGGSLRL SCAASGFTFS SYYMSWVRQA PGKGLEWVST IIKSGGYAYY     60
PDSVKDRFTI SRDNSKNTLY LQMNSLRAED TAVYYCVKGG QGAMDYWGQG TTVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447
```

```
SEQ ID NO: 839             moltype = AA   length = 214
FEATURE                    Location/Qualifiers
REGION                     1..214
                           note = antibody sequence
source                     1..214
                           mol_type = protein
                           organism = synthetic construct
SEQUENCE: 839
EIVLTQSPAT LSLSPGERAT LSCRASQSIG DYLHWYQQKP GQAPRLLIYY ASQSISGIPA     60
RFSGSGSGTD FTLTISSLEP EDFAVYYCQQ GYSFPYTFGG GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

```
SEQ ID NO: 840             moltype = DNA   length = 1341
FEATURE                    Location/Qualifiers
misc_feature               1..1341
                           note = antibody sequence
source                     1..1341
                           mol_type = other DNA
                           organism = synthetic construct
SEQUENCE: 840
gaagtgcagc tggtggaatc tggcggagga ctggttcagc tcggcggatc tctgagactg     60
tcttgtgccg ccagcggctt caccttcagc agctactaca tgagctgggt ccgacaggcc    120
cctggcaaag gacttgaatg ggtgtccacc atcatcaaga gcgcgggcta cgcctactat    180
cccgacagcg tgaaggaccg gttcaccatc tccagagaca acagcaagaa cacccctgtac   240
ctgcagatga acagcctgag agccgaggac accgccgtgt actactgtgt gaaaggtgga    300
cagggcgcca tggactattg gggccaggga acaacagtga ccgtgtcctc agccagcacc    360
aagggcccca gcgtgttccc tctggcccct agcagcaaga gcacatctgg cggaacagcc    420
gccctgggct gcctcgtgaa ggactacttt cccgagcccg tgaccgtgtc ctggaactct    480
ggcgctctga caagcggcgt gcacaccttt ccagccgtgc tgcagagcag cggcctgtac    540
tctctgagca gcgtcgtgac agtgcccagc agctctctgg gcacccagac ctacatctgc    600
aacgtgaacc acaagcccag caacaccaag gtggacaaga ggtggaacc caagagctgc    660
gacaagaccc acacctgtcc cccttgtcct gccccgaac tgctgggagg ccttccgtg     720
ttcctgttcc cccaaagcc caaggacacc ctgatgatca gccggacccc gaagtgacc    780
tgcgtggtgg tggatgtgtc ccacgaggac cctgaagtga agttcaattg gtacgtggac    840
ggcgtggaag tgcacaacgc caagaccaag cctagagagg aacagtacaa cagcacctac    900
cgggtggtgt ccgtgctgac agtgctgcac caggactggc tgaacggcaa agagtacaag    960
tgcaaggtgt ccaacaaggc cctgcctgcc cccatcgaga aaaccatcag caaggccaag   1020
ggccagcccc gcgaaccca ggtgtacaca ctgcccccaa gcagggacga gctgaccaag   1080
aaccaggtgt ccctgacctg tctcgtgaaa ggcttctacc cctccgatat cgccgtggaa   1140
tgggagagca acggccagcc cgagaacaac tacaagacca cccccctgt gctggacagc   1200
gacggctcat tcttcctgta cagcaagctg accgtggaca gtcccggtg gcagcaggg    1260
aacgtgttca gctgcagcgt gatgcacgag gccctgcaca accactacac ccagaagtcc   1320
ctgagcctga gccctggcaa g                                             1341
```

```
SEQ ID NO: 841             moltype = DNA   length = 642
FEATURE                    Location/Qualifiers
misc_feature               1..642
                           note = antibody sequence
source                     1..642
                           mol_type = other DNA
                           organism = synthetic construct
SEQUENCE: 841
gagattgtgc tgacacagtc tcccgccaca ctgtctctta gccctggcga aagagccaca     60
ctgagctgta gagccagcca gagcatcggc gattacctgc actggtatca gcagaagcct    120
ggacaggccc ctcggctgct gatctactat gccagccagt ccatcagcgg catccccgcc    180
agattttctg gcagcggctc tggcaccgat tcacccctga ccataagcag cctggaacct    240
```

```
gaggacttcg ccgtgtacta ctgccagcag ggctacagct tcccctacac atttggcgga    300
ggcaccaagc tggaaatcaa acgaaccgtg gccgctccca gcgtgttcat cttcccacct    360
agcgacgagc agctgaagtc cggcacagcc tctgtcgtgt gcctgctgaa caacttctac    420
ccccgcgagg ccaaggtgca gtggaaggtg gacaatgccc tgcagagcgg caacagccag    480
gaaagcgtga ccgagcagga cagcaaggac tccacctaca gcctgagcag cacccctgacc   540
ctgagcaagg ccgactacga gaagcacaag gtgtacgcct gcgaagtgac ccaccagggc    600
ctgtctagcc ccgtgaccaa gagcttcaac cggggcgagt gt                       642

SEQ ID NO: 842          moltype = AA   length = 117
FEATURE                 Location/Qualifiers
REGION                  1..117
                        note = antibody sequence
source                  1..117
                        mol_type = protein
                        organism = synthetic construct
SEQUENCE: 842
EVQLVESGGG LLQLGGSLRL SCAASGFTFS SYYMSWVRQA PGKGLEWVST IIKSGGYAYY     60
PDSVKDRFTI SRDNSKNTLN LQMNSLRAED TAVYYCVKGG QGAMDYWGQG TTVTVSS       117

SEQ ID NO: 843          moltype = AA   length = 5
FEATURE                 Location/Qualifiers
REGION                  1..5
                        note = antibody sequence
source                  1..5
                        mol_type = protein
                        organism = synthetic construct
SEQUENCE: 843
SYYMS                                                                  5

SEQ ID NO: 844          moltype = AA   length = 17
FEATURE                 Location/Qualifiers
REGION                  1..17
                        note = antibody sequence
source                  1..17
                        mol_type = protein
                        organism = synthetic construct
SEQUENCE: 844
TIIKSGGYAY YPDSVKD                                                    17

SEQ ID NO: 845          moltype = AA   length = 8
FEATURE                 Location/Qualifiers
REGION                  1..8
                        note = antibody sequence
source                  1..8
                        mol_type = protein
                        organism = synthetic construct
SEQUENCE: 845
GGQGAMDY                                                               8

SEQ ID NO: 846          moltype = AA   length = 107
FEATURE                 Location/Qualifiers
REGION                  1..107
                        note = antibody sequence
source                  1..107
                        mol_type = protein
                        organism = synthetic construct
SEQUENCE: 846
EIVLTQSPAT LSLSPGERAT LSCRASQSIG DYLHWYQQKP GQAPRLLIKY ASQSISGIPA     60
RFSGSGSGTD FTLTISSLEP EDFAVYYCQQ GYSFPYTFGG GTKLEIK                  107

SEQ ID NO: 847          moltype = AA   length = 11
FEATURE                 Location/Qualifiers
REGION                  1..11
                        note = antibody sequence
source                  1..11
                        mol_type = protein
                        organism = synthetic construct
SEQUENCE: 847
RASQSIGDYL H                                                          11

SEQ ID NO: 848          moltype = AA   length = 7
FEATURE                 Location/Qualifiers
REGION                  1..7
                        note = antibody sequence
source                  1..7
                        mol_type = protein
                        organism = synthetic construct
SEQUENCE: 848
YASQSIS                                                                7
```

```
SEQ ID NO: 849            moltype = AA  length = 9
FEATURE                   Location/Qualifiers
REGION                    1..9
                          note = antibody sequence
source                    1..9
                          mol_type = protein
                          organism = synthetic construct
SEQUENCE: 849
QQGYSFPYT                                                                 9

SEQ ID NO: 850            moltype = DNA  length = 351
FEATURE                   Location/Qualifiers
misc_feature              1..351
                          note = antibody sequence
source                    1..351
                          mol_type = other DNA
                          organism = synthetic construct
SEQUENCE: 850
gaagtgcagc tggtggaatc tggcggagga ctgctgcagc ttggcggatc tctgagactg    60
tcttgtgccg ccagcggctt caccttcagc agctactaca tgagctgggt ccgacaggcc   120
cctggcaaag gacttgaatg ggtgtccacc atcatcaaga gcggcggcta cgcctactat   180
cccgacagcg tgaaggaccg gttcaccatc tccagagaca acagcaagaa caccctgaac   240
ctgcagatga acagcctgag agccgaggac accgccgtgt actactgtgt gaaaggtgga   300
cagggcgcca tggactattg gggccaggga acaacagtga ccgtgtcctc a            351

SEQ ID NO: 851            moltype = DNA  length = 321
FEATURE                   Location/Qualifiers
misc_feature              1..321
                          note = antibody sequence
source                    1..321
                          mol_type = other DNA
                          organism = synthetic construct
SEQUENCE: 851
gagattgtgc tgacacagtc tcccgccaca ctgtctctta gccctggcga aagagccaca    60
ctgagctgta gagccagcca gagcatcggc gattacctgc actggtatca gcagaagcct   120
ggacaggccc ctcggctgct gattaagtac gccagccagt ccatcagcgg catccctgcc   180
agattttctg gcagcggctc tggcaccgat ttcaccctga ccataagcag cctggaacct   240
gaggacttcg ccgtgtacta ctgccagcag ggctacagct tcccctacac atttggcgga   300
ggcaccaagc tggaaatcaa a                                              321

SEQ ID NO: 852            moltype = AA  length = 447
FEATURE                   Location/Qualifiers
REGION                    1..447
                          note = antibody sequence
source                    1..447
                          mol_type = protein
                          organism = synthetic construct
SEQUENCE: 852
EVQLVESGGG LLQLGGSLRL SCAASGFTFS SYYMSWVRQA PGKGLEWVST IIKSGGYAYY    60
PDSVKDRFTI SRDNSKNTLN LQMNSLRAED TAVYYCVKGG QGAMDYWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                        447

SEQ ID NO: 853            moltype = AA  length = 214
FEATURE                   Location/Qualifiers
REGION                    1..214
                          note = antibody sequence
source                    1..214
                          mol_type = protein
                          organism = synthetic construct
SEQUENCE: 853
EIVLTQSPAT LSLSPGERAT LSCRASQSIG DYLHWYQQKP GQAPRLLIKY ASQSISGIPA    60
RFSGSGSGTD FTLTISSLEP EDFAVYYCQQ GYSFPYTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 854            moltype = DNA  length = 1341
FEATURE                   Location/Qualifiers
misc_feature              1..1341
                          note = antibody sequence
source                    1..1341
                          mol_type = other DNA
                          organism = synthetic construct
SEQUENCE: 854
```

```
gaagtgcagc tggtggaatc tggcggagga ctgctgcagc ttggcggatc tctgagactg   60
tcttgtgccg ccagcggctt caccttcagc agctactaca tgagctgggt ccgacaggcc  120
cctggcaaag gacttgaatg ggtgtccacc atcatcaaga gcggcggcta cgcctactat  180
cccgacagcg tgaaggaccg gttcaccatc tccagagaca acagcaagaa caccctgaac  240
ctgcagatga acagcctgag agccgaggac accgccgtgt actactgtgt gaaaggtgga  300
cagggcgcca tggactattg gggccaggga acaacagtga ccgtgtcctc agccagcacc  360
aagggcccca gcgtgttccc tctggcccct agcagcaaga gcacatctgg cggaacagcc  420
gccctgggct gcctcgtgaa ggactacttt cccgagcccg tgaccgtgtc ctggaactct  480
ggcgctctga caagcggcgt gcacaccttt ccagccgtgc tgcagagcag cggcctgtac  540
tctctgagca gcgtcgtgac agtgccagc agctctctgg gcacccagac ctacatctgc  600
aacgtgaacc acaagcccag caacaccaag gtggacaaga aggtggaacc caagagctgc  660
gacaagaccc acacctgtcc cccttgtcct gcccccgaac tgctgggagg cccttccgtg  720
ttcctgttcc cccaaagcc caaggacacc ctgatgatca gccggacccc gaagtgacc  780
tgcgtggtgg tggatgtgtc ccacgaggac cctgaagtga agttcaattg gtacgtggac  840
ggcgtggaag tgcacaacgc caagaccaag cctagagagg aacagtacaa cagcacctac  900
cgggtggtgt ccgtgctgac agtgctgcac caggactggc tgaacggcaa agagtacaag  960
tgcaaggtgt ccaacaaggc cctgcctgcc cccatcgaga aaaccatcag caaggccaag 1020
ggccagcccc gcgaacccca ggtgtacaca ctgcccccaa gcagggacga gctgaccaag 1080
aaccaggtgt ccctgacctg tctcgtgaaa ggcttctacc cctccgatat cgccgtggaa 1140
tgggagagca acggccagcc cgagaacaac tacaagacca cccccctgt gctgacagc 1200
gacggctcat tcttcctgta cagcaagctg accgtggaca agtcccggtg gcagcagggc 1260
aacgtgttca gctgcagcgt gatgcacgag gccctgcaca accactacac ccagaagtcc 1320
ctgagcctga gccctggcaa g                                          1341

SEQ ID NO: 855          moltype = DNA  length = 642
FEATURE                 Location/Qualifiers
misc_feature            1..642
                        note = antibody sequence
source                  1..642
                        mol_type = other DNA
                        organism = synthetic construct
SEQUENCE: 855
gagattgtgc tgacacagtc tcccgccaca ctgtctctta gccctggcga aagagccaca   60
ctgagctgta gagccagcca gagcatcggc gattaccctga actggtatca gcagaagcct  120
ggacaggccc ctcggctgct gattaagtac gccagccagt ccatcagcgg catccctgcc  180
agattttctg gcagcggctc tggcaccgat ttcaccctga ccataagcag cctggaacct  240
gaggacttcg ccgtgtacta ctgccagcag ggctacagct tccctacac atttggcgga  300
ggcaccagc tggaaatcaa acgaaccgtg gccgctccca gcgtgttcat cttcccacct  360
agcgacgagc agctgaagtc cggcacagcc tctgtcgtgt gcctgctgaa caacttctac  420
ccccgcgagg ccaaggtgca gtggaaggtg gacaatgccc tgcagagcgg caacagccag  480
gaaagcgtga ccgagcagga cagcaaggac tccacctaca gcctgagcag caccctgacc  540
ctgagcaagg ccgactacga aagcacaag gtgtacgcct gcgaagtgac ccaccagggc  600
ctgtctagcc ccgtgaccaa gagcttcaac cggggcgagt gt                    642

SEQ ID NO: 856          moltype = AA  length = 122
FEATURE                 Location/Qualifiers
REGION                  1..122
                        note = antibody sequence
source                  1..122
                        mol_type = protein
                        organism = synthetic construct
SEQUENCE: 856
EVQLLESGGG LVQPGGSLRL SCAASGFTFR SYAVHWVRQA PGKGLEWVSS TEGSGVGTSY   60
TDSVKGRFTI SRDNSKNTLY LQMNSLRAED TAVYYCARML GGGNPLDYLD YWGQGTLVTV  120
SS                                                                122

SEQ ID NO: 857          moltype = AA  length = 5
FEATURE                 Location/Qualifiers
REGION                  1..5
                        note = antibody sequence
source                  1..5
                        mol_type = protein
                        organism = synthetic construct
SEQUENCE: 857
SYAVH                                                               5

SEQ ID NO: 858          moltype = AA  length = 17
FEATURE                 Location/Qualifiers
REGION                  1..17
                        note = antibody sequence
source                  1..17
                        mol_type = protein
                        organism = synthetic construct
SEQUENCE: 858
STEGSGVGTS YTDSVKG                                                 17

SEQ ID NO: 859          moltype = AA  length = 13
FEATURE                 Location/Qualifiers
REGION                  1..13
```

```
                        note = antibody sequence
source                  1..13
                        mol_type = protein
                        organism = synthetic construct
SEQUENCE: 859
MLGGGNPLDY LDY                                                         13

SEQ ID NO: 860          moltype = AA  length = 111
FEATURE                 Location/Qualifiers
REGION                  1..111
                        note = antibody sequence
source                  1..111
                        mol_type = protein
                        organism = synthetic construct
SEQUENCE: 860
QSVLTQPPSA SGTPGQRVTI SCSGSSSNLG EGYDVHWYQQ LPGKAPKLLI YYSDFRPSGV       60
SDRFSGSKSG TSASLAISGL QSEDEADYYC AAWDDSLSSQ VFGGGTQVTV L               111

SEQ ID NO: 861          moltype = AA  length = 14
FEATURE                 Location/Qualifiers
REGION                  1..14
                        note = antibody sequence
source                  1..14
                        mol_type = protein
                        organism = synthetic construct
SEQUENCE: 861
SGSSSNLGEG YDVH                                                        14

SEQ ID NO: 862          moltype = AA  length = 7
FEATURE                 Location/Qualifiers
REGION                  1..7
                        note = antibody sequence
source                  1..7
                        mol_type = protein
                        organism = synthetic construct
SEQUENCE: 862
YSDFRPS                                                                 7

SEQ ID NO: 863          moltype = AA  length = 11
FEATURE                 Location/Qualifiers
REGION                  1..11
                        note = antibody sequence
source                  1..11
                        mol_type = protein
                        organism = synthetic construct
SEQUENCE: 863
AAWDDSLSSQ V                                                           11

SEQ ID NO: 864          moltype = DNA  length = 366
FEATURE                 Location/Qualifiers
misc_feature            1..366
                        note = antibody sequence
source                  1..366
                        mol_type = other DNA
                        organism = synthetic construct
SEQUENCE: 864
gaagttcagc tgctggaatc tggcggcgga ctggttcaac ctggcggatc tctgagactg       60
agctgtgccg ccagcggctt caccttagga agctatgccg tgcactgggt ccgacaggcc     120
cctggaaaag gactggaatg ggtgtccagc accgaaggct ctggcgtggg cacaagctac     180
accgattctg tgaagggcag attcaccatc agccgggaca acagcaagaa caccctgtac     240
ctgcagatga acagcctgag agccgaggac accgccgtgt actactgtgc agaatgctc      300
ggcgaggca accctctgga ctacctggat tattgggcc agggcaccct ggtcacagtc       360
tcttca                                                                366

SEQ ID NO: 865          moltype = DNA  length = 333
FEATURE                 Location/Qualifiers
misc_feature            1..333
                        note = antibody sequence
source                  1..333
                        mol_type = other DNA
                        organism = synthetic construct
SEQUENCE: 865
cagtctgttc tgacacagcc tcctagcgcc tctggcacac tggacagag agtgaccatc       60
agctgtagcg gcagcagctc caatctcggc gagggctatg acgtgcactg gtatcagcag     120
ctgcctggca aggcccctaa actgctgatc tactacagcg acttcagacc cagcggcgtg     180
tccgatagat tcagcggctc taagagcgga acatctgcca gcctggccat ctctggactg     240
cagagcgaag atgaggccga ctactattgc gccgctggg atgatagcct gagcagccaa     300
gttttttggcg gcggaaccca agtgaccgtg cta                                 333
```

```
SEQ ID NO: 866            moltype = AA   length = 452
FEATURE                   Location/Qualifiers
REGION                    1..452
                          note = antibody sequence
source                    1..452
                          mol_type = protein
                          organism = synthetic construct
SEQUENCE: 866
EVQLLESGGG LVQPGGSLRL SCAASGFTFR SYAVHWVRQA PGKGLEWVSS TEGSGVGTSY    60
TDSVKGRFTI SRDNSKNTLY LQMNSLRAED TAVYYCARML GGGNPLDYLD YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 867            moltype = AA   length = 217
FEATURE                   Location/Qualifiers
REGION                    1..217
                          note = antibody sequence
source                    1..217
                          mol_type = protein
                          organism = synthetic construct
SEQUENCE: 867
QSVLTQPPSA SGTPGQRVTI SCSGSSSNLG EGYDVHWYQQ LPGKAPKLLI YYSDFRPSGV    60
SDRFSGSKSG TSASLAISGL QSEDEADYYC AAWDDSLSSQ VFGGGTQVTV LGQPKAAPSV   120
TLFPPSSEEL QANKATLVCL ISDFYPGAVT VAWKADSSPV KAGVETTTPS KQSNNKYAAS   180
SYLSLTPEQW KSHRSYSCQV THEGSTVEKT VAPTECS                            217

SEQ ID NO: 868            moltype = DNA   length = 1356
FEATURE                   Location/Qualifiers
misc_feature              1..1356
                          note = antibody sequence
source                    1..1356
                          mol_type = other DNA
                          organism = synthetic construct
SEQUENCE: 868
gaagttcagc tgctggaatc tggcggcgga ctggttcaac ctggcggatc tctgagactg    60
agctgtgccg ccagcggctt cacctttaga agctatgccg tgcactgggt ccgacaggcc   120
cctggaaaag gactggaatg ggtgtccagc accgaaggct ctggcgtggg cacaagctac   180
accgattctg tgaagggcag attcaccatc agccgggaca cagcaagaa caccctgtac    240
ctgcaaatga cagcctgag agccgaggac accgccgtct actactgtgc cagaatgctc    300
ggcggaggca accctctgga ctacctggat tattgggcc agggcaccct ggtcacagtc   360
tcttcagcca gcaccaaggg ccccagcgtg ttccctctgg cccctagcag caagagcaca   420
tctggcgaa cagccgccct gggctgcctc gtgaaggact actttcccga gcccgtgacc    480
gtgtcctgga actctggcgc tctgacaagc ggcgtgcaca cctttccagc cgtgctgcag   540
agcagcggcc tgtactctct gagcagcgtc gtgacagtgc ccagcagctc tctgggcacc   600
cagacctaca tctgcaacgt gaaccacaag cccagcaaca ccaaggtgga caagaaggtg   660
gaacccaaga gctgcgacaa gacccacacc tgtcccccct tgtcctgccc cgaactgctg   720
ggaggcccct tccgtgttcct gttccccca aagcccaagg accctgat gatcagccgg    780
accccgaag tgacctgcgt ggtggtggat gtgtccacg aggaccctga agtgaagttc     840
aattggtacg tggacggcgt ggaagtgcac aacgccaaga ccaagcctag agaggaacag    900
tacaacagca cctaccgggt ggtgtccgtg ctgacagtgc tgcaccagga ctggctgaac    960
ggcaaagagt acaagtgcaa ggtgtccaac aaggccctgc ctgccccat cgagaaaacc   1020
atcagcaagg ccaagggcca gccccgcgaa cccaggtgt acacactgcc cccaagcagg   1080
gacgagctga ccaagaacca ggtgtccctg acctgtctcg tgaaaggctt ctaccctcc    1140
gatatcgccg tggaatggga gagcaacggc cagcccgaga caactacaa gaccacccc     1200
cctgtgctgg acagcgacgg ctcattcttc ctgtacagca agctgaccgt ggacaagtcc   1260
cggtggcagc agggcaacgt gttcagctgc agcgtgatgc acgaggccct gcacaaccac   1320
tacacccaga gtcccctgag cctgagccct ggcaag                              1356

SEQ ID NO: 869            moltype = DNA   length = 651
FEATURE                   Location/Qualifiers
misc_feature              1..651
                          note = antibody sequence
source                    1..651
                          mol_type = other DNA
                          organism = synthetic construct
SEQUENCE: 869
cagtctgttc tgacacagcc tcctagcgcc tctggcacac tggacagag agtgaccatc     60
agctgtagcg gcagcagctc caatctcggc gagggctatg acgtgcactg gtatcagcag   120
ctgcctggca aggcccctaa actgctgatc tactacagcg acttcagacc cagcggcgtg   180
tccgatagat tcagcggctc taagagcggc acatctgcca gcctggccat ctctggcctg   240
cagagcgaag atgaggccga ctactattgc gccgcctggg atgatagcct gagcagccaa   300
gttttttggcg gcggaaccca agtgaccgtg ctaggccagc ctaaagccgc ccctagcgtg   360
accctgttcc ctccaagcag cgaggaactg caggccaaca ggccaccct cgtgtgcctg    420
atcagcgact ctatcctgg cgccgtgacc gtggcctgga aggccgatag ctctcctgtg    480
aaggccggca ctggaaacca caccccctagc aagcagagca caacaaaata cgccgccagc    540
```

```
agctacctga gcctgacccc cgagcagtgg aagtcccaca gatcctacag ctgccaagtg    600
acccacgagg gcagcaccgt ggaaaagaca gtggccccta ccgagtgcag c             651
```

```
SEQ ID NO: 870              moltype = AA   length = 122
FEATURE                     Location/Qualifiers
REGION                      1..122
                            note = antibody sequence
source                      1..122
                            mol_type = protein
                            organism = synthetic construct
SEQUENCE: 870
EVQLLESGGG LVQPGGSLRL SCAASGFTFR SYAVHWVRQA PGKGLEWVSS TEGSGVGTSY    60
TDSVKGRFTI SRDNSKNTLY LQMNSLRAED TAVYYCARML GGGNPLDYLD YWGQGTLVTV    120
SS                                                                   122

SEQ ID NO: 871              moltype = AA   length = 5
FEATURE                     Location/Qualifiers
REGION                      1..5
                            note = antibody sequence
source                      1..5
                            mol_type = protein
                            organism = synthetic construct
SEQUENCE: 871
SYAVH                                                                5

SEQ ID NO: 872              moltype = AA   length = 17
FEATURE                     Location/Qualifiers
REGION                      1..17
                            note = antibody sequence
source                      1..17
                            mol_type = protein
                            organism = synthetic construct
SEQUENCE: 872
STEGSGVGTS YTDSVKG                                                   17

SEQ ID NO: 873              moltype = AA   length = 13
FEATURE                     Location/Qualifiers
REGION                      1..13
                            note = antibody sequence
source                      1..13
                            mol_type = protein
                            organism = synthetic construct
SEQUENCE: 873
MLGGGNPLDY LDY                                                       13

SEQ ID NO: 874              moltype = AA   length = 111
FEATURE                     Location/Qualifiers
REGION                      1..111
                            note = antibody sequence
source                      1..111
                            mol_type = protein
                            organism = synthetic construct
SEQUENCE: 874
QSVLTQPPSA SGTPGQRVTI SCSGSSSNLG EGYDVHWYQQ LPGKAPKLLI YYSDFRPSGV    60
SDRFSGSKSG TSASLAISGL QSEDEADYYC AAWDDSLSSQ VFGGGTQVTV L             111

SEQ ID NO: 875              moltype = AA   length = 14
FEATURE                     Location/Qualifiers
REGION                      1..14
                            note = antibody sequence
source                      1..14
                            mol_type = protein
                            organism = synthetic construct
SEQUENCE: 875
SGSSSNLGEG YDVH                                                      14

SEQ ID NO: 876              moltype = AA   length = 7
FEATURE                     Location/Qualifiers
REGION                      1..7
                            note = antibody sequence
source                      1..7
                            mol_type = protein
                            organism = synthetic construct
SEQUENCE: 876
YSDFRPS                                                              7

SEQ ID NO: 877              moltype = AA   length = 11
FEATURE                     Location/Qualifiers
REGION                      1..11
```

```
                       note = antibody sequence
source                 1..11
                       mol_type = protein
                       organism = synthetic construct
SEQUENCE: 877
AAWDDSLSSQ V                                                             11

SEQ ID NO: 878         moltype = DNA  length = 366
FEATURE                Location/Qualifiers
misc_feature           1..366
                       note = antibody sequence
source                 1..366
                       mol_type = other DNA
                       organism = synthetic construct
SEQUENCE: 878
gaagttcagc tgctggaatc tggcggcgga ctggttcaac ctggcggatc tctgagactg    60
agctgtgccg ccagcggctt cacctttaga agctatgccg tgcactgggt ccgacaggcc   120
cctggaaaag gactggaatg ggtgtccagc accgaaggct ctggcgtggg cacaagctac   180
accgattctg tgaagggcag attcaccatc agcggggaca cagcaagaa caccctgtac    240
ctgcagatga cagcctgag agccgaggac accgccgtgt actactgtgc cagaatgctc   300
ggcggaggca acccctctga ctacctggat tattggggcc agggcaccct ggtcacagtc   360
tcttca                                                              366

SEQ ID NO: 879         moltype = DNA  length = 333
FEATURE                Location/Qualifiers
misc_feature           1..333
                       note = antibody sequence
source                 1..333
                       mol_type = other DNA
                       organism = synthetic construct
SEQUENCE: 879
cagtctgttc tgacacagcc tcctagcgcc tctggcacac tggacagag agtgaccatc    60
agctgtagcg gcagcagctc caatctcggc gagggctatg acgtgcactg gtatcagcag   120
ctgcctggca aggcccctaa actgctgatc tactacagcg acttcagacc cagcggcgtg   180
tccgatagat tcagcggctc taagagcggc acatctgcca gcctggccat ctctggactg   240
cagagcgaag atgaggccga ctactattgc gccgccgtgg atgatagcct gagcagccaa   300
gttttttggcg gcggaaccca agtgaccgtg cta                               333

SEQ ID NO: 880         moltype = AA  length = 251
FEATURE                Location/Qualifiers
REGION                 1..251
                       note = antibody sequence
source                 1..251
                       mol_type = protein
                       organism = synthetic construct
SEQUENCE: 880
EVQLLESGGG LVQPGGSLRL SCAASGFTFR SYAVHWVRQA PGKGLEWVSS TEGSGVGTSY     60
TDSVKGRFTI SRDNSKNTLY LQMNSLRAED TAVYYCARML GGGNPLDYLD YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCAAGSE QKLISEEDLS    240
GSAAAHHHHH H                                                        251

SEQ ID NO: 881         moltype = AA  length = 217
FEATURE                Location/Qualifiers
REGION                 1..217
                       note = antibody sequence
source                 1..217
                       mol_type = protein
                       organism = synthetic construct
SEQUENCE: 881
QSVLTQPPSA SGTPGQRVTI SCSGSSSNLG EGYDVHWYQQ LPGKAPKLLI YYSDFRPSGV     60
SDRFSGSKSG TSASLAISGL QSEDEADYYC AAWDDSLSSQ VFGGGTQVTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 882         moltype = DNA  length = 753
FEATURE                Location/Qualifiers
misc_feature           1..753
                       note = antibody sequence
source                 1..753
                       mol_type = other DNA
                       organism = synthetic construct
SEQUENCE: 882
gaagttcagc tgctggaatc tggcggcgga ctggttcaac ctggcggatc tctgagactg     60
agctgtgccg ccagcggctt cacctttaga agctatgccg tgcactgggt ccgacaggcc   120
cctggaaaag gactggaatg ggtgtccagc accgaaggct ctggcgtggg cacaagctac   180
accgattctg tgaagggcag attcaccatc agcggggaca cagcaagaa caccctgtac    240
ctgcagatga cagcctgag agccgaggac accgccgtgt actactgtgc cagaatgctc   300
ggcggaggca acccctctga ctacctggat tattggggcc agggcaccct ggtcacagtc   360
```

```
tcttcagcct ccaccaaggg cccatcggtg ttccccctgg caccctcctc caagagcacc    420
tctgggggca cagcggccct gggctgcctg tcaaggact  acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgtcagc gggttctgaa caaaaactca tctcagaaga ggatctgtct   720
ggatcagcgg ccgcccatca tcatcatcat cat                                 753

SEQ ID NO: 883             moltype = DNA   length = 651
FEATURE                    Location/Qualifiers
misc_feature               1..651
                           note = antibody sequence
source                     1..651
                           mol_type = other DNA
                           organism = synthetic construct
SEQUENCE: 883
cagtctgttc tgacacagcc tcctagcgcc tctggcacac ctggacagag agtgaccatc    60
agctgtagcg gcagcagctc caatctcggc gagggctatg acgtgcactg gtatcagcag    120
ctgcctggca aggcccctaa actgctgatc tactacagcg acttcagacc cagcggcgtg    180
tccgatagat tcagcggctc taagagcggc acatctgcca gcctggccat ctctggactg    240
cagagcgaag atgaggccga ctactattgc gccgctgggg atgatagcct gagcagccaa    300
gttttggcg gcgcaaccca agtgaccgtg ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac caccccctagc aagcagagca caacaaata cgccgccagc    540
agctacctga gcctgacccc cgagcagtgg aagtcccaca gatcctacag ctgccaagtg    600
acccacgagg gcagcaccgt ggaaaagaca gtggccccta ccgagtgcag c            651

SEQ ID NO: 884             moltype = AA    length = 563
FEATURE                    Location/Qualifiers
source                     1..563
                           mol_type = protein
                           organism = Oryctolagus cuniculus
SEQUENCE: 884
NYQNGKNNVP RLKLSYKEML ESNNVITFNG LANSSSYHTF LLDEERSRLY VGAKDHIFSF    60
NLVNIKDFQK IAWPVSYTRR DECKWAGKDI LRECANFIKV LKVYNQTHLY ACGTGAFHPI    120
CTYVGIGHHP EDNIFKLEDS HFENGRGKSP YDPKLLTASL LIDGELYSGT AADFMGRDFA    180
IFRTLGQHHP IRTEQHDSRW LNDPRFISAH LIPESDNPED DKVYFFFREN AIDGEHSGKA    240
THARIGQICK NDFGGHRSLV NKWTTFLKAR LICSVPGPNG IDTHFDELQD VFLMNSKDPK    300
NPIVYGVFTT SSNIFRGSAV CMYSMSDVRR VFLGPYAHRD GPNYQWVPFQ GRVPYPRPGT    360
CPSKTFGGFE STKDLPDDVI TFARSHPAMY NPVFPINNRP IMVKTDVNYQ FTQIVVDRVD    420
AEDGQYDVMF IGTDVGTVLK VVSIPKETWH DLEEVLLEEM TVFREPTTIS AMELSTKQQQ    480
LYVGSAAGVA QLPLHRCDIY GKACAECCLA RDPYCAWDGS SCSRYFPTAK RRTRRQDIRN    540
GDPLTHCSDG GIEGRMDHHH HHH                                            563

SEQ ID NO: 885             moltype = DNA   length = 1689
FEATURE                    Location/Qualifiers
source                     1..1689
                           mol_type = other DNA
                           organism = Oryctolagus cuniculus
SEQUENCE: 885
aactatcaga acggcaagaa caacgtgccc cggctgaagc tgagctacaa agagatgctg    60
gaaagcaaca acgtgatcac cttcaacggc ctggccaaca gcagcagcta ccacaccttt    120
ctgctggacg aggaacggtc cagactgtac gtgggagcca aggaccacat cttcagcttc    180
aacctgtca acatcaagga cttccagaaa atcgcctggc ctgtgtccta caccagacgg    240
gatgagtgta aatgggccgg caaggacatc ctgagagagt gcgccaactt catcaaggtg    300
ctgaaggtgt acaatcagac ccacctgtac gcctgtggca ccggcgcttt tcaccctatc    360
tgtacctatg tcggcatcgg ccaccatcct gaggacaata tcttcaagct cgaggacagc    420
cacttcgaga acggcagagg caagagcccc tacgatccca aactgctgac agcctctctg    480
ctgatcgacg gcgagctgta ttctggcaca gccgccgatt tcatgggcag agacttcgcc    540
atcttcagaa ccctgggcca gcatcacccc atcagaaccg agcagcacga cagcagatgg    600
ctgaacgacc ccagattcat cagcgcccat ctgatccccg agagcgacaa ccccgaggac    660
gacaaggtgt acttcttctt ccgggaaaac gccatcgacg ggagcactc tggaaaagcc    720
acacacgcca gaatcggcca gatctgcaag aacgacttcg gcggccacag atccctcgtg    780
aacaagtgga ccaccttcct gaaggccagg ctgatctgtt ctgtgcccgg acctaatggc    840
atcgatccc acttcgacga gctgcaggac gtgttcctga tgaacagcaa ggaccccaag    900
aatcccatcg tgtacggcgt gttcaccacc agcagcaaca tctttagagg cagcgccgtg    960
tgcatgtaca gcatgtccga tgtgcggaga gtgtttctgg gcccctacgc tcacagagat    1020
ggcccccaat atcagtgggt gccattccag ggcagagtgc cctatcctag acctggcacc    1080
tgtcctagca agacctttgg cggcttcgag agcaccaagg acctgcctga cgatgtgatt    1140
acctttgcca gatctcaccc cgccatgtac aacccagtcc ttccccatcaa caaccggccc    1200
atcatggtca agaccgacgt gaactaccag ttcacccaga tcgtggtgga cagagtggat    1260
gccgaggacg gccagtacga cgtgatgttc atcggcaccg atgtgggcac cgtgctgaaa    1320
gtggtgtcta tccccaaaga gacatggcac gacctggaag aggtgctgct ggaagagatg    1380
accgtgttca gagagcccac caccatctcc gccatgaac tgagcacaaa acagcaacag    1440
ctgtatgtgg gctccgccgc tggtgttgct caactgcctc tgcacagatg cgacatctac    1500
```

-continued

```
ggcaaagcct gcgccgagtg ttgcctggcc agagatcctt actgtgcctg ggatggcagc  1560
agctgcagca gatactttcc caccgccaag cggagaacca gacggcagga tatcagaaac  1620
ggcgaccctc tgacacactg cagcgacggt ggcatcgagg gccgcatgga tcatcatcat  1680
caccatcat                                                          1689
```

ANTI-SEMA3A ANTIBODIES AND USES THEREOF

CROSS-REFERENCE TO RELATED APPLICATION

This application is a continuation of U.S. patent application Ser. No. 17/706,543, filed Mar. 28, 2022, which claims the benefit of, and priority to, European Patent Application Serial No. 21165960.2, filed Mar. 30, 2021. The entire disclosure of each of the above applications is hereby incorporated by reference.

SEQUENCE LISTING

This application contains references to amino acid sequences and/or nucleic acid sequences which have been submitted concurrently herewith as the sequence listing.xml file entitled "000034uscoa_SequenceListing.xml", file size 1,040,360 1,040,371 bytes, created on Jan. 9, 2024. The aforementioned sequence listing is hereby incorporated by reference in its entirety pursuant to 37 C.F.R. § 1.52 (e) (5).

FIELD

The present disclosure provides isolated antibodies or antigen-binding fragments thereof that bind to human semaphorin 3A (Sema3A). The isolated antibody or antigen-binding fragments according to the present disclosure i) bind to human Sema3A of the sequence of SEQ ID NO: 600 with a dissociation constant (KD)≤50 nM, ≤20 nM, ≤10 nM, ≤1 nM, or ≤0.1 nM; ii) cross-react with mouse, cynomolgus, rat, pig and/or dog Sema3A, particularly wherein said isolated antibodies or antigen-binding fragments thereof binds to mouse, cynomolgus, rat, pig and/or dog Sema3A with a dissociation constant (KD)≤50 nM, ≤20 nM, ≤10 nM, ≤1 nM, or ≤0.1 nM; iii) bind to human Sema3A of the sequence of SEQ ID NO: 600 with a binding activity as measured by surface plasmon resonance (SPR) of ≥60%, ≥70%, ≥80%, or ≥90%; iv) inhibit the activity of human Sema3A of the sequence of SEQ ID NO: 600 in an in vitro mesangial cell migration assay with an EC50 of ≤10 nM, ≤5 nM, ≤2.5 nM, or ≤1 nM; v) inhibit the activity of human Sema3A of the sequence of SEQ ID NO: 600 in an in vitro growth cone collapse assay with an EC50 of ≤50 nM, ≤25 nM, ≤10 nM, or ≤5 nM; and/or vi) inhibit the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM and/or vii) exhibiting an increased potency against cellular Sema3A, of the sequence of SEQ ID NO: 600, induced HUVEC repulsion. The present disclosure further provides isolated nucleic acid sequences encoding said antibodies or antigen-binding fragments thereof and vectors comprising same, isolated cells expressing said antibodies or antigen-binding fragments thereof, methods of producing said antibodies or antigen-binding fragments thereof and pharmaceutical compositions and kits comprising said antibodies or antigen-binding fragments thereof.

Antibodies according to the present disclosure can be used in the treatment of diseases associated with increased Sema3A levels or activity such as Alport syndrome, acute kidney injury (AKI) primary focal segmental glomerular sclerosis (FSGS), or chronic kidney disease (CKD).

BACKGROUND

Semaphorin 3A (Sema3A) is a secreted dimeric protein that acts as guidance protein. It forms a ternary complex with neuropilin-1 and different plexins which leads to the activation of different signaling pathways. It is a key regulator of cell migration, adhesion, cytoskeletal stabilization and apoptosis. Sema3A is expressed in podocyte in adult kidneys where it is induced after injury.

Excess of Sema3A interferes with the glomerular filtration barrier inducing ultrastructural changes of the filtration barrier leading to podocyte foot process effacement and albuminuria. Sema3A is also highly induced after AKI and exacerbates the injury by promoting tubular inflammation, tubular epithelial cell apoptosis and ultrastructural abnormalities of the filtration barrier. Genetic deficiency or pharmacological inhibition of Sema3A in rodents results in reduced renal damage in different animal models of kidney diseases.

Furthermore, Sema3A is expressed in retinal neurons and endothelium. It has been shown to increase vascular permeability, to promote retinal inflammation and cellular senescence and to inhibit retinal vascular regeneration in rodent models. Sema3A also plays a role in CNS disorders. Sema3A inhibition results in enhanced regeneration and/or preservation of injured axons, decreased apoptotic cell numbers and enhancement of angiogenesis, resulting in considerably better functional recovery.

WO 20141/23186 discloses an avian-mouse chimeric antibody (clone No. 4-2 strain-derived) and two humanized IgG1 variants thereof and suggests their suitability in the treatment of Alzheimer's disease.

WO 2017/074013 discloses anti-Sema3A IgG antibodies A08, C10 and F11 and suggests their suitability in the treatment of cancer.

Currently, no therapeutic option to inhibit Sema3A interaction with its receptors is available to treat patients with e.g. proteinuric kidney disease like Alport syndrome and it is presumed that monoclonal therapeutic Sema3A antibodies could be optimally suited for this. Thus, there exists a great need for novel therapeutic Sema3A antibodies useful for the treatment of diseases that are associated with elevated Sema3A levels or activity such as Alport syndrome, acute kidney injury (AKI) primary focal segmental glomerular sclerosis (FSGS), or chronic kidney disease (CKD) that has not been met so far.

Objects

In view of the prior art, it is an object of the present disclosure to provide novel therapeutic Sema3A antibodies that overcome the shortcomings of Sema3A antibodies of the prior art. In particular it is an object of the present disclosure to provide novel Sema3A antibodies that are high affinity binders of human Sema3A that efficiently block Sema3A activity. Desirable Sema3A antibodies are cross-reactive to Sema3A of multiple species in order to allow for preclinical experiments. They are non-immunogenic in human therapy, i.e. they are human or humanized antibodies. Desirable Sema3A antibodies are selective to Sema3A; they do not bind to off-targets and in particular do not cross-react with other semaphorin protein family members.

Such novel Sema3A antibodies would offer major advances in the treatment of diseases associated with elevated Sema3A levels or activity such as Alport syndrome, acute kidney injury (AKI) primary focal segmental glomerular sclerosis (FSGS), or chronic kidney disease (CKD).

SUMMARY

The above-mentioned object and other objects are achieved by the teaching of the present disclosure. The present disclosure is based on the discovery of novel antibodies that have a specific affinity for Sema3A and can deliver a therapeutic benefit to a subject.

Thus, in a first aspect, the present disclosure relates to an isolated antibody or antigen-binding fragment thereof that that binds to human Sema3A, wherein said isolated antibody or antigen-binding fragment thereof i) binds to human Sema3A of the sequence of SEQ ID NO: 600 with a dissociation constant (KD)≤50 nM, ≤20 nM, ≤10 nM, ≤1 nM, or ≤0.1 nM; ii) cross-reacts with mouse, cynomolgus, rat, pig and/or dog Sema3A, particularly wherein said isolated antibody or antigen-binding fragment thereof binds to mouse, cynomolgus, rat, pig and/or dog Sema3A with a dissociation constant (KD)≤50 nM, ≤20 nM, ≤10 nM, ≤1 nM, or ≤0.1 nM; iii) binds to human Sema3A of the sequence of SEQ ID NO: 600 with a binding activity as measured by surface plasmon resonance (SPR) of ≥60%, ≥70%, ≥80%, or ≥90%; iv) inhibits the activity of human Sema3A of the sequence of SEQ ID NO: 600 in an in vitro mesangial cell migration assay with an EC50 of ≤10 nM, ≤5 nM, ≤2.5 nM, or ≤1 nM; v) inhibits the activity of human Sema3A of the sequence of SEQ ID NO: 600 in an in vitro growth cone collapse assay with an EC50 of ≤50 nM, ≤25 nM, ≤10 nM, or ≤5 nM; vi) inhibits the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM and/or vii) exhibits an increased potency against cellular Sema3A, of the sequence of SEQ ID NO: 600, induced HUVEC repulsion.

The isolated antibody or antigen-binding fragment according to the present disclosure binds with high affinity to human Sema3A and inhibits its function. Thus, the isolated antibody or antigen-binding fragment according to the present disclosure may be used in the treatment of diseases associated with increased Sema3A levels or activity such as i) renal diseases, in particular acute and chronic kidney diseases, diabetic kidney diseases, Alport syndrome, acute and chronic renal failure, polycystic kidney disease (PCKD) and syndrome of inadequate ADH secretion (SIADH); ii) sequelae of renal insufficiency, in particular pulmonary edema, heart failure, uremia, anemia, electrolyte disturbances such as hyperkaliemia and hyponatremia and disturbances in bone and carbohydrate metabolism; iii) vascular hyperpermeability, diabetic retinopathy, deterioration of the blood retinal barrier, macular edema, particularly age related macular edema, non-proliferative age-related macular edema and non-proliferative diabetic macular edema; iv) diseases of the central or peripheral nervous system in particular neuropathic pain, spinal cord injury, multiple sclerosis, traumatic brain injury, brain edema and neurodegenerative diseases, particularly Alzheimer's disease, Parkinson's disease, Huntington's disease, amyotrophic lateral sclerosis, progressive supranuclear paralysis, black substance degeneration, Shy-Drager syndrome, olivopontocerebellar atrophy and spinocerebellar degeneration; v) cancer, in particular intestinal cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophageal cancer, liver cancer, squamous cell carcinoma of the head and neck, skin cancer, urinary tract cancer, prostate cancer, choriocarcinoma, pharyngeal cancer and larynx cancer.

The isolated antibody or antigen-binding fragment according to the present disclosure may further be used in the diagnosis of Sema3A-related disorders.

In a further aspect, the present disclosure relates to an isolated nucleic acid sequence that encodes the antibody or antigen-binding fragment according to the present disclosure.

In a further aspect, the present disclosure relates to a vector comprising a nucleic acid sequence according to the present disclosure.

In a further aspect, the present disclosure relates to an isolated cell expressing the antibody or antigen-binding fragment according to the present disclosure and/or comprising the nucleic acid according to the present disclosure or the vector according to the present disclosure.

In a further aspect, the present disclosure relates to a method of producing the isolated antibody or antigen-binding fragment according to the present disclosure comprising culturing of the cell according to the present disclosure and optionally purification of the antibody or antigen-binding fragment thereof.

In a further aspect, the present disclosure relates to a pharmaceutical composition comprising the isolated antibody or antigen-binding fragment according to the present disclosure or the antibody conjugate according to the present disclosure.

In a further aspect, the present disclosure relates to a kit comprising the isolated antibody or antigen-binding fragment according to the present disclosure or the conjugate according to the present disclosure and instructions for use.

DETAILED DESCRIPTION

The present disclosure may be understood more readily by reference to the following detailed description of the disclosure and the examples included therein.

Definitions

Unless defined otherwise, all technical and scientific terms used herein have the meaning commonly understood by one of ordinary skill in the art to which this disclosure belongs. The following references, however, can provide one of skill in the art to which this disclosure pertains with a general definition of many of the terms used in this disclosure, and can be referenced and used so long as such definitions are consistent with the meaning commonly understood in the art. Such references include, but are not limited to, Singleton et al., Dictionary of Microbiology and Molecular Biology (2nd ed. 1994); The Cambridge Dictionary of Science and Technology (Walker ed., 1988); Hale & Marham, The Harper Collins Dictionary of Biology (1991); Lackie et al., The Dictionary of Cell & Molecular Biology (3d ed. 1999); and Cellular and Molecular Immunology, Eds. Abbas, Lichtman and Pober, 2nd Edition, W.B. Saunders Company. Any additional technical resource available to the person of ordinary skill in the art providing definitions of terms used herein having the meaning commonly understood in the art can be consulted. For the purposes of the present disclosure, the following terms are further defined. Additional terms are defined elsewhere in the description. As used herein and in the appended claims, the singular forms "a," and "the" include plural reference unless the context clearly dictates otherwise. Thus, for example, reference to "a gene" is a reference to one or more genes and includes equivalents thereof known to those skilled in the art, and so forth.

In the context of the present disclosure, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

In this context, the term "about" or "approximately" means within 80% to 120%, alternatively within 90% to 110%, including within 95% to 105% of a given value or range.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Unless otherwise indicated, a particular polypeptide sequence also implicitly encompasses conservatively modified variants thereof.

As used herein "Sema3A" designates "semaphorin 3A", also known as "HH16", "SemD", "COLL1", "SEMA1", "SEMAD", "SEMAL", "coll-1", "Hsema-I", "SEMAIII", "Hsema-III", "collapsin 1", "semaphorin D", "semaphorin III", and "semaphorin L".

The terms "anti-Sema3A antibody" and "an antibody that binds to Sema3A" refer to an antibody that is capable of binding Sema3A with sufficient affinity such that the antibody is useful as a diagnostic and/or therapeutic agent in targeting Sema3A. In one embodiment, the extent of binding of an anti-Sema3A antibody to an unrelated, non-Sema3A protein is less than about 10%, less than about 5%, or less than about 2% of the binding of the antibody to Sema3A as measured, e.g., by standard ELISA procedure. In certain embodiments, an antibody that binds to Sema3A has a binding activity (EC50) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M). In certain embodiments, an anti-Sema3A antibody binds to an epitope of Sema3A that is conserved among Sema3A from different species.

The term "antibody", as used herein, is intended to refer to immunoglobulin molecules. Antibodies may comprise four polypeptide chains, two heavy (H) chains (about 50-70 kDa) and two light (L) chains (about 25 kDa) which are typically inter-connected by disulfide bonds. In particular embodiments, the antibody is composed of two identical pairs of polypeptide chains. The amino-terminal portion of each chain includes a "variable" region of about 100 to 110 or more amino acids primarily responsible for antigen recognition. The heavy chain variable region is abbreviated herein as VH, the light chain variable region is abbreviated herein as VL. The carboxyl-terminal portion of each chain defines a constant region primarily responsible for effector function. The heavy chain constant region can comprise e.g. three domains CH1, CH2 and CH3. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs, arranged from amino-terminus to carboxy-terminus e.g., in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (Kabat et al., Sequences of Proteins of Immunological Interest, 5th Ed. Public Health Service, National Institutes of Health, Bethesda, MD. (1991)) and/or those residues from a "hypervariable loop" (Chothia and Lesk; J Mol Biol 196: 901-917 (1987)). In some instances, a complementarity determining region can include amino acids from both a CDR region defined according to Kabat and a hypervariable loop.

"Framework" or FR residues are those variable domain residues other than the hypervariable region residues.

The phrase "constant region" refers to the portion of the antibody molecule that confers effector functions.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. In particular embodiments, the antibody according to the present disclosure is an IgG antibody. Several of these may be further divided into subclasses or isotypes, e.g. IgG1, IgG2, IgG3, IgG4, IgA1 and IgA2. In particular embodiments, the antibody according to the present disclosure is an IgG1, an IgG2, an IgG3 or an IgG4 antibody, more particularly an IgG1 or an IgG4 antibody. Different isotypes may have different effector functions. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hyper variable region(s) of an antibody, e.g., the CDR1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320).

Nonlimiting examples of "functional fragments" or "antigen-binding antibody fragments" include Fab, Fab', F(ab')2, Fv fragments, domain antibodies (dAb), complementarity determining region (CDR) fragments, single-chain antibodies (scFv), single chain antibody fragments, diabodies, triabodies, tetrabodies, minibodies, linear antibodies (Zapata et al., Protein Eng., 8 (10): 1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multispecific antibodies such as bi- and tri-specific antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "bispecific" or "bifunctional" antibody is understood to have each of its binding sites identical. The F(ab')$_2$ or Fab may be engineered to minimize or completely remove the intermolecular disulfide interactions that occur between the $C_{H1}$ and $C_L$ domains. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of Fvs see Pluckthun in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteine residues from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteine residues between them.

The term "mutein" or "variant" can be used interchangeably and refers to an antibody or antigen-binding fragment that contains at least one amino acid substitution, deletion, or insertion in the variable region or the portion equivalent to the variable region, provided that the mutein or variant retains the desired binding affinity or biological activity. Variants of the antibodies or antigen-binding antibody fragments contemplated in the disclosure are molecules in which the binding activity of the antibody or antigen-binding antibody fragment is maintained.

A "chimeric antibody" or antigen-binding fragment thereof is defined herein as one, wherein the variable domains are derived from a non-human origin and some or all constant domains are derived from a human origin.

"Humanized antibodies" contain CDR regions derived from a non-human species, such as mouse, that have, for example, been engrafted, along with any necessary framework back-mutations, into human sequence-derived V regions. Thus, for the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., Nature 332:323-27 (1988); and Presta, Curr. Opin. Struct. Biol. 2:593-96 (1992), each herein incorporated by reference.

"Human antibodies" or "fully human antibodies" comprise human derived CDRs, i.e. CDRs of human origin. Fully human antibodies may comprise a low number of germline deviations compared with the closest human germline reference determined based on the IMGT database (http://www.imgt.org). For example, a fully human antibody according to the current disclosure may comprise up to 1, 2, 3, 4, 5, 6, 7, 8, 9 or 10 germline deviations in the CDRs compared with the closest human germline reference. Fully human antibodies can be developed from human derived B cells by cloning techniques in combination with a cell enrichment or immortalization step. The majority of fully human antibodies, however, are isolated either from immunized mice transgenic for the human IgG locus or from sophisticated combinatorial libraries by phage display (Bruggemann M., Osborn M. J., Ma B., Hayre J., Avis S., Lundstrom B. and Buelow R., Human Antibody Production in Transgenic Animals, Arch Immunol Ther Exp (Warsz.) 63 (2015), 101-108; Carter P. J., Potent antibody therapeutics by design, Nat Rev Immunol 6 (2006), 343-357; Frenzel A., Schirrmann T. and Hust M., Phage display-derived human antibodies in clinical development and therapy, MAbs 8 (2016), 1177-1194; Nelson A. L., Dhimolea E. and Reichert J. M., Development trends for human monoclonal antibody therapeutics, Nat Rev Drug Discov 9 (2010), 767-774.)).

Several techniques are available to generate fully human antibodies (cf. WO2008/112640 A3). Cambridge Antibody Technologies (CAT) and Dyax have obtained antibody cDNA sequences from peripheral B cells isolated from immunized humans and devised phage display libraries for the identification of human variable region sequences of a particular specificity. Briefly, the antibody variable region sequences are fused either with the Gene III or Gene VIII structure of the M13 bacteriophage. These antibody variable region sequences are expressed either as Fab or single chain Fv (scFv) structures at the tip of the phage carrying the respective sequences. Through rounds of a panning process using different levels of antigen binding conditions (stringencies), phages expressing Fab or scFv structures that are specific for the antigen of interest can be selected and isolated. The antibody variable region cDNA sequences of selected phages can then be elucidated using standard sequencing procedures. These sequences may then be used for the reconstruction of a full antibody having the desired isotype using established antibody engineering techniques. Antibodies constructed in accordance with this method are considered fully human antibodies (including the CDRs). In order to improve the immunoreactivity (antigen binding affinity and specificity) of the selected antibody, an in vitro maturation process can be introduced, including a combinatorial association of different heavy and light chains, deletion/addition/mutation at the CDR3 of the heavy and light chains (to mimic V-J, and V-D-J recombination), and random mutations (to mimic somatic hypermutation). An example of a "fully human" antibody generated by this method is the anti-tumor necrosis factor α antibody, Humira (adalimumab).

"Human Engineered™" antibodies generated by altering the parent sequence according to the methods set forth in Studnicka et al., U.S. Pat. No. 5,766,886.

An antibody of the disclosure may be derived from a recombinant antibody gene library. The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function. Typically, heavy chain VH-CH1 and light chain VL-CL of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

A variety of procedures have been described for human antibodies deriving from phage-display libraries. Such libraries may be built on a single master framework, into which diverse in vivo-formed (i. e. human-derived) CDRs are allowed to recombine as described by Carlsson and Söderlind Exp. Rev. Mol. Diagn. 1 (1), 102-108 (2001), Söderlin et al., Nat. Biotech. 18, 852-856 (2000) and U.S. Pat. No. 6,989,250. Alternatively, such an antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064. For a review of phage display screening (for example see Hoet R M et al, Nat Biotechnol 2005; 23(3):344-8), the well-established hybridoma technology (for example see Köhler and Milstein Nature. 1975 Aug. 7; 256(5517):495-7), or immunization of mice inter alia immunization of hMAb mice (e.g. VelocImmune Mouse®).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. For example, the monoclonal antibodies to be used may be made by the hybridoma method first described by Kohler et al., Nature, 256: 495 [1975, or may be made by recombinant DNA methods (see, e.g., U.S. Pat. No. 4,816,567). The "monoclonal antibodies" may also be recombinant, chimeric, humanized, human, Human Engineered™, or antibody fragments, for example.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or non-proteinaceous solutes.

An "isolated" nucleic acid is one that has been identified and separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

As used herein, an antibody "binds specifically to", is "specific to/for" or "specifically recognizes" an antigen of interest, e.g. Sema3A, is one that binds the antigen with sufficient affinity such that the antibody is useful as a therapeutic agent in targeting a cell or tissue expressing the antigen. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent $K_D$ for the antigen of less than about $10^{-4}$ M, alternatively less than about $10^{-5}$ M, alternatively less than about $10^{-6}$ M, alternatively less than about $10^{-7}$ M, alternatively less than about $10^{-8}$ M, alternatively less than about $10^{-9}$ M, alternatively less than about $10^{-10}$ M, alternatively less than about $10^{-11}$ M, alternatively less than about $10^{-12}$ M, or less.

An antibody "binds selectively to," is "selective to/for" or "selectively recognizes" an antigen if such antibody is able to discriminate between such antigen and one or more reference antigen(s). In particular, an antibody that "binds selectively to" an antigen does not significantly cross-react with proteins other than orthologs and variants (e.g. mutant forms, splice variants, or proteolytically truncated forms) of the aforementioned antigen target. In its most general form, "selective binding", "binds selectively to", is "selective to/for" or "selectively recognizes" is referring to the ability of the antibody to discriminate between the antigen of interest and an unrelated antigen, as determined, for example, in accordance with one of the following methods. Such methods comprise but are not limited to surface plasmon resonance (SPR), Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative is more than 5-fold, 10-fold, 50-fold, and preferably more than 100-fold. Typically, determination of binding selectivity is performed by using not a single reference antigen, but a set of about three to five unrelated antigens, such as milk powder, BSA, transferrin or the like.

"Binding affinity" or "affinity" refers to the strength of the total sum of non-covalent interactions between a single binding site of a molecule and its binding partner. Unless indicated otherwise, as used herein, "binding affinity" refers to intrinsic binding affinity which reflects a 1:1 interaction between members of a binding pair (e.g. an antibody and an antigen). The dissociation constant "$K_D$" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. Affinity can be measured by common methods known in the art, including those described herein. In one embodiment, the "$K_D$" or "$K_D$ value" according to this disclosure is measured by using surface plasmon resonance assays using a Biacore T200 instrument (GE Healthcare Biacore, Inc.). Other suitable devices are BIACORE T100, BIACORE®-2000, BIACORe 4000, a BIACORE®-3000 (BIAcore, Inc., Piscataway, NJ), or ProteOn XPR36 instrument (Bio-Rad Laboratories, Inc.).

As used herein, the term "epitope" includes any protein determinant capable of specific binding to an immunoglobulin or T-cell receptor. Epitopic determinants usually consist of chemically active surface groupings of molecules such as amino acids or sugar side chains, or combinations thereof and usually have specific three-dimensional structural characteristics, as well as specific charge characteristics.

An "antibody that binds to the same epitope" as a reference antibody or "an antibody which competes for binding" to a reference antibody refers to an antibody that blocks binding of the reference antibody to its antigen in a competition assay by 10%, 20%, 30%, 40%, 50% or more, and conversely, the reference antibody blocks binding of the antibody to its antigen in a competition assay by 10%, 20%, 30%, 40%, 50% or more.

The term "maturated antibodies" or "maturated antigen-binding fragments" such as maturated Fab variants or "optimized" variants includes derivatives of an antibody or antibody fragment exhibiting stronger binding—i. e. binding with increased affinity—to a given antigen such as the extracellular domain of a target protein. Maturation is the process of identifying a small number of mutations within the six CDRs of an antibody or antibody fragment leading to this affinity increase. The maturation process is the combination of molecular biology methods for introduction of mutations into the antibody and screening for identifying the improved binders.

"Percent (%) sequence identity" with respect to a reference polynucleotide or polypeptide sequence, respectively, is defined as the percentage of nucleic acid or amino acid residues, respectively, in a candidate sequence that are identical with the nucleic acid or amino acid residues, respectively, in the reference polynucleotide or polypeptide sequence, respectively, after aligning the sequences and introducing gaps, if necessary, to achieve the maximum percent sequence identity. Conservative substitutions are not considered as part of the sequence identity. Preferred are un-gapped alignments. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

"Sequence homology" indicates the percentage of amino acids that either is identical or that represent conservative amino acid substitutions.

An "antagonistic" antibody or a "blocking" antibody is one which significantly inhibits (either partially or completely) a biological activity of the antigen it binds. In particular embodiments, the antibody or antigen-binding fragment according to the present disclosure is a Sema3A blocking antibody or antigen-binding fragment thereof.

The term "antibody conjugate" refers to an antibody conjugated to one or more molecules including drugs—in which case the antibody conjugate is referred to as "antibody-drug conjugate" ("ADC")—and high molecular weight molecules such as peptides or proteins.

The term "antibody-drug conjugate" or "ADC" refers to an antibody conjugated to one or more cytotoxic or cytostatic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). Immunoconjugates have been used for the local delivery of cytotoxic agents, i.e., drugs that kill or inhibit the growth or proliferation of cells, in the treatment of cancer (e.g. Liu et al., Proc Natl. Acad. Sci. (1996), 93, 8618-8623)). Immunoconjugates allow for the targeted delivery of a drug moiety to a tumor, and intracellular accumulation therein, where systemic administration of unconjugated drugs may result in unacceptable levels of toxicity to normal cells and/or tissues. Toxins used in antibody-toxin conjugates include bacterial toxins such as diphtheria toxin, plant toxins such as ricin, small molecule toxins such as geldanamycin. The toxins may exert their cytotoxic effects by mechanisms including tubulin binding, DNA binding, or topoisomerase inhibition.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell", "host cell line", and "host cell culture" are used interchangeably and refer to cells into which at least one exogenous nucleic acid has been introduced, including the progeny of such cells. Host cells include "transformants" and "transformed cells", "transfectants" and "transfected cells" and "transduced cells" which include the primary transformed/transfected/transduced cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

As used herein, the phrase "therapeutically effective amount" is meant to refer to an amount of therapeutic or prophylactic antibody that would be appropriate to elicit the desired therapeutic or prophylactic effect or response, including alleviating some or all of such symptoms of disease or reducing the predisposition to the disease, when administered in accordance with the desired treatment regimen.

The term "pharmaceutical formulation"/"pharmaceutical composition" refers to a preparation which is in such form as to permit the biological activity of an active ingredient contained therein to be effective, and which contains no additional components which are unacceptably toxic to a subject to which the formulation would be administered.

Antibodies According to the Present Disclosure

In one aspect the present disclosure relates to an isolated antibody or antigen-binding fragment thereof binding to human Sema3A, wherein said isolated antibody or antigen-binding fragment thereof binds to human Sema3A of the sequence of SEQ ID NO: 600 with a dissociation constant (KD)≤50 nM, ≤20 nM, ≤10 nM, ≤1 nM, or ≤0.1 nM. In particular embodiments, the isolated antibody or antigen-binding fragment thereof binds to the His-tagged human Sema3A domain of SEQ ID NO: 582 with a dissociation constant (KD)≤50 nM, ≤20 nM, ≤10 nM, ≤1 nM, or ≤0.1 nM.

In another aspect the present disclosure relates to an isolated antibody or antigen-binding fragment thereof binding to human Sema3A, wherein said isolated antibody or antigen-binding fragment thereof cross-reacts with mouse, cynomolgus, rat, pig and/or dog Sema3A, particularly wherein said isolated antibody or antigen-binding fragment thereof binds to mouse, cynomolgus, rat, pig and/or dog Sema3A with a dissociation constant (KD)≤50 nM, ≤20 nM, ≤10 nM, ≤1 nM, or ≤0.1 nM.

In particular such embodiments, said affinities are to mouse Sema3A of SEQ ID NO: 601, to cynomolgus Sema3A of SEQ ID NO: 602, to rat Sema3A of SEQ ID NO: 603, to pig Sema3A of SEQ ID NO: 604 and to dog Sema3A of SEQ ID NO: 605. In particular embodiments, said affinities are to His-tagged mouse Sema3A domain of SEQ ID NO: 583, to His-tagged cynomolgus Sema3A domain of SEQ ID NO: 586, to His-tagged rat Sema3A domain of SEQ ID NO: 584, to His-tagged pig Sema3A domain of SEQ ID NO: 587 and to His-tagged dog Sema3A domain of SEQ ID NO: 585.

In another aspect the present disclosure relates to an isolated antibody or antigen-binding fragment thereof binding to human Sema3A, wherein said isolated antibody or antigen-binding fragment thereof binds to human Sema3A with a binding activity as measured by surface plasmon resonance (SPR) of ≥60%, ≥70%, ≥80%, or ≥90%. In particular embodiments, the isolated antibody or antigen-binding fragment thereof bids to human Sema3A of the sequence of SEQ ID NO: 600 with a binding activity as measured by surface plasmin resonance (SPR) of ≥60%, ≥70%, ≥80%, or ≥90%. In particular embodiments, the isolated antibody or antigen-binding fragment thereof bids to His-tagged human Sema3A domain of the sequence of SEQ ID NO: 582 with a binding activity as measured by surface plasmon resonance (SPR) of ≥60%, ≥70%, ≥80%, or ≥90%.

In another aspect the present disclosure relates to an isolated antibody or antigen-binding fragment thereof binding to human Sema3A, wherein said isolated antibody or antigen-binding fragment thereof inhibits the activity of human Sema3A of the sequence of SEQ ID NO: 600 in an in vitro mesangial cell migration assay with an EC50 of ≤10 nM, ≤5 nM, ≤2.5 nM, or ≤1 nM.

In particular, the isolated antibody or antigen-binding fragment according to the present disclosure inhibits the activity of human Sema3A of the sequence of SEQ ID NO: 600 in an in vitro scratch assay using human primary mesangial cells and described in more detail in Example 9.

In another aspect the present disclosure relates to an isolated antibody or antigen-binding fragment thereof binding to human Sema3A, wherein said isolated antibody or antigen-binding fragment thereof inhibits the activity of human Sema3A of the sequence of SEQ ID NO: 600 in an in vitro growth cone collapse assay with an EC50 of ≤50 nM, ≤25 nM, ≤10 nM, or ≤5 nM.

In particular, the isolated antibody or antigen-binding fragment according to the present disclosure inhibits Sema3A-induced cytoskeletal collapse in an in vitro growth cone collapse assay using mouse dorsal root ganglion (DRG) neurons as described in more detail in Example 10. The in vitro growth cone assay described in Example 10 is a modified version of the growth cone assay described in Mikule et al. (PMID: 12077190).

In another aspect the present disclosure relates to an isolated antibody or antigen-binding fragment thereof binding to human Sema3A, wherein said isolated antibody or antigen-binding fragment thereof inhibits the activity of human Sema3A of the sequence of SEQ ID NO: 600 in an in vitro HUVEC repulsion assay with an EC50 of ≤1 nM, or ≤0.3 nM, ≤0.1 nM, ≤0.07 nM, ≤0.06 nM.

In particular, the isolated antibody or antigen-binding fragment according to the present disclosure inhibits Sema3A induced cell repulsion in an in vitro repulsion assay using Sema3A, of the sequence of SEQ ID NO: 600, expressing HEK293 cells seeded on a confluent monolayer of human umbilical vein endothelial cells (HUVEC) as described in Example 11.

In a further aspect, the present disclosure relates to an isolated antibody or antigen-binding fragment thereof binding to Sema3A, of the sequence of SEQ ID NO: 600, wherein said isolated antibody or antigen-binding fragment thereof exhibits an improved potency in HUVEC repulsion assay; i) wherein said isolated antibody or antigen-binding fragment thereof exhibits an improved potency in HUVEC repulsion assay in comparison to TPP-17755 with SEQ IDs 81, 85, 97, 98, or to TPP-11489 with SEQ IDs 1, 5, 17, 18, or to TPP-30788 with SEQ IDs 800, 804, 810, 811, or to TPP-30789 with SEQ IDs 814, 818, 824, 825, or to TPP-30790 with SEQ IDs 828, 832, 838, 839, or to TPP-30791 with SEQ IDs 842, 846, 852, 853; ii) wherein said isolated antibody or antigen-binding fragment thereof exhibits preferably a >400-fold, preferably a >50-fold, preferably >5-fold, preferably >2-fold increased potency against cellular Sema3A induced HUVEC repulsion based on the EC-50 values, in comparison to TPP-17755 with SEQ IDs 81, 85, 97, 98, or to TPP-11489 with SEQ IDs 1, 5, 17, 18, or to TPP-30788 with SEQ IDs 800, 804, 810, 811, or to TPP-30789 with SEQ IDs 814, 818, 824, 825, or to TPP-30790 with SEQ IDs 828, 832, 838, 839, or to TPP-30791 with SEQ IDs 842, 846, 852, 853; iii) wherein said isolated antibody or antigen-binding fragment thereof exhibits at least a 30% increased percent inhibition, preferably at least 50% increased percent inhibition of Sema3A in comparison to TPP-17755, to TPP-11489, to TPP-30788, to TPP-30789, TPP-30790, or to TPP-30791, with aforementioned sequences; iv) wherein said isolated antibody or antigen-binding fragment thereof has a two-digit picomolar activity against human Sema3A in vitro HUVEC repulsion assay, while prior art antibody potencies of TPP-17755, TPP-11489, TPP-30788, TPP-30789, TPP-30790, or TPP-30791, with aforementioned sequences, are in the three-digit picomolar or even nanomolar range; v) wherein said isolated antibody or antigen-binding fragment thereof inhibits the activity of human Sema3A in an in vitro HUVEC repulsion assay with an EC50 of ≤1 nM, or ≤0.3 nM, ≤0.1 nM, ≤0.07 nM, ≤0.06 nM, as described in Example 11.

The isolated antibody or antigen-binding fragment of the present disclosure show an improved potency in HUVEC repulsion assay compared to TPP-30788-TPP-30791 (BI clone I to IV), which might be due to a binding to a different epitope of human Sema3A.

In another aspect, the present disclosure relates to an isolated antibody or antigen-binding fragment thereof binding to Sema3A, wherein said isolated antibody or antigen-binding fragment thereof inhibits the activity of Sema3A in vivo, since the antibodies according to the present disclosure reduce Sema3A-induced urinary Albumin excretion. Thus in a further aspect, the present disclosure relates to an isolated antibody or antigen-binding fragment thereof binding to Sema3A, wherein said isolated antibody or antigen-binding fragment thereof exhibits an improved inhibitory activity of Sema3A in vivo, i) wherein said the antibodies exhibit an increased reduction of Sema3A-induced urinary Albumin excretion compared to TPP-30788 (BI clone I); ii) wherein said the antibodies exhibit an increased reduction of Sema3A-induced urinary Albumin excretion compared to TPP-17755 (Samsung); iii) wherein said the antibodies exhibit an increased reduction of Sema3A-induced urinary Albumin excretion compared to TPP-11489 (Chiome) as described in Example 12.

The isolated antibody or antigen-binding fragment of the present disclosure show an improved efficacy in an in vivo model for induced urinary Albumin excretion compared to TPP-30788-TPP-30791 (BI clone I to IV), which might be due to a binding to a different epitope of human Sema3A.

Thus, in a further aspect, the present disclosure relates to an isolated antibody or antigen-binding fragment thereof that binds to human Sema3A, wherein said isolated antibody or antigen-binding fragment thereof i) exhibits an increased stability (e.g. increased stress-stability when diluted in PBS to 25 mg/ml and incubated at 700 rpm and 40° C. for two weeks) compared to TPP-30788 (BI clone I); ii) wherein the increased stability exhibits an increased amount of monomeric anti-Sema3A antibody compared to TPP-30788 (BI clone I) measured by SEC; iii) wherein the increased stability exhibits a decreased percentage of the LC and HC of the anti-Sema3A antibody compared to TPP-30788 (BI clone I) measured by cGE, proving a reduced rate of degradation which is measured by the presence of remaining LC and HC, iv) wherein the increased stability exhibits that the amount of monomeric anti-Sema3A antibody is maintained, e.g. Δ % monomer=1 after the incubation at 40° C., 700 rpm for two weeks; v) wherein the increased stability exhibits that the amount of LC and HC of the anti-Sema3A antibody is maintained e.g. Δ % LC+HC<1 after the incubation at 40° C., 700 rpm for two weeks.

Thus, in a further aspect, the present disclosure relates to TPP-23298, that binds to human Sema3A, wherein said isolated antibody or antigen-binding fragment thereof i) exhibits an increased stability (e.g. increased stress-stability when diluted in PBS to 25 mg/ml and incubated at 700 rpm and 40° C. for two weeks) compared to TPP-30788 (BI clone I); ii) wherein the increased stability exhibits an increased amount of monomeric anti-Sema3A antibody compared to TPP-30788 (BI clone I) measured by SEC; iii) wherein the increased stability exhibits a decreased percentage of the LC and HC of the anti-Sema3A antibody compared to TPP-30788 (BI clone I) measured by cGE, proving a reduced rate of degradation which is measured by the presence of remaining LC and HC, iv) wherein the increased stability exhibits that the amount of monomeric anti-Sema3A antibody is maintained, e.g. Δ % monomer=1 after the incubation at 40° C., 700 rpm for two weeks; v) wherein the increased stability exhibits that the amount of LC and HC of the anti-Sema3A antibody is maintained e.g. Δ % LC+HC<1 after the incubation at 40° C., 700 rpm for two weeks.

Thus, in a further aspect, the present disclosure relates to an isolated antibody or antigen-binding fragment thereof that binds to human Sema3A, wherein said isolated antibody or antigen-binding fragment thereof i) exhibits an increased solubility; ii) wherein the increased solubility is measured in mg/ml after concentration at 90% recovery; iii) wherein the solubility is increased compared to TPP-30788 (BI clone I); iv) wherein the solubility is increased ≤1 fold, ≤1.5 fold, ≤2 fold compared to TPP-30788 (BI clone I); v) wherein the increased solubility exhibits that the percentage of monomeric anti-Sema3A antibody is not increased after concentration e.g. Δ % monomer<1 measured by SEC.

Thus, in a further aspect, the present disclosure relates to TPP-23298, that binds to human Sema3A, wherein said isolated antibody or antigen-binding fragment thereof i) exhibits an increased solubility; ii) wherein the increased solubility is measured in mg/ml after concentration at 90% recovery; iii) wherein the solubility is increased compared to TPP-30788 (BI clone I); iv) wherein the solubility is increased ≤1 fold, ≤1.5 fold, ≤2 fold compared to TPP-30788 (BI clone I); v) wherein the increased solubility exhibits that the percentage of monomeric anti-Sema3A antibody is not increased after concentration e.g. Δ % monomer<1 measured by SEC.

Thus, in a further aspect, the present disclosure relates to an isolated antibody or antigen-binding fragment thereof that binds to human Sema3A, wherein said isolated antibody or antigen-binding fragment thereof i) exhibits an increased viscosity compared to water or PBS; ii) exhibits a reduced viscosity in PBS compared to TPP-30788 (BI clone I); iii) wherein the viscosity is measured by a Viscosizer and exhibits a cP value of 5.1 (150 mg/ml).

Thus, in a further aspect, the present disclosure relates to TPP-23298, that binds to human Sema3A, wherein said isolated antibody or antigen-binding fragment thereof i) exhibits an increased viscosity compared to water or PBS; ii) exhibits a reduced viscosity in PBS compared to TPP-30788 (BI clone I); iii) wherein the viscosity is measured by a Viscosizer and exhibits a cP value of 5.1 (150 mg/ml).

In particular the isolated antibody or antigen-binding fragment according to the present disclosure shows a much higher solubility and stability, is more resistant to heat stress and is less viscous in PBS buffer than TPP-30788 as described in Example 17.

In particular TPP-23298 shows a much higher solubility and stability, is more resistant to heat stress and is less viscous in PBS buffer than TPP-30788 as described in Example 17.

In another aspect the present disclosure relates to an isolated antibody or antigen-binding fragment thereof binding to human Sema3A, which can be produced with high titers in mammalian cells; i) wherein high titer is ≤200 mg/L as described in Example 16.

In another aspect the present disclosure relates to an isolated antibody or antigen-binding fragment thereof binding to human Sema3A, wherein the antibody exhibits a higher binding selectivity to active Sema3A (TPP-13211) over cleaved Sema3A TPP-19068; i) wherein the antibody exhibits a higher binding selectivity to active Sema3A (TPP-13211) compared to the binding selectivity of TPP-30788-TPP-30791 to active Sema3A, as described in Example 8.

In another aspect the present disclosure relates to TPP-23298 binding to human Sema3A, wherein the antibody exhibits a higher binding selectivity to active Sema3A (TPP-13211) over cleaved Sema3A TPP-19068; i) wherein the antibody exhibits a higher binding selectivity to active Sema3A (TPP-13211) compared to the binding selectivity of TPP-30788-TPP-30791 to active Sema3A, as described in Example 8.

In another aspect the present disclosure relates to an isolated antibody or antigen-binding fragment thereof binding to human Sema3A, wherein the antibody binds a different epitope on Sema3A compared to TPP-30788; i) wherein the epitope binding is measured in SPR assay, as described in Example 5a. All antibodies binding the same epitope and competing with the binding of the isolated antibody or antigen-binding fragment according to the present disclosure are comprised by the present disclosure.

In another aspect the present disclosure relates to TPP-23298 binding to human Sema3A, wherein the antibody binds a different epitope on Sema3A compared to TPP-30788; i) wherein the epitope binding is measured in SPR assay, as described in Example 5a. All antibodies binding the same epitope and competing with the binding of the isolated antibody or antigen-binding fragment according to the present disclosure are comprised by the present disclosure.

In another aspect the present disclosure relates to an isolated antibody or antigen-binding fragment thereof that competes with the isolated antibody or antigen-binding fragment according to any one of the preceding claims for binding to Sema3A and wherein the isolated antibody or antigen-binding fragment does not compete with the binding of an antibody with the SEQ IDs NO 800, NO 804, NO 810 or NO 811 to Sema3A.

The isolated antibody or antigen-binding fragment according to the present disclosure may exhibit any combination of the above described characteristics.

The isolated antibody or antigen-binding fragment according to the present disclosure is a Sema3A blocking antibody or antigen-binding fragment thereof. In particular embodiments, the antibody binds specifically and more particularly selectively to the Sema3A domain of Semaphorin3A and interferes with the interaction of its receptor neuropilin-1.

In particular embodiments, the isolated antibody or antigen-binding fragment thereof according to the present disclosure cross-reacts with mouse, cynomolgus, rat, pig and/or dog Sema3A, particularly having an affinity to mouse, cynomolgus, rat, pig and/or dog Sema3A that is less than 100-fold, particularly less than 50-fold, more particularly less than 25-fold, even more particularly less than 10-fold and most particularly less than 5-fold different to that to human Sema3A.

In particular embodiments, the isolated antibody or antigen-binding fragment thereof according to the present disclosure does not significantly cross-react with human Sema3B, Sema3C, Sema3D, Sema3E, Sema3F and/or Sema3G. In particular, the isolated antibody or antigen-binding fragment thereof does not significantly cross-react with human Sema3G.

In particular embodiments, the isolated antibody or antigen-binding fragment thereof according to the present disclosure inhibits Sema3A-induced albuminuria and/or proteinuria.

In particular embodiments, the isolated antibody or antigen-binding fragment thereof according to the present disclosure inhibits Sema3A-induced fibrosis.

In particular embodiments, the isolated antibody or antigen-binding fragment according to the present disclosure comprises a heavy chain variable domain that is at least 90%, at least 95%, at least 98%, at least 99%, or 100% identical to SEQ ID NO: 141, and a light chain variable domain that is at least 90%, at least 95%, at least 98%, at least 99%, or 100% identical to SEQ ID NO: 145.

In particular other embodiments, the isolated antibody or antigen-binding fragment according to the present disclosure comprises a heavy chain variable domain that is at least 90%, at least 95%, at least 98%, at least 99%, or 100% identical to SEQ ID NO: 61, and a light chain variable domain that is at least 90%, at least 95%, at least 98%, at least 99%, or 100% identical to SEQ ID NO: 65.

In particular embodiments, the isolated antibody or antigen-binding fragment according to the present disclosure comprises a heavy chain antigen-binding region that comprises an H-CDR3 comprising the sequence RDDYTSRDAFDX (SEQ ID NO: 594), wherein X is selected from the group consisting of Y and V. Particularly, X is Y.

In particular embodiments, the isolated antibody or antigen-binding fragment according to the present disclosure comprises a light chain antigen-binding region that comprises an L-CDR3 comprising the sequence $X_1$AWDDSLN$X_2X_3X_4$V (SEQ ID NO: 598), wherein $X_1$ is selected from the group consisting of A and H, wherein $X_2$ is selected from the group consisting of V, D, and G, in particular wherein $X_2$ is selected from the group consisting of V and D, wherein $X_3$ is selected from the group consisting of I and Y, and wherein $X_4$ is selected from the group consisting of P and V.

In particular embodiments, the isolated antibody or antigen-binding fragment according to the present disclosure comprises a heavy chain antigen-binding region that comprises an H-CDR3 as defined above and a light chain antigen-binding region that comprises an L-CDR3 as defined above.

In particular embodiments, the isolated antibody or antigen-binding fragment according to the present disclosure comprises a heavy chain antigen-binding region that comprises an H-CDR3 comprising the sequence SGYSSSWFDPDFDY (SEQ ID NO: 64).

In particular embodiments, the isolated antibody or antigen-binding fragment according to the present disclosure comprises a light chain antigen-binding region that comprises an L-CDR3 comprising the sequence $X_1SYX_2GX_3NPYVV$ (SEQ ID NO: 599), wherein X1 is selected from the group consisting of S and Q; wherein $X_2$ is selected from the group consisting of E and A; and wherein $X_3$ is selected from the group consisting of P, I, and S. In particular, $X_3$ is selected from the group consisting of P and I.

In particular embodiments, the isolated antibody or antigen-binding fragment according to the present disclosure comprises a heavy chain antigen-binding region that comprises an H-CDR3 as defined above and a light chain antigen-binding region that comprises an L-CDR3 as defined above.

In particular embodiments, the isolated antibody or antigen-binding fragment according to the present disclosure comprises a heavy chain antigen-binding region that comprises an H-CDR1 comprising the sequence $SYX_1MX_2$ (SEQ ID NO: 588), wherein X1 is selected from G and A and wherein $X_2$ is selected from H, S and L. Particularly, the heavy chain antigen-binding region comprises an H-CDR1 comprising the sequence SYAMX (SEQ ID NO: 589), wherein X is selected from S and L.

In particular embodiments, the isolated antibody or antigen-binding fragment according to the present disclosure comprises a heavy chain antigen-binding region that comprises an H-CDR2 comprising the sequence $AIGX_1GGDTYYADSVX_2G$ (SEQ ID NO: 590), wherein $X_1$ is selected from T and Y, and wherein $X_2$ is selected from K and M. Particularly, the heavy chain antigen-binding region comprises an H-CDR2 comprising the sequence AIGXGGDTYYADSVKG (SEQ ID NO: 591), wherein X is selected from T and Y.

In particular embodiments, the isolated antibody or antigen-binding fragment according to the present disclosure comprises a heavy chain antigen-binding region that comprises an H-CDR3 comprising the sequence RDDYTSRDAFDX (SEQ ID NO: 594), wherein X is selected from the group consisting of Y and V. Particularly, X is Y.

In particular embodiments, the isolated antibody or antigen-binding fragment according to the present disclosure comprises a heavy chain antigen-binding region that comprises an H-CDR1, an H-CDR2 and an H-CDR3 as defined above.

In particular embodiments, the isolated antibody or antigen-binding fragment according to the present disclosure comprises a light chain antigen-binding region that comprises an L-CDR1 comprising the sequence SGSSSNIGSNTVN (SEQ ID NO: 46).

In particular embodiments, the isolated antibody or antigen-binding fragment according to the present disclosure comprises a light chain antigen-binding region that comprises an L-CDR2 comprising the sequence YDDLXPS (SEQ ID NO: 596), wherein X is selected from L and R. Particularly, the light chain antigen-binding region comprises an L-CDR2 comprising the sequence YDDLRPS (SEQ ID NO: 127).

In particular embodiments, the isolated antibody or antigen-binding fragment according to the present disclosure comprises a light chain antigen-binding region that comprises an L-CDR3 comprising the sequence $X_1AWDDSLNX_2X_3X_4V$ (SEQ ID NO: 598), wherein X1 is selected from the group consisting of A and H, wherein $X_2$ is selected from the group consisting of V, D, and G, in particular wherein $X_2$ is selected from the group consisting of V and D, wherein $X_3$ is selected from the group consisting of I and Y, and wherein $X_4$ is selected from the group consisting of P and V.

In particular embodiments, the isolated antibody or antigen-binding fragment according to the present disclosure comprises a light chain antigen-binding region that comprises an L-CDR1, and L-CDR2 and an L-CDR3 as defined above.

In particular embodiments, the isolated antibody or antigen-binding fragment according to the present disclosure comprises a heavy chain antigen-binding region that comprises an H-CDR1, an H-CDR2 and an H-CDR3 as defined above and a light chain antigen-binding region that comprises an L-CDR1, and L-CDR2 and an L-CDR3 as defined above.

In particular such embodiments, the amino acid residue directly adjacent to the H-CDR1 at its 5' end (corresponding to residue 30 of reference VH domain of SEQ ID NO: 121) is S or Y.

In particular other embodiments, the isolated antibody or antigen-binding fragment according to the present disclosure comprises a heavy chain antigen-binding region that comprises an H-CDR1 comprising the sequence SYEMN (SEQ ID NO: 62).

In particular embodiments, the isolated antibody or antigen-binding fragment according to the present disclosure comprises a heavy chain antigen-binding region that comprises an H-CDR2 comprising the sequence $GISWNSGX_1IX_2YADSVKG$ (SEQ ID NO: 592), wherein $X_1$ is selected from W and S and $X_2$ is selected from G and D. Particularly, the heavy chain antigen-binding region comprises an H-CDR2 comprising the sequence GISWNSGWIXYADSVKG (SEQ ID NO: 593), wherein X is selected from G and D.

In particular embodiments, the isolated antibody or antigen-binding fragment according to the present disclosure comprises a heavy chain antigen-binding region that comprises an H-CDR3 comprising the sequence SGYSSSWFDPDFDY (SEQ ID NO: 64).

In particular embodiments, the isolated antibody or antigen-binding fragment according to the present disclosure comprises a heavy chain antigen-binding region that comprises an H-CDR1, an H-CDR2 and an H-CDR3 as defined above.

In particular embodiments, the isolated antibody or antigen-binding fragment according to the present disclosure comprises a light chain antigen-binding region that comprises an L-CDR1 comprising the sequence TGSSSXIGAGYDVH (SEQ ID NO: 595), wherein X is selected from N and D.

In particular embodiments, the isolated antibody or antigen-binding fragment according to the present disclosure comprises a light chain antigen-binding region that comprises an L-CDR2 comprising the sequence GXSNRPS (SEQ ID NO: 597), wherein X is selected from N and A.

In particular embodiments, the isolated antibody or antigen-binding fragment according to the present disclosure comprises a light chain antigen-binding region that comprises an L-CDR3 comprising the sequence $X_1SYX_2GX_3NPYVV$ (SEQ ID NO: 599), wherein X1 is selected from the group consisting of S and Q, wherein $X_2$ is selected from the group consisting of E and A, and wherein $X_3$ is selected from the group consisting of P, I, and S. Particularly, $X_3$ is selected from the group consisting of P and I.

In particular embodiments, the isolated antibody or antigen-binding fragment according to the present disclosure comprises a light chain antigen-binding region that comprises an L-CDR1, and L-CDR2 and an L-CDR3 as defined above.

In particular embodiments, the isolated antibody or antigen-binding fragment according to the present disclosure comprises a heavy chain antigen-binding region that comprises an H-CDR1, an H-CDR2 and an H-CDR3 as defined above and a light chain antigen-binding region that comprises an L-CDR1, and L-CDR2 and an L-CDR3 as defined above.

In particular such embodiments, the three amino acid residues directly adjacent to the H-CDR1 at its 5' end (corresponding to residues 28 to 30 of reference VH domain of SEQ ID NO: 101) are $X_1FX_2$, wherein X1 is selected form T and D and $X_2$ is selected from S and D.

In particular embodiments, the isolated antibody or antigen-binding fragment according to the present disclosure comprises:

i) a heavy chain antigen-binding region that comprises an H-CDR3 comprising SEQ ID NO: 44 and a light chain antigen-binding region that comprises an L-CDR3 comprising SEQ ID NO: 48; or ii) a heavy chain antigen-binding region that comprises an H-CDR3 comprising SEQ ID NO: 64 and a light chain antigen-binding region that comprises an L-CDR3 comprising SEQ ID NO: 68; or.

iii) a heavy chain antigen-binding region that comprises an H-CDR3 comprising SEQ ID NO: 104 and a light chain antigen-binding region that comprises an L-CDR3 comprising SEQ ID NO: 108; or iv) a heavy chain antigen-binding region that comprises an H-CDR3 comprising SEQ ID NO: 124 and a light chain antigen-binding region that comprises an L-CDR3 comprising SEQ ID NO: 128; or v) a heavy chain antigen-binding region that comprises an H-CDR3 comprising SEQ ID NO: 144 and a light chain antigen-binding region that comprises an L-CDR3 comprising SEQ ID NO: 148; or vi) a heavy chain antigen-binding region that comprises an H-CDR3 comprising SEQ ID NO: 164 and a light chain antigen-binding region that comprises an L-CDR3 comprising SEQ ID NO: 168; or vii) a heavy chain antigen-binding region that comprises an H-CDR3 comprising SEQ ID NO: 184 and a light chain antigen-binding region that comprises an L-CDR3 comprising SEQ ID NO: 188; or viii) a heavy chain antigen-binding region that comprises an H-CDR3 comprising SEQ ID NO: 204 and a light chain antigen-binding region that comprises an L-CDR3 comprising SEQ ID NO: 208; or ix) a heavy chain antigen-binding region that comprises an H-CDR3 comprising SEQ ID NO: 224 and a light chain antigen-binding region that comprises an L-CDR3 comprising SEQ ID NO: 228; or x) a heavy chain antigen-binding region that comprises an H-CDR3 comprising SEQ ID NO: 244 and a light chain antigen-binding region that comprises an L-CDR3 comprising SEQ ID NO: 248; or xi) a heavy chain antigen-binding region that comprises an H-CDR3 comprising SEQ ID NO: 264 and a light chain antigen-binding region that comprises an L-CDR3 comprising SEQ ID NO: 268; or xii) a heavy chain antigen-binding region that comprises an H-CDR3 comprising SEQ ID NO: 284 and a light chain antigen-binding region that comprises an L-CDR3 comprising SEQ ID NO: 288; or xiii) a heavy chain antigen-binding region that comprises an H-CDR3 comprising SEQ ID NO: 304 and a light chain antigen-binding region that comprises an L-CDR3 comprising SEQ ID NO: 308; or xiv) a heavy chain antigen-binding region that comprises an H-CDR3 comprising SEQ ID NO: 324 and a light chain antigen-binding region that comprises an L-CDR3 comprising SEQ ID NO: 328; or xv) a heavy chain antigen-binding region that comprises an H-CDR3 comprising SEQ ID NO: 344 and a light chain antigen-binding region that comprises an L-CDR3 comprising SEQ ID NO: 348; or xvi) a heavy chain antigen-binding region that comprises an H-CDR3 comprising SEQ ID NO: 364 and a light chain antigen-binding region that comprises an L-CDR3 comprising SEQ ID NO: 368; or xvii) a heavy chain antigen-binding region that comprises an H-CDR3 comprising SEQ ID NO: 384 and a light chain antigen-binding region that comprises an L-CDR3 comprising SEQ ID NO: 388; or xviii) a heavy chain antigen-binding region that comprises an H-CDR3 comprising SEQ ID NO: 404 and a light chain antigen-binding region that comprises an L-CDR3 comprising SEQ ID NO: 408; or xix) a heavy chain antigen-binding region that comprises an H-CDR3 comprising SEQ ID NO: 424 and a light chain antigen-binding region that comprises an L-CDR3 comprising SEQ ID NO: 428; or xx) a heavy chain antigen-binding region that comprises an H-CDR3 comprising SEQ ID NO: 444 and a light chain antigen-binding region that comprises an L-CDR3 comprising SEQ ID NO: 448; or xxi) a heavy chain antigen-binding region that comprises an H-CDR3 comprising SEQ ID NO: 464 and a light chain antigen-binding region that comprises an L-CDR3 comprising SEQ ID NO: 468; or xxii) a heavy chain antigen-binding region that comprises an H-CDR3 comprising SEQ ID NO: 484 and a light chain antigen-binding region that comprises an L-CDR3 comprising SEQ ID NO: 488; or xxiii) a heavy chain antigen-binding region that comprises an H-CDR3 comprising SEQ ID NO: 504 and a light chain antigen-binding region that comprises an L-CDR3 comprising SEQ ID NO: 508; or xxiv) a heavy chain antigen-binding region that comprises an H-CDR3 comprising SEQ ID NO: 524 and a light chain antigen-binding region that comprises an L-CDR3 comprising SEQ ID NO: 528; or xxv) a heavy chain antigen-binding region that comprises an H-CDR3 comprising SEQ ID NO: 544 and a light chain antigen-binding region that comprises an L-CDR3 comprising SEQ ID NO: 548; or xxvi) a heavy chain antigen-binding region that comprises an H-CDR3 comprising SEQ ID NO: 564 and a light chain antigen-binding region that comprises an L-CDR3 comprising SEQ ID NO: 568.

In particular embodiments, the isolated antibody or antigen-binding fragment according to the present disclosure comprises a heavy chain antigen-binding region that comprises an H-CDR1 comprising any one of SEQ ID NOs: 42, 62, 102, 122, 142, 162, 182, 202, 222, 242, 262, 282, 302, 322, 342, 362, 382, 402, 422, 442, 462, 482, 502, 522, 542, and 562.

In particular embodiments, the isolated antibody or antigen-binding fragment according to the present disclosure comprises a heavy chain antigen-binding region that comprises an H-CDR2 comprising any one of SEQ ID NOs: 43, 63, 103, 123, 143, 163, 183, 203, 223, 243, 263, 283, 303, 323, 343, 363, 383, 403, 423, 443, 463, 483, 503, 523, 543, and 563.

In particular embodiments, the isolated antibody or antigen-binding fragment according to the present disclosure comprises a light chain antigen-binding region that comprises an L-CDR1 comprising any one of SEQ ID NOs: 46, 66, 106, 126, 146, 166, 186, 206, 226, 246, 266, 286, 306, 326, 346, 366, 386, 406, 426, 446, 466, 486, 506, 526, 546, and 566.

In particular embodiments, the isolated antibody or antigen-binding fragment according to the present disclosure comprises a light chain antigen-binding region that comprises an L-CDR2 comprising any one of SEQ ID NOs: 47, 67, 107, 127, 147, 167, 187, 207, 227, 247, 267, 287, 307, 327, 347, 367, 387, 407, 427, 447, 467, 487, 507, 527, 547, and 567.

In particular embodiments, the isolated antibody or antigen-binding fragment according to the present disclosure comprises:

i) a heavy chain antigen-binding region that comprises an H-CDR1 comprising SEQ ID NO: 42, an H-CDR2 comprising SEQ ID NO: 43, and an H-CDR3 comprising SEQ ID NO: 44 and a light chain antigen-binding region that comprises an L-CDR1 comprising SEQ ID NO: 46, an L-CDR2 comprising SEQ ID NO: 47, and an L-CDR3 comprising SEQ ID NO: 48; or ii) a heavy chain antigen-binding region that comprises an H-CDR1 comprising SEQ ID NO: 62, an H-CDR2 comprising SEQ ID NO: 63, and an H-CDR3 comprising SEQ ID NO: 64 and a light chain antigen-binding region that comprises an L-CDR1 comprising SEQ ID NO: 66, an L-CDR2 comprising SEQ ID NO: 67, and an L-CDR3 comprising SEQ ID NO: 68; or iii) a heavy chain antigen-binding region that comprises an H-CDR1 comprising SEQ ID NO: 102, an H-CDR2 comprising SEQ ID NO: 103, and an H-CDR3 comprising SEQ ID NO: 104 and a light chain antigen-binding region that comprises an L-CDR1 comprising SEQ ID NO: 106, an L-CDR2 comprising SEQ ID NO: 107, and an L-CDR3 comprising SEQ ID NO: 108; or iv) a heavy chain antigen-binding region that comprises an H-CDR1 comprising SEQ ID NO: 122, an H-CDR2 comprising SEQ ID NO: 123, and an H-CDR3 comprising SEQ ID NO: 124 and a light chain antigen-binding region that comprises an L-CDR1 comprising SEQ ID NO: 126, an L-CDR2 comprising SEQ ID NO: 127, and an L-CDR3 comprising SEQ ID NO: 128; or v) a heavy chain antigen-binding region that comprises an H-CDR1 comprising SEQ ID NO: 142, an H-CDR2 comprising SEQ ID NO: 143, and an H-CDR3 comprising SEQ ID NO: 144 and a light chain antigen-binding region that comprises an L-CDR1 comprising SEQ ID NO: 146, an L-CDR2 comprising SEQ ID NO: 147, and an L-CDR3 comprising SEQ ID NO: 148; or vi) a heavy chain antigen-binding region that comprises an H-CDR1 comprising SEQ ID NO: 162, an H-CDR2 comprising SEQ ID NO: 163, and an H-CDR3 comprising SEQ ID NO: 164 and a light chain antigen-binding region that comprises an L-CDR1 comprising SEQ ID NO: 166, an L-CDR2 comprising SEQ ID NO: 167, and an L-CDR3 comprising SEQ ID NO: 168; or vii) a heavy chain antigen-binding region that comprises an H-CDR1 comprising SEQ ID NO: 182, an H-CDR2 comprising SEQ ID NO: 183, and an H-CDR3 comprising SEQ ID NO: 184 and a light chain antigen-binding region that comprises an L-CDR1 comprising SEQ ID NO: 186, an L-CDR2 comprising SEQ ID NO: 187, and an L-CDR3 comprising SEQ ID NO: 188; or viii) a heavy chain antigen-binding region that comprises an H-CDR1 comprising SEQ ID NO: 202, an H-CDR2 comprising SEQ ID NO: 203, and an H-CDR3 comprising SEQ ID NO: 204 and a light chain antigen-binding region that comprises an L-CDR1 comprising SEQ ID NO: 206, an L-CDR2 comprising SEQ ID NO: 207, and an L-CDR3 comprising SEQ ID NO: 208; or ix) a heavy chain antigen-binding region that comprises an H-CDR1 comprising SEQ ID NO: 222, an H-CDR2 comprising SEQ ID NO: 223, and an H-CDR3 comprising SEQ ID NO: 224 and a light chain antigen-binding region that comprises an L-CDR1 comprising SEQ ID NO: 226, an L-CDR2 comprising SEQ ID NO: 227, and an L-CDR3 comprising SEQ ID NO: 228; or x) a heavy chain antigen-binding region that comprises an H-CDR1 comprising SEQ ID NO: 242, an H-CDR2 comprising SEQ ID NO: 243, and an H-CDR3 comprising SEQ ID NO: 244 and a light chain antigen-binding region that comprises an L-CDR1 comprising SEQ ID NO: 246, an L-CDR2 comprising SEQ ID NO: 247, and an L-CDR3 comprising SEQ ID NO: 248; or xi) a heavy chain antigen-binding region that comprises an H-CDR1 comprising SEQ ID NO: 262, an H-CDR2 comprising SEQ ID NO: 263, and an H-CDR3 comprising SEQ ID NO: 264 and a light chain antigen-binding region that comprises an L-CDR1 comprising SEQ ID NO: 266, an L-CDR2 comprising SEQ ID NO: 267, and an L-CDR3 comprising SEQ ID NO: 268; or xii) a heavy chain antigen-binding region that comprises an H-CDR1 comprising SEQ ID NO: 282, an H-CDR2 comprising SEQ ID NO: 283, and an H-CDR3 comprising SEQ ID NO: 284 and a light chain antigen-binding region that comprises an L-CDR1 comprising SEQ ID NO: 286, an L-CDR2 comprising SEQ ID NO: 287, and an L-CDR3 comprising SEQ ID NO: 288; or xiii) a heavy chain antigen-binding region that comprises an H-CDR1 comprising SEQ ID NO: 302, an H-CDR2 comprising SEQ ID NO: 303, and an H-CDR3 comprising SEQ ID NO: 304 and a light chain antigen-binding region that comprises an L-CDR1 comprising SEQ ID NO: 306, an L-CDR2 comprising SEQ ID NO: 307, and an L-CDR3 comprising SEQ ID NO: 308; or xiv) a heavy chain antigen-binding region that comprises an H-CDR1 comprising SEQ ID NO: 322, an H-CDR2 comprising SEQ ID NO: 323, and an H-CDR3 comprising SEQ ID NO: 324 and a light chain antigen-binding region that comprises an L-CDR1 comprising SEQ ID NO: 326, an L-CDR2 comprising SEQ ID NO: 327, and an L-CDR3 comprising SEQ ID NO: 328; or
xv) a heavy chain antigen-binding region that comprises an H-CDR1 comprising SEQ ID NO: 342, an H-CDR2 comprising SEQ ID NO: 343, and an H-CDR3 comprising SEQ ID NO: 344 and a light chain antigen-binding region that comprises an L-CDR1 comprising SEQ ID NO: 346, an L-CDR2 comprising SEQ ID NO: 347, and an L-CDR3 comprising SEQ ID NO: 348; or
xvi) a heavy chain antigen-binding region that comprises an H-CDR1 comprising SEQ ID NO: 362, an H-CDR2 comprising SEQ ID NO: 363, and an H-CDR3 comprising SEQ ID NO: 364 and a light chain antigen-binding region that comprises an L-CDR1 comprising SEQ ID NO: 366, an L-CDR2 comprising SEQ ID NO: 367, and an L-CDR3 comprising SEQ ID NO: 368; or
xvii) a heavy chain antigen-binding region that comprises an H-CDR1 comprising SEQ ID NO: 382, an H-CDR2 comprising SEQ ID NO: 383, and an H-CDR3 comprising SEQ ID NO: 384 and a light chain antigen-binding region that comprises an L-CDR1 comprising SEQ ID NO: 386, an L-CDR2 comprising SEQ ID NO: 387, and an L-CDR3 comprising SEQ ID NO: 388; or
xviii) a heavy chain antigen-binding region that comprises an H-CDR1 comprising SEQ ID NO: 402, an H-CDR2 comprising SEQ ID NO: 403, and an H-CDR3 comprising SEQ ID NO: 404 and a light chain antigen-binding region that comprises an L-CDR1 comprising SEQ ID NO: 406, an L-CDR2 comprising SEQ ID NO: 407, and an L-CDR3 comprising SEQ ID NO: 408; or
xix) a heavy chain antigen-binding region that comprises an H-CDR1 comprising SEQ ID NO: 422, an H-CDR2 comprising SEQ ID NO: 423, and an H-CDR3 comprising SEQ ID NO: 424 and a light chain antigen-binding region that comprises an L-CDR1 comprising SEQ ID NO: 426, an L-CDR2 comprising SEQ ID NO: 427, and an L-CDR3 comprising SEQ ID NO: 428; or
xx) a heavy chain antigen-binding region that comprises an H-CDR1 comprising SEQ ID NO: 442, an H-CDR2 comprising SEQ ID NO: 443, and an H-CDR3 comprising SEQ ID NO: 444 and a light chain antigen-binding region that comprises an L-CDR1 comprising SEQ ID NO: 446, an L-CDR2 comprising SEQ ID NO: 447, and an L-CDR3 comprising SEQ ID NO: 448; or
xxi) a heavy chain antigen-binding region that comprises an H-CDR1 comprising SEQ ID NO: 462, an H-CDR2 comprising SEQ ID NO: 463, and an H-CDR3 comprising SEQ ID NO: 464 and a light chain antigen-binding region that comprises an L-CDR1 comprising SEQ ID NO: 466, an L-CDR2 comprising SEQ ID NO: 467, and an L-CDR3 comprising SEQ ID NO: 468; or
xxii) a heavy chain antigen-binding region that comprises an H-CDR1 comprising SEQ ID NO: 482, an H-CDR2 comprising SEQ ID NO: 483, and an H-CDR3 comprising SEQ ID NO: 484 and a light chain antigen-binding region that comprises an L-CDR1 comprising SEQ ID NO: 486, an L-CDR2 comprising SEQ ID NO: 487, and an L-CDR3 comprising SEQ ID NO: 488; or
xxiii) a heavy chain antigen-binding region that comprises an H-CDR1 comprising SEQ ID NO: 502, an H-CDR2 comprising SEQ ID NO: 503, and an H-CDR3 comprising SEQ ID NO: 504 and a light chain antigen-binding region that comprises an L-CDR1 comprising SEQ ID NO: 506, an L-CDR2 comprising SEQ ID NO: 507, and an L-CDR3 comprising SEQ ID NO: 508; or
xxiv) a heavy chain antigen-binding region that comprises an H-CDR1 comprising SEQ ID NO: 522, an H-CDR2 comprising SEQ ID NO: 523, and an H-CDR3 comprising SEQ ID NO: 524 and a light chain antigen-binding region that comprises an L-CDR1 comprising SEQ ID NO: 526, an L-CDR2 comprising SEQ ID NO: 527, and an L-CDR3 comprising SEQ ID NO: 528; or
xxv) a heavy chain antigen-binding region that comprises an H-CDR1 comprising SEQ ID NO: 542, an H-CDR2 comprising SEQ ID NO: 543, and an H-CDR3 comprising SEQ ID NO: 544 and a light chain antigen-binding region that comprises an L-CDR1 comprising SEQ ID NO: 546, an L-CDR2 comprising SEQ ID NO: 547, and an L-CDR3 comprising SEQ ID NO: 548; or
xxvi) a heavy chain antigen-binding region that comprises an H-CDR1 comprising SEQ ID NO: 562, an H-CDR2 comprising SEQ ID NO: 563, and an H-CDR3 comprising SEQ ID NO: 564 and a light chain antigen-binding region that comprises an L-CDR1 comprising SEQ ID NO: 566, an L-CDR2 comprising SEQ ID NO: 567, and an L-CDR3 comprising SEQ ID NO: 568.

In particular embodiments, the isolated antibody or antigen-binding fragment according to the present disclosure comprises:
i) a variable heavy chain domain comprising SEQ ID NO: 41 and a variable light chain domain comprising SEQ ID NO: 45; or
ii) a variable heavy chain domain comprising SEQ ID NO: 61 and a variable light chain domain comprising SEQ ID NO: 65; or
iii) a variable heavy chain domain comprising SEQ ID NO: 101 and a variable light chain domain comprising SEQ ID NO: 105; or
iv) a variable heavy chain domain comprising SEQ ID NO: 121 and a variable light chain domain comprising SEQ ID NO: 125; or
v) a variable heavy chain domain comprising SEQ ID NO: 141 and a variable light chain domain comprising SEQ ID NO: 145; or
vi) a variable heavy chain domain comprising SEQ ID NO: 161 and a variable light chain domain comprising SEQ ID NO: 165; or
vii) a variable heavy chain domain comprising SEQ ID NO: 181 and a variable light chain domain comprising SEQ ID NO: 185; or
viii) a variable heavy chain domain comprising SEQ ID NO: 201 and a variable light chain domain comprising SEQ ID NO: 205; or
ix) a variable heavy chain domain comprising SEQ ID NO: 221 and a variable light chain domain comprising SEQ ID NO: 225; or
x) a variable heavy chain domain comprising SEQ ID NO: 241 and a variable light chain domain comprising SEQ ID NO: 245; or
xi) a variable heavy chain domain comprising SEQ ID NO: 261 and a variable light chain domain comprising SEQ ID NO: 265; or
xii) a variable heavy chain domain comprising SEQ ID NO: 281 and a variable light chain domain comprising SEQ ID NO: 285; or
xiii) a variable heavy chain domain comprising SEQ ID NO: 301 and a variable light chain domain comprising SEQ ID NO: 305; or
xiv) a variable heavy chain domain comprising SEQ ID NO: 321 and a variable light chain domain comprising SEQ ID NO: 325; or
xv) a variable heavy chain domain comprising SEQ ID NO: 341 and a variable light chain domain comprising SEQ ID NO: 345; or xvi) a variable heavy chain domain comprising SEQ ID NO: 361 and a variable light chain domain comprising SEQ ID NO: 365; or
xvii) a variable heavy chain domain comprising SEQ ID NO: 381 and a variable light chain domain comprising SEQ ID NO: 385; or
xviii) a variable heavy chain domain comprising SEQ ID NO: 401 and a variable light chain domain comprising SEQ ID NO: 405; or
xix) a variable heavy chain domain comprising SEQ ID NO: 421 and a variable light chain domain comprising SEQ ID NO: 425; or
xx) a variable heavy chain domain comprising SEQ ID NO: 441 and a variable light chain domain comprising SEQ ID NO: 445; or
xxi) a variable heavy chain domain comprising SEQ ID NO: 461 and a variable light chain domain comprising SEQ ID NO: 465; or
xxii) a variable heavy chain domain comprising SEQ ID NO: 481 and a variable light chain domain comprising SEQ ID NO: 485; or
xxiii) a variable heavy chain domain comprising SEQ ID NO: 501 and a variable light chain domain comprising SEQ ID NO: 505; or
xxiv) a variable heavy chain domain comprising SEQ ID NO: 521 and a variable light chain domain comprising SEQ ID NO: 525; or
xxv) a variable heavy chain domain comprising SEQ ID NO: 541 and a variable light chain domain comprising SEQ ID NO: 545; or
xxvi) a variable heavy chain domain comprising SEQ ID NO: 561 and a variable light chain domain comprising SEQ ID NO: 565.

In particular embodiments, the isolated antibody according to the present disclosure is an IgG antibody. In particular such embodiments, the isolated antibody according to the present disclosure is an IgG1, IgG2, IgG3 or an IgG4 antibody. Most particularly, the isolated antibody according to the present disclosure is an IgG1 or an IgG4 antibody.

In particular embodiments, the isolated antibody according to the present disclosure comprises:
i) a heavy chain comprising SEQ ID NO: 57 and a light chain comprising SEQ ID NO: 58; or
ii) a heavy chain comprising SEQ ID NO: 77 and a light chain comprising SEQ ID NO: 78; or
iii) a heavy chain comprising SEQ ID NO: 117 and a light chain comprising SEQ ID NO: 118; or
iv) a heavy chain comprising SEQ ID NO: 137 and a light chain comprising SEQ ID NO: 138; or
v) a heavy chain comprising SEQ ID NO: 157 and a light chain comprising SEQ ID NO: 158; or
vi) a heavy chain comprising SEQ ID NO: 177 and a light chain comprising SEQ ID NO: 178; or
vii) a heavy chain comprising SEQ ID NO: 197 and a light chain comprising SEQ ID NO: 198; or
viii) a heavy chain comprising SEQ ID NO: 217 and a light chain comprising SEQ ID NO: 218; or
ix) a heavy chain comprising SEQ ID NO: 237 and a light chain comprising SEQ ID NO: 238; or
x) a heavy chain comprising SEQ ID NO: 257 and a light chain comprising SEQ ID NO: 258; or
xi) a heavy chain comprising SEQ ID NO: 277 and a light chain comprising SEQ ID NO: 278; or
xii) a heavy chain comprising SEQ ID NO: 297 and a light chain comprising SEQ ID NO: 298; or
xiii) a heavy chain comprising SEQ ID NO: 317 and a light chain comprising SEQ ID NO: 318; or
xiv) a heavy chain comprising SEQ ID NO: 337 and a light chain comprising SEQ ID NO: 338; or
xv) a heavy chain comprising SEQ ID NO: 357 and a light chain comprising SEQ ID NO: 358; or
xvi) a heavy chain comprising SEQ ID NO: 377 and a light chain comprising SEQ ID NO: 378; or
xvii) a heavy chain comprising SEQ ID NO: 397 and a light chain comprising SEQ ID NO: 398; or
xviii) a heavy chain comprising SEQ ID NO: 417 and a light chain comprising SEQ ID NO: 418; or
xix) a heavy chain comprising SEQ ID NO: 437 and a light chain comprising SEQ ID NO: 438; or
xx) a heavy chain comprising SEQ ID NO: 457 and a light chain comprising SEQ ID NO: 458; or
xxi) a heavy chain comprising SEQ ID NO: 477 and a light chain comprising SEQ ID NO: 478; or
xxii) a heavy chain comprising SEQ ID NO: 497 and a light chain comprising SEQ ID NO: 498; or
xxiii) a heavy chain comprising SEQ ID NO: 517 and a light chain comprising SEQ ID NO: 518; or
xxiv) a heavy chain comprising SEQ ID NO: 537 and a light chain comprising SEQ ID NO: 538; or
xxv) a heavy chain comprising SEQ ID NO: 557 and a light chain comprising SEQ ID NO: 558; or
xxvi) a heavy chain comprising SEQ ID NO: 577 and a light chain comprising SEQ ID NO: 578.

In particular embodiments, the antigen-binding fragment according to the present disclosure is an scFv, Fab, Fab' fragment or a F(ab')2 fragment.

In particular embodiments, the isolated antibody or antigen-binding fragment according to the present disclosure is a monoclonal antibody or antigen-binding fragment thereof.

In particular embodiments, the isolated antibody or antigen-binding fragment according to the present disclosure is a human, humanized or chimeric antibody or antigen-binding fragment thereof, more particularly a fully human antibody or antigen-binding fragment thereof.

In particular embodiments, the isolated antibody or antigen-binding fragment according to the present disclosure is a monospecific antibody. In particular other embodiments, the isolated antibody or antigen-binding fragment according to the present disclosure is a multispecific antibody that binds to Sema3A and at least one further antigen, such as a bispecific, trispecific or tetraspecific antibody.

In another aspect the present disclosure relates to an isolated antibody or antigen-binding fragment thereof that competes with the isolated antibody or antigen-binding fragment according to the present disclosure for binding to human Sema3A.

In a further aspect, the present disclosure relates to an antibody conjugate, comprising the isolated antibody or antigen binding fragment according to the present disclosure. For example, an antibody could be conjugated to a cytotoxic agent, an immunotoxin, a toxophore or a radioisotope. Also provided are anti-Sema3A antibodies conjugated to a detectable marker. Preferred markers are a radiolabel, an enzyme, a chromophore or a fluorophore. The antibody may also be conjugated to high molecular weight molecules such as peptides or proteins, such as interleukins.

The ADC according to the present disclosure comprises an anti-Sema3A antibody conjugated to one or more cytotoxic agents, such as chemotherapeutic agents or drugs, growth inhibitory agents, toxins (e.g., protein toxins, enzymatically active toxins of bacterial, fungal, plant, human or animal origin, or fragments thereof), or radioactive isotopes.

In one embodiment, the ADC according to the present disclosure comprises an anti-Sema3A antibody as described herein conjugated to one or more drugs, including but not limited to a maytansinoid (see U.S. Pat. Nos. 5,208,020, 5,416,064 and European Patent EP0425235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof; an anthracycline such as daunomycin or doxorubicin; methotrexate; vindesine; a taxane such as docetaxel, paclitaxel, larotaxel, tesetaxel, and ortataxel; a trichothecene; and CC1065.

In another embodiment, the ADC according to the present disclosure comprises an anti-Sema3A antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alphasarcin, *Aleurites fordii* proteins, dianthin proteins, *Phytolaca americana* proteins (P API, P APII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, the ACD according to the present disclosure comprises and anti-Sema3A antibody as described herein conjugated to a radioactive atom to form a radioconjugate. A variety of radioactive isotopes are available for the production of radioconjugates. Examples include 227Th, 225Ac, 211At, 131I, 125I, 90Y, 186Re, 188Re, 153Sm, 212Bi, 32P, 212Pb and radioactive isotopes of Lu. When the radioconjugate is used for detection, it may comprise a radioactive atom for scintigraphic studies, for example Tc99m, or a spin label for nuclear magnetic resonance (NMR) imaging, such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52: 12 7-131 (1992).

The ACD according to the present disclosure includes ADCs prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A)

Amino acid and nucleic acid sequences of preferred antibodies according to the present disclosure and three prior art antibodies are listed in Table 1 and Table 1A.

Peptide Variants

Antibodies or antigen-binding fragments of the disclosure are not limited to the specific peptide sequences provided herein. Rather, the disclosure also embodies variants of these polypeptides. With reference to the instant disclosure and conventionally available technologies and references, the skilled worker will be able to prepare, test and utilize functional variants of the antibodies disclosed herein, while appreciating these variants having the ability to bind to Sema3A fall within the scope of the present disclosure.

A variant can include, for example, an antibody that has at least one altered complementary determining region (CDR) (hyper-variable) and/or framework (FR) (variable) domain/position, vis-à-vis a peptide sequence disclosed herein.

By altering one or more amino acid residues in a CDR or FR region, the skilled worker routinely can generate mutated or diversified antibody sequences, which can be screened against the antigen, for new or improved properties, for example.

A further preferred embodiment of the disclosure is an antibody or antigen-binding fragment thereof in which the VH and VL sequences are selected as shown in Table 1 and Table 1A. The skilled worker can use the data in Table 1 and Table 1A to design peptide variants that are within the scope of the present disclosure. It is preferred that variants are constructed by changing amino acids within one or more CDR regions; a variant might also have one or more altered framework regions. For example, a peptide FR domain might be altered where there is a deviation in a residue compared to a germline sequence.

Alternatively, the skilled worker could make the same analysis by comparing the amino acid sequences disclosed herein to known sequences of the same class of such antibodies, using, for example, the procedure described by Knappik A., et al., JMB 2000, 296:57-86.

Furthermore, variants may be obtained by using one antibody as starting point for further optimization by diversifying one or more amino acid residues in the antibody, preferably amino acid residues in one or more CDRs, and by screening the resulting collection of antibody variants for variants with improved properties. Particularly preferred is diversification of one or more amino acid residues in CDR3 of VL and/or VH. Diversification can be done e.g. by synthesizing a collection of DNA molecules using trinucleotide mutagenesis (TRIM) technology (Virnekäs B. et al., Nucl. Acids Res. 1994, 22: 5600.). Antibodies or antigen-binding fragments thereof include molecules with modifications/variations including but not limited to e.g. modifications leading to altered half-life (e.g. modification of the Fc part or attachment of further molecules such as PEG), altered binding affinity or altered ADCC or CDC activity.

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophane, and methionine; (b) polar neutral amino acids include glycine, serine, threonine, cysteine, tyrosine, asparagine, and glutamine; (c) positively charged (basic) amino acids include arginine, lysine, and histidine;

and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Glycosylation Variants

Where the antibody comprises an Fc region, the carbohydrate attached thereto may be altered. Native antibodies produced by mammalian cells typically comprise a branched, biantennary oligosaccharide that is generally attached by an N-linkage to Asn297 using Kabat EU numbering of the CH2 domain of the Fc region; see, e.g., Wright et al. Trends Biotechnol. 15: 26-32 (1997).

In certain embodiments, an antibody provided herein is altered to increase or decrease the extent to which the antibody is glycosylated. Addition or deletion of glycosylation sites to an antibody may be conveniently accomplished by altering the expression system (e.g. host cell) and/or by altering the amino acid sequence such that one or more glycosylation sites is created or removed.

In one embodiment of this disclosure, aglycosyl antibodies having decreased effector function or antibody derivatives are prepared by expression in a prokaryotic host. Suitable prokaryotic hosts for include but are not limited to E. coli, Bacillus subtilis, Salmonella typhimurium and various species within the genera Pseudomonas, Streptomyces, and Staphylococcus.

In one embodiment, antibody variants are provided having decreased effector function, which are characterized by a modification at the conserved N-linked site in the CH2 domains of the Fc portion of said antibody. In one embodiment of present disclosure, the modification comprises a mutation at the heavy chain glycosylation site to prevent glycosylation at the site. Thus, in one preferred embodiment of this disclosure, the aglycosyl antibodies or antibody derivatives are prepared by mutation of the heavy chain glycosylation site, —i.e., mutation of N297 using Kabat EU numbering and expressed in an appropriate host cell.

In another embodiment of the present disclosure, aglycosyl antibodies or antibody derivatives have decreased effector function, wherein the modification at the conserved N-linked site in the CH2 domains of the Fc portion of said antibody or antibody derivative comprises the removal of the CH2 domain glycans, —i.e., deglycosylation. These aglycosyl antibodies may be generated by conventional methods and then deglycosylated enzymatically. Methods for enzymatic deglycosylation of antibodies are well known in the art (e.g. Winkelhake & Nicolson (1976), J Biol Chem. 251(4):1074-80).

In another embodiment of this disclosure, deglycosylation may be achieved using the glycosylation inhibitor tunicamycin (Nose & Wigzell (1983), Proc Natl Acad Sci USA, 80(21):6632-6). That is, the modification is the prevention of glycosylation at the conserved N-linked site in the CH2 domains of the Fc portion of said antibody.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function.

Examples of publications related to "defucosylated" or "fucose-deficient" antibody variants include: Okazaki et al. J Mol. Biol. 336: 1239-1249 (2004); Yamane-Ohnuki et al. Biotech. Bioeng. 87: 614 (2004).

Examples of cell lines capable of producing defucosylated antibodies include Lec13 CHO cells deficient in protein fucosylation (Ripka et al. Arch. Biochem. Biophys. 249: 533-545 (1986); and WO 2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006)).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546.

Antibody variants with at least one galactose residue in the oligosaccharide attached to the Fc region are also provided. Such antibody variants may have improved CDC function. Such antibody variants are described, e.g., in WO1997/30087; WO1998/58964; and WO1999/22764.

FC Region Variants

In certain embodiments, one or more amino acid modifications (e.g. a substitution) may be introduced into the Fc region of an antibody (e.g., a human IgG1, IgG2, IgG3 or IgG4 Fc region) provided herein, thereby generating an Fc region variant.

In certain embodiments, the disclosure contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. In some embodiments, alterations are made in the Fc region that result in altered (i.e., either improved or diminished) C1q binding and/or Complement Dependent Cytotoxicity (CDC).

In certain embodiments, the disclosure contemplates an antibody variant that possesses an increased or decreased half-live. Antibodies with increased half-lives and improved binding to the neonatal Fc receptor (FcRn), which is responsible for the transfer of maternal IgGs to the fetus (Guyer et al., J Immunol. 117:587 (1976) and Kim et al., J Immunol. 24:249 (1994)), are described in US2005/0014934 (Hinton et al.). Those antibodies comprise an Fc region with one or more substitutions therein which improve binding of the Fc region to FcRn.

Antibody Generation

An antibody of the disclosure may be derived from a recombinant antibody library that is based on amino acid sequences that have been isolated from the antibodies of a large number of healthy volunteers e.g. using the n-CoDeR® technology the fully human CDRs are recombined into new antibody molecules (Carlson & Söderlind, Expert Rev Mol Diagn. 2001 May; 1(1):102-8). Or alternatively for example antibody libraries as the fully human antibody phage display library described in Hoet R M et al., Nat Biotechnol 2005; 23(3):344-8) can be used to isolate Sema3A-specific antibodies. Antibodies or antibody fragments isolated from human antibody libraries are considered human antibodies or human antibody fragments herein.

Human antibodies may be further prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. For example immunization of genetically engineered mice inter alia immunization of hMAb mice (e.g. VelocImmune Mouse® or XENOMOUSE®) may be performed.

Further antibodies may be generated using the hybridoma technology (for example see Köhler and Milstein Nature. 1975 Aug. 7; 256(5517):495-7), resulting in for example murine, rat, or rabbit antibodies which can be converted into chimeric or humanized antibodies. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Natl Acad. Sci. USA 86:10029-10033 (1989); U.S. Pat. Nos. 5,821,337, 7,527, 791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall' Acqua et al., Methods 36:43-60 (2005) (describing "FR shuffling"); and Osboum et al., Methods 36:61-68 (2005) and Klimka et al., Br. J. Cancer, 83:252-260 (2000) (describing the "guided selection" approach to FR shuffling).

Examples are provided for the generation of antibodies using a recombinant antibody library.

DNA Molecules According to the Present Disclosure

The present disclosure also relates to an isolated nucleic acid sequence that encodes the antibody or antigen-binding fragment according to the present disclosure. The isolated nucleic acid sequence encoding the antibody or antigen-binding fragment according to the present disclosure can for instance be produced by techniques described in Sambrook et al., 1989, and Ausubel et al., 1989, or alternatively, by chemically synthesis. (e.g. techniques described in Oligonucleotide Synthesis (1984, Gait, ed., IRL Press, Oxford)). The DNA sequences and respective SEQ IDs used for the antibodies expressed are given in Table 1 and 1A. These sequences are optimized in certain cases for mammalian expression. DNA molecules of the disclosure are not limited to the sequences disclosed herein, but also include variants thereof. DNA variants within the disclosure may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 supra and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

Functionally Equivalent DNA Variants

Yet another class of DNA variants within the scope of the disclosure may be described with reference to the product they encode. These functionally equivalent polynucleotides are characterized by the fact that they encode the same peptide sequences due to the degeneracy of the genetic code.

It is recognized that variants of DNA molecules provided herein can be constructed in several different ways. For example, they may be constructed as completely synthetic DNAs. Methods of efficiently synthesizing oligonucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present disclosure further provides recombinant DNA constructs comprising one or more of the nucleotide sequences according to the present disclosure. The recombinant constructs of the present disclosure can be used in connection with a vector, such as a plasmid, phagemid, phage or viral vector, into which a DNA molecule encoding an antibody of the disclosure or antigen-binding fragment thereof or variant thereof is inserted.

Thus, in one aspect, the present disclosure relates to a vector comprising a nucleic acid sequence according to the present disclosure.

An antibody, antigen binding portion, or variant thereof provided herein can be prepared by recombinant expression of nucleic acid sequences encoding light and heavy chains or portions thereof in a host cell. To express an antibody, antigen binding portion, or variant thereof recombinantly a host cell can be transfected with one or more recombinant expression vectors carrying DNA fragments encoding the light and/or heavy chains or portions thereof such that the light and heavy chains are expressed in the host cell. Standard recombinant DNA methodologies are used to prepare and/or obtain nucleic acids encoding the heavy and light chains, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, antigen binding fragments thereof or variants thereof standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic cells. Examples for prokaryotic host cells are e.g. bacteria, examples for eukaryotic hosts cells are yeasts, insects and insect cells, plants and plant cells, transgenic animals, or mammalian cells. Introduction of the recombinant construct into the host cell can be carried out using standard techniques such as calcium phosphate transfection, DEAE dextran mediated transfection, electroporation, transduction or phage infection.

In some embodiments, the DNAs encoding the heavy and light chains are inserted into separate vectors. In other embodiments, the DNA encoding the heavy and light chains is inserted into the same vector. It is understood that the design of the expression vector, including the selection of regulatory sequences is affected by factors such as the choice of the host cell, the level of expression of protein desired and whether expression is constitutive or inducible.

Thus, in a further aspect, the present disclosure relates to an isolated cell expressing the antibody or antigen-binding fragment according to the present disclosure and/or comprising the nucleic acid according to the present disclosure or the vector according to the present disclosure.

The isolated cell can be virtually any cell for which expression vectors are available. The isolated cell can for example a higher eukaryotic host cell, such as a mammalian cell, a lower eukaryotic host cell, such as a yeast cell, and may be a prokaryotic cell, such as a bacterial cell.

In a further aspect, the present disclosure relates to a method of producing the isolated antibody or antigen-binding fragment according to the present disclosure comprising culturing of the cell according to the present disclosure. In particular embodiments, the cell according to the present disclosure is cultivated under suitable conditions for antibody expression and the antibody or antigen-binding fragment thereof is recovered. In particular embodiments, the antibody or antigen-binding fragment thereof is purified, particularly to at least 95% homogeneity by weight.

Bacterial Expression

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include but are not limited to *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and a bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore, an embodiment of the present disclosure is an expression vector comprising a nucleic acid sequence encoding for the novel antibodies of the present disclosure.

Antibodies of the present disclosure or antigen-binding fragments thereof or variants thereof include naturally purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces*, and *Staphylococcus*, preferably, from *E. coli* cells.

Mammalian Expression

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Expression of the antibodies may be constitutive or regulated (e.g. inducible by addition or removal of small molecule inductors such as Tetracyclin in conjunction with Tet system). For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase (Bebbington et al., Biotechnology (N Y). 1992 February; 10(2):169-75), on a host cell into which the vector has been introduced. For example, the dihydrofolate reductase (DHFR) gene confers resistance to methotrexate, neo gene confers resistance to G418, the bsd gene from *Aspergillus terreus* confers resistance to blasticidin, puromycin N-acetyl-transferase confers resistance to puromycin, the Sh ble gene product confers resitance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

Transfection of the expression vector into a host cell can be carried out using standard techniques such as electroporation, nucleofection, calcium-phosphate precipitation, lipofection, polycation-based transfection such as polyethlylenimine (PEI)-based transfection and DEAE-dextran transfection.

Suitable mammalian host cells for expressing the antibodies, antigen binding fragments thereof or variants thereof provided herein include Chinese Hamster Ovary (CHO cells) such as CHO-K1, CHO-S, CHO-K1SV [including dhfr− CHO cells, described in Urlaub and Chasin, (1980) Proc. Natl. Acad. Sci. USA 77:4216-4220 and Urlaub et al., Cell. 1983 June; 33(2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109(4):1007-15], NSO myeloma cells, COS cells, HEK293 cells, HKB11 cells, BHK21 cells, CAP cells, EB66 cells, and SP2 cells.

Expression might also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for instance Durocher et al., Nucleic Acids Res. 2002 Jan. 15; 30(2):E9).

In some embodiments, the expression vector is designed such that the expressed protein is secreted into the culture medium in which the host cells are grown. The antibodies, antigen binding fragments thereof or variants thereof can be recovered from the culture medium using standard protein purification methods.

Purification

Antibodies of the disclosure or antigen-binding fragments thereof or variants thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present disclosure or antigen-binding fragments thereof or variants thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

In preferred embodiments, the antibody is purified (1) to greater than 95% by weight of antibody as determined e.g. by the Lowry method, UV-Vis spectroscopy or by by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

Therapeutic Methods

Therapeutic methods involve administering to a subject in need of treatment a therapeutically effective amount of an antibody or an antigen-binding fragment thereof or a variant thereof contemplated by the disclosure. A "therapeutically effective" amount hereby is defined as the amount of an antibody or antigen-binding fragment thereof that is of sufficient quantity to decrease Sema3A activity in a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, dog, monkey or other lower-order primate).

Thus, in one aspect, the present disclosure relates to the isolated antibody or antigen-binding fragment according the present disclosure or to a conjugate comprising the isolated antibody or antigen-binding fragment according the present disclosure or to a pharmaceutical composition comprising the isolated antibody or antigen-binding fragment according the present disclosure for use as a medicament.

The isolated antibody or antigen-binding fragment according to the present disclosure can be used as a therapeutic or a diagnostic tool in a variety of Sema3A-associated disorders.

Thus, in a further aspect, the present disclosure relates to the isolated antibody or antigen-binding fragment according the present disclosure or to a conjugate comprising the isolated antibody or antigen-binding fragment according the present disclosure or to a pharmaceutical composition comprising the isolated antibody or antigen-binding fragment according the present disclosure for use in the treatment and/or prevention of renal diseases, in particular of acute and chronic kidney diseases, diabetic kidney diseases, Alport syndrome and of acute and chronic renal failure. The general terms 'renal disease' or 'kidney disease' describes a class of conditions in which the kidneys fail to filter and remove waste products from the blood. There are two major forms of kidney disease: acute kidney disease (acute kidney injury, AKI) and chronic kidney disease (CKD). The isolated antibody or antigen-binding fragment according to the present disclosure or a conjugate or pharmaceutical composition comprising the same may further be used for the treatment and/or prevention of sequelae of acute kidney injury arising from multiple insults such as ischemia-reperfusion injury, radiocontrast administration, cardiopulmonary bypass surgery, shock and sepsis. In the context of the present disclosure, the terms renal failure and renal insufficiency comprise both acute and chronic manifestations of renal insufficiency, as well as underlying or related kidney diseases such as renal hypoperfusion, intradialytic hypotension, obstructive uropathy, glomerulopathies, IgA nephropathy, glomerulonephritis, acute glomerulonephritis, glomerulosclerosis, tubulointerstitial diseases, nephropathic diseases such as primary and congenital kidney disease, nephritis, Alport syndrome, kidney inflammation, immunological kidney diseases such as kidney transplant rejection, immune complex-induced kidney diseases, nephropathy induced by toxic substances, contrast medium-induced nephropathy; minimal change glomerulonephritis (lipoid); Membranous glomerulonephritis; focal segmental glomerulosclerosis (FSGS); hemolytic uremic syndrome (HUS), amyloidosis, Goodpasture's syndrome, Wegener's granulomatosis, Purpura Schönlein-Henoch, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphatemia and/or the need for dialysis. The present disclosure also relates to the isolated antibody or antigen-binding fragment according to the present disclosure or a conjugate or pharmaceutical composition comprising same for use in the treatment and/or prevention of sequelae of renal insufficiency, for example pulmonary edema, heart failure, uremia, anemia, electrolyte disturbances (e.g. hyperkaliemia, hyponatremia) and disturbances in bone and carbohydrate metabolism. The compounds according to the disclosure are also suitable for the treatment and/or prevention of polycystic kidney disease (PCKD) and of the syndrome of inadequate ADH secretion (SIADH).

Additionally, the isolated antibody or antigen-binding fragment according to the present disclosure or a conjugate or pharmaceutical composition comprising the same may be used for the treatment and/or prevention of vascular hyperpermeability, diabetic retinopathy, deterioration of the blood retinal barrier and consequent macular edema, preferably, age related macular edema, non-proliferative age-related macular edema and non-proliferative diabetic macular edema.

Further, the isolated antibody or antigen-binding fragment according to the present disclosure or a conjugate or pharmaceutical composition comprising same is suitable for the prevention or treatment of disease of the central or peripheral nervous system like neuropathic pain, spinal cord injury, multiple sclerosis, traumatic brain injury, brain edema or neurodegenerative diseases in which the neurodegenerative disease is Alzheimer's disease, Parkinson's disease, Huntington's disease, amyotrophic lateral sclerosis, progressive supranuclear paralysis, black substance degeneration, Shy-Drager syndrome, olivopontocerebellar atrophy or spinocerebellar degeneration.

Furthermore, the isolated antibody or antigen-binding fragment according to the present disclosure or a conjugate or pharmaceutical composition comprising the same may be useful for the treatment and/or prevention of cancer, wherein the cancer is intestinal cancer, colorectal cancer, lung cancer, breast cancer, brain cancer, melanoma, renal cell cancer, leukemia, lymphoma, T-cell lymphoma, stomach cancer, pancreatic cancer, cervical cancer, endometrial cancer, ovarian cancer, esophageal cancer, liver cancer, squamous cell carcinoma of the head and neck, skin cancer, urinary tract cancer, prostate cancer, choriocarcinoma, pharyngeal cancer or larynx cancer.

The disorders mentioned above have been well characterized in humans, but also exist with a similar etiology in other animals, including mammals, and can be treated by administering pharmaceutical compositions according to the present disclosure.

The antibody or the antigen-binding fragment according to the present disclosure or a variant thereof might be co-administered with known medicaments, and in some instances the antibody or antigen-binding fragment thereof might itself be modified. For example, an antibody or an antigen-binding fragment thereof or a variant thereof could be conjugated to a drug or to another peptide or protein to potentially further increase efficacy.

Antibodies of the present disclosure or antigen-binding fragments thereof or variants thereof may be administered as the sole pharmaceutical agent or in combination with one or more additional therapeutic agents where the combination causes no unacceptable adverse effects.

Thus, in a further aspect, the present disclosure relates to the isolated antibody or antigen-binding fragment according to the present disclosure or the conjugate according to the present disclosure or the pharmaceutical composition according to the present disclosure for use in simultaneous, separate, or sequential combination with one or more further therapeutically active compounds.

Non-limiting examples of therapeutically active compounds to be used in combination with the antibody or antigen-binding fragment according to the present disclosure are:

blood pressure lowering agents, for example and preferably from the group of calcium antagonists, angiotensin II antagonists, ACE inhibitors, NEP inhibitors, vasopeptidase inhibitors, endothelin antagonists, renin inhibitors, alpha-blockers, beta-blockers, mineralocorticoid receptor antagonists and diuretics;

antidiabetic agents (hypoglycemic or antihyperglycemic agents), such as for example and preferably insulin and derivatives, sulfonylureas, biguanides, thiazolidinediones, acarbose, DPP4 inhibitors, GLP-1 analogues, or SGLT inhibitors (gliflozins);

compounds inhibiting the signal transduction cascade, in particular tyrosine and/or serine/threonine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

anti-inflammatory drugs such as non-steroidal anti-inflammatory drugs (NSAIDs) including acetylsalicylic acid (aspirin), ibuprofen and naproxen, glucocorticoids such as for example and preferably prednison, prednisolon, methylprednisolon, triamcinolon, dexamethason, beclomethason, betamethason, flunisolid, budesonid or fluticason, or 5-aminosalicylic acid derivatives, leukotriene antagonists, TNF-alpha inhibitors and chemokine receptor antagonists such as CCR1, 2 and/or 5 inhibitors, NF-κB inhibitors and Nerf2 activators;

anti-fibrotic drugs such as TGFbeta antagonist, or microRNA-21 inhibitors;

organic nitrates and NO-donors, for example sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP), for example inhibitors of phosphodiesterases (PDE) 1, 2, 5 and/or 9, in particular PDE-5 inhibitors such as sildenafil, vardenafil, tadalafil, udenafil, dasantafil, avanafil, mirodenafil, lodenafil, CTP-499 or PF-00489791;

calcium sensitizers, such as for example and preferably levosimendan;

antithrombotic agents, particularly selected from the group consisting of platelet aggregation inhibitors, anticoagulants and profibrinolytic substances;

agents, that stimulate NO- and heme-dependent as well as NO- and heme-indipendent the synthesis of cGMP, for example and with preference soluble guanylate cyclase (sGC) modulators, for example and with preference riociguat, cinaciguat, vericiguat or BAY 1101042;

fat metabolism altering agents, for example and preferably from the group of thyroid receptor agonists, cholesterol synthesis inhibitors, such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

In particular embodiments, the isolated antibody or antigen-binding fragment according to the present disclosure is administered in combination with a platelet aggregation inhibitor, particularly aspirin, clopidogrel, ticlopidine or dipyridamole.

In particular embodiments, the isolated antibody or antigen-binding fragment according to the present disclosure is administered in combination with a thrombin inhibitor, particularly ximelagatran, dabigatran, melagatran, bivalirudin or enoxaparin.

In particular embodiments, the isolated antibody or antigen-binding fragment according to the present disclosure is administered in combination with a GPIIb/IIIa antagonist, particularly tirofiban or abciximab.

In particular embodiments, the isolated antibody or antigen-binding fragment according to the present disclosure is administered in combination with a factor Xa inhibitor, particularly selected from rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 and SSR-128428.

In particular embodiments, the isolated antibody or antigen-binding fragment according to the present disclosure is administered in combination with heparin or a low molecular weight (LMW) heparin derivative.

In particular embodiments, the isolated antibody or antigen-binding fragment according to the present disclosure is administered in combination with a vitamin K antagonist, particularly selected from coumarin.

Blood pressure lowering agents are particularly selected from the group consisting of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics.

In particular embodiments, the isolated antibody or antigen-binding fragment according to the present disclosure is administered in combination with a calcium antagonist, particularly selected from nifedipine, amlodipine, verapamil and diltiazem.

In particular embodiments, the isolated antibody or antigen-binding fragment according to the present disclosure is administered in combination with an angiotensin AII receptor antagonist, particularly selected from the group consisting of losartan, candesartan, valsartan, telmisartan, irbesartan, olmesartan, eprosartan, embursartan and azilsartan.

In particular embodiments, the isolated antibody or antigen-binding fragment according to the present disclosure is administered in combination with an ACE inhibitor, particularly selected from the group consisting of enalapril, captopril, lisinopril, ramipril, delapril, fosinopril, quinopril, perindopril, benazepril and trandopril.

In particular embodiments, the isolated antibody or antigen-binding fragment according to the present disclosure is administered in combination with an endothelin antagonist, particularly selected from the group consisting of bosentan, darusentan, ambrisentan, tezosentan, sitaxsentan, avosentan, macitentan and atrasentan.

In particular embodiments, the isolated antibody or antigen-binding fragment according to the present disclosure is administered in combination with a renin inhibitor, particularly selected from the group consisting of aliskiren, SPP-600 and SPP-800.

In particular embodiments, the isolated antibody or antigen-binding fragment according to the present disclosure is administered in combination with a mineralocorticoid receptor antagonist, particularly selected from the group consisting of finerenone, spironolactone, canrenone, potassium canrenoate, eplerenone, esaxerenone (CS-3150), or aparenone (MT-3995), CS-3150, and MT-3995.

In particular embodiments, the isolated antibody or antigen-binding fragment according to the present disclosure is administered in combination with a diuretic, particularly selected from the group consisting of furosemide, bumetanide, piretanide, torsemide, bendroflumethiazide, chlorothiazide, hydrochlorothiazide, xipamide, indapamide, hydroflumethiazide, methyclothiazide, polythiazide, trichloromethiazide, chlorothalidone, metolazone, quinethazone, acetazolamide, dichlorophenamide, methazolamide, glycerine, isosorbide, mannitol, amiloride and triamterene.

Fat metabolism altering agents are particularly selected from the group consisting of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In particular embodiments, the isolated antibody or antigen-binding fragment according to the present disclosure is administered in combination with a Nerf2 activator, particularly selected from Bardoxolone methyl.

In particular embodiments, the isolated antibody or antigen-binding fragment according to the present disclosure is administered in combination with a thyroid receptor agonist, particularly selected from the group consisting of D-thyroxin, 3,5,3'-triiodothyronin (T3), CGS 23425 and axitirome (CGS 26214).

In particular embodiments, the isolated antibody or antigen-binding fragment according to the present disclosure is administered in combination with an HMG-CoA-reductase inhibitor from the class of statins, particularly selected from the group consisting of lovastatin, simvastatin, pravastatin, fluvastatin, atorvastatin, rosuvastatin and pitavastatin.

In particular embodiments, the isolated antibody or antigen-binding fragment according to the present disclosure is administered in combination with a PPAR-gamma modulator, particularly selected from pioglitazone and rosiglitazone.

In particular embodiments, the isolated antibody or antigen-binding fragment according to the present disclosure is administered in combination with a PPAR-delta modulator, particularly selected from the group consisting of ASP1128, GW 501516 and BAY 68-5042.

In particular embodiments, the isolated antibody or antigen-binding fragment according to the present disclosure is administered in combination with a cholesterol absorption inhibitor, particularly selected from the group consisting of ezetimibe, tiqueside and pamaqueside.

In particular embodiments, the isolated antibody or antigen-binding fragment according to the present disclosure is administered in combination with a lipase inhibitor, particularly selected from orlistat.

In particular embodiments, the isolated antibody or antigen-binding fragment according to the present disclosure is administered in combination with a polymeric bile acid adsorber, particularly selected from the group consisting of cholestyramine, colestipol, colesolvam, CholestaGel and colestimide.

In particular embodiments, the isolated antibody or antigen-binding fragment according to the present disclosure is administered in combination with a bile acid reabsorption inhibitor, particularly selected from the group consisting of ASBT (IBAT) inhibitors such as AZD-7806, 5-8921, AK-105, BARI-1741, SC-435 and SC-635.

In particular embodiments, the isolated antibody or antigen-binding fragment according to the present disclosure is administered in combination with a lipoprotein(a) antagonist, particularly selected from the group consisting of gemcabene calcium (CI-1027) and nicotinic acid.

In particular embodiments, the isolated antibody or antigen-binding fragment according to the present disclosure is administered in combination with a TGFbeta antagonist, particularly selected from pirfenidone and fresolimumab.

In particular embodiments, the isolated antibody or antigen-binding fragment according to the present disclosure is administered in combination with anti-microRNA-21 oligonucleotides, particularly selected from Lademirsen.

In particular embodiments, the isolated antibody or antigen-binding fragment according to the present disclosure is administered in combination with HIF-PH inhibitors, particularly selected from molidustat and roxadustat.

In particular embodiments, the isolated antibody or antigen-binding fragment according to the present disclosure is administered in combination with a CCR2 antagonist, particularly selected from CCX-140.

In particular embodiments, the isolated antibody or antigen-binding fragment according to the present disclosure is administered in combination with a TNFalpha antagonist, particularly selected from adalimumab.

In particular embodiments, the isolated antibody or antigen-binding fragment according to the present disclosure is administered in combination with a galectin-3 inhibitor, particularly selected from GCS-100.

In particular embodiments, the isolated antibody or antigen-binding fragment according to the present disclosure is administered in combination with a hepatocyte growth factor mimeticmimetics, particularly selected from Refanalin.

In particular embodiments, the isolated antibody or antigen-binding fragment according to the present disclosure is administered in combination with a p53 modulator, particularly selected from QPI-1002.

In particular embodiments, the isolated antibody or antigen-binding fragment according to the present disclosure is administered in combination with a NOX1/4 inhibitor, particularly selected from GKT-137831.

In particular embodiments, the isolated antibody or antigen-binding fragment according to the present disclosure is administered in combination with a medicament which affects the vitamin D metabolism, particularly selected from cholecalciferol and paracalcitol.

In particular embodiments, the isolated antibody or antigen-binding fragment according to the present disclosure is administered in combination with a cytostatic agent, particularly selected from cyclophosphamide.

In particular embodiments, the isolated antibody or antigen-binding fragment according to the present disclosure is administered in combination with anti-VEGF therapy, particularly selected from the group consisting of ranibizumab, bevacizumab and aflibercept.

In particular embodiments, the isolated antibody or antigen-binding fragment according to the present disclosure is administered in combination with an immunosuppressive agent, particularly selected from ciclosporin.

In particular embodiments, the isolated antibody or antigen-binding fragment according to the present disclosure is administered in combination with a phosphate binder, particularly selected from sevelamer and lanthanum carbonate.

In particular embodiments, the isolated antibody or antigen-binding fragment according to the present disclosure is administered in combination with a calcimimetic for therapy of hyperparathyroidism.

In particular embodiments, the isolated antibody or antigen-binding fragment according to the present disclosure is administered in combination with agents for iron deficit therapy, particularly selected from iron products.

In particular embodiments, the isolated antibody or antigen-binding fragment according to the present disclosure is administered in combination with agents for the therapy of hyperurikaemia, particularly selected from allopurinol and rasburicase.

In particular embodiments, the isolated antibody or antigen-binding fragment according to the present disclosure is administered in combination with glycoprotein hormone for the therapy of anaemia, particularly selected from erythropoietin.

In particular embodiments, the isolated antibody or antigen-binding fragment according to the present disclosure is administered in combination with biologics for immune therapy, particularly selected from the group consisting of abatacept, rituximab, eculizumab and belimumab.

In particular embodiments, the isolated antibody or antigen-binding fragment according to the present disclosure is administered in combination with Jak inhibitors, particularly selected from the group consisting of ruxolitinib, tofacitinib, baricitinib, CYT387, GSK2586184, lestaurtinib, pacritinib (SB1518) and TG101348.

In particular embodiments, the isolated antibody or antigen-binding fragment according to the present disclosure is administered in combination with prostacyclin analogs for therapy of microthrombi.

In particular embodiments, the isolated antibody or antigen-binding fragment according to the present disclosure is administered in combination with an alkali therapy, particularly selected from sodium bicarbonate.

In particular embodiments, the isolated antibody or antigen-binding fragment according to the present disclosure is administered in combination with an mTOR inhibitor, particularly selected from everolimus and rapamycin.

In particular embodiments, the isolated antibody or antigen-binding fragment according to the present disclosure is administered in combination with an NHE3 inhibitor, particularly selected from AZD1722.

In particular embodiments, the isolated antibody or antigen-binding fragment according to the present disclosure is administered in combination with an eNOS modulator, particularly selected from sapropterin.

In particular embodiments, the isolated antibody or antigen-binding fragment according to the present disclosure is administered in combination with a CTGF inhibitor, particularly selected from FG-3019.

In particular embodiments, the isolated antibody or antigen-binding fragment according to the present disclosure is administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), and positive-inotropic agents.

In particular embodiments, the isolated antibody or antigen-binding fragment according to the present disclosure is administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), positive-inotropic agents, anti-inflammatory agents, immunosuppressive agents, phosphate binders and antibodies which modulate vitamin D metabolism.

Combination therapy includes administration of a single pharmaceutical dosage formulation which comprises the antibody or antigen-binding fragment according to the present disclosure or a variant thereof and one or more additional therapeutic agents, as well as administration of the antibody or antigen-binding fragment according to the present disclosure and each additional therapeutic agent in its own separate pharmaceutical dosage formulation. For example, an antibody of the disclosure or an antigen-binding fragment thereof or a variant thereof and a therapeutic agent may be administered to the patient together in a single liquid composition, or each agent may be administered in separate dosage formulation.

Where separate dosage formulations are used, the antibody or antigen-binding fragment according to the present disclosure or the variant thereof and one or more additional therapeutic agents may be administered at essentially the same time (e.g., concurrently) or at separately staggered times (e.g., sequentially).

The antibody or the antigen-binding fragment according to the present disclosure or a variant thereof might be used in combination with surgical interventions, including but not limited to:
major cardiovascular surgeries e.g. coronary artery bypass grafting (CABG), heart valve repair or replacement, insertion of a pacemaker or an implantable cardioverter defibrillator (ICD), maze surgery, aneurysm repair, arotid artery surgery/endarterectomy and thrombectomy;
major non-cardiac surgeries e.g., thoracic, orthopedic urologic surgeries.

Diagnostic Methods

Furthermore, the antibody or antigen-binding fragment according to the present disclosure may be utilized, as such or in compositions, in research and diagnostics, or as analytical reference standards, and the like.

Anti-Sema3A antibodies or antigen-binding fragments thereof can be used for detecting the presence of Sema3A. Thus, in a further aspect, the present disclosure relates to the isolated antibody or antigen-binding fragment according to the present disclosure or the antibody conjugate according to the present disclosure for use as a diagnostic agent.

Pharmaceutical Compositions and Administration

In a further aspect, the present disclosure relates to a pharmaceutical composition comprising the isolated antibody or antigen-binding fragment according to the present disclosure or the antibody conjugate according to the present disclosure. To treat any of the foregoing disorders, pharmaceutical compositions for use in accordance with the present disclosure may be formulated in any conventional manner using one or more physiologically acceptable carriers, excipients, or auxiliaries. Further details on techniques for formulation and administration may be found in the latest edition of Remington's Pharmaceutical Sciences (Ed. Maack Publishing Co, Easton, Pa.).

The antibody or antigen-binding fragment according to the present disclosure can be administered by any suitable means, which can vary, depending on the type of disorder being treated. Possible administration routes include oral, parenteral, and topical administration. Methods of parenteral delivery include intra-arterial, intramuscular, subcutaneous, intramedullary, intrathecal, intraventricular, intravenous, intraperitoneal, or intranasal administration. In addition, the antibody or antigen-binding fragment according to the present disclosure may be administered by pulse infusion, with, e.g., declining doses of the antibody. Preferably, administration is by injections, most preferably intravenous or subcutaneous injections, depending in part on whether the administration is brief or prolonged. The amount to be administered will depend on a variety of factors such as the clinical symptoms, weight of the individual, whether other drugs are administered, and the like. The skilled artisan will recognize that the route of administration will vary depending on the disorder or condition to be treated.

The pharmaceutical composition according to the present disclosure comprises the antibody or antigen-binding fragment according to the present disclosure alone or in combination with at least one other agent, such as a stabilizing compound. The antibody or antigen-binding fragment according to the present disclosure may be administered in any sterile, biocompatible pharmaceutical carrier, including, but not limited to, saline, buffered saline, dextrose, and water. In particular embodiments, the pharmaceutical composition according to the present disclosure may comprise one or more further pharmaceutically active compounds, in particular one or more further pharmaceutically active compounds that are suitable to treat Sema3A associated disorders. Any of these agents can be administered to a patient alone, or in combination with other agents or drugs, in pharmaceutical compositions where it is mixed with excipient(s) or pharmaceutically acceptable carriers. In particular embodiments, the pharmaceutically acceptable carrier is pharmaceutically inert.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methylcellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the disclosure may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present disclosure may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine or phosphate or Tris, 0.1%-2% sucrose and/or 2%-7% mannitol at a pH range of 4.5 to 7.5 optionally comprising additional substances like polysorbate that is combined with buffer prior to use.

After pharmaceutical compositions comprising a compound of the disclosure formulated in an acceptable carrier have been prepared, they can be placed in an appropriate container and labeled for treatment of an indicated condition. For administration of anti-Sema3A antibodies or antigen-binding fragment thereof, such labeling would include amount, frequency and method of administration.

Therapeutically Effective Dose

The determination of an effective dose is well within the capability of those skilled in the art. Determining a therapeutically effective amount of the novel antibody of this disclosure or an antigen-binding fragment thereof or a variant thereof, largely will depend on particular patient characteristics, route of administration, and the nature of the disorder being treated. General guidance can be found, for example, in the publications of the International Conference on Harmonization and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

For any compound, the therapeutically effective dose can be estimated initially either in cell culture assays, or in animal models, usually mice, rabbits, dogs, pigs or monkeys. The animal model is also used to achieve a desirable concentration range and route of administration. Such information can then be used to determine useful doses and routes for administration in humans.

A therapeutically effective dose refers to that amount of antibody or antigen-binding fragment thereof, that ameliorates the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Long acting pharmaceutical compositions might be administered for example every 3 to 4 days, every week, once every two weeks, or once every three weeks, depending on half-life and clearance rate of the particular formulation.

Normal dosage amounts may vary from 0.1 to 100,000 micrograms, up to a total dose of about 10 g, depending upon the route of administration. Guidance as to particular dosages and methods of delivery is provided in the literature. See U.S. Pat. Nos. 4,657,760; 5,206,344; or 5,225,212.

Kits

In a further aspect, the present disclosure relates to a kit comprising the isolated antibody or antigen-binding fragment according to the present disclosure or the conjugate according to the present disclosure and instructions for use. In particular embodiments, the kit comprises one or more containers filled with one or more of the ingredients of the aforementioned compositions of the disclosure. Associated with such container(s) can be a notice in the form prescribed by a governmental agency regulating the manufacture, use or sale of pharmaceuticals or biological products, reflecting approval by the agency of the manufacture, use or sale of the product for human administration.

DRAWINGS

FIG. 1A: Effects of Sema3A inhibition with TPP-15370 (grey bar), TPP-11489 (striped bar) and TPP-17755 (squared bar) on Sema3A-induced albumin excretion in mice. Shown are mean±S.D. (n=10). *, **: p<0.001 p<0.0001 vs. isotype control. Dunnett's post hoc test.

Figure 1B:
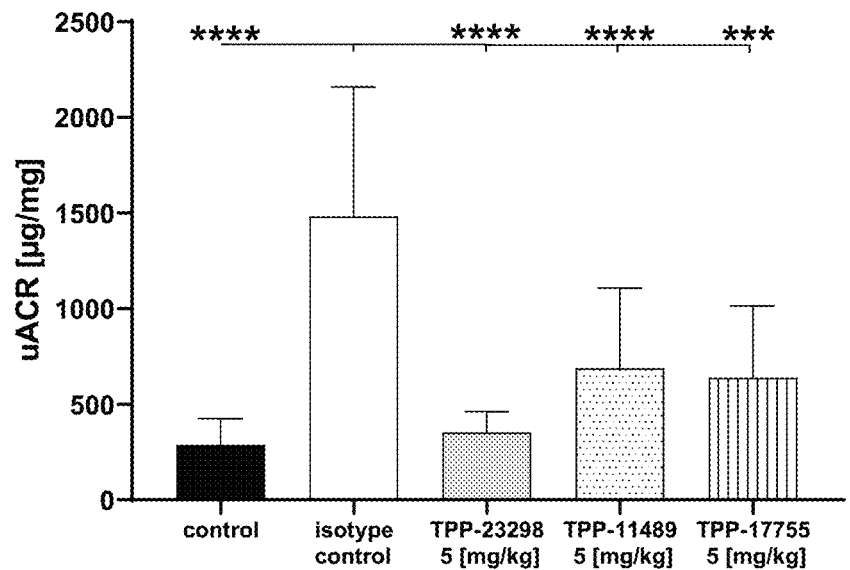

FIG. 1B: Effects of Sema3A inhibition with TPP-23298 (grey bars), TPP-11489 (dotted bar) and TPP-17755 (striped bar) on Sema3A-induced albumin excretion in mice. Shown are mean±S.D. (n=10). *, **: p<0.001 p<0.0001 vs. isotype control. Dunnett's post hoc test.

Figure 2A:
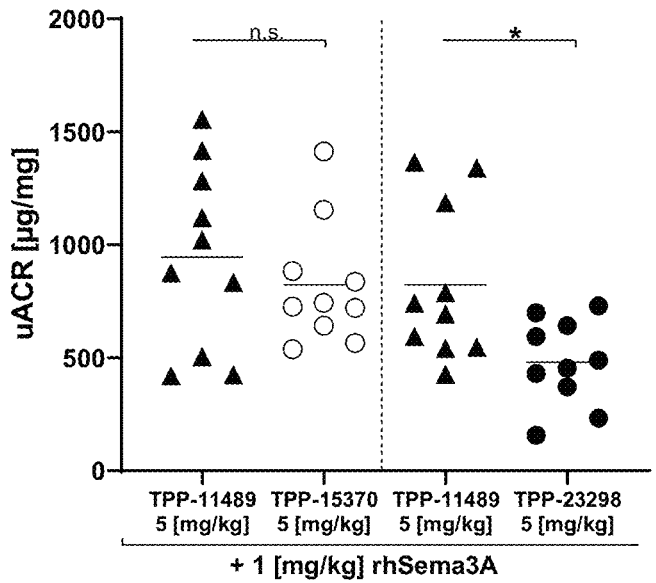

FIG. 2A: Sema3A induced albuminuria in mice after treatment with TPP-15370 (white circles) and TPP-23298 (black circles) in comparison to TPP-11489 (black triangles). The comparisons were performed in two separate experiments. Shown are mean values. (n=10). n.s.=statistically not significant vs. TPP-15370; *=p<0.05 vs. TPP-23298. Unpaired T-test.

Figure 2B:
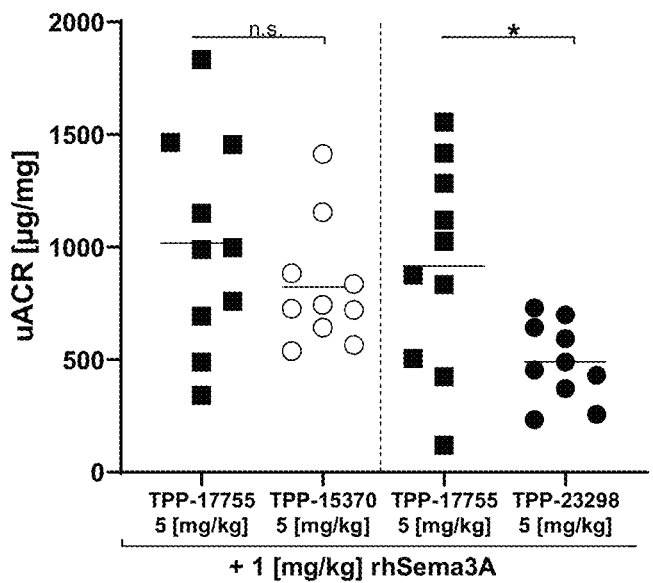

FIG. 2B: Sema3A induced albuminuria in mice after treatment with TPP-15370 (white circles) and TPP-23298 (black circles) in comparison to TPP-17755 (black squares). The comparisons were performed in two separate experiments. Shown are mean values. (n=10). n.s.=statistically not significant vs. TPP-15370; *=p<0.05 vs. TPP-23298. Unpaired T-test.

Figure 2C:
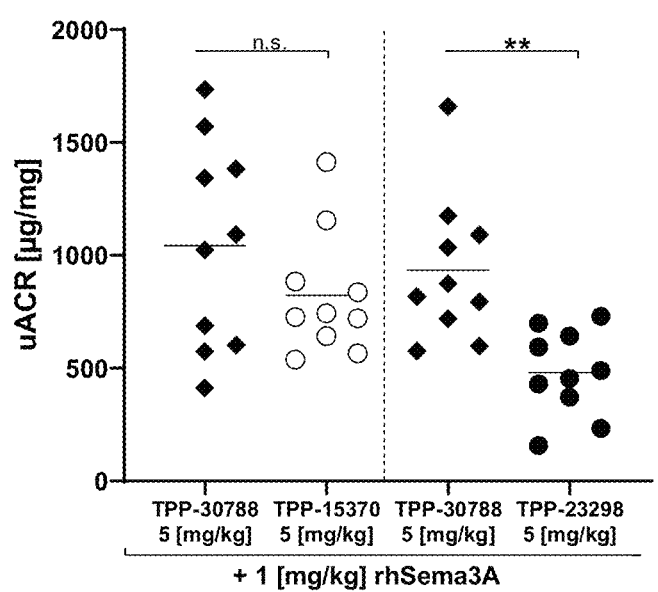

FIG. 2C: Sema3A induced albuminuria in mice after treatment with TPP-15370 (white circles) and TPP-23298 (black circles) in comparison to TPP-30788 (black rhombus). The comparisons were performed in two separate experiments. Shown are mean values. (n=10). n.s.=statistically not significant vs. TPP-15370; *=p<0.05 vs. TPP-23298. Unpaired T-test.

Figure 3A:
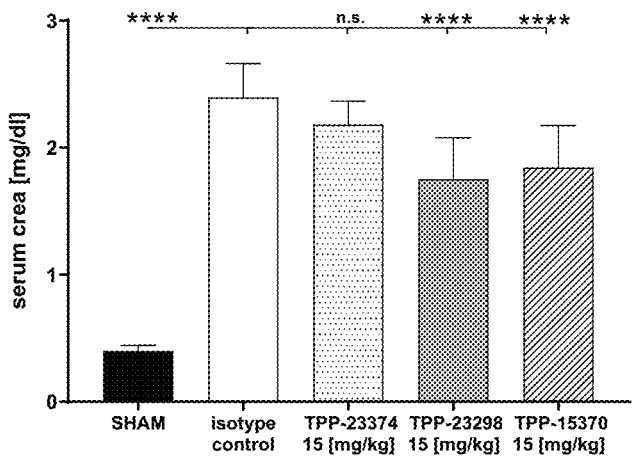
Figure 3B:
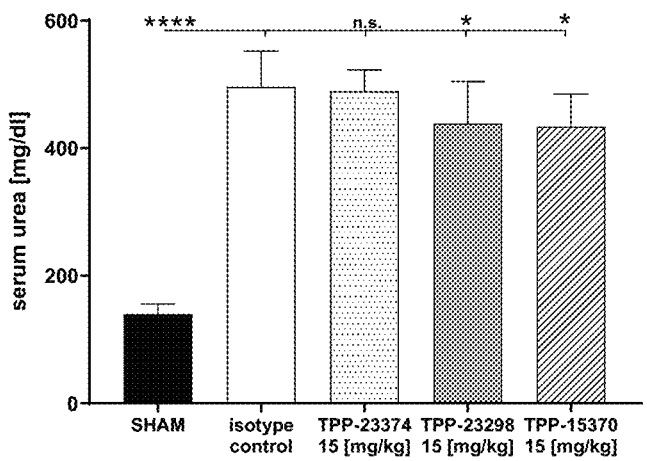
Figure 3C:
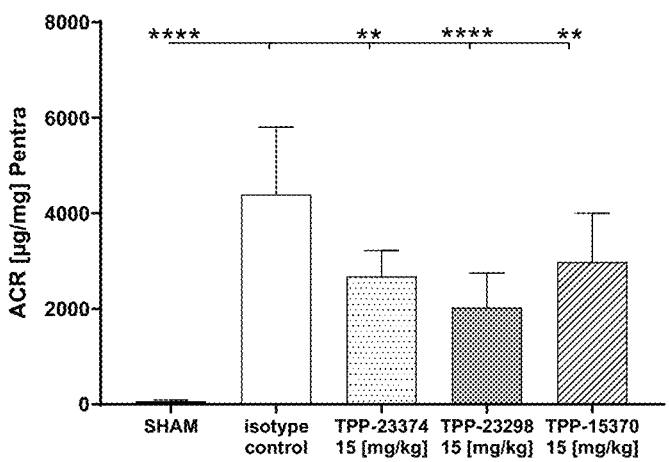

FIGS. 3A-3C: Effects of Sema3A inhibition with TPP-23374 (dotted bars) TPP-23298 (grey bars) and TPP-15370 (striped bars) on FIG. 3A: serum creatinine levels, FIG. 3B: serum urea levels and FIG. 3C: urinary albumin excretion after I/R injury in mice. Shown are mean±S.D. (n=8-10). *, , **: p<0.05, p<0.01, p<0.0001 vs. isotype control. Dunnett's post hoc test.

Figure 4A:
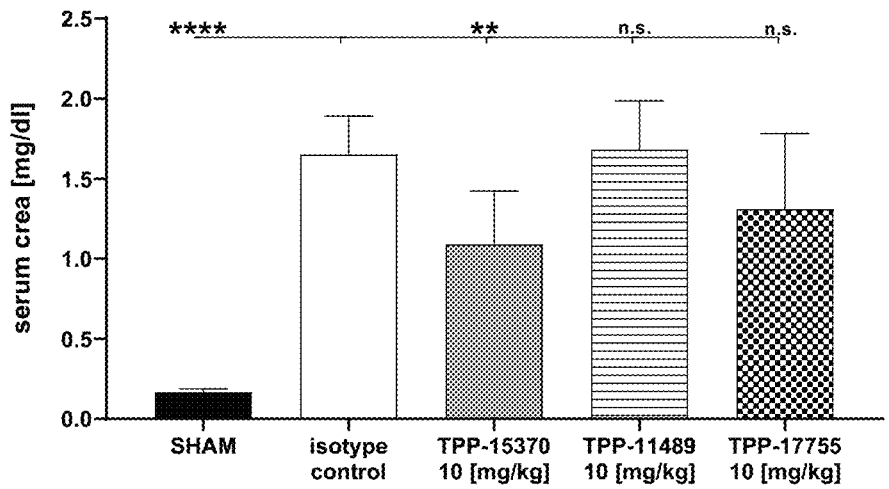
Figure 4B:
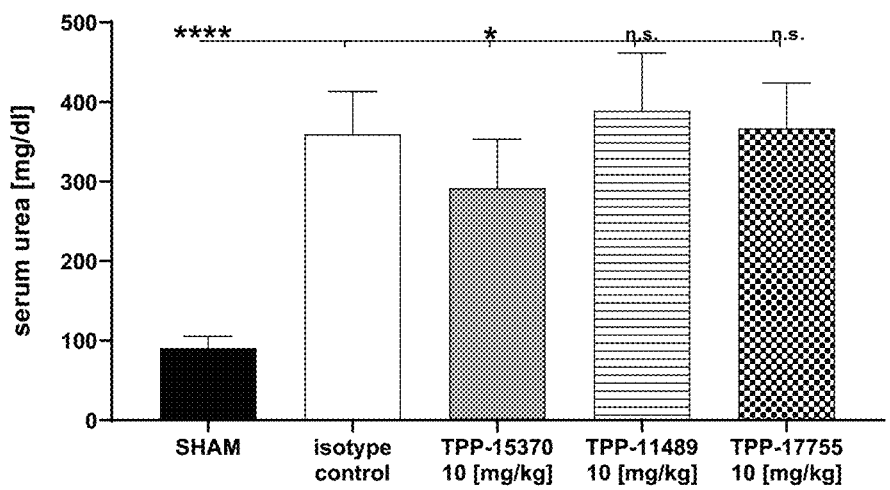
Figure 4C:
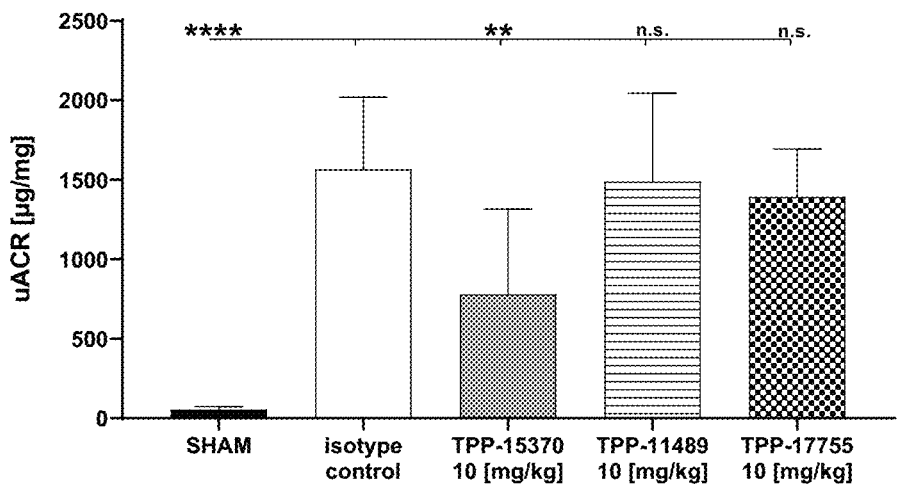

FIGS. 4A-4C: Effects of Sema3A inhibition with TPP-15370 (grey bars), TPP-11489 (striped bars) and TPP-17755 (squared bars) on FIG. 4A: serum creatinine levels, FIG. 4B: serum urea levels and FIG. 4C: urinary albumin excretion after I/R injury in mice. Shown are mean±S.D. (n=8-10). *, , **: p<0.05, p<0.01, p<0.0001 vs. isotype control. Dunnett's post hoc test.

Figure 5A:
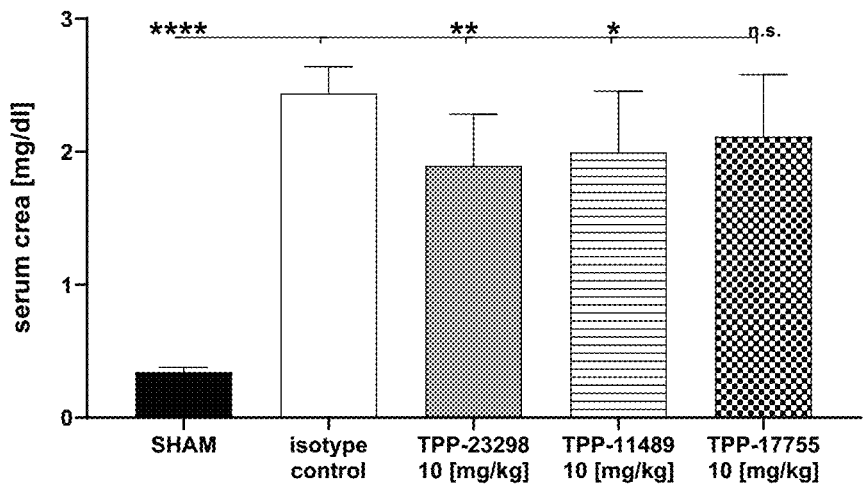
Figure 5B:
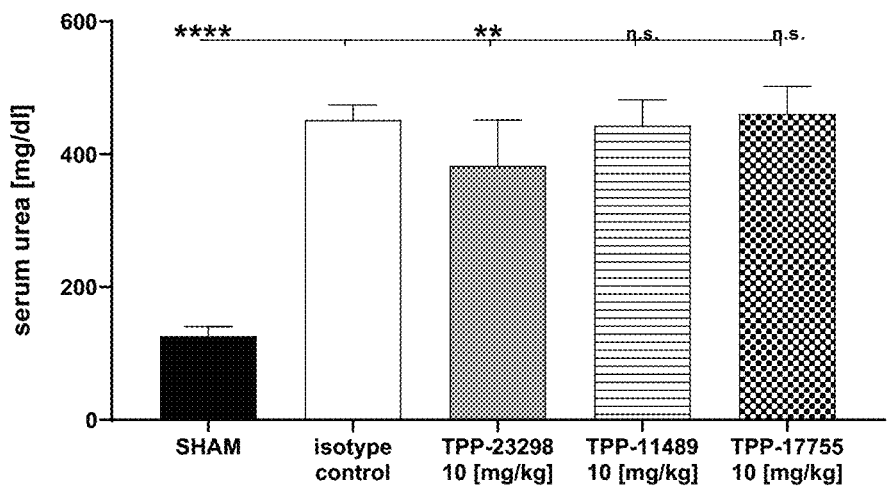
Figure 5C:
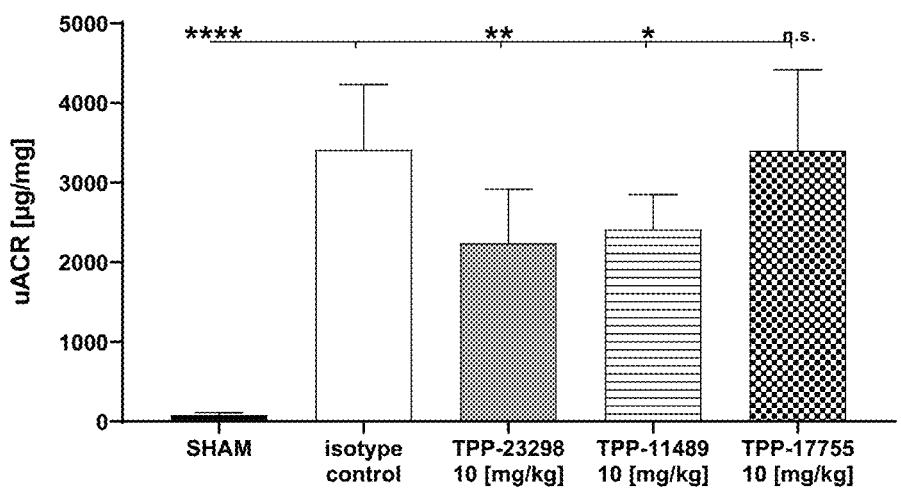

FIGS. 5A-5C: Effects of Sema3A inhibition with TPP-23298 (grey bars), TPP-11489 (striped bars) and TPP-17755 (squared bars) on FIG. 5A: serum creatinine levels, FIG. 5B: serum urea levels and FIG. 5C: urinary albumin excretion after I/R injury in mice. Shown are mean±S.D. (n=10-12). *, , **: p<0.05, p<0.01, p<0.0001 vs. isotype control. Dunnett's post hoc test.

Figure 6A:
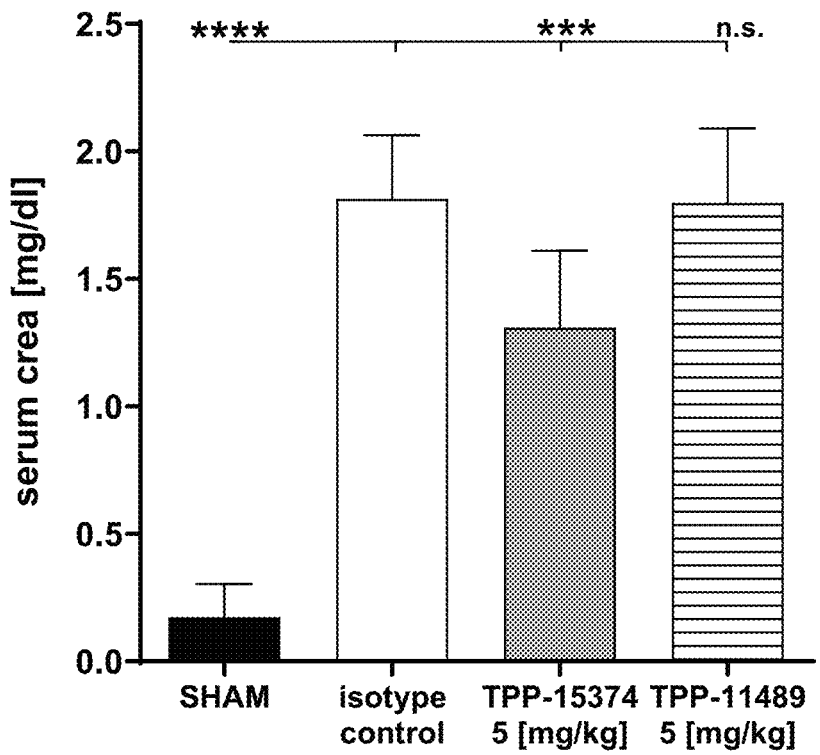
Figure 6B:
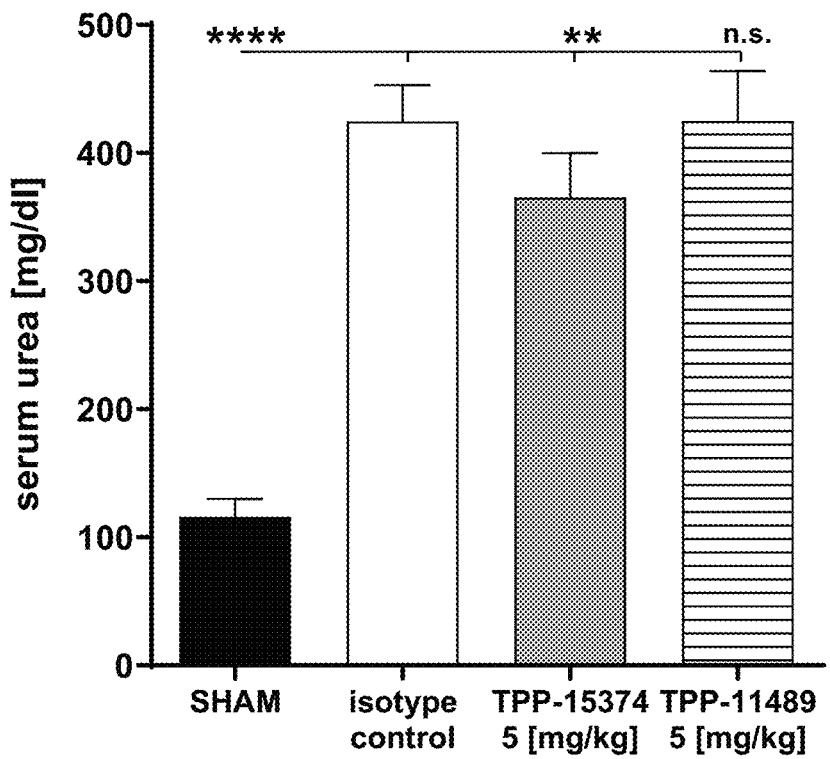
Figure 6C:
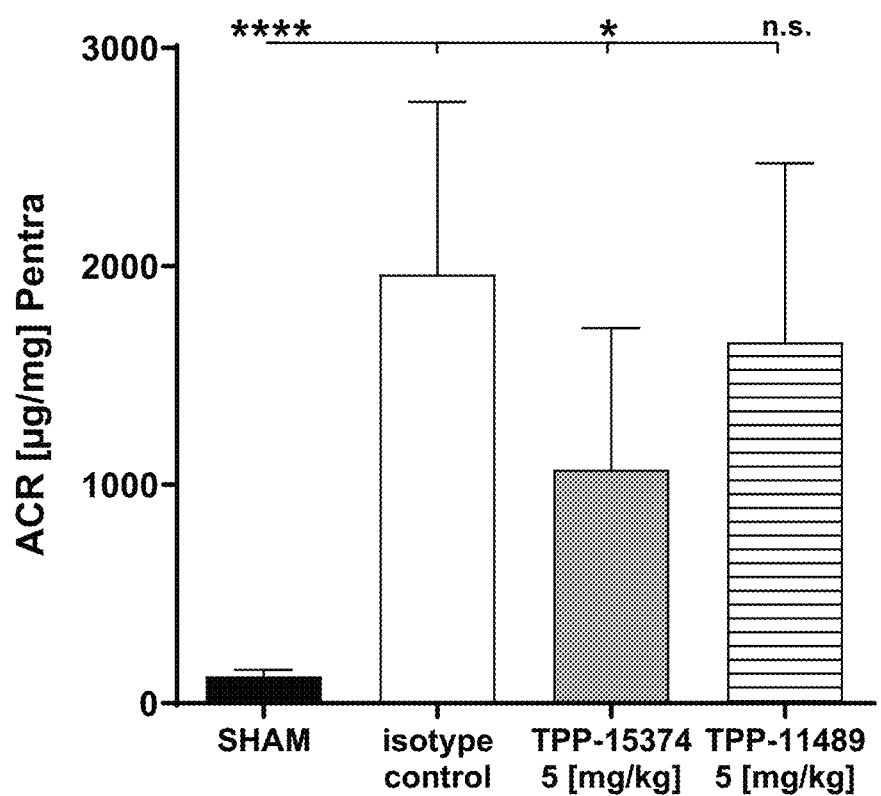

FIGS. 6A-6C: Effects of Sema3A inhibition with TPP-15374 (grey bars), TPP-11489 (striped bars) on FIG. 6A: serum creatinine levels, FIG. 6B: serum urea levels and FIG. 6C: urinary albumin excretion after I/R injury in mice. Shown are mean±S.D. (n=10-12). *, , *, ****: p<0.05, p<0.01, p<0.001 p<0.0001 vs. isotype control. Dunnett's post hoc test.

Figure 7:
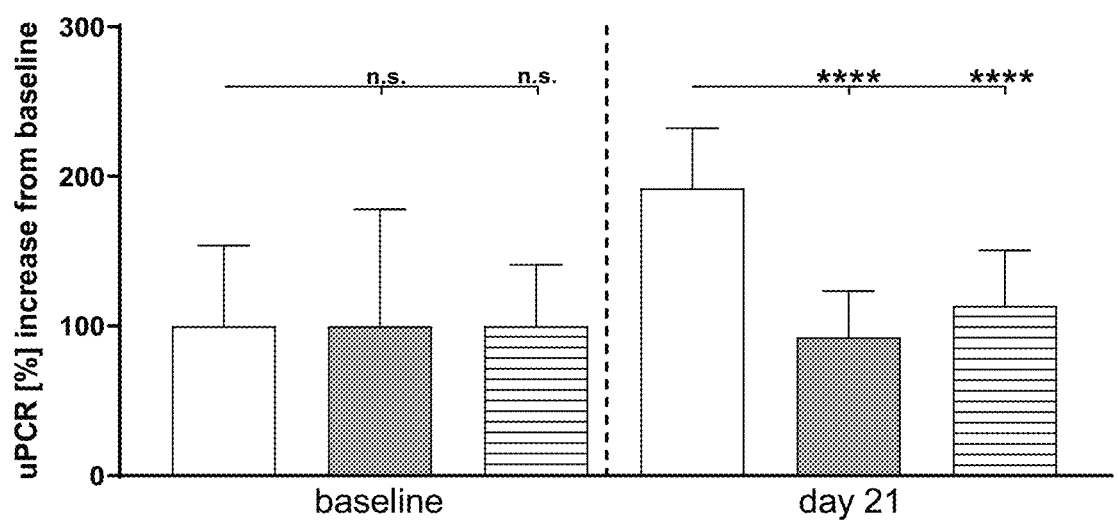
Figure 8A:
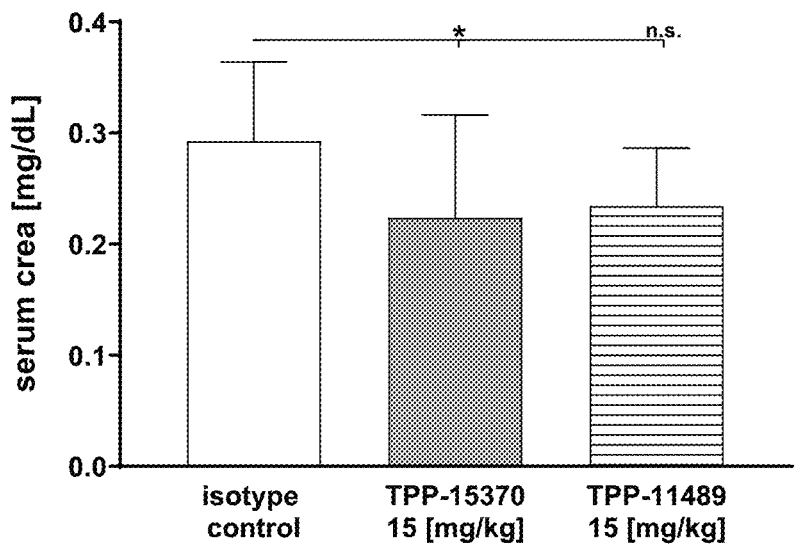
Figure 8B:
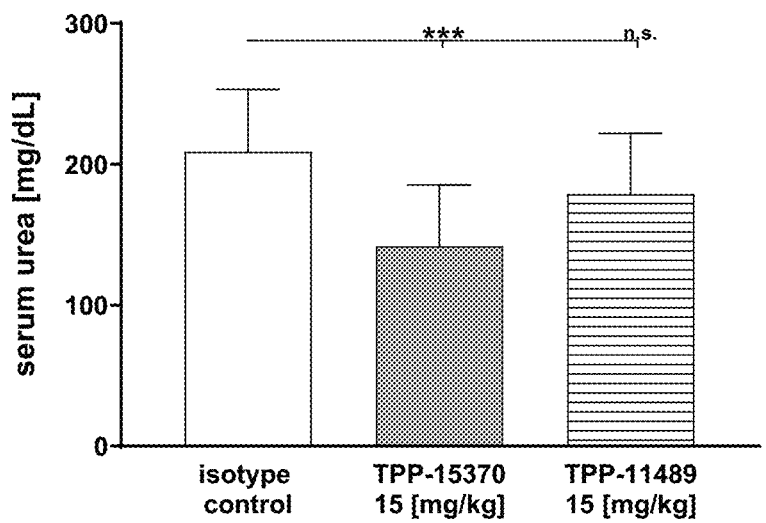
Figure 8C:
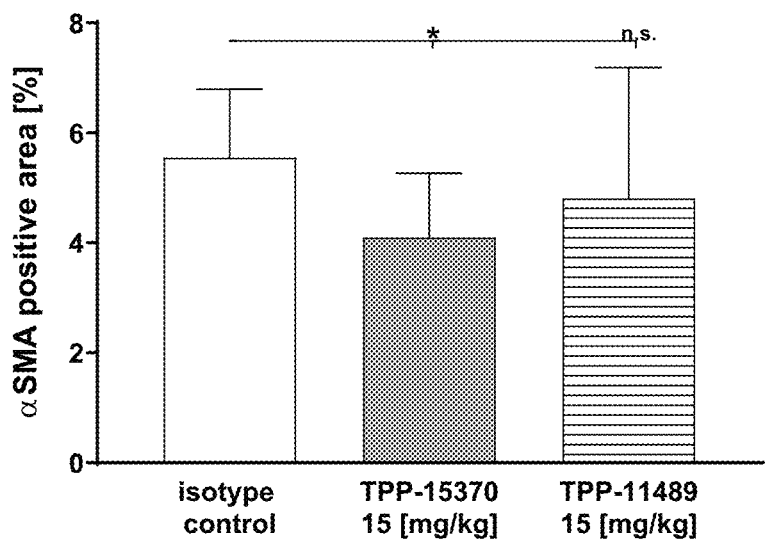
Figure 8D:
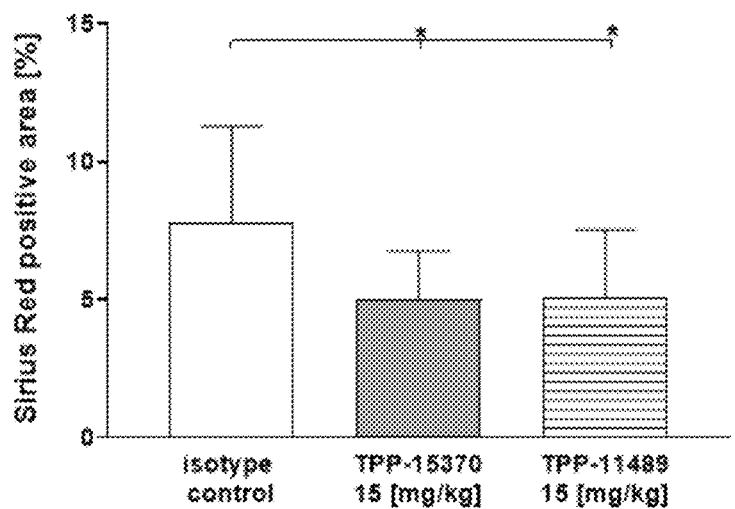

FIG. 7: Effects of Sema3A inhibition with TPP-15370 (grey bars), TPP-11489 (striped bars) on proteinuria in Alport mice. Shown are mean±S.D. (n=8-10). ****: p<0.0001 vs. isotype control. Dunnett's post hoc test.

FIGS. 8A-8D: Effects of Sema3A inhibition with TPP-15370 (grey bars), TPP-11489 (striped bars)) on FIG. 8A: serum creatinine levels, FIG. 8B: serum urea levels and fibrosis FIG. 8C: myofibroblast and FIG. 8D: collagen deposition in Alport mice. Shown are mean±S.D. (n=8-10). *, *, **: p<0.05, p<0.001, p<0.0001 vs. isotype control. Dunnett's post hoc test.

Figure 9A:
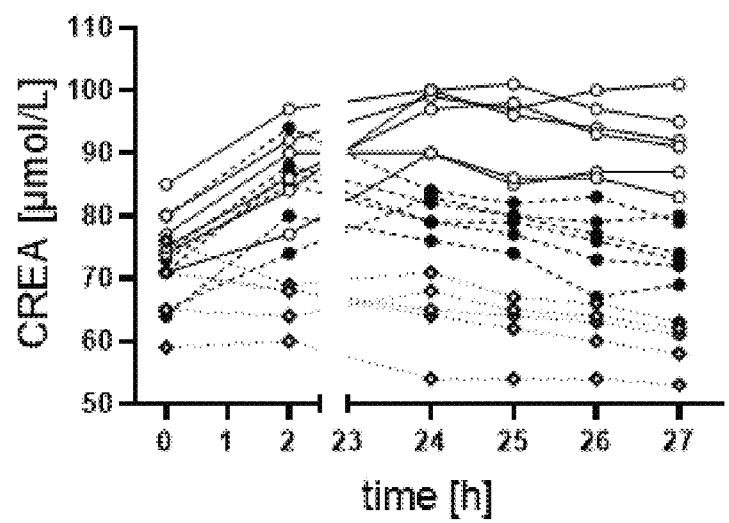
Figure 9B:
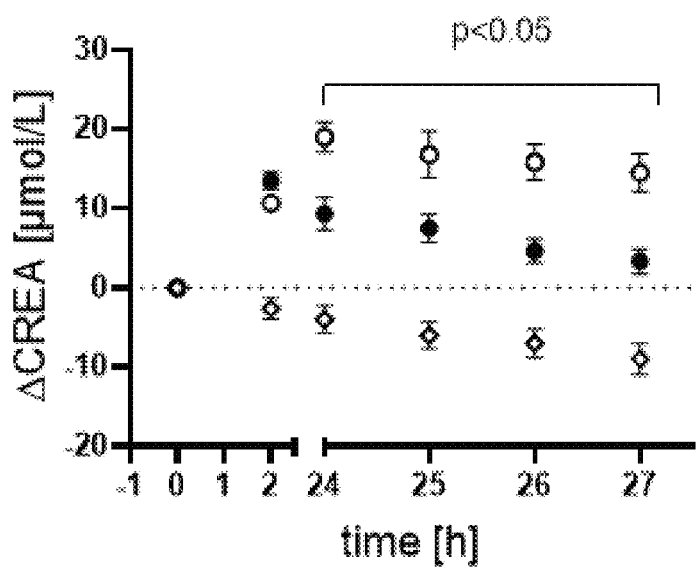
Figure 9C:
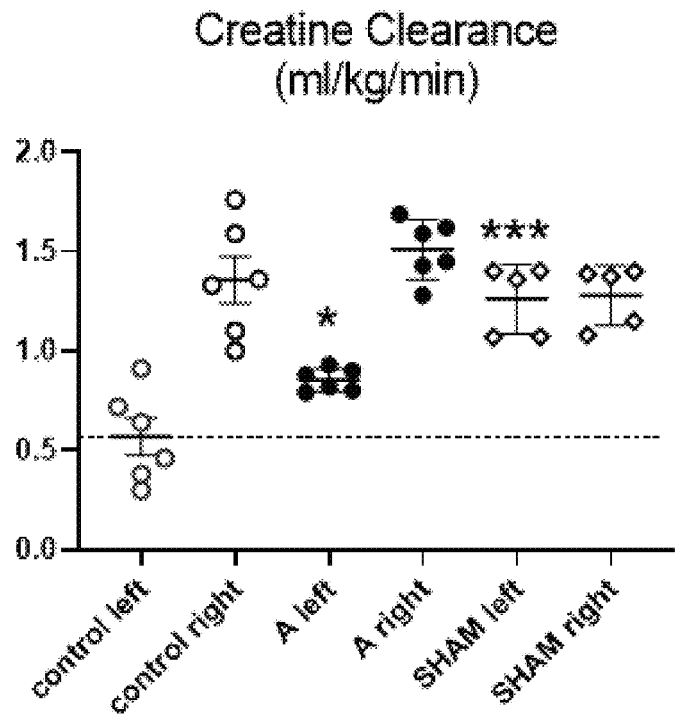
Figure 9D:
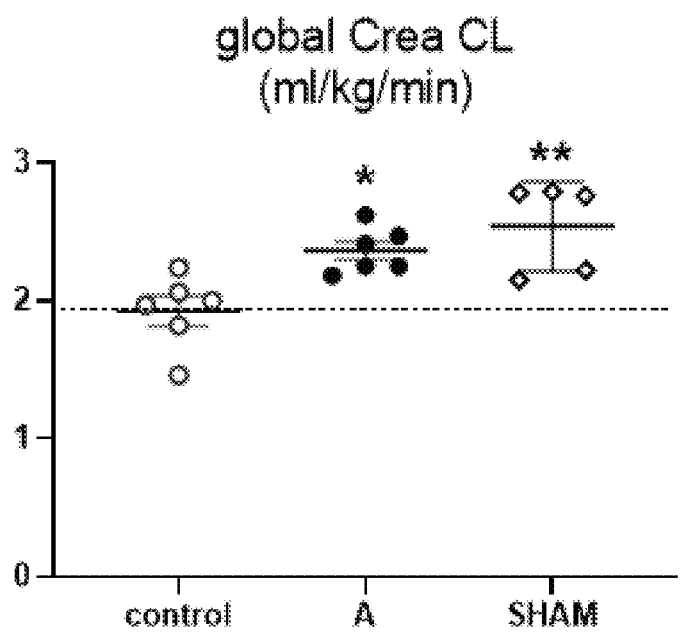

FIGS. 9A-9D: Effects of Sema3A inhibition with TPP-23298 in a single dose preventive setting in a unilateral kidney IRI model in pigs, 105 min of ischemia. TPP-23298 (FIG. 9A; black dots) or control IgG (open circles) (10 mg/kg) were given 30 min before inflating the balloon in the left renal artery. Values from SHAM animals are indicated diamonds. Time course of plasma creatinine concentrations of individual animals (FIG. 9A), and time course of mean change of creatinine plasma concentrations versus base line values at start of experimentation (0 h) (FIG. 9B). Mean values of creatinine clearance for 24-27 h interval. Creatinine clearance side separated for left (damaged) and right (non-damaged) kidneys and kidneys from sham animals (FIG. 9C). Global creatinine clearance (FIG. 9D); means±SEM, p-value in (FIG. 9B) from t-test, */*** in (FIG. 9C) and FIG. 9D): p<0.05/0.001, one-way ANOVA versus corresponding control followed by Dunnett's multiple comparison.

Figure 10A:
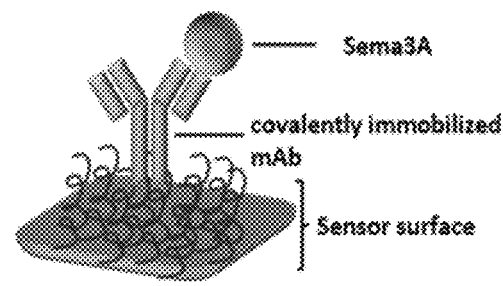
Figure 10A:
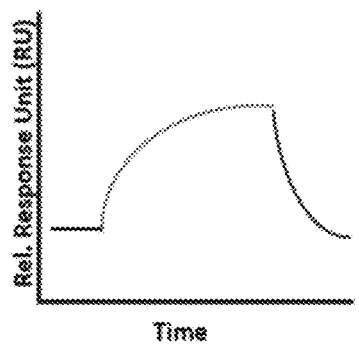
Figure 10B:
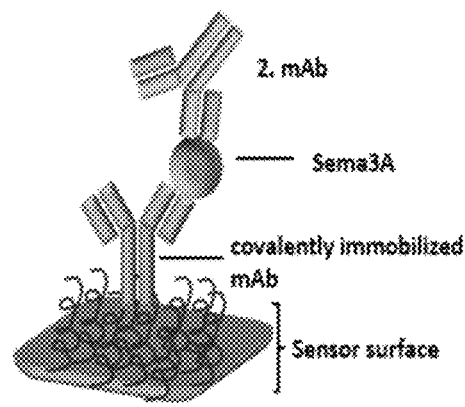
Figure 10B:
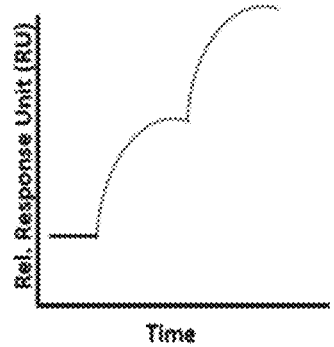
Figure 10C:
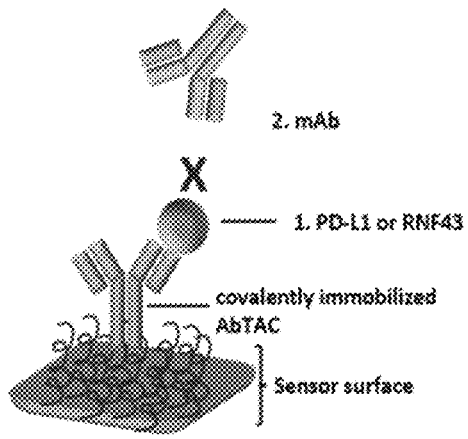
Figure 10C:
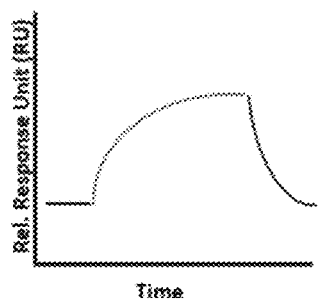

FIGS. 10A-10C: Schematic representation of a sandwich-based epitope binning experiment using SPR (see also Example 5A): FIG. 10A) One antibody is immobilized to a SPR chip, Sema3A is injected, and the binding is monitored; FIG. 10B) A second (competitive) antibody is injected on to the complex of the immobilized mAb bound to Sema3A, and the binding is monitored; FIG. 10C) A second (non-competitive) antibody is injected on to the complex of the immobilized mAb bound to Sema3A, and the binding is monitored.

Figure 11A:
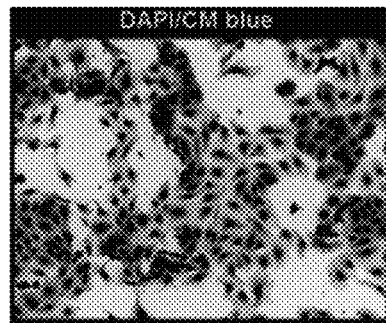
Figure 11B:
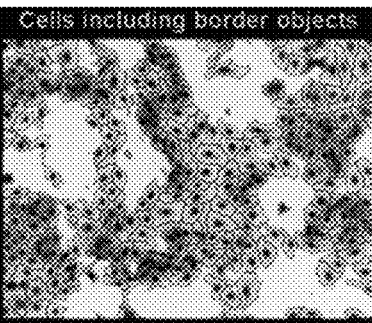
Figure 11C:
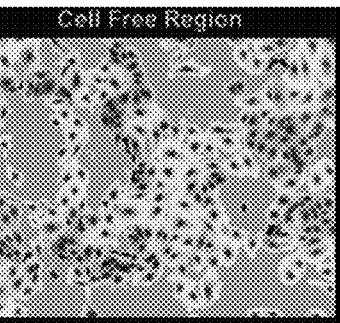

FIGS. 11A-11C: HRA image analysis steps: FIG. 11A) Fluorescence microscopy image of DAPI/CM cells; FIG. 11B) Identification of cells in the selected area; FIG. 11C) Calculation of cells-free region size (grey area).

Figure 12:
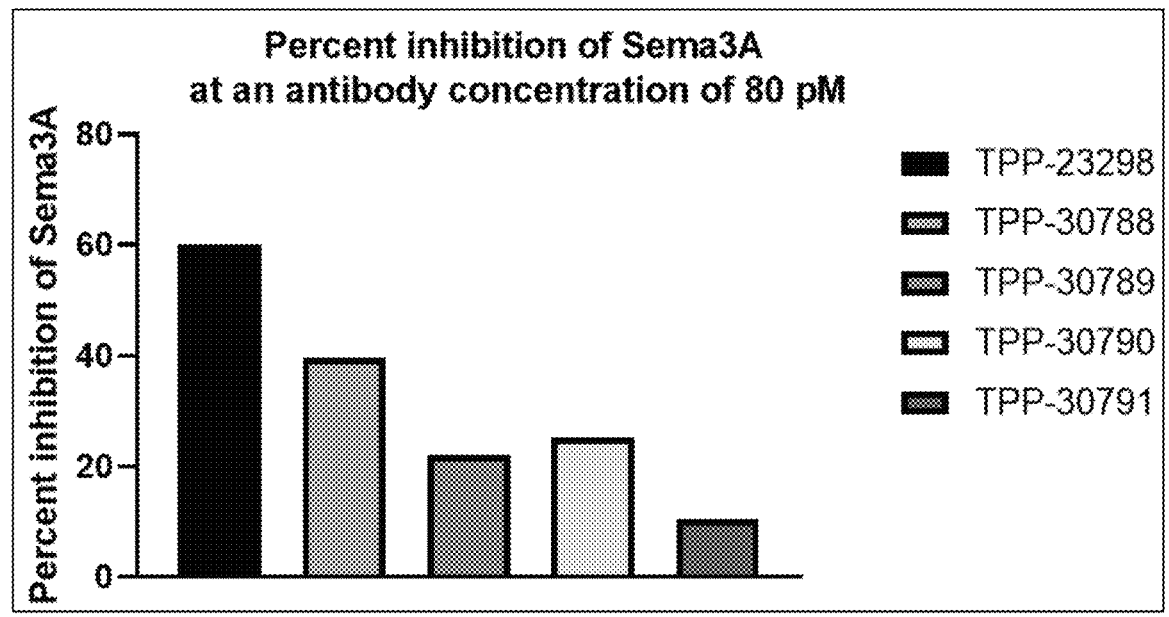

FIG. 12: The percent inhibition of Sema3A in a HUVEC repulsion assay at an antibody concentration of 80 pM is shown (see Example 11). Each column represents one antibody in the following left to right order: TPP-23298 (black column), TPP-30788, TPP-TPP-30789, TPP-30790, and TPP-30791.

EXAMPLES

Example 1: Sema3A Sequences and Tool Generation gies) and 4 mM Glutamax (Life Technologies). 24 h post-transfection, 1% FCS ultra-low IgG (Life Technologies) and 0.5 mM valproic acid (Sigma Aldrich) were added. Cell supernatant was sterile filtered and subsequently purified or concentrated via crossflow filtration prior to purification.

Sema3A domains were purified using a two-step purification consisting of affinity and size exclusion chromatography. In brief, cell culture supernatant was loaded on to a $Ni^{2+}$-NTA column (GE Healthcare) connected to an Äkta Avant system (GE Healthcare). Column was equilibrated with 4 CV of 50 mM $NaH_2PO_4$, 300 mM NaCl, pH 8 and washed afterwards with 10 CV of running buffer until baseline was reached. Elution was carried out using 6 CV of running buffer containing 250 mM imidazole, pH 8.0. Fractions of the elution peak were unified, concentrated using a Vivaflow 200 Hydrosart membrane (cut-off 10 kDa, Sartorius) and subjected to size exclusion chromatography using a Superdex 200 column (GE Healthcare) connected to an Äkta Pure 25 system. The column was equilibrated and run in DPBS, pH 7.4. Fractions of the domain elution peak were unified and concentrated using a Vivaflow 200 Hydrosart membrane (cut-off 10 kDa, Sartorius). The final protein quality was assessed on an analytical size exclusion chromatography (Superdex 200) for purity and monodispersity as well as SDS-PAGE. Sema domains were aliquoted and snap frozen in liquid nitrogen and stored at −80° C. until further use.

Example 2: Antibody Generation from BioInvent Antibody Libraries

A fully human antibody phage display library (BioInvent n-CoDeR Fab lambda library) was used to isolate human monoclonal antibodies of the present disclosure by selection against recombinant human Sema3A (TPP-13211, R&D

TABLE 2

Tools used in this disclosure

| TPP-No. | Protein | Bounderies [aa] | Uniprot ID | Catalog No. |
|---|---|---|---|---|
| TPP-13211 | Human Semaphorin3A-Fc (R&D Systems) | 26-771 | Q14563 | 1250-S3 |
| No TPP-No. | Human Semaphorin3G (Abnova) | 1-782 | Q9NS98 | H00056920-P01 |
| No TPP-No. | Human Semaphorin3F-Fc (R&D Systems) | 19-772 | Q13275 | 9878-S3 |
| TPP-13357 | Mouse Semaphorin3A-Fc (R&D Systems) | 21-747 | O08665 | 5926-S3 |
| TPP-19068 | Human Semaphorin3A-Sema Domain | 21-569 | Q14563 | Produced inhouse |
| TPP-19069 | Mouse Semaphorin3A-Sema Domain | 21-569 | O08665 | Produced inhouse |
| TPP-19122 | Cyno Semaphorin3A-Sema Domain | 21-569 | Q63548 | Produced inhouse |
| TPP-19120 | Rat Semaphorin3A-Sema Domain | 21-569 | E2QX94 | Produced inhouse |
| TPP-19121 | Dog Semaphorin3A-Sema Domain | 21-569 | A0A2K5VGJ0 | Produced inhouse |
| TPP-20176 | Pig Semaphorin3A-Sema Domain | 49-658 | A0A480WHT2 | Produced inhouse |

Sema3A domains were produced by mammalian cell culture using transiently transfected HEK293-6E cells (National Research Council Canada). All constructs were under the control of a CMV promoter and sequences contain a C-terminal FXa cleavage site followed by a 6×his-tag. Cell culture was performed using F17 medium (Life Technologies) supplemented with 0.1% pluronic F68 (Life Technolo- Systems) using the following protocol. Briefly, Immunotubes (Nunc) were coated for one hour at room temperature (RT) with the 100 µg of the target molecule (huSema3A) or an irrelevant Fc-containing off-target in 1 ml PBS (Phosphate Buffered Saline) with end-over-end rotation. The target and depletion antigen-coated immunotube as well as an empty immunotube were washed 4 times with PBS+

0.05% Tween20 (PBST) and subsequently blocked using 3 ml of a 3% Milk powder in PBST solution for 1 h at RT with end-over-end rotation. An aliquot of the phage library was thawed and allowed to block in a solution of 3% milk powder in PBST for 1 h at RT with end-over-end rotation. The non-coated depletion immunotube was washed 3 times in 4 ml PBS before addition of the blocked phage library and incubation with end-over-end rotation for 30 min at RT. This step was repeated for the non-target antigen-coated depletion immunotube. The huSema3A-coated immunotube was washed 3 times in 4 ml PBS before addition of the depleted library and incubation for 90 min at room temperature with end-over-end rotation. After stringent washing (4× with 4 ml PBST and 1× with 4 ml PBS) Fab-expressing phages binding specifically to the coated target were eluted using 500 µl 100 nM TEA, 10 min incubation at room temperature followed by neutralization by addition of 500 µl Tris-HCl pH 7.5. 500 µl of eluted phage were used to infect *Escherichia coli* strain HB101. Subsequently the phages were amplified in *Escherichia coli* strain HB101 using M13K07 Helper Phage (Invitrogen™). In two subsequent selection rounds the target concentration was decreased to 25 µg/ml. For a first qualitative assessment, 88 randomly picked Fab-expressing phage clones from each selection round were expressed in single wells and tested for binding to huSema3A compared to an irrelevant off-target. The clone pool from Round 3 in this example was found to contain a 60% positive hit rate and was chosen for further screening.

In a next step, the expression of soluble Fabs was enabled by bulk removal of the gene III fusion in this pool and 2208 single clones were picked for expression in *Escherichia coli* strain Top10 and evaluation of Fab-containing supernatants in a huSema3A binding ELISA. The VH and VL sequences for all 2208 clones was also determined using NGS methods. 154 distinct clones positive for binding to huSema3A were identified. These positive binding Fab fragments were tested in a confirmatory binding ELISA and were also evaluated for binding to mouse Sema3A-Fc (TPP-13357, R&D Systems) as well as specificity testing using an additional off target molecule, murine Sema3F (R&D Systems). Based on this analysis, 48 human/mouse cross-reactive Sema3A binding Fabs were prioritized. These Fab fragments were subsequently purified from 25 ml expression cultures using Capture Select CH1 matrix (LifeTechnologies), eluted using 12.5 mM Citric acid at pH 2.5 and finally buffer exchanged to PBS using a Zeba™ Spin desalting plate (ThermoFisher). A kinetic ranking was performed for all 48 purified Fab fragments by surface plasmon resonance (SPR), examining the binding to both human and mouse Sema3A and reformatted in to a full-length human IgG1 and again tested for binding in SPR (see Example 4).

Example 3: Sequence Optimization, Germlining & Affinity Maturation of Lead Antibodies TPP-15370 and TPP-15374

IgG1 antibodies TPP-15370 and TPP-15374 were subjected to lead optimization procedures aiming to (i) optimize its affinity, (ii) increase functional efficiency, (iii) reduce the risk of sequence-based immunogenicity and (iv) improve compatibility with downstream development processes.

Affinity maturation was done by a first single mutation gathering round followed by recombination of the most affinity- and potency-increasing amino acid exchanges in a germlined and sequence optimized antibody backbone.

For mutation gathering NNK (N=A or G or C or T, K=G or T) randomizations at the following individual amino acid positions were generated by site directed mutagenesis using synthetic oligonucleotides including NNK for codon-diversification. For TPP-15370 the following regions were analyzed for their effect on affinity: GFTFSSYGMH (residues 26 to 35 of VH SEQ ID NO: 41), WVSAIGTGGDTYY-ADSVMG (residues 47 to 65 of VH SEQ ID NO: 41), ARRDDYTSRDAFDV (residues 96 to 109 of VH SEQ ID NO:41), SGSSSNIGSNTVNWY (residues 23 to 37 of VL SEQ ID NO: 45), LLIYYDDLLPS (residues 47 to 57 of VL SEQ ID NO: 45), and AAWDDSLNGYVV (residues 90 to 101 of VL SEQ ID NO: 45).

For TPP-15374 the following regions were analyzed for their effect on affinity: GFTFSSYEMN (residues 26 to 35 of VH SEQ ID NO: 61), WVSGISWNSGSIGYADSVKG (residues 47 to 66 of VH SEQ ID NO: 61), ARSGYSSS-WFDPDFDY (residues 97 to 112 of VH SEQ ID NO: 61), TGSSSNIGAGYDVHWY (residues 23 to 38 of VL SEQ ID NO: 65), LLIYGNSNRPS (residues 48 to 58 of VL SEQ ID NO: 65), and SSYAGSNPYV (residues 91 to 101 of VL SEQ ID NO: 65).

The resulting single NNK libraries were sequenced and about 1000 single amino acid exchange variants of TPP15370 and TPP-15374, respectively, were identified. They were expressed by transient transfection of mammalian cells and resulting expression supernatants were normalized in terms of antibody concentrations to be screened in surface plasmon resonance and competition ELISA.

For the germlining and sequence optimization process of TPP-15370 and TPP-15374 the closest germline families for light and heavy chain were selected and scrutinized for potential CMC relevant residues. Deviations from closest human germlines in CDR regions and FW regions and potential CMC relevant residues in CDR regions were adjusted by site directed mutagenesis and tested for in functional and biophysical assays (unspecific binding, temperature stability in DSC). The resulting single reversions and following combinatorial IgG variants were expressed by transient transfection of mammalian cells and resulting expression supernatants were normalized in terms of antibody concentrations to be screened in binding assays (SPR, competition ELISA) and functional assays. This led to germlined and sequence optimized molecules TPP-21565 for TPP-15370 and TPP-18533 for TPP-15374. TPP-21565 carries in comparison to TPP-15370 reversions L55R and R80Q in the light chain and G33A, H35S, M64K and V109Y in the heavy chain. TPP-18533 carries in comparison to TPP-15374 reversions A10V, T13A, S78T, R81Q, S82A in the light chain.

For the final recombination library of TPP-21565 eight single substitution variants that were shown in the NNK library screening step to exhibit improved affinity and functional efficiency were selected. Light chain mutations A90H, G98D, G98V, Y99I and V100P and heavy chain mutations S30Y, S35L and T53Y were recombined in one recombination library (continuous amino acid nomenclature, reference is TPP-21565 as defined by SEQ ID NOs: 121—VH and 125—VL).

For the final recombination library of TPP-18533 eleven single substitution variants that were shown in the NNK library screening step to exhibit improved affinity and functional efficiency were selected. Light chain mutations N28D, N53A, S91K, S91Q, A94E, S96I and S96P and heavy chain mutations T28D, S30D, S57W and G59Y were recombined in one recombination library (continuous amino acid nomenclature, reference is TPP-18533 as defined by SEQ ID NOs: 101—VH and 105—VL).

For TPP-18533 oligonucleotides were generated to introduce selected mutations or the corresponding wild type amino acid at each selected position. Library construction was performed using sequential rounds of overlap extension PCR. The final PCR product was ligated into a mammalian IgG4 (S228P) expression vector and variants were sequenced using massive-parallel sequencing techniques. For TPP-21565 the recombinatorial variants were designed as distinct clones and cloned into an IgG4 (S228P) containing expression plasmid.

More than 1000 unique combinatorial amino acid exchange variants of TPP-18533 and more than 100 unique combinatorial variants of TPP-21565 were generated in that way, expressed by transient transfection of mammalian cells, and resulting expression supernatants were normalized in terms of antibody concentrations to be screened in varying number in SPR, competition ELISA and functional assays. Based on the result in these assays, mutants were either categorized as 'improved' or 'non-improved'.

Table 1 and 1A lists i.a. preferred antibodies candidates according to the present disclosure that were selected in the combination library screening step as being most potent in terms of binding to Sema3A and in terms of antagonizing the Sema3A-dependent biological activity as well as the respective amino acid and nucleic acid sequences of antibodies according to the present disclosure.

Example 4: Determination of Affinity and Species Cross-Reactivity Using Surface Plasmon Resonance To assess the binding kinetics and affinity of anti-Sema3A antibodies as well as their species cross-reactivity profile, binding assays were conducted using surface plasmon resonance (SPR). Binding assays were performed on a Biacore T200 instrument or on a Biacore 8K+ instrument (Cytiva) at 25° C. using assay buffer HBS P+, 300 mM NaCl, 0.75 mM $CaCl_2$, 2.5 mM $MgCl_2$, 1 mg/ml BSA, 0.05% $NaN_3$. Antibodies were captured either via anti-human Fc IgGs ("Human antibody capture kit", Order No. BR100839, Cytiva) or in case of Fc-tagged analytes by anti-human Fab IgGs ("Human Fab capture kit", Order No. 28958325, Cytiva) covalently amine coupled to a Series S CM5 sensor chip (Cytiva). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl, pH 8.5 ("Amine Coupling Kit" BR-1000-50, Cytiva.). For phage display hits Fc-tagged human and mouse Sema3A was used as analytes in a concentration range from 1.56-200 nM. Human, mouse, cynomolgus, rat, dog and pig monovalent Sema3A domain were used as analytes in a concentration series from 0.0.024-3.125 nM in multi cycle kinetics mode or in 100 nM for binding analysis only. The sensor surface was regenerated with glycine pH 2.0 after each antigen injection. Obtained sensorgrams were double referenced (subtraction of reference flow cell signal and buffer injection) and were fitted to a 1:1 Langmuir binding model to derive kinetic data using the Biacore T200 Evaluation software. Results are shown in Tables 3, 4 and 4a.

TABLE 3

Affinity of anti-Sema3A IgG1 antibodies derived from phage display hits determined by SPR using TPP-13211 and TPP-13357.

| Nomenclature | Mouse $K_D$ [M] | Human $K_D$ [M] |
| --- | --- | --- |
| TPP-15355 | 4.0E−09 | 3.5E−09 |
| TPP-15356 | n.b. | 3.2E−09 |
| TPP-15357 | 1.0E−07 | 5.0E−08 |
| TPP-15358 | 3.1E−09 | 9.5E−10 |
| TPP-15359 | n.b | 1.1E−08 |
| TPP-15360 | 1.1E−07 | 7.2E−09 |
| TPP-15361 | n.b. | 5.5E−09 |
| TPP-15362 | n.b. | n.b. |
| TPP-15363 | n.b. | 2.4E−09 |
| TPP-15364 | n.b. | 2.6E−09 |
| TPP-15365 | 2.4E−07 | 6.5E−08 |
| TPP-15366 | 1.4E−08 | 1.3E−08 |
| TPP-15367 | 5.4E−09 | 2.2E−09 |
| TPP-15368 | 8.2E−07 | 1.5E−07 |
| TPP-15369 | 4.1E−08 | 3.5E−08 |
| TPP-15370 | 3.2E−09 | 2.8E−09 |
| TPP-15371 | 7.4E−09 | 4.5E−09 |
| TPP-15372 | n.b. | 3.7E−09 |
| TPP-15373 | 2.0E−07 | 1.3E−07 |
| TPP-15374 | 1.8E−08 | 1.8E−08 |
| TPP-15375 | 5.8E−09 | 5.2E−09 |
| TPP-15376 | 8.4E−09 | 5.8E−09 |
| TPP-15377 | 3.3E−09 | 1.9E−09 |
| TPP-15378 | n.d. | 1.2E−08 |
| TPP-15379 | 4.3E−07 | 2.1E−07 |
| TPP-15380 | n.b. | n.b. |
| TPP-15381 | 9.9E−09 | 3.3E−09 |
| TPP-15382 | 2.5E−07 | 1.9E−07 |
| TPP-15383 | 5.3E−08 | 2.8E−08 |
| TPP-15384 | 9.6E−09 | 9.1E−09 |
| TPP-15385 | 8.5E−09 | 7.2E−09 |
| TPP-15386 | n.b. | n.b. |
| TPP-15387 | 1.6E−07 | 1.1E−07 |
| TPP-15388 | 1.7E−07 | 1.3E−08 |
| TPP-15389 | 4.2E−09 | 2.8E−09 |
| TPP-15390 | 9.8E−08 | 5.7E−08 |
| TPP-15391 | n.b. | 7.0E−09 |
| TPP-15392 | n.d. | n.d. |
| TPP-15393 | 5.9E−08 | 9.3E−09 |
| TPP-15394 | n.d. | n.d. |
| TPP-15395 | 1.1E−06 | 2.2E−07 |
| TPP-15396 | 6.2E−09 | 2.1E−09 |
| TPP-15397 | 2.7E−07 | 9.7E−09 |
| TPP-15398 | 8.5E−09 | 8.4E−09 |
| TPP-15399 | 1.9E−07 | 1.5E−07 |
| TPP-15400 | 4.9E−09 | 4.6E−09 |
| TPP-15401 | 7.6E−07 | 1.2E−08 | n.b. = no binding,
n.d. = not determinable

The majority of phage display hits bind to human and mouse dimeric Sema3A in the lower nanomolar range.

TABLE 4

Affinity of anti-Sema3A antibodies derived from TPP-15370 and TPP-15374 determined by SPR using TPP-19068, TPP-19069, TPP-19122, TPP-19120, TPP-19121, TPP-20176 as analytes as well as prior art antibodies (TPP-30972 was purified from HEK cell expression).

| Nomenclature | Mouse $K_D$ [M] | Pig $K_D$ [M] | Cyno $K_D$ [M] | Dog $K_D$ [M] | Human $K_D$ [M] | Rat $K_D$ [M] |
|---|---|---|---|---|---|---|
| TPP-11489 (Chiome) | 1.6E−07 | 1.0E−07 | 6.3E−08 | 5.0E−08 | 7.3E−08 | 3.3E−08 |
| TPP-17755 (Samsung) | 3.9E−09 | 4.0E−09 | 1.4E−08 | 7.5E−09 | 6.9E−09 | 5.4E−09 |
| TPP-30791 (BI clone IV) | 2.8E−11 | 2.9E−11 | 5.7E−11 | 7.8E−11 | 1.2E−11 | 1.7E−11 |
| TPP-30790 (BI clone III) | 4.0E−11 | 3.6E−11 | 7.7E−11 | 1.0E−10 | 1.5E−11 | 2.2E−11 |
| TPP-30789 (BI clone II) | 4.2E−11 | 3.9E−11 | 7.9E−11 | 1.1E−10 | 2.2E−11 | 2.6E−11 |
| TPP-30788 (BI clone I) | 4.3E−11 | 3.8E−11 | 7.8E−11 | 1.1E−10 | 1.8E−11 | 2.6E−11 |
| TPP-30792 (3H4 Univ Ramot) | no binding | no binding | no binding | no binding | no binding | no binding |
| TPP-15370 | 7.2E−09 | 9.0E−09 | 4.0E−08 | 2.2E−08 | 1.0E−08 | 1.4E−08 |
| TPP-23298 | 7.4E−11 | 6.7E−11 | 7.8E−11 | 7.0E−11 | 8.7E−11 | 3.0E−11 |
| TPP-23334 | 6.2E−11 | 1.4E−11 | 1.5E−11 | 8.4E−12 | 2.1E−11 | 5.6E−11 |
| TPP-23337 | 5.0E−11 | 1.1E−11 | 2.6E−11 | 4.5E−12 | 5.0E−11 | 1.1E−10 |
| TPP-23338 | 4.5E−11 | 4.6E−11 | 4.2E−11 | 5.3E−11 | 5.4E−11 | |
| TPP-23340 | 5.9E−11 | 6.2E−11 | 6.0E−11 | 5.8E−11 | 2.2E−11 | |
| TPP-23341 | 9.2E−11 | 8.6E−11 | 8.7E−11 | 8.4E−11 | 9.1E−11 | |
| TPP-23345 | 6.3E−11 | 5.5E−11 | 6.2E−11 | 4.6E−11 | 6.5E−11 | |
| TPP-23346 | 6.4E−11 | 5.8E−11 | 6.1E−11 | 6.1E−11 | 7.2E−11 | |
| TPP-23347 | 5.5E−11 | 5.3E−11 | 5.4E−11 | 5.1E−11 | 6.0E−11 | |
| TPP-23373 | 8.3E−11 | 7.8E−11 | 7.2E−11 | 1.0E−10 | 1.1E−10 | |
| TPP-23374 | 1.6E−11 | below 3 pM | below 3 pM | 7.3E−12 | 8.1E−12 | 3.3E−12 |
| TPP-23375 | 4.2E−11 | 4.7E−11 | 4.5E−11 | 4.5E−11 | 5.3E−11 | |
| TPP-15374 | 8.3E−09 | 7.2E−09 | 4.6E−08 | 1.9E−08 | 1.5E−08 | 9.8E−09 |
| TPP-18533 | 8.1E−09 | | 6.4E−09 | | 8.7E−09 | |
| TPP-25497 | | | | | 5.2E−11 | |
| TPP-25256 | | | | | 4.9E−11 | |
| TPP-25255 | | | | | 5.1E−11 | |
| TPP-25257 | | | | | 5.3E−11 | |
| TPP-25248 | | | | | 5.0E−11 | |
| TPP-25064 | | | | | 4.9E−11 | |
| TPP-26111 | | | | | 5.2E−11 | |
| TPP-25224 | | | | | 4.9E−11 | |
| TPP-25448 | | | | | 5.3E−11 | |
| TPP-25655 | | | | | 4.9E−11 | |

All derivative antibodies of TPP-15370 and TPP-15374 have a significantly increased affinity to the Sema3A domain in the lower picomolar range compared to their parental antibodies as well as to most prior art antibodies.

TABLE 4a

Affinity of anti-Sema3A IgG1 antibodies determined by SPR using 100 nM TPP-19068 (human) in a binding experiment.

| Nomenclature | Human $K_D$ [M] |
|---|---|
| TPP-23298 | 1.3E−10 |
| TPP-17755 (Samsung) | 6.2E−09 |
| TPP-11489 (Chiome) | n.d. |
| TPP-30788 (BI clone I) | 9.8E−11 |
| TPP-31357 (Fab of 3H4 Univ Ramot) | 3.5E−10 | n.d. = not determinable due to multiphasic behaviour

In contrast to the full length 3H4 IgG1 (TPP-30792) which showed no binding in SPR to Sema3A molecules, the Fab variant of TPP-30792, TPP-31357 shows binding to human Sema3A, but with less affinity as TPP-23298.

Example 5: Determination of Binding Activity Using Surface Plasmon Resonance To assess the binding activity of anti-Sema3A antibodies binding assays were conducted using surface plasmon resonance (SPR). Binding assays were performed on a Biacore T200 instrument (Cytiva) at 25° C. using assay buffer HBS P+, 300 mM NaCl, 0.75 mM $CaCl_2$, 2.5 mM $MgCl_2$, 1 mg/ml BSA, 0.05% $NaN_3$. Antibodies were captured via anti-human Fc IgGs ("Human antibody capture kit", Order No. BR100839, Cytiva) covalently amine coupled to a Series S CM5 sensor chip (Cytiva). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl, pH 8.5 ("Amine Coupling Kit" BR-1000-50, Cytiva.). Human, mouse, cynomolgus, rat, dog and pig monovalent Sema3A domain were used as analytes in a concentration series from 0.024-3.125 nM in multi cycle kinetics mode. The sensor surface was regenerated with glycine pH 2.0 after each antigen injection. Obtained sensorgrams were double referenced (subtraction of reference flow cell signal and buffer injection) and were fitted to a 1:1 Langmuir binding model using the Biacore T200 Evaluation software obtaining the experimental fitted $R_{Max}$ value. To calculate the binding activity first the theoretical $R_{Max}$ needs to be calculated according to equation 1:

$$R_{Max} = \frac{R_{Ligand} * Mr_{Analyte} * Valency_{Ligand}}{Mr_{Ligand}}$$

Equation 1: Theoretical calculation of $R_{Max}$. $R_{Ligand}$=Ligand Level in RU, Mr=molecular weight, Valency$_{Ligand}$=number of binding sites per antibody molecule, here 2

Binding activity was determined by dividing the experimental determined $R_{Max}$ by the theoretical calculated $R_{Max}$ according to equation 2:

$$\text{Activity in } \% = \frac{R_{Max\,experimental}}{R_{Max\,theoretical}} * 100$$

Equation 2: Calculation of binding activity in %

TABLE 5

Summary of ligand levels after capture, experimental, theoretical and binding activity of tested antibodies

| Ligand | Analyte | Ligand Level [RU] | Experimental Rmax [RU] | Theoretical Rmax [RU] | Binding Activity [%] |
|---|---|---|---|---|---|
| TPP-11489 (Chiome) | Rat Sema3A domain | 798 | 212 | 681 | 31 |
| TPP-15370 | | 53 | 51 | 45 | 113 |
| TPP-15374 | | 53 | 42 | 45 | 94 |
| TPP-17755 (Samsung) | | 54 | 26 | 46 | 56 |
| TPP-23298 | | 46 | 42 | 39 | 108 |
| TPP-30791 (BI clone IV) | | 46 | 42 | 39 | 109 |
| TPP-30790 (BI clone III) | | 62 | 50 | 53 | 94 |
| TPP-30789 (BI clone II) | | 50 | 44 | 42 | 104 |
| TPP-30788 (BI clone I) | | 46 | 43 | 40 | 109 |
| TPP-11489 (Chiome) | Dog Sema3A domain | 797 | 148 | 680 | 22 |
| TPP-15370 | | 53 | 51 | 45 | 114 |
| TPP-15374 | | 53 | 44 | 45 | 98 |
| TPP-17755 (Samsung) | | 54 | 25 | 46 | 55 |
| TPP-23298 | | 45 | 42 | 39 | 107 |
| TPP-30791 (BI clone IV) | | 47 | 43 | 40 | 106 |
| TPP-30790 (BI clone III) | | 61 | 48 | 52 | 92 |
| TPP-30789 (BI clone II) | | 50 | 44 | 43 | 102 |
| TPP-30788 (BI clone I) | | 47 | 42 | 40 | 106 |
| TPP-11489 (Chiome) | Pig Sema3A domain | 801 | 525 | 684 | 77 |
| TPP-15370 | | 53 | 50 | 45 | 111 |
| TPP-15374 | | 53 | 47 | 45 | 103 |
| TPP-17755 (Samsung) | | 54 | 28 | 46 | 60 |
| TPP-23298 | | 46 | 42 | 39 | 107 |
| TPP-30791 (BI clone IV) | | 49 | 44 | 42 | 105 |
| TPP-30790 (BI clone III) | | 61 | 48 | 52 | 92 |
| TPP-30789 (BI clone II) | | 51 | 45 | 43 | 103 |
| TPP-30788 (BI clone I) | | 47 | 43 | 40 | 107 |
| TPP-11489 (Chiome) | Cyno Sema3A domain | 800 | 85 | 682 | 13 |
| TPP-15370 | | 53 | 63 | 45 | 139 |
| TPP-15374 | | 53 | 47 | 45 | 104 |
| TPP-17755 (Samsung) | | 53 | 24 | 45 | 53 |
| TPP-23298 | | 46 | 41 | 39 | 106 |
| TPP-30791 (BI clone IV) | | 47 | 43 | 40 | 107 |
| TPP-30790 (BI clone III) | | 62 | 48 | 52 | 92 |
| TPP-30789 (BI clone II) | | 50 | 44 | 42 | 103 |
| TPP-30788 (BI clone I) | | 47 | 43 | 40 | 107 |
| TPP-11489 (Chiome) | Human Sema3A domain | 798 | 257 | 681 | 38 |
| TPP-15370 | | 53 | 51 | 45 | 112 |
| TPP-15374 | | 53 | 45 | 45 | 10 |
| TPP-17755 (Samsung) | | 54 | 25 | 46 | 55 |
| TPP-23298 | | 46 | 42 | 39 | 107 |
| TPP-30791 (BI clone IV) | | 48 | 44 | 41 | 107 |
| TPP-30790 (BI clone III) | | 61 | 48 | 52 | 93 |
| TPP-30789 (BI clone II) | | 49 | 45 | 42 | 106 |
| TPP-30788 (BI clone I) | | 47 | 43 | 40 | 107 |
| TPP-11489 (Chiome) | Mouse Sema3A domain | 796 | 803 | 680 | 118 |
| TPP-15370 | | 53 | 50 | 45 | 11. |
| TPP-15374 | | 53 | 48 | 45 | 106 |
| TPP-17755 (Samsung) | | 54 | 26 | 46 | 57 |
| TPP-23298 | | 46 | 42 | 39 | 108 |
| TPP-30791 (BI clone IV) | | 47 | 43 | 40 | 107 |
| TPP-30790 (BI clone III) | | 62 | 49 | 52 | 93 |
| TPP-30789 (BI clone II) | | 51 | 45 | 43 | 103 |
| TPP-30788 (BI clone I) | | 47 | 43 | 40 | 108 |

The binding activity calculated in the SPR experiment is a measure of the activity of the surface-attached ligand. As can be seen from Table 5, TPP-15370, TPP-15374, TPP-23298 and TPPs 30788-30791 are able to bind to all tested Sema3A domains with around 100% activity meaning all binding regions are fully able to bind. Prior art antibody TPP-17755 only reaches an activity level of 50-60% depending on the species. Prior art antibody TPP-11489 shows an even more reduced level of below 50%, except for mouse and pig where it is higher. Strikingly, to reach such an activity level, the ligand level of TPP-11489 needs to be over 10-fold higher as compared to the other antibodies pointing in general to a much lower binding activity as compared to TPP-15370, TPP-15374 and TPP-23298.

Example 6: Competition ELISA

For screening in a competition ELISA setup, human Sema3a (TPP-13211) was coated onto 384-well plates (Greiner bio-one, 781077) with a concentration of 0.5 µg/ml in coating buffer (Carbonate-Basis pH 9.6, Candor 121125) over night at 10° C. After washing the plates 3 times with 50 µl PBS 0.05% Tween the plates were blocked with 50 µl Smart Block® (Candor 113500) for 1 h at 20° C. and washed again 3 times as described.

Table 6 lists the values for the competition ELISA for selected recombination variants of TPP-15370 and TPP-15374. Depicted are the ratios vs. the isotype control antibody TPP-9809 in the measurement with a 1 to 5 or a 1 to 1 ratio, respectively.

TABLE 6

Values for the competition ELISA for recombination variants of TPP-15374 and TPP-15370. Depicted are the ratios vs. the isotype control antibody for selected recombination variants, respectively, when normalized to the isotype control antibody TPP-9809 in the measurement with a 1 to 5 or a 1 to 1 ratio, respectively.

| TPP-15374 family | | | TPP-15370 family | | |
| --- | --- | --- | --- | --- | --- |
| TPP Number | VAL norm to TPP-9809 (1 to 5 ratio) | VAL norm to TPP-9809 (1 to 1 ratio) | TPP Number | VAL norm to TPP-9809 (1 to 5 ratio) | VAL norm to TPP-9809 (1 to 1 ratio) |
| TPP-15374 | 0.41 | 0.69 | TPP-15370 | 0.54 | 0.67 |
| TPP-9809 | 1.00 | 1.00 | TPP-9809 | 1.00 | 1.00 |
| TPP-25497 | 0.26 | 0.39 | TPP-23298 | 0.09 | 0.18 |
| TPP-25256 | 0.15 | 0.41 | TPP-23334 | 0.11 | 0.28 |
| TPP-25255 | 0.17 | 0.37 | TPP-23337 | 0.14 | 0.27 |
| TPP-25257 | 0.18 | 0.36 | TPP-23338 | | 0.33 |
| TPP-25248 | 0.20 | 0.36 | TPP-23340 | | 0.40 |
| TPP-25064 | 0.19 | 0.48 | TPP-23341 | 0.18 | 0.38 |
| TPP-26111 | 0.18 | 0.49 | TPP-23345 | 0.08 | 0.27 |
| TPP-25224 | 0.17 | 0.43 | TPP-23346 | 0.13 | 0.22 |
| TPP-25448 | 0.19 | 0.47 | TPP-23347 | 0.16 | 0.30 |
| TPP-25655 | 0.23 | 0.39 | TPP-23373 | 0.20 | 0.35 |
| | | | TPP-23374 | 0.08 | 0.19 |
| | | | TPP-23375 | 0.16 | 0.30 |

Subsequently, 20 µl of pre-mixed antibody solution was added to the plates and incubate for 18 h at 10° C. For the pre-mixed antibody solution, for each well, one biotinylated, parental antibody being either TPP-15370 or TPP-15374 was mixed in a ratio 1:1, 1:5 or 5:1 with an antibody containing one or more amino acid variations within its CDR regions (recombination variants) and not containing any biotin tag. As additional controls an isotype control antibody not demonstrating any binding to human Sema3A was also used as competition antibody. The total concentration of the added antibody solution was 0.25 µg/ml. During the incubation time the antibodies bound to the plates in a competitive manner as they compete for the same epitope on the human Sema3A protein.

After subsequent washing with 50 µl PBS 0.05% Tween for 3 times, 20 µl of a Streptavidin-HRP solution (R&D Systems, DY998, 1:200 in PBS 0.05% Tween 10% Smart Block) were added and incubated for 1 h and 20° C. followed by subsequent washing 3 times with 50 µl PBS 0.05% Tween and addition of 20 µl Amplex Red solution (Invitrogen A12222, 1:1000 in NaP-buffer 50 mM pH7.6 with 1:10000 of 30% H2O2). After a final incubation for 20 min at 20° C. the signal was determined using an emission wavelength of 595 nm and excitation of 530 nm. Due to the biotinylation of the parental antibodies TPP-15370 and TPP-15374 only the binding of these variants can be detected. Hence, competition with an antibody variant demonstrating superior binding shows a lower binding signal in comparison to e.g. competition of the parental antibody with a non-bioinylated version of itself.

In total, 103 recombination variants of TPP-15370 and 1136 recombination variants for TPP-15374 were measured. For analysis, and to allow for correction of plate-to-plate variations, the ELISA raw values were normalized to the value of the competition with the isotype control antibody TPP-9809.

Example 5a: Epitope Binning Using Surface Plasmon Resonance (SPR)

An epitope binning experiment was performed to determine the epitope bins of anti-Sema3A antibodies using SPR by employing a classical sandwich approach. In this experiment, one antibody is immobilized to a SPR chip, Sema3A is injected, and the binding is monitored (FIG. 10A). After successful binding of Sema3A to the first antibody, a second antibody is injected on to the complex of the immobilized mAb bound to Sema3A and the additional binding is monitored (FIG. 10B and FIG. 10C). If the second antibody competes with the first antibody for the binding to Sema3A than no additional binding signal is detected after injection of the second antibody, showing that the two antibodies bind to the same or very adjacent Sema3A epitope (FIG. 10C). If the second antibody does not compete with the first antibody for the binding to Sema3A than an additional binding signal is detected after injection of the second antibody, showing that the two antibodies bind to different Sema3A epitopes (FIG. 10B).

Experiments were performed on a Biacore T200 instrument (Cytiva) at 25° C. using assay buffer HBS P+, 300 mM NaCl, 0.75 mM $CaCl_2$, 2.5 mM $MgCl_2$, 1 mg/ml BSA, 0.05% $NaN_3$. Antibodies were covalently amine coupled to a Series S CM5 sensor chip (Cytiva). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl, pH 8.5 ("Amine Coupling Kit" BR-1000-50, Cytiva.). Human, monovalent Sema3A domain was used as first analyte in a concentration of 200 nM followed by a second injection of the competitor antibody. This setup was performed with all possible combinations. The sensor surface was regenerated with glycine pH 2.0 after each antigen injection. Table 6a shows the binning results.

TABLE 6a

Matrix view of the epitope binning results
(+ = additional binding, − = no additional binding)

| First antibody/<br>second antibody | TPP-30788<br>(BI Clone I) | TPP-23298 | TPP-17755<br>(Samsung) |
|---|---|---|---|
| TPP-30788<br>(BI Clone I) | | + | + |
| TPP-23298 | + | | − |
| TPP-17755<br>(Samsung) | + | − | |

"+" means injection of second antibody resulted in additional binding signal showing that the two tested antibodies bind to two different Sema3A epitopes
"−" means injection of second antibody did not resulted in additional binding signal showing that the two tested antibodies compete for binding to overlapping or adjacent epitopes Sema3A epitopes The binning experiment strongly points to another epitope for TPP-23298 compared to TPP-30788 (BI clone I) meaning that both antibodies target an independent/different epitope on Sema3A, whereas TPP-23298 might have overlapping or adjacent epitopes with TPP-17755 (Samsung).

Example 7: Assessment of Binding to Off-Targets

To assess the specificity of an anti-Sema3A mAb (TPP-15370, parental mAb) an off-target screen using Retrogenix technology was conducted. For primary screening, 5484 expression vectors, encoding both ZsGreen1 and a full-length human plasma membrane protein or a cell-surface tethered human secreted protein, were arrayed in duplicate across 16 microarray slides. Human HEK293 cells were used for reverse transfection/expression.

The test antibody was added to each slide after cell fixation giving a final concentration of 20 µg/ml. Detection of binding was performed by using the same AF647 anti-hIgG Fc detection antibody as used in the Pre-screen. Two replicate slides were screened for each of the 16 slide-sets. Hits were classified as 'strong, medium, weak or very weak', depending on the intensity of the duplicate spots.

Following a screen for binding against fixed HEK293 cells expressing 5484 human plasma membrane proteins and human secreted proteins, Retrogenix's technology identified no specific off-target interactions for test antibody TPP-15370. Binding to Sema3A—its primary target—was observed. These data indicate high specificity of TPP-15370 for its primary target.

Example 8: Selectivity of Anti-Sema3A mAbs

Semaphorin proteins can be subdivided in five classes occurring in vertebrates (class 3-7). To assess the selectivity profile of parental anti-Sema3A mAbs TPP-15370 and TPP-15374 in the Semaphorin 3 class (Sema3A-G) an ELISA assay was conducted using Sema3A, Sema3B, Sema3C, Sema3D, Sema3E, and Sema3F molecules from R&D Systems. Both antibodies showed no binding to Sema3B, Sema3C, Sema3D, Sema3E and Sema3F.

Because Sema3G has been recently identified as kidney protective (PMID: 27180624), it was important to test whether the antibodies do not bind to Sema3G. For the assessment of binding selectivity to Sema3A vs Sema3G, 1 nM recombinant human Sema3A-Fc chimera (R&D Systems) or recombinant human GST—Sema3G (Abnova) were coated on Maxisorb plates, incubated with antibodies in a dose-response curve from 0.00015-10 µg/ml, and the binding of antibodies quantified using HRP coupled anti-human antiserum and chemiluminescent substrate.

TABLE 7

Off-target ELISA values for testing of Sema3G as off-target

| | EC50 [nM] | | Selectivity Score |
|---|---|---|---|
| Antibody | Coating: SEMA3A | Coating:<br>SEMA3G | SEMA3G/<br>SEMA3A |
| TPP-23298 | 1.6 | >66667 | >41666 |
| TPP-23334 | 9.2 | >66667 | >7220 |
| TPP-23337 | 15.5 | >66667 | >4308 |
| TPP-23338 | 9.6 | >66667 | >6949 |
| TPP-23340 | 12.3 | >66667 | >5435 |
| TPP-23341 | 21.3 | >66667 | >3133 |
| TPP-23347 | 8.4 | >66667 | >7918 |
| TPP-23373 | 17.6 | >66667 | >3786 |
| TPP-23374 | 6.1 | >66667 | >10951 |
| TPP-23375 | 7.7 | >66667 | >8651 |
| TPP-11489<br>(Chiome) | Weak binding<br>(EC50 not determinable) | >66667 | n.d. |
| TPP-17755<br>(Samsung) | Slight dose-response<br>(not determinable) | >66667 | n.d. |
| TPP-30791<br>(BI clone IV) | 0.08 | >66667 | >833337 |
| TPP-30790<br>(BI clone III) | 0.08 | >66667 | >833337 |
| TPP-30789<br>(BI clone II) | 0.10 | >66667 | >666670 |
| TPP-30788<br>(BI clone I) | 0.15 | >66667 | >444446 |

All tested antibodies of the present disclosure as well as prior art antibodies do not bind to kidney protective Sema3G, as shown in Table 7.

Sema3A is a secreted protein that contains two furin cleavage sites and is present in an active an inactive cleaved form. In the in vivo situation Sema3A exists in both forms side by side. To test if anti-Sema3A antibodies are able to differentiate between the inactive and active form and to test how antibodies perform in binding to active Sema3A (resembled by full-length Sema3A (TPP-13211) in contrast to a inactive version as it only contains the Sema3A domain (resembled by cleaved Sema3A TPP-19068), an ELISA assay was performed. As readout out the ELISA signals of the tested antibody to the active Sema3A has been divided by the ELISA signals of the tested antibody to the inactive Sema3A.

TABLE 7a

Ratio for binding of anti-Sema3A antibodies to active vs. inactive
Sema3A as determined by ELISA

| Antibody | Ratio ELISA binding<br>TPP-13211/TPP-19068* |
|---|---|
| TPPAntibody-23298 | 0.66 ± 0.14 |
| TPP-30788 (BI clone I) | 0.19 ± 0.03 |
| TPP-30789 (BI clone II) | 0.20 ± 0.07 |
| TPP-30790 (BI clone III) | 0.19 ± 0.03 |
| TPP-30791 (BI clone IV) | 0.21 ± 0.004 |

*A Ratio ELISA binding TPP-13211/TPP-19068 below 1 shows a higher binding activity to active Sema3A.
A Ratio ELISA binding TPP-13211/TPP-19068 above 1 shows a higher binding activity to inactive Sema3A.

The binding analysis as shown in Table 7a clearly showed that the antibody of the present disclosure (TPP-23298) shows increased binding to active Sema3A than TPP-30788-TPP-30791 (BI clones) presumably since they target a different epitope indicating a higher selectivity for active Sema3A.

Example 9: In Vitro Efficacy in a Mesangial Cell Migration Assay

A confluent monolayer of human primary mesangial cells was generated by seeding cells in serum-containing culture medium into image lock plates for 24 hours. After switching to serum-free culture medium, scratch wounds were created using the WoundMaker tool, after which the cells were treated with 1 nM recombinant human Sema3A-Fc chimera (R&D Systems) in the absence or presence of inhibitory antibodies. The cells were imaged in the Incucyte and after 24 hrs the extent of wound closure was assessed using the Incucyte Integrated Cell Migration Analysis software module.

TABLE 8

EC50 values for phage display hits and recombination variants in the MCM assay

| Antibody | EC50 [nM] |
|---|---|
| TPP-15051 (Chiome) | 42.87 |
| TPP-15354 | 31.87 |
| TPP-15355 | >200 |
| TPP-15356 | >200 |
| TPP-15357 | 158.13 |
| TPP-15358 | >200 |
| TPP-15359 | >200 |
| TPP-15360 | 37.47 |
| TPP-15361 | 118.67 |
| TPP-15362 | >200 |
| TPP-15363 | >200 |
| TPP-15364 | >200 |
| TPP-15365 | >200 |
| TPP-15366 | 2.27 |
| TPP-15367 | 148.07 |
| TPP-15368 | >200 |
| TPP-15369 | 45.47 |
| TPP-15370 | 4.13 |
| TPP-15371 | >200 |
| TPP-15372 | 86.87 |
| TPP-15373 | 123.53 |
| TPP-15374 | 5.07 |
| TPP-15375 | >200 |
| TPP-15376 | >200 |
| TPP-15377 | >200 |
| TPP-15378 | 67.00 |
| TPP-15379 | >200 |
| TPP-15380 | 125.53 |
| TPP-15381 | >200 |
| TPP-15382 | 199.87 |
| TPP-15384 | 1.60 |
| TPP-15385 | 1.20 |
| TPP-15386 | >200 |
| TPP-15387 | >200 |
| TPP-15388 | >200 |
| TPP-15389 | 103.60 |
| TPP-15390 | >200 |
| TPP-15391 | >200 |
| TPP-15392 | 62.53 |
| TPP-15393 | 131.93 |
| TPP-15394 | >200 |
| TPP-15395 | >200 |
| TPP-15396 | 82.67 |
| TPP-15397 | >200 |
| TPP-15398 | 6.00 |
| TPP-15399 | 197.13 |
| TPP-15400 | 4.73 |
| TPP-15401 | >200 |
| TPP-17755 (Samsung) | 11.33 |
| TPP-23298 | 0.40 |
| TPP-23334 | 0.67 |
| TPP-23337 | 0.33 |
| TPP-23338 | 0.60 |
| TPP-23340 | 0.87 |
| TPP-23341 | 0.90 |
| TPP-23345 | 0.93 |
| TPP-23346 | 1.27 |
| TPP-23347 | 0.67 |
| TPP-23373 | 0.63 |
| TPP-23374 | 0.30 |
| TPP-23375 | 1.03 |
| TPP-30788 (BI clone I) | 1.43 |

We identified antibodies with potencies in the three-digit picomolar range in the human Mesangial Cell Migration Assay, which is considerably more potent than the prior art antibodies, as shown in Table 8.

Example 10: In Vitro Efficacy in a Growth Cone Collapse Assay

In the direction of determining the potency of the antibodies against Sema3A induced cytoskeletal collapse, a growth cone collapse assay was used similarly as described (PMID: 12077190) with a few modifications. In brief, mouse dorsal root ganglion (DRG) neurons were isolated from E13 C57Bl/6J mouse embryos, cultured on poly-L-lysine and laminin-coated 96-wells with Neurobasal medium+100 ng/mL NGF+B-27+10% FCS. After 20 hours, the cells were treated for 1 hour with 10 nM recombinant human Sema3A-Fc chimera (RnD Systems) in the absence or presence of inhibitory antibodies followed by PFA fixation and staining with Alexa488-phalloidin. The extent of growth cone collapse was assessed using immunofluorescence microscopy via actin growth cone area/shape/texture for more than 100 growth cones per well.

TABLE 9

EC50 values for phage display hits and recombination variants in the GCC assay

| Antibody | EC50 (nM) |
|---|---|
| TPP-15051 (Chiome) | 243.40 |
| TPP-15354 | 67.73 |
| TPP-15355 | >200 |
| TPP-15356 | >200 |
| TPP-15357 | 50.73 |
| TPP-15358 | >200 |
| TPP-15359 | >200 |
| TPP-15360 | 31.07 |
| TPP-15361 | >200 |
| TPP-15362 | >200 |
| TPP-15363 | >200 |
| TPP-15364 | >200 |
| TPP-15365 | 142.87 |
| TPP-15366 | 4.13 |
| TPP-15367 | 170.87 |
| TPP-15368 | >200 |
| TPP-15369 | 76.60 |
| TPP-15370 | 4.33 |
| TPP-15371 | >200 |
| TPP-15372 | 109.47 |
| TPP-15373 | >200 |
| TPP-15374 | 8.13 |
| TPP-15375 | >200 |
| TPP-15376 | >200 |
| TPP-15377 | >200 |
| TPP-15378 | 138.60 |
| TPP-15379 | >200 |
| TPP-15380 | 135.40 |
| TPP-15381 | >200 |
| TPP-15382 | >200 |

TABLE 9-continued

EC50 values for phage display hits and recombination variants in the GCC assay

| Antibody | EC50 (nM) |
|---|---|
| TPP-15384 | 18.80 |
| TPP-15385 | 6.00 |
| TPP-15386 | >200 |
| TPP-15387 | >200 |
| TPP-15388 | >200 |
| TPP-15389 | 160.67 |
| TPP-15390 | >200 |
| TPP-15391 | >200 |
| TPP-15392 | >200 |
| TPP-15393 | >200 |
| TPP-15394 | >200 |
| TPP-15395 | 66.47 |
| TPP-15396 | 180.80 |
| TPP-15397 | >200 |
| TPP-15398 | 12.00 |
| TPP-15399 | >200 |
| TPP-15400 | 25.73 |
| TPP-15401 | >200 |
| TPP17755 (Samsung) | 52.67 |
| TPP-23298 | 2.40 |
| TPP-23334 | 2.24 |
| TPP-23337 | 2.12 |
| TPP-23374 | 2.19 |

The identified antibodies also show potencies in the single digit nanomolar range in the murine Growth Cone Collapse Assay, again considerably more potent than the tested prior art antibodies (two- to three-digit nanomolar potency), as shown in Table 9.

Example 11: In Vitro Efficacy in a HUVEC Repulsion Assay

Recombinant human Sema3A-Fc chimera (R&D Systems) is not identical to Sema3A in human biofluids because it contains several mutated amino acids and an extra protein fragment at its carboxy-terminus. Furthermore, the above described assays (human Mesangial Cell Migration Assay and murine Growth Cone Collapse Assay) use Sema3A in homogenous distribution, which is in contrast to the gradient distribution described for Sema3A in tissues. We hypothesized that these differences could result in a different potency of the antibodies towards recombinant versus endogenous protein. Therefore, we adapted an assay using a gradient of human wild-type Sema3A as agonist (PMID: 17569671). In brief, in this HUVEC repulsion assay, human embryonic kidney 293 cells (HEK293) cells expressing human Sema3A of the sequence of SEQ ID NO: 600, were seeded on a confluent monolayer of human umbilical vein endothelial cells (HUVEC) in EGM-2 medium in the absence or presence of inhibitory antibodies, cultured for 72 hours, fixed, stained with DAPI and the extent of cell repulsion assessed by immunofluorescence microscopy (measurement of cell free areas). Consequently, the substrate human Sema3A exists in excess.

Based on immunofluorescence microscopy images of the DAPI/CM stained cells (CM=HCS CellMask™ Stain, stains the whole cell in order to define the total cell area) data analysis is performed as follows: Cells are identified based on the DAPI/CM signals (FIG. 11B). The cell area for analysis is defined and selected. In this area the cell-free region is calculated (FIG. 11C). Percent inhibition is calculated based on the "cell free-region" that is induced by Sema3A in the antibody-treated wells in comparison to the isotype-treated wells. Percent inhibition is plotted over antibody concentration and EC-50 values of the respective antibodies are calculated.

In detail the following steps are performed for the data analysis:
1. Four fields are imaged per well which corresponds to 80% of the well area. All of these fields stitched together are used for the detection of the cells via the DAPI/CM fluorescence.
2. The "cell area" is calculated based on the DAPI/CM area.
3. The "cell-free region" is calculated based on the "total area" subtracted by the "cell area".
4. Percent inhibition is calculated based on the "cell free-region" that is induced by Sema3A in the antibody-treated wells vs the isotype-treated wells.
5. The software GraphPad Prism is used to determine the EC50 values using nonlinear regression (Variable slope model=four-parameter dose-response curve).

TABLE 10

EC50 values for selected antibodies in the repulsion assay, first experiment

| Antibody | EC50 (pM) |
|---|---|
| TPP-15370 | 800 |
| TPP-23298 | 80 |
| TPP-23334 | 120 |
| TPP-23337 | 170 |
| TPP-23340 | 180 |
| TPP-23341 | 113 |
| TPP-23373 | 180 |
| TPP-23374 | 77 |
| TPP-23375 | 123 |

TABLE 10a

EC50 values for TPP-23298 in the repulsion assay in a second experiment to compare to prior art antibodies

| Antibody | EC50 (pM) |
|---|---|
| TPP-23298 | 54 |
| TPP-30788 (BI clone I) | 104 |
| TPP-30789 (BI clone II) | 165 |
| TPP-30790 (BI clone III) | 121 |
| TPP-30791 (BI clone IV) | 221 |
| TPP-17755 (Samsung) | 2794 |
| TPP-11489 (Chiome) | >20000 |

The potency distinction to the prior art antibodies in the human Mesangial Cell Migration Assay and murine Growth Cone Collapse Assay above, is even more pronounced in this HUVEC Repulsion Assay that uses a gradient of native wt Sema3A (mixture of processed inactive and undigested active Sema3A) as shown in Table 10 and 10a. The improved potency in HUVEC repulsion assay in comparison to TPP-17755, to TPP-11489, to TPP-30788, to TPP-30789, TPP-30790, or to TPP-30791 is quantified measuring the picomolar activity as shown by the corresponding EC-50 values. While TPP-23298 shows two-digit picomolar activities, prior art antibody potencies of TPP-17755, TPP-11489, TPP-30788, TPP-30789, TPP-30790, or TPP-30791, are in the three-digit picomolar or even nanomolar range.

As an alternative illustration of the results, the improved potency in HUVEC repulsion assay is quantified by measuring the cell-free region at a specified concentration of 80 pM of the respective antibodies. TPP-23298 shows a higher percent inhibition of Sema3A than to TPP-30788, to TPP-30789, TPP-30790, or to TPP-30791 (FIG. 12).

Analyzing the data from both assays displayed in table 10 and 10a TPP-23298 shows the highest potency against cellular Sema3A induced HUVEC repulsion. The BI Antibodies TPP-30788, TPP-30798, TPP-30790 and TPP-30791 exhibited slightly higher EC50 values (2-5-fold). The Samsung Antibody TPP-17755 has a significantly lower potency than the TPP-23298 (50-fold). The Chiome Antibody TPP-11489 did only show inhibitory activity at the highest tested concentrations resulting in a predicted EC50 value>400-fold above antibody according to the present disclosure.

That shows that under conditions, that resembles a native environment without any spiked exogenous, recombinant semaphorin3A, the antibodies according to the present disclosure inhibit Sema3A-induced cell repulsion with the strongest activity, as shown in Table 10 and 10a.

Example 12: In Vivo Assay for Detecting Protective Renal Effects: Inhibition of Sema3A-Induced Albuminuria in Mice Sema3A inhibitors decrease urinary albumin excretion induced via systemic injection of recombinant Sema3A. The beneficial effect of the compounds on albuminuria reduction were investigated in a Sema3A-induced albuminuria model as follows:

Male C57Bl/6 mice (8- to 10-wk-old) purchased from Taconic were injected intravenously with anti-Sema3A antibodies. Thirty minutes after antibody application albuminuria was induced by intravenous injection of human recombinant Sema3A (1.0 mg/kg, R&D Systems). Animals were placed into metabolic cages and urine was collected for 4 h. Urinary creatinine was measured via clinical biochemistry analyzer (Pentra400). For the assessment of urinary albumin, a mouse specific Albumin ELISA (Abcam) was used according to manufacturer's protocol. Both urinary creatinine and albumin were used to calculate urinary albumin to creatine ratio (ACR). Differences between groups were analyzed by one-way ANOVA with Dunnett's corrections for multiple comparisons. Statistical significance is defined as $p<0.05$. All statistical analyses were done using GraphPad Prism 8.

Table 11-15a show dose-response experiments with TPP-15370, TPP-15374, TPP-11489, TPP-17755, TPP-30788 and TPP-23298 in the Sema3A-induced albuminuria model in mice. Effects on albuminuria reduction with TPP-15370, TPP-23298 in comparison to TPP-11489 and/or TPP-17755 and/or TPP-30788 are shown in FIGS. 1A-2C.

The antibodies according to the present disclosure reduce Sema3A-induced urinary Albumin excretion.

TABLE 11

Dose-response of Sema3A-induced albuminuria reduction after treatment with TPP-15370

| | urinary albumin to creatinine ratio [μg/mg] |
|---|---|
| control; Mean ± SD | 345.30 ± 102.15**** |
| 15 [mg/kg] isotype control; Mean ± SD | 1392.80 ± 350.70 |
| 1 [mg/kg] TPP-15370; Mean ± SD | 1030.80 ± 216.27** |

TABLE 11-continued

Dose-response of Sema3A-induced albuminuria reduction after treatment with TPP-15370

| | urinary albumin to creatinine ratio [μg/mg] |
|---|---|
| 5 [mg/kg] TPP-15370; Mean ± SD | 693.84 ± 203.18**** |
| 15 [mg/kg] TPP-15370; Mean ± SD | 273.10 ± 146.02**** |

8-10 animal/group, One-way ANOVA with Dunnett's corrections for multiple comparisons, *//*/**** = significant with $p < 0.05/0.01/0.001/0.0001$ vs isotype control

TABLE 12

Dose-response of Sema3A-induced albuminuria reduction after treatment with TPP-15374

| | urinary albumin to creatinine ratio [μg/mg] |
|---|---|
| Control; Mean ± SD | 226.40 ± 65.50**** |
| 15 [mg/kg] isotype control; Mean ± SD | 1061.43 ± 216.47 |
| 1 [mg/kg] TPP-15374; Mean ± SD | 782.60 ± 122.43** |
| 5 [mg/kg] TPP-15374; Mean ± SD | 690.19 ± 190.27**** |
| 15 [mg/kg] TPP-15374; Mean ± SD | 592.87 ± 123.93**** |

8-10 animal/group, One-way ANOVA with Dunnett's corrections for multiple comparisons, *//*/**** = significant with $p < 0.05/0.01/0.001/0.0001$ vs isotype control

TABLE 13

Dose-response of Sema3A-induced albuminuria reduction after treatment with TPP-23298

| | urinary albumin to creatinine ratio [μg/mg] |
|---|---|
| Control; Mean ± SD | 345.30 ± 102.15**** |
| 15 [mg/kg] isotype control; Mean ± SD | 1281.65 ± 447.14 |
| 1 [mg/kg] TPP-23298; Mean ± SD | 623.37 ± 240.41**** |
| 5 [mg/kg] TPP-23298; Mean ± SD | 471.07 ± 164.97**** |
| 15 [mg/kg] TPP-23298; Mean ± SD | 320.60 ± 166.36**** |

8-10 animal/group, One-way ANOVA with Dunnett's corrections for multiple comparisons, *//*/**** = significant with $p < 0.05/0.01/0.001/0.0001$ vs isotype control

TABLE 14

Dose-response of Sema3A-induced albuminuria reduction after treatment with TPP-11489

| | urinary albumin to creatinine ratio [μg/mg] |
|---|---|
| Control; Mean ± SD | 237.23 ± 92.61**** |
| 15 [mg/kg] isotype control; Mean ± SD | 1404.81 ± 411.55 |
| 1 [mg/kg] TPP-11489; Mean ± SD | 1204.81 ± 426.64 |
| 5 [mg/kg] TPP-11489; Mean ± SD | 664.02 ± 228.96**** |
| 15 [mg/kg] TPP-11489; Mean ± SD | 572.42 ± 211.05**** |

8-10 animal/group, One-way ANOVA with Dunnett's corrections for multiple comparisons, *//*/**** = significant with $p < 0.05/0.01/0.001/0.0001$ vs isotype control

TABLE 15

Dose-response of Sema3A-induced albuminuria reduction after treatment with TPP-17755

|  | urinary albumin to creatinine ratio [µg/mg] |
|---|---|
| Control; Mean ± SD | 298.02 ± 91.06**** |
| 15 [mg/kg] isotype control; Mean ± SD | 1053.75 ± 162.28 |
| 1 [mg/kg] TPP-17755; Mean ± SD | 932.57 ± 221.09 |
| 5 [mg/kg] TPP-17755; Mean ± SD | 823.11 ± 196.93* |
| 15 [mg/kg] TPP-17755; Mean ± SD | 711.09 ± 181.65*** |

8-10 animal/group, One-way ANOVA with Dunnett's corrections for multiple comparisons, *//*/**** = significant with p < 0.05/0.01/0.001/0.0001 vs isotype control

TABLE 15a

Dose-response of Sema3A-induced albuminuria reduction after treatment with TPP-30788

|  | urinary albumin to creatinine ratio [µg/mg] |
|---|---|
| Control; Mean ± SD | 266.67 ± 115.66**** |
| 15 [mg/kg] isotype control; Mean ± SD | 1546.59 ± 312.43 |
| 1 [mg/kg] TPP-30788; Mean ± SD | 1234.13 ± 353.48 |
| 5 [mg/kg] TPP-30788; Mean ± SD | 958.30 ± 196.93*** |
| 15 [mg/kg] TPP-30788; Mean ± SD | 841.46 ± 438.51**** |

8-10 animal/group, One-way ANOVA with Dunnett's corrections for multiple comparisons, *//*/**** = significant with p < 0.05/0.01/0.001/0.0001 vs isotype control

Example 13: In Vivo Assay for Detecting Protective Renal Effects: Acute Ischemia/Reperfusion Injury (I/RI) Model in Mice Unilaterally nephrectomized mice may benefit from treatment with Sema3A inhibitors after ischemia reperfusion injury. The beneficial effect of Sema3A antibodies on kidney function was investigated in a kidney ischemia-reperfusion injury model in mice as follows:

Laboratory bred male C57Bl/6J mice 6-8 weeks old were obtained from Charles River. Mice were maintained under standard laboratory conditions, 12-hour light-dark cycles with access to normal chow and drinking water at libitum. For the ischemia reperfusion injury model, a total of 8-10 was used in each control and experimental group.

Animals were anesthetized with continuous inhaled isoflurane. Right nephrectomy was performed through a right flank incision 7 days before the ischemic procedures in the contralateral kidneys. One-hour before the initiation of renal ischemia antibodies and adequate isotype control were administrated to mice via i.v. injection. Mice were anesthetized and a left flank incision was made. Renal vessels were exposed by dissection of the left renal pedicle. Non-traumatic vascular clamps were used to stop blood flow (artery and vein) during 25 min (mice) of ischemia. Reperfusion was established by removing the clamps. The abdominal wall (muscular layer and skin) was closed with 5.0 polypropylene sutures. Temgesic® (Buprenorphin, 0.025 mg/kg s.c.) was applied as an analgesic.

Urine of each animal was collected in metabolic cages over night before sacrifice at 24 h post ischemia. Urinary creatinine was measured by a clinical biochemistry analyzer (Pentra400). For the assessment of urinary albumin, a mouse specific Albumin Kit (Hitachi) was used within the Pentra analyzer. Both urinary creatinine and albumin were used to determine Albuminuria (albumin/creatinine ratio). Upon sacrifice, blood samples were obtained under terminal anesthesia. After centrifugation of the blood samples, serum was isolated. Both serum creatinine and serum urea were measured via clinical biochemistry analyzer (Pentra 400). Differences between groups were analyzed by one-way ANOVA with Dunnett's corrections for multiple comparisons. Statistical significance is defined as p<0.05. All statistical analyses were done using GraphPad Prism 8.

Table 16-20 show dose-response experiments with TPP-15370, TPP-15374, TPP-11489, TPP-17755 and TPP-23298 in an acute renal ischemia/reperfusion injury model in mice. FIGS. 3A-3C show the efficacy of TPP-23374, TPP-23298 and TPP-15370 after treatment with 15 mg/kg in the I/RI model. Treatment effects with TPP-15370, TPP-23298 and TPP-15374 in comparison to TPP-11489 and/or TPP-17755 are shown in FIGS. 4A-6C.

The antibodies attenuated ischemia/reperfusion induced kidney damage by reducing serum creatinine and serum urea (surrogates for glomerular filtration rate) and excretion of urinary albumin.

TABLE 16

Dose-response of TPP-15370 in mouse I/R injury model

|  | serum creatinine [mg/dl] | serum urea [mg/dl] | urinary albumin to creatinine ratio [µg/mg] |
|---|---|---|---|
| SHAM Mean ± SD | 0.34 ± 0.05**** | 102.78 ± 9.45**** | 58.50 ± 19.22**** |
| 15 [mg/kg] isotype control Mean ± SD | 1.72 ± 0.30 | 385.63 ± 41.69 | 1699.47 ± 461.60 |
| 1 [mg/kg] TPP-15370 Mean ± SD | 1.61 ± 0.52 | 396.51 ± 86.91 | 1165.37 ± 445.50** |
| 5 [mg/kg] TPP-15370 Mean ± SD | 1.22 ± 0.32* | 297.92 ± 70.02** | 705.21 ± 192.26** |
| 15 [mg/kg] TPP-15370 Mean ± SD | 0.89 ± 0.27**** | 261.95 ± 27.76*** | 554.52 ± 133.99**** |

8-10 animal/group, One-way ANOVA with Dunnett's corrections for multiple comparisons, *//*/**** = significant with p < 0.05/0.01/0.001/0.0001 vs isotype control

TABLE 17

Dose-response of TPP-15374 in mouse I/R injury model

|  | serum creatinine [mg/dl] | serum urea [mg/dl] | urinary albumin to creatinine ratio [µg/mg] |
|---|---|---|---|
| SHAM Mean ± SD | 0.26 ± 0.02**** | 113.90 ± 29.95**** | 39.36 ± 10.19**** |
| 15 [mg/kg] isotype control Mean ± SD | 2.09 ± 0.19 | 494.52 ± 29.75 | 3942.50 ± 1790.29 |
| 1 [mg/kg] TPP-15374 Mean ± SD | 1.84 ± 0.39 | 478.10 ± 66.55 | 2774.43 ± 946.18 |
| 5 [mg/kg] TPP-15374 Mean ± SD | 1.66 ± 0.32* | 416.49 ± 98.47* | 2195.95 ± 900.56* |
| 15 [mg/kg] TPP-15374 Mean ± SD | 1.43 ± 0.34**** | 389.02 ± 5128** | 1495.88 ± 560.06** |

8-10 animal/group, One-way ANOVA with Dunnett's corrections for multiple comparisons, TABLE 17-continued Dose-response of TPP-15374 in mouse I/R injury model

| | serum creatinine [mg/dl] | serum urea [mg/dl] | urinary albumin to creatinine ratio [µg/mg] |
|---|---|---|---|

*//*/**** = significant with p < 0.05/0.01/0.001/0.0001 vs isotype control

TABLE 18

Dose-response of TPP-11489 in mouse I/R injury model

| | serum creatinine [mg/dl] | serum urea [mg/dl] | urinary albumin to creatinine ratio [µg/mg] |
|---|---|---|---|
| SHAM Mean ± SD | 0.22 ± 0.02**** | 57.64 ± 14.62**** | 27.87 ± 13.55**** |
| 15 [mg/kg] isotype control Mean ± SD | 1.99 ± 0.29 | 410.18 ± 39.80 | 1569.47 ± 277.70 |
| 1 [mg/kg] TPP-11489 Mean ± SD | 2.00 ± 0.12 | 453.84 ± 26.54 | 1600.96 ± 338.48 |
| 5 [mg/kg] TPP-11489 Mean ± SD | 1.92 ± 0.16 | 416.87 ± 49.81 | 1437.08 ± 323.46 |
| 15 [mg/kg] TPP-11489 Mean ± SD | 1.68 ± 0.42* | 367.67 ± 39.32 | 1186.32 ± 366.49* |

8-10 animal/group, One-way ANOVA with Dunnett's corrections for multiple comparisons,
*//*/**** = significant with p < 0.05/0.01/0.001/0.0001 vs isotype control

TABLE 19

Dose-response of TPP-17755 antibody in mouse I/R injury model

| | serum creatinine [mg/dl] | serum urea [mg/dl] | urinary albumin to creatinine ratio [µg/mg] |
|---|---|---|---|
| SHAM Mean ± SD | 0.21 ± 0.06**** | 91.20 ± 34.20**** | 75.45 ± 42.78**** |
| 15 [mg/kg] isotype control Mean ± SD | 1.75 ± 0.30 | 444.25 ± 64.25 | 1791.23 ± 543.46 |
| 1 [mg/kg] TPP-17755 Mean ± SD | 1.74 ± 0.27 | 430.30 ± 75.96 | 1659.08 ± 577.99 |
| 5 [mg/kg] TPP-17755 Mean ± SD | 1.84 ± 0.24 | 439.83 ± 73.68 | 1661.14 ± 460.41 |
| 15 [mg/kg] TPP-17755 Mean ± SD | 1.31 ± 0.37** | 346.62 ± 78.14** | 1351.64 ± 795.59 |

8-10 animal/group, One-way ANOVA with Dunnett's corrections for multiple comparisons,
*//*/**** = significant with p < 0.05/0.01/0.001/0.0001 vs isotype control

TABLE 20

Dose-response of TPP-23298 antibody in mouse I/R injury model

| | serum creatinine [mg/dl] | serum urea [mg/dl] | urinary albumin to creatinine ratio [µg/mg] |
|---|---|---|---|
| SHAM Mean ± SD | 0.26 ± 0.04**** | 115.80 ± 6.76**** | 71.05 ± 865.39**** |
| 15 [mg/kg] isotype control Mean ± SD | 2.53 ± 0.15 | 498.92 ± 45.45 | 3968.71 ± 453.52 |
| 1 [mg/kg] TPP-23298 Mean ± SD | 2.38 ± 0.22 | 482.06 ± 25.84 | 2383.77 ± 1111.94** |
| 5 [mg/kg] TPP-23298 Mean ± SD | 2.20 ± 0.36* | 425.64 ± 58.85* | 1966.11 ± 677.69**** |
| 15 [mg/kg] TPP-23298 Mean ± SD | 2.02 ± 0.28*** | 422.79 ± 71.44** | 1949.56 ± 700.58**** |

8-10 animal/group, One-way ANOVA with Dunnett's corrections for multiple comparisons. One-way ANOVA with Dunnett's corrections for multiple comparisons,
*//*/**** = significant with p < 0.05/0.01/0.001/0.0001 vs isotype control Example 14: In Vivo Assay for Detecting Protective Renal Effects: Alport Syndrome Model (Col4α3 Deficient Mice)

The phenotype of Alport mice is similar to that of Alport patients, including characteristic thickening and splitting of the glomerular basement membrane as well as strong proteinuria. Alport mice may benefit from treatment with Sema3A inhibitors due to increased Sema3A expression in kidneys of those mice. The beneficial effect of Sema3A blocking antibodies on kidney function was investigated in the Alport mouse model as follows: A colony of knockout Col4α3 (129-Col4a3<tm1Dec>/J) mice (Jackson Laboratory, USA) was established by mating heterozygous animals within the breeding facilities at Bayer AG, Wuppertal, Germany. Male and female homozygous and wild-type Col4α3 mice at an age of 4-5 weeks were obtained from the animal breeding facilities at Bayer AG and used for this study.

The homozygous mice (HOM) were randomized into groups (n=10 each group) according to their age and gender. Mice were dosed once weekly with isotype control and TPP-15370 and TPP-23298. TPP-11489 was administered biweekly. Urine of each animal was collected in metabolic cages once weekly starting before initiation of treatment. Urinary creatinine as well as total protein was measured by a clinical biochemistry analyzer (Pentra400). Both urinary creatinine and albumin were used to determine proteinuria (protein/creatinine ratio). Upon sacrifice at day 21 or day 28 post treatment start, blood samples were obtained under terminal anesthesia. After centrifugation of the blood samples, serum was isolated. Both serum creatinine and serum urea were measured via clinical biochemistry analyzer (Pentra 400).

Kidneys were collected and divided in two parts. One part was snap-frozen in liquid nitrogen for mRNA analysis. The other part was stored in Davidson's fixative for the preparation of histological sections. Total RNA was isolated from parts of harvested kidneys. Kidney tissue was homogenized, and RNA was obtained and transcribed to cDNA. Using TaqMan real time PCR renal mRNA expression of pro-fibrotic markers was analyzed in kidney tissues. For the assessment of fibrosis on the protein level paraffin tissue sections were stained with alpha-smooth muscle actin (αSMA) and Sirius Red/Fast Green Collagen staining using standard procedures.

Quantitative measurements of alpha-smooth muscle actin (αSMA)-positive as well as Sirius Red (Collagen) positive areas within the kidneys were obtained by computer image analysis using the Axio Scan Z1 (Zeiss) microscope and the Zen software.

All data are expressed as means±S.D. Differences between groups were analyzed by one-way ANOVA with Dunnett's corrections for multiple comparisons. Statistical significance was defined as $p<0.05$. All statistical analyses were done using GraphPad Prism 8.

Tables 21A-21C and 22A-22C show effects on proteinuria, kidney function and kidney fibrosis obtained after treatment with TPP-15370 and TPP-23298 in the Alport model. Effects after treatment with TPP-15370 in comparison to TPP-11489 on proteinuria, kidney function and kidney fibrosis are displayed in FIGS. 7 and 8A-8D.

The antibodies according to the present disclosure stopped the progression of kidney disease in a mouse model of Alport syndrome. The antibodies according to the present disclosure reduced the excretion of urinary protein, reduced creatinine and serum urea (surrogates for glomerular filtration rate) as well as fibrosis quantified via myofibroblasts staining and collagen deposition.

TABLE 21A

Effects of TPP-15370 on proteinuria progression in Alport mouse model

| | urinary protein to creatinine ratio [%] increase from baseline | | | |
|---|---|---|---|---|
| | baseline | day 7 | day 14 | day 21 |
| HOM 15 [mg/kg] isotype control Mean ± SD | 100.00 ± 53.71 | 118.65 ± 47.18 | 167.49 ± 55.77 | 192.03 ± 40.23 |
| HOM 5 [mg/kg] TPP-15370 Mean ± SD | 100.00 ± 54.02 | 114.61 ± 50.48 | 149.35 ± 95.41 | 164.92 ± 47.18 |
| HOM 15 [mg/kg] TPP-15370 Mean ± SD | 100.00 ± 65.59 | 114.61 ± 50.48 | 95.41 ± 52.50** | 93.04 ± 31.26**** |

10 animal/group, data are expressed as relative means ± SD percentage values calculated vs. baseline (set to 100). Differences between groups were analyzed by one-way ANOVA with Dunnett's corrections for multiple comparisons. Statistical significance was defined as $p \leq 0.05$.

TABLE 21B

Effects of TPP-15370 on functional parameters at day 21 in Alport mouse model

| | serum creatinine [mg/dl] | serum urea [mg/dl] |
|---|---|---|
| HOM 15 [mg/kg] isotype control Mean ± SD | 0.71 ± 0.26 | 380.61 ± 120.28 |
| HOM 5 [mg/kg] TPP-15370 Mean ± SD | 0.39 ± 0.16** | 255.25 ± 56.80** |
| HOM 15 [mg/kg] TPP-15370 Mean ± SD | 0.44 ± 0.21** | 256.71 ± 95.03** |

10-15 animal/group, One-way ANOVA with Dunnett's corrections for multiple comparisons. One-way ANOVA with Dunnett's corrections for multiple comparisons, /*/**** = significant with $p < 0.05/0.01/0.001/0.0001$ vs isotype control

TABLE 21C

Effects of TPP-15370 on fibrosis at day 28 in Alport mouse model

| | Myofibroblasts % αSMA reduction | Collagen % Sirius Red reduction |
|---|---|---|
| HOM 15 [mg/kg] isotype control Mean ± SD | 100.00 ± 53.53 | 100.00 ± 47.78 |
| HOM 5 [mg/kg] TPP-15370 Mean ± SD | 50.18 ± 21.00** | 80.08 ± 51.58 |
| HOM 15 [mg/kg] TPP-15370 Mean ± SD | 54.86 ± 17.60** | 100.26 ± 50.97 |

10-15 animal/group, One-way ANOVA with Dunnett's corrections for multiple comparisons. One-way ANOVA with Dunnett's corrections for multiple comparisons, /*/**** = significant with $p < 0.05/0.01/0.001/0.0001$ vs isotype control

TABLE 22A

Effects of TPP-23298 on proteinuria progression in Alport mouse model

| | urinary protein to creatinine ratio [%] increase from baseline | | | |
|---|---|---|---|---|
| | baseline | day 14 | day 21 | day 28 |
| HOM 15 [mg/kg] isotype control Mean ± SD | 100.00 ± 70.94 | 185.29 ± 88.09 | 228.62 ± 160.68 | 283.62 ± 77.37 |
| HOM 5 [mg/kg] TPP-23298 Mean ± SD | 100.00 ± 55.72 | 148.01 ± 77.13 | 155.25 ± 61.60 | 151.82 ± 45.84**** |
| HOM 15 [mg/kg] TPP-23298 Mean ± SD | 100.00 ± 56.02 | 154.58 ± 91.21 | 120.54 ± 37.21**** | 125.71 ± 34.25**** |

10 animal/group, data are expressed as relative means ± SD percentage values calculated vs. baseline (set to 100). Differences between groups were analyzed by one-way ANOVA with Dunnett's corrections for multiple comparisons. Statistical significance was defined as p ≤ 0.05.

TABLE 22B

Effects of TPP-23298 on functional parameters at day 28 in Alport mouse model

| | serum creatinine [mg/dl] | serum urea [mg/dl] |
|---|---|---|
| HOM 15 [mg/kg] isotype control Mean ± SD | 0.29 ± 0.07 | 208.89 ± 0.07 |
| HOM 5 [mg/kg] TPP-23298 Mean ± SD | 0.22 ± 0.09* | 175.54 ± 0.03 |
| HOM 15 [mg/kg] TPP-23298 Mean ± SD | 0.19 ± 0.03*** | 141.84 ± 0.03*** |

10-15 animal/group, One-way ANOVA with Dunnett's corrections for multiple comparisons. One-way ANOVA with Dunnett's corrections for multiple comparisons, /*/**** = significant with p < 0.05/0.01/0.001/0.0001 vs isotype control

TABLE 22C

Effects of TPP-23298 on fibrosis at day 28 in Alport mouse model

| | Myofibroblasts % αSMA positive area | Collagen % Sirius Red positive area |
|---|---|---|
| HOM 15 [mg/kg] isotype control Mean ± SD | 100.00 ± 53.53 | 100.00 ± 47.78 |
| HOM 5 [mg/kg] TPP-23298 Mean ± SD | 50.18 ± 21.00** | 80.08 ± 51.58 |
| HOM 15 [mg/kg] TPP-23298 Mean ± SD | 54.86 ± 17.60** | 100.26 ± 50.97 |

10-15 animal/group, One-way ANOVA with Dunnett's corrections for multiple comparisons. One-way ANOVA with Dunnett's corrections for multiple comparisons, /*/**** = significant with p < 0.05/0.01/0.001/0.0001 vs isotype control Example 15: In Vivo Assay for Detecting Protective Renal Effects: Unilateral Kidney IRI Model in Pigs TPP-23298 was tested in a minimal invasive, unilateral kidney artery balloon-catheter occlusion model in adult minipigs with a post-reperfusion follow-up of about 24 hours. Female Gottingen mini pigs of a body weight range 14 to 17 kg (Ellegaard, Denmark) were used for the experiments. Animals were randomly assigned to experimental groups.

TPP-23298 was administered in a blinded, controlled study to 6 animals in comparison to 6 matched IgG-treated controls. Animals which were subjected to all treatment procedures without kidney artery occlusion and received phosphate buffered saline vehicle only served as sham treated reference group.

TPP-23298 was administered at weight adjusted doses in a final volume of 1 ml/kg phosphate buffered saline as a bolus by slow intravenous injection before start of kidney artery occlusion (preventive setting).

For the intervention on day 1 of experimentation pigs were anesthetized by a combination of Propofol and Fentanyl and artificially ventilated over an oro-tracheal tube under muscular relaxation by Pancuronium. Volume was continuously substituted by continuous infusion of Ringer lactate solution. Before starting surgery, antibiotic and thrombosis prophylaxis were provided by administration of Enrofloxacin i.m. and Heparin i.v., respectively. Blood pressure and heart rate were monitored with a non-invasive veterinary device equipped with a foreleg cuff.

All following interventions were performed under strictly aseptic conditions. A catheter was tunneled subcutaneously through the dorsal neck skin to a jugular vein for drug administration. A sheath was placed into the—preferably left—femoral artery and fixed, through which a hockey-stick catheter with a balloon catheter inside was advanced upstream into the abdominal aorta and inserted with its tip into the orifice of the left or right kidney artery. The balloon catheter was then protruded, and the balloon was inflated to interrupt blood flow to the kidney. Correct positioning of the balloon was controlled by Doppler ultrasound using a commercial ultrasound diagnostic apparatus. Plasma samples were collected at baseline and 2 h after start of ischemia.

Kidney ischemia was relieved exactly at pre-defined time points after start of occlusion (ranging from 90 to 120 min) by deflating the balloon and withdrawing the catheter and the sheath. After vascular suture and wound closure animals were re-awakened from anesthesia and after onset of spontaneous breathing extubated.

About 22 to 23 hours after the kidney artery occlusion animals were re-anesthetized by a combination of Ketaset/Dormicum and Pancuronium and artificially ventilated as described. Blood pressure and heart rate were invasively monitored via a carotid artery catheter. Volume substitution was provided at a flow rate of 10 ml/kg/h Ringer Lactate intravenously. Via a small incision in the lower abdomen both ureters were dissected on the urinary bladder wall and catheters were inserted to collect urine side separately for volume determination and urinalysis. Recordings and sample collections were started when all parameters were stable, which was typically the case 24 hours after occlusion. Blood samples were collected at baseline and every hour for three hours (24-27 h interval). In parallel urine was collected for three intervals of 1 h.

After urine volume flow ($V_U$) and urinary creatinine concentrations ($[Crea]_U$) were determined creatinine clearance ($CL_{Crea}$) was calculated separately according to the standard formula $CL_{Crea}=V_U*[Crea]_U/[Crea]_{Pl}$ in which $[Crea]_{Pl}$ stands for plasma creatinine concentration. Global $CL_{Crea}$ was calculated by adding $CL_{Crea}$ of left and right kidney of each animal.

The results are depicted in FIGS. 9A-9D. TPP-23298 when administered in a preventive manner 30 min before occlusion prevented deterioration of ischemia/reperfusion-induced creatinine clearance significantly in this experimental setting after a unilateral kidney artery occlusion of 105 min.

Example 16: Expression Titer of Anti-Sema3A Antibodies in Mammalian Cell Culture HEK293-6E cells were transfected with pTT5 plasmids coding for the heavy and light chain of anti-Sema3A antibodies or with the Fab fragment of TPP-30792 (TPP-31357). Two days prior to transfection, HEK293-6E cells were split to a density of 5×10^5 cells/mL in FreeStyle™ F17 Expression Medium (Gibco, A1383501) with 0.1% Pluronic F68 (Gibco, 24040032) and 4 mM GlutaMax (Gibco, 35050061) in a shake flask, making up 90% of the desired expression volume. HEK293-6E cells were cultivated at 37° C., 5% $CO_2$ shaking at 75 rpm.

For transfection, the DNA and polyethylenimine (Polysciences, 29366) are mixed in FreeStyle™ F17 Expression Medium (Gibco, A1383501) with 4 mM GlutaMax (Gibco, 35050061) making up 10% of the final expression volume. The solution is incubated for 10 minutes and added to the shake flask.

24 hours after transfection, 1% (v/v) ultra-low IgG FBS (Gibco, 16250078) and 0.05% (v/v) iN valproic acid (Sigma, P4543) are added to the shake flask.

The cell viability and density are monitored every day starting 4 days post transfection, the supernatant is harvested by centrifugation and sterile filtration when the viability is determined to be 70%. To determine the production titer, 100 μL of the harvested supernatant are loaded to a 0.1 mL Poros A affinity column (Thermo Scientific, 2100100) via HPLC-system (Agilent, 1100 HPLC system) using 50 mM sodium phosphate (Sigma, S0751, S9763), 150 mM NaCl (Sigma, S6546), 5% 2-propanol (sigma, 34863), pH 7.2 as running buffer. Subsequently, the protein is eluted using 12 mM HCl (Sigma, H9892), 150 mM NaCl, 5% 2-propanol pH 2. A calibration curve from 5 μg/mL to 150 μg/mL is set up using a protein of known size and is applied to the Poros A column via HPLC-system as well. Taking the size and extinction coefficient of the protein in the supernatant into consideration, the exact titer can be calculated using the standard curve. Expression in CHO is similar to HEK cells except that plasmid pTT22AKT was used for TPP-30792.

TABLE 23

Expression Titer of anti-Sema3A antibodies in mammalian cells in mg/L

|  | Titer [mg/L] |
| --- | --- |
| TPP-23298 | 203.6 |
| TPP-17755 (Samsung) | 277.0 |
| TPP-11489 (Chiome) | 132.0 |
| TPP-30791 (BI clone IV) | 333.0 |
| TPP-30790 (BI clone III) | 160.9 |
| TPP-30789 (BI clone II) | 187.6 |
| TPP-30788 (BI clone I) | 240.2 |
| TPP-30792 (3H4 Univ Ramot) | 3.0 (HEK), 3.2 (CHO) |
| TPP-31357 (Fab of TPP-30792) | Not determined |

The antibody of the present disclosure as well as all prior art antibodies except TPP-30792 can be produced with high titers in mammalian cells, as shown in Table 23. TPP-30792 could not be expressed in a significant amount in either HEK or CHO cells. In total 125 μg of TPP-30792 could be purified out of 4.5 liters of HEK293 cell culture. Similarly, the Fab fragment of TPP30792 (TPP-31357) yielded only 200 μg purified Fab out of 5 liters HEK293 cell culture.

Example 17: Analysis of CMC Parameter Stability and Solubility of Anti-Sema3A Antibodies It is known that high concentrated protein solutions of more than 50 mg/ml usually exhibit also higher viscosities compared to lower concentrated protein solutions. Increased viscosity negatively affects the deliverability of the protein solutions especially in low application volumes and it may increase the injection time and pain at the site of injection. In addition to that, high viscosity impacts high-scale protein production in the industry. Thus, reducing viscosity of high concentrated protein solutions while maintaining stability for a long shelf life is i.a. important for the therapeutical in vivo setting.

Proteins in high concentrated solutions are often less stable than in diluted solutions, since the proteins tend to aggregate and may reversibly self-associate at higher concentrations. Aggregation may negatively impact structural integrity and therefore also the amount of functional, bioavailable protein in the therapeutical in vivo setting. This further complicates delivery by injection.

Solubility of proteins is another important quality criterion. Increased solubility of the isolated protein allows for the preparation of highly concentrated solutions required for the therapeutical in vivo setting.

Thus, providing a high concentrated protein solution with reduced viscosity and increased stability and solubility is beneficial for therapeutic applicability of therapeutic molecules.

To assess the CMC (Chemistry, Manufacturing, Control) parameters stability, solubility and viscosity of anti-Sema3A antibodies for potential therapeutic use, antibodies TPP-23289 and TPP-30788 (BI clone I) were diluted in PBS to 25 mg/ml and incubated at 700 rpm and 40° C. for two weeks. While antibodies are usually stored at 4°–10° C. for short-term or frozen at ≤−18° C. or ≥−81° C. for long term an exposure of mammalian antibodies to temperatures higher than ≥40° C. (mammalian average body temperature is 36° C.-39° C.) resembles a thermal stress condition. In this thermal stress condition accelerated protein stability/stress stability is tested. Analysis of stability was assessed by size-exclusion chromatography using a Superdex 200 column (Cytiva) coupled to an Äkta system (Cytiva) in PBS buffer as well as capillary gel electrophoresis using a Caliper system (Perkin Elmer). Changes in profile were calculated as percentage to non-stressed starting material. Solubility was determined by concentrating anti-Sema3A antibodies using an Amicon spin filter (Millipore) with a cut-off of 30 kDa in PBS buffer. The solubility was determined at 90% recovery from the concentrator and protein concentration was measured using Absorption at UV280 nm.

TABLE 24

Overview of CMC parameters for TPP-23298 and TPP-30788; SEC = size-exclusion chromatography, cGE = capillary gel electrophoresis

| CMC Parameter | Method | Analysis | TPP-23298 | TPP-30788 (BI clone I) |
|---|---|---|---|---|
| Stability at 40° C. | SEC* | Δ % monomer | 1 | −5.5 |
|  | cGE** | Δ % LC + HC | <1 | −4.7 |
| Solubility | concentrator | mg/ml at 90% recovery | 225 | 105 |
| Viscosity | SEC* Viscosizer | Δ % monomer cP | <1 5.1 (150 mg/ml) | <1 5.3 (127 mg/ml) |

*SEC = Size exclusion chromatography;
**cGE = capillary gel electrophoresis

Stability, solubility and viscosity are critical CMC parameters for therapeutic molecules as described above. The structural integrity after a thermal stress condition, like exposure to 40° C., or concentrating step is analyzed via SEC and/or cGE to see the effect of the applied stress on the structural integrity. Less than 1% change after the applied stress compared to the start points to a stable molecule whereas deviations>1% points to instabilities in the molecule. TPP-23289 shows a much higher solubility in PBS compared to TPP-30788 by a factor>2 which is very beneficial for e.g. enabling low application volume. Furthermore, TPP-23298 is more stable and more resistant to heat stress than TPP-30788 and is less viscous in PBS buffer.

Sequences

TABLE 1

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-11489 | Chiome Prior Art (hIgG1) | VH | PRT | SEQ ID NO: 1 |
| TPP-11489 | Chiome Prior Art (hIgG1) | HCDR1 | PRT | SEQ ID NO: 2 |
| TPP-11489 | Chiome Prior Art (hIgG1) | HCDR2 | PRT | SEQ ID NO: 3 |
| TPP-11489 | Chiome Prior Art (hIgG1) | HCDR3 | PRT | SEQ ID NO: 4 |
| TPP-11489 | Chiome Prior Art (hIgG1) | VL | PRT | SEQ ID NO: 5 |
| TPP-11489 | Chiome Prior Art (hIgG1) | LCDR1 | PRT | SEQ ID NO: 6 |
| TPP-11489 | Chiome Prior Art (hIgG1) | LCDR2 | PRT | SEQ ID NO: 7 |
| TPP-11489 | Chiome Prior Art (hIgG1) | LCDR3 | PRT | SEQ ID NO: 8 |
| TPP-11489 | Chiome Prior Art (hIgG1) | VH | DNA | SEQ ID NO: 9 |
| TPP-11489 | Chiome Prior Art (hIgG1) | HCDR1 | DNA | SEQ ID NO: 10 |
| TPP-11489 | Chiome Prior Art (hIgG1) | HCDR2 | DNA | SEQ ID NO: 11 |
| TPP-11489 | Chiome Prior Art (hIgG1) | HCDR3 | DNA | SEQ ID NO: 12 |
| TPP-11489 | Chiome Prior Art (hIgG1) | VL | DNA | SEQ ID NO: 13 |
| TPP-11489 | Chiome Prior Art (hIgG1) | LCDR1 | DNA | SEQ ID NO: 14 |
| TPP-11489 | Chiome Prior Art (hIgG1) | LCDR2 | DNA | SEQ ID NO: 15 |
| TPP-11489 | Chiome Prior Art (hIgG1) | LCDR3 | DNA | SEQ ID NO: 16 |
| TPP-11489 | Chiome Prior Art (hIgG1) | Heavy Chain | PRT | SEQ ID NO: 17 |
| TPP-11489 | Chiome Prior Art (hIgG1) | Light Chain | PRT | SEQ ID NO: 18 |
| TPP-11489 | Chiome Prior Art (hIgG1) | Heavy Chain | DNA | SEQ ID NO: 19 |
| TPP-11489 | Chiome Prior Art (hIgG1) | Light Chain | DNA | SEQ ID NO: 20 |
| TPP-15051 | Chiome Prior Art (mIgG1) | VH | PRT | SEQ ID NO: 21 |
| TPP-15051 | Chiome Prior Art (mIgG1) | HCDR1 | PRT | SEQ ID NO: 22 |
| TPP-15051 | Chiome Prior Art (mIgG1) | HCDR2 | PRT | SEQ ID NO: 23 |
| TPP-15051 | Chiome Prior Art (mIgG1) | HCDR3 | PRT | SEQ ID NO: 24 |
| TPP-15051 | Chiome Prior Art (mIgG1) | VL | PRT | SEQ ID NO: 25 |
| TPP-15051 | Chiome Prior Art (mIgG1) | LCDR1 | PRT | SEQ ID NO: 26 |
| TPP-15051 | Chiome Prior Art (mIgG1) | LCDR2 | PRT | SEQ ID NO: 27 |
| TPP-15051 | Chiome Prior Art (mIgG1) | LCDR3 | PRT | SEQ ID NO: 28 |
| TPP-15051 | Chiome Prior Art (mIgG1) | VH | DNA | SEQ ID NO: 29 |
| TPP-15051 | Chiome Prior Art (mIgG1) | HCDR1 | DNA | SEQ ID NO: 30 |
| TPP-15051 | Chiome Prior Art (mIgG1) | HCDR2 | DNA | SEQ ID NO: 31 |
| TPP-15051 | Chiome Prior Art (mIgG1) | HCDR3 | DNA | SEQ ID NO: 32 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788- TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-15051 | Chiome Prior Art (mIgG1) | VL | DNA | SEQ ID NO: 33 |
| TPP-15051 | Chiome Prior Art (mIgG1) | LCDR1 | DNA | SEQ ID NO: 34 |
| TPP-15051 | Chiome Prior Art (mIgG1) | LCDR2 | DNA | SEQ ID NO: 35 |
| TPP-15051 | Chiome Prior Art (mIgG1) | LCDR3 | DNA | SEQ ID NO: 36 |
| TPP-15051 | Chiome Prior Art (mIgG1) | Heavy Chain | PRT | SEQ ID NO: 37 |
| TPP-15051 | Chiome Prior Art (mIgG1) | Light Chain | PRT | SEQ ID NO: 38 |
| TPP-15051 | Chiome Prior Art (mIgG1) | Heavy Chain | DNA | SEQ ID NO: 39 |
| TPP-15051 | Chiome Prior Art (mIgG1) | Light Chain | DNA | SEQ ID NO: 40 |
| TPP-15370 | IgG1, hit from panning | VH | PRT | SEQ ID NO: 41 |
| TPP-15370 | IgG1, hit from panning | HCDR1 | PRT | SEQ ID NO: 42 |
| TPP-15370 | IgG1, hit from panning | HCDR2 | PRT | SEQ ID NO: 43 |
| TPP-15370 | IgG1, hit from panning | HCDR3 | PRT | SEQ ID NO: 44 |
| TPP-15370 | IgG1, hit from panning | VL | PRT | SEQ ID NO: 45 |
| TPP-15370 | IgG1, hit from panning | LCDR1 | PRT | SEQ ID NO: 46 |
| TPP-15370 | IgG1, hit from panning | LCDR2 | PRT | SEQ ID NO: 47 |
| TPP-15370 | IgG1, hit from panning | LCDR3 | PRT | SEQ ID NO: 48 |
| TPP-15370 | IgG1, hit from panning | VH | DNA | SEQ ID NO: 49 |
| TPP-15370 | IgG1, hit from panning | HCDR1 | DNA | SEQ ID NO: 50 |
| TPP-15370 | IgG1, hit from panning | HCDR2 | DNA | SEQ ID NO: 51 |
| TPP-15370 | IgG1, hit from panning | HCDR3 | DNA | SEQ ID NO: 52 |
| TPP-15370 | IgG1, hit from panning | VL | DNA | SEQ ID NO: 53 |
| TPP-15370 | IgG1, hit from panning | LCDR1 | DNA | SEQ ID NO: 54 |
| TPP-15370 | IgG1, hit from panning | LCDR2 | DNA | SEQ ID NO: 55 |
| TPP-15370 | IgG1, hit from panning | LCDR3 | DNA | SEQ ID NO: 56 |
| TPP-15370 | IgG1, hit from panning | Heavy Chain | PRT | SEQ ID NO: 57 |
| TPP-15370 | IgG1, hit from panning | Light Chain | PRT | SEQ ID NO: 58 |
| TPP-15370 | IgG1, hit from panning | Heavy Chain | DNA | SEQ ID NO: 59 |
| TPP-15370 | IgG1, hit from panning | Light Chain | DNA | SEQ ID NO: 60 |
| TPP-15374 | IgG1, hit from panning | VH | PRT | SEQ ID NO: 61 |
| TPP-15374 | IgG1, hit from panning | HCDR1 | PRT | SEQ ID NO: 62 |
| TPP-15374 | IgG1, hit from panning | HCDR2 | PRT | SEQ ID NO: 63 |
| TPP-15374 | IgG1, hit from panning | HCDR3 | PRT | SEQ ID NO: 64 |
| TPP-15374 | IgG1, hit from panning | VL | PRT | SEQ ID NO: 65 |
| TPP-15374 | IgG1, hit from panning | LCDR1 | PRT | SEQ ID NO: 66 |
| TPP-15374 | IgG1, hit from panning | LCDR2 | PRT | SEQ ID NO: 67 |
| TPP-15374 | IgG1, hit from panning | LCDR3 | PRT | SEQ ID NO: 68 |
| TPP-15374 | IgG1, hit from panning | VH | DNA | SEQ ID NO: 69 |
| TPP-15374 | IgG1, hit from panning | HCDR1 | DNA | SEQ ID NO: 70 |
| TPP-15374 | IgG1, hit from panning | HCDR2 | DNA | SEQ ID NO: 71 |
| TPP-15374 | IgG1, hit from panning | HCDR3 | DNA | SEQ ID NO: 72 |
| TPP-15374 | IgG1, hit from panning | VL | DNA | SEQ ID NO: 73 |
| TPP-15374 | IgG1, hit from panning | LCDR1 | DNA | SEQ ID NO: 74 |
| TPP-15374 | IgG1, hit from panning | LCDR2 | DNA | SEQ ID NO: 75 |
| TPP-15374 | IgG1, hit from panning | LCDR3 | DNA | SEQ ID NO: 76 |
| TPP-15374 | IgG1, hit from panning | Heavy Chain | PRT | SEQ ID NO: 77 |
| TPP-15374 | IgG1, hit from panning | Light Chain | PRT | SEQ ID NO: 78 |
| TPP-15374 | IgG1, hit from panning | Heavy Chain | DNA | SEQ ID NO: 79 |
| TPP-15374 | IgG1, hit from panning | Light Chain | DNA | SEQ ID NO: 80 |
| TPP-17755 | Samsung Prior Art F11 | VH | PRT | SEQ ID NO: 81 |
| TPP-17755 | Samsung Prior Art F11 | HCDR1 | PRT | SEQ ID NO: 82 |
| TPP-17755 | Samsung Prior Art F11 | HCDR2 | PRT | SEQ ID NO: 83 |
| TPP-17755 | Samsung Prior Art F11 | HCDR3 | PRT | SEQ ID NO: 84 |
| TPP-17755 | Samsung Prior Art F11 | VL | PRT | SEQ ID NO: 85 |
| TPP-17755 | Samsung Prior Art F11 | LCDR1 | PRT | SEQ ID NO: 86 |
| TPP-17755 | Samsung Prior Art F11 | LCDR2 | PRT | SEQ ID NO: 87 |
| TPP-17755 | Samsung Prior Art F11 | LCDR3 | PRT | SEQ ID NO: 88 |
| TPP-17755 | Samsung Prior Art F11 | VH | DNA | SEQ ID NO: 89 |
| TPP-17755 | Samsung Prior Art F11 | HCDR1 | DNA | SEQ ID NO: 90 |
| TPP-17755 | Samsung Prior Art F11 | HCDR2 | DNA | SEQ ID NO: 91 |
| TPP-17755 | Samsung Prior Art F11 | HCDR3 | DNA | SEQ ID NO: 92 |
| TPP-17755 | Samsung Prior Art F11 | VL | DNA | SEQ ID NO: 93 |
| TPP-17755 | Samsung Prior Art F11 | LCDR1 | DNA | SEQ ID NO: 94 |
| TPP-17755 | Samsung Prior Art F11 | LCDR2 | DNA | SEQ ID NO: 95 |
| TPP-17755 | Samsung Prior Art F11 | LCDR3 | DNA | SEQ ID NO: 96 |
| TPP-17755 | Samsung Prior Art F11 | Heavy Chain | PRT | SEQ ID NO: 97 |
| TPP-17755 | Samsung Prior Art F11 | Light Chain | PRT | SEQ ID NO: 98 |
| TPP-17755 | Samsung Prior Art F11 | Heavy Chain | DNA | SEQ ID NO: 99 |
| TPP-17755 | Samsung Prior Art F11 | Light Chain | DNA | SEQ ID NO: 100 |

TABLE 1-continued

Amino acid sequences and nucleic acid sequences of preferred
antibodies according to the present disclosure and of three
prior art antibodies. TPP-11489 corresponds to Chiome antibody
Humanized-2 derived of clone No. 4-2 strain (WO 2014/123186);
TPP-15051 respresents a murine IgG1 variant thereof. TPP-30788-
TPP-30791 corresponds to Böhringer Ingelheim antibody (BI)
Clone I-IV (WO 2020/225400). TPP-30792 corresponds to
University Ramot antibody clone I (WO 2020/261281).

| TPP ID | Antibody Description | Sequence Region | Sequence Type | SEQ ID |
|---|---|---|---|---|
| TPP-18533 | germline IgG1 of TPP-15374 | VH | PRT | SEQ ID NO: 101 |
| TPP-18533 | germline IgG1 of TPP-15374 | HCDR1 | PRT | SEQ ID NO: 102 |
| TPP-18533 | germline IgG1 of TPP-15374 | HCDR2 | PRT | SEQ ID NO: 103 |
| TPP-18533 | germline IgG1 of TPP-15374 | HCDR3 | PRT | SEQ ID NO: 104 |
| TPP-18533 | germline IgG1 of TPP-15374 | VL | PRT | SEQ ID NO: 105 |
| TPP-18533 | germline IgG1 of TPP-15374 | LCDR1 | PRT | SEQ ID NO: 106 |
| TPP-18533 | germline IgG1 of TPP-15374 | LCDR2 | PRT | SEQ ID NO: 107 |
| TPP-18533 | germline IgG1 of TPP-15374 | LCDR3 | PRT | SEQ ID NO: 108 |
| TPP-18533 | germline IgG1 of TPP-15374 | VH | DNA | SEQ ID NO: 109 |
| TPP-18533 | germline IgG1 of TPP-15374 | HCDR1 | DNA | SEQ ID NO: 110 |
| TPP-18533 | germline IgG1 of TPP-15374 | HCDR2 | DNA | SEQ ID NO: 111 |
| TPP-18533 | germline IgG1 of TPP-15374 | HCDR3 | DNA | SEQ ID NO: 112 |
| TPP-18533 | germline IgG1 of TPP-15374 | VL | DNA | SEQ ID NO: 113 |
| TPP-18533 | germline IgG1 of TPP-15374 | LCDR1 | DNA | SEQ ID NO: 114 |
| TPP-18533 | germline IgG1 of TPP-15374 | LCDR2 | DNA | SEQ ID NO: 115 |
| TPP-18533 | germline IgG1 of TPP-15374 | LCDR3 | DNA | SEQ ID NO: 116 |
| TPP-18533 | germline IgG1 of TPP-15374 | Heavy Chain | PRT | SEQ ID NO: 117 |
| TPP-18533 | germline IgG1 of TPP-15374 | Light Chain | PRT | SEQ ID NO: 118 |
| TPP-18533 | germline IgG1 of TPP-15374 | Heavy Chain | DNA | SEQ ID NO: 119 |
| TPP-18533 | germline IgG1 of TPP-15374 | Light Chain | DNA | SEQ ID NO: 120 |
| TPP-21565 | germline IgG1 of TPP-15370 | VH | PRT | SEQ ID NO: 121 |
| TPP-21565 | germline IgG1 of TPP-15370 | HCDR1 | PRT | SEQ ID NO: 122 |
| TPP-21565 | germline IgG1 of TPP-15370 | HCDR2 | PRT | SEQ ID NO: 123 |
| TPP-21565 | germline IgG1 of TPP-15370 | HCDR3 | PRT | SEQ ID NO: 124 |
| TPP-21565 | germline IgG1 of TPP-15370 | VL | PRT | SEQ ID NO: 125 |
| TPP-21565 | germline IgG1 of TPP-15370 | LCDR1 | PRT | SEQ ID NO: 126 |
| TPP-21565 | germline IgG1 of TPP-15370 | LCDR2 | PRT | SEQ ID NO: 127 |
| TPP-21565 | germline IgG1 of TPP-15370 | LCDR3 | PRT | SEQ ID NO: 128 |
| TPP-21565 | germline IgG1 of TPP-15370 | VH | DNA | SEQ ID NO: 129 |
| TPP-21565 | germline IgG1 of TPP-15370 | HCDR1 | DNA | SEQ ID NO: 130 |
| TPP-21565 | germline IgG1 of TPP-15370 | HCDR2 | DNA | SEQ ID NO: 131 |
| TPP-21565 | germline IgG1 of TPP-15370 | HCDR3 | DNA | SEQ ID NO: 132 |
| TPP-21565 | germline IgG1 of TPP-15370 | VL | DNA | SEQ ID NO: 133 |
| TPP-21565 | germline IgG1 of TPP-15370 | LCDR1 | DNA | SEQ ID NO: 134 |
| TPP-21565 | germline IgG1 of TPP-15370 | LCDR2 | DNA | SEQ ID NO: 135 |
| TPP-21565 | germline IgG1 of TPP-15370 | LCDR3 | DNA | SEQ ID NO: 136 |
| TPP-21565 | germline IgG1 of TPP-15370 | Heavy Chain | PRT | SEQ ID NO: 137 |
| TPP-21565 | germline IgG1 of TPP-15370 | Light Chain | PRT | SEQ ID NO: 138 |
| TPP-21565 | germline IgG1 of TPP-15370 | Heavy Chain | DNA | SEQ ID NO: 139 |
| TPP-21565 | germline IgG1 of TPP-15370 | Light Chain | DNA | SEQ ID NO: 140 |
| TPP-23298 | Recombi Variant of TPP-15370 | VH | PRT | SEQ ID NO: 141 |
| TPP-23298 | Recombi Variant of TPP-15370 | HCDR1 | PRT | SEQ ID NO: 142 |
| TPP-23298 | Recombi Variant of TPP-15370 | HCDR2 | PRT | SEQ ID NO: 143 |
| TPP-23298 | Recombi Variant of TPP-15370 | HCDR3 | PRT | SEQ ID NO: 144 |
| TPP-23298 | Recombi Variant of TPP-15370 | VL | PRT | SEQ ID NO: 145 |
| TPP-23298 | Recombi Variant of TPP-15370 | LCDR1 | PRT | SEQ ID NO: 146 |
| TPP-23298 | Recombi Variant of TPP-15370 | LCDR2 | PRT | SEQ ID NO: 147 |
| TPP-23298 | Recombi Variant of TPP-15370 | LCDR3 | PRT | SEQ ID NO: 148 |
| TPP-23298 | Recombi Variant of TPP-15370 | VH | DNA | SEQ ID NO: 149 |
| TPP-23298 | Recombi Variant of TPP-15370 | HCDR1 | DNA | SEQ ID NO: 150 |
| TPP-23298 | Recombi Variant of TPP-15370 | HCDR2 | DNA | SEQ ID NO: 151 |
| TPP-23298 | Recombi Variant of TPP-15370 | HCDR3 | DNA | SEQ ID NO: 152 |
| TPP-23298 | Recombi Variant of TPP-15370 | VL | DNA | SEQ ID NO: 153 |
| TPP-23298 | Recombi Variant of TPP-15370 | LCDR1 | DNA | SEQ ID NO: 154 |
| TPP-23298 | Recombi Variant of TPP-15370 | LCDR2 | DNA | SEQ ID NO: 155 |
| TPP-23298 | Recombi Variant of TPP-15370 | LCDR3 | DNA | SEQ ID NO: 156 |
| TPP-23298 | Recombi Variant of TPP-15370 | Heavy Chain | PRT | SEQ ID NO: 157 |
| TPP-23298 | Recombi Variant of TPP-15370 | Light Chain | PRT | SEQ ID NO: 158 |
| TPP-23298 | Recombi Variant of TPP-15370 | Heavy Chain | DNA | SEQ ID NO: 159 |
| TPP-23298 | Recombi Variant of TPP-15370 | Light Chain | DNA | SEQ ID NO: 160 |
| TPP-23334 | Recombi Variant of TPP-15370 | VH | PRT | SEQ ID NO: 161 |
| TPP-23334 | Recombi Variant of TPP-15370 | HCDR1 | PRT | SEQ ID NO: 162 |
| TPP-23334 | Recombi Variant of TPP-15370 | HCDR2 | PRT | SEQ ID NO: 163 |
| TPP-23334 | Recombi Variant of TPP-15370 | HCDR3 | PRT | SEQ ID NO: 164 |
| TPP-23334 | Recombi Variant of TPP-15370 | VL | PRT | SEQ ID NO: 165 |
| TPP-23334 | Recombi Variant of TPP-15370 | LCDR1 | PRT | SEQ ID NO: 166 |
| TPP-23334 | Recombi Variant of TPP-15370 | LCDR2 | PRT | SEQ ID NO: 167 |
| TPP-23334 | Recombi Variant of TPP-15370 | LCDR3 | PRT | SEQ ID NO: 168 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23334 | Recombi Variant of TPP-15370 | VH | DNA | SEQ ID NO: 169 |
| TPP-23334 | Recombi Variant of TPP-15370 | HCDR1 | DNA | SEQ ID NO: 170 |
| TPP-23334 | Recombi Variant of TPP-15370 | HCDR2 | DNA | SEQ ID NO: 171 |
| TPP-23334 | Recombi Variant of TPP-15370 | HCDR3 | DNA | SEQ ID NO: 172 |
| TPP-23334 | Recombi Variant of TPP-15370 | VL | DNA | SEQ ID NO: 173 |
| TPP-23334 | Recombi Variant of TPP-15370 | LCDR1 | DNA | SEQ ID NO: 174 |
| TPP-23334 | Recombi Variant of TPP-15370 | LCDR2 | DNA | SEQ ID NO: 175 |
| TPP-23334 | Recombi Variant of TPP-15370 | LCDR3 | DNA | SEQ ID NO: 176 |
| TPP-23334 | Recombi Variant of TPP-15370 | Heavy Chain | PRT | SEQ ID NO: 177 |
| TPP-23334 | Recombi Variant of TPP-15370 | Light Chain | PRT | SEQ ID NO: 178 |
| TPP-23334 | Recombi Variant of TPP-15370 | Heavy Chain | DNA | SEQ ID NO: 179 |
| TPP-23334 | Recombi Variant of TPP-15370 | Light Chain | DNA | SEQ ID NO: 180 |
| TPP-23337 | Recombi Variant of TPP-15370 | VH | PRT | SEQ ID NO: 181 |
| TPP-23337 | Recombi Variant of TPP-15370 | HCDR1 | PRT | SEQ ID NO: 182 |
| TPP-23337 | Recombi Variant of TPP-15370 | HCDR2 | PRT | SEQ ID NO: 183 |
| TPP-23337 | Recombi Variant of TPP-15370 | HCDR3 | PRT | SEQ ID NO: 184 |
| TPP-23337 | Recombi Variant of TPP-15370 | VL | PRT | SEQ ID NO: 185 |
| TPP-23337 | Recombi Variant of TPP-15370 | LCDR1 | PRT | SEQ ID NO: 186 |
| TPP-23337 | Recombi Variant of TPP-15370 | LCDR2 | PRT | SEQ ID NO: 187 |
| TPP-23337 | Recombi Variant of TPP-15370 | LCDR3 | PRT | SEQ ID NO: 188 |
| TPP-23337 | Recombi Variant of TPP-15370 | VH | DNA | SEQ ID NO: 189 |
| TPP-23337 | Recombi Variant of TPP-15370 | HCDR1 | DNA | SEQ ID NO: 190 |
| TPP-23337 | Recombi Variant of TPP-15370 | HCDR2 | DNA | SEQ ID NO: 191 |
| TPP-23337 | Recombi Variant of TPP-15370 | HCDR3 | DNA | SEQ ID NO: 192 |
| TPP-23337 | Recombi Variant of TPP-15370 | VL | DNA | SEQ ID NO: 193 |
| TPP-23337 | Recombi Variant of TPP-15370 | LCDR1 | DNA | SEQ ID NO: 194 |
| TPP-23337 | Recombi Variant of TPP-15370 | LCDR2 | DNA | SEQ ID NO: 195 |
| TPP-23337 | Recombi Variant of TPP-15370 | LCDR3 | DNA | SEQ ID NO: 196 |
| TPP-23337 | Recombi Variant of TPP-15370 | Heavy Chain | PRT | SEQ ID NO: 197 |
| TPP-23337 | Recombi Variant of TPP-15370 | Light Chain | PRT | SEQ ID NO: 198 |
| TPP-23337 | Recombi Variant of TPP-15370 | Heavy Chain | DNA | SEQ ID NO: 199 |
| TPP-23337 | Recombi Variant of TPP-15370 | Light Chain | DNA | SEQ ID NO: 200 |
| TPP-23338 | Recombi Variant of TPP-15370 | VH | PRT | SEQ ID NO: 201 |
| TPP-23338 | Recombi Variant of TPP-15370 | HCDR1 | PRT | SEQ ID NO: 202 |
| TPP-23338 | Recombi Variant of TPP-15370 | HCDR2 | PRT | SEQ ID NO: 203 |
| TPP-23338 | Recombi Variant of TPP-15370 | HCDR3 | PRT | SEQ ID NO: 204 |
| TPP-23338 | Recombi Variant of TPP-15370 | VL | PRT | SEQ ID NO: 205 |
| TPP-23338 | Recombi Variant of TPP-15370 | LCDR1 | PRT | SEQ ID NO: 206 |
| TPP-23338 | Recombi Variant of TPP-15370 | LCDR2 | PRT | SEQ ID NO: 207 |
| TPP-23338 | Recombi Variant of TPP-15370 | LCDR3 | PRT | SEQ ID NO: 208 |
| TPP-23338 | Recombi Variant of TPP-15370 | VH | DNA | SEQ ID NO: 209 |
| TPP-23338 | Recombi Variant of TPP-15370 | HCDR1 | DNA | SEQ ID NO: 210 |
| TPP-23338 | Recombi Variant of TPP-15370 | HCDR2 | DNA | SEQ ID NO: 211 |
| TPP-23338 | Recombi Variant of TPP-15370 | HCDR3 | DNA | SEQ ID NO: 212 |
| TPP-23338 | Recombi Variant of TPP-15370 | VL | DNA | SEQ ID NO: 213 |
| TPP-23338 | Recombi Variant of TPP-15370 | LCDR1 | DNA | SEQ ID NO: 214 |
| TPP-23338 | Recombi Variant of TPP-15370 | LCDR2 | DNA | SEQ ID NO: 215 |
| TPP-23338 | Recombi Variant of TPP-15370 | LCDR3 | DNA | SEQ ID NO: 216 |
| TPP-23338 | Recombi Variant of TPP-15370 | Heavy Chain | PRT | SEQ ID NO: 217 |
| TPP-23338 | Recombi Variant of TPP-15370 | Light Chain | PRT | SEQ ID NO: 218 |
| TPP-23338 | Recombi Variant of TPP-15370 | Heavy Chain | DNA | SEQ ID NO: 219 |
| TPP-23338 | Recombi Variant of TPP-15370 | Light Chain | DNA | SEQ ID NO: 220 |
| TPP-23340 | Recombi Variant of TPP-15370 | VH | PRT | SEQ ID NO: 221 |
| TPP-23340 | Recombi Variant of TPP-15370 | HCDR1 | PRT | SEQ ID NO: 222 |
| TPP-23340 | Recombi Variant of TPP-15370 | HCDR2 | PRT | SEQ ID NO: 223 |
| TPP-23340 | Recombi Variant of TPP-15370 | HCDR3 | PRT | SEQ ID NO: 224 |
| TPP-23340 | Recombi Variant of TPP-15370 | VL | PRT | SEQ ID NO: 225 |
| TPP-23340 | Recombi Variant of TPP-15370 | LCDR1 | PRT | SEQ ID NO: 226 |
| TPP-23340 | Recombi Variant of TPP-15370 | LCDR2 | PRT | SEQ ID NO: 227 |
| TPP-23340 | Recombi Variant of TPP-15370 | LCDR3 | PRT | SEQ ID NO: 228 |
| TPP-23340 | Recombi Variant of TPP-15370 | VH | DNA | SEQ ID NO: 229 |
| TPP-23340 | Recombi Variant of TPP-15370 | HCDR1 | DNA | SEQ ID NO: 230 |
| TPP-23340 | Recombi Variant of TPP-15370 | HCDR2 | DNA | SEQ ID NO: 231 |
| TPP-23340 | Recombi Variant of TPP-15370 | HCDR3 | DNA | SEQ ID NO: 232 |
| TPP-23340 | Recombi Variant of TPP-15370 | VL | DNA | SEQ ID NO: 233 |
| TPP-23340 | Recombi Variant of TPP-15370 | LCDR1 | DNA | SEQ ID NO: 234 |
| TPP-23340 | Recombi Variant of TPP-15370 | LCDR2 | DNA | SEQ ID NO: 235 |
| TPP-23340 | Recombi Variant of TPP-15370 | LCDR3 | DNA | SEQ ID NO: 236 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23340 | Recombi Variant of TPP-15370 | Heavy Chain | PRT | SEQ ID NO: 237 |
| TPP-23340 | Recombi Variant of TPP-15370 | Light Chain | PRT | SEQ ID NO: 238 |
| TPP-23340 | Recombi Variant of TPP-15370 | Heavy Chain | DNA | SEQ ID NO: 239 |
| TPP-23340 | Recombi Variant of TPP-15370 | Light Chain | DNA | SEQ ID NO: 240 |
| TPP-23341 | Recombi Variant of TPP-15370 | VH | PRT | SEQ ID NO: 241 |
| TPP-23341 | Recombi Variant of TPP-15370 | HCDR1 | PRT | SEQ ID NO: 242 |
| TPP-23341 | Recombi Variant of TPP-15370 | HCDR2 | PRT | SEQ ID NO: 243 |
| TPP-23341 | Recombi Variant of TPP-15370 | HCDR3 | PRT | SEQ ID NO: 244 |
| TPP-23341 | Recombi Variant of TPP-15370 | VL | PRT | SEQ ID NO: 245 |
| TPP-23341 | Recombi Variant of TPP-15370 | LCDR1 | PRT | SEQ ID NO: 246 |
| TPP-23341 | Recombi Variant of TPP-15370 | LCDR2 | PRT | SEQ ID NO: 247 |
| TPP-23341 | Recombi Variant of TPP-15370 | LCDR3 | PRT | SEQ ID NO: 248 |
| TPP-23341 | Recombi Variant of TPP-15370 | VH | DNA | SEQ ID NO: 249 |
| TPP-23341 | Recombi Variant of TPP-15370 | HCDR1 | DNA | SEQ ID NO: 250 |
| TPP-23341 | Recombi Variant of TPP-15370 | HCDR2 | DNA | SEQ ID NO: 251 |
| TPP-23341 | Recombi Variant of TPP-15370 | HCDR3 | DNA | SEQ ID NO: 252 |
| TPP-23341 | Recombi Variant of TPP-15370 | VL | DNA | SEQ ID NO: 253 |
| TPP-23341 | Recombi Variant of TPP-15370 | LCDR1 | DNA | SEQ ID NO: 254 |
| TPP-23341 | Recombi Variant of TPP-15370 | LCDR2 | DNA | SEQ ID NO: 255 |
| TPP-23341 | Recombi Variant of TPP-15370 | LCDR3 | DNA | SEQ ID NO: 256 |
| TPP-23341 | Recombi Variant of TPP-15370 | Heavy Chain | PRT | SEQ ID NO: 257 |
| TPP-23341 | Recombi Variant of TPP-15370 | Light Chain | PRT | SEQ ID NO: 258 |
| TPP-23341 | Recombi Variant of TPP-15370 | Heavy Chain | DNA | SEQ ID NO: 259 |
| TPP-23341 | Recombi Variant of TPP-15370 | Light Chain | DNA | SEQ ID NO: 260 |
| TPP-23345 | Recombi Variant of TPP-15370 | VH | PRT | SEQ ID NO: 261 |
| TPP-23345 | Recombi Variant of TPP-15370 | HCDR1 | PRT | SEQ ID NO: 262 |
| TPP-23345 | Recombi Variant of TPP-15370 | HCDR2 | PRT | SEQ ID NO: 263 |
| TPP-23345 | Recombi Variant of TPP-15370 | HCDR3 | PRT | SEQ ID NO: 264 |
| TPP-23345 | Recombi Variant of TPP-15370 | VL | PRT | SEQ ID NO: 265 |
| TPP-23345 | Recombi Variant of TPP-15370 | LCDR1 | PRT | SEQ ID NO: 266 |
| TPP-23345 | Recombi Variant of TPP-15370 | LCDR2 | PRT | SEQ ID NO: 267 |
| TPP-23345 | Recombi Variant of TPP-15370 | LCDR3 | PRT | SEQ ID NO: 268 |
| TPP-23345 | Recombi Variant of TPP-15370 | VH | DNA | SEQ ID NO: 269 |
| TPP-23345 | Recombi Variant of TPP-15370 | HCDR1 | DNA | SEQ ID NO: 270 |
| TPP-23345 | Recombi Variant of TPP-15370 | HCDR2 | DNA | SEQ ID NO: 271 |
| TPP-23345 | Recombi Variant of TPP-15370 | HCDR3 | DNA | SEQ ID NO: 272 |
| TPP-23345 | Recombi Variant of TPP-15370 | VL | DNA | SEQ ID NO: 273 |
| TPP-23345 | Recombi Variant of TPP-15370 | LCDR1 | DNA | SEQ ID NO: 274 |
| TPP-23345 | Recombi Variant of TPP-15370 | LCDR2 | DNA | SEQ ID NO: 275 |
| TPP-23345 | Recombi Variant of TPP-15370 | LCDR3 | DNA | SEQ ID NO: 276 |
| TPP-23345 | Recombi Variant of TPP-15370 | Heavy Chain | PRT | SEQ ID NO: 277 |
| TPP-23345 | Recombi Variant of TPP-15370 | Light Chain | PRT | SEQ ID NO: 278 |
| TPP-23345 | Recombi Variant of TPP-15370 | Heavy Chain | DNA | SEQ ID NO: 279 |
| TPP-23345 | Recombi Variant of TPP-15370 | Light Chain | DNA | SEQ ID NO: 280 |
| TPP-23346 | Recombi Variant of TPP-15370 | VH | PRT | SEQ ID NO: 281 |
| TPP-23346 | Recombi Variant of TPP-15370 | HCDR1 | PRT | SEQ ID NO: 282 |
| TPP-23346 | Recombi Variant of TPP-15370 | HCDR2 | PRT | SEQ ID NO: 283 |
| TPP-23346 | Recombi Variant of TPP-15370 | HCDR3 | PRT | SEQ ID NO: 284 |
| TPP-23346 | Recombi Variant of TPP-15370 | VL | PRT | SEQ ID NO: 285 |
| TPP-23346 | Recombi Variant of TPP-15370 | LCDR1 | PRT | SEQ ID NO: 286 |
| TPP-23346 | Recombi Variant of TPP-15370 | LCDR2 | PRT | SEQ ID NO: 287 |
| TPP-23346 | Recombi Variant of TPP-15370 | LCDR3 | PRT | SEQ ID NO: 288 |
| TPP-23346 | Recombi Variant of TPP-15370 | VH | DNA | SEQ ID NO: 289 |
| TPP-23346 | Recombi Variant of TPP-15370 | HCDR1 | DNA | SEQ ID NO: 290 |
| TPP-23346 | Recombi Variant of TPP-15370 | HCDR2 | DNA | SEQ ID NO: 291 |
| TPP-23346 | Recombi Variant of TPP-15370 | HCDR3 | DNA | SEQ ID NO: 292 |
| TPP-23346 | Recombi Variant of TPP-15370 | VL | DNA | SEQ ID NO: 293 |
| TPP-23346 | Recombi Variant of TPP-15370 | LCDR1 | DNA | SEQ ID NO: 294 |
| TPP-23346 | Recombi Variant of TPP-15370 | LCDR2 | DNA | SEQ ID NO: 295 |
| TPP-23346 | Recombi Variant of TPP-15370 | LCDR3 | DNA | SEQ ID NO: 296 |
| TPP-23346 | Recombi Variant of TPP-15370 | Heavy Chain | PRT | SEQ ID NO: 297 |
| TPP-23346 | Recombi Variant of TPP-15370 | Light Chain | PRT | SEQ ID NO: 298 |
| TPP-23346 | Recombi Variant of TPP-15370 | Heavy Chain | DNA | SEQ ID NO: 299 |
| TPP-23346 | Recombi Variant of TPP-15370 | Light Chain | DNA | SEQ ID NO: 300 |
| TPP-23347 | Recombi Variant of TPP-15370 | VH | PRT | SEQ ID NO: 301 |
| TPP-23347 | Recombi Variant of TPP-15370 | HCDR1 | PRT | SEQ ID NO: 302 |
| TPP-23347 | Recombi Variant of TPP-15370 | HCDR2 | PRT | SEQ ID NO: 303 |
| TPP-23347 | Recombi Variant of TPP-15370 | HCDR3 | PRT | SEQ ID NO: 304 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788- TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23347 | Recombi Variant of TPP-15370 | VL | PRT | SEQ ID NO: 305 |
| TPP-23347 | Recombi Variant of TPP-15370 | LCDR1 | PRT | SEQ ID NO: 306 |
| TPP-23347 | Recombi Variant of TPP-15370 | LCDR2 | PRT | SEQ ID NO: 307 |
| TPP-23347 | Recombi Variant of TPP-15370 | LCDR3 | PRT | SEQ ID NO: 308 |
| TPP-23347 | Recombi Variant of TPP-15370 | VH | DNA | SEQ ID NO: 309 |
| TPP-23347 | Recombi Variant of TPP-15370 | HCDR1 | DNA | SEQ ID NO: 310 |
| TPP-23347 | Recombi Variant of TPP-15370 | HCDR2 | DNA | SEQ ID NO: 311 |
| TPP-23347 | Recombi Variant of TPP-15370 | HCDR3 | DNA | SEQ ID NO: 312 |
| TPP-23347 | Recombi Variant of TPP-15370 | VL | DNA | SEQ ID NO: 313 |
| TPP-23347 | Recombi Variant of TPP-15370 | LCDR1 | DNA | SEQ ID NO: 314 |
| TPP-23347 | Recombi Variant of TPP-15370 | LCDR2 | DNA | SEQ ID NO: 315 |
| TPP-23347 | Recombi Variant of TPP-15370 | LCDR3 | DNA | SEQ ID NO: 316 |
| TPP-23347 | Recombi Variant of TPP-15370 | Heavy Chain | PRT | SEQ ID NO: 317 |
| TPP-23347 | Recombi Variant of TPP-15370 | Light Chain | PRT | SEQ ID NO: 318 |
| TPP-23347 | Recombi Variant of TPP-15370 | Heavy Chain | DNA | SEQ ID NO: 319 |
| TPP-23347 | Recombi Variant of TPP-15370 | Light Chain | DNA | SEQ ID NO: 320 |
| TPP-23373 | Recombi Variant of TPP-15370 | VH | PRT | SEQ ID NO: 321 |
| TPP-23373 | Recombi Variant of TPP-15370 | HCDR1 | PRT | SEQ ID NO: 322 |
| TPP-23373 | Recombi Variant of TPP-15370 | HCDR2 | PRT | SEQ ID NO: 323 |
| TPP-23373 | Recombi Variant of TPP-15370 | HCDR3 | PRT | SEQ ID NO: 324 |
| TPP-23373 | Recombi Variant of TPP-15370 | VL | PRT | SEQ ID NO: 325 |
| TPP-23373 | Recombi Variant of TPP-15370 | LCDR1 | PRT | SEQ ID NO: 326 |
| TPP-23373 | Recombi Variant of TPP-15370 | LCDR2 | PRT | SEQ ID NO: 327 |
| TPP-23373 | Recombi Variant of TPP-15370 | LCDR3 | PRT | SEQ ID NO: 328 |
| TPP-23373 | Recombi Variant of TPP-15370 | VH | DNA | SEQ ID NO: 329 |
| TPP-23373 | Recombi Variant of TPP-15370 | HCDR1 | DNA | SEQ ID NO: 330 |
| TPP-23373 | Recombi Variant of TPP-15370 | HCDR2 | DNA | SEQ ID NO: 331 |
| TPP-23373 | Recombi Variant of TPP-15370 | HCDR3 | DNA | SEQ ID NO: 332 |
| TPP-23373 | Recombi Variant of TPP-15370 | VL | DNA | SEQ ID NO: 333 |
| TPP-23373 | Recombi Variant of TPP-15370 | LCDR1 | DNA | SEQ ID NO: 334 |
| TPP-23373 | Recombi Variant of TPP-15370 | LCDR2 | DNA | SEQ ID NO: 335 |
| TPP-23373 | Recombi Variant of TPP-15370 | LCDR3 | DNA | SEQ ID NO: 336 |
| TPP-23373 | Recombi Variant of TPP-15370 | Heavy Chain | PRT | SEQ ID NO: 337 |
| TPP-23373 | Recombi Variant of TPP-15370 | Light Chain | PRT | SEQ ID NO: 338 |
| TPP-23373 | Recombi Variant of TPP-15370 | Heavy Chain | DNA | SEQ ID NO: 339 |
| TPP-23373 | Recombi Variant of TPP-15370 | Light Chain | DNA | SEQ ID NO: 340 |
| TPP-23374 | Recombi Variant of TPP-15370 | VH | PRT | SEQ ID NO: 341 |
| TPP-23374 | Recombi Variant of TPP-15370 | HCDR1 | PRT | SEQ ID NO: 342 |
| TPP-23374 | Recombi Variant of TPP-15370 | HCDR2 | PRT | SEQ ID NO: 343 |
| TPP-23374 | Recombi Variant of TPP-15370 | HCDR3 | PRT | SEQ ID NO: 344 |
| TPP-23374 | Recombi Variant of TPP-15370 | VL | PRT | SEQ ID NO: 345 |
| TPP-23374 | Recombi Variant of TPP-15370 | LCDR1 | PRT | SEQ ID NO: 346 |
| TPP-23374 | Recombi Variant of TPP-15370 | LCDR2 | PRT | SEQ ID NO: 347 |
| TPP-23374 | Recombi Variant of TPP-15370 | LCDR3 | PRT | SEQ ID NO: 348 |
| TPP-23374 | Recombi Variant of TPP-15370 | VH | DNA | SEQ ID NO: 349 |
| TPP-23374 | Recombi Variant of TPP-15370 | HCDR1 | DNA | SEQ ID NO: 350 |
| TPP-23374 | Recombi Variant of TPP-15370 | HCDR2 | DNA | SEQ ID NO: 351 |
| TPP-23374 | Recombi Variant of TPP-15370 | HCDR3 | DNA | SEQ ID NO: 352 |
| TPP-23374 | Recombi Variant of TPP-15370 | VL | DNA | SEQ ID NO: 353 |
| TPP-23374 | Recombi Variant of TPP-15370 | LCDR1 | DNA | SEQ ID NO: 354 |
| TPP-23374 | Recombi Variant of TPP-15370 | LCDR2 | DNA | SEQ ID NO: 355 |
| TPP-23374 | Recombi Variant of TPP-15370 | LCDR3 | DNA | SEQ ID NO: 356 |
| TPP-23374 | Recombi Variant of TPP-15370 | Heavy Chain | PRT | SEQ ID NO: 357 |
| TPP-23374 | Recombi Variant of TPP-15370 | Light Chain | PRT | SEQ ID NO: 358 |
| TPP-23374 | Recombi Variant of TPP-15370 | Heavy Chain | DNA | SEQ ID NO: 359 |
| TPP-23374 | Recombi Variant of TPP-15370 | Light Chain | DNA | SEQ ID NO: 360 |
| TPP-23375 | Recombi Variant of TPP-15370 | VH | PRT | SEQ ID NO: 361 |
| TPP-23375 | Recombi Variant of TPP-15370 | HCDR1 | PRT | SEQ ID NO: 362 |
| TPP-23375 | Recombi Variant of TPP-15370 | HCDR2 | PRT | SEQ ID NO: 363 |
| TPP-23375 | Recombi Variant of TPP-15370 | HCDR3 | PRT | SEQ ID NO: 364 |
| TPP-23375 | Recombi Variant of TPP-15370 | VL | PRT | SEQ ID NO: 365 |
| TPP-23375 | Recombi Variant of TPP-15370 | LCDR1 | PRT | SEQ ID NO: 366 |
| TPP-23375 | Recombi Variant of TPP-15370 | LCDR2 | PRT | SEQ ID NO: 367 |
| TPP-23375 | Recombi Variant of TPP-15370 | LCDR3 | PRT | SEQ ID NO: 368 |
| TPP-23375 | Recombi Variant of TPP-15370 | VH | DNA | SEQ ID NO: 369 |
| TPP-23375 | Recombi Variant of TPP-15370 | HCDR1 | DNA | SEQ ID NO: 370 |
| TPP-23375 | Recombi Variant of TPP-15370 | HCDR2 | DNA | SEQ ID NO: 371 |
| TPP-23375 | Recombi Variant of TPP-15370 | HCDR3 | DNA | SEQ ID NO: 372 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-23375 | Recombi Variant of TPP-15370 | VL | DNA | SEQ ID NO: 373 |
| TPP-23375 | Recombi Variant of TPP-15370 | LCDR1 | DNA | SEQ ID NO: 374 |
| TPP-23375 | Recombi Variant of TPP-15370 | LCDR2 | DNA | SEQ ID NO: 375 |
| TPP-23375 | Recombi Variant of TPP-15370 | LCDR3 | DNA | SEQ ID NO: 376 |
| TPP-23375 | Recombi Variant of TPP-15370 | Heavy Chain | PRT | SEQ ID NO: 377 |
| TPP-23375 | Recombi Variant of TPP-15370 | Light Chain | PRT | SEQ ID NO: 378 |
| TPP-23375 | Recombi Variant of TPP-15370 | Heavy Chain | DNA | SEQ ID NO: 379 |
| TPP-23375 | Recombi Variant of TPP-15370 | Light Chain | DNA | SEQ ID NO: 380 |
| TPP-25064 | Recombi Variant of TPP-15374 | VH | PRT | SEQ ID NO: 381 |
| TPP-25064 | Recombi Variant of TPP-15374 | HCDR1 | PRT | SEQ ID NO: 382 |
| TPP-25064 | Recombi Variant of TPP-15374 | HCDR2 | PRT | SEQ ID NO: 383 |
| TPP-25064 | Recombi Variant of TPP-15374 | HCDR3 | PRT | SEQ ID NO: 384 |
| TPP-25064 | Recombi Variant of TPP-15374 | VL | PRT | SEQ ID NO: 385 |
| TPP-25064 | Recombi Variant of TPP-15374 | LCDR1 | PRT | SEQ ID NO: 386 |
| TPP-25064 | Recombi Variant of TPP-15374 | LCDR2 | PRT | SEQ ID NO: 387 |
| TPP-25064 | Recombi Variant of TPP-15374 | LCDR3 | PRT | SEQ ID NO: 388 |
| TPP-25064 | Recombi Variant of TPP-15374 | VH | DNA | SEQ ID NO: 389 |
| TPP-25064 | Recombi Variant of TPP-15374 | HCDR1 | DNA | SEQ ID NO: 390 |
| TPP-25064 | Recombi Variant of TPP-15374 | HCDR2 | DNA | SEQ ID NO: 391 |
| TPP-25064 | Recombi Variant of TPP-15374 | HCDR3 | DNA | SEQ ID NO: 392 |
| TPP-25064 | Recombi Variant of TPP-15374 | VL | DNA | SEQ ID NO: 393 |
| TPP-25064 | Recombi Variant of TPP-15374 | LCDR1 | DNA | SEQ ID NO: 394 |
| TPP-25064 | Recombi Variant of TPP-15374 | LCDR2 | DNA | SEQ ID NO: 395 |
| TPP-25064 | Recombi Variant of TPP-15374 | LCDR3 | DNA | SEQ ID NO: 396 |
| TPP-25064 | Recombi Variant of TPP-15374 | Heavy Chain | PRT | SEQ ID NO: 397 |
| TPP-25064 | Recombi Variant of TPP-15374 | Light Chain | PRT | SEQ ID NO: 398 |
| TPP-25064 | Recombi Variant of TPP-15374 | Heavy Chain | DNA | SEQ ID NO: 399 |
| TPP-25064 | Recombi Variant of TPP-15374 | Light Chain | DNA | SEQ ID NO: 400 |
| TPP-25224 | Recombi Variant of TPP-15374 | VH | PRT | SEQ ID NO: 401 |
| TPP-25224 | Recombi Variant of TPP-15374 | HCDR1 | PRT | SEQ ID NO: 402 |
| TPP-25224 | Recombi Variant of TPP-15374 | HCDR2 | PRT | SEQ ID NO: 403 |
| TPP-25224 | Recombi Variant of TPP-15374 | HCDR3 | PRT | SEQ ID NO: 404 |
| TPP-25224 | Recombi Variant of TPP-15374 | VL | PRT | SEQ ID NO: 405 |
| TPP-25224 | Recombi Variant of TPP-15374 | LCDR1 | PRT | SEQ ID NO: 406 |
| TPP-25224 | Recombi Variant of TPP-15374 | LCDR2 | PRT | SEQ ID NO: 407 |
| TPP-25224 | Recombi Variant of TPP-15374 | LCDR3 | PRT | SEQ ID NO: 408 |
| TPP-25224 | Recombi Variant of TPP-15374 | VH | DNA | SEQ ID NO: 409 |
| TPP-25224 | Recombi Variant of TPP-15374 | HCDR1 | DNA | SEQ ID NO: 410 |
| TPP-25224 | Recombi Variant of TPP-15374 | HCDR2 | DNA | SEQ ID NO: 411 |
| TPP-25224 | Recombi Variant of TPP-15374 | HCDR3 | DNA | SEQ ID NO: 412 |
| TPP-25224 | Recombi Variant of TPP-15374 | VL | DNA | SEQ ID NO: 413 |
| TPP-25224 | Recombi Variant of TPP-15374 | LCDR1 | DNA | SEQ ID NO: 414 |
| TPP-25224 | Recombi Variant of TPP-15374 | LCDR2 | DNA | SEQ ID NO: 415 |
| TPP-25224 | Recombi Variant of TPP-15374 | LCDR3 | DNA | SEQ ID NO: 416 |
| TPP-25224 | Recombi Variant of TPP-15374 | Heavy Chain | PRT | SEQ ID NO: 417 |
| TPP-25224 | Recombi Variant of TPP-15374 | Light Chain | PRT | SEQ ID NO: 418 |
| TPP-25224 | Recombi Variant of TPP-15374 | Heavy Chain | DNA | SEQ ID NO: 419 |
| TPP-25224 | Recombi Variant of TPP-15374 | Light Chain | DNA | SEQ ID NO: 420 |
| TPP-25248 | Recombi Variant of TPP-15374 | VH | PRT | SEQ ID NO: 421 |
| TPP-25248 | Recombi Variant of TPP-15374 | HCDR1 | PRT | SEQ ID NO: 422 |
| TPP-25248 | Recombi Variant of TPP-15374 | HCDR2 | PRT | SEQ ID NO: 423 |
| TPP-25248 | Recombi Variant of TPP-15374 | HCDR3 | PRT | SEQ ID NO: 424 |
| TPP-25248 | Recombi Variant of TPP-15374 | VL | PRT | SEQ ID NO: 425 |
| TPP-25248 | Recombi Variant of TPP-15374 | LCDR1 | PRT | SEQ ID NO: 426 |
| TPP-25248 | Recombi Variant of TPP-15374 | LCDR2 | PRT | SEQ ID NO: 427 |
| TPP-25248 | Recombi Variant of TPP-15374 | LCDR3 | PRT | SEQ ID NO: 428 |
| TPP-25248 | Recombi Variant of TPP-15374 | VH | DNA | SEQ ID NO: 429 |
| TPP-25248 | Recombi Variant of TPP-15374 | HCDR1 | DNA | SEQ ID NO: 430 |
| TPP-25248 | Recombi Variant of TPP-15374 | HCDR2 | DNA | SEQ ID NO: 431 |
| TPP-25248 | Recombi Variant of TPP-15374 | HCDR3 | DNA | SEQ ID NO: 432 |
| TPP-25248 | Recombi Variant of TPP-15374 | VL | DNA | SEQ ID NO: 433 |
| TPP-25248 | Recombi Variant of TPP-15374 | LCDR1 | DNA | SEQ ID NO: 434 |
| TPP-25248 | Recombi Variant of TPP-15374 | LCDR2 | DNA | SEQ ID NO: 435 |
| TPP-25248 | Recombi Variant of TPP-15374 | LCDR3 | DNA | SEQ ID NO: 436 |
| TPP-25248 | Recombi Variant of TPP-15374 | Heavy Chain | PRT | SEQ ID NO: 437 |
| TPP-25248 | Recombi Variant of TPP-15374 | Light Chain | PRT | SEQ ID NO: 438 |
| TPP-25248 | Recombi Variant of TPP-15374 | Heavy Chain | DNA | SEQ ID NO: 439 |
| TPP-25248 | Recombi Variant of TPP-15374 | Light Chain | DNA | SEQ ID NO: 440 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-25255 | Recombi Variant of TPP-15374 | VH | PRT | SEQ ID NO: 441 |
| TPP-25255 | Recombi Variant of TPP-15374 | HCDR1 | PRT | SEQ ID NO: 442 |
| TPP-25255 | Recombi Variant of TPP-15374 | HCDR2 | PRT | SEQ ID NO: 443 |
| TPP-25255 | Recombi Variant of TPP-15374 | HCDR3 | PRT | SEQ ID NO: 444 |
| TPP-25255 | Recombi Variant of TPP-15374 | VL | PRT | SEQ ID NO: 445 |
| TPP-25255 | Recombi Variant of TPP-15374 | LCDR1 | PRT | SEQ ID NO: 446 |
| TPP-25255 | Recombi Variant of TPP-15374 | LCDR2 | PRT | SEQ ID NO: 447 |
| TPP-25255 | Recombi Variant of TPP-15374 | LCDR3 | PRT | SEQ ID NO: 448 |
| TPP-25255 | Recombi Variant of TPP-15374 | VH | DNA | SEQ ID NO: 449 |
| TPP-25255 | Recombi Variant of TPP-15374 | HCDR1 | DNA | SEQ ID NO: 450 |
| TPP-25255 | Recombi Variant of TPP-15374 | HCDR2 | DNA | SEQ ID NO: 451 |
| TPP-25255 | Recombi Variant of TPP-15374 | HCDR3 | DNA | SEQ ID NO: 452 |
| TPP-25255 | Recombi Variant of TPP-15374 | VL | DNA | SEQ ID NO: 453 |
| TPP-25255 | Recombi Variant of TPP-15374 | LCDR1 | DNA | SEQ ID NO: 454 |
| TPP-25255 | Recombi Variant of TPP-15374 | LCDR2 | DNA | SEQ ID NO: 455 |
| TPP-25255 | Recombi Variant of TPP-15374 | LCDR3 | DNA | SEQ ID NO: 456 |
| TPP-25255 | Recombi Variant of TPP-15374 | Heavy Chain | PRT | SEQ ID NO: 457 |
| TPP-25255 | Recombi Variant of TPP-15374 | Light Chain | PRT | SEQ ID NO: 458 |
| TPP-25255 | Recombi Variant of TPP-15374 | Heavy Chain | DNA | SEQ ID NO: 459 |
| TPP-25255 | Recombi Variant of TPP-15374 | Light Chain | DNA | SEQ ID NO: 460 |
| TPP-25256 | Recombi Variant of TPP-15374 | VH | PRT | SEQ ID NO: 461 |
| TPP-25256 | Recombi Variant of TPP-15374 | HCDR1 | PRT | SEQ ID NO: 462 |
| TPP-25256 | Recombi Variant of TPP-15374 | HCDR2 | PRT | SEQ ID NO: 463 |
| TPP-25256 | Recombi Variant of TPP-15374 | HCDR3 | PRT | SEQ ID NO: 464 |
| TPP-25256 | Recombi Variant of TPP-15374 | VL | PRT | SEQ ID NO: 465 |
| TPP-25256 | Recombi Variant of TPP-15374 | LCDR1 | PRT | SEQ ID NO: 466 |
| TPP-25256 | Recombi Variant of TPP-15374 | LCDR2 | PRT | SEQ ID NO: 467 |
| TPP-25256 | Recombi Variant of TPP-15374 | LCDR3 | PRT | SEQ ID NO: 468 |
| TPP-25256 | Recombi Variant of TPP-15374 | VH | DNA | SEQ ID NO: 469 |
| TPP-25256 | Recombi Variant of TPP-15374 | HCDR1 | DNA | SEQ ID NO: 470 |
| TPP-25256 | Recombi Variant of TPP-15374 | HCDR2 | DNA | SEQ ID NO: 471 |
| TPP-25256 | Recombi Variant of TPP-15374 | HCDR3 | DNA | SEQ ID NO: 472 |
| TPP-25256 | Recombi Variant of TPP-15374 | VL | DNA | SEQ ID NO: 473 |
| TPP-25256 | Recombi Variant of TPP-15374 | LCDR1 | DNA | SEQ ID NO: 474 |
| TPP-25256 | Recombi Variant of TPP-15374 | LCDR2 | DNA | SEQ ID NO: 475 |
| TPP-25256 | Recombi Variant of TPP-15374 | LCDR3 | DNA | SEQ ID NO: 476 |
| TPP-25256 | Recombi Variant of TPP-15374 | Heavy Chain | PRT | SEQ ID NO: 477 |
| TPP-25256 | Recombi Variant of TPP-15374 | Light Chain | PRT | SEQ ID NO: 478 |
| TPP-25256 | Recombi Variant of TPP-15374 | Heavy Chain | DNA | SEQ ID NO: 479 |
| TPP-25256 | Recombi Variant of TPP-15374 | Light Chain | DNA | SEQ ID NO: 480 |
| TPP-25257 | Recombi Variant of TPP-15374 | VH | PRT | SEQ ID NO: 481 |
| TPP-25257 | Recombi Variant of TPP-15374 | HCDR1 | PRT | SEQ ID NO: 482 |
| TPP-25257 | Recombi Variant of TPP-15374 | HCDR2 | PRT | SEQ ID NO: 483 |
| TPP-25257 | Recombi Variant of TPP-15374 | HCDR3 | PRT | SEQ ID NO: 484 |
| TPP-25257 | Recombi Variant of TPP-15374 | VL | PRT | SEQ ID NO: 485 |
| TPP-25257 | Recombi Variant of TPP-15374 | LCDR1 | PRT | SEQ ID NO: 486 |
| TPP-25257 | Recombi Variant of TPP-15374 | LCDR2 | PRT | SEQ ID NO: 487 |
| TPP-25257 | Recombi Variant of TPP-15374 | LCDR3 | PRT | SEQ ID NO: 488 |
| TPP-25257 | Recombi Variant of TPP-15374 | VH | DNA | SEQ ID NO: 489 |
| TPP-25257 | Recombi Variant of TPP-15374 | HCDR1 | DNA | SEQ ID NO: 490 |
| TPP-25257 | Recombi Variant of TPP-15374 | HCDR2 | DNA | SEQ ID NO: 491 |
| TPP-25257 | Recombi Variant of TPP-15374 | HCDR3 | DNA | SEQ ID NO: 492 |
| TPP-25257 | Recombi Variant of TPP-15374 | VL | DNA | SEQ ID NO: 493 |
| TPP-25257 | Recombi Variant of TPP-15374 | LCDR1 | DNA | SEQ ID NO: 494 |
| TPP-25257 | Recombi Variant of TPP-15374 | LCDR2 | DNA | SEQ ID NO: 495 |
| TPP-25257 | Recombi Variant of TPP-15374 | LCDR3 | DNA | SEQ ID NO: 496 |
| TPP-25257 | Recombi Variant of TPP-15374 | Heavy Chain | PRT | SEQ ID NO: 497 |
| TPP-25257 | Recombi Variant of TPP-15374 | Light Chain | PRT | SEQ ID NO: 498 |
| TPP-25257 | Recombi Variant of TPP-15374 | Heavy Chain | DNA | SEQ ID NO: 499 |
| TPP-25257 | Recombi Variant of TPP-15374 | Light Chain | DNA | SEQ ID NO: 500 |
| TPP-25448 | Recombi Variant of TPP-15374 | VH | PRT | SEQ ID NO: 501 |
| TPP-25448 | Recombi Variant of TPP-15374 | HCDR1 | PRT | SEQ ID NO: 502 |
| TPP-25448 | Recombi Variant of TPP-15374 | HCDR2 | PRT | SEQ ID NO: 503 |
| TPP-25448 | Recombi Variant of TPP-15374 | HCDR3 | PRT | SEQ ID NO: 504 |
| TPP-25448 | Recombi Variant of TPP-15374 | VL | PRT | SEQ ID NO: 505 |
| TPP-25448 | Recombi Variant of TPP-15374 | LCDR1 | PRT | SEQ ID NO: 506 |
| TPP-25448 | Recombi Variant of TPP-15374 | LCDR2 | PRT | SEQ ID NO: 507 |
| TPP-25448 | Recombi Variant of TPP-15374 | LCDR3 | PRT | SEQ ID NO: 508 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
|---|---|---|---|---|
| TPP-25448 | Recombi Variant of TPP-15374 | VH | DNA | SEQ ID NO: 509 |
| TPP-25448 | Recombi Variant of TPP-15374 | HCDR1 | DNA | SEQ ID NO: 510 |
| TPP-25448 | Recombi Variant of TPP-15374 | HCDR2 | DNA | SEQ ID NO: 511 |
| TPP-25448 | Recombi Variant of TPP-15374 | HCDR3 | DNA | SEQ ID NO: 512 |
| TPP-25448 | Recombi Variant of TPP-15374 | VL | DNA | SEQ ID NO: 513 |
| TPP-25448 | Recombi Variant of TPP-15374 | LCDR1 | DNA | SEQ ID NO: 514 |
| TPP-25448 | Recombi Variant of TPP-15374 | LCDR2 | DNA | SEQ ID NO: 515 |
| TPP-25448 | Recombi Variant of TPP-15374 | LCDR3 | DNA | SEQ ID NO: 516 |
| TPP-25448 | Recombi Variant of TPP-15374 | Heavy Chain | PRT | SEQ ID NO: 517 |
| TPP-25448 | Recombi Variant of TPP-15374 | Light Chain | PRT | SEQ ID NO: 518 |
| TPP-25448 | Recombi Variant of TPP-15374 | Heavy Chain | DNA | SEQ ID NO: 519 |
| TPP-25448 | Recombi Variant of TPP-15374 | Light Chain | DNA | SEQ ID NO: 520 |
| TPP-25497 | Recombi Variant of TPP-15374 | VH | PRT | SEQ ID NO: 521 |
| TPP-25497 | Recombi Variant of TPP-15374 | HCDR1 | PRT | SEQ ID NO: 522 |
| TPP-25497 | Recombi Variant of TPP-15374 | HCDR2 | PRT | SEQ ID NO: 523 |
| TPP-25497 | Recombi Variant of TPP-15374 | HCDR3 | PRT | SEQ ID NO: 524 |
| TPP-25497 | Recombi Variant of TPP-15374 | VL | PRT | SEQ ID NO: 525 |
| TPP-25497 | Recombi Variant of TPP-15374 | LCDR1 | PRT | SEQ ID NO: 526 |
| TPP-25497 | Recombi Variant of TPP-15374 | LCDR2 | PRT | SEQ ID NO: 527 |
| TPP-25497 | Recombi Variant of TPP-15374 | LCDR3 | PRT | SEQ ID NO: 528 |
| TPP-25497 | Recombi Variant of TPP-15374 | VH | DNA | SEQ ID NO: 529 |
| TPP-25497 | Recombi Variant of TPP-15374 | HCDR1 | DNA | SEQ ID NO: 530 |
| TPP-25497 | Recombi Variant of TPP-15374 | HCDR2 | DNA | SEQ ID NO: 531 |
| TPP-25497 | Recombi Variant of TPP-15374 | HCDR3 | DNA | SEQ ID NO: 532 |
| TPP-25497 | Recombi Variant of TPP-15374 | VL | DNA | SEQ ID NO: 533 |
| TPP-25497 | Recombi Variant of TPP-15374 | LCDR1 | DNA | SEQ ID NO: 534 |
| TPP-25497 | Recombi Variant of TPP-15374 | LCDR2 | DNA | SEQ ID NO: 535 |
| TPP-25497 | Recombi Variant of TPP-15374 | LCDR3 | DNA | SEQ ID NO: 536 |
| TPP-25497 | Recombi Variant of TPP-15374 | Heavy Chain | PRT | SEQ ID NO: 537 |
| TPP-25497 | Recombi Variant of TPP-15374 | Light Chain | PRT | SEQ ID NO: 538 |
| TPP-25497 | Recombi Variant of TPP-15374 | Heavy Chain | DNA | SEQ ID NO: 539 |
| TPP-25497 | Recombi Variant of TPP-15374 | Light Chain | DNA | SEQ ID NO: 540 |
| TPP-25655 | Recombi Variant of TPP-15374 | VH | PRT | SEQ ID NO: 541 |
| TPP-25655 | Recombi Variant of TPP-15374 | HCDR1 | PRT | SEQ ID NO: 542 |
| TPP-25655 | Recombi Variant of TPP-15374 | HCDR2 | PRT | SEQ ID NO: 543 |
| TPP-25655 | Recombi Variant of TPP-15374 | HCDR3 | PRT | SEQ ID NO: 544 |
| TPP-25655 | Recombi Variant of TPP-15374 | VL | PRT | SEQ ID NO: 545 |
| TPP-25655 | Recombi Variant of TPP-15374 | LCDR1 | PRT | SEQ ID NO: 546 |
| TPP-25655 | Recombi Variant of TPP-15374 | LCDR2 | PRT | SEQ ID NO: 547 |
| TPP-25655 | Recombi Variant of TPP-15374 | LCDR3 | PRT | SEQ ID NO: 548 |
| TPP-25655 | Recombi Variant of TPP-15374 | VH | DNA | SEQ ID NO: 549 |
| TPP-25655 | Recombi Variant of TPP-15374 | HCDR1 | DNA | SEQ ID NO: 550 |
| TPP-25655 | Recombi Variant of TPP-15374 | HCDR2 | DNA | SEQ ID NO: 551 |
| TPP-25655 | Recombi Variant of TPP-15374 | HCDR3 | DNA | SEQ ID NO: 552 |
| TPP-25655 | Recombi Variant of TPP-15374 | VL | DNA | SEQ ID NO: 553 |
| TPP-25655 | Recombi Variant of TPP-15374 | LCDR1 | DNA | SEQ ID NO: 554 |
| TPP-25655 | Recombi Variant of TPP-15374 | LCDR2 | DNA | SEQ ID NO: 555 |
| TPP-25655 | Recombi Variant of TPP-15374 | LCDR3 | DNA | SEQ ID NO: 556 |
| TPP-25655 | Recombi Variant of TPP-15374 | Heavy Chain | PRT | SEQ ID NO: 557 |
| TPP-25655 | Recombi Variant of TPP-15374 | Light Chain | PRT | SEQ ID NO: 558 |
| TPP-25655 | Recombi Variant of TPP-15374 | Heavy Chain | DNA | SEQ ID NO: 559 |
| TPP-25655 | Recombi Variant of TPP-15374 | Light Chain | DNA | SEQ ID NO: 560 |
| TPP-26111 | Recombi Variant of TPP-15374 | VH | PRT | SEQ ID NO: 561 |
| TPP-26111 | Recombi Variant of TPP-15374 | HCDR1 | PRT | SEQ ID NO: 562 |
| TPP-26111 | Recombi Variant of TPP-15374 | HCDR2 | PRT | SEQ ID NO: 563 |
| TPP-26111 | Recombi Variant of TPP-15374 | HCDR3 | PRT | SEQ ID NO: 564 |
| TPP-26111 | Recombi Variant of TPP-15374 | VL | PRT | SEQ ID NO: 565 |
| TPP-26111 | Recombi Variant of TPP-15374 | LCDR1 | PRT | SEQ ID NO: 566 |
| TPP-26111 | Recombi Variant of TPP-15374 | LCDR2 | PRT | SEQ ID NO: 567 |
| TPP-26111 | Recombi Variant of TPP-15374 | LCDR3 | PRT | SEQ ID NO: 568 |
| TPP-26111 | Recombi Variant of TPP-15374 | VH | DNA | SEQ ID NO: 569 |
| TPP-26111 | Recombi Variant of TPP-15374 | HCDR1 | DNA | SEQ ID NO: 570 |
| TPP-26111 | Recombi Variant of TPP-15374 | HCDR2 | DNA | SEQ ID NO: 571 |
| TPP-26111 | Recombi Variant of TPP-15374 | HCDR3 | DNA | SEQ ID NO: 572 |
| TPP-26111 | Recombi Variant of TPP-15374 | VL | DNA | SEQ ID NO: 573 |
| TPP-26111 | Recombi Variant of TPP-15374 | LCDR1 | DNA | SEQ ID NO: 574 |
| TPP-26111 | Recombi Variant of TPP-15374 | LCDR2 | DNA | SEQ ID NO: 575 |
| TPP-26111 | Recombi Variant of TPP-15374 | LCDR3 | DNA | SEQ ID NO: 576 |

TABLE 1-continued

Amino acid sequences and nucleic acid sequences of preferred antibodies according to the present disclosure and of three prior art antibodies. TPP-11489 corresponds to Chiome antibody Humanized-2 derived of clone No. 4-2 strain (WO 2014/123186); TPP-15051 respresents a murine IgG1 variant thereof. TPP-30788-TPP-30791 corresponds to Böhringer Ingelheim antibody (BI) Clone I-IV (WO 2020/225400). TPP-30792 corresponds to University Ramot antibody clone I (WO 2020/261281).

| TPP ID | Antibody Description | Sequence Region | Sequence Type | SEQ ID |
| --- | --- | --- | --- | --- |
| TPP-26111 | Recombi Variant of TPP-15374 | Heavy Chain | PRT | SEQ ID NO: 577 |
| TPP-26111 | Recombi Variant of TPP-15374 | Light Chain | PRT | SEQ ID NO: 578 |
| TPP-26111 | Recombi Variant of TPP-15374 | Heavy Chain | DNA | SEQ ID NO: 579 |
| TPP-26111 | Recombi Variant of TPP-15374 | Light Chain | DNA | SEQ ID NO: 580 |
| TPP-13211 | huSema3a_FXaFc | Chain 1 | PRT | SEQ ID NO: 581 |
| TPP-19068 | human Sema3a_FXaHis6 | Chain 1 | PRT | SEQ ID NO: 582 |
| TPP-19069 | mouse Sema3a_FXaHis6 | Chain 1 | PRT | SEQ ID NO: 583 |
| TPP-19120 | rat-Sema3a_FXaHis6 | Chain 1 | PRT | SEQ ID NO: 584 |
| TPP-19121 | dog-Sema3a_FXaHis6 | Chain 1 | PRT | SEQ ID NO: 585 |
| TPP-19122 | cyno-Sema3a_FXaHis6 | Chain 1 | PRT | SEQ ID NO: 586 |
| TPP-20176 | pigSema3A_FXaHis6 | Chain 1 | PRT | SEQ ID NO: 587 |
| TPP-30788 | Böhringer (BI) Clone I | VH | PRT | SEQ ID NO: 800 |
| TPP-30788 | Böhringer (BI) Clone I | HCDR1 | PRT | SEQ ID NO: 801 |
| TPP-30788 | Böhringer (BI) Clone I | HCDR2 | PRT | SEQ ID NO: 802 |
| TPP-30788 | Böhringer (BI) Clone I | HCDR3 | PRT | SEQ ID NO: 803 |
| TPP-30788 | Böhringer (BI) Clone I | VL | PRT | SEQ ID NO: 804 |
| TPP-30788 | Böhringer (BI) Clone I | LCDR1 | PRT | SEQ ID NO: 805 |
| TPP-30788 | Böhringer (BI) Clone I | LCDR2 | PRT | SEQ ID NO: 806 |
| TPP-30788 | Böhringer (BI) Clone I | LCDR3 | PRT | SEQ ID NO: 807 |
| TPP-30788 | Böhringer (BI) Clone I | VH | DNA | SEQ ID NO: 808 |
| TPP-30788 | Böhringer (BI) Clone I | VL | DNA | SEQ ID NO: 809 |
| TPP-30788 | Böhringer (BI) Clone I | Heavy Chain | PRT | SEQ ID NO: 810 |
| TPP-30788 | Böhringer (BI) Clone I | Light Chain | PRT | SEQ ID NO: 811 |
| TPP-30788 | Böhringer (BI) Clone I | Heavy Chain | DNA | SEQ ID NO: 812 |
| TPP-30788 | Böhringer (BI) Clone I | Light Chain | DNA | SEQ ID NO: 813 |
| TPP-30789 | Böhringer (BI) Clone II | VH | PRT | SEQ ID NO: 814 |
| TPP-30789 | Böhringer (BI) Clone II | HCDR1 | PRT | SEQ ID NO: 815 |
| TPP-30789 | Böhringer (BI) Clone II | HCDR2 | PRT | SEQ ID NO: 816 |
| TPP-30789 | Böhringer (BI) Clone II | HCDR3 | PRT | SEQ ID NO: 817 |
| TPP-30789 | Böhringer (BI) Clone II | VL | PRT | SEQ ID NO: 818 |
| TPP-30789 | Böhringer (BI) Clone II | LCDR1 | PRT | SEQ ID NO: 819 |
| TPP-30789 | Böhringer (BI) Clone II | LCDR2 | PRT | SEQ ID NO: 820 |
| TPP-30789 | Böhringer (BI) Clone II | LCDR3 | PRT | SEQ ID NO: 821 |
| TPP-30789 | Böhringer (BI) Clone II | VH | DNA | SEQ ID NO: 822 |
| TPP-30789 | Böhringer (BI) Clone II | VL | DNA | SEQ ID NO: 823 |
| TPP-30789 | Böhringer (BI) Clone II | Heavy Chain | PRT | SEQ ID NO: 824 |
| TPP-30789 | Böhringer (BI) Clone II | Light Chain | PRT | SEQ ID NO: 825 |
| TPP-30789 | Böhringer (BI) Clone II | Heavy Chain | DNA | SEQ ID NO: 826 |
| TPP-30789 | Böhringer (BI) Clone II | Light Chain | DNA | SEQ ID NO: 827 |
| TPP-30790 | Böhringer (BI) Clone III | VH | PRT | SEQ ID NO: 828 |
| TPP-30790 | Böhringer (BI) Clone III | HCDR1 | PRT | SEQ ID NO: 829 |
| TPP-30790 | Böhringer (BI) Clone III | HCDR2 | PRT | SEQ ID NO: 830 |
| TPP-30790 | Böhringer (BI) Clone III | HCDR3 | PRT | SEQ ID NO: 831 |
| TPP-30790 | Böhringer (BI) Clone III | VL | PRT | SEQ ID NO: 832 |
| TPP-30790 | Böhringer (BI) Clone III | LCDR1 | PRT | SEQ ID NO: 833 |
| TPP-30790 | Böhringer (BI) Clone III | LCDR2 | PRT | SEQ ID NO: 834 |
| TPP-30790 | Böhringer (BI) Clone III | LCDR3 | PRT | SEQ ID NO: 835 |
| TPP-30790 | Böhringer (BI) Clone III | VH | DNA | SEQ ID NO: 836 |
| TPP-30790 | Böhringer (BI) Clone III | VL | DNA | SEQ ID NO: 837 |
| TPP-30790 | Böhringer (BI) Clone III | Heavy Chain | PRT | SEQ ID NO: 838 |
| TPP-30790 | Böhringer (BI) Clone III | Light Chain | PRT | SEQ ID NO: 839 |
| TPP-30790 | Böhringer (BI) Clone III | Heavy Chain | DNA | SEQ ID NO: 840 |
| TPP-30790 | Böhringer (BI) Clone III | Light Chain | DNA | SEQ ID NO: 841 |
| TPP-30791 | Böhringer (BI) Clone IV | VH | PRT | SEQ ID NO: 842 |
| TPP-30791 | Böhringer (BI) Clone IV | HCDR1 | PRT | SEQ ID NO: 843 |
| TPP-30791 | Böhringer (BI) Clone IV | HCDR2 | PRT | SEQ ID NO: 844 |
| TPP-30791 | Böhringer (BI) Clone IV | HCDR3 | PRT | SEQ ID NO: 845 |
| TPP-30791 | Böhringer (BI) Clone IV | VL | PRT | SEQ ID NO: 846 |
| TPP-30791 | Böhringer (BI) Clone IV | LCDR1 | PRT | SEQ ID NO: 847 |
| TPP-30791 | Böhringer (BI) Clone IV | LCDR2 | PRT | SEQ ID NO: 848 |
| TPP-30791 | Böhringer (BI) Clone IV | LCDR3 | PRT | SEQ ID NO: 849 |
| TPP-30791 | Böhringer (BI) Clone IV | VH | DNA | SEQ ID NO: 850 |
| TPP-30791 | Böhringer (BI) Clone IV | VL | DNA | SEQ ID NO: 851 |
| TPP-30791 | Böhringer (BI) Clone IV | Heavy Chain | PRT | SEQ ID NO: 852 |
| TPP-30791 | Böhringer (BI) Clone IV | Light Chain | PRT | SEQ ID NO: 853 |
| TPP-30791 | Böhringer (BI) Clone IV | Heavy Chain | DNA | SEQ ID NO: 854 |
| TPP-30791 | Böhringer (BI) Clone IV | Light Chain | DNA | SEQ ID NO: 855 |
| TPP-30792 | 3H4 (Ramot) Clon I | VH | PRT | SEQ ID NO: 856 |

TABLE 1-continued

Amino acid sequences and nucleic acid sequences of preferred
antibodies according to the present disclosure and of three
prior art antibodies. TPP-11489 corresponds to Chiome antibody
Humanized-2 derived of clone No. 4-2 strain (WO 2014/123186);
TPP-15051 respresents a murine IgG1 variant thereof. TPP-30788-
TPP-30791 corresponds to Böhringer Ingelheim antibody (BI)
Clone I-IV (WO 2020/225400). TPP-30792 corresponds to
University Ramot antibody clone I (WO 2020/261281).

| TPP ID | Antibody Description | Sequence Region | Sequence Type | SEQ ID |
|---|---|---|---|---|
| TPP-30792 | 3H4 (Ramot) Clon I | HCDR1 | PRT | SEQ ID NO: 857 |
| TPP-30792 | 3H4 (Ramot) Clon I | HCDR2 | PRT | SEQ ID NO: 858 |
| TPP-30792 | 3H4 (Ramot) Clon I | HCDR3 | PRT | SEQ ID NO: 859 |
| TPP-30792 | 3H4 (Ramot) Clon I | VL | PRT | SEQ ID NO: 860 |
| TPP-30792 | 3H4 (Ramot) Clon I | LCDR1 | PRT | SEQ ID NO: 861 |
| TPP-30792 | 3H4 (Ramot) Clon I | LCDR2 | PRT | SEQ ID NO: 862 |
| TPP-30792 | 3H4 (Ramot) Clon I | LCDR3 | PRT | SEQ ID NO: 863 |
| TPP-30792 | 3H4 (Ramot) Clon I | VH | DNA | SEQ ID NO: 864 |
| TPP-30792 | 3H4 (Ramot) Clon I | VL | DNA | SEQ ID NO: 865 |
| TPP-30792 | 3H4 (Ramot) Clon I | Heavy Chain | PRT | SEQ ID NO: 866 |
| TPP-30792 | 3H4 (Ramot) Clon I | Light Chain | PRT | SEQ ID NO: 867 |
| TPP-30792 | 3H4 (Ramot) Clon I | Heavy Chain | DNA | SEQ ID NO: 868 |
| TPP-30792 | 3H4 (Ramot) Clon I | Light Chain | DNA | SEQ ID NO: 869 |
| TPP-31357 | Fab of 3H4 Univ Ramot | VH | PRT | SEQ ID NO: 870 |
| TPP-31357 | Fab of 3H4 Univ Ramot | HCDR1 | PRT | SEQ ID NO: 871 |
| TPP-31357 | Fab of 3H4 Univ Ramot | HCDR2 | PRT | SEQ ID NO: 872 |
| TPP-31357 | Fab of 3H4 Univ Ramot | HCDR3 | PRT | SEQ ID NO: 873 |
| TPP-31357 | Fab of 3H4 Univ Ramot | VL | PRT | SEQ ID NO: 874 |
| TPP-31357 | Fab of 3H4 Univ Ramot | LCDR1 | PRT | SEQ ID NO: 875 |
| TPP-31357 | Fab of 3H4 Univ Ramot | LCDR2 | PRT | SEQ ID NO: 876 |
| TPP-31357 | Fab of 3H4 Univ Ramot | LCDR3 | PRT | SEQ ID NO: 877 |
| TPP-31357 | Fab of 3H4 Univ Ramot | VH | DNA | SEQ ID NO: 878 |
| TPP-31357 | Fab of 3H4 Univ Ramot | VL | DNA | SEQ ID NO: 879 |
| TPP-31357 | Fab of 3H4 Univ Ramot | Heavy Chain | PRT | SEQ ID NO: 880 |
| TPP-31357 | Fab of 3H4 Univ Ramot | Light Chain | PRT | SEQ ID NO: 881 |
| TPP-31357 | Fab of 3H4 Univ Ramot | Heavy Chain | DNA | SEQ ID NO: 882 |
| TPP-31357 | Fab of 3H4 Univ Ramot | Light Chain | DNA | SEQ ID NO: 883 |

TABLE 1A

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 1 | PRT | EVQLLESGGGLVQPGGSLRLSCAASGFTFSSYPMGWVRQAPGKGLEWV AGIDDDGDSDTRYAPAVKGRATISRDNSKNTVYLQMNSLRAEDTAVYY CAKHTGIGANSAGSIDAWGQGTLVTVSS |
| 2 | PRT | SYPMG |
| 3 | PRT | GIDDDGDSDTRYAPAVKG |
| 4 | PRT | HTGIGANSAGSIDA |
| 5 | PRT | SYELTQPPSVSVSPGQTARITCSGGGSYTGSYYYGWYQQKPGQAPVTVI YYNNKRPSDIPERFSGSLSGTTNTLTISGVQAEDEADYYCGSADNSGDAF GTGTKVTVL |
| 6 | PRT | SGGGSYTGSYYYG |
| 7 | PRT | YNNKRPS |
| 8 | PRT | GSADNSGDA |
| 9 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ATCCTATGGGCTGGGTCCGACAGGCCCCTGGCAAAGGACTTGAATGG GTGGCCGGCATCGACGACGATGGCGATAGCGATACAAGATACGCCC CTGCCGTGAAGGGCAGAGCCACCATCTCCAGAGACAACAGCAAGAA CACCGTGTACCTGCAGATGAACAGCCTGAGAGCCGAGGACACCGCC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | GTGTACTATTGTGCCAAGCACACAGGCATCGGCGCCAATTCTGCCGG<br>CTCTATTGATGCCTGGGGCCAGGGAACACTGGTCACAGTTTCTTCA |
| 10 | DNA | AGCTATCCTATGGGC |
| 11 | DNA | GGCATCGACGACGATGGCGATAGCGATACAAGATACGCCCCTGCCGT<br>GAAGGGC |
| 12 | DNA | CACACAGGCATCGGCGCCAATTCTGCCGGCTCTATTGATGCC |
| 13 | DNA | AGCTATGAGCTGACACAGCCTCCAAGCGTGTCCGTGTCTCCTGGACA<br>GACCGCCAGAATCACATGTAGCGGCGGAGGCAGCTACACCGGCAGC<br>TACTACTATGGCTGGTATCAGCAGAAGCCCGGACAGGCCCCTGTGAC<br>CGTGATCTACTACAACAACAAGCGGCCCAGCGACATCCCCGAGAGAT<br>TTTCTGGCTCTCTGAGCGGCACCACCAACACACTGACAATCTCTGGC<br>GTGCAGGCCGAGGACGAGGCCGATTACTATTGTGGCAGCGCCGATAA<br>TAGCGGCGACGCCTTTGGCACCGGCACCAAAGTTACAGTGCTA |
| 14 | DNA | AGCGGCGGAGGCAGCTACACCGGCAGCTACTACTATGGC |
| 15 | DNA | TACAACAACAAGCGGCCCAGC |
| 16 | DNA | GGCAGCGCCGATAATAGCGGCGACGCC |
| 17 | PRT | EVQLLESGGGLVQPGGSLRLSCAASGFTFSSYPMGWVRQAPGKGLEWV<br>AGIDDDGDSDTRYAPAVKGRATISRDNSKNTVYLQMNSLRAEDTAVYY<br>CAKHTGIGANSAGSIDAWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPG |
| 18 | PRT | SYELTQPPSVSVSPGQTARITCSGGGSYTGSYYYGWYQQKPGQAPVTVI<br>YYNNKRPSDIPERFSGSLSGTTNTLTISGVQAEDEADYYCGSADNSGDAF<br>GVGTKVTVLGQPKAAPSVTLFPPSSEELQANKATLVCLISDFYPGAVTVA<br>WKADSSPVKAGVETTTPSKQSNNKYAASSYLSLTPEQWKSHRSYSCQV<br>THEGSTVEKTVAPTECS |
| 19 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATCCTATGGGCTGGGTCCGACAGGCCCCTGGCAAAGGACTTGAATGG<br>GTGGCCGGCATCGACGACGATGGCGATAGCGATACAAGATACGCCC<br>CTGCCGTGAAGGGCAGAGCCACCATCTCCAGAGACAACAGCAAGAA<br>CACCGTGTACCTGCAGATGAACAGCCTGAGAGCCGAGGACACCGCC<br>GTGTACTATTGTGCCAAGCACACAGGCATCGGCGCCAATTCTGCCGG<br>CTCTATTGATGCCTGGGGCCAGGGAACACTGGTCACAGTTTCTTCAG<br>CCAGCACCAAGGGCCCCAGCGTGTTCCCTCTGGCCCCTAGCAGCAAG<br>AGCACATCTGGCGGAACAGCCGCCCTGGGCTGCCTCGTGAAGGACTA<br>CTTTCCCGAGCCCGTGACCGTGTCCTGGAACTCTGGCGCTCTGACAA<br>GCGGCGTGCACACCTTTCCAGCCGTGCTGCAGAGCAGCGGCCTGTAC<br>TCTCTGAGCAGCGTCGTGACAGTGCCCAGCAGCTCTCTGGGCACCCA<br>GACCTACATCTGCAACGTGAACCACAAGCCCAGCAACACCAAGGTG<br>GACAAGAAGGTGGAACCCAAGAGCTGCGACAAGACCCACACCTGTC<br>CCCCTTGTCCTGCCCCCGAACTGCTGGGAGGCCCTTCCGTGTTCCTGT<br>TCCCCCCAAAGCCCAAGGACACCCTGATGATCAGCCGGACCCCCGAA<br>GTGACCTGCGTGGTGGTGGATGTGTCCCACGAGGACCCTGAAGTGAA<br>GTTCAATTGGTACGTGGACGGCGTGGAAGTGCACAACGCCAAGACCA<br>AGCCTAGAGAGGAACAGTACAACAGCACCTACCGGGTGGTGTCCGT<br>GCTGACAGTGCTGCACCAGGACTGGCTGAACGGCAAAGAGTACAAG<br>TGCAAGGTGTCCAACAAGGCCCTGCCTGCCCCCATCGAGAAAACCAT<br>CAGCAAGGCCAAGGGCCAGCCCCGCGAACCCCAGGTGTACACACTG<br>CCCCCAAGCAGGGACGAGCTGACCAAGAACCAGGTGTCCCTGACCTG<br>TCTCGTGAAAGGCTTCTACCCCTCCGATATCGCCGTGGAATGGGAGA<br>GCAACGGCCAGCCCGAGAACAACTACAAGACCACCCCCCCTGTGCTG<br>GACAGCGACGGCTCATTCTTCCTGTACAGCAAGCTGACCGTGGACAA<br>GTCCCGGTGGCAGCAGGGCAACGTGTTCAGCTGCAGCGTGATGCACG<br>AGGCCCTGCACAACCACTACACCCAGAAGTCCCTGAGCCTGAGCCCT<br>GGC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 20 | DNA | AGCTATGAGCTGACACAGCCTCCAAGCGTGTCCGTGTCTCCTGGACA GACCGCCAGAATCACATGTAGCGGCGGAGGCAGCTACACCGGCAGC TACTACTATGGCTGGTATCAGCAGAAGCCCGGACAGGCCCCTGTGAC CGTGATCTACTACAACAACAAGCGGCCCAGCGACATCCCCGAGAGAT TTTCTGGCTCTCTGAGCGGCACCACCAACACACTGACAATCTCTGGC GTGCAGGCCGAGGACGAGGCCGATTACTATTGTGGCAGCGCCGATAA TAGCGGCGACGCCTTTGGCACCGGCACCAAAGTTACAGTGCTAGGCC AGCCTAAAGCCGCCCCTAGCGTGACCCTGTTCCCTCCAAGCAGCGAG GAACTGCAGGCCAACAAGGCCACCCTCGTGTGCCTGATCAGCGACTT CTATCCTGGCGCCGTGACCGTGGCCTGGAAGGCCGATAGCTCTCCTG TGAAGGCCGGCGTGGAAACCACCACCCCTAGCAAGCAGAGCAACAA CAAATACGCCGCCAGCAGCTACCTGAGCCTGACCCCCGAGCAGTGGA AGTCCCACAGATCCTACAGCTGCCAAGTGACCCACGAGGGCAGCACC GTGGAAAAGACAGTGGCCCCTACCGAGTGCAGC |
| 21 | PRT | EVQLLESGGGLVQPGGSLRLSCAASGFTFSSYPMGWVRQAPGKGLEWV AGIDDDGDSDTRYAPAVKGRATISRDNSKNTVYLQMNSLRAEDTAVYY CAKHTGIGANSAGSIDAWGQGTLVTVSS |
| 22 | PRT | SYPMG |
| 23 | PRT | GIDDDGDSDTRYAPAVKG |
| 24 | PRT | HTGIGANSAGSIDA |
| 25 | PRT | SYELTQPPSVSVSPGQTARITCSGGGSYTGSYYYGWYQQKPGQAPVTVI YYNNKRPSDIPERFSGSLSGTTNTLTISGVQAEDEADYYCGSADNSGDAF GTGTKVTVL |
| 26 | PRT | SGGGSYTGSYYYG |
| 27 | PRT | YNNKRPS |
| 28 | PRT | GSADNSGDA |
| 29 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ATCCTATGGGCTGGGTCCGACAGGCCCCTGGCAAAGGACTTGAATGG GTGGCCGGCATCGACGACGATGGCGATAGCGATACAAGATACGCCC CTGCCGTGAAGGGCAGAGCCACCATCTCCAGAGACAACAGCAAGAA CACCGTGTACCTGCAGATGAACAGCCTGAGAGCCGAGGACACCGCC GTGTACTATTGTGCCAAGCACACAGGCATCGGCGCCAATTCTGCCGG CTCTATTGATGCCTGGGGCCAGGGAACACTGGTCACAGTTTCTTCA |
| 30 | DNA | AGCTATCCTATGGGC |
| 31 | DNA | GGCATCGACGACGATGGCGATAGCGATACAAGATACGCCCCTGCCGT GAAGGGC |
| 32 | DNA | CACACAGGCATCGGCGCCAATTCTGCCGGCTCTATTGATGCC |
| 33 | DNA | AGCTATGAGCTGACACAGCCTCCAAGCGTGTCCGTGTCTCCTGGACA GACCGCCAGAATCACATGTAGCGGCGGAGGCAGCTACACCGGCAGC TACTACTATGGCTGGTATCAGCAGAAGCCCGGACAGGCCCCTGTGAC CGTGATCTACTACAACAACAAGCGGCCCAGCGACATCCCCGAGAGAT TTTCTGGCTCTCTGAGCGGCACCACCAACACACTGACAATCTCTGGC GTGCAGGCCGAGGACGAGGCCGATTACTATTGTGGCAGCGCCGATAA TAGCGGCGACGCCTTTGGCACCGGCACCAAAGTTACAGTGCTA |
| 34 | DNA | AGCGGCGGAGGCAGCTACACCGGCAGCTACTACTATGGC |
| 35 | DNA | TACAACAACAAGCGGCCCAGC |
| 36 | DNA | GGCAGCGCCGATAATAGCGGCGACGCC |
| 37 | PRT | EVQLLESGGGLVQPGGSLRLSCAASGFTFSSYPMGWVRQAPGKGLEWV AGIDDDGDSDTRYAPAVKGRATISRDNSKNTVYLQMNSLRAEDTAVYY CAKHTGIGANSAGSIDAWGQGTLVTVSSAKTTPPSVYPLAPGSAAQTNS MVTLGCLVKGYFPEPVTVTWNSGSLSSGVHTFPAVLQSDLYTLSSSVTV PSSTWPSETVTCNVAHPASSTKVDKKIVPRDCGCKPCICTVPEVSSVFIFP |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
| --- | --- | --- |
| | | PKPKDVLTITLTPKVTCVVVDISKDDPEVQFSWFVDDVEVHTAQTQPRE EQFNSTFRSVSELPIMHQDWLNGKEFKCRVNSAAFPAPIEKTISKTKGRP KAPQVYTIPPPKEQMAKDKVSLTCMITDFFPEDITVEWQWNGQPAENYK NTQPIMDTDGSYFVYSKLNVQKSNWEAGNTFTCSVLHEGLHNHHTEKS LSHSPGK |
| 38 | PRT | SYELTQPPSVSVSPGQTARITCSGGGSYTGSYYYGWYQQKPGQAPVTVI YYNNKRPSDIPERFSGSLSGTTNTLTISGVQAEDEADYYCGSADNSGDAF GTGTKVTVLGQPKSSPSVTLFPPSSEELETNKATLVCTITDFYPGVVTVD WKVDGTPVTQGMETTQPSKQSNNKYMASSYLTLTARAWERHSSYSCQ VTHEGHTVEKSLSRADCS |
| 39 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ATCCTATGGGCTGGGTCCGACAGGCCCCTGGCAAAGGACTTGAATGG GTGGCCGGCATCGACGACGATGGCGATAGCGATACAAGATACGCCC CTGCCGTGAAGGGCAGAGCCACCATCTCCAGAGACAACAGCAAGAA CACCGTGTACCTGCAGATGAACAGCCTGAGAGCCGAGGACACCGCC GTGTACTATTGTGCCAAGCACACAGGCATCGGCGCCAATTCTGCCGG CTCTATTGATGCCTGGGGCCAGGGAACACTGGTCACAGTTTCTTCAG CCAAGACCACCCCCCCCAGCGTGTACCCTCTGGCTCCTGGATCTGCC GCCCAGACCAACAGCATGGTCACCCTGGGCTGCCTCGTGAAGGGCTA CTTCCCTGAGCCTGTGACCGTGACCTGGAACAGCGGCTCTCTGTCTAG CGGCGTGCACACCTTTCCAGCCGTGCTGCAGAGCGACCTGTACACCC TGAGCAGCAGCGTGACCGTGCCTAGCAGCACCTGGCCTAGCGAGACA GTGACCTGCAACGTGGCCCACCCTGCCAGCAGCACAAAGGTGGACA AGAAAATCGTGCCCCGGGACTGCGGCTGCAAGCCCTGTATCTGTACC GTGCCCGAGGTGTCCAGCGTGTTCATCTTCCCACCCAAGCCCAAGGA CGTGCTGACCATCACCCTGACCCCCAAAGTGACCTGTGTGGTGGTGG ACATCAGCAAGGACGACCCCGAGGTGCAGTTCAGTTGGTTCGTGGAC GACGTGGAAGTGCACACAGCCCAGACCCAGCCCAGAGAGGAACAGT TCAACAGCACCTTCAGAAGCGTGTCCGAGCTGCCCATCATGCACCAG GACTGGCTGAACGGCAAAGAGTTCAAGTGCAGAGTGAACAGCGCCG CCTTCCCTGCCCCCATCGAGAAAACCATCTCCAAGACCAAGGGCAGA CCCAAGGCCCCTCAGGTGTACACAATCCCCCCACCCAAGAACAGAT GGCCAAGGACAAGGTGTCCCTGACCTGCATGATCACCGATTTCTTCC CAGAGGACATCACCGTGGAATGGCAGTGGAACGGCCAGCCCGCCGA GAACTACAAGAACACCCAGCCTATCATGGACACCGACGGCAGCTACT TCGTGTACAGCAAGCTGAACGTGCAGAAGTCCAACTGGGAGGCGG CAACACCTTCACCTGTAGCGTGCTGCACGAGGGCCTGCACAATCACC ACACCGAGAAGTCCCTGTCCCACAGCCCTGGCAAG |
| 40 | DNA | AGCTATGAGCTGACACAGCCTCCAAGCGTGTCCGTGTCTCCTGGACA GACCGCCAGAATCACATGTAGCGGCGGAGGCAGCTACACCGGCAGC TACTACTATGGCTGGTATCAGCAGAAGCCCGGACAGGCCCCTGTGAC CGTGATCTACTACAACAACAAGCGGCCCAGCGACATCCCCGAGAGAT TTTCTGGCTCTCTGAGCGGCACCACCAACACACTGACAATCTCTGGC GTGCAGGCCGAGGACGAGGCCGATTACTATTGTGGCAGCGCCGATAA TAGCGGCGACGCCTTTGGCACCGGCACCAAAGTTACAGTGCTAGGCC AGCCCAAGAGCAGCCCTAGCGTGACCCTGTTCCCTCCAAGCAGCGAG GAACTGGAAACAAACAAGGCCACCCTCGTGTGCACCATCACCGACTT CTACCCCGGCGTCGTGACCGTGGACTGGAAGGTGGACGGCACCCCAG TGACCCAGGGCATGGAAACCACCCAGCCCAGCAAGCAGAGCAACAA CAAGTACATGGCCAGCAGCTACCTGACCCTGACCGCCAGAGCCTGGG AGAGACACAGCTCCTACAGCTGCCAAGTGACCCACGAGGGCCACAC CGTGGAAAAGAGCCTGAGCAGAGCCGACTGCAGC |
| 41 | PRT | EVQLLESGGGLVQPGGSLRLSCAASGFTFSSYGMHWVRQAPGKGLEWV SAIGTGGDTYYADSVMGRFTISRDNSKNTLYLQMNSLRAEDTAVYYCA RRDDYTSRDAFDVWGQGTLVTVSS |
| 42 | PRT | SYGMH |
| 43 | PRT | AIGTGGDTYYADSVMG |
| 44 | PRT | RDDYTSRDAFDV |
| 45 | PRT | QSVLTQPPSASGTPGQRVTISCSGSSSNIGSNTVNWYQQLPGTAPKLLIYY DDLLPSGVPDRFSGSKSGTSASLAISGLRSEDEADYYCAAWDDSLNGYV VFGGGTKLTVL |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 46 | PRT | SGSSSNIGSNTVN |
| 47 | PRT | YDDLLPS |
| 48 | PRT | AAWDDSLNGYVV |
| 49 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATGGCATGCACTGGGTCCGACAGGCCCCTGGCAAAGGACTTGAATGG<br>GTGTCCGCCATCGGCACAGGCGGCGATACCTACTATGCCGATAGCGT<br>GATGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGATGCCTTCGATGTGT<br>GGGGCCAGGGAACACTGGTTACCGTTTCTTCA |
| 50 | DNA | AGCTATGGCATGCAC |
| 51 | DNA | GCCATCGGCACAGGCGGCGATACCTACTATGCCGATAGCGTGATGGG<br>C |
| 52 | DNA | AGGGACGACTACACCAGCAGGGATGCCTTCGATGTG |
| 53 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCTGCCTAGCGGCGTGCCCGATAGAT<br>TTTCTGGCAGCAAGAGCGGCACAAGCGCCAGCCTGGCTATCTCTGGA<br>CTGAGATCTGAGGACGAGGCCGACTACTATTGCGCCGCCTGGGACGA<br>TAGCCTGAACGGCTATGTGGTTTTCGGCGGAGGCACCAAGCTGACCG<br>TGCTA |
| 54 | DNA | AGCGGCAGCAGCTCCAACATCGGCAGCAACACCGTGAAC |
| 55 | DNA | TACGACGACCTGCTGCCTAGC |
| 56 | DNA | GCCGCCTGGGACGATAGCCTGAACGGCTATGTGGTT |
| 57 | PRT | EVQLLESGGGLVQPGGSLRLSCAASGFTFSSYGMHWVRQAPGKGLEWV<br>SAIGTGGDTYYADSVMGRFTISRDNSKNTLYLQMNSLRAEDTAVYYCA<br>RRDDYTSRDAFDVWGQGTLVTVSSASTKGPSVFPLAPSSKSTSGGTAAL<br>GCLVKDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISKA<br>KGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHY<br>TQKSLSLSPG |
| 58 | PRT | QSVLTQPPSASGTPGQRVTISCSGSSSNIGSNTVNWYQQLPGTAPKLLIYY<br>DDLLPSGVPDRFSGSKSGTSASLAISGLRSEDEADYYCAAWDDSLNGYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 59 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ATGGCATGCACTGGGTCCGACAGGCCCCTGGCAAAGGACTTGAATGG<br>GTGTCCGCCATCGGCACAGGCGGCGATACCTACTATGCCGATAGCGT<br>GATGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGATGCCTTCGATGTGT<br>GGGGCCAGGGAACACTGGTTACCGTTTCTTCAGCCAGCACCAAGGGC<br>CCCAGCGTGTTCCCTCTGGCCCCTAGCAGCAAGAGCACATCTGGCGG<br>AACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCTCTCTGGGCACCCAGACCTACATCTGCA<br>ACGTGAACCACAAGCCCAGCAACACCAAGGTGGACAAGAAGGTGGA<br>ACCCAAGAGCTGCGACAAGACCCACACCTGTCCCCCTTGTCCTGCCC<br>CCGAACTGCTGGGAGGCCCTTCCGTGTTCCTGTTCCCCCCAAAGCCCA<br>AGGACACCCTGATGATCAGCCGGACCCCCGAAGTGACCTGCGTGGTG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from *Homo sapiens* (SEQ ID 581, 582), *Mus Musculus*
(SEQ ID 583), *Rattus norvegicus* (SEQ ID 584), *Canis lupus familiaris* (SEQ ID 585), *Macaca
fascicularis* (SEQ ID 586), *Sus scrofa* (SEQ ID 587).

| SEQ ID No | SEQ Type | SEQUENCE |
|---|---|---|
| | | GTGGATGTGTCCCACGAGGACCCTGAAGTGAAGTTCAATTGGTACGT |
| | | GGACGGCGTGGAAGTGCACAACGCCAAGACCAAGCCTAGAGAGGAA |
| | | CAGTACAACAGCACCTACCGGGTGGTGTCCGTGCTGACAGTGCTGCA |
| | | CCAGGACTGGCTGAACGGCAAAGAGTACAAGTGCAAGGTGTCCAAC |
| | | AAGGCCCTGCCTGCCCCCATCGAGAAAACCATCAGCAAGGCCAAGG |
| | | GCCAGCCCCGCGAACCCCAGGTGTACACACTGCCCCCAAGCAGGGAC |
| | | GAGCTGACCAAGAACCAGGTGTCCCTGACCTGTCTCGTGAAAGGCTT |
| | | CTACCCCTCCGATATCGCCGTGGAATGGGAGAGCAACGGCCAGCCCG |
| | | AGAACAACTACAAGACCACCCCCCCTGTGCTGGACAGCGACGGCTCA |
| | | TTCTTCCTGTACAGCAAGCTGACCGTGGACAAGTCCCGGTGGCAGCA |
| | | GGGCAACGTGTTCAGCTGCAGCGTGATGCACGAGGCCCTGCACAACC |
| | | ACTACACCCAGAAGTCCCTGAGCCTGAGCCCTGGC |
| 60 | DNA | CAGTCTGTTCTGACACAGCCTCCTAGCGCCTCTGGCACACCTGGACA |
| | | GAGAGTGACCATCAGCTGTAGCGGCAGCAGCTCCAACATCGGCAGC |
| | | AACACCGTGAACTGGTATCAGCAGCTGCCTGGCACAGCCCCTAAACT |
| | | GCTGATCTACTACGACGACCTGCTGCCTAGCGGCGTGCCCGATAGAT |
| | | TTTCTGGCAGCAAGAGCGGCACAAGCGCCAGCCTGGCTATCTCTGGA |
| | | CTGAGATCTGAGGACGAGGCCGACTACTATTGCGCCGCCTGGGACGA |
| | | TAGCCTGAACGGCTATGTGGTTTTCGGCGGAGGCACCAAGCTGACCG |
| | | TGCTAGGCCAGCCTAAAGCCGCCCCTAGCGTGACCCTGTTCCCTCCA |
| | | AGCAGCGAGGAACTGCAGGCCAACAAGGCCACCCTCGTGTGCCTGAT |
| | | CAGCGACTTCTATCCTGGCGCCGTGACCGTGGCCTGGAAGGCCGATA |
| | | GCTCTCCTGTGAAGGCCGGCGTGGAAACCACCACCCCTAGCAAGCAG |
| | | AGCAACAACAAATACGCCGCCAGCAGCTACCTGAGCCTGACCCCCGA |
| | | GCAGTGGAAGTCCCACAGATCCTACAGCTGCCAAGTGACCCACGAGG |
| | | GCAGCACCGTGGAAAAGACAGTGGCCCCTACCGAGTGCAGC |
| 61 | PRT | EVQLLESGGGLVQPGGSLRLSCAASGFTFSSYEMNWVRQAPGKGLEWV |
| | | SGISWNSGSIGYADSVKGRFTISRDNSKNTLYLQMNSLRAEDTAVYYCA |
| | | RSGYSSSWFDPDFDYWGQGTLVTVSS |
| 62 | PRT | SYEMN |
| 63 | PRT | GISWNSGSIGYADSVKG |
| 64 | PRT | SGYSSSWFDPDFDY |
| 65 | PRT | QSVLTQPPSASGTPGQRVTISCTGSSSNIGAGYDVHWYQQLPGTAPKLLI |
| | | YGNSNRPSGVPDRFSGSKSGTSASLAISGLRSEDEADYYCSSYAGSNPYV |
| | | VFGGGTKLTVL |
| 66 | PRT | TGSSSNIGAGYDVH |
| 67 | PRT | GNSNRPS |
| 68 | PRT | SSYAGSNPYVV |
| 69 | DNA | GAAGTTCAGCTGCTGGAATCTGGCGGCGGACTGGTTCAACCTGGCGG |
| | | ATCTCTGAGACTGAGCTGTGCCGCCAGCGGCTTCACCTTTAGCAGCT |
| | | ACGAGATGAACTGGGTCCGACAGGCCCCTGGCAAAGGCCTTGAATG |
| | | GGTGTCCGGCATCAGCTGGAATAGCGGCTCTATCGGCTACGCCGACA |
| | | GCGTGAAGGGCAGATTCACCATCAGCCGGGACAACAGCAAGAACAC |
| | | CCTGTACCTGCAGATGAACAGCCTGAGAGCCGAGGACACCGCCGTGT |
| | | ACTACTGTGCCAGAAGCGGCTACAGCAGCTCTTGGTTTGACCCCGAC |
| | | TTCGACTATTGGGGCCAGGGCACACTGGTCACAGTCTCTTCA |
| 70 | DNA | AGCTACGAGATGAAC |
| 71 | DNA | GGCATCAGCTGGAATAGCGGCTCTATCGGCTACGCCGACAGCGTGAA<br>GGGC |
| 72 | DNA | AGCGGCTACAGCAGCTCTTGGTTTGACCCCGACTTCGACTAT |
| 73 | DNA | CAGTCTGTTCTGACACAGCCTCCTAGCGCCTCTGGCACACCTGGACA |
| | | GAGAGTGACCATCAGCTGTACCGGCAGCAGCTCCAATATCGGAGCCG |
| | | GCTATGACGTGCACTGGTATCAGCAGCTGCCTGGCACAGCCCCTAAA |
| | | CTGCTGATCTACGGCAACAGCAACAGACCCAGCGGCGTGCCCGATAG |
| | | ATTTTCCGGCTCTAAGAGCGGCACAAGCGCCAGCCTGGCTATCTCTG |
| | | GACTGAGATCTGAGGACGAGGCCGACTACTACTGCAGCAGCTATGCC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | GGCAGCAACCCCTACGTTGTGTTTGGCGGAGGCACCAAGCTGACCGT TCTA |
| 74 | DNA | ACCGGCAGCAGCTCCAATATCGGAGCCGGCTATGACGTGCAC |
| 75 | DNA | GGCAACAGCAACAGACCCAGC |
| 76 | DNA | AGCAGCTATGCCGGCAGCAACCCCTACGTTGTG |
| 77 | PRT | EVQLLESGGGLVQPGGSLRLSCAASGFTFSSYEMNWVRQAPGKGLEWV SGISWNSGSIGYADSVKGRFTISRDNSKNTLYLQMNSLRAEDTAVYYCA RSGYSSSWFDPDFDYWGQGTLVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPG |
| 78 | PRT | QSVLTQPPSASGTPGQRVTISCTGSSSNIGAGYDVHWYQQLPGTAPKLLI YGNSNRPSGVPDRFSGSKSGTSASLAISGLRSEDEADYYCSSYAGSNPYV VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 79 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGAGATGAACTGGGTCCGACAGGCCCCTGGCAAAGGCCTTGAATG GGTGTCCGGCATCAGCTGGAATAGCGGCTCTATCGGCTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGC |
| 80 | DNA | CAGTCTGTTCTGACACAGCCTCCTAGCGCCTCTGGCACACCTGGACA GAGAGTGACCATCAGCTGTACCGGCAGCAGCTCCAATATCGGAGCCG GCTATGACGTGCACTGGTATCAGCAGCTGCCTGGCACAGCCCCTAAA CTGCTGATCTACGGCAACAGCAACAGACCCAGCGGCGTGCCCGATAG ATTTTCCGGCTCTAAGAGCGGCACAAGCGCCAGCCTGGCTATCTCTG GACTGAGATCTGAGGACGAGGCCGACTACTACTGCAGCAGCTATGCC GGCAGCAACCCCTACGTTGTGTTTGGCGGAGGCACCAAGCTGACCGT TCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| 81 | PRT | EVQLLESGGGLVQTGGSLRLSCAASGFTFSDYAMSWVRQAPGKGLEWV SWIYYDSGSKYYADSVKGRFTISRDNSKNTLYLQMNSLRAEDTAVYYC AKLNGDFDYWGQGTLVTVSS |
| 82 | PRT | DYAMS |
| 83 | PRT | WIYYDSGSKYYADSVKG |
| 84 | PRT | LNGDFDY |
| 85 | PRT | QSVLTQPPSASGTPGQRVTISCSGSSSNIGNNDVSWYQQLPGTAPKLLIY ADSHRPSGVPDRFSGSKSGTSASLAISGLRSEDEADYYCGAWDSSLSGY VFGGGTKLTVL |
| 86 | PRT | SGSSSNIGNNDVS |
| 87 | PRT | ADSHRPS |
| 88 | PRT | GAWDSSLSGYV |
| 89 | DNA | GAAGTTCAGCTGCTGGAATCTGGCGGCGGACTGGTTCAAACAGGCGG CTCTCTGAGACTGAGCTGTGCCGCCTCTGGCTTCACCTTCAGCGATTA CGCCATGAGCTGGGTCCGACAGGCCCCTGGAAAAGGCCTTGAATGGG TGTCCTGGATCTACTACGACAGCGGCAGCAAGTACTACGCCGACAGC GTGAAGGGCAGATTCACCATCAGCCGGGACAACAGCAAGAACACCC TGTACCTGCAGATGAACAGCCTGAGAGCCGAGGACACCGCCGTGTAC TATTGCGCCAAGCTGAACGGCGACTTCGACTATTGGGGCCAGGGCAC ACTGGTCACAGTCTCTTCA |
| 90 | DNA | GATTACGCCATGAGC |
| 91 | DNA | TGGATCTACTACGACAGCGGCAGCAAGTACTACGCCGACAGCGTGAA GGGC |
| 92 | DNA | CTGAACGGCGACTTCGACTAT |
| 93 | DNA | CAGTCTGTTCTGACACAGCCTCCTAGCGCCTCTGGCACACCTGGACA GAGAGTGACCATCAGCTGTAGCGGCAGCAGCTCCAACATCGGCAAC AACGACGTGTCCTGGTATCAGCAGCTGCCTGGCACAGCCCCTAAACT GCTGATCTACGCCGACAGCCACAGACCTAGCGGCGTGCCAGATAGAT TCAGCGGCTCTAAGAGCGGCACATCTGCCAGCCTGGCCATCTCTGGA CTGAGATCTGAGGACGAGGCCGACTACTATTGCGGCGCCTGGGATTC TAGCCTGAGCGGCTATGTTTTTGGCGGAGGCACCAAGCTGACCGTGC TA |
| 94 | DNA | AGCGGCAGCAGCTCCAACATCGGCAACAACGACGTGTCC |
| 95 | DNA | GCCGACAGCCACAGACCTAGC |
| 96 | DNA | GGCGCCTGGGATTCTAGCCTGAGCGGCTATGTT |
| 97 | PRT | EVQLLESGGGLVQTGGSLRLSCAASGFTFSDYAMSWVRQAPGKGLEWV SWIYYDSGSKYYADSVKGRFTISRDNSKNTLYLQMNSLRAEDTAVYYC AKLNGDFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPG |
| 98 | PRT | QSVLTQPPSASGTPGQRVTISCSGSSSNIGNNDVSWYQQLPGTAPKLLIY ADSHRPSGVPDRFSGSKSGTSASLAISGLRSEDEADYYCGAWDSSLSGY VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 99 | DNA | GAAGTTCAGCTGCTGGAATCTGGCGGCGGACTGGTTCAAACAGGCGG CTCTCTGAGACTGAGCTGTGCCGCCTCTGGCTTCACCTTCAGCGATTA CGCCATGAGCTGGGTCCGACAGGCCCCTGGAAAAGGCCTTGAATGGG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from *Homo sapiens* (SEQ ID 581, 582), *Mus Musculus*
(SEQ ID 583), *Rattus norvegicus* (SEQ ID 584), *Canis lupus familiaris* (SEQ ID 585), *Macaca
fascicularis* (SEQ ID 586), *Sus scrofa* (SEQ ID 587).

| SEQ ID No | SEQ Type | SEQUENCE |
|---|---|---|
| | | TGTCCTGGATCTACTACGACAGCGGCAGCAAGTACTACGCCGACAGC<br>GTGAAGGGCAGATTCACCATCAGCCGGGACAACAGCAAGAACACCC<br>TGTACCTGCAGATGAACAGCCTGAGAGCCGAGGACACCGCCGTGTAC<br>TATTGCGCCAAGCTGAACGGCGACTTCGACTATTGGGGCCAGGGCAC<br>ACTGGTCACAGTCTCTTCAGCCAGCACCAAGGGCCCCAGCGTGTTCC<br>CTCTGGCCCCTAGCAGCAAGAGCACATCTGGCGGAACAGCCGCCCTG<br>GGCTGCCTCGTGAAGGACTACTTTCCCGAGCCCGTGACCGTGTCCTG<br>GAACTCTGGCGCTCTGACAAGCGGCGTGCACACCTTTCCAGCCGTGC<br>TGCAGAGCAGCGGCCTGTACTCTCTGAGCAGCGTCGTGACAGTGCCC<br>AGCAGCTCTCTGGGCACCCAGACCTACATCTGCAACGTGAACCACAA<br>GCCCAGCAACACCAAGGTGGACAAGAAGGTGGAACCCAAGAGCTGC<br>GACAAGACCCACACCTGTCCCCCTTGTCCTGCCCCCGAACTGCTGGG<br>AGGCCCTTCCGTGTTCCTGTTCCCCCAAAGCCCAAGGACACCCTGAT<br>GATCAGCCGGACCCCCGAAGTGACCTGCGTGGTGGTGGATGTGTCCC<br>ACGAGGACCCTGAAGTGAAGTTCAATTGGTACGTGGACGGCGTGGA<br>AGTGCACAACGCCAAGACCAAGCCTAGAGAGGAACAGTACAACAGC<br>ACCTACCGGGTGGTGTCCGTGCTGACAGTGCTGCACCAGGACTGGCT<br>GAACGGCAAAGAGTACAAGTGCAAGGTGTCCAACAAGGCCCTGCCT<br>GCCCCCATCGAGAAAACCATCAGCAAGGCCAAGGGCCAGCCCCGCG<br>AACCCCAGGTGTACACACTGCCCCCAAGCAGGGACGAGCTGACCAA<br>GAACCAGGTGTCCCTGACCTGTCTCGTGAAAGGCTTCTACCCCTCCG<br>ATATCGCCGTGGAATGGGAGAGCAACGGCCAGCCCGAGAACAACTA<br>CAAGACCACCCCCCCTGTGCTGGACAGCGACGGCTCATTCTTCCTGT<br>ACAGCAAGCTGACCGTGGACAAGTCCCGGTGGCAGCAGGGCAACGT<br>GTTCAGCTGCAGCGTGATGCACGAGGCCCTGCACAACCACTACACCC<br>AGAAGTCCCTGAGCCTGAGCCCTGGC |
| 100 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAAC<br>AACGACGTGTCCTGGTATCAGCAGCTGCCTGGCACAGCCCCTAAACT<br>GCTGATCTACGCCGACAGCCACAGACCTAGCGGCGTGCCAGATAGAT<br>TCAGCGGCTCTAAGAGCGGCACATCTGCCAGCCTGGCCATCTCTGGA<br>CTGGAGATCTGAGGACGAGGCCGACTACTATTGCGGCGCCTGGGATTC<br>TAGCCTGAGCGGCTATGTTTTTGGCGGAGGCACCAAGCTGACCGTGC<br>TAGGCCAGCCTAAAGCCGCCCCTAGCGTGACCCTGTTCCCTCCAAGC<br>AGCGAGGAACTGCAGGCCAACAAGGCCACCCTCGTGTGCCTGATCAG<br>CGACTTCTATCCTGGCGCCGTGACCGTGGCCTGGAAGGCCGATAGCT<br>CTCCTGTGAAGGCCGGCGTGGAAACCACCACCCCTAGCAAGCAGAGC<br>AACAACAAATACGCCGCCAGCAGCTACCTGAGCCTGACCCCCGAGCA<br>GTGGAAGTCCCACAGATCCTACAGCTGCCAAGTGACCCACGAGGGCA<br>GCACCGTGGAAAAGACAGTGGCCCCTACCGAGTGCAGC |
| 101 | PRT | EVQLLESGGGLVQPGGSLRLSCAASGFTFSSYEMNWVRQAPGKGLEWV<br>SGISWNSGSIGYADSVKGRFTISRDNSKNTLYLQMNSLRAEDTAVYYCA<br>RSGYSSSWFDPDFDYWGQGTLVTVSS |
| 102 | PRT | SYEMN |
| 103 | PRT | GISWNSGSIGYADSVKG |
| 104 | PRT | SGYSSSWFDPDFDY |
| 105 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCSSYAGSNPY<br>VVFGGGTKLTVL |
| 106 | PRT | TGSSSNIGAGYDVH |
| 107 | PRT | GNSNRPS |
| 108 | PRT | SSYAGSNPYVV |
| 109 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGAGATGAACTGGGTCCGACAGGCCCCTGGCAAAGGCCTTGAATG<br>GGTGTCCGGCATCAGCTGGAATAGCGGCTCTATCGGCTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 110 | DNA | AGCTACGAGATGAAC |
| 111 | DNA | GGCATCAGCTGGAATAGCGGCTCTATCGGCTACGCCGACAGCGTGAAGGGC |
| 112 | DNA | AGCGGCTACAGCAGCTCTTGGTTTGACCCCGACTTCGACTAT |
| 113 | DNA | CAGTCTGTTCTGACACAGCCTCCATCTGTGTCTGGCGCCCCTGGACAGAGAGTGACCATCAGCTGTACAGGCAGCAGCTCCAATATCGGAGCCGGCTATGACGTGCACTGGTATCAGCAGCTGCCTGGCACAGCCCCTAAACTGCTGATCTACGGCAACAGCAACAGACCCAGCGGCGTGCCCGATAGATTTTCCGGCTCTAAGAGCGGCACAAGCGCCAGCCTGGCTATTACTGGACTGCAGGCCGAGGACGAGGCCGACTACTACTGTTCTAGCTACGCCGGCAGCAACCCCTACGTGGTGTTTGGCGGAGGCACCAAGCTGACAGTTCTA |
| 114 | DNA | ACAGGCAGCAGCTCCAATATCGGAGCCGGCTATGACGTGCAC |
| 115 | DNA | GGCAACAGCAACAGACCCAGC |
| 116 | DNA | TCTAGCTACGCCGGCAGCAACCCCTACGTGGTG |
| 117 | PRT | EVQLLESGGGLVQPGGSLRLSCAASGFTFSSYEMNWVRQAPGKGLEWVSGISWNSGSIGYADSVKGRFTISRDNSKNTLYLQMNSLRAEDTAVYYCARSGYSSSWFDPDFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| 118 | PRT | QSVLTQPPSVSGAPGQRVTISCTGSSSNIGAGYDVHWYQQLPGTAPKLLIYGNSNRPSGVPDRFSGSKSGTSASLAITGLQAEDEADYYCSSYAGSNPYVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 119 | DNA | GAAGTTCAGCTGCTGGAATCTGGCGGCGGACTGGTTCAACCTGGCGGATCTCTGAGACTGAGCTGTGCCGCCAGCGGCTTCACCTTTAGCAGCTACGAGATGAACTGGGTCCGACAGGCCCCTGGCAAAGGCCTTGAATGGGTGTCCGGCATCAGCTGGAATAGCGGCTCTATCGGCTACGCCGACAGCGTGAAGGGCAGATTCACCATCAGCCGGGACAACAGCAAGAACACCCTGTACCTGCAGATGAACAGCCTGAGAGCCGAGGACACCGCCGTGTACTACTGTGCCAGAAGCGGCTACAGCAGCTCTTGGTTTGACCCCGACTTCGACTATTGGGGCCAGGGCACACTGGTCACAGTCTCTTCAGCCAGCACCAAGGGCCCCAGCGTGTTCCCTCTGGCCCCTAGCAGCAAGAGCACATCTGGCGGAACAGCCGCCCTGGGCTGCCTCGTGAAGGACTACTTTCCCGAGCCCGTGACCGTGTCCTGGAACTCTGGCGCTCTGACAAGCGGCGTGCACACCTTTCCAGCCGTGCTGCAGAGCAGCGGCCTGTACTCTCTGAGCAGCGTCGTGACAGTGCCCAGCAGCTCTCTGGGCACCCAGACCTACATCTGCAACGTGAACCACAAGCCCAGCAACACCAAGGTGGACAAGAAGGTGGAACCCAAGAGCTGCGACAAGACCCACACCTGTCCCCCTTGTCCTGCCCCCGAACTGCTGGGAGGCCCTTCCGTGTTCCTGTTCCCCCCAAAGCCCAAGGACACCCTGATGATCAGCCGGACCCCCGAAGTGACCTGCGTGGTGGTGGATGTGTCCCACGAGGACCCTGAAGTGAAGTTCAATTGGTACGTGGACGGCGTGGAAGTGCACAACGCCAAGACCAAGCCTAGAGAGGAACAGTACAACAGCACCTACCGGGTGGTGTCCGTGCTGACAGTGCTGCACCAGGACTGGCTGAACGGCAAAGAGTACAAGTGCAAGGTGTCCAACAAGGCCCTGCCTGCCCCCATCGAGAAAACCATCAGCAAGGCCAAGGGCCAGCCCCGCGAACCCCAGGTGTACACACTGCCCCCAAGCAGGGACGAGCTGACCAAGAACCAGGTGTCCCTGACCTGTCTCGTGAAAGGCTTCTACCCCTCCGATATCGCCGTGGAATGGGAGAGCAACGGCCAGCCCGAGAACAACTACAAGACCACCCCCCCTGTGCTGGACAGCGACGGCTCATTCTTCCTGTACAGCAAGCTGACCGTGGACAAGTCCCGGTGGCAGCAGGGCAACGTGTTCAGCTGCAGCGTGATGCACGAGGCCCTGCACAACCACTACACCCAGAAGTCCCTGAGCCTGAGCCCTGGC |
| 120 | DNA | CAGTCTGTTCTGACACAGCCTCCATCTGTGTCTGGCGCCCCTGGACAGAGAGTGACCATCAGCTGTACAGGCAGCAGCTCCAATATCGGAGCCGG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | CTATGACGTGCACTGGTATCAGCAGCTGCCTGGCACAGCCCCTAAAC |
|  |  | TGCTGATCTACGGCAACAGCAACAGACCCAGCGGCGTGCCCGATAGA |
|  |  | TTTTCCGGCTCTAAGAGCGGCACAAGCGCCAGCCTGGCTATTACTGG |
|  |  | ACTGCAGGCCGAGGACGAGGCCGACTACTACTGTTCTAGCTACGCCG |
|  |  | GCAGCAACCCCTACGTGGTGTTTGGCGGAGGCACCAAGCTGACAGTT |
|  |  | CTAGGCCAGCCTAAAGCCGCCCCTAGCGTGACCCTGTTCCCTCCAAG |
|  |  | CAGCGAGGAACTGCAGGCCAACAAGGCCACCCTCGTGTGCCTGATCA |
|  |  | GCGACTTCTATCCTGGCGCCGTGACCGTGGCCTGGAAGGCCGATAGC |
|  |  | TCTCCTGTGAAGGCCGGCGTGGAAACCACCACCCCTAGCAAGCAGAG |
|  |  | CAACAACAAATACGCCGCCAGCAGCTACCTGAGCCTGACCCCCGAGC |
|  |  | AGTGGAAGTCCCACAGATCCTACAGCTGCCAAGTGACCCACGAGGGC |
|  |  | AGCACCGTGGAAAAGACAGTGGCCCCTACCGAGTGCAGC |
| 121 | PRT | EVQLLESGGGLVQPGGSLRLSCAASGFTFSSYAMSWVRQAPGKGLEWV |
|  |  | SAIGTGGDTYYADSVKGRFTISRDNSKNTLYLQMNSLRAEDTAVYYCA |
|  |  | RRDDYTSRDAFDYWGQGTLVTVSS |
| 122 | PRT | SYAMS |
| 123 | PRT | AIGTGGDTYYADSVKG |
| 124 | PRT | RDDYTSRDAFDY |
| 125 | PRT | QSVLTQPPSASGTPGQRVTISCSGSSSNIGSNTVNWYQQLPGTAPKLLIYY |
|  |  | DDLRPSGVPDRFSGSKSGTSASLAISGLQSEDEADYYCAAWDDSLNGYV |
|  |  | VFGGGTKLTVL |
| 126 | PRT | SGSSSNIGSNTVN |
| 127 | PRT | YDDLRPS |
| 128 | PRT | AAWDDSLNGYVV |
| 129 | DNA | GAAGTTCAGCTGCTGGAATCTGGCGGCGGACTGGTTCAACCTGGCGG |
|  |  | ATCTCTGAGACTGAGCTGTGCCGCCAGCGGCTTCACCTTTAGCAGCT |
|  |  | ACGCCATGAGCTGGGTCCGACAGGCTCCTGGCAAAGGCCTTGAATGG |
|  |  | GTGTCCGCCATTGGCACAGGCGGCGATACCTACTACGCCGACTCTGT |
|  |  | GAAGGGCAGATTCACCATCAGCCGGGACAACAGCAAGAACACCCTG |
|  |  | TACCTGCAGATGAACAGCCTGAGAGCCGAGGACACCGCCGTGTACTA |
|  |  | TTGCGCCAGAAGGGACGACTACACCAGCAGGGACGCCTTCGATTATT |
|  |  | GGGGCCAGGGCACACTGGTCACCGTTTCTTCA |
| 130 | DNA | AGCTACGCCATGAGC |
| 131 | DNA | GCCATTGGCACAGGCGGCGATACCTACTACGCCGACTCTGTGAAGGG C |
| 132 | DNA | AGGGACGACTACACCAGCAGGGACGCCTTCGATTAT |
| 133 | DNA | CAGTCTGTTCTGACACAGCCTCCTAGCGCCTCTGGCACACCTGGACA |
|  |  | GAGAGTGACCATCAGCTGTAGCGGCAGCAGCTCCAACATCGGCAGC |
|  |  | AACACCGTGAACTGGTATCAGCAGCTGCCTGGCACAGCCCCTAAACT |
|  |  | GCTGATCTACTACGACGACCTGCGGCCTAGCGGCGTGCCAGATAGAT |
|  |  | TTTCTGGCAGCAAGAGCGGCACCTCTGCCAGCCTGGCTATTTCTGGA |
|  |  | CTGCAGAGCGAGGACGAGGCCGACTATTATTGTGCCGCCTGGGACGA |
|  |  | CAGCCTGAACGGCTATGTTGTTTTCGGCGGAGGCACCAAGCTGACCG |
|  |  | TTCTA |
| 134 | DNA | AGCGGCAGCAGCTCCAACATCGGCAGCAACACCGTGAAC |
| 135 | DNA | TACGACGACCTGCGGCCTAGC |
| 136 | DNA | GCCGCCTGGGACGACAGCCTGAACGGCTATGTTGTT |
| 137 | PRT | EVQLLESGGGLVQPGGSLRLSCAASGFTFSSYAMSWVRQAPGKGLEWV |
|  |  | SAIGTGGDTYYADSVKGRFTISRDNSKNTLYLQMNSLRAEDTAVYYCA |
|  |  | RRDDYTSRDAFDYWGQGTLVTVSSASTKGPSVFPLAPSSKSTSGGTAAL |
|  |  | GCLVKDYFPEPVTVSWNSGALTSGVHTFPAVLQSSGLYSLSSVVTVPSSS |
|  |  | LGTQTYICNVNHKPSNTKVDKKVEPKSCDKTHTCPPCPAPELLGGPSVFL |
|  |  | FPPKPKDTLMISRTPEVTCVVVDVSHEDPEVKFNWYVDGVEVHNAKTK |
|  |  | PREEQYNSTYRVVSVLTVLHQDWLNGKEYKCKVSNKALPAPIEKTISKA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | KGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHY<br>TQKSLSLSPG |
| 138 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNGYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 139 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATTGGCACAGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCAGCCAGCACCAAGGGC<br>CCCAGCGTGTTCCCTCTGGCCCCTAGCAGCAAGAGCACATCTGGCGG<br>AACAGCCGCCCTGGGCTGCCTCGTGAAGGACTACTTTCCCGAGCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCTCTCTGGGCACCCAGACCTACATCTGCA<br>ACGTGAACCACAAGCCCAGCAACACCAAGGTGGACAAGAAGGTGGA<br>ACCCAAGAGCTGCGACAAGACCCACACCTGTCCCCCTTGTCCTGCCC<br>CCGAACTGCTGGGAGGCCCTTCCGTGTTCCTGTTCCCCCCAAAGCCCA<br>AGGACACCCTGATGATCAGCCGGACCCCCGAAGTGACCTGCGTGGTG<br>GTGGATGTGTCCCACGAGGACCCTGAAGTGAAGTTCAATTGGTACGT<br>GGACGGCGTGGAAGTGCACAACGCCAAGACCAAGCCTAGAGAGGAA<br>CAGTACAACAGCACCTACCGGGTGGTGTCCGTGCTGACAGTGCTGCA<br>CCAGGACTGGCTGAACGGCAAAGAGTACAAGTGCAAGGTGTCCAAC<br>AAGGCCCTGCCTGCCCCCATCGAGAAAACCATCAGCAAGGCCAAGG<br>GCCAGCCCCGCGAACCCCAGGTGTACACACTGCCCCCAAGCAGGGAC<br>GAGCTGACCAAGAACCAGGTGTCCCTGACCTGTCTCGTGAAAGGCTT<br>CTACCCCTCCGATATCGCCGTGGAATGGGAGAGCAACGGCCAGCCCG<br>AGAACAACTACAAGACCACCCCCCCTGTGCTGGACAGCGACGGCTCA<br>TTCTTCCTGTACAGCAAGCTGACCGTGGACAAGTCCCGGTGGCAGCA<br>GGGCAACGTGTTCAGCTGCAGCGTGATGCACGAGGCCCTGCACAACC<br>ACTACACCCAGAAGTCCCTGAGCCTGAGCCCTGGC |
| 140 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGGCTATGTTGTTTTCGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 141 | PRT | EVQLLESGGGLVQPGGSLRLSCAASGFTFYSYAMSWVRQAPGKGLEWV<br>SAIGTGGDTYYADSVKGRFTISRDNSKNTLYLQMNSLRAEDTAVYYCA<br>RRDDYTSRDAFDYWGQGTLVTVSS |
| 142 | PRT | SYAMS |
| 143 | PRT | AIGTGGDTYYADSVKG |
| 144 | PRT | RDDYTSRDAFDY |
| 145 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDYV<br>VFGGGTKLTVL |
| 146 | PRT | SGSSSNIGSNTVN |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 147 | PRT | YDDLRPS |
| 148 | PRT | AAWDDSLNDYVV |
| 149 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCACAGGCGGCGATACCTACTATGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCA |
| 150 | DNA | AGCTACGCCATGAGC |
| 151 | DNA | GCCATCGGCACAGGCGGCGATACCTACTATGCCGACTCTGTGAAGGG<br>C |
| 152 | DNA | AGGGACGACTACACCAGCAGGGACGCCTTCGATTAT |
| 153 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACTACGTTGTGTTTGGCGGAGGCACCAAGCTGACCG<br>TTCTA |
| 154 | DNA | AGCGGCAGCAGCTCCAACATCGGCAGCAACACCGTGAAC |
| 155 | DNA | TACGACGACCTGCGGCCTAGC |
| 156 | DNA | GCCGCCTGGGACGACAGCCTGAACGACTACGTTGTG |
| 157 | PRT | EVQLLESGGGLVQPGGSLRLSCAASGFTFYSYAMSWVRQAPGKGLEWV<br>SAIGTGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 158 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 159 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCACAGGCGGCGATACCTACTATGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCAGCAGCACCAAGGGCC<br>CCAGCGTGTTCCCTCTGGCCCCTTGTAGCAGAAGCACCAGCGAGTCT<br>ACAGCCGCCCTGGGCTGCCTCGTGAAGGACTACTTTCCCGAGCCCGT<br>GACCGTGTCCTGGAACTCTGGCGCTCTGACAAGCGGCGTGCACACCT<br>TTCCAGCCGTGCTGCAGAGCAGCGGCCTGTACTCTCTGAGCAGCGTC<br>GTGACAGTGCCCAGCAGCAGCCTGGGCACCAAGACCTACACCTGTAA<br>CGTGGACCACAAGCCCAGCAACACCAAGGTGGACAAGCGGGTGGAA<br>TCTAAGTACGCCCCTCCCTGCCCTCCTTGCCCAGCCCCTGAATTTCTG<br>GGCGGACCCTCCGTGTTCCTGTTCCCCCCAAAGCCCAAGGACACCCT<br>GATGATCAGCCGGACCCCCGAAGTGACCTGCGTGGTGGTGGATGTGT<br>CCCAGGAAGATCCCGAGGTGCAGTTCAATTGGTACGTGGACGGCGTG<br>GAAGTGCACAACGCCAAGACCAAGCCCAGAGAGGAACAGTTCAACA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | GCACCTACCGGGTGGTGTCCGTGCTGACAGTGCTGCACCAGGACTGG<br>CTGAACGGCAAAGAGTACAAGTGCAAGGTGTCCAACAAGGGCCTGC<br>CCAGCTCCATCGAGAAAACCATCAGCAAGGCCAAGGGCCAGCCCCG<br>CGAACCCCAGGTGTACACACTGCCTCCAAGCCAGGAAGAGATGACC<br>AAGAACCAGGTGTCCCTGACCTGTCTCGTGAAAGGCTTCTACCCCTC<br>CGATATCGCCGTGGAATGGGAGAGCAACGGCCAGCCCGAGAACAAC<br>TACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 160 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACTACGTTGTGTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 161 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 162 | PRT | SYAMS |
| 163 | PRT | AIGYGGDTYYADSVKG |
| 164 | PRT | RDDYTSRDAFDY |
| 165 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDIV<br>VFGGGTKLTVL |
| 166 | PRT | SGSSSNIGSNTVN |
| 167 | PRT | YDDLRPS |
| 168 | PRT | AAWDDSLNDIVV |
| 169 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 170 | DNA | AGCTACGCCATGAGC |
| 171 | DNA | GCCATCGGCTATGGCGGCGATACCTACTACGCCGACTCTGTGAAGGG<br>C |
| 172 | DNA | AGGGACGACTACACCAGCAGGGACGCCTTCGATTAT |
| 173 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACATCGTTGTTTTCGGCGGAGGCACCAAGCTGACCG<br>TTCTA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 174 | DNA | AGCGGCAGCAGCTCCAACATCGGCAGCAACACCGTGAAC |
| 175 | DNA | TACGACGACCTGCGGCCTAGC |
| 176 | DNA | GCCGCCTGGGACGACAGCCTGAACGACATCGTTGTT |
| 177 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 178 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDIV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 179 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCAGCCAGCACCAAGGGC<br>CCCAGCGTGTTCCCTCTGGCCCCTTGTAGCAGAAGCACCAGCGAGTC<br>TACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCAGCCTGGGCACCAAGACCTACACCTGTA<br>ACGTGGACCACAAGCCCAGCAACACCAAGGTGGACAAGCGGGTGGA<br>ATCTAAGTACGGCCCTCCCTGCCCTCCTTGCCCAGCCCCTGAATTTCT<br>GGGCGGACCCTCCGTGTTCCTGTTCCCCCCAAAGCCCAAGGACACCC<br>TGATGATCAGCCGGACCCCCGAAGTGACCTGCGTGGTGGTGGATGTG<br>TCCCAGGAAGATCCCGAGGTGCAGTTCAATTGGTACGTGGACGGCGT<br>GGAAGTGCACAACGCCAAGACCAAGCCCAGAGAGGAACAGTTCAAC<br>AGCACCTACCGGGTGGTGTCCGTGCTGACAGTGCTGCACCAGGACTG<br>GCTGAACGGCAAAGAGTACAAGTGCAAGGTGTCCAACAAGGGCCTG<br>CCCAGCTCCATCGAGAAAACCATCAGCAAGGCCAAGGGCCAGCCCC<br>GCGAACCCCAGGTGTACACACTGCCTCCAAGCCAGGAAGAGATGAC<br>CAAGAACCAGGTGTCCCTGACCTGTCTCGTGAAAGGCTTCTACCCCT<br>CCGATATCGCCGTGGAATGGGAGAGCAACGGCCAGCCCGAGAACAA<br>CTACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 180 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACATCGTTGTTTTCGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 181 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 182 | PRT | SYAMS |
| 183 | PRT | AIGYGGDTYYADSVKG |
| 184 | PRT | RDDYTSRDAFDY |
| 185 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNVYP<br>VFGGGTKLTVL |
| 186 | PRT | SGSSSNIGSNTVN |
| 187 | PRT | YDDLRPS |
| 188 | PRT | AAWDDSLNVYPV |
| 189 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 190 | DNA | AGCTACGCCATGAGC |
| 191 | DNA | GCCATCGGCTATGGCGGCGATACCTACTACGCCGACTCTGTGAAGGG<br>C |
| 192 | DNA | AGGGACGACTACACCAGCAGGGACGCCTTCGATTAT |
| 193 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGTGTACCCTGTTTTTGGCGGAGGCACCAAGCTGACCG<br>TTCTA |
| 194 | DNA | AGCGGCAGCAGCTCCAACATCGGCAGCAACACCGTGAAC |
| 195 | DNA | TACGACGACCTGCGGCCTAGC |
| 196 | DNA | GCCGCCTGGGACGACAGCCTGAACGTGTACCCTGTT |
| 197 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 198 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNVYP<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 199 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | TTGCGCCAGAAGGGACGACTACACCAGCAGGGACGCCTTCGATTATT |
| | | GGGGCCAGGGCACACTGGTCACCGTTTCTTCAGCCAGCACCAAGGGC |
| | | CCCAGCGTGTTCCCTCTGGCCCCTTGTAGCAGAAGCACCAGCGAGTC |
| | | TACAGCCGCCCTGGGCTGCCTCGTGAAGGACTACTTTCCCGAGCCCG |
| | | TGACCGTGTCCTGGAACTCTGGCGCTCTGACAAGCGGCGTGCACACC |
| | | TTTCCAGCCGTGCTGCAGAGCAGCGGCCTGTACTCTCTGAGCAGCGT |
| | | CGTGACAGTGCCCAGCAGCAGCCTGGGCACCAAGACCTACACCTGTA |
| | | ACGTGGACCACAAGCCCAGCAACACCAAGGTGGACAAGCGGGTGGA |
| | | ATCTAAGTACGGCCCTCCCTGCCCTCCTTGCCCAGCCCCTGAATTTCT |
| | | GGGCGGACCCTCCGTGTTCCTGTTCCCCCCAAAGCCCAAGGACACCC |
| | | TGATGATCAGCCGGACCCCCGAAGTGACCTGCGTGGTGGTGGATGTG |
| | | TCCCAGGAAGATCCCGAGGTGCAGTTCAATTGGTACGTGGACGGCGT |
| | | GGAAGTGCACAACGCCAAGACCAAGCCCAGAGAGGAACAGTTCAAC |
| | | AGCACCTACCGGGTGGTGTCCGTGCTGACAGTGCTGCACCAGGACTG |
| | | GCTGAACGGCAAAGAGTACAAGTGCAAGGTGTCCAACAAGGGCCTG |
| | | CCCAGCTCCATCGAGAAAACCATCAGCAAGGCCAAGGGCCAGCCCC |
| | | GCGAACCCCAGGTGTACACACTGCCTCCAAGCCAGGAAGAGATGAC |
| | | CAAGAACCAGGTGTCCCTGACCTGTCTCGTGAAAGGCTTCTACCCCT |
| | | CCGATATCGCCGTGGAATGGGAGAGCAACGGCCAGCCCGAGAACAA |
| | | CTACAAGACCACCCCCCCTGTGCTGGACAGCGACGGCTCATTCTTCCT |
| | | GTACAGCAGACTGACCGTGGACAAGAGCCGGTGGCAGGAAGGCAAC |
| | | GTGTTCAGCTGCAGCGTGATGCACGAGGCCCTGCACAACCACTACAC |
| | | CCAGAAGTCCCTGTCTCTGAGCCTGGGCAAG |
| 200 | DNA | CAGTCTGTTCTGACACAGCCTCCTAGCGCCTCTGGCACACCTGGACA |
| | | GAGAGTGACCATCAGCTGTAGCGGCAGCAGCTCCAACATCGGCAGC |
| | | AACACCGTGAACTGGTATCAGCAGCTGCCTGGCACAGCCCCTAAACT |
| | | GCTGATCTACTACGACGACCTGCGGCCTAGCGGCGTGCCAGATAGAT |
| | | TTTCTGGCAGCAAGAGCGGCACCTCTGCCAGCCTGGCTATTTCTGGA |
| | | CTGCAGAGCGAGGACGAGGCCGACTATTATTGTGCCGCCTGGGACGA |
| | | CAGCCTGAACGTGTACCCTGTTTTTGGCGGAGGCACCAAGCTGACCG |
| | | TTCTAGGCCAGCCTAAAGCCGCCCCTAGCGTGACCCTGTTCCCTCCAA |
| | | GCAGCGAGGAACTGCAGGCCAACAAGGCCACCCTCGTGTGCCTGATC |
| | | AGCGACTTCTATCCTGGCGCCGTGACCGTGGCCTGGAAGGCCGATAG |
| | | CTCTCCTGTGAAGGCCGGCGTGGAAACCACCACCCCTAGCAAGCAGA |
| | | GCAACAACAAATACGCCGCCAGCAGCTACCTGAGCCTGACCCCCGAG |
| | | CAGTGGAAGTCCCACAGATCCTACAGCTGCCAAGTGACCCACGAGGG |
| | | CAGCACCGTGGAAAAGACAGTGGCCCCTACCGAGTGCAGC |
| 201 | PRT | EVQLLESGGGLVQPGGSLRLSCAASGFTFSSYAMSWVRQAPGKGLEWV |
| | | SAIGYGGDTYYADSVKGRFTISRDNSKNTLYLQMNSLRAEDTAVYYCA |
| | | RRDDYTSRDAFDYWGQGTLVTVSS |
| 202 | PRT | SYAMS |
| 203 | PRT | AIGYGGDTYYADSVKG |
| 204 | PRT | RDDYTSRDAFDY |
| 205 | PRT | QSVLTQPPSASGTPGQRVTISCSGSSSNIGSNTVNWYQQLPGTAPKLLIYY |
| | | DDLRPSGVPDRFSGSKSGTSASLAISGLQSEDEADYYCHAWDDSLNDIV |
| | | VFGGGTKLTVL |
| 206 | PRT | SGSSSNIGSNTVN |
| 207 | PRT | YDDLRPS |
| 208 | PRT | HAWDDSLNDIVV |
| 209 | DNA | GAAGTTCAGCTGCTGGAATCTGGCGGCGGACTGGTTCAACCTGGCGG |
| | | ATCTCTGAGACTGAGCTGTGCCGCCAGCGGCTTCACCTTTAGCAGCT |
| | | ACGCCATGAGCTGGGTCCGACAGGCTCCTGGCAAAGGCCTTGAATGG |
| | | GTGTCCGCCATCGGCTATGGCGGCGATACCTACTACGCCGACTCTGT |
| | | GAAGGGCAGATTCACCATCAGCCGGGACAACAGCAAGAACACCCTG |
| | | TACCTGCAGATGAACAGCCTGAGAGCCGAGGACACCGCCGTGTACTA |
| | | TTGCGCCAGAAGGGACGACTACACCAGCAGGGACGCCTTCGATTATT |
| | | GGGGCCAGGGCACACTGGTCACCGTTTCTTCA |
| 210 | DNA | AGCTACGCCATGAGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
| --- | --- | --- |
| 211 | DNA | GCCATCGGCTATGGCGGCGATACCTACTACGCCGACTCTGTGAAGGGC |
| 212 | DNA | AGGGACGACTACACCAGCAGGGACGCCTTCGATTAT |
| 213 | DNA | CAGTCTGTTCTGACACAGCCTCCTAGCGCCTCTGGCACACCTGGACAGAGAGTGACCATCAGCTGTAGCGGCAGCAGCTCCAACATCGGCAGCAACACCGTGAACTGGTATCAGCAGCTGCCTGGCACAGCCCCTAAACTGCTGATCTACTACGACGACCTGCGGCCTAGCGGCGTGCCAGATAGATTTTCTGGCAGCAAGAGCGGCACCTCTGCCAGCCTGGCTATTTCTGGACTGCAGAGCGAGGACGAGGCCGACTACTATTGTCACGCCTGGGACGACAGCCTGAACGACATCGTGGTTTTTGGCGGAGGCACCAAGCTGACCGTTCTA |
| 214 | DNA | AGCGGCAGCAGCTCCAACATCGGCAGCAACACCGTGAAC |
| 215 | DNA | TACGACGACCTGCGGCCTAGC |
| 216 | DNA | CACGCCTGGGACGACAGCCTGAACGACATCGTGGTT |
| 217 | PRT | EVQLLESGGGLVQPGGSLRLSCAASGFTFSSYAMSWVRQAPGKGLEWVSAIGYGGDTYYADSVKGRFTISRDNSKNTLYLQMNSLRAEDTAVYYCARRDDYTSRDAFDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 218 | PRT | QSVLTQPPSASGTPGQRVTISCSGSSSNIGSNTVNWYQQLPGTAPKLLIYYDDLRPSGVPDRFSGSKSGTSASLAISGLQSEDEADYYCHAWDDSLNDIVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 219 | DNA | GAAGTTCAGCTGCTGGAATCTGGCGGCGGACTGGTTCAACCTGGCGGATCTCTGAGACTGAGCTGTGCCGCCAGCGGCTTCACCTTTAGCAGCTACGCCATGAGCTGGGTCCGACAGGCTCCTGGCAAAGGCCTTGAATGGGTGTCCGCCATCGGCTATGGCGGCGATACCTACTACGCCGACTCTGTGAAGGGCAGATTCACCATCAGCCGGGACAACAGCAAGAACACCCTGTACCTGCAGATGAACAGCCTGAGAGCCGAGGACACCGCCGTGTACTATTGCGCCAGAAGGGACGACTACACCAGCAGGGACGCCTTCGATTATTGGGGCCAGGGCACACTGGTCACCGTTTCTTCAGCCAGCACCAAGGGCCCCAGCGTGTTCCCTCTGGCCCCTTGTAGCAGAAGCACCAGCGAGTCTACAGCCGCCCTGGGCTGCCTCGTGAAGGACTACTTTCCCGAGCCCGTGACCGTGTCCTGGAACTCTGGCGCTCTGACAAGCGGCGTGCACACCTTTCCAGCCGTGCTGCAGAGCAGCGGCCTGTACTCTCTGAGCAGCGTCGTGACAGTGCCCAGCAGCAGCCTGGGCACCAAGACCTACACCTGTAACGTGGACCACAAGCCCAGCAACACCAAGGTGGACAAGCGGGTGGAATCTAAGTACGGCCCTCCCTGCCCTCCTTGCCCAGCCCCTGAATTTCTGGGCGGACCCTCCGTGTTCCTGTTCCCCCCAAAGCCCAAGGACACCCTGATGATCAGCCGGACCCCCGAAGTGACCTGCGTGGTGGTGGATGTGTCCCAGGAAGATCCCGAGGTGCAGTTCAATTGGTACGTGGACGGCGTGGAAGTGCACAACGCCAAGACCAAGCCCAGAGAGGAACAGTTCAACAGCACCTACCGGGTGGTGTCCGTGCTGACAGTGCTGCACCAGGACTGGCTGAACGGCAAAGAGTACAAGTGCAAGGTGTCCAACAAGGGCCTGCCCAGCTCCATCGAGAAAACCATCAGCAAGGCCAAGGGCCAGCCCCGCGAACCCCAGGTGTACACACTGCCTCCAAGCCAGGAAGAGATGACCAAGAACCAGGTGTCCCTGACCTGTCTCGTGAAAGGCTTCTACCCCTCCGATATCGCCGTGGAATGGGAGAGCAACGGCCAGCCCGAGAACAACTACAAGACCACCCCCCCTGTGCTGGACAGCGACGGCTCATTCTTCCTGTACAGCAGACTGACCGTGGACAAGAGCCGGTGGCAGGAAGGCAACGTGTTCAGCTGCAGCGTGATGCACGAGGCCCTGCACAACCACTACACCCAGAAGTCCCTGTCTCTGAGCCTGGGCAAG |
| 220 | DNA | CAGTCTGTTCTGACACAGCCTCCTAGCGCCTCTGGCACACCTGGACAGAGAGTGACCATCAGCTGTAGCGGCAGCAGCTCCAACATCGGCAGCAACACCGTGAACTGGTATCAGCAGCTGCCTGGCACAGCCCCTAAACT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGACATCGTGGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 221 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 222 | PRT | SYAMS |
| 223 | PRT | AIGYGGDTYYADSVKG |
| 224 | PRT | RDDYTSRDAFDY |
| 225 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNDYP<br>VFGGGTKLTVL |
| 226 | PRT | SGSSSNIGSNTVN |
| 227 | PRT | YDDLRPS |
| 228 | PRT | HAWDDSLNDYPV |
| 229 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 230 | DNA | AGCTACGCCATGAGC |
| 231 | DNA | GCCATCGGCTATGGCGGCGATACCTACTACGCCGACTCTGTGAAGGG<br>C |
| 232 | DNA | AGGGACGACTACACCAGCAGGGACGCCTTCGATTAT |
| 233 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGACTACCCTGTTTTTGGCGGAGGCACCAAGCTGACCG<br>TTCTA |
| 234 | DNA | AGCGGCAGCAGCTCCAACATCGGCAGCAACACCGTGAAC |
| 235 | DNA | TACGACGACCTGCGGCCTAGC |
| 236 | DNA | CACGCCTGGGACGACAGCCTGAACGACTACCCTGTT |
| 237 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | KTTPPVLDSDGSFFLYSRLTVDKSRWQEGNVFSCSVMHEALHNHYTQK SLSLSLGK |
| 238 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCHAWDDSLNDYP VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 239 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCAGCCAGCACCAAGGGC CCCAGCGTGTTCCCTCTGGCCCCTTGTAGCAGAAGCACCAGCGAGTC TACAGCCGCCCTGGGCTGCCTCGTGAAGGACTACTTTCCCGAGCCCG TGACCGTGTCCTGGAACTCTGGCGCTCTGACAAGCGGCGTGCACACC TTTCCAGCCGTGCTGCAGAGCAGCGGCCTGTACTCTCTGAGCAGCGT CGTGACAGTGCCCAGCAGCAGCCTGGGCACCAAGACCTACACCTGTA ACGTGGACCACAAGCCCAGCAACACCAAGGTGGACAAGCGGGTGGA ATCTAAGTACGGCCCTCCCTGCCCTCCTTGCCCAGCCCCTGAATTTCT GGGCGGACCCTCCGTGTTCCTGTTCCCCCCAAAGCCCAAGGACACCC TGATGATCAGCCGGACCCCCGAAGTGACCTGCGTGGTGGTGGATGTG TCCCAGGAAGATCCCGAGGTGCAGTTCAATTGGTACGTGGACGGCGT GGAAGTGCACAACGCCAAGACCAAGCCCAGAGAGGAACAGTTCAAC AGCACCTACCGGGTGGTGTCCGTGCTGACAGTGCTGCACCAGGACTG GCTGAACGGCAAAGAGTACAAGTGCAAGGTGTCCAACAAGGGCCTG CCCAGCTCCATCGAGAAAACCATCAGCAAGGCCAAGGGCCAGCCCC GCGAACCCCAGGTGTACACACTGCCTCCAAGCCAGGAAGAGATGAC CAAGAACCAGGTGTCCCTGACCTGTCTCGTGAAAGGCTTCTACCCCT CCGATATCGCCGTGGAATGGGAGAGCAACGGCCAGCCCGAGAACAA CTACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 240 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTACTATTGTCACGCCTGGGACGA CAGCCTGAACGACTACCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 241 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSS |
| 242 | PRT | SYAMS |
| 243 | PRT | AIGYGGDTYYADSVKG |
| 244 | PRT | RDDYTSRDAFDY |
| 245 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCHAWDDSLNVYP VFGGGTKLTVL |
| 246 | PRT | SGSSSNIGSNTVN |
| 247 | PRT | YDDLRPS |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 248 | PRT | HAWDDSLNVYPV |
| 249 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 250 | DNA | AGCTACGCCATGAGC |
| 251 | DNA | GCCATCGGCTATGGCGGCGATACCTACTACGCCGACTCTGTGAAGGG<br>C |
| 252 | DNA | AGGGACGACTACACCAGCAGGGACGCCTTCGATTAT |
| 253 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGTACCCTGTTTTTGGCGGAGGCACCAAGCTGACCG<br>TTCTA |
| 254 | DNA | AGCGGCAGCAGCTCCAACATCGGCAGCAACACCGTGAAC |
| 255 | DNA | TACGACGACCTGCGGCCTAGC |
| 256 | DNA | CACGCCTGGGACGACAGCCTGAACGTGTACCCTGTT |
| 257 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 258 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVYP<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 259 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCAGCCAGCACCAAGGGC<br>CCCAGCGTGTTCCCTCTGGCCCCTTGTAGCAGAAGCACCAGCGAGTC<br>TACAGCCGCCCTGGGCTGCCTCGTGAAGGACTACTTTCCCGAGCCCG<br>TGACCGTGTCCTGGAACTCTGGCGCTCTGACAAGCGGCGTGCACACC<br>TTTCCAGCCGTGCTGCAGAGCAGCGGCCTGTACTCTCTGAGCAGCGT<br>CGTGACAGTGCCCAGCAGCAGCCTGGGCACCAAGACCTACACCTGTA<br>ACGTGGACCACAAGCCCAGCAACACCAAGGTGGACAAGCGGGTGGA<br>ATCTAAGTACGGCCCTCCCTGCCCTCCTTGCCCAGCCCCTGAATTTCT<br>GGGCGGACCCTCCGTGTTCCTGTTCCCCCCAAAGCCCAAGGACACCC<br>TGATGATCAGCCGGACCCCCGAAGTGACCTGCGTGGTGGTGGATGTG<br>TCCCAGGAAGATCCCGAGGTGCAGTTCAATTGGTACGTGGACGGCGT<br>GGAAGTGCACAACGCCAAGACCAAGCCCAGAGAGGAACAGTTCAAC<br>AGCACCTACCGGGTGGTGTCCGTGCTGACAGTGCTGCACCAGGACTG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | GCTGAACGGCAAAGAGTACAAGTGCAAGGTGTCCAACAAGGGCCTG<br>CCCAGCTCCATCGAGAAAACCATCAGCAAGGCCAAGGGCCAGCCC<br>GCGAACCCCAGGTGTACACACTGCCTCCAAGCCAGGAAGAGATGAC<br>CAAGAACCAGGTGTCCCTGACCTGTCTCGTGAAAGGCTTCTACCCCT<br>CCGATATCGCCGTGGAATGGGAGAGCAACGGCCAGCCCGAGAACAA<br>CTACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 260 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGACGA<br>CAGCCTGAACGTGTACCCTGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 261 | PRT | EVQLLESGGGLVQPGGSLRLSCAASGFTFSSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 262 | PRT | SYAMS |
| 263 | PRT | AIGYGGDTYYADSVKG |
| 264 | PRT | RDDYTSRDAFDY |
| 265 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVIPV<br>FGGGTKLTVL |
| 266 | PRT | SGSSSNIGSNTVN |
| 267 | PRT | YDDLRPS |
| 268 | PRT | HAWDDSLNVIPV |
| 269 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGCAGCT<br>ACGCCATGAGCTGGGTCCGACAGGCTCCTGGCAAAGGCCTTGAATGG<br>GTGTCCGCCATCGGCTATGGCGGCGATACCTACTACGCCGACTCTGT<br>GAAGGGCAGATTCACCATCAGCCGGGACAACAGCAAGAACACCCTG<br>TACCTGCAGATGAACAGCCTGAGAGCCGAGGACACCGCCGTGTACTA<br>TTGCGCCAGAAGGGACGACTACACCAGCAGGGACGCCTTCGATTATT<br>GGGGCCAGGGCACACTGGTCACCGTTTCTTCA |
| 270 | DNA | AGCTACGCCATGAGC |
| 271 | DNA | GCCATCGGCTATGGCGGCGATACCTACTACGCCGACTCTGTGAAGGG<br>C |
| 272 | DNA | AGGGACGACTACACCAGCAGGGACGCCTTCGATTAT |
| 273 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGATCCCTGTTTTTGGCGGAGGCACCAAGCTGACCG<br>TTCTA |
| 274 | DNA | AGCGGCAGCAGCTCCAACATCGGCAGCAACACCGTGAAC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 275 | DNA | TACGACGACCTGCGGCCTAGC |
| 276 | DNA | CACGCCTGGGACGACAGCCTGAACGTGATCCCTGTT |
| 277 | PRT | EVQLLESGGGLVQPGGSLRLSCAASGFTFSSYAMSWVRQAPGKGLEWV SAIGYGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 278 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCHAWDDSLNVIPV FGGGTKLTVLGQPKAAPSVTLFPPSSEELQANKATLVCLISDFYPGAVTV AWKADSSPVKAGVETTTPSKQSNNKYAASSYLSLTPEQWKSHRSYSCQ VTHEGSTVEKTVAPTECS |
| 279 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGCAGCT ACGCCATGAGCTGGGTCCGACAGGCTCCTGGCAAAGGCCTTGAATGG GTGTCCGCCATCGGCTATGGCGGCGATACCTACTACGCCGACTCTGT GAAGGGCAGATTCACCATCAGCCGGGACAACAGCAAGAACACCCTG TACCTGCAGATGAACAGCCTGAGAGCCGAGGACACCGCCGTGTACTA TTGCGCCAGAAGGGACGACTACACCAGCAGGGACGCCTTCGATTATT GGGGCCAGGGCACACTGGTCACCGTTTCTTCAGCCAGCACCAAGGGC CCCAGCGTGTTCCCTCTGGCCCCTTGTAGCAGAAGCACCAGCGAGTC TACAGCCGCCCTGGGCTGCCTCGTGAAGGACTACTTTCCCGAGCCCG TGACCGTGTCCTGGAACTCTGGCGCTCTGACAAGCGGCGTGCACACC TTTCCAGCCGTGCTGCAGAGCAGCGGCCTGTACTCTCTGAGCAGCGT CGTGACAGTGCCCAGCAGCAGCCTGGGCACCAAGACCTACACCTGTA ACGTGGACCACAAGCCCAGCAACACCAAGGTGGACAAGCGGGTGGA ATCTAAGTACGGCCCTCCCTGCCCTCCTTGCCCAGCCCCTGAATTTCT GGGCGGACCCTCCGTGTTCCTGTTCCCCCCAAAGCCCAAGGACACCC TGATGATCAGCCGGACCCCCGAAGTGACCTGCGTGGTGGTGGATGTG TCCCAGGAAGATCCCGAGGTGCAGTTCAATTGGTACGTGGACGGCGT GGAAGTGCACAACGCCAAGACCAAGCCCAGAGAGGAACAGTTCAAC AGCACCTACCGGGTGGTGTCCGTGCTGACAGTGCTGCACCAGGACTG GCTGAACGGCAAAGAGTACAAGTGCAAGGTGTCCAACAAGGGCCTG CCCAGCTCCATCGAGAAAACCATCAGCAAGGCCAAGGGCCAGCCCC GCGAACCCCAGGTGTACACACTGCCTCCAAGCCAGGAAGAGATGAC CAAGAACCAGGTGTCCCTGACCTGTCTCGTGAAAGGCTTCTACCCCT CCGATATCGCCGTGGAATGGGAGAGCAACGGCCAGCCCGAGAACAA CTACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 280 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTACTATTGTCACGCCTGGGACGA CAGCCTGAACGTGATCCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 281 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSS |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
| --- | --- | --- |
| 282 | PRT | SYAML |
| 283 | PRT | AIGTGGDTYYADSVKG |
| 284 | PRT | RDDYTSRDAFDY |
| 285 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDYV<br>VFGGGTKLTVL |
| 286 | PRT | SGSSSNIGSNTVN |
| 287 | PRT | YDDLRPS |
| 288 | PRT | AAWDDSLNDYVV |
| 289 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGCTGTGGGTCCGACAGGCCCCTGGAAAAGGCCTTGAATGGG<br>TGTCCGCCATCGGCACAGGCGGCGATACCTACTATGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCA |
| 290 | DNA | AGCTACGCCATGCTG |
| 291 | DNA | GCCATCGGCACAGGCGGCGATACCTACTATGCCGACTCTGTGAAGGG<br>C |
| 292 | DNA | AGGGACGACTACACCAGCAGGGACGCCTTCGATTAT |
| 293 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACTACGTTGTGTTTGGCGGAGGCACCAAGCTGACCG<br>TTCTA |
| 294 | DNA | AGCGGCAGCAGCTCCAACATCGGCAGCAACACCGTGAAC |
| 295 | DNA | TACGACGACCTGCGGCCTAGC |
| 296 | DNA | GCCGCCTGGGACGACAGCCTGAACGACTACGTTGTG |
| 297 | PRT | EVQLLESGGGLVQPGGSLRLSCAASGFTFYSYAMLWVRQAPGKGLEWV<br>SAIGTGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 298 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 299 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGCTGTGGGTCCGACAGGCCCCTGGAAAAGGCCTTGAATGGG<br>TGTCCGCCATCGGCACAGGCGGCGATACCTACTATGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | GGGCCAGGGCACACTGGTCACCGTTTCTTCAGCCAGCACCAAGGGCC CCAGCGTGTTCCCTCTGGCCCCTTGTAGCAGAAGCACCAGCGAGTCT ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGGCCCTCCCTGCCCTCCTTGCCCAGCCCCTGAATTTCTG GGCGGACCCTCCGTGTTCCTGTTCCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 300 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGACTACGTTGTGTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 301 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSS |
| 302 | PRT | SYAML |
| 303 | PRT | AIGTGGDTYYADSVKG |
| 304 | PRT | RDDYTSRDAFDY |
| 305 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVYV VFGGGTKLTVL |
| 306 | PRT | SGSSSNIGSNTVN |
| 307 | PRT | YDDLRPS |
| 308 | PRT | AAWDDSLNVYVV |
| 309 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGCTGTGGGTCCGACAGGCCCCTGGAAAAGGCCTTGAATGGG TGTCCGCCATCGGCACAGGCGGCGATACCTACTATGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCA |
| 310 | DNA | AGCTACGCCATGCTG |
| 311 | DNA | GCCATCGGCACAGGCGGCGATACCTACTATGCCGACTCTGTGAAGGG C |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 312 | DNA | AGGGACGACTACACCAGCAGGGACGCCTTCGATTAT |
| 313 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA CAGCCTGAACGTGTACGTTGTGTTTGGCGGAGGCACCAAGCTGACCG TTCTA |
| 314 | DNA | AGCGGCAGCAGCTCCAACATCGGCAGCAACACCGTGAAC |
| 315 | DNA | TACGACGACCTGCGGCCTAGC |
| 316 | DNA | GCCGCCTGGGACGACAGCCTGAACGTGTACGTTGTG |
| 317 | PRT | EVQLLESGGGLVQPGGSLRLSCAASGFTFYSYAMLWVRQAPGKGLEWV SAIGTGGDTYYADSVKGRFTISRDNSKNTLYLQMNSLRAEDTAVYYCA RRDDYTSRDAFDYWGQGTLVTVSSASTKGPSVFPLAPCSRSTSESTAAL GCLVKDYFPEPVTVSWNSGALTSGVHTFPAVLQSSGLYSLSSVVTVPSSS LGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPRE EQFNSTYRVVSVLTVLHQDWLNGKEYKCKVSNKGLPSSIEKTISKAKGQ PREPQVYTLPPSQEEMTKNQVSLTCLVKGFYPSDIAVEWESNGQPENNY KTTPPVLDSDGSFFLYSRLTVDKSRWQEGNVFSCSVMHEALHNHYTQK SLSLSLGK |
| 318 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNVYV VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 319 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGCTGTGGGTCCGACAGGCCCCTGGAAAAGGCCTTGAATGGG TGTCCGCCATCGGCACAGGCGGCGATACCTACTATGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCAGCCAGCACCAAGGGCC CCAGCGTGTTCCCTCTGGCCCCTTGTAGCAGAAGCACCAGCGAGTCT ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGGCCCTCCCTGCCCTCCTTGCCCAGCCCCTGAATTTCTG GGCGGACCCTCCGTGTTCCTGTTCCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 320 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTATTATTGTGCCGCCTGGGACGA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | CAGCCTGAACGTGTACGTTGTGTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 321 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 322 | PRT | SYAMS |
| 323 | PRT | AIGYGGDTYYADSVKG |
| 324 | PRT | RDDYTSRDAFDY |
| 325 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCHAWDDSLNVYP<br>VFGGGTKLTVL |
| 326 | PRT | SGSSSNIGSNTVN |
| 327 | PRT | YDDLRPS |
| 328 | PRT | HAWDDSLNVYPV |
| 329 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCA |
| 330 | DNA | AGCTACGCCATGAGC |
| 331 | DNA | GCCATCGGCTATGGCGGCGATACCTACTACGCCGACTCTGTGAAGGG<br>C |
| 332 | DNA | AGGGACGACTACACCAGCAGGGACGCCTTCGATTAT |
| 333 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTACTATTGTCACGCCTGGGACGA<br>CAGCCTGAACGTGTACCCTGTTTTTGGCGGAGGCACCAAGCTGACCG<br>TTCTA |
| 334 | DNA | AGCGGCAGCAGCTCCAACATCGGCAGCAACACCGTGAAC |
| 335 | DNA | TACGACGACCTGCGGCCTAGC |
| 336 | DNA | CACGCCTGGGACGACAGCCTGAACGTGTACCCTGTT |
| 337 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| 338 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCHAWDDSLNVYP VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 339 | DNA | GAAGTTCAGCTGCTGGAATCTGGCGGCGGACTGGTTCAACCTGGCGG ATCTCTGAGACTGAGCTGTGCCGCCAGCGGCTTCACCTTTTACAGCTA CGCCATGAGCTGGGTCCGACAGGCCCCTGGAAAAGGCCTTGAATGGG TGTCCGCCATCGGCTATGGCGGCGATACCTACTACGCCGACTCTGTG AAGGGCAGATTCACCATCAGCCGGGACAACAGCAAGAACACCCTGT ACCTGCAGATGAACAGCCTGAGAGCCGAGGACACCGCCGTGTACTAT TGCGCCAGAAGGGACGACTACACCAGCAGGGACGCCTTCGATTATTG GGGCCAGGGCACACTGGTCACCGTTTCTTCAGCAGCACCAAGGGCC CCAGCGTGTTCCCTCTGGCCCCTTGTAGCAGAAGCACCAGCGAGTCT ACAGCCGCCCTGGGCTGCCTCGTGAAGGACTACTTTCCCGAGCCCGT GACCGTGTCCTGGAACTCTGGCGCTCTGACAAGCGGCGTGCACACCT TTCCAGCCGTGCTGCAGAGCAGCGGCCTGTACTCTCTGAGCAGCGTC GTGACAGTGCCCAGCAGCAGCCTGGGCACCAAGACCTACACCTGTAA CGTGGACCACAAGCCCAGCAACACCAAGGTGGACAAGCGGGTGGAA TCTAAGTACGCCCTCCCTGCCCTCCTTGCCCAGCCCCTGAATTTCTG GGCGGACCCTCCGTGTTCCTGTTCCCCCAAAGCCCAAGGACACCCT GATGATCAGCCGGACCCCCGAAGTGACCTGCGTGGTGGTGGATGTGT CCCAGGAAGATCCCGAGGTGCAGTTCAATTGGTACGTGGACGGCGTG GAAGTGCACAACGCCAAGACCAAGCCCAGAGAGGAACAGTTCAACA GCACCTACCGGGTGGTGTCCGTGCTGACAGTGCTGCACCAGGACTGG CTGAACGGCAAAGAGTACAAGTGCAAGGTGTCCAACAAGGGCCTGC CCAGCTCCATCGAGAAAACCATCAGCAAGGCCAAGGGCCAGCCCCG CGAACCCCAGGTGTACACACTGCCTCCAAGCCAGGAAGAGATGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAGACTGACCGTGGACAAGAGCCGGTGGCAGGAAGGCAAC GTGTTCAGCTGCAGCGTGATGCACGAGGCCCTGCACAACCACTACAC CCAGAAGTCCCTGTCTCTGAGCCTGGGCAAG |
| 340 | DNA | CAGTCTGTTCTGACACAGCCTCCTAGCGCCTCTGGCACACCTGGACA GAGAGTGACCATCAGCTGTAGCGGCAGCAGCTCCAACATCGGCAGC AACACCGTGAACTGGTATCAGCAGCTGCCTGGCACAGCCCCTAAACT GCTGATCTACTACGACGACCTGCGGCCTAGCGGCGTGCCAGATAGAT TTTCTGGCAGCAAGAGCGGCACCTCTGCCAGCCTGGCTATTTCTGGA CTGCAGAGCGAGGACGAGGCCGACTACTATTGTCACGCCTGGGACGA CAGCCTGAACGTGTACCCTGTTTTTGGCGGAGGCACCAAGCTGACCG TTCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 341 | PRT | EVQLLESGGGLVQPGGSLRLSCAASGFTFYSYAMSWVRQAPGKGLEWV SAIGYGGDTYYADSVKGRFTISRDNSKNTLYLQMNSLRAEDTAVYYCA RRDDYTSRDAFDYWGQGTLVTVSS |
| 342 | PRT | SYAMS |
| 343 | PRT | AIGYGGDTYYADSVKG |
| 344 | PRT | RDDYTSRDAFDY |
| 345 | PRT | QSVLTQPPSASGTPGQRVTISCSGSSSNIGSNTVNWYQQLPGTAPKLLIYY DDLRPSGVPDRFSGSKSGTSASLAISGLQSEDEADYYCAAWDDSLNDIPV FGGGTKLTVL |
| 346 | PRT | SGSSSNIGSNTVN |
| 347 | PRT | YDDLRPS |
| 348 | PRT | AAWDDSLNDIPV |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 349 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCA |
| 350 | DNA | AGCTACGCCATGAGC |
| 351 | DNA | GCCATCGGCTATGGCGGCGATACCTACTACGCCGACTCTGTGAAGGG<br>C |
| 352 | DNA | AGGGACGACTACACCAGCAGGGACGCCTTCGATTAT |
| 353 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACATCCCTGTTTTTGGCGGAGGCACCAAGCTGACCG<br>TTCTA |
| 354 | DNA | AGCGGCAGCAGCTCCAACATCGGCAGCAACACCGTGAAC |
| 355 | DNA | TACGACGACCTGCGGCCTAGC |
| 356 | DNA | GCCGCCTGGGACGACAGCCTGAACGACATCCCTGTT |
| 357 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 358 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNDIPV<br>FGGGTKLTVLGQPKAAPSVTLFPPSSEELQANKATLVCLISDFYPGAVTV<br>AWKADSSPVKAGVETTTPSKQSNNKYAASSYLSLTPEQWKSHRSYSCQ<br>VTHEGSTVEKTVAPTECS |
| 359 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCAGCAGCACCAAGGGCC<br>CCAGCGTGTTCCCTCTGGCCCCTTGTAGCAGAAGCACCAGCGAGTCT<br>ACAGCCGCCCTGGGCTGCCTCGTGAAGGACTACTTTCCCGAGCCCGT<br>GACCGTGTCCTGGAACTCTGGCGCTCTGACAAGCGGCGTGCACACCT<br>TTCCAGCCGTGCTGCAGAGCAGCGGCCTGTACTCTCTGAGCAGCGTC<br>GTGACAGTGCCCAGCAGCAGCCTGGGCACCAAGACCTACACCTGTAA<br>CGTGGACCACAAGCCCAGCAACACCAAGGTGGACAAGCGGGTGGAA<br>TCTAAGTACGGCCCTCCCTGCCCTCCTTGCCCAGCCCCTGAATTTCTG<br>GGCGGACCCTCCGTGTTCCTGTTCCCCCCAAAGCCCAAGGACACCCT<br>GATGATCAGCCGGACCCCCGAAGTGACCTGCGTGGTGGTGGATGTGT<br>CCCAGGAAGATCCCGAGGTGCAGTTCAATTGGTACGTGGACGGCGTG<br>GAAGTGCACAACGCCAAGACCAAGCCCAGAGAGGAACAGTTCAACA<br>GCACCTACCGGGTGGTGTCCGTGCTGACAGTGCTGCACCAGGACTGG<br>CTGAACGGCAAAGAGTACAAGTGCAAGGTGTCCAACAAGGGCCTGC<br>CCAGCTCCATCGAGAAAACCATCAGCAAGGCCAAGGGCCAGCCCCG<br>CGAACCCCAGGTGTACACACTGCCCTCCAAGCCAGGAAGAGATGACC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
|  |  | AAGAACCAGGTGTCCCTGACCTGTCTCGTGAAAGGCTTCTACCCCTC<br>CGATATCGCCGTGGAATGGGAGAGCAACGGCCAGCCCGAGAACAAC<br>TACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 360 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGACATCCCTGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 361 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSS |
| 362 | PRT | SYAMS |
| 363 | PRT | AIGYGGDTYYADSVKG |
| 364 | PRT | RDDYTSRDAFDY |
| 365 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNVIPV<br>FGGGTKLTVL |
| 366 | PRT | SGSSSNIGSNTVN |
| 367 | PRT | YDDLRPS |
| 368 | PRT | AAWDDSLNVIPV |
| 369 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGT<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCA |
| 370 | DNA | AGCTACGCCATGAGC |
| 371 | DNA | GCCATCGGCTATGGCGGCGATACCTACTACGCCGACTCTGTGAAGGG<br>C |
| 372 | DNA | AGGGACGACTACACCAGCAGGGACGCCTTCGATTAT |
| 373 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGTGATCCCTGTTTTTGGCGGAGGCACCAAGCTGACCG<br>TTCTA |
| 374 | DNA | AGCGGCAGCAGCTCCAACATCGGCAGCAACACCGTGAAC |
| 375 | DNA | TACGACGACCTGCGGCCTAGC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 376 | DNA | GCCGCCTGGGACGACAGCCTGAACGTGATCCCTGTT |
| 377 | PRT | EVQLLESGGGLVQPGGSLRLSCAASGFTFYSYAMSWVRQAPGKGLEWV<br>SAIGYGGDTYYADSVKGRFTISRDNSKNTLYLQMNSLRAEDTAVYYCA<br>RRDDYTSRDAFDYWGQGTLVTVSSASTKGPSVFPLAPCSRSTSESTAAL<br>GCLVKDYFPEPVTVSWNSGALTSGVHTFPAVLQSSGLYSLSSVVTVPSSS<br>LGTKTYTCNVDHKPSNTKVDKRVESKYGPPCPPCPAPEFLGGPSVFLFPP<br>KPKDTLMISRTPEVTCVVVDVSQEDPEVQFNWYVDGVEVHNAKTKPRE<br>EQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNY<br>KTTPPVLDSDGSFFLYSRLTVDKSRWQEGNVFSCSVMHEALHNHYTQK<br>SLSLSLGK |
| 378 | PRT | QSVLTQPPSASGTPGQRVTISCSGSSSNIGSNTVNWYQQLPGTAPKLLIYY<br>DDLRPSGVPDRFSGSKSGTSASLAISGLQSEDEADYYCAAWDDSLNVIPV<br>FGGGTKLTVLGQPKAAPSVTLFPPSSEELQANKATLVCLISDFYPGAVTV<br>AWKADSSPVKAGVETTTPSKQSNNKYAASSYLSLTPEQWKSHRSYSCQ<br>VTHEGSTVEKTVAPTECS |
| 379 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTTACAGCTA<br>CGCCATGAGCTGGGTCCGACAGGCCCCTGGAAAAGGCCTTGAATGGG<br>TGTCCGCCATCGGCTATGGCGGCGATACCTACTACGCCGACTCTGTG<br>AAGGGCAGATTCACCATCAGCCGGGACAACAGCAAGAACACCCTGT<br>ACCTGCAGATGAACAGCCTGAGAGCCGAGGACACCGCCGTGTACTAT<br>TGCGCCAGAAGGGACGACTACACCAGCAGGGACGCCTTCGATTATTG<br>GGGCCAGGGCACACTGGTCACCGTTTCTTCAGCCAGCACCAAGGGCC<br>CAGCGTGTTCCCTCTGGCCCCTTGTAGCAGAAGCACCAGCGAGTCT<br>ACAGCCGCCCTGGGCTGCCTCGTGAAGGACTACTTTCCCGAGCCCGT<br>GACCGTGTCCTGGAACTCTGGCGCTCTGACAAGCGGCGTGCACACCT<br>TTCCAGCCGTGCTGCAGAGCAGCGGCCTGTACTCTCTGAGCAGCGTC<br>GTGACAGTGCCCAGCAGCAGCCTGGGCACCAAGACCTACACCTGTAA<br>CGTGGACCACAAGCCCAGCAACACCAAGGTGGACAAGCGGGTGGAA<br>TCTAAGTACGCCCTCCCTGCCCTCCTTGCCCAGCCCCTGAATTTCTG<br>GGCGGACCCTCCGTGTTCCTGTTCCCCCAAAGCCCAAGGACACCCT<br>GATGATCAGCCGGACCCCCGAAGTGACCTGCGTGGTGGTGGATGTGT<br>CCCAGGAAGATCCCGAGGTGCAGTTCAATTGGTACGTGGACGGCGTG<br>GAAGTGCACAACGCCAAGACCAAGCCCAGAGAGGAACAGTTCAACA<br>GCACCTACCGGGTGGTGTCCGTGCTGACAGTGCTGCACCAGGACTGG<br>CTGAACGGCAAAGAGTACAAGTGCAAGGTGTCCAACAAGGGCCTGC<br>CCAGCTCCATCGAGAAAACCATCAGCAAGGCCAAGGGCCAGCCCCG<br>CGAACCCCAGGTGTACACACTGCCTCCAAGCCAGGAAGAGATGACC<br>AAGAACCAGGTGTCCCTGACCTGTCTCGTGAAAGGCTTCTACCCCTC<br>CGATATCGCCGTGGAATGGGAGAGCAACGGCCAGCCCGAGAACAAC<br>TACAAGACCACCCCCCCTGTGCTGGACAGCGACGGCTCATTCTTCCT<br>GTACAGCAGACTGACCGTGGACAAGAGCCGGTGGCAGGAAGGCAAC<br>GTGTTCAGCTGCAGCGTGATGCACGAGGCCCTGCACAACCACTACAC<br>CCAGAAGTCCCTGTCTCTGAGCCTGGGCAAG |
| 380 | DNA | CAGTCTGTTCTGACACAGCCTCCTAGCGCCTCTGGCACACCTGGACA<br>GAGAGTGACCATCAGCTGTAGCGGCAGCAGCTCCAACATCGGCAGC<br>AACACCGTGAACTGGTATCAGCAGCTGCCTGGCACAGCCCCTAAACT<br>GCTGATCTACTACGACGACCTGCGGCCTAGCGGCGTGCCAGATAGAT<br>TTTCTGGCAGCAAGAGCGGCACCTCTGCCAGCCTGGCTATTTCTGGA<br>CTGCAGAGCGAGGACGAGGCCGACTATTATTGTGCCGCCTGGGACGA<br>CAGCCTGAACGTGATCCCTGTTTTTGGCGGAGGCACCAAGCTGACCG<br>TTCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 381 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 382 | PRT | SYEMN |
| 383 | PRT | GISWNSGWIDYADSVKG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 384 | PRT | SGYSSSWFDPDFDY |
| 385 | PRT | QSVLTQPPSVSGAPGQRVTISCTGSSSDIGAGYDVHWYQQLPGTAPKLLI YGNSNRPSGVPDRFSGSKSGTSASLAITGLQAEDEADYYCSSYAGPNPY VVFGGGTKLTVL |
| 386 | PRT | TGSSSDIGAGYDVH |
| 387 | PRT | GNSNRPS |
| 388 | PRT | SSYAGPNPYVV |
| 389 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 390 | DNA | AGCTACGAGATGAAC |
| 391 | DNA | GGCATCAGCTGGAATAGCGGCTGGATCGACTACGCCGACAGCGTGA AGGGC |
| 392 | DNA | AGCGGCTACAGCAGCTCTTGGTTTGACCCCGACTTCGACTAT |
| 393 | DNA | CAGTCTGTTCTGACACAGCCTCCATCTGTGTCTGGCGCCCCTGGACAG AGAGTGACCATCAGCTGTACAGGCAGCAGCTCCGATATTGGCGCCGG ATACGACGTGCACTGGTATCAGCAACTGCCTGGCACAGCCCCTAAGC TGCTGATCTACGGCAACAGCAACAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGCTG GCCCCAATCCTTACGTGGTGTTTGGCGGCGGAACAAAGCTGACCGTT CTA |
| 394 | DNA | ACAGGCAGCAGCTCCGATATTGGCGCCGGATACGACGTGCAC |
| 395 | DNA | GGCAACAGCAACAGACCTAGC |
| 396 | DNA | AGCAGCTACGCTGGCCCCAATCCTTACGTGGTG |
| 397 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 398 | PRT | QSVLTQPPSVSGAPGQRVTISCTGSSSDIGAGYDVHWYQQLPGTAPKLLI YGNSNRPSGVPDRFSGSKSGTSASLAITGLQAEDEADYYCSSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 399 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT |

| TABLE 1A-continued |
| --- |
| Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587). |

| SEQ ID No | SEQ Type | SEQUENCE |
| --- | --- | --- |
|  |  | CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 400 | DNA | CAGTCTGTTCTGACACAGCCTCCATCTGTGTCTGGCGCCCTGGACAG AGAGTGACCATCAGCTGTACAGGCAGCAGCTCCGATATTGGCGCCGG ATACGACGTGCACTGGTATCAGCAACTGCCTGGCACAGCCCCTAAGC TGCTGATCTACGGCAACAGCAACAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGCTG GCCCCAATCCTTACGTGGTGTTTGGCGGCGGAACAAAGCTGACCGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 401 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSS |
| 402 | PRT | SYEMN |
| 403 | PRT | GISWNSGWIDYADSVKG |
| 404 | PRT | SGYSSSWFDPDFDY |
| 405 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGINPY VVFGGGTKLTVL |
| 406 | PRT | TGSSSNIGAGYDVH |
| 407 | PRT | GNSNRPS |
| 408 | PRT | QSYAGINPYVV |
| 409 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 410 | DNA | AGCTACGAGATGAAC |
| 411 | DNA | GGCATCAGCTGGAATAGCGGCTGGATCGACTACGCCGACAGCGTGA AGGGC |
| 412 | DNA | AGCGGCTACAGCAGCTCTTGGTTTGACCCCGACTTCGACTAT |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| 413 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGAGCTACGCCG<br>GCATCAACCCCTACGTGGTGTTTGGCGGAGGCACCAAGCTGACAGTT<br>CTA |
| 414 | DNA | ACAGGCAGCAGCTCCAATATCGGAGCCGGCTATGACGTGCAC |
| 415 | DNA | GGCAACAGCAACAGACCCAGC |
| 416 | DNA | CAGAGCTACGCCGGCATCAACCCCTACGTGGTG |
| 417 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPGK |
| 418 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGINPY<br>VVFGGGTKLTVLGQPKAAPSVTLFPPSSEELQANKATLVCLISDFYPGAV<br>TVAWKADSSPVKAGVETTTPSKQSNNKYAASSYLSLTPEQWKSHRSYS<br>CQVTHEGSTVEKTVAPTECS |
| 419 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCCAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 420 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGAGCTACGCCG<br>GCATCAACCCCTACGTGGTGTTTGGCGGAGGCACCAAGCTGACAGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 421 | PRT | EVQLLESGGGLVQPGGSLRLSCAASGFDFSSYEMNWVRQAPGKGLEWV<br>SGISWNSGWIGYADSVKGRFTISRDNSKNTLYLQMNSLRAEDTAVYYC<br>ARSGYSSSWFDPDFDYWGQGTLVTVSS |
| 422 | PRT | SYEMN |
| 423 | PRT | GISWNSGWIGYADSVKG |
| 424 | PRT | SGYSSSWFDPDFDY |
| 425 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGPNPY<br>VVFGGGTKLTVL |
| 426 | PRT | TGSSSNIGAGYDVH |
| 427 | PRT | GNSNRPS |
| 428 | PRT | QSYAGPNPYVV |
| 429 | DNA | GAAGTTCAGCTGCTGGAATCTGGCGGCGGACTGGTTCAACCTGGCGG<br>ATCTCTGAGACTGAGCTGTGCCGCCAGCGGCTTCGATTTCAGCAGCT<br>ACGAGATGAACTGGGTCCGACAGGCCCCTGGCAAAGGCCTTGAATG<br>GGTGTCCGGCATCAGCTGGAATAGCGGCTGGATCGGCTACGCCGATA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 430 | DNA | AGCTACGAGATGAAC |
| 431 | DNA | GGCATCAGCTGGAATAGCGGCTGGATCGGCTACGCCGATAGCGTGAA<br>GGGC |
| 432 | DNA | AGCGGCTACAGCAGCTCTTGGTTTGACCCCGACTTCGACTAT |
| 433 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTA |
| 434 | DNA | ACAGGCAGCAGCTCCAATATCGGAGCCGGCTATGACGTGCAC |
| 435 | DNA | GGCAACAGCAACAGACCCAGC |
| 436 | DNA | CAGTCTTACGCTGGCCCCAATCCTTACGTGGTG |
| 437 | PRT | EVQLLESGGGLVQPGGSLRLSCAASGFDFSSYEMNWVRQAPGKGLEWV<br>SGISWNSGWIGYADSVKGRFTISRDNSKNTLYLQMNSLRAEDTAVYYC<br>ARSGYSSSWFDPDFDYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPGK |
| 438 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGPNPY<br>VVFGGGTKLTVLGQPKAAPSVTLFPPSSEELQANKATLVCLISDFYPGAV |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | TVAWKADSSPVKAGVETTTPSKQSNNKYAASSYLSLTPEQWKSHRSYS CQVTHEGSTVEKTVAPTECS |
| 439 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT ACGAGATGAACTGGGTCCGACAGGCCCCTGGCAAAGGCCTTGAATG GGTGTCCGGCATCAGCTGGAATAGCGGCTGGATCGGCTACGCCGATA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 440 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 441 | PRT | EVQLLESGGGLVQPGGSLRLSCAASGFDFSSYEMNWVRQAPGKGLEWV SGISWNSGWIDYADSVKGRFTISRDNSKNTLYLQMNSLRAEDTAVYYC ARSGYSSSWFDPDFDYWGQGTLVTVSS |
| 442 | PRT | SYEMN |
| 443 | PRT | GISWNSGWIDYADSVKG |
| 444 | PRT | SGYSSSWFDPDFDY |
| 445 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVL |
| 446 | PRT | TGSSSNIGAGYDVH |
| 447 | PRT | GNSNRPS |
| 448 | PRT | QSYAGPNPYVV |
| 449 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT ACGAGATGAACTGGGTCCGACAGGCCCCTGGCAAAGGCCTTGAATG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 450 | DNA | AGCTACGAGATGAAC |
| 451 | DNA | GGCATCAGCTGGAATAGCGGCTGGATCGACTACGCCGACAGCGTGA<br>AGGGC |
| 452 | DNA | AGCGGCTACAGCAGCTCTTGGTTTGACCCCGACTTCGACTAT |
| 453 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTA |
| 454 | DNA | ACAGGCAGCAGCTCCAATATCGGAGCCGGCTATGACGTGCAC |
| 455 | DNA | GGCAACAGCAACAGACCCAGC |
| 456 | DNA | CAGTCTTACGCTGGCCCCAATCCTTACGTGGTG |
| 457 | PRT | EVQLLESGGGLVQPGGSLRLSCAASGFDFSSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPGK |
| 458 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGPNPY<br>VVFGGGTKLTVLGQPKAAPSVTLFPPSSEELQANKATLVCLISDFYPGAV<br>TVAWKADSSPVKAGVETTTPSKQSNNKYAASSYLSLTPEQWKSHRSYS<br>CQVTHEGSTVEKTVAPTECS |
| 459 | DNA | GAAGTTCAGCTGCTGGAATCTGGCGGCGGACTGGTTCAACCTGGCGG<br>ATCTCTGAGACTGAGCTGTGCCGCCAGCGGCTTCGATTTCAGCAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCCAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 460 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 461 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 462 | PRT | SYEMN |
| 463 | PRT | GISWNSGWIDYADSVKG |
| 464 | PRT | SGYSSSWFDPDFDY |
| 465 | PRT | QSVLTQPPSVSGAPGQRVTISCTGSSSNIGAGYDVHWYQQLPGTAPKLLI<br>YGNSNRPSGVPDRFSGSKSGTSASLAITGLQAEDEADYYCQSYAGPNPY<br>VVFGGGTKLTVL |
| 466 | PRT | TGSSSNIGAGYDVH |
| 467 | PRT | GNSNRPS |
| 468 | PRT | QSYAGPNPYVV |
| 469 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 470 | DNA | AGCTACGAGATGAAC |
| 471 | DNA | GGCATCAGCTGGAATAGCGGCTGGATCGACTACGCCGACAGCGTGA<br>AGGGC |
| 472 | DNA | AGCGGCTACAGCAGCTCTTGGTTTGACCCCGACTTCGACTAT |
| 473 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTA |
| 474 | DNA | ACAGGCAGCAGCTCCAATATCGGAGCCGGCTATGACGTGCAC |
| 475 | DNA | GGCAACAGCAACAGACCCAGC |
| 476 | DNA | CAGTCTTACGCTGGCCCCAATCCTTACGTGGTG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 477 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 478 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 479 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 480 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 481 | PRT | EVQLLESGGGLVQPGGSLRLSCAASGFDFDSYEMNWVRQAPGKGLEW VSGISWNSGWIDYADSVKGRFTISRDNSKNTLYLQMNSLRAEDTAVYY CARSGYSSSWFDPDFDYWGQGTLVTVSS |
| 482 | PRT | SYEMN |
| 483 | PRT | GISWNSGWIDYADSVKG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 484 | PRT | SGYSSSWFDPDFDY |
| 485 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVL |
| 486 | PRT | TGSSSNIGAGYDVH |
| 487 | PRT | GNSNRPS |
| 488 | PRT | QSYAGPNPYVV |
| 489 | DNA | GAAGTTCAGCTGCTGGAATCTGGCGGCGGACTGGTTCAACCTGGCGG ATCTCTGAGACTGAGCTGTGCCGCCAGCGGCTTCGACTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 490 | DNA | AGCTACGAGATGAAC |
| 491 | DNA | GGCATCAGCTGGAATAGCGGCTGGATCGACTACGCCGACAGCGTGA AGGGC |
| 492 | DNA | AGCGGCTACAGCAGCTCTTGGTTTGACCCCGACTTCGACTAT |
| 493 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTCAGTCTTACGCTG GCCCCAATCCTTACGTGGTGTTTGGCGGCGGAACAAAGCTGACCGTT CTA |
| 494 | DNA | ACAGGCAGCAGCTCCAATATCGGAGCCGGCTATGACGTGCAC |
| 495 | DNA | GGCAACAGCAACAGACCCAGC |
| 496 | DNA | CAGTCTTACGCTGGCCCCAATCCTTACGTGGTG |
| 497 | PRT | EVQLLESGGGLVQPGGSLRLSCAASGFDFDSYEMNWVRQAPGKGLEW VSGISWNSGWIDYADSVKGRFTISRDNSKNTLYLQMNSLRAEDTAVYY CARSGYSSSWFDPDFDYWGQGTLVTVSSASTKGPSVFPLAPSSKSTSGG TAALGCLVKDYFPEPVTVSWNSGALTSGVHTFPAVLQSSGLYSLSSVVT VPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEAL HNHYTQKSLSLSPGK |
| 498 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCQSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 499 | DNA | GAAGTTCAGCTGCTGGAATCTGGCGGCGGACTGGTTCAACCTGGCGG ATCTCTGAGACTGAGCTGTGCCGCCAGCGGCTTCGACTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 500 | DNA | CAGTCTGTTCTGACACAGCCTCCATCTGTGTCTGGCGCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCAACAGCAACAGACCCAGCGGCGTGCCCGATAGA<br>TTTTCCGGCTCTAAGAGCGGCACAAGCGCCAGCCTGGCTATTACTGG<br>ACTGCAGGCCGAGGACGAGGCCGACTACTACTGTCAGTCTTACGCTG<br>GCCCCAATCCTTACGTGGTGTTTGGCGGCGGAACAAAGCTGACCGTT<br>CTAGGCCAGCCTAAAGCCGCCCCTAGCGTGACCCTGTTCCCTCCAAG<br>CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 501 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSS |
| 502 | PRT | SYEMN |
| 503 | PRT | GISWNSGWIDYADSVKG |
| 504 | PRT | SGYSSSWFDPDFDY |
| 505 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCQSYAGINPY<br>VVFGGGTKLTVL |
| 506 | PRT | TGSSSDIGAGYDVH |
| 507 | PRT | GNSNRPS |
| 508 | PRT | QSYAGINPYVV |
| 509 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 510 | DNA | AGCTACGAGATGAAC |
| 511 | DNA | GGCATCAGCTGGAATAGCGGCTGGATCGACTACGCCGACAGCGTGA<br>AGGGC |
| 512 | DNA | AGCGGCTACAGCAGCTCTTGGTTTGACCCCGACTTCGACTAT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
| --- | --- | --- |
| 513 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGTCAGAGCTACGCCG<br>GCATCAACCCCTACGTGGTGTTTGGCGGAGGCACCAAGCTGACAGTT<br>CTA |
| 514 | DNA | ACAGGCAGCAGCTCCGATATTGGCGCCGGATACGACGTGCAC |
| 515 | DNA | GGCAACAGCAACAGACCTAGC |
| 516 | DNA | CAGAGCTACGCCGGCATCAACCCCTACGTGGTG |
| 517 | PRT | EVQLLESGGGLVQPGGSLRLSCAASGFTFDSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPGK |
| 518 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCQSYAGINPY<br>VVFGGGTKLTVLGQPKAAPSVTLFPPSSEELQANKATLVCLISDFYPGAV<br>TVAWKADSSPVKAGVETTTPSKQSNNKYAASSYLSLTPEQWKSHRSYS<br>CQVTHEGSTVEKTVAPTECS |
| 519 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCCAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG<br>GCCAGCCCGAGAACAACTACAAGACCACCCCCCCTGTGCTGGACAGC<br>GACGGCTCATTCTTCCTGTACAGCAAGCTGACCGTGGACAAGTCCCG<br>GTGGCAGCAGGGCAACGTGTTCAGCTGCAGCGTGATGCACGAGGCCC<br>TGCACAACCACTACACCCAGAAGTCCCTGAGCCTGAGCCCTGGCAAG |
| 520 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGTCAGAGCTACGCCG<br>GCATCAACCCCTACGTGGTGTTTGGCGGAGGCACCAAGCTGACAGTT<br>CTAGGCCAGCCTAAAGCCGCCCCTAGCGTGACCCTGTTCCCTCCAAG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | CAGCGAGGAACTGCAGGCCAACAAGGCCACCCTCGTGTGCCTGATCA<br>GCGACTTCTATCCTGGCGCCGTGACCGTGGCCTGGAAGGCCGATAGC<br>TCTCCTGTGAAGGCCGGCGTGGAAACCACCACCCCTAGCAAGCAGAG<br>CAACAACAAATACGCCGCCAGCAGCTACCTGAGCCTGACCCCCGAGC<br>AGTGGAAGTCCCACAGATCCTACAGCTGCCAAGTGACCCACGAGGGC<br>AGCACCGTGGAAAAGACAGTGGCCCCTACCGAGTGCAGC |
| 521 | PRT | EVQLLESGGGLVQPGGSLRLSCAASGFDFDSYEMNWVRQAPGKGLEW<br>VSGISWNSGWIDYADSVKGRFTISRDNSKNTLYLQMNSLRAEDTAVYY<br>CARSGYSSSWFDPDFDYWGQGTLVTVSS |
| 522 | PRT | SYEMN |
| 523 | PRT | GISWNSGWIDYADSVKG |
| 524 | PRT | SGYSSSWFDPDFDY |
| 525 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCSSYEGINPYV<br>VFGGGTKLTVL |
| 526 | PRT | TGSSSDIGAGYDVH |
| 527 | PRT | GNSNRPS |
| 528 | PRT | SSYEGINPYVV |
| 529 | DNA | GAAGTTCAGCTGCTGGAATCTGGCGGCGGACTGGTTCAACCTGGCGG<br>ATCTCTGAGACTGAGCTGTGCCGCCAGCGGCTTCGACTTCGATAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 530 | DNA | AGCTACGAGATGAAC |
| 531 | DNA | GGCATCAGCTGGAATAGCGGCTGGATCGACTACGCCGACAGCGTGA<br>AGGGC |
| 532 | DNA | AGCGGCTACAGCAGCTCTTGGTTTGACCCCGACTTCGACTAT |
| 533 | DNA | CAGTCTGTTCTGACACAGCCTCCATCTGTGTCTGGCGCCCCTGGACAG<br>AGAGTGACCATCAGCTGTACAGGCAGCAGCTCCGATATTGGCGCCGG<br>ATACGACGTGCACTGGTATCAGCAACTGCCTGGCACAGCCCCTAAGC<br>TGCTGATCTACGGCAACAGCAACAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGCAGCAGCTACGAG<br>GGCATCAACCCCTACGTGGTGTTTGGCGGCGGAACAAAGCTGACCGT<br>TCTA |
| 534 | DNA | ACAGGCAGCAGCTCCGATATTGGCGCCGGATACGACGTGCAC |
| 535 | DNA | GGCAACAGCAACAGACCTAGC |
| 536 | DNA | AGCAGCTACGAGGGCATCAACCCCTACGTGGTG |
| 537 | PRT | EVQLLESGGGLVQPGGSLRLSCAASGFDFDSYEMNWVRQAPGKGLEW<br>VSGISWNSGWIDYADSVKGRFTISRDNSKNTLYLQMNSLRAEDTAVYY<br>CARSGYSSSWFDPDFDYWGQGTLVTVSSASTKGPSVFPLAPSSKSTSGG<br>TAALGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEK<br>TISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEAL<br>HNHYTQKSLSLSPGK |
| 538 | PRT | QSVLTQPPSVSGAPGQRVTISCTGSSSDIGAGYDVHWYQQLPGTAPKLLI<br>YGNSNRPSGVPDRFSGSKSGTSASLAITGLQAEDEADYYCSSYEGINPYV |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | VFGGGTKLTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 539 | DNA | GAAGTTCAGCTGCTGGAATCTGGCGGCGGACTGGTTCAACCTGGCGG ATCTCTGAGACTGAGCTGTGCCGCCAGCGGCTTCGACTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 540 | DNA | CAGTCTGTTCTGACACAGCCTCCATCTGTGTCTGGCGCCCCTGGACAG AGAGTGACCATCAGCTGTACAGGCAGCAGCTCCGATATTGGCGCCGG ATACGACGTGCACTGGTATCAGCAACTGCCTGGCACAGCCCCTAAGC TGCTGATCTACGGCAACAGCAACAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGAG GGCATCAACCCCTACGTGGTGTTTGGCGGCGGAACAAAGCTGACCGT TCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 541 | PRT | EVQLLESGGGLVQPGGSLRLSCAASGFDFSSYEMNWVRQAPGKGLEWV SGISWNSGWIDYADSVKGRFTISRDNSKNTLYLQMNSLRAEDTAVYYC ARSGYSSSWFDPDFDYWGQGTLVTVSS |
| 542 | PRT | SYEMN |
| 543 | PRT | GISWNSGWIDYADSVKG |
| 544 | PRT | SGYSSSWFDPDFDY |
| 545 | PRT | QSVLTQPPSVSGAPGQRVTISCTGSSSNIGAGYDVHWYQQLPGTAPKLLI YGASNRPSGVPDRFSGSKSGTSASLAITGLQAEDEADYYCSSYEGPNPYV VFGGGTKLTVL |
| 546 | PRT | TGSSSNIGAGYDVH |
| 547 | PRT | GASNRPS |
| 548 | PRT | SSYEGPNPYVV |
| 549 | DNA | GAAGTTCAGCTGCTGGAATCTGGCGGCGGACTGGTTCAACCTGGCGG ATCTCTGAGACTGAGCTGTGCCGCCAGCGGCTTCGATTTCAGCAGCT |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
| --- | --- | --- |
| | | ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCA |
| 550 | DNA | AGCTACGAGATGAAC |
| 551 | DNA | GGCATCAGCTGGAATAGCGGCTGGATCGACTACGCCGACAGCGTGA<br>AGGGC |
| 552 | DNA | AGCGGCTACAGCAGCTCTTGGTTTGACCCCGACTTCGACTAT |
| 553 | DNA | CAGTCTGTTCTGACACAGCCTCCATCTGTGTCTGGCGCCCCTGGACAG<br>AGAGTGACCATCAGCTGTACAGGCAGCAGCTCCAATATCGGAGCCGG<br>CTATGACGTGCACTGGTATCAGCAGCTGCCTGGCACAGCCCCTAAAC<br>TGCTGATCTACGGCGCCAGCAATAGACCTAGCGGCGTGCCCGATAGA<br>TTCAGCGGCTCTAAGTCTGGCACAAGCGCCAGCCTGGCCATTACTGG<br>ACTGCAGGCCGAAGATGAGGCCGACTACTACTGCAGCAGCTACGAG<br>GGCCCCAATCCTTACGTGGTGTTTGGCGGCGGAACAAAGCTGACCGT<br>TCTA |
| 554 | DNA | ACAGGCAGCAGCTCCAATATCGGAGCCGGCTATGACGTGCAC |
| 555 | DNA | GGCGCCAGCAATAGACCTAGC |
| 556 | DNA | AGCAGCTACGAGGGCCCCAATCCTTACGTGGTG |
| 557 | PRT | EVQLLESGGGLVQPGGSLRLSCAASGFDFSSYEMNWVRQAPGKGLEWV<br>SGISWNSGWIDYADSVKGRFTISRDNSKNTLYLQMNSLRAEDTAVYYC<br>ARSGYSSSWFDPDFDYWGQGTLVTVSSASTKGPSVFPLAPSSKSTSGGT<br>AALGCLVKDYFPEPVTVSWNSGALTSGVHTFPAVLQSSGLYSLSSVVTV<br>PSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNG<br>QPENNYKTTPPVLDSDGSFFLYSKLTVDKSRWQQGNVFSCSVMHEALH<br>NHYTQKSLSLSPGK |
| 558 | PRT | QSVLTQPPSVSGAPGQRVTISCTGSSSNIGAGYDVHWYQQLPGTAPKLLI<br>YGASNRPSGVPDRFSGSKSGTSASLAITGLQAEDEADYYCSSYEGPNPYV<br>VFGGGTKLTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |
| 559 | DNA | GAAGTTCAGCTGCTGGAATCTGGCGGCGGACTGGTTCAACCTGGCGG<br>ATCTCTGAGACTGAGCTGTGCCGCCAGCGGCTTCGATTTCAGCAGCT<br>ACGAGATGAACTGGGTCCGACAGGCCCCTGGCAAAGGCCTTGAATG<br>GGTGTCCGGCATCAGCTGGAATAGCGGCTGGATCGACTACGCCGACA<br>GCGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAAGCGGCTACAGCAGCTCTTGGTTTGACCCCGAC<br>TTCGACTATTGGGGCCAGGGCACACTGGTCACAGTCTCTTCAGCTAG<br>CACCAAGGGCCCCAGCGTGTTCCCTCTGGCCCCTAGCAGCAAGAGCA<br>CATCTGGCGGAACAGCCGCCCTGGGCTGCCTCGTGAAGGACTACTTT<br>CCCGAGCCCGTGACCGTGTCCTGGAACTCTGGCGCTCTGACAAGCGG<br>CGTGCACACCTTTCCAGCCGTGCTGCAGAGCAGCGGCCTGTACTCTCT<br>GAGCAGCGTCGTGACAGTGCCCAGCAGCTCTCTGGGCACCCAGACCT<br>ACATCTGCAACGTGAACCACAAGCCCAGCAACACCAAGGTGGACAA<br>GAAGGTGGAACCCAAGAGCTGCGACAAGACCCACACCTGTCCCCCTT<br>GTCCTGCCCCCGAACTGCTGGGAGGCCCTTCCGTGTTCCTGTTCCCCC<br>CAAAGCCCAAGGACACCCTGATGATCAGCCGGACCCCCGAAGTGAC<br>CTGCGTGGTGGTGGATGTGTCCCACGAGGACCCTGAAGTGAAGTTCA<br>ATTGGTACGTGGACGGCGTGGAAGTGCACAACGCCAAGACCAAGCC<br>TAGAGAGGAACAGTACAACAGCACCTACCGGGTGGTGTCCGTGCTGA<br>CAGTGCTGCACCAGGACTGGCTGAACGGCAAAGAGTACAAGTGCAA<br>GGTGTCCAACAAGGCCCTGCCTGCCCCCATCGAGAAAACCATCAGCA<br>AGGCCAAGGGCCAGCCCCGCGAACCCCAGGTGTACACACTGCCCCCA<br>AGCAGGGACGAGCTGACCAAGAACCAGGTGTCCCTGACCTGTCTCGT<br>GAAAGGCTTCTACCCCTCCGATATCGCCGTGGAATGGGAGAGCAACG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 560 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCGCCAGCAATAGACCTAGCGGCGTGCCCGATAGA TTCAGCGGCTCTAAGTCTGGCACAAGCGCCAGCCTGGCCATTACTGG ACTGCAGGCCGAAGATGAGGCCGACTACTACTGCAGCAGCTACGAG GGCCCCAATCCTTACGTGGTGTTTGGCGGCGGAACAAAGCTGACCGT TCTAGGCCAGCCTAAAGCCGCCCCTAGCGTGACCCTGTTCCCTCCAA GCAGCGAGGAACTGCAGGCCAACAAGGCCACCCTCGTGTGCCTGATC AGCGACTTCTATCCTGGCGCCGTGACCGTGGCCTGGAAGGCCGATAG CTCTCCTGTGAAGGCCGGCGTGGAAACCACCACCCCTAGCAAGCAGA GCAACAACAAATACGCCGCCAGCAGCTACCTGAGCCTGACCCCCGAG CAGTGGAAGTCCCACAGATCCTACAGCTGCCAAGTGACCCACGAGGG CAGCACCGTGGAAAAGACAGTGGCCCCTACCGAGTGCAGC |
| 561 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSS |
| 562 | PRT | SYEMN |
| 563 | PRT | GISWNSGWIDYADSVKG |
| 564 | PRT | SGYSSSWFDPDFDY |
| 565 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCSSYAGPNPY VVFGGGTKLTVL |
| 566 | PRT | TGSSSNIGAGYDVH |
| 567 | PRT | GNSNRPS |
| 568 | PRT | SSYAGPNPYVV |
| 569 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCA |
| 570 | DNA | AGCTACGAGATGAAC |
| 571 | DNA | GGCATCAGCTGGAATAGCGGCTGGATCGACTACGCCGACAGCGTGA AGGGC |
| 572 | DNA | AGCGGCTACAGCAGCTCTTGGTTTGACCCCGACTTCGACTAT |
| 573 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTAGCTCTTACGCTG GCCCCAATCCTTACGTGGTGTTTGGCGGCGGAACAAAGCTGACCGTT CTA |
| 574 | DNA | ACAGGCAGCAGCTCCAATATCGGAGCCGGCTATGACGTGCAC |
| 575 | DNA | GGCAACAGCAACAGACCCAGC |
| 576 | DNA | AGCTCTTACGCTGGCCCCAATCCTTACGTGGTG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| 577 | PRT | EVQLLESGGGLVQPGGSLRLSCAASGFTFDSYEMNWVRQAPGKGLEWV SGISWNSGWIDYADSVKGRFTISRDNSKNTLYLQMNSLRAEDTAVYYC ARSGYSSSWFDPDFDYWGQGTLVTVSSASTKGPSVFPLAPSSKSTSGGT AALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALH NHYTQKSLSLSPGK |
| 578 | PRT | QSVLTQPPSVSGAPGQRVTISCTGSSSNIGAGYDVHWYQQLPGTAPKLLI YGNSNRPSGVPDRFSGSKSGTSASLAITGLQAEDEADYYCSSYAGPNPY VVFGGGTKLTVLGQPKAAPSVTLFPPSSEELQANKATLVCLISDFYPGAV TVAWKADSSPVKAGVETTTPSKQSNNKYAASSYLSLTPEQWKSHRSYS CQVTHEGSTVEKTVAPTECS |
| 579 | DNA | GAAGTTCAGCTGCTGGAATCTGGCGGCGGACTGGTTCAACCTGGCGG ATCTCTGAGACTGAGCTGTGCCGCCAGCGGCTTCACCTTCGATAGCT ACGAGATGAACTGGGTCCGACAGGCCCCTGGCAAAGGCCTTGAATG GGTGTCCGGCATCAGCTGGAATAGCGGCTGGATCGACTACGCCGACA GCGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAAGCGGCTACAGCAGCTCTTGGTTTGACCCCGAC TTCGACTATTGGGGCCAGGGCACACTGGTCACAGTCTCTTCAGCCAG CACCAAGGGCCCCAGCGTGTTCCCTCTGGCCCCTAGCAGCAAGAGCA CATCTGGCGGAACAGCCGCCCTGGGCTGCCTCGTGAAGGACTACTTT CCCGAGCCCGTGACCGTGTCCTGGAACTCTGGCGCTCTGACAAGCGG CGTGCACACCTTTCCAGCCGTGCTGCAGAGCAGCGGCCTGTACTCTCT GAGCAGCGTCGTGACAGTGCCCAGCAGCTCTCTGGGCACCCAGACCT ACATCTGCAACGTGAACCACAAGCCCAGCAACACCAAGGTGGACAA GAAGGTGGAACCCAAGAGCTGCGACAAGACCCACACCTGTCCCCCTT GTCCTGCCCCCGAACTGCTGGGAGGCCCTTCCGTGTTCCTGTTCCCCC CAAAGCCCAAGGACACCCTGATGATCAGCCGGACCCCCGAAGTGAC CTGCGTGGTGGTGGATGTGTCCCACGAGGACCCTGAAGTGAAGTTCA ATTGGTACGTGGACGGCGTGGAAGTGCACAACGCCAAGACCAAGCC TAGAGAGGAACAGTACAACAGCACCTACCGGGTGGTGTCCGTGCTGA CAGTGCTGCACCAGGACTGGCTGAACGGCAAAGAGTACAAGTGCAA GGTGTCCAACAAGGCCCTGCCTGCCCCCATCGAGAAAACCATCAGCA AGGCCAAGGGCCAGCCCCGCGAACCCCAGGTGTACACACTGCCCCCA AGCAGGGACGAGCTGACCAAGAACCAGGTGTCCCTGACCTGTCTCGT GAAAGGCTTCTACCCCTCCGATATCGCCGTGGAATGGGAGAGCAACG GCCAGCCCGAGAACAACTACAAGACCACCCCCCCTGTGCTGGACAGC GACGGCTCATTCTTCCTGTACAGCAAGCTGACCGTGGACAAGTCCCG GTGGCAGCAGGGCAACGTGTTCAGCTGCAGCGTGATGCACGAGGCCC TGCACAACCACTACACCCAGAAGTCCCTGAGCCTGAGCCCTGGCAAG |
| 580 | DNA | CAGTCTGTTCTGACACAGCCTCCATCTGTGTCTGGCGCCCCTGGACAG AGAGTGACCATCAGCTGTACAGGCAGCAGCTCCAATATCGGAGCCGG CTATGACGTGCACTGGTATCAGCAGCTGCCTGGCACAGCCCCTAAAC TGCTGATCTACGGCAACAGCAACAGACCCAGCGGCGTGCCCGATAGA TTTTCCGGCTCTAAGAGCGGCACAAGCGCCAGCCTGGCTATTACTGG ACTGCAGGCCGAGGACGAGGCCGACTACTACTGTAGCTCTTACGCTG GCCCCAATCCTTACGTGGTGTTTGGCGGCGGAACAAAGCTGACCGTT CTAGGCCAGCCTAAAGCCGCCCCTAGCGTGACCCTGTTCCCTCCAAG CAGCGAGGAACTGCAGGCCAACAAGGCCACCCTCGTGTGCCTGATCA GCGACTTCTATCCTGGCGCCGTGACCGTGGCCTGGAAGGCCGATAGC TCTCCTGTGAAGGCCGGCGTGGAAACCACCACCCCTAGCAAGCAGAG CAACAACAAATACGCCGCCAGCAGCTACCTGAGCCTGACCCCCGAGC AGTGGAAGTCCCACAGATCCTACAGCTGCCAAGTGACCCACGAGGGC AGCACCGTGGAAAAGACAGTGGCCCCTACCGAGTGCAGC |
| 581 | PRT | HHHHHHKNNVPRLKLSYKEMLESNNVITFNGLANSSSYHTFLLDEERSR LYVGAKDHIFSFDLVNIKDFQKIVWPVSYTRRDECKWAGKDILKECANF IKVLKAYNQTHLYACGTGAFHPICTYIEIGHHPEDNIFKLENSHFENGRG KSPYDPKLLTASLLIDGELYSGTAADFMGRDFAIFRTLGHHHPIRTEQHD SRWLNDPKFISAHLISESDNPEDDKVYFFFRENAIDGEHSGKATHARIGQI CKNDFGGHRSLVNKWTTFLKARLICSVPGPNGIDTHFDELQDVFLMNFK DPKNPVVYGVFTTSSNIFKGSAVCMYSMSDVRRVFLGPYAHRDGPNYQ WVPYQGRVPYPRPGTCPSKTFGGFDSTKDLPDDVITFARSHPAMYNPVF PMNNRPIVIKTDVNYQFTQIVVDRVDAEDGQYDVMFIGTDVGTVLKVV |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | SIPKETWYDLEEVLLEEMTVFREPTAISAMELSTKQQQLYIGSTAGVAQL<br>PLHRCDIYGKACAECCLARDPYCAWDGSACSRYFPTAKRATRAQDIRN<br>GDPLTHCSDLHHDNHHGHSPEERIIYGVENSSTFLECSPKSQRALVYWQF<br>QRRNEERKEEIRVDDHIIRTDQGLLLRSLQQKDSGNYLCHAVEHGFIQTL<br>LKVTLEVIDTEHLEELLHKDDDGDGSKTKEMSNSMTPSQKVWYRDFMQ<br>LINHPNLNTMDEFCEQVWKRDRKQRRQRPGHTPGNSNKWKHLQENKK<br>GRNRRTHEFERAPRSVDIEGRMDPKSCDKTHTCPPCPAPELLGGPSVFLF<br>PPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYT<br>QKSLSLSPGK |
| 582 | PRT | NYQNGKNNVPRLKLSYKEMLESNNVITFNGLANSSSYHTFLLDEERSRL<br>YVGAKDHIFSFDLVNIKDFQKIVWPVSYTRRDECKWAGKDILKECANFI<br>KVLKAYNQTHLYACGTGAFHPICTYIEIGHHPEDNIFKLENSHFENGRGK<br>SPYDPKLLTASLLIDGELYSGTAADFMGRDFAIFRTLGHHHPIRTEQHDS<br>RWLNDPKFISAHLISESDNPEDDKVYFFFRENAIDGEHSGKATHARIGQIC<br>KNDFGGHRSLVNKWTTFLKARLICSVPGPNGIDTHFDELQDVFLMNFKD<br>PKNPVVYGVFTTSSNIFKGSAVCMYSMSDVRRVFLGPYAHRDGPNYQW<br>VPYQGRVPYPRPGTCPSKTFGGFDSTKDLPDDVITFARSHPAMYNPVFP<br>MNNRPIVIKTDVNYQFTQIVVDRVDAEDGQYDVMFIGTDVGTVLKVVSI<br>PKETWYDLEEVLLEEMTVFREPTAISAMELSTKQQQLYIGSTAGVAQLP<br>LHRCDIYGKACAECCLARDPYCAWDGSACSRYFPTAKARTRAQDIRNG<br>DPLTHCSDGGIEGRMDHHHHHH |
| 583 | PRT | NYANGKNNVPRLKLSYKEMLESNNVITFNGLANSSSYHTFLLDEERSRL<br>YVGAKDHIFSFNLVNIKDFQKIVWPVSYTRRDECKWAGKDILKECANFI<br>KVLEAYNQTHLYACGTGAFHPICTYIEVGHHPEDNIFKLQDSHFENGRG<br>KSPYDPKLLTASLLIDGELYSGTAADFMGRDFAIFRTLGHHHPIRTEQHD<br>SRWLNDPRFISAHLIPESDNPEDDKVYFFFRENAIDGEHSGKATHARIGQI<br>CKNDFGGHRSLVNKWTTFLKARLICSVPGPNGIDTHFDELQDVFLMNSK<br>DPKNPIVYGVFTTSSNIFKGSAVCMYSMSDVRRVFLGPYAHRDGPNYQ<br>WVPYQGRVPYPRPGTCPSKTFGGFDSTKDLPDDVITFARSHPAMYNPVF<br>PINNRPIMIKTDVNYQFTQIVVDRVDAEDGQYDVMFIGTDVGTVLKVVS<br>VPKETWHDLEEILLEEMTVFREPTTISAMELSTKQQQLYIGSTAGVAQLP<br>LHRCDIYGKACAECCLARDPYCAWDGSSCSRYFPTAKARTRAQDIRNG<br>DPLTHCSDGGIEGRMDHHHHHH |
| 584 | PRT | NYANGKNNVPRLKLSYKEMLESNNVITFNGLANSSSYHTFLLDEERSRL<br>YVGAKDHIFSFNLVNIKDFQKIVWPVSYTRRDECKWAGKDILKECANFI<br>KVLKAYNQTHLYACGTGAFHPICTYIEVGHHPEDNIFKLQDSHFENGRG<br>KSPYDPKLLTASLLIDGELYSGTAADFMGRDFAIFRTLGHHHPIRTEQHD<br>SRWLNDPRFISAHLIPESDNPEDDKVYFFFRENAIDGEHSGKATHARIGQI<br>CKNDFGGHRSLVNKWTTFLKARLICSVPGPNGIDTHFDELQDVFLMNSK<br>DPKNPIVYGVFTTSSNIFKGSAVCMYSMSDVRRVFLGPYAHRDGPNYQ<br>WVPYQGRVPYPRPGTCPSKTFGGFDSTKDLPDDVITFARSHPAMYNPVF<br>PINNRPIMIKTDVNYQFTQIVVDRVDAEDGQYDVMFIGTDVGTVLKVVS<br>VPKETWHDLEEVLLEEMTVFREPTTISAMELSTKQQQLYIGSTAGVAQL<br>PLHRCDIYGKACAECCLARDPYCAWDGSSCSRYFPTAKARTRAQDIRNG<br>DPLTHCSDGGIEGRMDHHHHHH |
| 585 | PRT | NYQNGKNNVPRLKLSYKEMLESNSVITFNGLANSSSYHTFLLDEERSRL<br>YVGAKDHIFSFNLVNIKDFQKIVWPVSYTRRDECKWAGKDIQKECANFI<br>KVLKAYNQTHLYACGTGAFHPICTYIEIGHHPEDNIFKLEDSHFENGRGK<br>SPYDPKLLTASLLIDGELYSGTAADFMGRDFAIFRTLGHHHPIRTEQHDS<br>RWLNDPRFISAHLIPESDNPEDDKVYFFFRENAIDGEHTGKATHARIGQIC<br>KNDFGGHRSLVNKWTTFLKARLICSVPGPNGIDTHFDELQDVFLMNSKD<br>PKNPIVYGVFTTSSNIFKGSAVCMYSMSDVRRVFLGPYAHRDGPNYQW<br>VPYQGRVPYPRPGTCPSKTFGGFDSTKDLPDDVITFARSHPAMYNPVFPI<br>NNRPIMIKTDVNYQFTQIVVDRVDAEDGQYDVMFIGTDVGTVLKVVSIP<br>KETWHDLEEVLLEEMTVFREPTPISAMELSTKQHQLYAGSPAGLAQLPL<br>QRCAAYGRACAECCLARDPYCAWDGAACSRYFPAAKARTRAQDIRNG<br>DPLTHCSDGGIEGRMDHHHHHH |
| 586 | PRT | NYQNGKNNVPRLKLSYKEMLESNNVITFNGLANSSSYHTFLLDEERSRL<br>YVGAKDHIFSFNLVNIKDFQKIVWPVSYTRRDECKWAGKDILKECANFI<br>KVLKAYNQTHLYACGTGAFHPICTYIEIGHHPEDNIFKLENSHFENGRGK<br>SPYDPKLLTASLLIDGELYSGTAADFMGRDFAIFRTLGHHHPIRTEQHDS<br>RWLNDPRFISAHLIPESDNPEDDKVYFFFRENAIDGEHSGKATHARIGQIC<br>KNDFGGHRSLVNKWTTFLKARLICSVPGPNGIDTHFDELQDVFLMNFKD |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | PKNPIVYGVFTTSSNIFKGSAVCMYSMSDVRRVFLGPYAHRDGPNYQW VPYQGRVPYPRPGTCPSKTFGGFDSTKDLPDDVITFARSHPAMYNPVFPI NNRPIMIKTDVNYQFTQIVVDRVDAEDGQYDVMFIGTDVGTVLKVVSIP KETWHDLEEVLLEEMTVFREPTTISAMELSTKQQQLYIGSTAGIAQLPLH RCDIYGKACAECCLARDPYCAWDGSSCSRYFPTAKARTRAQDIRNGDPL THCSDGGIEGRMDHHHHHH |
| 587 | PRT | NYQNGKNNVPRLKLSYKEMLESNNVITFNGLANSSSYHTFLLDEERSRL YVGAKDHIFSFNLVNIKDFQKIVWPVSYTRRDECKWAGKDILKECANFI KVLKAYNQTHLYACGTGAFHPICTYIEIGHHPEDNIFKLEDSHFENGRGK SPYDPKLLTASLLIDGELYSGTAADFMGRDFAIFRTLGHHHPIRTEQHDS RWLNDPRFISAHLIPESDNPEDDKVYFFFRENAIDGEHTGKATHARIGQIC KNDFGGHRSLVNKWTTFLKARLICSVPGPNGIDTHFDELQDVFLMNSKD PKNPVVYGVFTTSSNIFKGSAVCMYSMSDVRRVFLGPYAHRDGPNYQW VPYQGRVPYPRPGTCPSKTFGGFDSTKDLPDDVITFARSHPAMYNPVFPI NNRPIMIKTDVNYQFTQIVVDRVDAEDGQYDVMFIGTDVGTVLKVVSIP KETWHDLEEVLLEEMTVFREPTTISAMELSTKQQQLYVGSAAGVAQLPL HRCDIYGKACAECCLARDPYCAWDGSSCSRYFPTAKARTRAQDIRNGD PLTHCSDGGIEGRMDHHHHHH |
| 800 | PRT | EVQLVESGGGLVQPGGSLRLSCAASGFTFSSYYMSWVRQAPGKGLEWV STIIKSGGYAYYPDSVKDRFTISRDNSKNTLYLQMSSLRAEDTAVYYCVR GGQGAMDYWGQGTTVTVSS |
| 801 | PRT | SYYMS |
| 802 | PRT | TIIKSGGYAYYPDSVKD |
| 803 | PRT | GGQGAMDY |
| 804 | PRT | EIVLTQSPATLSLSPGERATLSCRASQSIGDYLHWYQQKPGQAPRLLIKY ASQSISGIPARFSGSGSGTDFTLTITSLEPEDFAVYYCQQGYSFPYTFGGG TKLEIK |
| 805 | PRT | RASQSIGDYLH |
| 806 | PRT | YASQSIS |
| 807 | PRT | QQGYSFPYT |
| 808 | DNA | GAAGTGCAGCTGGTGGAATCTGGCGGAGGACTGGTTCAACCTGGCGG CTCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GTACCTGCAGATGAGCAGCCTGAGAGCCGAGGATACCGCCGTGTACT ACTGTGTTAGAGGCGGACAGGGCGCCATGGATTATTGGGGCCAGGG AACCACAGTGACCGTGTCATCA |
| 809 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATTAAGTACGCCAGCCAGTCCATCAGCGGCATCCCTGCCAGATTTTCT GGCAGCGGCTCTGGCACCGATTTCACCCTGACCATCACCAGCCTGGA ACCTGAGGACTTCGCCGTGTACTACTGCCAGCAGGGCTACAGCTTCC CCTACACATTTGGCGGAGGCACCAAGCTGGAAATCAAA |
| 810 | PRT | EVQLVESGGGLVQPGGSLRLSCAASGFTFSSYYMSWVRQAPGKGLEWV STIIKSGGYAYYPDSVKDRFTISRDNSKNTLYLQMSSLRAEDTAVYYCVR GGQGAMDYWGQGTTVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQK SLSLSPGK |
| 811 | PRT | EIVLTQSPATLSLSPGERATLSCRASQSIGDYLHWYQQKPGQAPRLLIKY ASQSISGIPARFSGSGSGTDFTLTITSLEPEDFAVYYCQQGYSFPYTFGGG TKLEIKRTVAAPSVFIFPPSDEQLKSGTASVVCLLNNFYPREAKVQWKVD |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | NALQSGNSQESVTEQDSKDSTYSLSSTLTLSKADYEKHKVYACEVTHQG LSSPVTKSFNRGEC |
| 812 | DNA | GAAGTGCAGCTGGTGGAATCTGGCGGAGGACTGGTTCAACCTGGCGG CTCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GTACCTGCAGATGAGCAGCCTGAGAGCCGAGGATACCGCCGTGTACT ACTGTGTTAGAGGCGGACAGGGCGCCATGGATTATTGGGGCCAGGG AACCACAGTGACCGTGTCATCAGCCAGCACCAAGGGCCCCAGCGTGT TCCCTCTGGCCCCTAGCAGCAAGAGCACATCTGGCGGAACAGCCGCC CTGGGCTGCCTCGTGAAGGACTACTTTCCCGAGCCCGTGACCGTGTC CTGGAACTCTGGCGCTCTGACAAGCGGCGTGCACACCTTTCCAGCCG TGCTGCAGAGCAGCGGCCTGTACTCTCTGAGCAGCGTCGTGACAGTG CCCAGCAGCTCTCTGGGCACCCAGACCTACATCTGCAACGTGAACCA CAAGCCCAGCAACACCAAGGTGGACAAGAAGGTGGAACCCAAGAGC TGCGACAAGACCCACACCTGTCCCCCTTGTCCTGCCCCGAACTGCTG GGAGGCCCTTCCGTGTTCCTGTTCCCCCCAAAGCCCAAGGACACCCT GATGATCAGCCGGACCCCCGAAGTGACCTGCGTGGTGGTGGATGTGT CCCACGAGGACCCTGAAGTGAAGTTCAATTGGTACGTGGACGGCGTG GAAGTGCACAACGCCAAGACCAAGCCTAGAGAGGAACAGTACAACA GCACCTACCGGGTGGTGTCCGTGCTGACAGTGCTGCACCAGGACTGG CTGAACGGCAAAGAGTACAAGTGCAAGGTGTCCAACAAGGCCCTGC CTGCCCCCATCGAGAAAACCATCAGCAAGGCCAAGGGCCAGCCCCG CGAACCCCAGGTGTACACACTGCCCCCAAGCAGGGACGAGCTGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAAGCTGACCGTGGACAAGTCCCGGTGGCAGCAGGGCAAC GTGTTCAGCTGCAGCGTGATGCACGAGGCCCTGCACAACCACTACAC CCAGAAGTCCCTGAGCCTGAGCCCTGGCAAG |
| 813 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATTAAGTACGCCAGCCAGTCCATCAGCGGCATCCCTGCCAGATTTTCT GGCAGCGGCTCTGGCACCGATTTCACCCTGACCATCACCAGCCTGGA ACCTGAGGACTTCGCCGTGTACTACTGCCAGCAGGGCTACAGCTTCC CCTACACATTTGGCGGAGGCACCAAGCTGGAAATCAAACGAACCGTG GCCGCTCCCAGCGTGTTCATCTTCCCACCTAGCGACGAGCAGCTGAA GTCCGGCACAGCCTCTGTCGTGTGCCTGCTGAACAACTTCTACCCCCG CGAGGCCAAGGTGCAGTGGAAGGTGGACAATGCCCTGCAGAGCGGC AACAGCCAGGAAAGCGTGACCGAGCAGGACAGCAAGGACTCCACCT ACAGCCTGAGCAGCACCCTGACCCTGAGCAAGGCCGACTACGAGAA GCACAAGGTGTACGCCTGCGAAGTGACCCACCAGGGCCTGTCTAGCC CCGTGACCAAGAGCTTCAACCGGGGCGAGTGT |
| 814 | PRT | EVQLVESGGGLVQPGGSLRLSCAASGFPFSSYYMSWVRQAPGKGLEWV STIIKSGGYAYYPDSVKDRFTISRDNSKNTLYLQMSSLRAEDTAVYYCVR GGQGAMDYWGQGTTVTVSS |
| 815 | PRT | SYYMS |
| 816 | PRT | TIIKSGGYAYYPDSVKD |
| 817 | PRT | GGQGAMDY |
| 818 | PRT | EIVLTQSPATLSLSPGERATLSCRASQSIGDYLHWYQQKPGQAPRLLIKY ASQSISGIPARFSGSGSGTDFTLTITSLEPEDFAVYYCQQGYSFPYTFGGG TKLEIK |
| 819 | PRT | RASQSIGDYLH |
| 820 | PRT | YASQSIS |
| 821 | PRT | QQGYSFPYT |
| 822 | DNA | GAAGTGCAGCTGGTGGAATCTGGCGGAGGACTGGTTCAACCTGGCGG CTCTCTGAGACTGTCTTGTGCCGCCTCTGGCTTCCCATTCAGCAGCTA CTACATGAGCTGGGTCCGACAGGCCCCTGGCAAAGGACTTGAATGGG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| | | TGTCCACCATCATCAAGAGCGGCGGCTACGCCTACTATCCCGACAGC |
| | | GTGAAGGACCGGTTCACCATCAGCCGGGACAACAGCAAGAACACCC |
| | | TGTACCTGCAGATGAGCAGCCTGAGAGCCGAGGATACCGCCGTGTAC |
| | | TACTGTGTTAGAGGCGGACAGGGCGCCATGGATTATTGGGGCCAGGG |
| | | AACCACAGTGACCGTGTCATCA |
| 823 | DNA | GAGATTGTGCTGACACAGTCTCCCGCCACACTGTCTCTTAGCCCTGGC |
| | | GAAAGAGCCACACTGAGCTGTAGAGCCAGCCAGAGCATCGGCGATT |
| | | ACCTGCACTGGTATCAGCAGAAGCCTGGACAGGCCCCTCGGCTGCTG |
| | | ATTAAGTACGCCAGCCAGTCCATCAGCGGCATCCCTGCCAGATTTTCT |
| | | GGCAGCGGCTCTGGCACCGATTTCACCCTGACCATCACCAGCCTGGA |
| | | ACCTGAGGACTTCGCCGTGTACTACTGCCAGCAGGGCTACAGCTTCC |
| | | CCTACACATTTGGCGGAGGCACCAAGCTGGAAATCAAA |
| 824 | PRT | EVQLVESGGGLVQPGGSLRLSCAASGFPFSSYYMSWVRQAPGKGLEWV |
| | | STIIKSGGYAYYPDSVKDRFTISRDNSKNTLYLQMSSLRAEDTAVYYCVR |
| | | GGQGAMDYWGQGTTVTVSSASTKGPSVFPLAPSSKSTSGGTAALGCLV |
| | | KDYFPEPVTVSWNSGALTSGVHTFPAVLQSSGLYSLSSVVTVPSSLGTQ |
| | | TYICNVNHKPSNTKVDKKVEPKSCDKTHTCPPCPAPELLGGPSVFLFPPK |
| | | PKDTLMISRTPEVTCVVVDVSHEDPEVKFNWYVDGVEVHNAKTKPREE |
| | | QYNSTYRVVSVLTVLHQDWLNGKEYKCKVSNKALPAPIEKTISKAKGQ |
| | | PREPQVYTLPPSRDELTKNQVSLTCLVKGFYPSDIAVEWESNGQPENNY |
| | | KTTPPVLDSDGSFFLYSKLTVDKSRWQQGNVFSCSVMHEALHNHYTQK |
| | | SLSLSPGK |
| 825 | PRT | EIVLTQSPATLSLSPGERATLSCRASQSIGDYLHWYQQKPGQAPRLLIKY |
| | | ASQSISGIPARFSGSGSGTDFTLTITSLEPEDFAVYYCQQGYSFPYTFGGG |
| | | TKLEIKRTVAAPSVFIFPPSDEQLKSGTASVVCLLNNFYPREAKVQWKVD |
| | | NALQSGNSQESVTEQDSKDSTYSLSSTLTLSKADYEKHKVYACEVTHQG |
| | | LSSPVTKSFNRGEC |
| 826 | DNA | GAAGTGCAGCTGGTGGAATCTGGCGGAGGACTGGTTCAACCTGGCGG |
| | | CTCTCTGAGACTGTCTTGTGCCGCCTCTGGCTTCCCATTCAGCAGCTA |
| | | CTACATGAGCTGGGTCCGACAGGCCCCTGGCAAAGGACTTGAATGGG |
| | | TGTCCACCATCATCAAGAGCGGCGGCTACGCCTACTATCCCGACAGC |
| | | GTGAAGGACCGGTTCACCATCAGCCGGGACAACAGCAAGAACACCC |
| | | TGTACCTGCAGATGAGCAGCCTGAGAGCCGAGGATACCGCCGTGTAC |
| | | TACTGTGTTAGAGGCGGACAGGGCGCCATGGATTATTGGGGCCAGGG |
| | | AACCACAGTGACCGTGTCATCAGCCAGCACCAAGGGCCCCAGCGTGT |
| | | TCCCTCTGGCCCCTAGCAGCAAGAGCACATCGGCGGAACAGCCGCC |
| | | CTGGGCTGCCTCGTGAAGGACTACTTTCCCGAGCCCGTGACCGTGTC |
| | | CTGGAACTCTGGCGCTCTGACAAGCGGCGTGCACACCTTTCCAGCCG |
| | | TGCTGCAGAGCAGCGGCCTGTACTCTCTGAGCAGCGTCGTGACAGTG |
| | | CCCAGCAGCTCTCTGGGCACCCAGACCTACATCTGCAACGTGAACCA |
| | | CAAGCCCAGCAACACCAAGGTGGACAAGAAGGTGGAACCCAAGAGC |
| | | TGCGACAAGACCCACACCTGTCCCCCTTGTCCTGCCCCCGAACTGCTG |
| | | GGAGGCCCTTCCGTGTTCCTGTTCCCCCCAAAGCCCAAGGACACCCT |
| | | GATGATCAGCCGGACCCCCGAAGTGACCTGCGTGGTGGTGGATGTGT |
| | | CCCACGAGGACCCTGAAGTGAAGTTCAATTGGTACGTGGACGGCGTG |
| | | GAAGTGCACAACGCCAAGACCAAGCCTAGAGAGGAACAGTACAACA |
| | | GCACCTACCGGGTGGTGTCCGTGCTGACAGTGCTGCACCAGGACTGG |
| | | CTGAACGGCAAAGAGTACAAGTGCAAGGTGTCCAACAAGGCCCTGC |
| | | CTGCCCCCATCGAGAAAACCATCAGCAAGGCCAAGGGCCAGCCCCG |
| | | CGAACCCCAGGTGTACACACTGCCCCCAAGCAGGGACGAGCTGACC |
| | | AAGAACCAGGTGTCCCTGACCTGTCTCGTGAAAGGCTTCTACCCCTC |
| | | CGATATCGCCGTGGAATGGGAGAGCAACGGCCAGCCCGAGAACAAC |
| | | TACAAGACCACCCCCCCTGTGCTGGACAGCGACGGCTCATTCTTCCT |
| | | GTACAGCAAGCTGACCGTGGACAAGTCCCGGTGGCAGCAGGGCAAC |
| | | GTGTTCAGCTGCAGCGTGATGCACGAGGCCCTGCACAACCACTACAC |
| | | CCAGAAGTCCCTGAGCCTGAGCCCTGGCAAG |
| 827 | DNA | GAGATTGTGCTGACACAGTCTCCCGCCACACTGTCTCTTAGCCCTGGC |
| | | GAAAGAGCCACACTGAGCTGTAGAGCCAGCCAGAGCATCGGCGATT |
| | | ACCTGCACTGGTATCAGCAGAAGCCTGGACAGGCCCCTCGGCTGCTG |
| | | ATTAAGTACGCCAGCCAGTCCATCAGCGGCATCCCTGCCAGATTTTCT |
| | | GGCAGCGGCTCTGGCACCGATTTCACCCTGACCATCACCAGCCTGGA |
| | | ACCTGAGGACTTCGCCGTGTACTACTGCCAGCAGGGCTACAGCTTCC |
| | | CCTACACATTTGGCGGAGGCACCAAGCTGGAAATCAAACGAACCGTG |
| | | GCCGCTCCCAGCGTGTTCATCTTCCCACCTAGCGACGAGCAGCTGAA |
| | | GTCCGGCACAGCCTCTGTCGTGTGCCTGCTGAACAACTTCTACCCCCG |
| | | CGAGGCCAAGGTGCAGTGGAAGGTGGACAATGCCCTGCAGAGCGGC |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
|  |  | AACAGCCAGGAAAGCGTGACCGAGCAGGACAGCAAGGACTCCACCT<br>ACAGCCTGAGCAGCACCCTGACCCTGAGCAAGGCCGACTACGAGAA<br>GCACAAGGTGTACGCCTGCGAAGTGACCCACCAGGGCCTGTCTAGCC<br>CCGTGACCAAGAGCTTCAACCGGGGCGAGTGT |
| 828 | PRT | EVQLVESGGGLVQLGGSLRLSCAASGFTFSSYYMSWVRQAPGKGLEWV<br>STIIKSGGYAYYPDSVKDRFTISRDNSKNTLYLQMNSLRAEDTAVYYCV<br>KGGQGAMDYWGQGTTVTSS |
| 829 | PRT | SYYMS |
| 830 | PRT | TIIKSGGYAYYPDSVKD |
| 831 | PRT | GGQGAMDY |
| 832 | PRT | EIVLTQSPATLSLSPGERATLSCRASQSIGDYLHWYQQKPGQAPRLLIYY<br>ASQSISGIPARFSGSGSGTDFTLTISSLEPEDFAVYYCQQGYSFPYTFGGGT<br>KLEIK |
| 833 | PRT | RASQSIGDYLH |
| 834 | PRT | YASQSIS |
| 835 | PRT | QQGYSFPYT |
| 836 | DNA | GAAGTGCAGCTGGTGGAATCTGGCGGAGGACTGGTTCAGCTCGGCGG<br>ATCTCTGAGACTGTCTTGTGCCGCCAGCGGCTTCACCTTCAGCAGCTA<br>CTACATGAGCTGGGTCCGACAGGCCCCTGGCAAAGGACTTGAATGGG<br>TGTCCACCATCATCAAGAGCGGCGGCTACGCCTACTATCCCGACAGC<br>GTGAAGGACCGGTTCACCATCTCCAGAGACAACAGCAAGAACACCCT<br>GTACCTGCAGATGAACAGCCTGAGAGCCGAGGACACCGCCGTGTACT<br>ACTGTGTGAAAGGTGGACAGGGCGCCATGGACTATTGGGGCCAGGG<br>AACAACAGTGACCGTGTCCTCA |
| 837 | DNA | GAGATTGTGCTGACACAGTCTCCCGCCACACTGTCTCTTAGCCCTGGC<br>GAAAGAGCCACACTGAGCTGTAGAGCCAGCCAGAGCATCGGCGATT<br>ACCTGCACTGGTATCAGCAGAAGCCTGGACAGGCCCCTCGGCTGCTG<br>ATCTACTATGCCAGCCAGTCCATCAGCGGCATCCCCGCCAGATTTTCT<br>GGCAGCGGCTCTGGCACCGATTTCACCCTGACCATAAGCAGCCTGGA<br>ACCTGAGGACTTCGCCGTGTACTACTGCCAGCAGGGCTACAGCTTCC<br>CCTACACATTTGGCGGAGGCACCAAGCTGGAAATCAAA |
| 838 | PRT | EVQLVESGGGLVQLGGSLRLSCAASGFTFSSYYMSWVRQAPGKGLEWV<br>STIIKSGGYAYYPDSVKDRFTISRDNSKNTLYLQMNSLRAEDTAVYYCV<br>KGGQGAMDYWGQGTTVTVSSASTKGPSVFPLAPSSKSTSGGTAALGCL<br>VKDYFPEPVTVSWNSGALTSGVHTFPAVLQSSGLYSLSSVVTVPSSSLGT<br>QTYICNVNHKPSNTKVDKKVEPKSCDKTHTCPPCPAPELLGGPSVFLFPP<br>KPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQ<br>KSLSLSPGK |
| 839 | PRT | EIVLTQSPATLSLSPGERATLSCRASQSIGDYLHWYQQKPGQAPRLLIYY<br>ASQSISGIPARFSGSGSGTDFTLTISSLEPEDFAVYYCQQGYSFPYTFGGGT<br>KLEIKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQG<br>LSSPVTKSFNRGEC |
| 840 | DNA | GAAGTGCAGCTGGTGGAATCTGGCGGAGGACTGGTTCAGCTCGGCGG<br>ATCTCTGAGACTGTCTTGTGCCGCCAGCGGCTTCACCTTCAGCAGCTA<br>CTACATGAGCTGGGTCCGACAGGCCCCTGGCAAAGGACTTGAATGGG<br>TGTCCACCATCATCAAGAGCGGCGGCTACGCCTACTATCCCGACAGC<br>GTGAAGGACCGGTTCACCATCTCCAGAGACAACAGCAAGAACACCCT<br>GTACCTGCAGATGAACAGCCTGAGAGCCGAGGACACCGCCGTGTACT<br>ACTGTGTGAAAGGTGGACAGGGCGCCATGGACTATTGGGGCCAGGG<br>AACAACAGTGACCGTGTCCTCAGCCAGCACCAAGGGCCCCAGCGTGT<br>TCCCTCTGGCCCCTAGCAGCAAGAGCACATCTGGCGGAACAGCCGCC<br>CTGGGCTGCCTCGTGAAGGACTACTTTCCCGAGCCCGTGACCGTGTC<br>CTGGAACTCTGGCGCTCTGACAAGCGGCGTGCACACCTTTCCAGCCG<br>TGCTGCAGAGCAGCGGCCTGTACTCTCTGAGCAGCGTCGTGACAGTG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from Homo sapiens (SEQ ID 581, 582), Mus Musculus (SEQ ID 583), Rattus norvegicus (SEQ ID 584), Canis lupus familiaris (SEQ ID 585), Macaca fascicularis (SEQ ID 586), Sus scrofa (SEQ ID 587).

| SEQ ID No | SEQ Type | SEQUENCE |
|---|---|---|
| | | CCCAGCAGCTCTCTGGGCACCCAGACCTACATCTGCAACGTGAACCA CAAGCCCAGCAACACCAAGGTGGACAAGAAGGTGGAACCCAAGAGC TGCGACAAGACCCACACCTGTCCCCCTTGTCCTGCCCCCGAACTGCTG GGAGGCCCTTCCGTGTTCCTGTTCCCCCCAAAGCCCAAGGACACCCT GATGATCAGCCGGACCCCCGAAGTGACCTGCGTGGTGGTGGATGTGT CCCACGAGGACCCTGAAGTGAAGTTCAATTGGTACGTGGACGGCGTG GAAGTGCACAACGCCAAGACCAAGCCTAGAGAGGAACAGTACAACA GCACCTACCGGGTGGTGTCCGTGCTGACAGTGCTGCACCAGGACTGG CTGAACGGCAAAGAGTACAAGTGCAAGGTGTCCAACAAGGCCCTGC CTGCCCCCATCGAGAAAACCATCAGCAAGGCCAAGGGCCAGCCCCG CGAACCCCAGGTGTACACACTGCCCCCAAGCAGGGACGAGCTGACC AAGAACCAGGTGTCCCTGACCTGTCTCGTGAAAGGCTTCTACCCCTC CGATATCGCCGTGGAATGGGAGAGCAACGGCCAGCCCGAGAACAAC TACAAGACCACCCCCCCTGTGCTGGACAGCGACGGCTCATTCTTCCT GTACAGCAAGCTGACCGTGGACAAGTCCCGGTGGCAGCAGGGCAAC GTGTTCAGCTGCAGCGTGATGCACGAGGCCCTGCACAACCACTACAC CCAGAAGTCCCTGAGCCTGAGCCCTGGCAAG |
| 841 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATCTACTATGCCAGCCAGTCCATCAGCGGCATCCCCGCCAGATTTTCT GGCAGCGGCTCTGGCACCGATTTCACCCTGACCATAAGCAGCCTGGA ACCTGAGGACTTCGCCGTGTACTACTGCCAGCAGGGCTACAGCTTCC CCTACACATTTGGCGGAGGCACCAAGCTGGAAATCAAACGAACCGTG GCCGCTCCCAGCGTGTTCATCTTCCCACCTAGCGACGAGCAGCTGAA GTCCGGCACAGCCTCTGTCGTGTGCCTGCTGAACAACTTCTACCCCCG CGAGGCCAAGGTGCAGTGGAAGGTGGACAATGCCCTGCAGAGCGGC AACAGCCAGGAAAGCGTGACCGAGCAGGACAGCAAGGACTCCACCT ACAGCCTGAGCAGCACCCTGACCCTGAGCAAGGCCGACTACGAGAA GCACAAGGTGTACGCCTGCGAAGTGACCCACCAGGGCCTGTCTAGCC CCGTGACCAAGAGCTTCAACCGGGGCGAGTGT |
| 842 | PRT | EVQLVESGGGLLQLGGSLRLSCAASGFTFSSYYMSWVRQAPGKGLEWV STIIKSGGYAYYPDSVKDRFTISRDNSKNTLNLQMNSLRAEDTAVYYCV KGGQGAMDYWGQGTTVTVSS |
| 843 | PRT | SYYMS |
| 844 | PRT | TIIKSGGYAYYPDSVKD |
| 845 | PRT | GGQGAMDY |
| 846 | PRT | EIVLTQSPATLSLSPGERATLSCRASQSIGDYLHWYQQKPGQAPRLLIKY ASQSISGIPARFSGSGSGTDFTLTISSLEPEDFAVYYCQQGYSFPYTFGGGT KLEIK |
| 847 | PRT | RASQSIGDYLH |
| 848 | PRT | YASQSIS |
| 849 | PRT | QQGYSFPYT |
| 850 | DNA | GAAGTGCAGCTGGTGGAATCTGGCGGAGGACTGCTGCAGCTTGGCGG ATCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GAACCTGCAGATGAACAGCCTGAGAGCCGAGGACACCGCCGTGTAC TACTGTGTGAAAGGTGGACAGGGCGCCATGGACTATTGGGGCCAGG GAACAACAGTGACCGTGTCCTCA |
| 851 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATTAAGTACGCCAGCCAGTCCATCAGCGGCATCCCTGCCAGATTTTCT GGCAGCGGCTCTGGCACCGATTTCACCCTGACCATAAGCAGCCTGGA ACCTGAGGACTTCGCCGTGTACTACTGCCAGCAGGGCTACAGCTTCC CCTACACATTTGGCGGAGGCACCAAGCTGGAAATCAAA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 852 | PRT | EVQLVESGGGLLQLGGSLRLSCAASGFTFSSYYMSWVRQAPGKGLEWV STIIKSGGYAYYPDSVKDRFTISRDNSKNTLNLQMNSLRAEDTAVYYCV KGGQGAMDYWGQGTTVTVSSASTKGPSVFPLAPSSKSTSGGTAALGCL VKDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQ KSLSLSPGK |
| 853 | PRT | EIVLTQSPATLSLSPGERATLSCRASQSIGDYLHWYQQKPGQAPRLLIKY ASQSISGIPARFSGSGSGTDFTLTISSLEPEDFAVYYCQQGYSFPYTFGGGT KLEIKRTVAAPSVFIFPPSDEQLKSGTASVVCLLNNFYPREAKVQWKVD NALQSGNSQESVTEQDSKDSTYSLSSTLTLSKADYEKHKVYACEVTHQG LSSPVTKSFNRGEC |
| 854 | DNA | GAAGTGCAGCTGGTGGAATCTGGCGGAGGACTGCTGCAGCTTGGCGG ATCTCTGAGACTGTCTTGTGCCGCCAGCGGCTTCACCTTCAGCAGCTA CTACATGAGCTGGGTCCGACAGGCCCCTGGCAAAGGACTTGAATGGG TGTCCACCATCATCAAGAGCGGCGGCTACGCCTACTATCCCGACAGC GTGAAGGACCGGTTCACCATCTCCAGAGACAACAGCAAGAACACCCT GAACCTGCAGATGAACAGCCTGAGAGCCGAGGACACCGCCGTGTAC TACTGTGTGAAAGGTGGACAGGGCGCCATGGACTATTGGGGCCAGG GAACAACAGTGACCGTGTCCTCAGCCAGCACCAAGGGCCCCAGCGTG TTCCCTCTGGCCCCTAGCAGCAAGAGCACATCTGGCGGAACAGCCGC CCTGGGCTGCCTCGTGAAGGACTACTTTCCCGAGCCCGTGACCGTGT CCTGGAACTCTGGCGCTCTGACAAGCGGCGTGCACACCTTTCCAGCC GTGCTGCAGAGCAGCGGCCTGTACTCTCTGAGCAGCGTCGTGACAGT GCCCAGCAGCTCTCTGGGCACCCAGACCTACATCTGCAACGTGAACC ACAAGCCCAGCAACACCAAGGTGGACAAGAAGGTGGAACCCAAGAG CTGCGACAAGACCCACACCTGTCCCCCTTGTCCTGCCCCCGAACTGCT GGGGAGGCCCTTCCGTGTTCCTGTTCCCCCCAAAGCCCAAGGACACCC TGATGATCAGCCGGACCCCCGAAGTGACCTGCGTGGTGGTGGATGTG TCCCACGAGGACCCTGAAGTGAAGTTCAATTGGTACGTGGACGGCGT GGAAGTGCACAACGCCAAGACCAAGCCTAGAGAGGAACAGTACAAC AGCACCTACCGGGTGGTGTCCGTGCTGACAGTGCTGCACCAGGACTG GCTGAACGGCAAAGAGTACAAGTGCAAGGTGTCCAACAAGGCCCTG CCTGCCCCCATCGAGAAAACCATCAGCAAGGCCAAGGGCCAGCCCC GCGAACCCCAGGTGTACACACTGCCCCCAAGCAGGGACGAGCTGAC CAAGAACCAGGTGTCCCTGACCTGTCTCGTGAAAGGCTTCTACCCCT CCGATATCGCCGTGGAATGGGAGAGCAACGGCCAGCCCGAGAACAA CTACAAGACCACCCCCCCTGTGCTGGACAGCGACGGCTCATTCTTCCT GTACAGCAAGCTGACCGTGGACAAGTCCCGGTGGCAGCAGGGCAAC GTGTTCAGCTGCAGCGTGATGCACGAGGCCCTGCACAACCACTACAC CCAGAAGTCCCTGAGCCTGAGCCCTGGCAAG |
| 855 | DNA | GAGATTGTGCTGACACAGTCTCCCGCCACACTGTCTCTTAGCCCTGGC GAAAGAGCCACACTGAGCTGTAGAGCCAGCCAGAGCATCGGCGATT ACCTGCACTGGTATCAGCAGAAGCCTGGACAGGCCCCTCGGCTGCTG ATTAAGTACGCCAGCCAGTCCATCAGCGGCATCCCTGCCAGATTTTCT GGCAGCGGCTCTGGCACCGATTTCACCCTGACCATAAGCAGCCTGGA ACCTGAGGACTTCGCCGTGTACTACTGCCAGCAGGGCTACAGCTTCC CCTACACATTTGGCGGAGGCACCAAGCTGGAAATCAAACGAACCGTG GCCGCTCCCAGCGTGTTCATCTTCCCACCTAGCGACGAGCAGCTGAA GTCCGGCACAGCCTCTGTCGTGTGCCTGCTGAACAACTTCTACCCCCG CGAGGCCAAGGTGCAGTGGAAGGTGGACAATGCCCTGCAGAGCGGC AACAGCCAGGAAAGCGTGACCGAGCAGGACAGCAAGGACTCCACCT ACAGCCTGAGCAGCACCCTGACCCTGAGCAAGGCCGACTACGAGAA GCACAAGGTGTACGCCTGCGAAGTGACCCACCAGGGCCTGTCTAGCC CCGTGACCAAGAGCTTCAACCGGGGCGAGTGT |
| 856 | PRT | EVQLLESGGGLVQPGGSLRLSCAASGFTFRSYAVHWVRQAPGKGLEWV SSTEGSGVGTSYTDSVKGRFTISRDNSKNTLYLQMNSLRAEDTAVYYCA RMLGGGNPLDYLDYWGQGTLVTVSS |
| 857 | PRT | SYAVH |
| 858 | PRT | STEGSGVGTSYTDSVKG |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 859 | PRT | MLGGGNPLDYLDY |
| 860 | PRT | QSVLTQPPSASGTPGQRVTISCSGSSSNLGEGYDVHWYQQLPGKAPKLLI YYSDFRPSGVSDRFSGSKSGTSASLAISGLQSEDEADYYCAAWDDSLSSQ VFGGGTQVTVL |
| 861 | PRT | SGSSSNLGEGYDVH |
| 862 | PRT | YSDFRPS |
| 863 | PRT | AAWDDSLSSQV |
| 864 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGAAGCT ATGCCGTGCACTGGGTCCGACAGGCCCCTGGAAAAGGACTGGAATG GGTGTCCAGCACCGAAGGCTCTGGCGTGGGCACAAGCTACACCGATT CTGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAATGCTCGGCGGAGGCAACCCTCTGGACTACCTG GATTATTGGGGCCAGGGCACCCTGGTCACAGTCTCTTCA |
| 865 | DNA | CAGTCTGTTCTGACACAGCCTCCTAGCGCCTCTGGCACACCTGGACA GAGAGTGACCATCAGCTGTAGCGGCAGCAGCTCCAATCTCGGCGAGG GCTATGACGTGCACTGGTATCAGCAGCTGCCTGGCAAGGCCCCTAAA CTGCTGATCTACTACAGCGACTTCAGACCCAGCGGCGTGTCCGATAG ATTCAGCGGCTCTAAGAGCGGCACATCTGCCAGCCTGGCCATCTCTG GACTGCAGAGCGAAGATGAGGCCGACTACTATTGCGCCGCCTGGGAT GATAGCCTGAGCAGCCAAGTTTTTGGCGGCGGAACCCAAGTGACCGT GCTA |
| 866 | PRT | EVQLLESGGGLVQPGGSLRLSCAASGFTFRSYAVHWVRQAPGKGLEWV SSTEGSGVGTSYTDSVKGRFTISRDNSKNTLYLQMNSLRAEDTAVYYCA RMLGGGNPLDYLDYWGQGTLVTVSSASTKGPSVFPLAPSSKSTSGGTAA LGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK |
| 867 | PRT | QSVLTQPPSASGTPGQRVTISCSGSSSNLGEGYDVHWYQQLPGKAPKLLI YYSDFRPSGVSDRFSGSKSGTSASLAISGLQSEDEADYYCAAWDDSLSSQ VFGGGTQVTVLGQPKAAPSVTLFPPSSEELQANKATLVCLISDFYPGAVT VAWKADSSPVKAGVETTTPSKQSNNKYAASSYLSLTPEQWKSHRSYSC QVTHEGSTVEKTVAPTECS |
| 868 | DNA | GAAGTTCAGCTGCTGGAATCTGGCGGCGGACTGGTTCAACCTGGCGG ATCTCTGAGACTGAGCTGTGCCGCCAGCGGCTTCACCTTTAGAAGCT ATGCCGTGCACTGGGTCCGACAGGCCCCTGGAAAAGGACTGGAATG GGTGTCCAGCACCGAAGGCTCTGGCGTGGGCACAAGCTACACCGATT CTGTGAAGGGCAGATTCACCATCAGCCGGGACAACAGCAAGAACAC CCTGTACCTGCAGATGAACAGCCTGAGAGCCGAGGACACCGCCGTGT ACTACTGTGCCAGAATGCTCGGCGGAGGCAACCCTCTGGACTACCTG GATTATTGGGGCCAGGGCACCCTGGTCACAGTCTCTTCAGCCAGCAC CAAGGGCCCCAGCGTGTTCCCTCTGGCCCCTAGCAGCAAGAGCACAT CTGGCGGAACAGCCGCCCTGGGCTGCCTCGTGAAGGACTACTTTCCC GAGCCCGTGACCGTGTCCTGGAACTCTGGCGCTCTGACAAGCGGCGT GCACACCTTTCCAGCCGTGCTGCAGAGCAGCGGCCTGTACTCTCTGA GCAGCGTCGTGACAGTGCCCAGCAGCTCTCTGGGCACCCAGACCTAC ATCTGCAACGTGAACCACAAGCCCAGCAACACCAAGGTGGACAAGA AGGTGGAACCCAAGAGCTGCGACAAGACCCACACCTGTCCCCCTTGT CCTGCCCCCGAACTGCTGGGAGGCCCTTCCGTGTTCCTGTTCCCCCCA AAGCCCAAGGACACCCTGATGATCAGCCGGACCCCCGAAGTGACCTG CGTGGTGGTGGATGTGTCCCACGAGGACCCTGAAGTGAAGTTCAATT GGTACGTGGACGGCGTGGAAGTGCACAACGCCAAGACCAAGCCTAG AGAGGAACAGTACAACAGCACCTACCGGGTGGTGTCCGTGCTGACA GTGCTGCACCAGGACTGGCTGAACGGCAAAGAGTACAAGTGCAAGG TGTCCAACAAGGCCCTGCCTGCCCCCATCGAGAAAACCATCAGCAAG GCCAAGGGCCAGCCCCGCGAACCCCAGGTGTACACTGCCCCCAAG CAGGGACGAGCTGACCAAGAACCAGGTGTCCCTGACCTGTCTCGTGA |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from *Homo sapiens* (SEQ ID 581, 582), *Mus Musculus*
(SEQ ID 583), *Rattus norvegicus* (SEQ ID 584), *Canis lupus familiaris* (SEQ ID 585), *Macaca
fascicularis* (SEQ ID 586), *Sus scrofa* (SEQ ID 587).

| SEQ ID No | SEQ Type | SEQUENCE |
|---|---|---|
| | | AAGGCTTCTACCCCTCCGATATCGCCGTGGAATGGGAGAGCAACGGC<br>CAGCCCGAGAACAACTACAAGACCACCCCCCCTGTGCTGGACAGCGA<br>CGGCTCATTCTTCCTGTACAGCAAGCTGACCGTGGACAAGTCCCGGT<br>GGCAGCAGGGCAACGTGTTCAGCTGCAGCGTGATGCACGAGGCCCTG<br>CACAACCACTACACCCAGAAGTCCCTGAGCCTGAGCCCTGGCAAG |
| 869 | DNA | CAGTCTGTTCTGACACAGCCTCCTAGCGCCTCTGGCACACCTGGACA<br>GAGAGTGACCATCAGCTGTAGCGGCAGCAGCTCCAATCTCGGCGAGG<br>GCTATGACGTGCACTGGTATCAGCAGCTGCCTGGCAAGGCCCCTAAA<br>CTGCTGATCTACTACAGCGACTTCAGACCCAGCGGCGTGTCCGATAG<br>ATTCAGCGGCTCTAAGAGCGGCACATCTGCCAGCCTGGCCATCTCTG<br>GACTGCAGAGCGAAGATGAGGCCGACTACTATTGCGCCGCCTGGGAT<br>GATAGCCTGAGCAGCCAAGTTTTTGGCGGCGGAACCCAAGTGACCGT<br>GCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 870 | PRT | EVQLLESGGGLVQPGGSLRLSCAASGFTFRSYAVHWVRQAPGKGLEWV<br>SSTEGSGVGTSYTDSVKGRFTISRDNSKNTLYLQMNSLRAEDTAVYYCA<br>RMLGGGNPLDYLDYWGQGTLVTVSS |
| 871 | PRT | SYAVH |
| 872 | PRT | STEGSGVGTSYTDSVKG |
| 873 | PRT | MLGGGNPLDYLDY |
| 874 | PRT | QSVLTQPPSASGTPGQRVTISCSGSSSNLGEGYDVHWYQQLPGKAPKLLI<br>YYSDFRPSGVSDRFSGSKSGTSASLAISGLQSEDEADYYCAAWDDSLSSQ<br>VFGGGTQVTVL |
| 875 | PRT | SGSSSNLGEGYDVH |
| 876 | PRT | YSDFRPS |
| 877 | PRT | AAWDDSLSSQV |
| 878 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGAAGCT<br>ATGCCGTGCACTGGGTCCGACAGGCCCCTGGAAAAGGACTGGAATG<br>GGTGTCCAGCACCGAAGGCTCTGGCGTGGGCACAAGCTACACCGATT<br>CTGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAATGCTCGGCGGAGGCAACCCTCTGGACTACCTG<br>GATTATTGGGGCCAGGGCACCCTGGTCACAGTCTCTTCA |
| 879 | DNA | CAGTCTGTTCTGACACAGCCTCCTAGCGCCTCTGGCACACCTGGACA<br>GAGAGTGACCATCAGCTGTAGCGGCAGCAGCTCCAATCTCGGCGAGG<br>GCTATGACGTGCACTGGTATCAGCAGCTGCCTGGCAAGGCCCCTAAA<br>CTGCTGATCTACTACAGCGACTTCAGACCCAGCGGCGTGTCCGATAG<br>ATTCAGCGGCTCTAAGAGCGGCACATCTGCCAGCCTGGCCATCTCTG<br>GACTGCAGAGCGAAGATGAGGCCGACTACTATTGCGCCGCCTGGGAT<br>GATAGCCTGAGCAGCCAAGTTTTTGGCGGCGGAACCCAAGTGACCGT<br>GCTA |
| 880 | PRT | EVQLLESGGGLVQPGGSLRLSCAASGFTFRSYAVHWVRQAPGKGLEWV<br>SSTEGSGVGTSYTDSVKGRFTISRDNSKNTLYLQMNSLRAEDTAVYYCA<br>RMLGGGNPLDYLDYWGQGTLVTVSSASTKGPSVFPLAPSSKSTSGGTAA<br>LGCLVKDYFPEPVTVSWNSGALTSGVHTFPAVLQSSGLYSLSSVVTVPSS<br>SLGTQTYICNVNHKPSNTKVDKKVEPKSCAAGSEQKLISEEDLSGSAAA<br>HHHHHH |
| 881 | PRT | QSVLTQPPSASGTPGQRVTISCSGSSSNLGEGYDVHWYQQLPGKAPKLLI<br>YYSDFRPSGVSDRFSGSKSGTSASLAISGLQSEDEADYYCAAWDDSLSSQ<br>VFGGGTQVTVLGQPKAAPSVTLFPPSSEELQANKATLVCLISDFYPGAVT<br>VAWKADSSPVKAGVETTTPSKQSNNKYAASSYLSLTPEQWKSHRSYSC<br>QVTHEGSTVEKTVAPTECS |

TABLE 1A-continued

Corresponding amino acid sequences and nucleic acid sequences of antibodies according
to the present disclosure mentioned in table 1 under the respective SEQ IDs. SEQ ID 581 to 587 being
the corresponding Sema3A protein sequences from Homo sapiens (SEQ ID 581, 582), Mus Musculus
(SEQ ID 583), Rattus norvegicus (SEQ ID 584), Canis lupus familiaris (SEQ ID 585), Macaca
fascicularis (SEQ ID 586), Sus scrofa (SEQ ID 587).

| SEQ ID No | SEQ Type | SEQUENCE |
|---|---|---|
| 882 | DNA | GAAGTTCAGCTGCTGGAATCTGGCGGCGGACTGGTTCAACCTGGCGG<br>ATCTCTGAGACTGAGCTGTGCCGCCAGCGGCTTCACCTTTAGAAGCT<br>ATGCCGTGCACTGGGTCCGACAGGCCCCTGGAAAAGGACTGGAATG<br>GGTGTGTCCAGCACCGAAGGCTCTGGCGTGGGCACAAGCTACACCGATT<br>CTGTGAAGGGCAGATTCACCATCAGCCGGGACAACAGCAAGAACAC<br>CCTGTACCTGCAGATGAACAGCCTGAGAGCCGAGGACACCGCCGTGT<br>ACTACTGTGCCAGAATGCTCGGCGGAGGCAACCCTCTGGACTACCTG<br>GATTATTGGGGCCAGGGCACCCTGGTCACAGTCTCTTCAGCCTCCAC<br>CAAGGGCCCATCGGTGTTCCCCCTGGCACCCTCCTCCAAGAGCACCT<br>CTGGGGGCACAGCGGCCCTGGGCTGCCTGGTCAAGGACTACTTCCCC<br>GAACCGGTGACGGTGTCGTGGAACTCAGGCGCCCTGACCAGCGGCGT<br>GCACACCTTCCCGGCTGTCCTACAGTCCTCAGGACTCTACTCCCTCAG<br>CAGCGTGGTGACCGTGCCCTCCAGCAGCTTGGGCACCCAGACCTACA<br>TCTGCAACGTGAATCACAAGCCCAGCAACACCAAGGTGGACAAGAA<br>AGTTGAGCCCAAATCTTGTGCAGCGGGTTCTGAACAAAAACTCATCT<br>CAGAAGAGGATCTGTCTGGATCAGCGGCCGCCCATCATCATCATCAT<br>CAT |
| 883 | DNA | CAGTCTGTTCTGACACAGCCTCCTAGCGCCTCTGGCACACCTGGACA<br>GAGAGTGACCATCAGCTGTAGCGGCAGCAGCTCCAATCTCGGCGAGG<br>GCTATGACGTGCACTGGTATCAGCAGCTGCCTGGCAAGGCCCCTAAA<br>CTGCTGATCTACTACAGCGACTTCAGACCCAGCGGCGTGTCCGATAG<br>ATTCAGCGGCTCTAAGAGCGGCACATCTGCCAGCCTGGCCATCTCTG<br>GACTGCAGAGCGAAGATGAGGCCGACTACTATTGCGCCGCCTGGGAT<br>GATAGCCTGAGCAGCCAAGTTTTTGGCGGCGGAACCCAAGTGACCGT<br>GCTAGGCCAGCCTAAAGCCGCCCCTAGCGTGACCCTGTTCCCTCCAA<br>GCAGCGAGGAACTGCAGGCCAACAAGGCCACCCTCGTGTGCCTGATC<br>AGCGACTTCTATCCTGGCGCCGTGACCGTGGCCTGGAAGGCCGATAG<br>CTCTCCTGTGAAGGCCGGCGTGGAAACCACCACCCCTAGCAAGCAGA<br>GCAACAACAAATACGCCGCCAGCAGCTACCTGAGCCTGACCCCCGAG<br>CAGTGGAAGTCCCACAGATCCTACAGCTGCCAAGTGACCCACGAGGG<br>CAGCACCGTGGAAAAGACAGTGGCCCCTACCGAGTGCAGC |
| 884 | PRT | NYQNGKNNVPRLKLSYKEMLESNNVITFNGLANSSSYHTFLLDEERSRL<br>YVGAKDHIFSFNLVNIKDFQKIAWPVSYTRRDECKWAGKDILRECANFI<br>KVLKVYNQTHLYACGTGAFHPICTYVGIGHHPEDNIFKLEDSHFENGRG<br>KSPYDPKLLTASLLIDGELYSGTAADFMGRDFAIFRTLGQHHPIRTEQHD<br>SRWLNDPRFISAHLIPESDNPEDDKVYFFFRENAIDGEHSGKATHARIGQI<br>CKNDFGGHRSLVNKWTTFLKARLICSVPGPNGIDTHFDELQDVFLMNSK<br>DPKNPIVYGVFTTSSNIFRGSAVCMYSMSDVRRVFLGPYAHRDGPNYQ<br>WVPFQGRVPYPRPGTCPSKTFGGFESTKDLPDDVITFARSHPAMYNPVFP<br>INNRPIMVKTDVNYQFTQIVVDRVDAEDGQYDVMFIGTDVGTVLKVVSI<br>PKETWHDLEEVLLEEMTVFREPTTISAMELSTKQQQLYVGSAAGVAQLP<br>LHRCDIYGKACAECCLARDPYCAWDGSSCSRYFPTAKRRTRRQDIRNG<br>DPLTHCSDGGIEGRMDHHHHHH |
| 885 | DNA | AACTATCAGAACGGCAAGAACAACGTGCCCCGGCTGAAGCTGAGCT<br>ACAAAGAGATGCTGGAAAGCAACAACGTGATCACCTTCAACGGCCT<br>GGCCAACAGCAGCAGCTACCACACCTTTCTGCTGGACGAGGAACGGT<br>CCAGACTGTACGTGGGAGCCAAGGACCACATCTTCAGCTTCAACCTG<br>GTCAACATCAAGGACTTCCAGAAAATCGCCTGGCCTGTGTCCTACAC<br>CAGACGGGATGAGTGTAAATGGGCCGGCAAGGACATCCTGAGAGAG<br>TGCGCCAACTTCATCAAGGTGCTGAAGGTGTACAATCAGACCCACCT<br>GTACGCCTGTGGCACCGGCGCTTTTCACCCTATCTGTACCTATGTCGG<br>CATCGGCCACCATCCTGAGGACAATATCTTCAAGCTCGAGGACAGCC<br>ACTTCGAGAACGGCAGAGGCAAGAGCCCCTACGATCCCAAACTGCTG<br>ACAGCCTCTCTGCTGATCGACGGCGAGCTGTATTCTGGCACAGCCGC<br>CGATTTCATGGGCAGAGACTTCGCCATCTTCAGAACCCTGGGCCAGC<br>ATCACCCCATCAGAACCGAGCAGCACGACAGCAGATGGCTGAACGA<br>CCCCAGATTCATCAGCGCCCATCTGATCCCCGAGAGCGACAACCCCG<br>AGGACGACAAGGTGTACTTCTTCTTCCGGGAAAACGCCATCGACGGG<br>GAGCACTCTGGAAAAGCCACACACGCCAGAATCGGCCAGATCTGCA<br>AGAACGACTTCGGCGGCCACAGATCCCTCGTGAACAAGTGGACCACC<br>TTCCTGAAGGCCCGGCTGATCTGTTCTGTGCCCGGACCTAATGGCATC<br>GATCCCACTTCGACGAGCTGCAGGACGTGTTCCTGATGAACAGCAA<br>GGACCCCAAGAATCCCATCGTGTACGGCGTGTTCACCACCAGCAGCA<br>ACATCTTTAGAGGCAGCGCCGTGTGCATGTACAGCATGTCCGATGTG<br>CGGAGAGTGTTTCTGGGCCCCTACGCTCACAGAGATGGCCCCAATTA<br>TCAGTGGGTGCCATTCCAGGGCAGAGTGCCCTATCCTAGACCTGGCA<br>CCTGTCCTAGCAAGACCTTTGGCGGCTTCGAGAGCACCAAGGACCTG |

TABLE 1A-continued

Corresponding amino acid sequences and nucleic acid sequences of antibodies according to the present disclosure mentioned in table 1 under the respective SEQ IDs. SEQ ID 581 to 587 being the corresponding Sema3A protein sequences from *Homo sapiens* (SEQ ID 581, 582), *Mus Musculus* (SEQ ID 583), *Rattus norvegicus* (SEQ ID 584), *Canis lupus familiaris* (SEQ ID 585), *Macaca fascicularis* (SEQ ID 586), *Sus scrofa* (SEQ ID 587).

| SEQ ID No | SEQ Type | SEQUENCE |
|---|---|---|
| | | CCTGACGATGTGATTACCTTCGCCAGATCTCACCCCGCCATGTACAAC CCTGTGTTCCCCATCAACAACAGGCCCATCATGGTCAAGACCGACGT GAACTACCAGTTCACCCAGATCGTGGTGGACAGAGTGGATGCCGAGG ACGGCCAGTACGACGTGATGTTCATCGGCACCGATGTGGGCACCGTG CTGAAAGTGGTGTCTATCCCCAAAGAGACATGGCACGACCTGGAAGA GGTGCTGCTGGAAGAGATGACCGTGTTCAGAGAGCCCACCACCATCT CCGCCATGGAACTGAGCACAAAACAGCAACAGCTGTATGTGGGCTCC GCCGCTGGTGTTGCTCAACTGCCTCTGCACAGATGCGACATCTACGG CAAAGCCTGCGCCGAGTGTTGCCTGGCCAGAGATCCTTACTGTGCCT GGGATGGCAGCAGCTGCAGCAGATACTTTCCCACCGCCAAGCGGAG AACCAGACGGCAGGATATCAGAAACGGCGACCCTCTGACACACTGC AGCGACGGTGGCATCGAGGGCCGCATGGATCATCATCATCACCATCA T |

---

What is claimed is:

1. An isolated antibody or antigen-binding fragment thereof for binding to human Sema3A, wherein said isolated antibody or antigen-binding fragment thereof comprises:
   a heavy chain antigen-binding region comprising:
   an H-CDR1 comprising SEQ ID NO: 142,
   an H-CDR2 comprising SEQ ID NO: 143, and
   an H-CDR3 comprising SEQ ID NO: 144 and
   a light chain antigen-binding region comprising:
   an L-CDR1 comprising SEQ ID NO: 146,
   an L-CDR2 comprising SEQ ID NO: 147, and
   an L-CDR3 comprising SEQ ID NO: 148.

2. The isolated antibody or antigen-binding fragment according to claim 1 comprising a variable heavy chain domain that is at least 98% identical to SEQ ID NO: 141 and a variable light chain domain that is at least 98%, identical to SEQ ID NO: 145.

3. The isolated antibody or antigen-binding fragment according to claim 1 comprising a variable heavy chain domain comprising SEQ ID NO: 141 and a variable light chain domain comprising SEQ ID NO: 145.

4. The isolated antibody according to claim 1, wherein said isolated antibody is an IgG1 or an IgG4 antibody.

5. The isolated antibody according to claim 1 comprising a heavy chain comprising SEQ ID NO: 157 and a light chain comprising SEQ ID NO: 158.

6. The antigen-binding fragment according to claim 1, which is an scFv, Fab, Fab' fragment or a F (ab') 2 fragment.

7. An antibody conjugate, comprising the isolated antibody or antigen binding fragment according to claim 1.

8. A pharmaceutical composition comprising the isolated antibody or antigen-binding fragment according to claim 1 or an antibody conjugate comprising the isolated antibody or antigen binding fragment.

9. A kit comprising the isolated antibody or antigen-binding fragment according to claim 1, a conjugate comprising the isolated antibody or antigen binding fragment, a pharmaceutical composition comprising the isolated antibody or antigen binding fragment, or a pharmaceutical composition comprising the conjugate comprising the isolated antibody or antigen binding fragment, and instructions for use.

* * * * *